United States Patent
Ueno et al.

(10) Patent No.: US 6,875,761 B2
(45) Date of Patent: Apr. 5, 2005

(54) CERTAIN 1,3-DISUBSTITUTED ISOQUINOLINE DERIVATIVES

(75) Inventors: Kohshi Ueno, Ibaraki (JP); Atsushi Sasaki, Ibaraki (JP); Koki Kawano, Ibaraki (JP); Tadashi Okabe, Ibaraki (JP); Noritaka Kitazawa, Ibaraki (JP); Keiko Takahashi, Ibaraki (JP); Noboru Yamamoto, Ibaraki (JP); Yuichi Suzuki, Ibaraki (JP); Manabu Matsunaga, Ibaraki (JP); Atsuhiko Kubota, Tsuchiura (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/796,673

(22) Filed: Mar. 10, 2004

(65) Prior Publication Data
US 2004/0204421 A1 Oct. 14, 2004

Related U.S. Application Data

(62) Division of application No. 09/852,850, filed on May 11, 2001, now Pat. No. 6,790,844, which is a division of application No. 09/509,778, filed as application No. PCT/JP98/04465 on Oct. 2, 1998, now Pat. No. 6,340,759.

(30) Foreign Application Priority Data

Oct. 2, 1997 (JP) .............................................. 9-284290

(51) Int. Cl.$^7$ ........................ A61K 31/33; A61K 31/47; A61K 31/495; C07D 241/04; C07D 217/00
(52) U.S. Cl. .................. 514/183; 514/253.03; 514/307; 514/309; 514/310; 514/300; 544/358; 544/363; 546/139; 546/143; 546/18; 546/113
(58) Field of Search ................................ 514/183, 307, 514/253.05, 309, 310, 300; 544/358, 363; 546/139, 143, 18, 113

(56) References Cited

U.S. PATENT DOCUMENTS

| 3,857,944 A | 12/1974 | Simpson et al. ....... 514/253.05 |
| 4,942,163 A | 7/1990 | Behrens ..................... 514/309 |

FOREIGN PATENT DOCUMENTS

| CH | 438 308 | 6/1967 |
| DE | 2 314 985 | 10/1974 |
| FR | 2268524 | 11/1975 |
| GB | 1 545 767 | 5/1979 |
| GB | 1545767 | * 5/1979 |
| JP | 56-92871 A | 7/1981 |
| NL | 8002119 | 10/1980 |

OTHER PUBLICATIONS

Chemical Abstract DN 94:174912, also cited as NL 8002113, dated Oct. 1980.*
Chemical Abstract DN85:160167, also cited asFR 2268524, dated Nov. 1975.*
Chemical Abstract DN 69:35972, also cited as CH 438308, dated Dec. 1967.*
Nair M.D., Chemical Abstract DN 77:164414, also cityed as Indian J. Chem. 10/4,337–40(1972).*

* cited by examiner

Primary Examiner—Richard L. Raymond
Assistant Examiner—Sudhaker B. Patel
(74) Attorney, Agent, or Firm—Birch, Stewart, Kolasch & Birch, LLP

(57) ABSTRACT

Condensed pyridine compounds represented by formula (I):

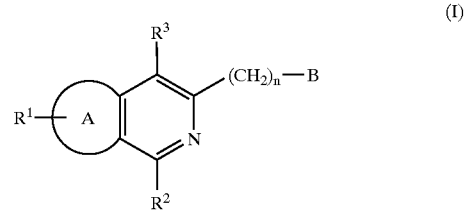

wherein: $R^1$ and $R^3$ are, independently, hydrogen, lower alkyl, or lower alkoxy; $R^2$ represent an amino substituent; ring A is a benzene ring, pyridine ring, thiophene ring, or furan ring; and B represents a substituent containing a ring structure. Also, pharmaceutically acceptable salt and hydrates thereof. These compounds are clinically useful medicaments having serotonin antagonism, and in particular, for treating, ameliorating, or preventing spastic paralysis. They are also useful as central muscle relaxants for ameliorating myotonia.

8 Claims, No Drawings

CERTAIN 1,3-DISUBSTITUTED ISOQUINOLINE DERIVATIVES

This application is a divisional of application Ser. No. 09/852,850, filed May 11, 2001 now U.S. Pat. No. 6,790,844, which is a divisional of Ser. No. 09/509,778, filed on Mar. 31, 2000 (now U.S. Pat. No. 6,340,759B1) and for which priority is claimed under 35 U.S.C. §120. Application Ser. No. 09/509,778 is the national phase under 35 U.S.C. §371 of PCT International Application No. PCT/JP98/04465 filed on Oct. 2, 1998. The entire contents of each of the above-identified applications is hereby incorporated by reference. This application also claims priority under 35 U.S.C. §119 to Application Ser. No. 9-284290 filed in Japan on Oct. 2, 1997.

FIELD OF THE INVENTION

The present invention relates to a clinically useful medicament having a serotonin antagonism, in particular, that for treating, ameliorating and preventing spastic paralysis or central muscle relaxants for ameliorating myotonia.

BACKGROUND OF THE INVENTION

Myotonia, which seriously restrains daily life, is induced by any of a number of factors or a combination thereof, for example, cervico-omo-brachial syndromes accompanying stiffness or pain in the neck, shoulder, arm, lumbar and dorsal skeletal muscles due to abnormal posture, fatigue, changes in the backbone with ageing etc., shoulder periarthritis accompanying inflammation in the tissues constituting the shoulder joint due to charges in the shoulder joint caused by trauma, etc., and spastic paralysis wherein accelerated limb muscle tonus hinders voluntary movements.

In particular, spastic paralysis is a disease which accompanies limb muscle tonus, stiffening, walking difficulty, etc. and thus seriously restrains daily life.

PRIOR ART

It has been a practice to treat these diseases mainly with the use of medicaments. At the present stage, central muscle relaxants or peripheral muscle relaxants are administered to patients with these diseases.

Particular examples of used central muscle relaxants include Tolperisone hydrochloride, Baclofen, Tizanidine hydrochloride, Chlorzoxazone and Diazepam.

On the other hand, particular examples of used peripheral muscle relaxants include suxamethoniun chloride, Pancuronium bromide and dantrolene sodium.

Central muscle relaxants act selectively on the central nervous system so as to relax muscles. Therefore, it is expected that those action on the upper center would exhibit a more potent muscle relaxant effect. However, there arise at the same time some problems including extrapyramidal symptoms and neurologic manifestations such as sleepiness, sluggishness and atony. Namely, there has been known hitherto no medicament capable of achieving well-balanced principal action and side effects.

Diazepam, which is inherently a minor tranquilizer, is efficacious against diseases accompanying metal symptoms such as anxiety, tension and depression. However, its effect is too potent to merely ameliorate myotonia. With the use of diazepam, therefore, spastic paralysis can be relieved but there arise some problems such as dizziness.

On the other hand, suxamethonium chloride and Pancuronium bromide which are peripheral muscle relaxants are marketed exclusively as injections, which makes the chronic administration thereof difficult.

Dantrolene sodium is processed into injections and preparations for oral use and has a relatively potent muscle relaxant effect. However, it suffers from problems of having only a low margin of safety and frequently induced muscular atony. Accordingly, it is difficult for those other than medical specialists to administer this medicine.

As discussed above, there has been known hitherto no medicaments for treating and ameliorating myotonia in spastic paralysis etc., which is clinically useful and has a high safety.

DISCLOSURE OF THE INVENTION

Under these circumstances, the present inventors have conducted extensive studies to develop medicaments for treating, ameliorating and preventing spastic paralysis or central muscle relaxants which have a potent effect of ameliorating myotonia while sustaining a high safety and newly paid their attention to compounds having a serotonin antagonism. As a result, they have successfully found that a novel condensed pyridine compound represented by the following formula or a pharmacologically acceptable salt thereof has an excellent central muscle relaxant effect and a high safety and thus makes it possible to solve the above problems, thus completing the present invention.

Accordingly, the present invention aims at providing clinically useful novel medicaments which have well-balanced principal action and side effects and make it possible to overcome the problem encountering in the prior art that those acting on the upper center would exhibit a more potent muscle relaxant effect but at the same time suffer from problems including extrapyramidal symptoms and neurologic manisfestations such as sleepiness, sluggishness and weakness.

Because of the anti-serotonin effect, it is expected that the condensed pyridine compound of the present invention is moreover useable in preventing, treating and ameliorating depression, emotional disorders, schizophrenia, sleep disturbance, anxiety, spinal cord injury, thrombosis, hypertension, brain circulatory disturbances, peripheral circulatory disturbances, drug addition, etc.

In addition to the condensed pyridine compound, the present invention provides medicinal composition which comprises a pharmaceutically effective dose of the condensed pyridine compound, its pharmaceutically acceptable salt or hydrates thereof and pharmaceutically acceptable carriers. Further, it provides an agent for treating, ameliorating or preventing diseases against which serontonin antagonism is efficacious, an agent for treating, ameliorating or preventing spastic paralysis and a muscle relaxant, which comprise the above-mentioned active ingredient.

Further, it provides a treating, ameliorating or prophylactic agent comprising the above-mentioned effective ingredient for diseases for which the serotonin antagonism is efficacious or, a therapeutic, ameliorating and prophylactic agents or spastic paralysis and a muscle relaxation agent.

Furthermore, it provides a method for treating diseases against which the serotonin antagonism is efficacious or spastic paralysis, or ameliorating myotonia, which comprising the step of administering a pharmacologically effective dose of the condensed pyridine compound, its pharmacologically acceptable salt or hydrates thereof to a patient. Additionally, it provides the use of the effective ingedient for producing the above-mentioned medicaments.

Herein, the condensed pyridine compound (I) of the present invention is represented by the following formula:

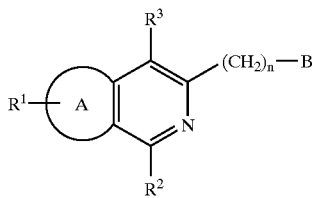
(I)

wherein, ring A represents benzene ring, pyridine ring, thiophene ring or furan ring;

$R^1$ represents hydrogen atom, halogen atom, a lower alkyl group or a lower alkoxyl group;

$R^2$ represents 4-morpholinyl group, 1-imidazolyl group, 1-lower alkyl homopiperazin-4-yl group or any one selected from the groups represented by the following formulae:

(wherein, T represents nitrogen atom or methine group;

$R^1$ represents hydrogen atom, halogen atom, a lower alkyl group or a lower alkoxyl group;

$R^4$ represents hydrogen atom, a lower alkyl group, a hydroxy lower alkyl group, a halogenated lower alkyl group, a lower cycloalkyl group, an aryl group, an aralkyl group, 1-piperidyl group, an alkenyl group, a cyano lower alkyl group, a carbamoyl lower alkyl group, a lower acyl group, an aromatic acyl group, a lower alkoxyl carbonyl group, an aryloxycarbonyl group or an aralkyloxycarbonyl group;

$R^5$ and $R^6$ are the same as or different from each other and each represents hydrogen atom, a lower alkyl group, a di lower alkyl aminoalkyl group, an optionally substituted heteroaryl lower alkyl group);

n represents 0 or an integer of 1 to 6; and

B represents an optionally substituted aryl group, an optionally substituted heteroaryl group, an optionally substituted aralkyloxy group, an aryl (hydroxy) alkyl group, an aromatic acyl amino group, an arylsulfonylamino group, a lower alkoxyl arylsulfonylamino group, a hydroxy lower alkoxyl styryl group, a lower alkoxyl aryloxy group, 4-phenylpiperidin-1-yl group, 4-pyridylpiperidin-1-yl group, an optionally substituted arylalkenyl group, an optionally substituted arylalkynyl group, an optinally substituted heteroarylalkenyl group, an optionally substituted heteroarylalkynyl group, an aromatic acyl alkynyl group, an optionally N-substituted amino lower alkyl group, an optionally substituted arylamino group, an optionally substituted aralkylamino group or any one selected from the groups represented by the following formulae:

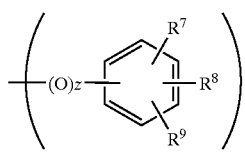

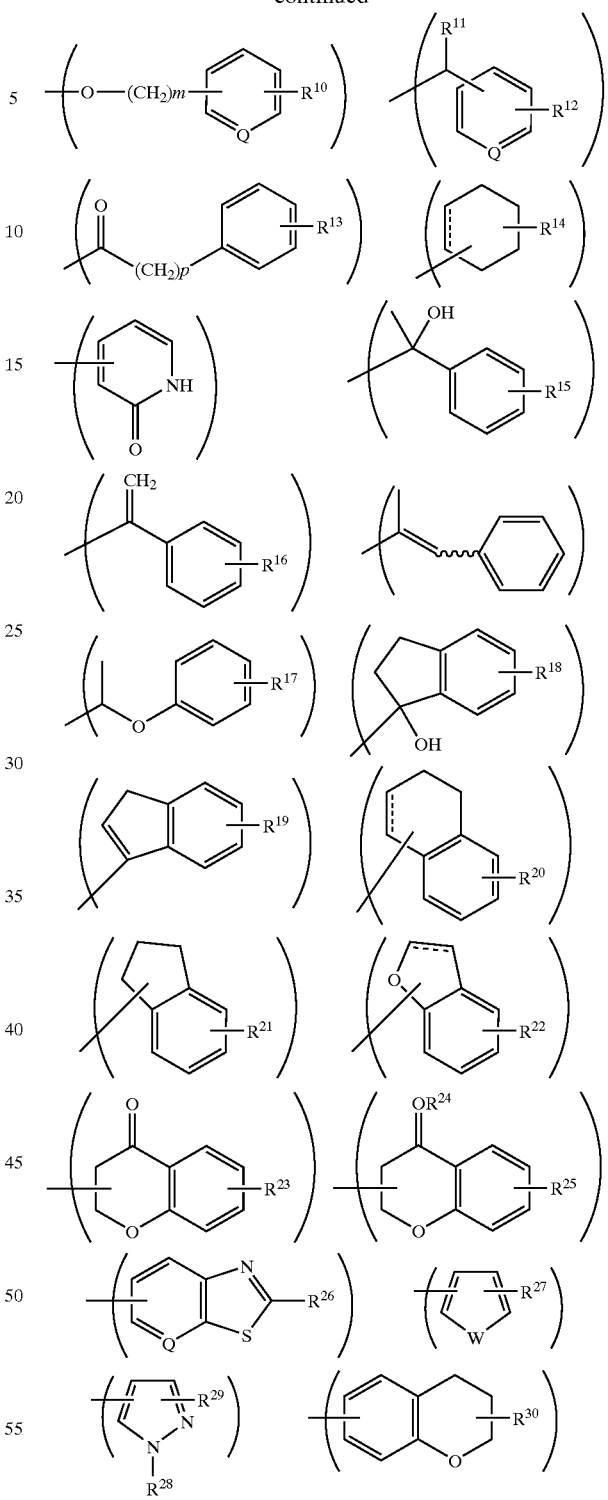

(wherein z represents 0 or 1;

Q represents nitrogen atom or methine group;

$R^7$, $R^8$ are $R^9$ are the same as or different from each other and each represents hydrogen atom, halogen atom, hydroxyl group, a lower alkyl group, a lower alkenyl group, a lower alkynyl group, a lower alkoxy group, a lower thioalkoxyl group, a hydroxy lower thioalkoxyl group, an arylthio group, a heteroarylthio group, a heteroaryl (hydroxy) alkyl group, a halogenated lower alkyl group, a hydroxy lower alkyl group, a dihydroxy lower alkyl group, a halogenated (hydroxy) lower alkyl group, a hydroxyalkenyl group, a hydroxyalkynyl group, a hydroxy lower cycloalkenyl group, a lower alkoxy (hydroxy) alkyl group, a lower alkoxy (hydroxy) alkoxy group, a lower alkoxyalkyl group, a lower alkoxyalkyl group, a lower thioalkoxyalkoxy group, a lower alkylsulfonylakoxy group, a hydroxy lower alkoxy group, a dihydroxy lower alkoxy group, a hydroxy lower alkylalkoxy group, a hydroxyamino lower alkyl group, a lower cycloalkyl (hydroxyl) alkyl group, an aralkyl group, a hydroxyaralkyl group, cyano group, a cyano lower alkyl group, amide group (carbamoyl group), an N-lower alkylamide group, an N-lowre cycloalkylamide group, an N,N-di lower alkylamide group, an N-hydroxy lower alkylamide group, an N-hydroxy lower alkyl-N-lower alkylamide group, an N-arylamide group, cyclic aminocarbonyl group, carbamoyl group, an N-lower alkyl carbamoyl group, an N,N-di lower alkyl carbamoyl group, aminosulfonyl group, cyclic aminosulfonyl group, an N-lower alkylaminosulfonyl group, an N-lower cycloalkylaminosulfonyl group, an N,N-di lower alkylaminosulfonyl group, an N-hydroxy lower alkylaminosulfonyl group, an N-lower alkoxyalkylaminosulfonyl group, an N-halogenated lower alkylsulfonyl group, pyrrolidinylsulfonyl group, a lower alkylsulfonylaminoalkyl group, an N-lower alkylaminosulfonylalkyl group, an N,N-di lower alkylaminosulfonylalkyl group, a lower acyl group, a lower acylalkyl group, a lower cycloalkyl (hydroxy) methyl group, tetrahydropyranol group, hydroxytetrahydropyranyl group, a hydroxy lower alkyltetrahydropyranyl group, a lower acylaminoalkyl group, (thiazol-2-yl)hydroxymethyl group, di (thiazol-2-yl)hydroxymethyl group, a lower alkylsulfonyl group, a lower alkoxyalkylsulfonyl group, a hydroxy lower alkylsulfonyl group, a lower alkylsulfonyl group, an N-lower alkylamidealkyl group, an aryl group, an aralkyl group, a heteroaryl group, a heteroaryl lower alkyl group, a heteroaryl lower alkoxy group, a heteroarylsulfonyl group, 4-morpholinylsulfonyl group, 4-oxythiomorpholinylsulfonyl group, 4-dioxythiomorpholinylsulfonyl group, 4-morpholinylsulfonyl group, a hydroxy lower cycloalkyl group, a hydroxy lower cycloalkyloxy group, a hydroxycycloalkenyl group, a halogenatedhydroxy lower alkyl group, 4-hydroxypiperidyl group, a 4-lower alkoxypiperidyl group, an ω,ω-lower alkylenedioxyalkyl group, an ω,ω-lower alkylenedioxyalkoxy group, a lower cycloalkylhydroxymethyl group, an aryloxy group, an arylaminosulfonyl group, amino group, a lower alkylamino group, a di lower alkylamino group, a hydroxy lower alkylamino group, a lower acylamino group, a hydroxy lower acylamino group, a lower alkylsulfonylamino group, a pyridyl lower alkoxygroup, a lower alkylpyridylalkoxy group, a lower alkoxyhydroxyalkoxy group, a lower thioalkoxyalkoxy group, a lower alkylsulfonylalkoxy group, an N-lower alkylcarbamoyl group, an N,N-di lower alkylcarbamoyl group, an N-hydroxy lower alkylcarbamoyl group, an N-hydroxy lower alkyl-N-lower alkylcarbamoyl group, a halogenated lower alkoxy group, a cyano lower alkoxy group, a hydroxy lower cycloalkoxy group, trifluoromethyl group, trifluoromethoxy group, an amino lower alkoxy group, an N-lower alkyl aminoalkoxy group, an N,N-di lower alkylaminoalkoxy group, a lower acylalkoxy group, a lower acylaminoalkoxy group, a (1,3-dioxolanyl) lower alkyl group, a (1,3-dioxolanyl) lower alkoxyl group, an amide lower alkoxy group, a 4-(hydroxyalkyl) tetrahydropyran-4-yl group, 2,3-dihydrobenzofuranyl group, a 2-hydroxy-2-alkyl-2,3-dihydrobenzofuranyl group, indanonyl group, hydroxyindanyl group, an imidazolyl lower alkoxyl group, succinimide group or 2-oxazolidon-3-yl group;

furthermore, $R^7$ represents hydrogen atom, while $R^8$ and $R^9$ form cyclopentanone ring, hydroxycyclopentane ring, a hydroxyalkylcyclopentane ring, cyclohexanone ring, hydroxycyclohexane ring, a hydroxyalkylcyclohexane ring, 2-hydroxymethyl-2-methylcyclopentanone ring, 1,2-ethylenedioxy ring or methylenedioxy ring;

m or p represent 0 or an integer of 1 to 6;

$R^{10}, R^{12}, R^{13}, R^{14}, R^{15}, R^{16}, R^{17}, R^{18}, R^{19}, R^{20}, R^{21}, R^{22}, R^{23}, R^{25}, R^{27}$ and $R^{29}$ independently represent hydrogen atom, halogen atom, hydroxyl group, a lower alkyl group, a lower alkoxy group, a hydroxy lower alkyl group, a hydroxy lower alkoxy group or tetrahydropyranyl group;

$R^{11}$ represents hydrogen atom, halogen atom, hydroxy group, a lower alkyl group or a lower alkoxy group;

$R^{24}$ represent hydrogen atom or a lower alkyl group;

$R^{26}$ represent hydrogen atom or a hydroxy lower alkyl group;

$R^{28}$ represent hydrogen atom or a lower alkyl group;

$R^{30}$ represents hydrogen atom, a lower alkyl group, a lower alkoxy group, a hydroxy lower alkyl group or a hydroxy lower alkoxy group;

W represent sulfur atom or oxygen atom;

the bond represented by the following formula:

----- represent a single or double bond; and the bond represented by the following formula:

∿∿∿ represent trans or cis bond.).

Among these condensed pyridine compounds, the condensed pyridine compound (II) represented by the following formula is more preferable:

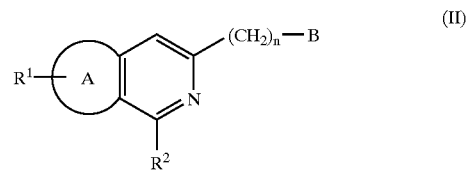

wherein, ring A represents benzene ring, thiophene ring or furan ring;

$R^1$ represents hydrogen atom, halogen atom, a lower alkyl group or a lower alkoxy group;

$R^2$ represents 4-morpholinyl group, 1-imidazolyl group, a 1-lower alkylhomopiperazin-4-yl group or any one selected from the groups represented by the following formulae:

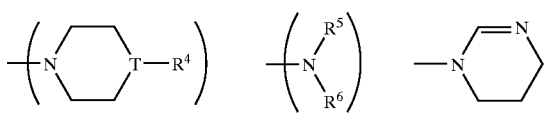

(wherein, T represents nitrogen atom or methine group;

R⁴ represents hydrogen atom, a lower alkyl group, a hydroxy lower alkyl group, a halogenated lower alkyl group, a lower cycloalkyl group, an aryl group, an aralkyl group, 1-piperidyl group, an alkenyl group, a cyano lower alkyl group, a carbamoyl lower alkyl group, a lower acyl group, an aromatic acyl group, a lower alkoxy carbonyl group, an aryloxycarbonyl group or an aralkyloxycarbonyl group; and R⁵ and R⁶ are the same as or different from each other and each represents hydrogen atom, a lower alkyl group, a di lower alkylaminoalkyl group, an optionally substituted heteroaryl lower alkyl group.);

n represents 0 or an integer of 1 to 6; and

B represents an optionally substituted aryl group, an optionally substituted heteroaryl group, an optionally substituted aralkyloxy group, an aryl (hydroxy)alkyl group, an aromaticacylamino group, an arylsulfonylamino group, a lower alkoxyarylsufonylamino group, a hydroxy lower alkoxystyryl group, a lower alkoxyaryloxy group, 4-phenylpiperidin-1-yl group, 4-pyridylpiperidin-1-yl group, an optionally substituted arylalkenyl group, an optionally substituted arylalkynyl group, an optionally substituted heteroarylalkenyl group, an optionally substituted heteroarylalkynyl group, an aromaticacylalkynyl group, an optionally N-substituted amino lower alkyl group, an optionally substituted arylamino group, an optionally substituted aralkylamino group or any one selected from the groups represented by the following formulae:

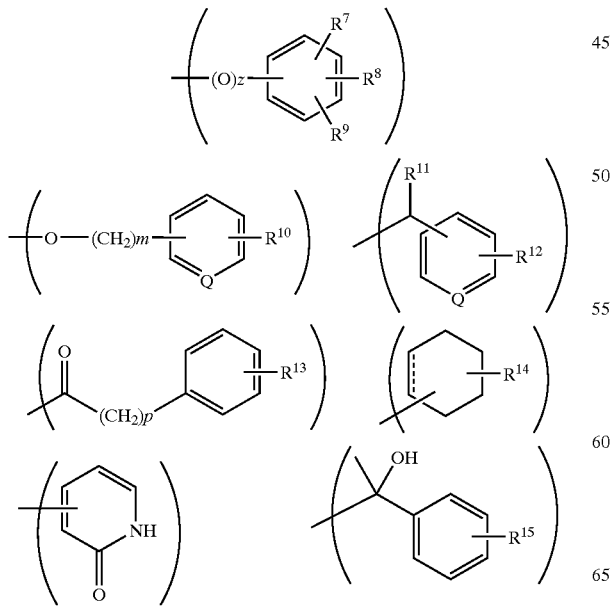

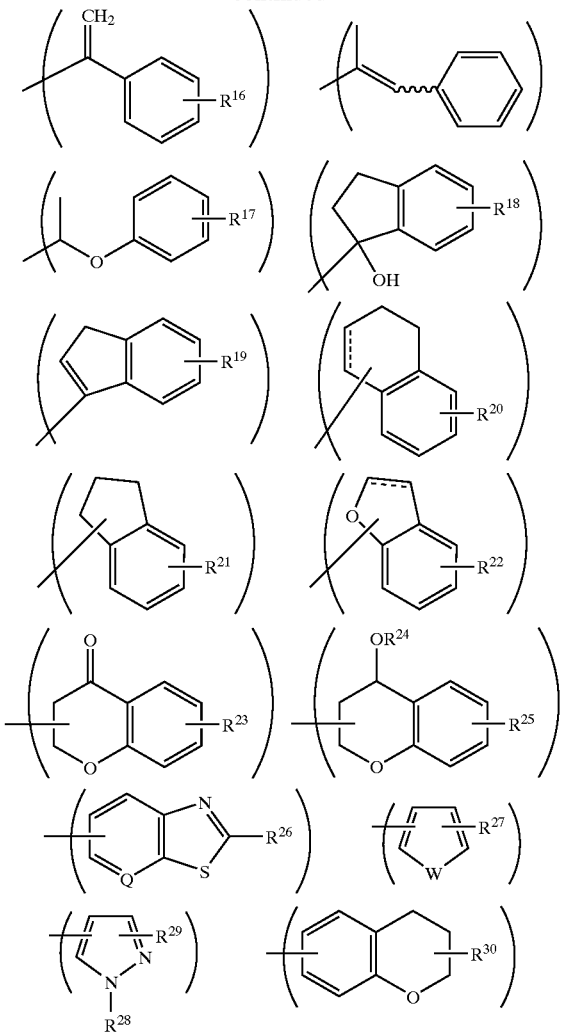

(wherein, z represents 0 or 1;

Q represents nitrogen atom or methine group;

R⁷, R⁸ and R⁹ are the same as or different from each other and each represents hydrogen atom, halogen atom, hydroxy group, a lower alkyl group, a lower alkenyl group, a lower alkynyl group, a lower alkoxy group, a lower thioalkoxy group, a hydroxy lower thioalkoxy group, an arylthio group, a heteroarylthio group, a heteroaryl(hydroxy)alkyl group, a halogenated lower alkyl group, a hydroxy lower alkyl group, a dihydroxy lower alkyl group, a halogenated(hydroxy) lower alkyl group, a hydroxyalkenyl group, a hydroxyalkynyl group, a hydroxy lower cycloalkenyl group, a lower alkoxy(hydroxy)alkyl group, a lower alkoxy(hydroxy) alkoxy group, a lower alkoxyalkyl group, a lower alkoxyalkoxy group, a lower thioalkoxyalkoxy group, a lower alkyl sulfonylalkoxy group, a hydroxy lower alkoxy group, a dihydroxy lower alkoxy group, a hydroxy lower alkylakoxy group, a hydroxyimino lower alkyl group, a lower cycloalkyl (hydroxy) alkyl group, an aralkyl group, a hydroxyaralkyl group, cyano group, an cyano lower alkyl group, amide group (carbamoyl group), an N-lower alkyl amide group, an N-lower cycloalkyl amide group, an N,N-di lower alkyl amide group, an N-hydroxy lower alkyl amide group, an N-hydroxy lower alkyl-N-lower alkyl amide group, an N-arylamide group, a cyclic amino carbonyl group, carbamoyl group, an N-lower alkyl carbamoyl group, an N,N-di-lower alkyl carbamoyl group, aminosulfonyl group, a cyclic amino sulfonyl group, an N-lower alkyl aminosulfonyl group, an N-lower cycloalkylaminosulfonyl group, an N,N-di lower alkyl aminosulfonyl group, an N-hydroxy lower alkylaminosulfonyl group, an N-lower alkoxyalkylaminosulfonyl group, an N-halogenated lower alkylsulfonyl group, pyrrolidinylsulfonyl group, a lower alkylsulfonylaminoalkyl group, an N-lower alkylaminosulfonylalkyl group, an N,N-di lower alkylaminosulfonylalkyl group, a lower acyl group, a lower acylalkyl group, a lower cycloalkyl (hydroxy)methyl group, tetrahydropyranyl group, hydroxytetrahydropyranyl group, a hydroxy lower alkyltetrahydropyranyl group, a lower acylaminoalkyl group, (thiazol-2-yl)hydroxymethyl group, di(thiazol-2-yl)hydroxymethyl group, a lower alkylsulfonyl group, a lower alkoxyalkylsulfonyl group, a hydroxy lower alkyl sulfonyl group, a lower alkyl sulfonylalkyl group, an N-lower alkyl amidealkyl group, an aryl group, an aralkyl group, a heteroaryl group, a heteroaryl lower alkyl group, a heteroaryl lower alkoxy group, a heteroarylsulfonyl group, 4-morpholinylsulfonyl group, 4-oxythiomorpholinylsulfonyl group, 4-dioxythiomorpholinylsulfonyl group, 4-morpholinylsulfonyl group, a hydroxy lower cycloalkyl group, a hydroxy lower cycloalkyloxy group, a hydroxycycloalkenyl group, a halogenated hydroxy lower alkyl group, 4-hydroxypiperidyl group, a 4-lower alkoxy piperidyl group, an ω,ω-lower alkylene dioxyalkyl group, an ω,ω-lower alkylene dioxylalkoxy group, a lower cycloalkyl hydroxymethyl group, an aryloxy group, an arylaminosulfonyl group, amino group, a lower alkylamino group, a di lower alkylamino group, a hydroxy lower alkylamino group, a lower acylamino group, a hydroxy lower acylamino group, a lower alkylsulfonylamino group, a pyridyl lower alkoxy group, a lower alkylpyridylalkoxy group, a lower alkoxyhydroxyalkoxy group, a lower thioalkoxyalkoxy group, a lower alkylsulfonylalkoxy group, an N-lower alkylcarbamoyl group, an N,N-di lower alkylcarbamoyl group, an N-hydroxy lower alkylcarbamoyl group, an N-hydroxy lower alkyl-N-lower alkylcarbamoyl group, a halogenated lower alkoxy group, a cyano lower alkoxy group, a hydroxy lower cycloalkoxy group, trifluoromethyl group, trifluoromethoxy group, an amino lower alkoxy group, an N-lower alkyl aminoalkoxy group, an N,N-di lower alkylaminoalkoxy group, a lower acylalkoxy group, a lower acylaminoalkoxy group, a (1,3-dioxolanyl) lower alkyl group, a (1,3-dioxolanyl) lower alkoxy group, an amide lower alkoxy group, a 4-(hydroxyalkyl) tetrahydropyran-4-yl group, 2,3-dihydrobenzofuranyl group, a 2-hydroxy-2-alkyl-2,3-dihydrobenzofuranyl group, indanonyl group, hydroxyindanyl group, an imidazolyl lower alkoxy group, succinimide group or 2-oxazolidon-3-yl group;

furthermore, $R^7$ represents hydrogen atom, while $R^8$ and $R^9$ may form cyclopentanon ring, hydroxycyclopentane ring, a hydroxyalkylcyclopentane ring, cyclohexanone ring, hydroxycyclohexane ring, a hydroxyalkylcyclohexane ring, 2-hydroxymethyl-2-methylcyclopentanone ring, 1,2-ethylenedioxy ring or methylenedioxy ring;

m or p represents 0 or an integer of 1 to 6;

$R^{10}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{25}$, $R^{27}$ and $R^{29}$ independently represent hydrogen atom, halogen atom, hydroxy group, a lower alkyl group, a lower alkoxy group, a hydroxy lower alkyl group, a hydroxy lower alkoxy group or tetrahydropyranyl group;

the concrete examples of the heteroaryl group include 4-morpholinyl group, 2,6-dimethyl-4-morpholinyl group, 4-thiomorpholinyl group, 4-oxythiomorpholinyl group, 4-dioxythiomorpholinyl group, 1,3-dioxanyl group, 1,4-dioxanyl group, tetrahydrofuranyl group, dihydropyranyl group, 4,4-ethylenedioxypiperidin-1-yl group, 4-hydroxypiperidin-1-yl group, 4-methoxypiperidin-1-yl group, 4-acetylpiperazin-1-yl group, a 4-hydroxy lower alkyl piperidin-1-yl group and the like;

the concrete examples of the heteroaryl lower alkyl group include 4-morpholinylmethyl group, 4-thiomorpholinylmethyl group, a (tetrahydropyran-4-yl) lower alkyl group, pyridylmethyl group and the like;

$R^{11}$ represents hydrogen atom, halogen atom, hydroxy group, a lower alkyl group or a lower alkoxy group;

$R^{24}$ represents hydrogen atom or a lower alkyl group;

$R^{26}$ represents hydrogen atom or a hydroxy lower alkyl group;

$R^{28}$ represents hydrogen atom or a lower alkyl group;

$R^{30}$ represents hydrogen atom or a lower alkyl group, a lower alkoxy group, a hydroxy lower alkyl group or a hydroxy lower alkoxy group;

W represents sulfur atom or oxygen atom;

the bond represented by the following formula:

----- represents a single or double bond; and the bond represented by the following formula:

∿∿∿ represents trans or bis bond.).

More specifically, the condensed pyridine compound of the present invention preferably include the condensed pyridine compounds represented by the following formulae:

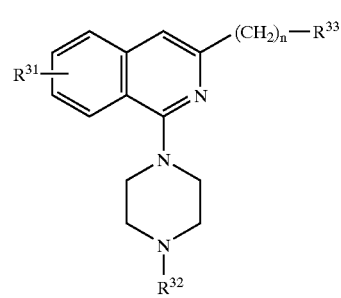

(1)

-continued (2)

(3)

(4)

(5)

(6)

(7)

(8)

(9)

(10)

(11)

wherein R³¹ has the same meaning as that of the above R¹, R³² has the same meaning as that of the above R² and R³³ has the same meaning as that of the above B, respectively.

More specifically, the condensed pyridine compound of the present invention preferably includes the following ones:
(1) 3-(4-benzyloxybutyl)-1-(4-ethylpiperazin-1-yl)isoquinoline,
(2) 1-(1-methylpiperazin-4-yl)-3-(4-methoxyphenyl)isoquinoline,
(3) 1-(1-methylpiperazin-4-yl)-3-[4-(2-hydroxyethoxy)phenyl]isoquinoline,
(4) 1-(4-ethylpiperazin-1-yl)-3-(4-trifluoromethylphenyl)isoquinoline,
(5) 1-(4-ethylpiperazin-1-yl)-3-[4-(1-fluoropropyl)phenyl]isoquinoline,
(6) 1-(4-ethylpiperazin-1-yl)-3-(2-hydroxyphenyl)isoquinoline,
(7) 1-(4-ethylpiperazin-1-yl)-3-(4-hydroxyphenyl)isoquinoline,
(8) 1-(4-ethylpiperazin-1-yl)-3-(2-methoxyphenyl)isoquinoline,
(9) 1-(4-ethylpiperazin-1-yl)-3-(3-methoxyphenyl)isoquinoline,
(10) 1-(4-ethylpiperazin-1-yl)-3-(4-methoxyphenyl)isoquinoline,
(11) 3-(2,3-dimethoxyphenyl)-1-(4-ethylpiperazin-1-yl)isoquinoline,
(12) 3-(2,4-dimethoxyphenyl)-1-(4-ethylpiperazin-1-yl)isoquinoline,
(13) 3-(2,5-dimethoxyphenyl)-1-(4-ethylpiperazin-1-yl)isoquinoline,
(14) 3-(3,4-dimethoxyphenyl)-1-(4-ethylpiperazin-1-yl)isoquinoline,
(15) 3-(3,5-dimethoxyphenyl)-1-(4-ethylpiperazin-1-yl)isoquinoline,
(16) 1-(4-ethylpiperazin-1-yl)-3-(2,4,5-trimethoxyphenyl)isoquinoline,
(17) 1-(4-ethylpiperazin-1-yl)-3-(4-hydroxymethylphenyl)isoquinoline,
(18) 3-[2-(2-hydroxyethoxy)phenyl]-1-(4-ethylpiperazin-1-yl)isoquinoline,
(19) 1-(4-ethylpiperazin-1-yl)-3-[4-(1-hydroxypropyl)phenyl]isoquinoline,
(20) 1-(4-ethylpiperazin-1-yl)-3-[4-(3-hydroxypropyl)phenyl]isoquinoline,
(21) 1-(4-ethylpiperazin-1-yl)-3-[4-(1-hydroxybutyl)phenyl]isoquinoline,
(22) 1-(4-ethylpiperazin-1-yl)-3-[4-(3-hydroxybutyl)phenyl]isoquinoline,
(23) 3-[4-(4-hydroxybutyl)phenyl]-1-(4-ethylpiperazin-1-yl)isoquinoline,
(24) 3-[4-(1,3-dihydroxypropyl)phenyl]-1-(4-ethylpiperazin-1-yl)isoquinoline,
(25) 3-[4-(1,3-dihydroxy-3-methylbutyl)phenyl]-1-(4-ethylpiperazin-1-yl)isoquinoline,
(26) 3-[4-(3-hydroxy-1-methoxybutyl)phenyl]-1-(4-ethylpiperazin-1-yl)isoquinoline,
(27) 1-(1-ethylpiperazin-4-yl)-3-[4-(3-hydroxy-1-fluoropropyl)phenyl]isoquinoline,
(28) 1-(4-ethylpiperazin-1-yl)-3-[4-(4-hydroxymethyl-3-fluoro)phenyl]isoquinoline,
(29) 1-(4-ethylpiperazin-1-yl)-3-[3-fluoro-4-(1-hydroxypropyl)phenyl]isoquinoline,
(30) 3-[3-chloro-4-(3-hydroxypropyl)phenyl]-1-(4-ethylpiperazin-1-yl)isoquinoline,
(31) 3-[3-carboxamide-4-(3-hydroxypropyl)phenyl]-1-(4-ethylpiperazin-1-yl)isoquinoline,
(32) 3-[3-cyano-4-(3-hydroxypropyl)phenyl]-1-(4-ethylpiperazin-1-yl)isoquinoline,
(33) 1-(4-ethylpiperazin-1-yl)-3-[4-(3-hydroxypropyl)-3-methoxyphenyl]isoquinoline,
(34) 3-[3-(3-hydroxypropyl)-4-methoxyphenyl]-1-(4-ethylpiperazin-1-yl)isoquinoline,
(35) 3-[3-(4-hydroxybutyl)-4-methoxyphenyl]-1-(4-ethylpiperazin-1-yl)isoquinoline,
(36) 1-[4-ethylpiperazin-1-yl)-3-[4-(2-hydroxyethoxy)phenyl]isoquinoline,
(37) 3-[3,4-(2-dihydroxyethoxy)phenyl]-1-(4-ethylpiperazin-1-yl)isoquinoline,
(38) 3-[3,5-(2-dihydroxyethyoxy)phenyl]-1-(4-ethylpiperazin-1-yl)isoquinoline,
(39) 3-[3-chloro-4-(2-hydroxyethoxy)phenyl]-1-(4-ethylpiperazin-1-yl)isoquinoline,
(40) 3-[3-methyl-4-(2-hydroxyethoxy)phenyl]-1-(4-ethylpiperazin-1-yl)isoquinoline,
(41) 3-[3-isopropyl-4-(2-hydroxyethoxy)phenyl]-1-(4-ethylpiperazin-1-yl)isoquinoline,
(42) 1-(4-ethylpiperazin-1-yl)-3-[4-(2-methoxyethoxy)phenyl]isoquinoline,
(43) 3-[3,4-(2-dimethoxyethoxy)phenyl]-1-(4-ethylpiperazin-1-yl)isoquinoline,
(44) 3-[4-(2-hydroxyethoxy)methylphenyl]-1-(4-ethylpiperazin-1-yl)isoquinoline,
(45) 1-(4-ethylpiperazin-1-yl)-3-[4-(2-fluoroethoxy)phenyl]isoquinoline,
(46) 3-(3,4-methylenedioxyphenyl)-1-(4-ethylpiperazin-1-yl)isoquinoline,
(47) 1-(1-ethylpiperazin-4-yl)-3-(4-acetonyloxyphenyl)isoquinoline,
(48) 3-[4-(3-aminopropoxy)phenyl]-1-(4-ethylpiperazin-1-yl)isoquinoline,
(49) 1-(4-ethylpiperazin-1-yl)-3-[4-(2-dimethylaminoethoxy)phenyl]isoquinoline,
(50) 3-[4-(3-acetamidepropoxy)phenyl]-1-(4-ethylpiperazin-1-yl)isoquinoline,
(51) 3-(4-cyanomethoxyphenyl)-1-(4-ethylpiperazin-1-yl)isoquinoline,
(52) 3-[4-(2-cyanoethoxy)phenyl]-1-(4-ethylpiperazin-1-yl)isoquinoline,
(53) 3-[4-(3-cyanopropoxy)phenyl]-1-(4-ethylpiperazin-1-yl)isoquinoline,
(54) 3-[4-(3-methylthiopropoxy)phenyl]-1-(4-ethylpiperazin-1-yl)isoquinoline,
(55) 3-[4-(3-methylsulfonpropoxy)phenyl]-1-(4-ethylpiperazin-1-yl)isoquinoline,
(56) 3-[4-[2-(1-imidazonyl)ethoxy]phenyl]-1-(4-ethylpiperazin-1-yl)isoquinoline,
(57) 3-{4-[3-(4-pyridyl)propoxy]phenyl}-1-(4-ethylpiperazin-1-yl)isoquinoline,
(58) 3-{4-[2-(2-methylpyridin-5-yl)ethoxy]phenyl}-1-(4-ethylpiperazin-1yl)isoqinoline,
(59) 1-(1-ethylpiperazin-4-yl)-3-[4-(N-ethylcarbamyl)phenyl]isoquinoline,
(60) (Z)-1-(4-ethylpiperazin-1-yl)-3-(4-hydroxyiminomethylphenyl)isoquinoline,
(61) (E)-1-(4-ethylpiperazin-1-yl)-3-(4-hydroxyiminomethylphenyl)isoquinoline,
(62) 3-(4-cyanophenyl)-1-(4-ethylpiperazin-1-yl)isoquinoline,
(63) 1-(4-ethylpiperazin-1-yl)-3-(4-N-propylaminocarbonylphenyl) isoquinolin,
(64) 3-[4-(4-hydroxy-1-cyclohexen-1-yl)phenyl]-1-(4-ethylpiperazin-1-yl)isoquinoline,
(65) 3-(4-aminophenyl)-1-(4-ethylpiperazin-1-yl)isoquinoline,

(66) 3-[4-(N,N-dimethylamino)phenyl]-1-(4-ethylpiperazin-1-yl)isoquinoline,
(67) 3-[4-(2-hydroxyethyl)aminophenyl]-1-(4-ethylpiperazin-1-yl)isoquinoline,
(68) 3-(4-acetamidephenyl)-1-(4-ethylpiperazin-1-yl)isoquinoline,
(69) 3-(4-ethylcarbonylaminophenyl)-1-(4-ethylpiperazin-1-yl)isoquinoline,
(70) 3-(4-propylcarbonylaminophenyl)-1-(4-ethylpiperazin-1-yl)isoquinoline,
(71) 3-(4-ethylsulfonylaminophenyl)-1-(4-ethylpiperazin-1-yl)isoquinoline,
(72) 3-(4-propylsulfonylaminophenyl)-1-(4-ethylpiperazin-1-yl)isoquinoline,
(73) 3-(4-butylsulfonylaminophenyl)-1-(4-ethylpiperazin-1-yl)isoquinoline,
(74) 3-(4-sulfonamidephenyl)-1-(4-ethylpiperazin-1-yl)isoquinoline,
(75) 3-[(4-morpholinyl) sulfonylphenyl]-1-(4-ethylpiperazin-1-yl)isoquinoline,
(76) 3-[(4-thiomorpholinyl) sulfonylphenyl]-1-(4-ethylpiperazin-1-yl)isoquinoline,
(77) 3-[(1,1-dioxythiomorpholinyl) sulfonylphenyl]-1-(4-ethylpiperazin-1-yl)isoquinoline,
(78) 3-(4-ethylsulfonylaminomethylphenyl)-1-(4-ethylpiperazin-1-yl)isoquinoline,
(79) 3-(4-ethylsulfonylaminoethylphenyl)-1-(4-ethylpiperazin-1-yl)isoquinoline,
(80) 3-(4-ethylaminosulfonylmethylphenyl)-1-(4-ethylpiperazin-1-yl)isoquinoline,
(81) 3-(4-propylaminosulfonylmethylphenyl)-1-(4-ethylpiperazin-1-yl)isoquinoline,
(82) 3-[4-N,N-diethylamino)sulfonylmethylphenyl]-1-(4-ethylpiperazin-1-yl)isoquinoline,
(83) 3-[4-(tetrahydropyran-4-yl)phenyl]-1-(4-ethylpiperazin-1-yl)isoquinoline,
(84) 3-[4-(5,6-dihydro-2H-pyran-4-yl)phenyl]-1-(4-ethylpiperazin-1-yl)isoquinoline,
(85) 3-(4-ethylcarbonylaminomethylphenyl)-1-(4-ethylpiperazin-1-yl)isoquinoline,
(86) 3-(4-propylcarbonylaminoethylphenyl]-1-(4-ethylpiperazin-1-yl)isoquinoline,
(87) 3-(4-ethylaminocarbonylmethylphenyl)-1-(4-ethylpiperazin-1-yl)isoquinoline,
(88) 3-(4-propylaminocarbonylmethylphenyl)-1-(4-ethylpiperazin-1-yl)isoquinoline,
(89) 3-(4-butylaminocarbonylmethylphenyl)-1-(4-ethylpiperazin-1-yl)isoquinoline,
(90) 3-(4-methylsulfonylmethylphenyl)-1-(4-ethylpiperazin-1-yl)isoquinoline,
(91) 3-(3-chloro-4-ethylsulfonylaminomethylphenyl)-1-(4-ethylpiperazin-1-yl)isoquinoline,
(92) 3-(3-chloro-4-propylsulfonylaminomethylphenyl)-1-(4-ethylpiperazin-1-yl)isoquinoline,
(93) 3-(4-morpholinymethylphenyl)-1-(4-ethylpiperazin-1-yl) isoquinone,
(94) 3-(4-thiomorpholinymethylphenyl)-1-(4-ethylpiperazin-1-yl)isoquinoline,
(95) 3-[4-(3-oxazolidionone)phenyl]-1-(4-ethylpiperazin-1yl)isoquinoline,
(96) 3-[4-(4,4-ethylenedioxypiperidin-1-yl)phenyl]-1-(4-ethylpiperazin-1-yl)isoquinoline,
(97) 1-(4-ethylpiperazin-1-yl)-3-[4-(4-hydroxypiperidin-1-yl)phenyl]isoquinoline,
(98) 1-(4-ethylpiperazin-1-yl)-3-[4-[4-methoxypiperidin-1-yl]phenyl]isoquinoline,
(99) 3-[2-(4-acetylpiperazin-1-yl)pyridin-5-yl]-1-(4-ethylpiperazin-1-yl)isoquinoline,
(100) 3-[4-(4-acetylpiperazin-1-yl)phenyl]-1-(4-ethylpiperazin-1-yl)isoquinoline,
(101) 3-(2-methoxybenzyl)-1-(4-ethylpiperazin-1-yl)isoquinoline,
(102) 3-($\alpha$-methyl-(4-methoxybenzyl)]-1-(4-ethylpiperazin-1-yl)isoquinoline,
(103) 3-[$\alpha$-hydroxy-(2-methoxybenzyl)]-1-(4-ethylpiperazin-1-yl)isoquinoline,
(104) 3-[$\alpha$-hydroxy-(4-methoxybenzyl)]-1-(4-ethylpiperazin-1-yl)isoquinoline,
(105) 3-[$\alpha$-methyl-$\alpha$-hydroxy-(4-methoxybenzyl)]-1-(4-ethylpiperazin-1-yl)isoquinoline,
(106) 1-(1-ethylpiperazin-4-yl)-3-(4-methoxyphenethyl)isoquinoline,
(107) 1-(1-ethylpiperazin-4-yl)-3-[2-(2-hydroxyethoxy)phenethyl]isoquinoline,
(108) 1-(1-ethylpiperazin-4-yl)-3-[3-(2-hydroxyethoxy)phenethyl]isoquinoline,
(109) 1-(1-ethylpiperazin-4-yl)-3-[4-(2-hydroxyethoxy)phenethyl]isoquinoline,
(110) 1-(1-ethylpiperazin-4-yl)-3-[3-[2-(2-hydroxyethoxy)phenyl]propyl]isoquinoline,
(111) 3-(2-methoxyphenylcarbonyl)-1-(4-ethylpiperazin-1-yl)isoquinoline,
(112) 3-(4-methoxyphenylcarbonyl)-1-(4-ethylpiperazin-1-yl)isoquinoline,
(113) 3-(4-methoxyindan-1-yl)-1-(4-ethylpiperazin-1-yl)isoquinoline,
(114) 3-(6-methoxyindan-1-yl)-1-(4-ethylpiperazin-1-yl)isoquinoline,
(115) 3-[4-(2-hydroxyethoxy)indan-1-yl]-1-(4-ethylpiperazin-1-yl)isoquinoline,
(116) 3-(8-methoxy-1,2-dihydronaphthalen-4-yl)-1-(4-ethylpiperazin-1-yl)isoquinoline,
(117) 3-(7-methoxy-1,2-dihydronaphthalen-4-yl)-1-(4-ethylpiperazin-1-yl)isoquinoline,
(118) 3-(6-methoxy-1,2-dihydronaphthalen-4-yl)-1-(4-ethylpiperazin-1-yl)isoquinoline,
(119) 3-(5-methoxy-1,2,3,4-tetrahydronaphthalen-1-yl)-1-(4-ethylpiperazin-1yl)isoquinoline,
(120) 3-(6-methoxy-1,2,3,4-tetrahydronaphthalen-1-yl)-1-(4-ethylpiperazin-1-yl)isoquinoline,
(121) 3-(7-methoxy-1,2,3,4-tetrahydronaphthalen-1-yl)-1-(4-ethylpiperazin-1-yl)isoquinoline,
(122) 3-(3-hydroxymethylchroman-6-yl)-1-(4-ethylpiperazin-1-yl)isoquinoline,
(123) 1-(4-ethylpiperazin-1-yl)-3-(2-pyridyl)isoquinoline,
(124) 1-(4-ethylpiperazin-4-yl)-3-[5-(2-hydroxyethoxy)pyridin-2-yl]isoquinoline,
(125) 1-(1-ethylpiperazin-4-yl)-3-[2-(2-hydroxyethoxy)pyridin-5-yl]isoquinoline,
(126) 1-(1-ethylpiperazin-4-yl)-3-[2-(2-methoxyethoxy)pyridin-5-yl]isoquinoline,
(127) 1-(1-ethylpiperazin-4-yl)-3-[5-(2-methoxyethoxy)pyridin-2-yl]isoquinoline,
(128) 3-(2-propylcarbonylaminopyridin-5-yl)-1-(4-ethylpiperazin-1-yl)isoquinoline,
(129) 3-[2-methylsulfonylpyridin)-5-yl]-1-(4-ethylpiperazin-1-yl)isoquinoline,
(130) 3-[2-ethylsulfonylpyridin)-5-yl)-1-(4-ethylpiperazin-1-yl)isoquinoline,
(131) 1-(1-ethylpiperazin-4-yl)-3-(2-butylpyridin-5-yl)isoquinoline,
(132) 1-(1-ethylpiperazin-4-yl)-3-[5-(3-fluoropropyl)pyridin-2-yl]isoquinoline,
(133) 1-(1-ethylpiperazin-4-yl)-3-[2-(3-fluoropropyl)pyridin-5-yl]isoquinoline, (134) 1-(1-ethylpiperazin-4-yl)-3-[5-(3-hydroxypropyl)pyridin-2-yl]isoquinoline,
(135) 1-(1-ethylpiperazin-4-yl)-3-[2-(3-hydroxypropyl)pyridin-5-yl]isoquinoline,
(136) 1-(1-ethylpiperazin-4-yl)-3-[2-(3-hydroxybutyl)pyridin-5-yl]isoquinoline,
(137) 1-(1-ethylpiperazin-4-yl)-3-[2-(4-hydroxybutyl)pyridin-5-yl]isoquinoline,
(138) 1-(1-ethylpiperazin-4-yl)-3-[2-(3-hydroxy-3-methylbutyl)pyridin-5-yl]isoquinoline,
(139) 1-(1-ethylpiperazin-4-yl)-3-[2-(3-methoxypropyl)pyridin-5-yl]isoquinoline,
(140) 1-(1-ethylpiperazin-4-yl)-3-[3-(3-methoxypropyl)pyridin-5-yl]isoquinoline,
(141) 1-(1-ethylpiperazin-4-yl)-3-[5-(3-methoxypropyl)pyridin-2-yl]isoquinoline,
(142) 1-(1-ethylpiperazin-4-yl)-3-[2-(3-ethoxypropyl)pyridin-5-yl]isoquinoline,
(143) 1-(1-ethylpiperazin-4-yl)-3-[2-[3-(2-propoxy)propyl]pyridin-5-yl]isoquinoline,
(144) 1-(1-ethylpiperazin-4-yl)-3-[2-(3-methoxybutyl)pyridin-5-yl]isoquinoline,
(145) 1-(1-ethylpiperazin-4-yl)-3-{2-[2-(2-hydroxy-2-cyclohexyl)ethynyl]pyridin-4-yl}isoquinoline,
(146) 1-(1-ethylpiperazin-4-yl)-3-[2-(1-butyn-1-yl)pyridin-5yl]isoquinoline,
(147) 1-(4-ethylpiperazin-1-yl)-3-[2-(morpholin-4-yl)pyridin-5-yl]isoquinoline,
(148) 1-(4-ethylpiperazin-1-yl)-3-[5-(morpholin-4-yl)pyridin-2-yl]isoquinoline,
(149) 3-[2-(2,6-dimethylmorpholin-4-yl)pyridin-5-yl]-1-(4-ethylpiperazin-1-yl)isoquinoline,
(150) 1-(4-ethylpiperazin-1-yl)-3-[2-thiomorpholin-4-yl)pyridin-5-yl]isoquinoline,
(151) 1-(4-ethylpiperazin-1-yl)-3-[2(S-oxythiomorpholin-4-yl)pyridin-5-yl]isoquinoline,
(152) 1-(4-ethylpiperazin-1-yl)-3-[2-(4-hydroxypiperidin-1-yl)pyridin-5-yl]isoquinoline,
(153) 1-(4-ethylpiperazin-1-yl)-3-[2-(4-methoxypiperidin-1-yl)pyridin-5-yl]isoquinoline,
(154) 1-(4-ethylpiperazin-1-yl)-3-[2-(4-hydroxymethylpiperidin-1-yl)pyridin-5-yl]isoquinoline,
(155) 3-[2-(5,6-dihydro-2H-pyran-4-yl)pyridin-5-yl]-1-(4-ethylpiperazin-1-yl)isoquinoline,
(156) 3-[2-(tetrahydropyran-4-yl)pyridin-5-yl]-1-(4-ethylpiperazin-1-yl)isoquinoline,
(157) 3-[4-[3-(3-pyridyl)propoxy]phenyl]-1-(4-ethylpiperazin-1-yl)isoquinoline,
(158) 1-(1-ethylpiperazin-4-yl)-3-(1-phenylpiperazin-4-yl)isoquinoline,
(159) 1-(1-ethylpiperazin-4-yl)-3-[1-(2-pyridyl) piperazin-4-yl]isoquinoline,
(160) 3-[4-(4-morpholinyl)phenyl]-1-(4-ethylpiperazin-1-yl)isoquinoline,
(161) 1-(1-ethylpiperazin-4-yl)-3-(2-hydroxymethylthiophen-4-yl)isoquinoline,
(162) 1-(1-ethylpiperazin-4-yl)-3-(2-hydroxymethylthiophen-5-yl)isoquinoline,
(163) 1-(1-ethylpiperazin-4-yl)-3-[2-(2-hydroxyethyl)thiophen-5-yl]isoquinoline,
(164) 1-(1-ethylpiperazin-4-yl)-3-[2-(1-hydroxypropyl)thiophen-4-yl]isoquinoline,
(165) 1-(1-ethylpiperazin-4-yl)-3-[2-(1-hydroxypropyl)thiophen-5-yl]isoquinoline,
(166) 3-[2-(tetrahydropyran-4-yl) thiophen-5-yl]-1-(4-ethylpiperazin-1yl)isoquinoline,
(167) 1-(1-ethylpiperazin-4-yl)-3-[4-methyl-5-(2-hydroxyethyl)thiazol-2-yl]isoquinoline,
(168) 1-(1-ethylpiperazin-4-yl)-3-(2-hydroxymethylthiazol-5-yl)isoquinoline,
(169) 1-(1-ethylpiperazin-4-yl)-3-[1-(2-hydroxyethyl)pyrazol-3-yl]isoquinoline,
(170) 1-(1-ethylpiperazin-4-yl)-3-[(1-hydroxypropyl)thiazol-5-yl]isoquinoline,
(171) 1-(1-ethylpiperaziin-4-yl)-3-[2-(3-hydroxypropyl)thiazol-5-yl]isoquinoline,
(172) 1-(1-ethylpiperazin-4-yl)-3-[2-(3-methoxypropyl)thiazol-5-yl]isoquinoline,
(173) 1-(1-ethylpiperazin-4-yl)-3-[2-(4-morpholinyl)thiazol-5-yl]isoquinoline,
(174) 3-(2-propylcarbonylaminopyrimidin-5-yl)-1-(4-ethylpiperazin-1-yl)isoquinoline,
(175) 3-[2-(5,6-dihydro-2H-pyran-4-yl)thiophen-4-yl]-1-(4-ethylpiperazin-1-yl)isoquinoline,
(176) 3-[2-(5,6-dihydro-2H-pyran-4-yl)thiophen-5-yl]-1-(4-ethylpiperazin-1-yl)isoquinoline,
(177) 1-(1-ethylpiperazin-4-yl)-3-(phenylethynyl)isoquinoline,
(178) 1-(1-ethylpiperazin-4-yl)-3-(4-methoxyphenyl)ethynylisoquinoline,
(179) 1-(1-ethylpiperazin-4-yl)-3-(2-pyridyl)ethynylisoquinoline,
(180) 3-[3-(4-morpholinyl)-1-propynl]-1-(4-ethylpiperazin-1-yl)isoquinoline,
(181) 1-(1-ethylpiperazin-4-yl)-3-(3-phenyl-1-propynyl)isoquinoline,
(182) 1-(1-ethylpiperazin-4-yl)-3-(4-phenyl-1-butynyl)isoquinoline,
(183) 1-(1-ethylpiperazin-4-yl)-3-[4-(2-hydroxyethoxy)phenylethynyl]isoquinoline,
(184) 1-(1-ethylpiperazin-4-yl)-3-benzoylethynylisoquinoline,
(185) 1-(1-ethylpiperazin-4-yl)-3-(2,4-dimethoxyphenylethynyl)isoquinoline,
(186) 1-(1-ethylpiperazin-4-yl)-3-[3-(3-methoxypropyl)-5-pyridyl]ethynylisoquinoline,
(187) 1-(1-ethylpiperazin-4-yl)-3-[2-(2-hydroxyethoxy)phenyl]ethynylisoquinoline,
(188) 1-(1-ethylpiperazin-4-yl)-3-[3-(2-hydroxyethoxy)-2-pyridyl]ethynylisoquinoline,
(189) 1-(1-ethylpiperazin-4-yl)-3-(trans-2-phenylethenyl)isoquinoline,
(190) 1-(1-ethylpiperazin-4-yl)-3-[trans-2-(4-methoxyphenyl)ethenyl]isoquinoline,
(191) 1-(1-ethylpiperazin-4-yl)-3-[cis-2-(4-methoxyphenyl)ethenyl]isoquinoline,
(192) 1-(1-ethylpiperazin-4-yl)-3-(cis-1-methyl-2-phenylethenyl)isoquinoline,
(193) 1-(1-ethylpiperazin-4-yl)-3-(trans-1-methyl-2-phenylethyenyl)isoquinoline,
(194) 1-(1-ethylpiperazin-4-yl)-3-[trans-2-(2-hydroxyethoxyphenyl)ethenyl]isoquinoline,
(195) 1-(1-ethylpiperazin-4-yl)-3-[trans-2-(2-methoxyphenyl)ethenyl]isoquinoline,
(196) 1-(1-ethylpiperazin-4-yl)-3-(trans-2-methyl-2-phenylethen-1-yl)isoquinoline,
(197) 1-(1-ethylpiperazin-4-yl)-3-[trans-2-(2-fluorophenyl)ethenyl]isoquinoline,
(198) 1-(1-ethylpiperazin-4-yl)-3-[(E)-4-(2-hydroxyethoxy)styryl]isoquinoline,
(199) 1-(1-ethylpiperazin-4-yl)-3-{trans-2-[3-(2-hydroxyethoxy)phenyl]ethenyl}isoquinoline,
(200) 3-{(E)-2-[2-(4-morpholinyl)pyridin-5-yl]ethenyl}-1-(4-ethylpiperazin-1-yl)isoquinoline,
(201) 3-[(E)-2-(4-methylsulfonylphenyl)ethenyl]-1-(4-ethylpiperazin-1-yl)isoquinoline, (202) 3-[(E)-2-(2-methylsulfonylphenyl)ethenyl]-1-(4-ethylpiperazin-1-yl)isoquinoline,
(203) 3-[(E)-2-(4-methylsulfonylmethylphenyl)ethenyl]-1-(4-ethylpiperazin-1-yl)isoquinoline,
(204) 3-{(E)-2-(3-(4-morpholinyl)phenyl]ethenyl}-1-(4-ethylpiperazin-1-yl)isoquinoline,
(205) 3-{(E)-2-[4-(4-morpholinyl)phenyl]ethenyl}-1-(4-ethylpiperazin-1-yl)isoquinoline,
(206) 3-{(E)-2-methyl-2-[4-(4-morpholinyl)phenyl]ethenyl}-1-(4-ethylpiperaziin-1-yl)isoquinoline,
(207) 3-{(E)-2-methyl-2-[3-(4-morpholinyl)phenyl]ethenyl}-1-(4-ethylpiperazin-1-yl)isoquinoline,
(208) 3-[(E)-2-methoxymethyl-2-phenylethenyl]-1-(4-ethylpiperazin-1-yl)isoquinoline,
(209) 1-(1-ethylpiperazin-4-yl)-3-[trans-2-(2-pyridyl)ethenyl]isoquinoline,
(210) 1-(1-ethylpiperazin-4-yl)-3-[trans-2-(4-pyridyl)ethenyl]isoquinoline,
(211) 1-(1-ethylpiperazin-4-yl)-3-[3-(2-methoxy)phenyl-2-propenyl]isoquinoline,
(212) 1-(1-ethylpiperazin-4-yl)-3-[3-(2-hydroxyethoxy)phenyl-1-propenyl]isoquinoline,
(213) 3-{(E)-2-[2-(4-morpholinyl)pyridin-5-yl]ethenyl}-1-(4-ethylpiperazin-1-yl)isoquinoline,
(214) 3-{(E)-2-[3-(4-morpholinyl)pyridazin-6-yl]ethenyl}-1-(4-ethylpiperazin-1-yl)isoquinoline,
(215) 3-{(E)-2-[4-(4-morpholinyl)pyrimidin-6-yl]ethenyl}-1-(4-ethylpiperazin-1-yl)isoquinoline,
(216) 3-{(E)-2-[2-(4-morpholinyl)pyrazin-6-yl]ethenyl}-1-(4-ethylpiperazin-1-yl)isoquinoline,
(217) 3-[1-(4-methoxyphenyl)ethenyl]-1-(4-ethylpiperazin-1-yl)isoquinoline,
(218) 1-(1-ethylpiperazin-4-yl)-N-phenyl-3-isoquinolinecarboxamide,
(219) 1-(1-ethylpiperazin-4-yl)-3-(4-methoxyanilinomethyl)isoquinoline,
(220) 1-(1-ethylpiperazin-4-yl)-3-(4-methoxybenzylamino)isoquinoline,
(221) 1-(1-ethylpiperazin-4-yl)-4-methoxy-3-(4-methoxyphenyl)isoquinoline,
(222) 1-(1-ethylpiperazin-4-yl)-5-methyl-3-(4-methoxyphenyl)isoquinoline,
(223) 1-(4-ethylpiperazin-1-yl)-3-[4-(2-hydroxyethoxy)phenyl]-6-fluoroisoquinoline,
(224) 1-(1-ethylpiperazin-4-yl)-6-fluoro-3-(4-methoxyphenyl)isoquinoline,
(225) 1-(1-ethylpiperazin-4-yl)-6-methyl-3-(4-methoxyphenyl)isoquinoline,
(226) 1-(4-ethylpiperazin-1-yl)-6-methoxy-3-(4-trifluoromethylphenyl)isoquinoline,
(227) 1-(4-ethylpiperazin-1-yl)-6-methoxy-3-(4-methoxyphenyl)isoquinoline,
(228) 1-(1-ethylpiperazin-4-yl)-7-methyl-3-(4-methoxyphenyl)isoquinoline,
(229) 1-(4-ethylpiperazin-1-yl)-7-fluoro-3-(4-methoxyphenyl)isoquinoline,
(230) 1-(4-ethylpiperazin-1-yl)-3-[4-(2-hydroxyethoxy)phenyl]-7-fluoroisoquinoline,
(231) 1-(4-ethylpiperazin-1-yl)-7-methoxy-3-phenylisoquinoline,
(232) 1-(4-ethylpiperazin-1-yl)-7-methoxy-3-(2-methoxyphenyl)isoquinoline,
(233) 1-(1-ethylpiperazin-4-yl)-8-fluoro-3-(4-methoxyphenyl)isoquinoline,
(234) 1-(1-ethylpiperazin-4-yl)-8-fluoro-3-[4-(2-hydroxyethoxy)phenyl]isoquinoline,
(235) 1-(1-ethylpiperazin-4-yl)-8-methoxy-3-(4-methoxyphenyl)isoquinoline,
(236) 1-(1-propylpiperazin-4-yl)-3-(4-methoxyphenyl)isoquinoline,
(237) 1-(1-propylpiperazin-4-yl)-3-[4-(2-hydroxyethoxy)phenyl]isoquinoline,
(238) 1-(1-isopropylpiperazin-4-yl)-3-(4-methoxyphenyl)isoquinoline,
(239) 1-(1-cyclopropylpiperazin-4-yl)-3-(4-methoxyphenyl)isoquinoline,
(240) 1-(1-allylpiperazin-4-yl)-3-(4-methoxyphenyl)isoquinoline,
(241) 1-[1-(2-fluoroethyl)piperazin-4-yl]-3-(4-methoxyphenyl)isoquinoline,
(242) 1-[4-(2-hydroxyethyl)piperazin-1-yl]-3-(4-methoxyphenyl)isoquinoline,
(243) 1-(4-ethylsulfonylaminomethylphenyl)-1-[4-(2-hydroxyethyl)piperazin-1-yl]isoquinoline,
(244) 8-(4-ethylpiperazin-1-yl)-6-(4-methoxyphenyl)pyrido[2,3-c]pyridine,
(245) 8-(1-ethylpiperazin-4-yl)-6-[4-(2-hydroxyethoxy)phenyl]-1,7-naphthyridine,
(246) 8-(1-ethylpiperazin-4-yl)-6-[4-[(S)-2-hydroxypropoxy]phenyl]-1,7-naphthyridine,
(247) 8-(1-ethylpiperazin-4-yl)-6-[4-(3-hydroxypropyl)phenyl]-1,7-naphthyridine,
(248) 8-(1-ethylpiperazin-4-yl)-6-[4-(3-hydroxybutyl)phenyl]-1,7-naphthyridine,
(249) 8-(1-ethylpiperazin-4-yl)-6-[4-(3-hydroxy-1-fluoropropyl)phenyl]-1,7-naphthyridine,
(250) 8-(1-ethylpiperazin-4-yl)-6-[4-(2-hydroxy-2-methylpropoxy)phenyl]-1,7-naphthyridine,
(251) 1-(1-ethylpiperazin-4-yl)-3-(4-methoxyphenyl)-2,6-naphthyridine,
(252) 5-(1-ethylpiperazin-4-yl)-7-(4-methoxyphenyl)-1,6-naphthyridine,
(253) 5-[4-(2-hydroxyethoxy)phenyl]-7-(4-methylpiperazin-1-yl)thieno[2,3-c]pyridine,
(254) 7-(1-ethylpiperazin-4-yl)-5-[4-(1-hydroxypentyl)phenyl]thieno[2,3-c]pyridine,
(255) 7-(1-ethylpiperazin-4-yl)-5-(1-hydroxy-3-methylbutyl)phenyl]thieno[2,3-c]pyridine,
(256) 7-(1-ethylpiperazin-4-yl)-5-[4-(3-hydroxy-1-fluoropropyl)phenyl]thieno(2,3-c]pyridine,
(257) 5-[4-(3-hydroxypropyl)-3-chlorophenyl]-7-(4-ethylpiperazin-1-yl)thieno[2,3-c]pyridine,
(258) 7-(1-ethylpiperazin-4-yl)-5-[3-(2-hydroxyethoxy)phenyl]thieno[2,3-c]pyridine,
(259) 7-(4-ethylpiperazin-1-yl)-5-(4-hydroxyethyoxyphenyl)thieno[2,3-c]pyridine,
(260) 7-(1-ethylpiperazin-4-yl)-5-[4-(2-hydroxy-2-methylpropoxy)phenyl]thieno[2,3-c]pyridine,
(261) 5-[3-(3-hydroxypropyl)-4-methoxyphenyl]-7-(4-ethylpiperazin-1-yl)thieno[2,3-c]pyridine,
(262) 5-[4-(3-hydroxypropyl)-3-cyanophenyl]-7-(4-ethylpiperazin-1-yl)thieno[2,3-c]pyridine,
(263) 5-[2-(4-morpholinyl)pyridin-5-yl]-7-(4-ethylpiperazin-1-yl)thieno[2,3-c]pyridine,
(264) 5-[2-(4-thiomorpholinyl)pyrindin-5-yl]-7-(4-ethylpiperazin-1-yl)thieno[2,3-c]pyridine,
(265) 5-[2-(4-hydroxypiperidin-1-yl]pyridin-5-yl]-7-(4-ethylpiperazin-1-yl)thieno[2,3-c]pyridine,
(266) 5-[4-(5,6-dihydro-2H-pyran-4-yl)phenyl]-7-(4-ethylpiperazin-1-yl)thieno[2,3-c]pyridine,
(267) 5-[2-(2-methoxyethoxy-2-methyl)pyridin-5-yl]-7-(4-ethylpiperazin-1-yl)thieno[2,3-c]pyridine,
(268) 5-[2-hydroxyethoxy)pyridin-5-yl]-7-(4-ethylpiperazin-1-yl)thieno[2,3-c]pyridine,
(269) 5-[2-(2-methoxyethoxy)pyridin-5-yl]-7-(4-ethylpiperazin-1-yl)thieno[2,3-c]pyridine, (270) 5-[4-(4-hydroxycyclohexen-1-yl)phenyl]-7-(4-ethylpiperazin-1-yl)thieno[2,3-c]pyridine,
(271) 7-(1-ethylpiperazin-4-yl)-5-(4-pentanoylphenyl)thieno[2,3-c]pyridine,
(272) 7-(1-ethylpiperazin-4-yl)-5-[4-(3-methylbutanoyl)phenyl]thieno[2,3-c]pyridine,
(273) 7-(1-ethylpiperazin-4-yl)-5-[4-(N-cyclohexylamide)phenyl]thieno[2,3-c]-pyridinecarboxamide,
(274) 7-(1-ethylpiperazin-4-yl)-5-[4-(pyrrolidinyl-1-carbonyl)phenyl]thieno[2,3-c]pyridine,
(275) 5-[4-(2-hydroxyethoxy)phenyl]-7-[4-(2-hydroxyethyl)piperazin-1-yl]thieno[3,2-c]pyridine,
(276) 5-(4-methoxyphenyl)-7-[4-(2-hydroxyethyl)piperazin-1-yl]thieno[2,3-c]pyridine,
(277) 4-(4-ethylpiperazin-1-yl)-6-(4-methoxyphenyl)thieno[3,4-c]pyridine,
(278) 4-(4-ethylpiperazin-1-yl)-6-[4-(2-hydroxyethoxy)phenyl]thieno[3,4-c]pyridine,
(279) 4-(4-methylpiperazin-1-yl)-6-[4-(2-hydroxyethoxy)phenyl]thieno [3,2-c]pyridine,
(280) 4-(4-ethylpiperazin-1-yl)-6-(4-hydroxyphenyl)thieno[3,2-c]pyridine,
(281) 4-(4-ethylpiperarazin-1-yl)-6-[4-(1-hydroxyethyl)phenyl]thieno[3,2-c]pyridine,
(282) 4-(4-ethylpiperazin-1-yl)-6-[4-(1-hydroxypropyl)phenyl]thieno[3,2-c]pyridine,
(283) 4-(4-ethylpiperazin-1-yl)-6-[4-(1-hydroxybutyl)phenyl]thienol[3,2-c]pyridine,
(284) 4-(1-ethylpiperazin-4-yl)-6-[3-(2-hydroxyethyoxy)phenyl]thieno[3,2-c]pyridine,
(285) 4-(1-ethylpiperazin-4-yl)-6-[4-(3-hydroxybutyl)phenyl]thieno[3,2-c]pyridine,
(286) 4-ethylpiperazin-1-yl)-6-[4-(2-hydroxyethoxy)phenyl]thieno[3,2-c]pyridine,
(287) 4-(4-ethylpiperazin-1-yl)-6-[4-(2-hydroxypropoxy)phenyl]thieno[3,2-c]pyridine,
(288) 6-[4-(2-methyl-2-hydroxypropoxy)phenyl]-4-(4-methylpiperazin-1-yl)thieno[3,2-c]pyridine,
(289) 6-[4-(2-methyl-2-hydroxypropoxy)phenyl]-4-(4-propylpiperazin-1-yl)thieno[3,2-c]pyridine,
(290) 6-[4-(2-methyl-2-hydroxypropoxy)phenyl]-4-(4-ethylpiperazin-1-yl)thieno[3,2-c]pyridine,
(291) 4-(4-ethylpiperazin-1-yl)-6-[4-(3-hydroxy-3-methylbutyl)phenyl]thieno[3,2-c]pyridine,
(292) 6-[4-(4-methyl-4-hydroxypentyloxy)phenyl]-4-(4-ethylpiperazin-1-yl)thieno[3,2-c]pyridine,
(293) 4-(4-propylpiperazin-1-yl)-6-[4-(2-hydroxyethoxy)phenyl]thieno[3,2-c]pyridine,
(294) 6-[4-(2-methyl-2-hydroxypropoxy)phenyl]-4-[4-(2-fluoroethyl)piperazin-1-yl]thieno[3,2-c]pyridine,
(295) 4-[4-(2-fluoroethyl)piperazin-1-yl]-6-[4-(2-hydroxyethoxy)phenyl]thieno[3,2-c]pyridine,
(296) 6-[4-(2-methyl-2-hydroxypropoxy)phenyl]-4-[4-(2-hydroxyethyl)piperazin-1-yl]thieno[3,2-c]pyridine,
(297) 6-[4-(2-methyl-2-hydroxypropoxy)phenyl]-4-[4-(2-phenylethyl)piperazin-yl]thieno[3,2-c]pyridine,
(298) 7-(1-ethylpiperazin-4-yl)-5-[3-(2-hydroxyethoxy)phenyl]furo[2,3-c]pyridine,
(299) 7-(1-ethylpiperarin-4-yl)-5-[4-(3-hydroxypropyl)phenyl]furo[2,3-c]pyridine,
(300) 7-(1-ethylpiperazin-4-yl)-5-[4-(3-hydroxybutyl)phenyl]furo[2,3-c]pyridine,
(301) 7-(1-ethylpiperazin-4-yl)-5-[4-(2-hydroxyethoxy)phenyl]furo[2,3-c]pyridine,
(302) 7-(1-ethylpiperazin-4-yl)-5-[4-[(R)-2-hydroxy-1-methylethoxy]phenyl]furo[2,3c]pyridine,
(303) 7-(1-ethylpiperazin-4-yl)-5-{4-[(S)-2-hydroxy-1-methylethoxy]phenyl}furo[2,3-c]pyridine,
(304) 7-(1-ethylpiperazin-4-yl)-5-{4-[(S)-2-hydroxypropoxy]phenyl}furo[2,3-c]pyridine,
(305) 7-(1-ethylpiperazin-4-yl)-5-{4-[(R)-2-hydroxypropoxy]phenyl}furo[2,3-c]pyridine,
(306) 7-(1-ethylpiperazin-4-yl)-5-[4-(3-hydroxy-3-methylbutoxy)phenyl]furo[2,3-c]pyridine,
(307) 7-(1-ethylpiperazin-4-yl)-5-[trans-2-[4-(2-hydroxyethoxy)phenyl]ethenyl]furo[2,3-c]pyridine,
(308) 7-(1-ethylpiperazin-4-yl)-5-[trans-2-[b 2-(2-hydroxyethoxy)phenyl]ethenyl]furo[2,3-c]pyridine,
(309) 1-(1-ethylpiperazin-4-yl)-3-[4-(2-hydroxy-2-methylpropoxy)phenyl]isoquinoline,
(310) 1-(1-ethylpiperazin-4-yl)-3-(3-phenyl-3-hydroxy-1-propynyl)isoquinoline,
(311) 1-(1-ethylpiperazin-4-yl)-8-methyl-3-(4-methoxyphenyl)isoquinoline,
(312) 1-(1-ethylpiperazin-4-yl)-4-methyl-3-(4-methoxyphenyl)isoquinoline,
(313) 1-[1-(2-cyanoethyl)piperazin-4yl]-3-(4-methoxyphenyl)isoquinoline,
(314) 1-[1-(carbamoylmethyl)piperazin-4-yl]-3-(4-methoxyphenyl)isoquinoline,
(315) 1-(4-ethylsulfonylpiperazin-1-yl)-3-(4-methoxyphenyl)isoquinoline,
(316) 4-piperidinyl-6-[4-(2-methyl-2-hydroxypropoxy)phenyl]thieno[3,2-c]pyridine,
(317) 7-(1-ethylpiperazin-4-yl)-5-[4-(3-hydroxypropoxy)phenyl]furo[2,3-c]pyridine,
(318) 1-(4-ethylpiperazin-1-yl)-3-(4-methoxyphenyl)isoquinoline,
(319) 1-{N-[2-(2-dimethylamino)ethyl]-N-methylamino}-3-(4-methoxyphenyl)isoquinoline,
(320) 1-(4-morpholinyl)-3-(4-methoxyphenyl)isoquinoline,
(321) 1-(1-ethyl-2-pyrrolidinyl) methylamino-3-(4-methoxyphenyl)isoquinoline,
(322) 3-(4-methoxyphenyl)-1-[2-(2-pyridyl)ethyl]aminoisoquinoline,
(323) 1-[2-(4-morpholinyl)ethyl]amino-3-(4-methoxyphenyl)isoquinoline,
(324) 1-(1-imidazolyl)-3-(4-methoxyphenyl)isoquinoline,
(325) 1-[4-(piperidin-1-yl)piperidin-1-yl]-3-(4-methoxyphenyl)isoquinoline,
(326) 1-(1,4,5,6-tetrahydropyrimidin-1-yl)-3-(4-methoxyphenyl)isoquinoline,
(327) 1-(1-ethylhomopiperazin-4-yl)-3-(4-methoxyphenyl)isoquinoline,
(328) 3-(4-methoxyphenyl)-1-(4-ethylpiperazin-1-yl)methylisoquinoline,
(329) 1-(4-ethylpiperazin-1-yl)-3-[3-(2-hydroxyethoxy)phenyl]isoquinoline,
(330) 1-(4-ethylpiperazin-1-yl)-3-(4-ethoxyphenyl)isoquinoline,
(331) 1-(4-ethylpiperazin-1-yl)-3-[4-(3-hydroxypropoxy)phenyl]isoquinoline,
(332) 1-(4-ethylpiperazin-1-yl)-3-(3,4-ethylenedioxyphenyl)isoquinoline,
(333) 1-(4-ethylpiperazin-1-yl)-3-[4-(3-methoxyphenyl)phenyl]isoquinoline,
(334) 1-(4-ethylpiperazin-1-yl)-3-[4-(n-butyl)phenyl]isoquinoline,
(335) 1-(4-ethylpiperazin-1-yl)-3-(4-methoxypyridin-2-yl)isoquinoline,
(336) 1-(4-ethylpiperazin-1-yl)-3-[4-(1,3-dioxolan-2-ylmethyloxy)phenyl]isoquinoline,
(337) 1-(4-ethylpiperazin-1-yl)-3-[4-(2,3-dihydroxypropoxy)phenyl]isoquinoline,
(338) 1-(4-ethylpiperazin-1-yl)-3-(4-carbamoylmethoxyphenyl)isoquinoline, (339) 1-(4-ethylpiperazin-1-yl)-3-(4-trifluoromethoxyphenyl)isoquinoline,
(340) 1-(4-ethylpiperazin-1-yl)-3-[4-(2-hydroxyethoxy)-3-methoxyphenyl)isoquinoline,
(341) 1-(4-ethylpiperazin-1-yl)-3-(4-methylthiophenyl)isoquinoline,
(342) 1-(4-ethylpiperazin-1-yl)-3-(4-methylsulfonylphenyl)isoquinoline,
(343) 1-(4-ethylpiperazin-1-yl)-3-[4-(2-hydroxy-3-methoxypropoxy)phenyl]isoquinoline,
(344) 1-(4-ethylpiperazin-1-yl)-3-(2-methoxypyridin-5-yl)isoquinoline,
(345) 1-(4-ethylpiperazin-1-yl)-3-[4-(1-hydroxy-1-methylethyl)phenyl]isoquinoline,
(346) 1-(4-ethylpiperazin-1-yl)-3-[4-[N-(2-hydroxyethyl)carbamoyl]phenyl]isoquinoline,
(347) 1-(4-ethylpiperazin-1-yl)-3-[4-[N-(2-hydroxyethyl)sulfamoyl]pehnyl]isoquinoline,
(348) 1-(4-ethylpiperazin-1-yl)-3-[4-(1-hydroxyethyl)phenyl]isoquinoline,
(349) 1-(4-ethylpiperazin-1-yl)-3-[4-(propylsulfonyl)phenyl]isoquinoline,
(350) 1-(4-ethylpiperazin-1-yl)-3-[4-[(3-methoxypropyl)sulfonyl]phenyl]isoquinoline,
(351) 1-(4-ethylpiperazin-1-yl)-3-[4-(2-hydroxyethyl)phenyl]isoquinoline,
(352) 1-(4-ethylpiperazin-1-yl)-3-[4-(3-hydroxypropyl)sulfonylphenyphenyl]isoquinoline,
(353) 1-(4-ethylpiperazin-1-yl)-3-[4-(N-propylsulfamoyl)phenyl]isoquinoline,
(354) 1-(4-ethylpiperazin-1-yl)-3-{4-[N-(2-methoxyethyl)sulfamoyl]phenyl}isoquinoline,
(355) 1-(4-ethylpiperazin-1-yl)-3-[4-(3-fluoropropyl)sulfonylphenyl]isoquinoline,
(356) 1-(4-ethylpiperazin-1-yl)-3-[4-(pyrrolidin-1-yl)sulfonylphenyl]isoquinoline,
(357) 1-(4-ethylpiperazin-1-yl)-3-[4-(N-ethylsulfamoyl)phenyl]isoquinoline,
(358) 1-(4-ethylpiperazin-1-yl)-3-[4-(N-methyl-N-propylsulfamoyl)phenyl]isoquinoline,
(359) 1-(4-ethylpiperazin-1-yl)-3-[4-(N,N-diethylsulfamoyl)phenyl]isoquinoline,
(360) 1-(4-ethylpiperazin-1-yl)-3-{4-[N-(1-methylpropyl)sulfamoyl]phenyl}isoquinoline,
(361) 1-(4-ethylpiperazin-1-yl)-3-[4-(N-methylsulfamoyl)phenyl]isoquinoline,
(362) 1-(4-ethylpiperaziin-1-yl)-3-[4-[N,N-dimethylsulfamoyl]phenyl]isoquinoline,
(363) 1-(4-ethylpiperazin-1-yl)-3-[4-(N-cyclopropylsulfamoyl)phenyl]isoquinoline,
(364) 1-(4-ethylpiperazin-1-yl)-3-[4-(N-ethylcarbamoyl)phenyl]isoquinoline,
(365) 1-(4-ethylpiperazin-1-yl)-3-[4-(N-methylcarbamoyl)phenyl]isoquinoline,
(366) 1-(4-ethylpiperazin-1-yl)-3-[4-(ethylsulfonyl)phenyl]isoquinoline,
(367) 1-(4-ethylpiperazin-1-yl)-3-(3-fluoro-4-methoxyethoxyphenyl)isoquinoline,
(368) 1-(4-ethylpiperazin-1-yl)-3-(3,5-difluoro-4-methoxyethoxyphenyl)isoquinoline,
(369) 1-(4-ethylpiperazin-1-yl)-3-[3-fluoro-4-(2-hydroxyethoxy)phenyl]isoquinoline,
(370) 1-(4-ethylpiperazin-1-yl)-3-(3,5-difluoro-4-(2-hydroxyethoxy)phenyl]isoquinoline,
(371) 1-(4-ethylpiperazin-1-yl)-3-(3,5-difluoro-4-(2-fluoroethoxy)phenyl]isoquinoline,
(372) 1-[4-(2-hydroxyethyl)piperazin-1-yl]-3-[4-(N-ethylsulfamoyl)phenyl]isoquinoline,
(373) 1-[4-(2-hydroxyethyl)piperazin-1-yl]-3-[4-(propylsulfonyl)phenyl]isoquinoline,
(374) 1-(4-ethylpiperazin-1-yl)-3-phenylthio)isoquinoline,
(375) 1-(4-ethylpiperazin-1-yl)-3-[4-(2-oxopropyl)phenyl]isoquinoline,
(376) 1-(4-ethylpiperazin-1-yl)-3-[4-(2-hydroxypropyl)phenyl]isoquinoline,
(377) 1-(4-ethylpiperazin-1-yl)-3-[4-(2-hydroxy-2-methylpropyl)phenyl]isoquinoline,
(378) 1-(4-ethylpiperazin-1-yl)-3-(2-pyridylthio)isoquinoline,
(379) 1-(4-ethylpiperazin-1-yl)-3-(4-butyrylphenyl)isoquinoline,
(380) 1-(4-ethylpiperazin-1-yl)-3-[4-(1-hydroxyiminobutyl)phenyl]isoquinoline,
(381) 1-(4-ethylpiperazin-1-yl)-3-[4-(N-methyl-N-propylcarbamoyl)phenyl]isoquinoline,
(382) 1-(4-ethylpiperazin-1-yl)-3-{4-[N-(2-hydroxyethyl)-N-methylcarbamoyl]phenyl}isoquinoline,
(383) 1-(4-ethylpiperazin-1-yl)-3-[4-(3-hydroxy-1-methylpropyl)phenyl]isoquinoline,
(384) 1-(4-ethylpiperazin-1-yl)-3-[4-(N-propylcarbamoyl)-3-fluorophenyl]isoquinoline,
(385) 1-(4-ethylpiperazin-1-yl)-3-[3-fluoro-4-(2-hydroxyethyl) phenyl]isoquinoline,
(386) 1-(4-ethylpiperazin-1-yl)-3-[4-(3-hydroxy-2-methylpropyl)phenyl]isoquinoline,
(387) 1-(4-ethylpiperazin-1-yl)-3-[4-(1,2-dihydroxyethyl)phenyl]isoquinoline,
(388) 1-(4-ethylpiperazin-1-yl)-3-[4-(3-hydroxy-3-methylbutyl)phenyl]isoquinoline,
(389) 1-(4-ethylpiperazin-1-yl)-3-[4-(3-hydroxy-2,2-dimethylpropyl)phenyl]isoquinoline,
(390) 1-(4-ethylpiperazin-1-yl)-3-[4-(3-hydroxy-1,1-dimethylpropyl)phenyl]isoquinoline,
(391) 1-(4-ethylpiperazin-1-yl)-3-[4-(1,3-dihydroxy-2,2-dimethylpropyl)phenyl]isoquinoline,
(392) 1-(4-ethylpiperazin-1-yl)-3-[4-[4-(2-hydroxyethyl)tetrahydropyran-4-yl]phenyl]isoquinoline,
(393) 1-(4-ethylpiperazin-1-yl)-3-(2-hydroxymethylindan-5-yl)isoquinoline,
(394) 1-(4-ethylpiperazin-1-yl)-3-[(3,4-dihydroxymethyl)phenyl]isoquinoline,
(395) 1-(4-ethylpiperazin-1-yl)-3-[4-(1,4-dioxan-2-yl)phenyl]isoquinoline,
(396) 1-(4-ethylpiperazin-1-yl)-3-[4-tetrahydrofuran-2-yl)phenyl]isoquinoline,
(397) 1-(4-ethylpiperazin-1-yl)-3-[4-(cis-4-hydroxycyclohexy)phenyl]isoquinoline,
(398) 1-(4-ethylpiperazin-1-yl)-3-[4-(trans-4-hydroxycyclohexyl)phenyl]isoquinoline,
(399) 1-(4-ethylpiperazin-1-yl)-3-[4-(tetrahydropyran-4-yl)methylphenyl]isoquinoline,
(400) 4-chloro-1-(4-ethylpiperazin-1-yl)-3-(4-methoxyphenyl)isoquinoline,
(401) 1-(4-ethylpiperazin-1-yl)-3-[4-(cis-4-hydroxytetrahydropyran-2-yl)phenyl]isoquinoline,
(402) 1-(4-ethylpiperazin-1-yl)-3-[4-(trans-4-hydroxytetrahydropyran-2-yl)phenyl]isoquinoline,
(403) 1-(4-ethylpiperazin-1-yl)-3-[4-(2-hydroxypropoxy)phenyl]isoquinoline,
(404) 1-(4-ethylpiperazin-1-yl)-3-[4-(2-hydroxy-1-methylethoxy)phenyl]isoquinoline,
(405) 1-(4-ethylpiperazin-1-yl)-3-(2-methoxypyridin-4-yl)isoquinoline,
(406) 1-(4-ethylpiperazin-1-yl)-3-(2-benzyloxypyridin-4-yl)isoquinoline and 1-(4-ethylpiperazin-1-yl)-3-(2-chloropyridin-4-yl)isoquinoline, (407) 1-(4-ethylpiperazin-1-yl)-3-[2-(2-methoxyethoxy)pyridin-4-yl]isoquinoline,
(408) 1-(4-ethylpiperazin-1-yl)-3-(4-carbamoylphenyl)isoquinoline
(409) 1-(4-ethylpiperazin-1-yl)-3-[4-(cyclohexylhydroxymethyl)phenyl]isoquinoline,
(410) 1-(4-ethylpiperazin-1-yl)-3-[4-(4-hydroxytetrahydropyran-4-yl)phenyl]isoquinoline,
(411) 1-(4-ethylpiperazin-1-yl)-3-[4-[bis(1,3-thiazol-2-yl)hydroxymethyl]phenyl]isoquinoline,
(412) 1-(4-ethylpiperazin-1-yl)-3-[4-(1,3-thiazol-2-yl)hydroxymethylphenyl]isoquinoline,
(413) 1-(4-ethylpiperazin-1-yl)-3-[(3-pyridyl)hydroxymethyl]isoquinoline,
(414) 1-(4-ethylpiperazin-1-yl)-3-(1-indanon-5-yl)isoquinoline,
(415) 1-(4-ethylpiperazin-1-yl)-3-(1-hydroxyindan-5-yl)isoquinoline,
(416) 1-(4-ethylpiperazin-1-yl)-3-[4-(3-hydroxy-3-methylbutyl)-3-fluorophenyl]isoquinoline,
(417) 1-(4-ethylpiperazin-1-yl)-3-[3-cyano-4-(2-hydroxyethoxy)phenyl]isoquinoline,
(418) 1-(4-ethylpiperazin-1-yl)-3-[3-(3-hydroxypropyl)phenyl]isoquinoline,
(419) 1-(4-ethylpiperazin-1-yl)-3-benzylisoquinoline,
(420) 1-(4-ethylpiperazin-1-yl)-3-(2-hydroxy-2-phenylethyl)isoquinoline,
(421) 3-benzamide-1-(4-ethylpiperazin-1-yl)isoquinoline,
(422) 3-benzenesulfoneamide-1-(4-ethylpiperazin-1-yl)isoquinoline,
(423) 1-(4-ethylpiperazin-1-yl)-3-(4-methoxybenzenesulfonamide)isoquinoline,
(424) 1-(4-ethylpiperazin-1-yl)-3-(4-methoxyphenoxymethyl)isoquinoline,
(425) 1-(4-ethylpiperazin-1-yl)-3-[4-(2-hydroxyethoxy)-2-methoxyphenyl]isoquinoline,
(426) 1-(4-ethylpiperazin-1-yl)-3-[4-(2-hydroxycyclohexyloxy)phenyl]isoquinoline,
(427) 4-(4-ethylpiperazin-1-yl)-2-(4-methoxyphenyl)quinazoline,
(428) 1-(4-ethylpiperazin-1-yl)-3-(4-methoxyphenyl)-7-azaisoquinoline,
(429) 7-(4-ethylpiperazin-1-yl)-5-[2-(3-hydroxypropyl)pyridin-5-yl]thieno[2,3-c]pyridine,
(430) 7-(4-ethylpiperazin-1-yl)-5-[3-(2-hydroxyethoxy)styryl]thieno[2,3-c]pyridine,
(431) 7-(4-ethylpiperazin-1-yl)-5-[4-(2-hydroxyethoxy)styryl]thieno[2,3-c]pyridine,
(432) 7-(4-ethylpiperazin-1-yl)-5-[4-(3-hydroxypropyl)phenyl]thieno[2,3-c]pyridine,
(433) 7-(4-ethylpiperazin-1-yl)-5-[4-(3-hydroxypropyl)-3-methoxyphenyl]thieno[2,3-c]pyridine,
(434) 7-(4-ethylpiperazin-1-yl)-5-[4-(3-hydroxypropoxy)phenyl]thieno[2,3-c]pyridine,
(435) 7-(4-ethylpiperazin-1-yl)-5-[4-(2-hydroxypropoxy)phenyl]thieno[2,3-c]pyridine,
(436) 7-(4-ethylpiperazin-1-yl)-5-[4-(2-hydroxypropyl)phenyl]thieno[2,3-c]pyridine,
(437) 7-(4-ethylpiperazin-1-yl)-5-[3-chloro-4-(2-hydroxyethoxy)phenyl]thieno[2,3-c]pyridine,
(438) 7-(4-ethylpiperazin-1-yl)-5-[4-(1-methyl-2-hydroxyethoxy)phenyl]thieno[2,3-c]pyridine,
(439) 7-(4-ethylpiperazin-1-yl)-5-[4-(3-hydroxy-3-methylbutyl)phenyl]thieno[2,3-c]pyridine,
(440) 7-(4-ethylpiperazin-1-yl)-5-[4-(3-hydroxybutyl)phenyl]thieno[2,3-c]pyridine,
(441) 7-(4-ethylpiperazin-1-yl)-5-[4-(3-hydroxy-2-methylpropyl)phenyl]thieno[2,3-c]pyridine,
(442) 7-(4-ethylpiperazin-1-yl)-5-[4-(3-hydroxy-2,2-dimethylpropyl)phenyl]thieno[2,3-c]pyridine,
(443) 7-(4-ethylpiperazin-1-yl)-5-[4-(3-hydroxy-1,1-dimethylpropyl)phenyl]thieno[2,3-c]pyridine,
(444) 7-(4-ethylpiperazin-1-yl)-5-[4-(2-hydroxypropylthio)phenyl]thieno[2,3-c]pyridine,
(445) 7-(4-ethylpiperazin-1-yl)-5-(4-methanesulfonylphenyl)thieno[2,3-c]pyridine,
(446) 7-(4-ethylpiperazin-1-yl)-5-[4-(1-hydroxybutyl)phenyl]thieno[2,3-c]pyridine,
(447) 7-(4-ethylpiperazin-1-yl)-4-[4-(N-methylcarbamoyl)phenyl]thieno[2,3-c]pyridine,
(448) 7-(4-ethylpiperazin-1-yl)-5-[4-(N-ethylcarbamoyl)phenyl]thieno[2,3-c]pyridine,
(449) 7-(4-ethylpiperazin-1-yl)-5-[4-(N-propylcarbamoyl)phenyl]thieno[2,3-c]pyridine,
(450) 7-(4-ethylpiperazin-1-yl)-5-(4-ethanesulfonylphenyl]thieno[2,3-c]pyridine,
(451) 7-(4-ethylpiperazin-1-yl)-5-(4-propanesulfonylphenyl)thieno[2,3-c]pyridine,
(452) 7-(4-ethylpiperazin-1-yl)-5-[4-(N-butylcarbamoyl)phenyl]thieno[2,3-c]pyridine,
(453) 7-(4-ethylpiperazin-1-yl)-5-[4-(N-cyclopentylcarbamoyl)phenyl]thieno[2,3-c]pyridine,
(454) 7-(4-ethylpiperazin-1-yl)-5-[4-(cis-4-hydroxytetrahydropyran-2-yl)phenyl]thieno[2,3-c]pyridine,
(455) 7-(4-ethylpiperazin-1-yl)-5-[4-(trans-4-hydroxytetrahydropyran-2-yl)phenyl]thieno[2,3-c]pyridine,
(456) 7-(4-ethylpiperazin-1-yl)-5-(2,3-dihydro-2-hydroxymethyl-2-methylbenzofuran-5-yl)phenyl]thieno[2,3-c]pyridine,
(457) 7-(4-ethylpiperazin-1-yl)-5-[4-(cyclohexylhydroxymethyl)phenyl]thieno[2,3-c]pyridine,
(458) 7-(4-ethylpiperazin-1-yl)-5-[4-(cyclopentylhydroxymethyl)phenyl]thieno[2,3-c]pyridine,
(459) 7-(4-ethylpiperazin-1-yl)-5-(4-methoxyphenyl)thieno[2,3-c]pyridine,
(460) 4-(4-ethylpiperazin-1-yl)-6-[4-(1,3-dioxolan-2-yl)methoxyphenyl]thieno[3,2-c]pyridine,
(461) 4-(4-ethylpiperazin-1-yl)-6-[4-(2-hydroxyethoxy)phenyl]thieno[3,2-c]pyridine,
(462) 4-(4-ethylpiperazin-1-yl)-6-[4-(3-hydroxypropoxy)phenyl]thieno[3,2-c]pyridine,
(463) 4-(4-ethylpiperazin-1-yl)-6-[4-(2-hydroxy-1-methylethoxy)phenyl]thieno[3,2-c]pyridine,
(464) 4-(4-ethylpiperazin-1-yl)-6-[4-(3-hydroxy-1-propynyl)phenyl]thieno[3,2-c]pyridine,
(465) 4-(4-(ethylpiperazin-1-yl)-6-[4-(3-hydroxypropyl)phenyl]thieno[3,2-c]pyridine,
(466) 4-(4-ethylpiperazin-1-yl)-6-[4-(3-hydroxy-3-methyl-1-butynyl)phenyl]thieno[3,2-c]pyridine,
(467) 7-(4-ethylpiperazin-1-yl)-5-(4-methoxyphenyl)furo[2,3-c]pyridine and
(468) 4-(4-ethylpiperazin-1-yl)-6-(4-methoxyphenyl)furo[3,2-c]pyridine.

Among the condensed pyridine compound according to the present invention, those which are particularly preferable from the viewpoint of pharmacological effects or safety are, for example, the following ones:

(1) 1-(4-ethylpiperazin-1-yl)-3-[4-(1-hydroxypropyl)phenyl]isoquinoline,
(2) 1-(4-ethylpiperazin-1-yl)-3-[4-(3-hydroxypropyl)phenyl]isoquinoline,
(3) 1-(4-ethylpiperazin-1-yl)-3-[4-(3-hydroxybutyl)phenyl]isoquinoline, (4) 1-(4-ethylpiperazin-1-yl)-3-[4-(2-hydroxyethoxy) phenyl]isoquinoline,
(5) 1-(4-ethylpiperazin-1-yl)-3-[4-(2-methoxyethoxy) phenyl]isoquinoline,
(6) 1-(4-ethylpiperazin-1-yl)-3-[4-(2-fluoroethoxy)phenyl] isoquinoline,
(7) 3-[4-(2-cyanoethoxy)phenyl]-1-(4-ethylpiperazin-1-yl) isoquinoline,
(8) 7-(4-ethylpiperazin-1-yl)-5-(4-hydroxyethoxyphenyl) thieno[2,3-c]pyridine,
(9) (4-ethylpiperazin-1-yl)-6-[4-(2-hydroxyethoxy)phenyl] thieno[2,3-c]pyridine,
(10) 4-(4-ethylpiperazin-1-yl)-6-[4-(2-hydroxypropoxy) phenyl]thieno[3,2-c]pyridine and
(11) 6-[4-(2-methyl-2-hydroxy)propoxyphenyl]-(4-ethylpiperazin-1-yl)thieno[3,2-c]pyridine.

Although some of the condensed pyridine compound of the present invention occur as stereomers, either one of these stereomers or a mixture thereof may be used in the present invention without restriction. Similarly, either one of geometrical isomers or a mixture thereof may be employed herein without any restriction. In the case of polymorphic crystals, either one of the crystal forms or a mixture thereof may be used in the present invention without restriction, too. Moreover, use may be made of both anhydrides and hydrates.

The pharmacologically acceptable salts to be used in the present invention may be arbitrary salts of the condensed pyridine compound of the present invention without particular restriction. Examples thereof include inorganic acid addition salts such as hydrochlorides, sulfates, nitrates, hydrobromides, hydriodides, perchlorates and phosphates, organic acid addition salts such as oxaolates, maleates, fumarates and succinates, sulfonic acid addition salts such as methanesulfonates, ethanesulfonates, benzenesulfonates, p-toluenesulfonates and camphorsulfonates, and amino acid addition salts. Among all, it is preferable to use hydrochlorides and oxalates thereof.

Sequentially, a general process of producing the compound of the present invention will be described below, with no limitation. It can be prepared by other synthetic routes.

(1) The formula of the condensed pyridine compound (I) according to the present invention, in which ring A is benzene ring The compound can be prepared by reacting isoquinolin-1-compound (III) with a halogenating agent to give 1-halogenated isoquinoline compound (IV), and reacting the resulting compound which piperazine or 1-substituted piperazine. (See the following formulae. In the formulae, $R^3$, $R^{31}$, $R^{32}$, $R^{33}$ and n have the same meanings as described above. X represents halogen atom.)

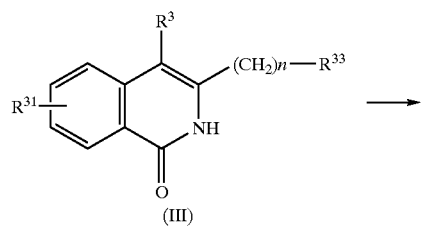
(III)

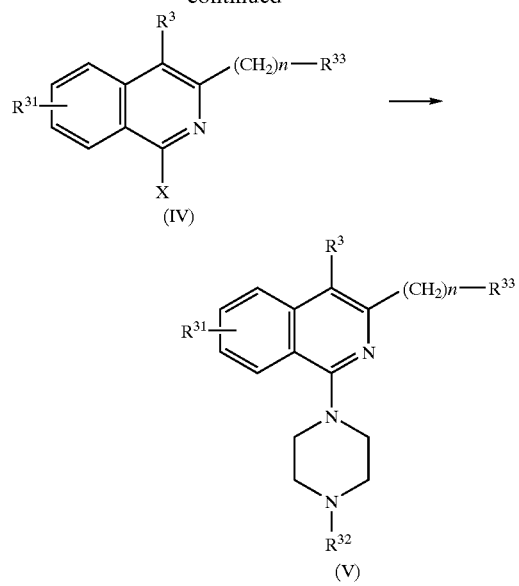
(IV)

(V)

Herein, the isoquinolin-1-one compound (III) includes a great number of known compounds, which are available as industrial raw materials or reagents. And, These compound can be produced by methods described in known references.

The isoquinolin-1-one compound (III) can be halogenated by general methods. Herein, any type of halogenating agents can be used, with no limitation. Generally, phosphorus oxychloride, phosphorus trichloride, phosphorus pentachloride, thionyl chloride, sulfuryl chloride, oxazolyl chloride, phosphorus oxybromide, phosphorus tribromide and the like are used; among them, phosphorus oxychloride is preferable.

The reaction of the 1-halogenated isoquinoline compound (IV) with piperazine or 1-substituted piperazine can be effected by general methods for N-alkylation.

By chemically modifying the substituent of the 1-piperidylisoquinoline compound (V) thus prepared, furthermore, a novel 1-piperidylisoquinoline compound (V) can be derived.

(2) The formula of the condensed pyridine compound (I) according to the present invention, in which ring A is pyridine ring Also in this case, in the same manner as described above in (1), the compound can be prepared by reacting dihydrpyridopyridin-8-one compound (VI) with a halogenating agent to give 8-halogenated pyridopyridine compound (VII), and then reacting the resulting compound with piperazine or 1-substituted piperazine. (See the following formulae. In the formulae, $R^3$, $R^{31}$, $R^{32}$, $R^{33}$ and n have the same meanings as described above. X represents halogen atom.)

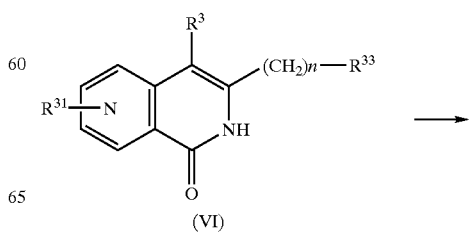
(VI)

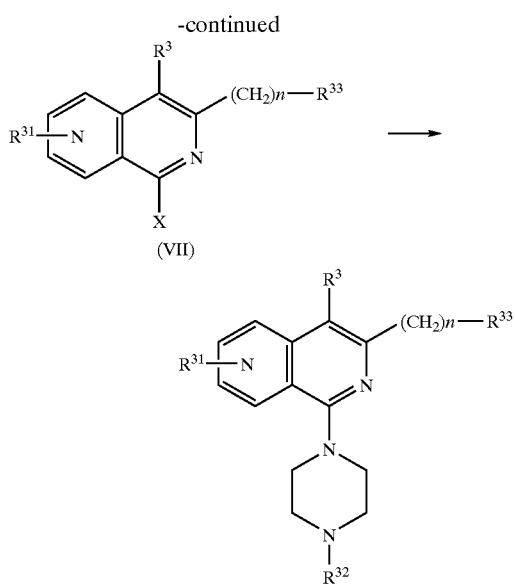

(VII)

(3) The formula of the condensed pyridine compound (I) according to the present invention, in which ring A is thiophene ring Also in this case, in the same manner as described above in (1) or (2), the compound can be prepared by reacting thienopyridopyridin-7-compound (VIII) with a halogenating agent to give 7-halogenated thienopyridine compound (IX), and then reacting the resulting compound with piperazine or 1-substituted piperazine. (See the following formulae. In the formulae, $R^3$, $R^{31}$, $R^{32}$, $R^{33}$ and n have the same meanings as described above. X represents halogen atom.)

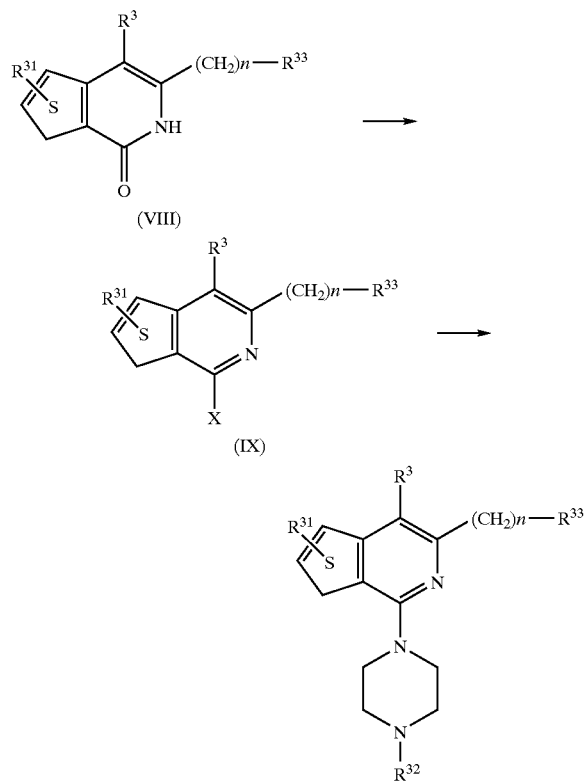

(4) The formula of the condensed pyridine compound (I) according to the present invention, in which ring A is furan ring Also in this case, in the same manner as described above in any of (1) to (3), the compound can be prepared by reacting furopyridin-7-one compound (X) with a halogenating agent to give 7-halogenated furopyridine compound (XI), and then reacting the resulting compound with piperazine or 1-substituted piperazine. (See the following formulae. In the formulae, $R^3$, $R^{31}$, $R^{32}$, $R^{33}$ and n have the same meanings as described above. X represents halogen atom.)

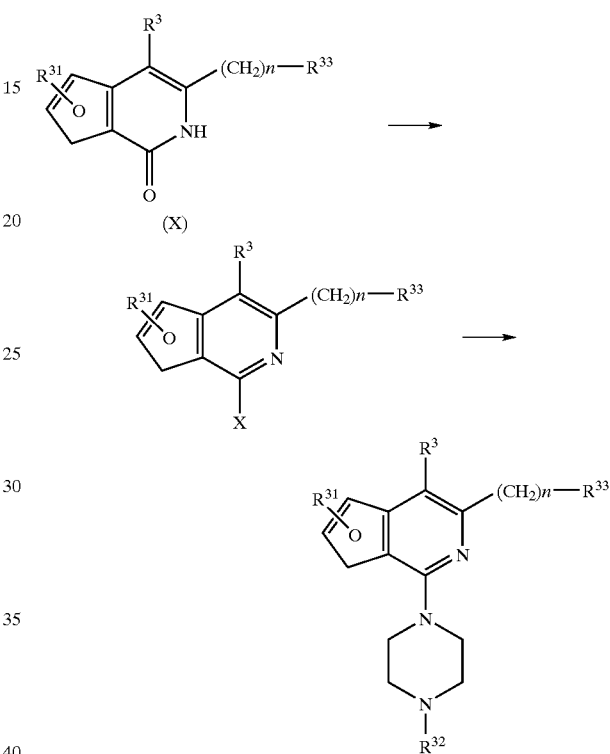

Examples of the dosage forms of the compounds of the present invention include oral preparations such as powders, fine granules, granules, tablets, coated tablets and capsules, external preparations such as ointments, patches and suppositories, and injections. These preparations may be produced by the conventional methods with the use of pharmaceutical carriers commonly employed in the art.

Namely, oral preparations may be produced by blending the 1,4-substituted cyclic amine derivatives or a pharmacologically acceptable salt thereof with fillers optionally together with binders, disintegrating agents, lubricating agents, coloring agents, corrigents, etc. and then processing the resultant blends into powders, fine granules, granules, tablets, coated tablets, capsules, etc. by the conventional methods.

As the fillers, use may be made of, for example, lactose, corn starch, sucrose, glucose, mannitol, sorbitol, crystalline cellulose and silicon dioxide. As the binders, use may be made of, for example, polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, polypropylene glycol/polyoxyethylene block polymers and meglumine. As the disintegrating agents, use may be made of, for example, starch, agar, gelatin powder, crystalline cellulose, calcium carbonate, sodium hydrogencarbonate, calcium citrate, dextrin, pectin and calcium carboxymethylcellulose. As the lubricating agents, use may be made of, for example, magnesium stearate, talc, polyethylene glycol, silica and hardened vegetable oils. As the coloring agents, use may be made of those authorized as pharmaceutical additives. As the corrigents, use may be made of, for example, cocoa powder, mentha, aromatic powder, mentha oil, borneol and powdered cinnamon bark. Needless to say, these tablets and granules may be appropriately coated with sugar, etc., if necessary.

Injections are produced by blending the condensed pyridine compound or a pharmacologically acceptable salt thereof with pH regulating agents, resolvents, tonicity agents, etc., optionally together with dissolution aids, stabilizers, etc. and processing the resultant blends into preparations by the conventional methods.

External preparations may be produced by the conventional methods without restriction. As the bases, therefore, use can be made of various materials commonly used in drugs, quasi drugs, cosmetics, etc.

Particular examples of the base materials include animal and vegetable oils, mineral oils, ester oils, waxes, higher alcohols, fatty acids, silicone oils, surfactants, phospholipids, alcohols, polyhydric alcohols, water-soluble polymers, clay minerals and purified water. If needed, it is possible to further add pH regulating agents, antioxidants, chelating agents, antiseptics, fungicides, coloring agents, perfumes, etc., through the materials usable as the base in the external preparations of the present invention are not restricted thereto. If necessary, it is also possible to furthermore add other ingredients capable of inducing differentiation, blood flow accelerators, bactericides, antiinflammatory agents, cell activators, vitamins, amino acids, humectants, keratolytic agents, etc. The above materials may be added in such amounts as to give the concentrations thereof commonly employed in the production of external preparations.

The clinical dose of the condensed pyridine compound of the present invention or a pharmacologically acceptable salt thereof is not restricted but varies depending on the symptoms, severity, age, complications, etc. Also, the dose thereof varies depending on the type of the salt, administration route, etc. In general, these compounds are administered to an adult in a dose of from 0.01 to 1000 mg, preferably from 0.1 to 500 mg and still preferably from 0.5 to 100 mg, per day orally, intravenously, as suppositories or percutaneously.

Next, the results of a binding test on the compounds of the present invention to serotonin 1A and serotonin 2 receptors will be given so as to illustrate the effects of the present invention. Moreover, the results of a binding test on these compounds to an $\alpha_1$ adrenalin receptor will be given so as to illustrate the safety thereof.

It is reported in, for example, the following publications that compounds with a serotonin antagonism are usable as medicament for treating, ameliorating and preventing spastic paralysis or central muscle relaxants for ameliorating myotonia:
(1) Saishin Igaku Jiten, 3rd impression of 1st edition, p. 809 "SEROTONIN", Iyaku Shuppan
(2) Stedman's Medical Dictionary, 24th edition, p. 1227 "serotonin", Williams & Wilkins
(3) Shinkei Shinpo, 37(3), 459–467, 1993.
(4) Iyaku Journal, 30(8), 2030–2068, 1994.
(5) DN & P, 5(8), 453–460, 1992.
(6) Annals of Neurology, 30(4), 533–541, 1991.

Compounds poor in the ability to bind to an $\alpha_1$ adrenalin receptor are medicines which would scarcely affect blood pressure in orthostatic hypotension, etc. and have a higher safety.

(1) Binding test on serotonin 1A, serotonin 2 and $\alpha_1$ adrenalin receptors
Method
(Reagent)
The following reagents were employed in this test.
1) Serotonin binoxalate (5-HT binoxalate, mfd. by Sigma Chemical Co.).
2) Methysergide maleate (mfd. by RBI).
As radioisotope-labeled compounds, use was made of the following reagents (mfd. by NEN).
3) [$^3$H] 8-Hydroxy-dipropylaminotetralin (8-OH-DPAT).
4) [$^3$H] Ketanserin hydrochloride.
5) [$^3$H] Prazosin.

These compounds and test compounds, when insoluble in water, were dissolved in ethanol and then diluted with distilled water so as to each give an ethanol concentration of 10%. Methysergide maleate was dissolved in distilled water before using.

(Animal)
Use was made of SD rats aged 6 to 8 weeks.
(Preparation of receptor source)
The rats were sacrificed by decapitation to extirpate the cerebra. The hippocampus and cortex were separated therefrom and employed in the binding tests respectively on the serotonin 1A receptor and the serotonin 2 receptor.

The hippocampus was mixed with 50 times (on the wet weight basis) as much as 0.32 M sucrose solution while the cortex was mixed with 10 times as much the same solution. Each mixture was homogenized by using a Teflon glass homogenizer and centrifuged as 1,000× g for 10 min. The supernatant thus obtained was further centrifuged at 20,000× g for 20 min. The obtained precipitate was re-suspended in 50 times (based on the initial wet weight; in the case of the hippocampus) or 10 times (in the case of the cortex) as much a 50 Tris hydrochloride (pH 7.4) and incubated at room temperature for 30 min. After centrifuging at 20,000× g for 20 min, the obtained precipitate was further suspended and centrifuged twice each in the same manner. The precipitate thus obtained was suspended in 100 times (based on the initial wet weight; in the case of the hippocampus) or 20 times (in the case of the cortex) as much a 50 mM Tris hydrochloride solution (pH 7.4) to thereby give a receptor fraction. This receptor fraction was stored at −80° C. until using.

(Binding test on [$^3$H] 8-hydroxy-dipropylaminotetralin)
To the receptor fraction of the hippocampus were added a test compound and 0.5 nM of [$^3$H] 8-hydroxy-dipropylaminotetralin and the resultant mixture was incubated at room temperature for 30 min. Next, it was filtered through a glass filter with the use of a cell harvester. After washing the glass filter with 50 mM Tris hydrochloride (pH 7.4), the radioactivity of the receptor was measured with a liquid scintillation counter. The binding detected in the presence of 10 µM of serotonin binoxalate was referred to as the nonspecific binding.

(Binding test on [$^3$H] ketanserin)
To the receptor fraction of the cerebral cortex were added a test compound and 0.3 nM of [$^3$H] ketanserin and the resultant mixture was incubated at 37° C. for 15 min. Next, it was filtered through a glass filter with the use of a cell harvester. After washing the glass filter with 50 mM Tris hydrochloride (pH 7.4), the radioactivity of the receptor was measured with a liquid scintillation counter. The binding detected in the presence of 1 µM of methysergide was referred to as the nonspecific binding.

IC$_{50}$ was calculated by the probit method, while Ki was determined in accordance with the following formula:

$$Ki=IC_{50}(1+c/Kd)$$

wherein c represents the concentration of the radioisotope-labeled compound, and Kd represents the dissociation constant of the radioisotope-labeled compound with respect to the receptor determined by Scatchard's analysis.

(Binding test on [$^3$H] prazosin)

To the receptor fraction of the cerebral cortex were added a test compound and about 0.2 nM of [$^3$H] prazosin and the resultant mixture was incubated at room temperature for 60 min. Next, it was filtered through a glass filter with the use of a cell harvester. After washing the glass filter with 50 mM Tris hydrochloride (pH 7.4), the radioactivity of the receptor was measured with a liquid scintillation counter. The binding detected in the presence of 10 μM of phentolamine was referred to as the nonspecific binding.

The following tables show the abilities of typical examples of the compounds of the present invention to bind to the serotonin (5HT)1A and serotin (5HT)2 receptors, wherein the number of each compound corresponds to the number of Example described below. Also, comparison was made with cyproheptadine hydrochloride and cyclobenzaprine hydrochloride which were employed as positive controls having anti-serotonin effects.

| Example No. | 5HT1 (nM) | 5HT2 (nM) |
|---|---|---|
| 1 | 21.2 | 36.4 |
| 3 | 65 | 3.8 |
| 4 | 71 | 74.9 |
| 5 | 21 | 2.2 |
| 7 | 27.9 | 81.3 |
| 9 | 57 | 24.5 |
| 10 | 60 | 11 |
| 12 | 140 | 5.32 |
| 14 | 23 | 35 |
| 15 | 55.5 | 19.5 |
| 16 | 30 | 44 |
| 17 | 11.1 | 26.8 |
| 19 | 6.9 | 1.6 |
| 20 | 14.5 | 2.6 |
| 21 | 17.2 | 4.3 |
| 22 | 9.4 | 1.5 |
| 23 | 16.8 | 6.4 |
| 24 | 11.7 | 7.4 |
| 25 | 21.5 | 3.4 |
| 26 | 8.5 | 55 |
| 27 | 29.42 | 2.47 |
| 28 | 24.4 | 9.1 |
| 29 | 9.6 | 3.5 |
| 30 | 10.7 | 6.3 |
| 31 | 10.7 | 30.3 |
| 32 | 10.1 | 7.8 |
| 33 | 7.9 | 10.9 |
| 34 | 23.5 | 17.3 |
| 35 | 35.3 | 5.7 |
| 36 | 18.8 | 3.9 |
| 38 | 20.8 | 75.7 |
| 39 | 26 | 4.9 |
| 40 | 26.7 | 3.1 |
| 41 | 40.1 | 45.6 |
| 42 | 33.1 | 4.4 |
| 43 | 29.3 | 66.6 |
| 44 | 55.4 | 9 |
| 45 | 45 | 1.1 |
| 46 | 58 | 12.7 |
| 47 | 25.3 | 2.6 |
| 50 | 25.2 | 21.9 |
| 51 | 102.77 | 1.87 |
| 52 | 23.5 | 0.6 |

-continued

| Example No. | 5HT1 (nM) | 5HT2 (nM) |
|---|---|---|
| 53 | 61.25 | 1.78 |
| 54 | 62.1 | 4.9 |
| 55 | 10.4 | 15.3 |
| 56 | 37.4 | 59.5 |
| 57 | 57.2 | 4.6 |
| 58 | 23.3 | 18.7 |
| 59 | 16.3 | 14.3 |
| 60 | 21.3 | 9.1 |
| 61 | 11.7 | 8.2 |
| 62 | 14.8 | 4 |
| 63 | 18.1 | 0.84 |
| 64 | 86.99 | 8.5 |
| 65 | 60.1 | 33.5 |
| 66 | 52.7 | 21.6 |
| 67 | 27.3 | 6.6 |
| 68 | 30.9 | 94.1 |
| 69 | 17.2 | 17.3 |
| 70 | 23.3 | 5.5 |
| 71 | 2 | 1.5 |
| 72 | 15 | 3.6 |
| 73 | 13 | 3.3 |
| 74 | 4.6 | 7.7 |
| 75 | 7.7 | 10 |
| 76 | 5.7 | 8.9 |
| 77 | 13.6 | 90.5 |
| 78 | 0.56 | 1.9 |
| 79 | 5.8 | 23 |
| 80 | 0.8 | 16.3 |
| 81 | 1.1 | 15.1 |
| 82 | 0.2 | 10.8 |
| 83 | 75.6 | 4.3 |
| 84 | 72.1 | 0.9 |
| 85 | 18.7 | 9.7 |
| 86 | 11.7 | 5.3 |
| 87 | 16.9 | 17 |
| 88 | 9.4 | 11.7 |
| 89 | 6.3 | 10 |
| 90 | 4.5 | 12.9 |
| 91 | 1.1 | 1.6 |
| 92 | 0.9 | 0.7 |
| 93 | 10.8 | 56.7 |
| 94 | 6.4 | 41.2 |
| 95 | 7.8 | 21.2 |
| 96 | 138.4 | 0.1 |
| 97 | 34.7 | 13.3 |
| 98 | 61.6 | 2.7 |
| 99 | 3.5 | 6.2 |
| 100 | 12.7 | 5.6 |
| 102 | 129.36 | 132.01 |
| 104 | 108.71 | 100.93 |
| 106 | 70 | 30.6 |
| 108 | 156.65 | 33.76 |
| 110 | 58.62 | 108.98 |
| 111 | 10.28 | 89.9 |
| 114 | 167.03 | 49.89 |
| 122 | 40.1 | 19.9 |
| 123 | 34 | 29.1 |
| 125 | 27.1 | 6.9 |
| 126 | 26.4 | 5.7 |
| 128 | 22.2 | 3 |
| 129 | 21.6 | 18.4 |
| 130 | 24.4 | 17 |
| 131 | 6.4 | 5.8 |
| 132 | 1.5 | 23.4 |
| 133 | 2.9 | 6.2 |
| 134 | 4.9 | 12.4 |
| 135 | 3.4 | 18.9 |
| 136 | 3.7 | 11.6 |
| 137 | 7.2 | 32.5 |
| 138 | 13.5 | 5.5 |
| 139 | 2.7 | 5.1 |
| 140 | 22.1 | 36.7 |
| 141 | 2.9 | 20.4 |
| 142 | 3.3 | 15.2 |
| 143 | 2.2 | 17.4 |
| 144 | 4.8 | 12.4 |
| 145 | 7.5 | 3.7 |

-continued

| Example No. | 5HT1 (nM) | 5HT2 (nM) |
|---|---|---|
| 146 | 170.5 | 2.9 |
| 147 | 6.5 | 1.7 |
| 148 | 6.33 | 7.85 |
| 149 | 37.2 | 21.8 |
| 150 | 10.7 | 0.8 |
| 151 | 7 | 79.2 |
| 152 | 6.1 | 12.4 |
| 153 | 12.9 | 1.5 |
| 154 | 1.6 | 8.8 |
| 155 | 19.98 | 4.34 |
| 156 | 10.93 | 0.01 |
| 157 | 29.7 | 4.9 |
| 158 | 0.41 | 1.08 |
| 159 | 0.65 | 13.25 |
| 160 | 22.2 | 0.7 |
| 161 | 10.7 | 23.8 |
| 162 | 10.7 | 84.7 |
| 163 | 25.1 | 19.2 |
| 164 | 9.38 | 11.88 |
| 165 | 32.58 | 25.38 |
| 166 | 81.89 | 11.49 |
| 170 | 3 | 25.4 |
| 171 | 4.7 | 21.9 |
| 172 | 4.7 | 36.2 |
| 173 | 3.9 | 4.8 |
| 174 | 29.1 | 7.3 |
| 176 | 154.55 | 12.38 |
| 177 | 45 | 0.5 |
| 178 | 56.4 | 0.2 |
| 179 | 5.3 | 0.4 |
| 181 | 17.9 | 6.7 |
| 182 | 10 | 15.89 |
| 183 | 14.1 | 3.36 |
| 184 | 30.85 | 122.2 |
| 185 | 21.21 | 2 |
| 186 | 2.83 | 4.5 |
| 187 | 9.81 | 2.53 |
| 188 | 4.47 | 106.9 |
| 189 | 37.17 | 0.44 |
| 190 | 35 | 3.85 |
| 191 | 12.98 | 0.93 |
| 192 | 66.74 | 7.85 |
| 194 | 11.21 | 33.72 |
| 195 | 22.96 | 37.22 |
| 196 | 66.74 | 6.44 |
| 197 | 70.69 | 4.26 |
| 198 | 45.5 | 9.08 |
| 199 | 3.27 | 3.8 |
| 200 | 77.3 | 7.33 |
| 201 | 35.9 | 2.96 |
| 202 | 14.61 | 2.22 |
| 203 | 5.5 | 0.52 |
| 204 | 25.46 | 18.54 |
| 205 | 33.15 | 0.98 |
| 206 | 77.12 | 2.59 |
| 207 | 22.23 | 17.95 |
| 208 | 91.61 | 7.62 |
| 209 | 3.28 | 2.35 |
| 210 | 6.56 | 3.95 |
| 211 | 5.17 | 40.2 |
| 213 | 21.1 | 31.82 |
| 214 | 15.59 | 7.59 |
| 215 | 51.93 | 20.86 |
| 216 | 16.55 | 15.53 |
| 219 | 2.99 | 5.92 |
| 220 | 0.53 | 2.01 |
| 233 | 200 | 1.97 |
| 234 | 128.78 | 1.11 |
| 243 | 13 | 6.7 |
| 244 | 27.14 | 78.55 |
| 245 | 109.44 | 72.17 |
| 246 | 86.99 | 13.91 |
| 247 | 25.08 | 28.72 |
| 248 | 42.98 | 31.57 |
| 249 | 37.96 | 28.08 |
| 250 | 122.76 | 7.67 |
| 253 | 75.37 | 5.98 |
| 254 | 59.73 | 29.18 |
| 255 | 75.37 | 40.04 |
| 256 | 9.22 | 19.48 |
| 257 | 12.58 | 23.23 |
| 258 | 24.72 | 35.1 |
| 259 | 9.26 | 18.86 |
| 260 | 67.79 | 0.54 |
| 261 | 53.74 | 0.06 |
| 262 | 9.04 | 0.25 |
| 263 | 6.42 | 0.89 |
| 264 | 61.35 | 3.34 |
| 265 | 9.73 | 113.91 |
| 266 | 97.26 | 13.78 |
| 267 | 10.39 | 68.74 |
| 268 | 16.51 | 85.99 |
| 269 | 15.53 | 58.38 |
| 270 | 42.96 | 30.32 |
| 272 | 159.51 | 22.45 |
| 273 | 51.44 | 9.11 |
| 276 | 159.51 | 0.45 |
| 277 | 71.36 | 52.06 |
| 278 | 41.28 | 4.61 |
| 279 | 76.43 | 1.44 |
| 281 | 15.03 | 16.92 |
| 282 | 10.79 | 6.46 |
| 283 | 5.71 | 6.43 |
| 284 | 91.86 | 75.86 |
| 285 | 22.18 | 1.96 |
| 286 | 6.95 | 3.95 |
| 287 | 27.91 | 0.87 |
| 288 | 80.94 | 0.14 |
| 290 | 54.67 | 1.35 |
| 291 | 43.3 | 1.44 |
| 292 | 68.62 | 22.45 |
| 298 | 1.72 | 5.37 |
| 299 | 0.37 | 30.14 |
| 300 | 0.49 | 9.06 |
| 301 | 9.15 | 12.73 |
| 302 | 0.53 | 30 |
| 303 | 0.53 | 44.42 |
| 304 | 15.44 | 19.42 |
| 305 | 18.47 | 33.12 |
| 306 | 47.73 | 0.82 |
| 307 | 7.7 | 11.47 |
| 308 | 6.49 | 19.46 |
| 309 | 91 | 0.01 |
| 310 | 4.4 | 10.18 |
| 317 | 12.24 | 105.36 |
| 329 | 31.6 | 73.6 |
| 331 | 23.6 | 5.9 |
| 332 | 13.9 | 12.1 |
| 333 | 17.1 | 6.1 |
| 335 | 60.1 | 20.3 |
| 336 | 45.7 | 2.6 |
| 337 | 25.7 | 5.6 |
| 338 | 14.1 | 61.9 |
| 339 | 214 | 18.9 |
| 340 | 26.0 | 20.7 |
| 342 | 6.2 | 14.9 |
| 343 | 35.7 | 5.7 |
| 344 | 10.7 | 35.9 |
| 345 | 11.3 | 1.4 |
| 346 | 31.8 | 41.7 |
| 347 | 8.0 | 24.2 |
| 348 | 11.0 | 1.6 |
| 349 | 3.2 | 5.0 |
| 350 | 2.6 | 16.7 |
| 351 | 15.7 | 6.4 |
| 352 | 4.0 | 54.6 |
| 353 | 1.1 | 0.24 |
| 354 | 3.0 | 1.3 |
| 355 | 2.6 | 4.9 |
| 356 | 2.1 | 24.2 |
| 357 | 2.8 | 0.58 |
| 358 | 6.4 | 19.1 |
| 359 | 6.1 | 3.2 |
| 360 | 2.0 | 1.5 |

| Example No. | | 5HT1 (nM) | 5HT2 (nM) |
|---|---|---|---|
| 361 | | 3.5 | 2.6 |
| 362 | | 4.5 | 24.1 |
| 363 | | 3.5 | 0.61 |
| 364 | | 21.7 | 3.9 |
| 365 | | 26.2 | 9.9 |
| 366 | | 3.8 | 7.2 |
| 367 | | 55.2 | 3.3 |
| 368 | | 32.0 | 9.1 |
| 369 | | 28.2 | 2.5 |
| 370 | | 23.9 | 3.4 |
| 371 | | 41.0 | 4.3 |
| 374 | | 44.5 | 24.7 |
| 375 | | 30.5 | 7.6 |
| 376 | | 19.5 | 6.3 |
| 377 | | 28.5 | 16.5 |
| 378 | | 42.7 | 95.2 |
| 380 | | 31.2 | 23.0 |
| 381 | | 11.1 | 27.3 |
| 383 | | 7.4 | 3.4 |
| 384 | | 27.3 | 0.1 |
| 385 | | 14.8 | 21.6 |
| 386 | | 8.9 | 2.4 |
| 387 | | 25.1 | 24.7 |
| 388 | | 21.5 | 0.7 |
| 389 | | 14.2 | 7.3 |
| 390 | | 7.5 | 11.1 |
| 391 | | 3.6 | 12.8 |
| 393 | | 13.1 | 1.8 |
| 394 | | 10.7 | 32.9 |
| 395 | | 37.3 | 4.8 |
| 396 | | 50.4 | 2.6 |
| 397 | | 53.3 | 0.9 |
| 398 | | 8.0 | 5.9 |
| 399 | | 53.0 | 17.2 |
| 401 | | 31.3 | 3.4 |
| 402 | | 23.7 | 2.1 |
| 403 | | 28.35 | 0.78 |
| 404 | | 18.76 | 1.07 |
| 405 | | 22.6 | 10.2 |
| 406 | 2-Benzyloxy | 46.0 | 88.1 |
| | 2-chloro | 12.2 | 11.1 |
| 407 | | 17.8 | 26.1 |
| 408 | | 19.8 | 36.3 |
| 409 | | 16.4 | 9.7 |
| 410 | | 21.1 | 2.1 |
| 412 | | 19.1 | 41.4 |
| 414 | | 17.3 | 4.2 |
| 415 | | 3.6 | 11.6 |
| 416 | | 31.2 | 0.7 |
| 417 | | 13.4 | 4.5 |
| 418 | | 54.5 | 17.4 |
| 419 | | 94.8 | 16.4 |
| 420 | | 117.4 | 22.4 |
| 421 | | 9.47 | 129.2 |
| 422 | | 5.32 | 175.3 |
| 423 | | 9.81 | 332.47 |
| 424 | | 61.6 | 1.93 |
| 425 | | 320.58 | 2.55 |
| 426 | | 132.70 | 7.10 |
| 427 | | 80.94 | 300.37 |
| 430 | | 2.48 | 11.68 |
| 431 | | 1.98 | 2.11 |
| 432 | | 1.98 | 28.48 |
| 433 | | 20.63 | 3.53 |
| 434 | | 64.88 | 60.48 |
| 435 | | 61.18 | 1.14 |
| 436 | | 8.64 | 26.03 |
| 437 | | 30.49 | 18.11 |
| 438 | | 62.94 | 18.83 |
| 439 | | 44.18 | 6.03 |
| 440 | | 21.83 | 0.72 |
| 441 | | 15.23 | 0.41 |
| 442 | | 23.23 | 2.66 |
| 443 | | 10.24 | 1.85 |
| 444 | | 43.16 | 11.98 |
| 445 | | 5.46 | 90.37 |
| 446 | | 12.20 | 29.96 |
| 448 | | 22.60 | 345.80 |
| 449 | | 24.04 | 43.79 |
| 450 | | 6.89 | 15.16 |
| 451 | | 7.72 | 37.86 |
| 452 | | 19.61 | 7.04 |
| 453 | | 22.18 | 45.39 |
| 454 | | 67.41 | 26.53 |
| 455 | | 50.33 | 39.99 |
| 456 | | 63.33 | 16.21 |
| 457 | | 63.33 | 280.93 |
| 458 | | 75.37 | 93.12 |
| 459 | | 107.86 | 60.15 |
| 460 | | 5.32 | 175.3 |
| 461 | | 0.17 | 15.21 |
| 462 | | 4.83 | 2.84 |
| 463 | | 6.98 | 20.86 |
| 464 | | 47.81 | 1.40 |
| 465 | | 6.28 | 7.11 |
| 466 | | 49.8 | 1.0 |
| 467 | | 20.55 | 93.11 |
| Cyproheptadine | | 29.5 | 1.68 |
| Cyclobenzaprine | 25 | 29 | |

Subsequently, the abilities of typical examples of the compounds of the present invention to bind to the $\alpha_1$ adrenalin receptor were evaluated by the test method described above. The following table shows the results, wherein the number of each compound corresponds to the number of Example described below.

| Example No. | $\alpha 1$ (nM) |
|---|---|
| 1 | >2000 |
| 7 | 521 |
| 12 | 4111 |
| 19 | 373 |
| 20 | 868 |
| 21 | 636 |
| 22 | 3095 |
| 23 | 1253 |
| 29 | 668 |
| 32 | 500 |
| 33 | 758 |
| 36 | 1220 |
| 42 | 2450 |
| 45 | 1220 |
| 52 | 555 |
| 63 | 252 |
| 70 | 1260 |
| 73 | 699 |
| 109 | >2000 |
| 123 | 553 |
| 126 | 382 |
| 139 | 374 |
| 160 | 536 |
| 173 | 284 |
| 179 | 208 |
| 181 | 920 |
| 183 | 577 |
| 185 | 741 |
| 187 | 969 |
| 200 | 755 |
| 202 | >2000 |
| 220 | 3803 |
| 242 | 1788 |
| 259 | 405 |
| 281 | 345 |
| 286 | 305 |
| 289 | 1306 |
| 300 | >2000 |
| 331 | 721.5 |
| 393 | 241.8 |

| Example No. | α 1 (nM) |
|---|---|
| 416 | 173.5 |
| Cyproheptadine | 1900 |

The above results indicate that the condensed pyridine compound of the present invention are useful as medicaments with a serotonin antagonism and have clinical usefulness and a high safety, in particular, those for treating, ameliorating and preventing spastic paralysis or central muscle relaxants for ameliorating myotonia.

Moreover, it is also evident that the compounds of the present invention are superior in safety, since they have low abilities to bond to the $\alpha_1$ adrenalin receptor and scarcely affect blood pressure.

Next, to illustrate the present invention in detail, Examples will be given below. However, it is needless to say that the present invention is not restricted thereto.

EXAMPLES

Example 1

Synthesis of 3-(4-benzyloxybutyl)-1-(4-ethylpiperazin-1-yl)isoquinoline Dihydrochloride (1-1) 2-[2-(4-Benzyloxybutyl)ethynyl]-5-methoxybenzaldehyde

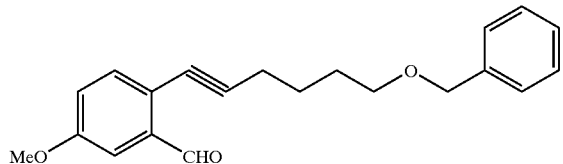

6-Benzyloxy-1-hexyne (5.60 g) and 2-bromobenzaldehyde (2.90 g) were reacted in dimethylformamide (30 ml), in the presence of dichloro-bis-triphenylphosphinepalladium (0.40 g), cuprous iodide (0.20 g) and triethylamine (2.5 ml) in nitrogen atmosphere at 50° C. for 6 hr. The resulting reaction solution was evaporated, and ethyl acetate and water were added to the resulting residue. The resulting organic layer was washed with water and brine, and dried over magnesium sulfate. The solvent was evaporated, and the resulting residue was purified by silica gel column chromatography (ethyl acetate/hexane system), to give 2.60 g of the title compound as a pale yellow oil.

(1-2) 3-(4-Benzyloxybutyl)isoquinoline-2-oxide

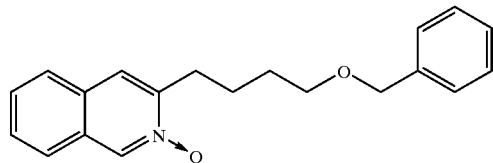

2-[2-(4-Benzyloxybutyl)ethynyl]-5-methoxybenzaldehyde (2.60 g), hydroxylamine hydrochloride (0.63 g) and sodium acetate (0.78 g) were reacted in ethanol (30 ml) at 60° C. for 2 hr. Potassium carbonate (2.0 g) and water (5 ml) were added to the resulting reaction mixture, which was then heated under reflux for 12 hr. The reaction solution was evaporated, and the resulting residue was extracted with methylene chloride, washed with brine, and then dried. The solvent was removed and the resulting residue was purified by silica gel column chromatography (methylene chloride/methanol system), to give 2.0 g of the title compound as a brown amorphous.

(1-3) 3-(4-Benzyloxybutyl)-1-(4-ethylpiperazin-1-yl)isoquinoline

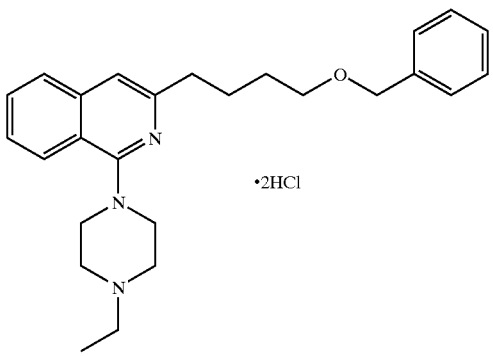

3-(4-Benzyloxybutyl)isoquinoline-2-oxide (2.0 g) and phosphorous oxychloride (5 ml) were reacted at 110° C. for 2 hr. The reaction solution was evaporated, to the resulting residue were added ethyl acetate and aqueous solution of saturated sodium bicarbonate, and the resulting organic layer was washed with water and brine. The organic layer was dried over magnesium sulfate followed by evaporating the solvent. The resulting 1-chloro-3-(4-benzyloxybutyl)isoquinoline obtained as a yellow oil was reacted with N-ethylpiperazine (5 ml) and potassium carbonate (0.5 g) at 120° C. for 5 hr. The reaction solution was then cooled and then partitioned by adding ethyl acetate and water thereto. The resulting organic layer was washe with water and brine, and dried over magnesium sulfate. The solvent was evaporated, and the resulting residue was purified by silica gel column chromatography (methylene chloride/methanol system) to give 1.32 g of the free compound of the title compound as a pale yellow oil.

Free compound:

$^1$H-NMR (400 MHz, CDCl$_3$): δ (ppm) 1.17(t,J=7.2 Hz, 3H), 1.64–1.75(m,2H), 1.80–1.92(m,2H), 2.54(q,J=7.2 Hz,2H), 2.74(m,4H), 2.80(t,J=7.2 Hz,2H), 3.41–3.56(m, 4H), 4.49(s,2H), 7.02(s,1H), 7.22–7.36(m,5H), 7.40(t,J=8.0 Hz,1H), 7.53(t,J=8.0 Hz,1H), 7.64(d,J=8.0 Hz,2H), 8.01(d, J=8.0 Hz,2H).

MS(FAB) m/z 404(M+H)$^-$.

The resulting free compound was converted into a hydrochloride in a conventional manner, and then recrystallized from ethanol/ether, to give 1.14 g of the title compound as a yellow amorphous.

Example 2

Synthesis of 1-(1-methylpiperazin-4-yl)-3-(4-methoxyphenyl)isoquinoline

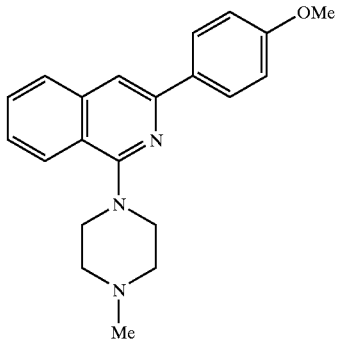

1-Chloro-3-(4-methoxyphenyl)isoquinoline (526 mg) and 1-methylpiperazine (4.4 ml) were stirred at 120° C. overnight. The reaction mixture was evaporated, aqueous solution of saturated sodium bicarbonate was added thereto, followed by extracting with ethyl acetate. The resulting organic layer was washed with water, dried (over MgSO$_4$), evaporated, and then purified by silica gel column chromatography (methylene chloride/methanol system). The resulting product was converted into a hydrochloride in a conventional manner, and then recrystallized from ethanol, to give the hydrochloride of the title compound as pale yellow crystals (320 mg, yield: 40%).
Hydrochloride:
m.p.; 134–136° C.
$^1$H-NMR(400 MHz, DMSO-d$_6$); δ (ppm) 2.86(3H,d,J× 4.4 Hz), 3.26–3.44(4H,m), 3.54(2H,d,J=11.6 Hz), 3.80(3H,s), 3.97(2H,d,J=11.6 Hz), 7.05(2H,d,J=8.8 Hz), 7.55(1H,ddd,J=8.2 Hz,6.8 Hz,1.2 Hz), 7.70(1H,ddd,J=8.2 Hz,6.8 Hz,1.2 Hz), 7.93(1H,d,J=8.4 Hz), 7.98(1H,s), 8.06(1H,d,J=8.4 Hz), 8.13(2H,d,J=8.8 Hz).
ESI-Mass; 334(MH$^+$).

Example 3

Synthesis of 1-(1-methylpiperazin-4-yl)-3-[4-(2-hydroxyethoxy)phenyl]isoquinoline
(3-1) 1-(1-Methylpiperazin-4-yl)-3-(4-hydroxyphenyl)isoquinoline

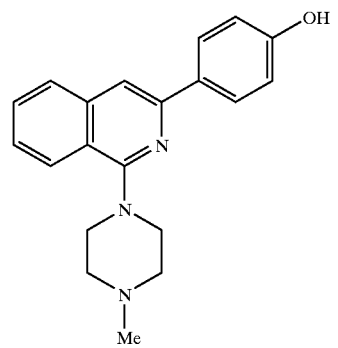

To 1-(1-methylpiperazin-4-yl)-3-(4-methoxy-1-phenyl)isoquinoline (2.07 g) was added 47% hydrobromic acid (28 ml), and the resulting mixture was heated under reflux for 6.5 hr. After the resulting solution was left for cooling, it was basified (pH=10) by adding 5N sodium hydroxide thereto, and then extracted with chloroform. The resulting organic layer was washed with water, dried (over MgSO$_4$) and evaporated. Methanol was added thereto, and the insoluble matter was collected by filtration and dried, to give the title compound as a pale red solid (946 mg, yield; 50%).
$^1$H-NMR (400 MHz,CDCl$_3$); δ (ppm) 2.28(3H,s), 2.60 (4H,br-s), 3.40(4H,br-s), 6.85(2H,d,J=8.8 Hz), 7.48(1H,dd, J=8 Hz,7 Hz), 7.63(1H,dd,J=8 Hz,7 Hz), 7.79(1H,s), 7.86 (1H,d,J=8 Hz), 8.00(1H,d,J=8 Hz), 8.01(2H,d,J=8.8 Hz), 9.62(1H,s).
(3-2) 1-(1-Methylpiperazin-4-yl)-3-[4-(ethoxycarbonylmethoxy)phenyl]isoquinoline

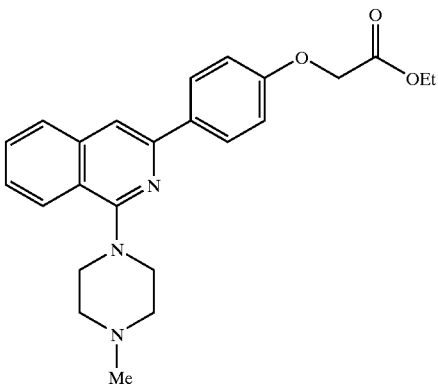

1-(1-Methylpiperazin-4-yl)-3-(4-hydroxy-1-phenyl) isoquinoline (320 mg) was dissolved in N,N-dimethylformamide (5 ml), to which was then added 60% sodium hydride (48 mg) under ice-cooling. The resulting mixture was stirred at room temperature for 1 hr. It was ice-cooled again, to which was then added ethyl 2-bromoacetate (166 ml), for agitation for 6 hours. The reaction mixture was partitioned between ethyl acetate and water, and the resulting organic layer was washed with water, dried (over MgSO$_4$) and evaporated. The resulting residue was purified by silica gel column chromatography (methylene chloride/methanol system), to give the title compound as a pale yellow oil (171 mg, yield; 40%).
$^1$H-NMR(400 MHz,CDCl$_3$); δ (ppm) 1.31(3H,t,J=7.2 Hz), 2.41(3H,s), 2.71(4H,t,J=4.4 Hz), 3.56(4H,t,J=4.4 Hz), 4.28(2H,q,J=7.2 Hz), 4.67(2H,s), 7.01(2H,d,J=8.8 Hz), 7.43 (1H,ddd,J=8 Hz,7 Hz,1.2 Hz), 7.55(1H,ddd,J=8 Hz,7 Hz,1.2 Hz), 7.60(1H,s), 7.75(1H,d,8 Hz), 8.04(1H,d,J=8 Hz), 8.11 (2H,d,8.8 Hz).
(3-3) 1-(1-Methylpiperazin-4-yl)-3-[4-(2-hydroxyethoxy)phenyl]isoquinoline

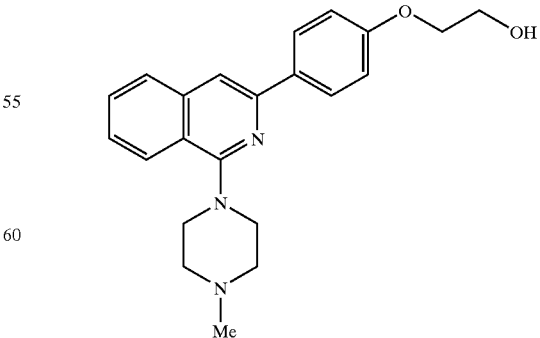

1-(1-Methylpiperazin-4-yl)-3-[4-(ethoxycarbonylmethoxy)phenyl]isoquinoline (320 mg) was dissolved in tetrahydrofuran (5 ml), to which was added lithium aluminium hydride (16 mg) under ice-cooling, followed by stirring for 5 min. To the resulting reaction mixture were then added water (16 ml), 5N sodium hydroxide (16 ml) and water (48 ml) in this order. After diluting with ethyl acetate, it was filtered through Celite and evaporated. The resulting residue was purified by silica gel column chromatography (methylene chloride/methanol system), which was converted into a hydrochloride in a conventional manner, and then recrystallized from in ethanol, to give the hydrochlroide of the title compound as yellow crystals (105 mg, yield; 50%).

Hydrochloride:
m.p.; 131–144° C.
$^1$H-NMR(400 MHz,DMSO-$d_6$); δ (ppm) 2.85(3H,d,J=4.4 Hz), 3.36(1H,t,J=11 Hz), 3.38(1H,t,J=11 Hz), 3.42(1H,t,J=12.6 Hz), 3.45(1H,t,J=12.6 Hz), 3.54(2H,d,J=11 Hz), 3.73 (2H,t,J=5 Hz), 3.96(1H,d,J=12.6 Hz), 4.04(2H,t,J=5 Hz), 7.05(2H,d,J=8.8 Hz), 7.55(1H,ddd,J=8 Hz,7 Hz,1.2 Hz), 7.70(1H,ddd,J=8 Hz,7 Hz,1.2 Hz), 7.93(1H,d,J=8 Hz), 7.97 (1H,s), 8.06(1H,d,J=8 Hz), 8.12(2H,d,J=8.8 Hz), 10.95(1H, br-s).
ESI-Mass; 364(MH$^+$).

Example 4

Synthesis of 1-(4-ethylpiperazin-1-yl)-3-(4-trifluoromethylphenyl)isoquinoline Dihydrochloride

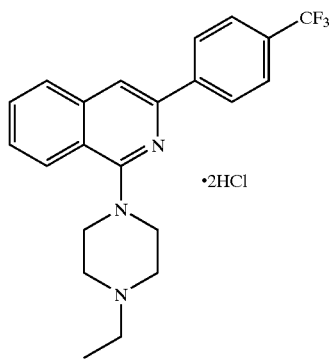

3-(4-Trifluoromethylphenyl)isoquinolin-1-one obtained by reacting N-methyl-o-toluamide (1.0 g) and 4-trifluoromethylbenzonitrile (1.15 g) according to Example 10-1 was added to phosphorous oxychloride (10 ml), and the resulting mixture was heated at 110° C. for 3 hr. The reaction solution was evaporated, and ethyl acetate and water were added to the resulting residue. The resulting organic layer was washed with water, an aqueous solution of sodium bicarbonate and brine, and then dried over magnesium sulfate. The solvent was evaporated, and the resulting 1-chloro-3-(4-trifluoromethylphenyl)isoquinoline was reacted with N-ethylpiperazine (10 ml) at 120° C. for 5 hr. The reaction solution was evaporated, and ethyl acetate and water were added to the resulting residue. The resulting organic layer was washed with water and brine, and dried over magnesium sulfate. The solvent was evaporated, and the resulting residue was purified by silica gel column chromatography (methylene chloride/methanol system), to give the free compound of the title compound as a pale yellow oil.

Free compound:
$^1$H-NMR(400 MHz,CDCl$_3$); δ (ppm) 1.18(t,J=7.6 Hz,3H), 2.57(q,J=7.6 Hz,2H), 2.78(m,4H), 3.60(m,4H), 7.50(br-t,1H), 7.62(br-t,1H), 7.71(d,J=8.4 Hz,2H), 7.74(s, 1H), 7.81(d,J=8.4 Hz,1H), 8.09(br-d,1H), 8.26(d,J=8.4 Hz,2H).

The resulting free compound was converted into a hydrochloride in a conventional manner, and then recrystallized from ethanol/ether, to give 0.19 g of the title compound as a yellow powder.

Hydrochloride:
m.p.; 131–133° C.
$^1$H-NMR(400 MHz, DMSO-$d_6$); δ (ppm) 1.34(t,J=7.2 Hz,3H), 3.19–3.27(m,2H), 3.30–3.41(m,2H), 3.52–3.65(m, 4H), 4.02(br-d,2H), 7.67(ddd,J=8.4,7.2,1.2 Hz,2H), 7.79 (ddd,J=7.6,7.2,0.8 Hz,1H), 7.88(d,J=8.4 Hz,1H), 8.04(d,J= 7.6 Hz,1H), 8.16(d,J=8.4 Hz,1H), 8.25(s,2H), 8.16(d,J=8.4 Hz,1H), 11.27(br-s,1H).
MS(FAB) m/z 416(M+H)$^+$.

Example 5

Synthesis of 1-(4-ethylpiperazin-1-yl)-3-[4-(1-fluoropropyl)phenyl]isoquinoline Hydrochloride

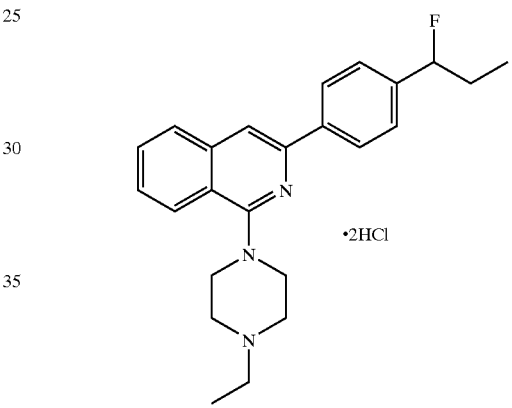

Diethylaminosulfur trifluoride (0.27 g) was added to a solution of 1-(4-ethylpiperazin-1-yl)-3-[4-(1-hydroxypropyl)phenyl]isoquinoline (0.53 g) obtained in Example 19 in methylene chloride (30 ml) at −78° C. After stirring the resulting mixture for 1 hr, it was returned to room temperature. An aqueous solution of saturated sodium bicarbonate and ethyl acetate were added to the resulting reaction solution, for partitioning. The resulting organic layer was washed with water and brine, dried and concentrated. The resulting residue was purified by silica gel column chromatography (methylene chloride/methanol system) (0.38 g), and was then converted into a hydrochloride in a conventional manner, to give 0.36 g of the title compound as a yellow powder.

Free compound:
$^1$H-NMR(400 MHz,CDCl$_3$); δ (ppm) 1.01(t,J=7.2 Hz,3H), 1.17(t,J=7.2 Hz,3H), 1.82–2.10(m,2H), 2.56(q,J= 7.2 Hz,2H), 2.76(m,4H), 3.59(m,4H), 5.35–5.50(m,1H), 7.42(t,J=8.0 Hz,2H), 7.45(t,J=8.0 Hz,1H), 7.58(t,J=8.0 Hz,2H), 7.68(s,1H), 7.79(d,J=8.0 Hz,1H), 8.08(d,J=8.0 Hz,1H), 8.17(d,J=8.0 Hz,2H).

Hydrochloride:
m.p.; 147–149° C.
MS(FAB) m/z 378(M+H)$^+$.

Example 6

Synthesis of 1-(4-ethylpiperazin-1-yl)-3-(2-hydroxyphenyl)isoquinoline

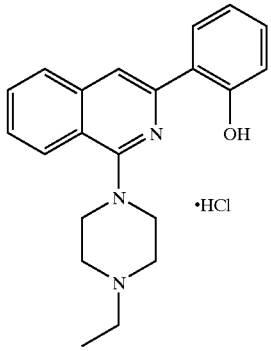

1-(4-Ethylpiperazin-1-yl)-3-(2-methoxyphenyl)isoquinoline (0.38 g) obtained in Example 8 was dissolved in 48% hydrobromic acid (15 ml) and reacted at 120° C. for 1.5 hr. The reaction solution was evaporated to a final half volume, and then ice-cooled. The resulting precipitates were collected by filtration and washed with a small amount of ice-cold water. The resulting precipitates were treated with a 2N aqueous solutiong of sodium hydroxide. The resulting precipitates were collected by filtration, and washed with water and ether/n-hexane, to give 0.23 g of the free compound of the title compound. 70 mg of the free compound was converted into a hydrochloride in a conventional manner, to give 71 mg of the hydrochloride of the title compound title compound as a yellow powder.

Hydrochloride:
m.p.; 228–230° C.
$^1$H-NMR(400 MHz,DMSO-d$_6$); δ (ppm) 1.31(t,J=7.2 Hz,3H), 3.20–3.30(m,2H), 3.36–3.52(m,4H), 3.63–3.70(m,2H), 3.90–4.08(m,2H), 6.95(d,J=8.0 Hz,2H), 6.95(t,J=8.0 Hz,1H), 7.65(t,J=8.0 Hz,2H), 7.80(t,J=8.0 Hz,2H), 8.00–8.09(m,2H), 8.15(d,J=8.0 Hz,2H), 8.27(s,1H).
MS(FAB) m/z 334(M+H)$^+$.

Example 7

Synthesis of 1-(4-ethylpiperazin-1-yl)-3-(4-hydroxyphenyl)isoquinoline

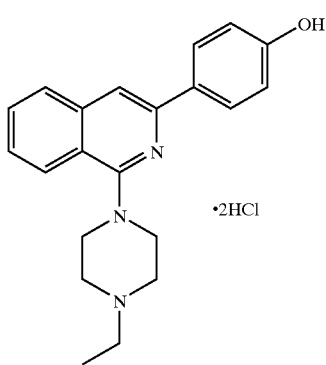

1-(4-Ethylpiperazin-1-yl)-3-(4-methoxyphenyl)isoquinoline (1.50 g) obtained in Example 10 was dissolved in 48% hydrobromic acid (15 ml) and reacted at 120° C. for 1.5 hr. The reaction solution was evaporated to a final half volume, and ice-cooled. The resulting precipitates were collected by filtration, and then washed with a small amount of ice-cooled water. The precipitates were treated with a 2N aqueous solution of sodium hydroxide, followed by collecting the precipitates by filtration, washed with water and ether/n-hexane, and then dried in warm air, to give the title compound (1.08 g, yield; 75%).

Free compound:
m.p.; 204–206° C.
$^1$H-NMR(400 MHz,DMSO-d$_6$); δ (ppm) 1.08(t,J=7.2 Hz,3H), 2.38–2.52(m,2H), 2.68(br,4H), 3.42(br,4H), 6.87(d, J=8.8 Hz,2H), 7.51(ddd,J=8.0,7.2,0.8 Hz,1H), 6.87(ddd,J= 8.0,7.2,0.8 Hz,1H), 7.82(s,1H), 7.88(d,J=8.0 Hz,1H), 8.02–8.06(m,1H), 8.03(d,J=8.8 Hz,2H), 9.66(s,1H).
MS(FAB) m/z 334(M+H)$^+$.

Example 8

Synthesis of 1-(4-ethylpiperazin-1-yl)-3-(2-methoxyphenyl)isoquinoline Dihydrochloride

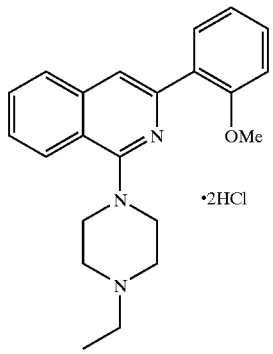

To 3-(2-methoxyphenyl)isoquinolin-1-one obtained by reacting N-methyl-o-toluamide (2.30 g) and 2-methoxybenzonitrile (2.0 g) according to Example 10-1 was added phosphorous oxychloride (10 ml), and the resulting mixture was heated at 100° C. for 2 hr. The reaction solution was evaporated, and to the resulting residue were added ethyl acetate and water, for partitioning. The resulting organic layer was washed with water, an aqueous solution of sodium bicarbonate and brine, and then dried over magnesium sulfate. The solvent was evaporated, and the resulting 1-chloro-3-(2-methoxyphenyl)isoquinoline was reacting with N-ethylpiperazine (10 ml) at 120° C. for 8 hr. The reaction solution was evaporated, and to the resulting residue were added ethyl acetate and water. The resulting organic layer was washed with water and brine, and dried over magnesium sulfate. The solvent was evaporated and the resulting residue was purified by silica gel column chromatography (methylene chloride/methanol system), to give the free compound of the title compound as a pale yellow oil.

Free compound:
$^1$H-NMR(400 MHz,CDCl$_3$); δ (ppm) 1.17(t,J=8.0 Hz,3H), 2.56(q,J=8.0 Hz,2H), 2.75(m,4H), 3.55(m,4H), 3.93(s,3H), 7.02(d,J=9.4 Hz,1H), 7.10(t,J=9.4 Hz,1), 7.32 (br-t,1H), 7.45(t,J=9.4 Hz,1H), 7.58(t,J=9.2 Hz,1H), 7.78(d, J=9.2 Hz,1H), 7.98(s,1H), 8.08(d,J=9.2 Hz,1H), 8.15(d,J= 4.5 Hz,1H).

The resulting free compound was converted into a hydrochloride in a conventional manner, and recrystallized from ethanol/ether, to give 0.42 g of the title compound as a yellow powder.

Hydrochloride:

m.p.: 133–135° C.

$^1$H-NMR(400 MHz,DMSO-d$_6$): δ (ppm) 1.33(t,J=7.2 Hz,3H), 3.19–3.26(m,2H), 3.29–3.41(m,2H), 3.53–3.65(m,4H), 3.90(s,3H), 3.97(br-d,2H), 7.11(br-t,1H), 7.19(d,J=8.0 Hz,1H), 7.42(br-t,1H), 7.65(br-t,1H), 7.78(br-t,1H), 7.98(d, J=8.0 Hz,2H), 8.06(s,1H), 8.15(d,J=8.8 Hz,1H), 11.30(br-s, 1H).

MS(FAB) m/z 348(M+H)$^+$.

Example 9

Synthesis of 1-(4-ethylpiperazin-1-yl)-3-(3-methoxyphenyl)isoquinone Dihydrochloride

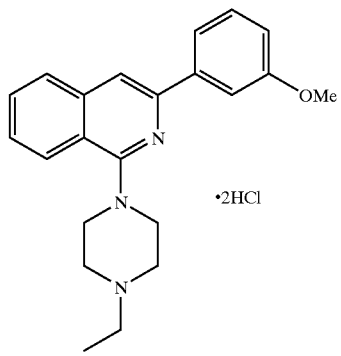

3-(4-Methoxyphenyl)isoquinone-1-one obtained by reacting N-methyl-o-toluamide (1.49 g) and 3-methoxybenzonitrile (1.33 g) according to Example 10-1 was reacted with phosphorus oxychloride (10 ml) according to Example 10-2, to give 1-chloro-3-(3-methoxyphenyl) isoquinoline. Then, it was reacted with N-ethylpiperazine (10 ml) at 120° C. for 6 hr. The reaction solution was evaporated, and ethyl acetate and water were added to the resulting residue. The resulting organic layer was washed with water and brine, and then dried over magnesium sulfate. The solvent was evaporated, and the resulting residue was purified by silica gel column chromatography (methylene chloride/methanol system), to give the free compound of the title compound as a pale yellow oil.

Free compound:

$^1$H-NMR(400 MHz,CDCl$_3$); δ (ppm) 1.17(t,J=7.6 Hz,3H), 2.55(q,J=7.6 Hz,2H), 2.76(m,4H), 3.58(m,4H), 3.90(s,3H), 6.93(dd,J=8.4,2.4 Hz,1H), 7.37(t,J=8.4 Hz,1H), 7.45(br-t,1H), 7.59(br-t,1H), 7.69(s,1H), 7.70–7.75(m,1H), 7.77–7.82(m,2H), 8.17(d,J=8.0 Hz,1H).

The resulting free compound was converted into a hydrochloride in a conventional manner and recrystallized from ethanol/ether, to give 0.27 g of the title compound as a yellow powder.

Hydrochloride:

m.p.; 108–110° C.

$^1$H-NMR(400 MHz,DMSO-d$_6$); δ (ppm) 1.34(t,J=7.2 Hz,3H), 3.18–3.27(m2H), 3.35(q,J=7.2 Hz,2H), 3.52–3.66 (m,4H), 3.87(s,3H), 3.96–4.04(m,2H), 7.01(br-d,1H), 7.44 (t,J=8.0 Hz,1H), 7.63(br-t,1H), 7.73–7.82(m,3H), 8.10(d,J= 8.0 Hz,1H), 8.13(s,1H), 8.13(d,J=8.4 Hz,1H), 11.25(br-s, 1H).

MS(FAB) m/z 348(M+H)$^+$.

Example 10

Synthesis of 1-(4-ethylpiperazin-1-yl)-3-(4-methoxyphenyl)isoquinone (10-1) 3-(4-Methoxyphenyl)isoquinolin-1-one

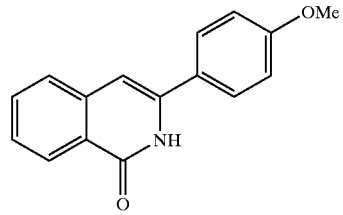

To a solution of N-methyl-o-toluamide (4.47 g) in THF (100 ml) was added dropwise 1.6 M n-BuLi (40 ml, 2.2 equivalents) in nitrogen atmosphere at 0° C. After stirring for 2 hr, the resulting solution was cooled in a dry ice/acetone bath to −70° C., followed by the addition of anisole (4.0 g) at once. The reaction mixture was drawn out of dry ice/acetone bath, and then returned to room temperature. Three hours later, an aqueous solution of saturated ammonium chloride and ether were added thereto, which was stirred for further 1 hr. The resulting white precipitates were collected by filtration, and then washed with water, ether and n-hexane, in this order. The resulting precipitates were dried, to give the title compound (1.72 g, yield; 24%).

$^1$H-NMR(400 MHz,DMSO-d$_6$); δ (ppm) 3.84(s,3H), 6.85 (s,1H), 7.05(d,J=8.4 Hz,2H), 7.46(m,1H), 7.69(s,1H), 7.65–7.72(m,1H), 7.78(d,J=8.4 Hz,2H), 8.20(d,J=8.0 Hz,1H).

(10-2) 1-Chloro-3-(4-methoxyphenyl)isoquinoline

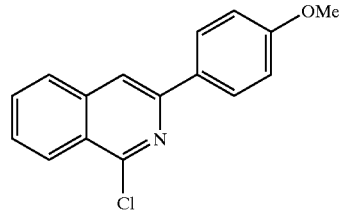

3-(4-Methoxyphenyl)isoquinolin-1-one (1.70 g) was added to phosphorus oxychloride (10 ml), and the resulting mixture was heated at 110° C. for 3 hr. The reaction mixture was evaporated, and to the resulting residue were added ethyl acetate and water. The resulting organic layer was washed with water, an aqueous solution of sodium bicarbonate and brine, and then dried over magnesium sulfate. The solvent was evaporated, and the resulting residue was purified by silica gel column chromatography (ethyl acetate/hexane system), to give the title compound as a white powder (1.76 g, yield; 96%).

$^1$H-NMR(400 MHz,CDCl$_3$); δ (ppm) 3.87(s,3H), 7.02(d, J=8.4 Hz,2H), 7.61(br-t,1H), 7.71(br-t,1H), 7.84(d,J=8.0 Hz,1H), 7.92(s,1H), 8.07(d,J=8.4 Hz,2H), 8.32(d,J=8.0 Hz,1H).

(10-3) 1-(4-Ethylpiperazin-1-yl)-3-(4-methoxyphenyl)isoquinoline

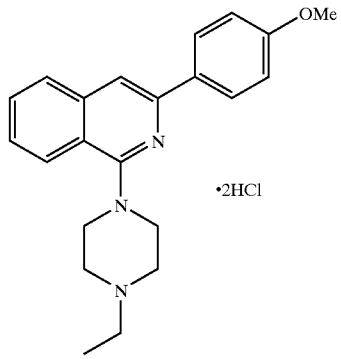

A mixture of 1-chloro-3-(4-methoxyphenyl)isoquinoline (0.89 g), N-ethylpiperazine (0.86 g) and potassium carbonate (1.10 g) was heated in dimethylformamide (20 ml) at 90° C. for 12 hr. The reaction mixture was evaporated, water was added to the resulting residue, and then it was extracted with ethyl acetate. The resulting organic layer was washed with water and brine, dried over magnesium sulfate, and then the solvent was romoved. The resulting residue was purified by silica gel column chromatography (methylene chloride/methanol system), to give the title compound as a pale brown oil (1.02 g, yield; 88%).

$^1$H-NMR(400 MHz,CDCl$_3$); δ (ppm) 1.18(t,J=7.2 Hz,3H), 2.55(q,J=7.2 Hz,2H), 2.76(br,4H), 3.59(br,4H), 3.87(s,3H), 7.00(d,J=8.4 Hz,2H), 7.43(t,J=8.0 Hz,1H), 7.56 (t,J=8.0 Hz,1H), 7.61(s,1H), 7.76(d,J=8.0 Hz,1H), 8.06(d, J=8.0 Hz,1H), 8.12(d,J=8.4 Hz,2H).

Example 11

Synthesis of 3-(2,3-dimethoxyphenyl)-1-(4-ethylpiperazin-1-yl)isoquinoline Dihydrochloride

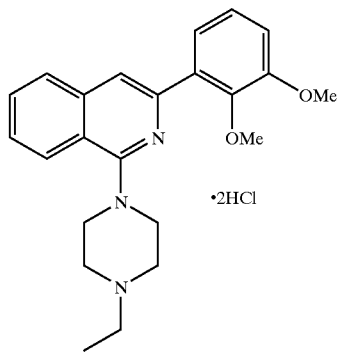

3-(2,3-Dimethoxyphenyl)isoquinolin-1-one obtained by reacting N-methyl-o-toluamide (1.49 g) and 2,3-dimethoxybenzonitrile (1.63 g) according to Example 10-1 was added to phosphorus oxychloride (10 ml), and the resulting mixture was heated at 110° C. for 3 hr. The reaction solution was evaporated, and to the resulting residue were added ethyl acetate and water. The resulting organic layer was washed with water, an aqueous solution of sodium bicarbonate and brine, and then dried over magnesium sulfate. The solvent was evaporated, and the resulting 1-chloro-3-(2,3-dimethoxyphenyl)isoquinoline was reacted with N-ethylpiperazine (15 ml) at 120° C. for 5 hr. The reaction solution was evaporated, and to the resulting residue were added ethyl acetate and water. The resulting organic layer was washed with water and brine, and was then dried over magnesium sulfate. The solvent was evaporated, and the resulting residue was purified by silica gel column chromatography (methylene chloride/methanol system), to give the free compound of the title compound as a pale yellow oil.

Free compound:
$^1$H-NMR(400 MHz,CDCl$_3$); δ (ppm) 1.18(t,J=7.2 Hz,3H), 2.55(q,J=7.2 Hz,2H), 2.76(m,4H), 3.55(m,4H), 3.78(s,3H), 3.92(s,3H), 6.94(d,J=7.5 Hz,1H), 7.16(t,J=7.5 Hz,2H), 7.47(dt,J=7.6,1.2 Hz,1H), 7.56–7.19(m,2H), 7.78 (d,J=7.6 Hz,2H), 7.96(s,1H), 8.10(d,J=7.6 Hz,1H).

The resulting free compound was converted into a hydrochloride in a conventional manner, and recrystallized from ethanol/ether, to give 0.19 g of the title compound as a yellow powder.

Hydrochloride:
m.p.; 122–123° C.
$^1$H-NMR(400 MHz,DMSO-d$_6$); δ (ppm) 1.33(t,J=7.2 Hz,3H), 3.18–3.27(m,2H), 3.35(q,J=7.2 Hz,3H), 3.53(br-t, 2H), 3.62(br-d,2H), 3.74(s,3H), 3.88(s,3H), 3.94(br-d,2H), 7.14(dd,J=8.0,1.6 Hz,1H), 7.20(t,J=8.0 Hz,1H), 7.49(dd,J= 8.4,1.6 Hz,1H), 7.65(t,J=7.2 Hz,1H), 7.77(t,J=7.2 Hz,1H), 7.97(s,1H), 8.00(d,J=8.4 Hz,1H), 8.15(d,J=8.4 Hz,1H), 11.19(br-s,1H).
MS(FAB) m/z 378(M+H)$^+$.

Example 12

Synthesis of 3-(2,4-dimethoxyphenyl)-1-(4-ethylpiperazin-1-yl)isoquinolin Dihydrochloride

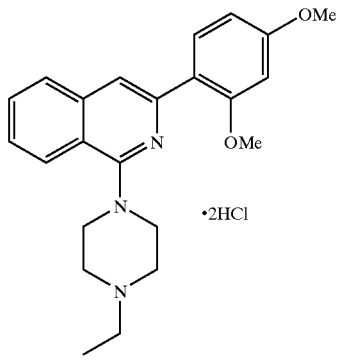

Phosphorus oxychloride (10 ml) was added to 3-(2,4-dimethoxyphenyl)isoquinolin-1-one obtained by reacting N-methyl-o-toluamide (2.20 g) and 2,4-dimethoxybenzonitrile (2.40 g) according to Example 10-1, and the resulting mixture was heated at 100° C. for 1 hr. The reaction solution was evaporated, and to the resulting residue were added ethyl acetate and water. The resulting organic layer was washed with water, an aqueous solution of sodium bicarbonate and brine, and was then dried over magnesium sulfate. The solvent was evaporated, and the resulting 1-chloro-3-(2,4-dimethoxyphenyl)isoquinoline was reacted with N-ethylpiperazine (15 ml) at 110° C. for 12 hr. The reaction solution was evaporated, and to the resulting residue were added ethyl acetate and water. The resulting organic layer was washed with water and brine, and was then dried over magneisum sulfate. The solvent was evaporated, and the resulting residue was purified by silica gel column chromatography (methylene chloride/methanol system), to give the free compound of the title compound as a pale yellow oil.

Free compound:
¹H-NMR(400 MHz,CDCl₃); δ (ppm) 1.15(t,J=7.2 Hz,3H), 2.55(q,J=7.2 Hz,2H), 2.70(m,4H), 3.55(m,4H), 3.85(s,3H), 3.91(s,3H), 6.57(d,J=4.0 Hz,1H), 6.64(dd,J=8.8, 4.0 Hz,1H), 7.43(t,J=8.0 Hz,1H), 7.56(t,J=8.0 Hz,1H), 7.77 (d,J=8.0 Hz,1H), 7.95(s,1H), 8.04(d,J=8.0 Hz,1H), 8.13(d, J=8.8 Hz,1H).

The resulting free compound was converted into a hydrochloride in a conventional manner, and recrystallization from ethanol/ether, to give 0.12 g of the title compound as a yellow powder.
Hydrochloride:
m.p.; 145–148° C.
¹H-NMR(400 MHz,DMSO-d₆); δ (ppm) 1.36(t,J=7.4 Hz,3H), 3.35(q,J=7.4 Hz,2H), 3.44–3.55(m,2H), 3.64–3.75 (m,2H), 3.77–3.88(m,2H), 3.84(s,3H), 3.86(s,3H), 4.17–4.26(m,2H), 6.66(br-s,1H), 6.67–6.82(m,1H), 7.57(dd, J=8.4,1.2 Hz,1H), 7.66–7.74(m,2H), 7.88–7.84(m,2H), 8.08 (br-d,1H).
MS(FAB) m/z 378(M+H)⁺.

Example 13

Synthesis of 3-(2,5-dimethoxyphenyl)-1-(4-ethylpiperazin-1-yl)isoquinoline Dihydrochloride

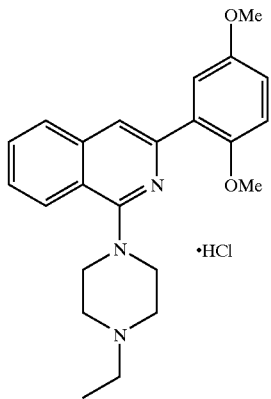

3-(2,5-Dimethoxyphenyl)isoquinolin-1-one (0.61 g) obtained by reacting N-methyl-o-toluamide (1.64 g) and 2,5-dimethoxybenzonitrile (1.80 g) according to Example 10-1 was reacted with phosphorus oxychloride (10 ml) according to Example 10-2, to give 1-chloro-3-(2,5-dimethoxyphenyl)isoquinoline, which was then reacted with N-ethylpiperazine (15 ml) at 100° C. for 8 hr. The reaction solution was evaporated, and to the resulting residue were added ethyl acetate and water. The resulting organic layer was washed with water and brine, and then dried over magnesium sulfate. The solvent was evaporated, and the resulting residue was purified by silica gel column chromatography (methylene chloride/methanol system), to give the free compound of the title compound as a pale yellow oil.
Free compound:
¹H-NMR(400 MHz,CDCl₃); δ (ppm) 1.16(t,J=7.2 Hz,3H), 2.55(q,J=7.2 Hz,2H), 2.76(m,4H), 3.55(m,4H), 3.86(s,3H), 3.88(s,3H), 6.88(dd,J=8.1,2.4 Hz,1H), 6.96(t,J= 8.1 Hz,1H), 7.46(br-t,1H), 7.57(br-t,1H), 7.76–7.84(m,1H), 8.04(s,1H), 8.08(s,1H), 8.12(d,J=8.0 Hz,1H).

The resulting free compound was converted into a hydrochloride in a conventional manner, and recrystallized from ethanol/ether, to give 0.55 g of the title compound as a yellow powder.

Hydrochloride:
m.p.; 189–191° C.
¹H-NMR(400 MHz,DMSO-d₆); δ (ppm) 1.32(t,J=7.2 Hz,3H), 3.19–3.28(m,2H), 3.36(q,J=7.2 Hz,2H), 3.48(br-t, 2H), 3.63(br-d,2H), 3.79(s,3H), 3.86(s,3H), 3.97(br-d,2H), 6.98(dd,J=8.0,3.2 Hz,1H), 7.12(d,J=9.2 Hz,1H), 7.61–7.66 (m,2H), 7.51(t,J=7.2 Hz,1H), 7.97(d,J=8.4 Hz,1H), 8.12(s, 1H), 8.11–8.16(m,1H), 10.73(br-s,1H).
MS(FAB) m/z 378(M+H)⁺.

Example 14

Synthesis of 3-(3,4-dimethoxyphenyl)-1-(4-ethylpiperazin-1-yl)isoquinoline Dihydrochloride

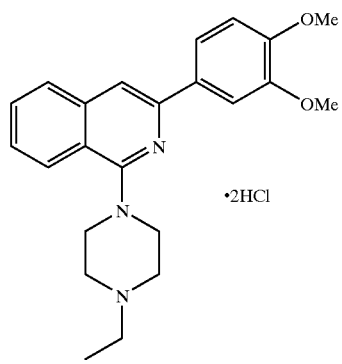

3-(3,4-Dimethoxyphenyl)isoquinolin-1-one (0.98 g) obtained by reacting N-methyl-o-toluamide (2.60 g) and 3,4-dimethoxybenzonitrile (2.83 g) according to Example 10-1 was reacted with phosphorus oxychloride (15 ml) at 80° C. for 3 hr. The reaction solution was evaporated, and to the resulting residue was added ethyl acetate and water. The resulting organic layer was washed with water, an aqueous solution of sodium bicarbonate and brine, and then dried over magnesium sulfate. The solvent was evaporated, and the resulting 1-chloro-3-(3,4-dimethoxyphenyl)isoquinoline was reacted with N-ethylpiperazine (15 ml) at 100° C. for 5 hr. The reaction solution was evaporated, and to the resulting residue were added ethyl acetate and water. The resulting organic layer was washed with water and brine, and then dried over magnesium sulfate. The solvent was evaporated, and the resulting residue was purified by silica gel column chromatography (methylene chloride/methanol system), to give the free compound of the title compound as a pale yellow oil.
Free compound:
¹H-NMR(400 MHz,CDCl₃); δ (ppm) 1.19(t,J=7.2 Hz,3H), 2.78(m,4H), 3.59(m,4H), 3.95(s,3H), 4.01(s,3H), 6.98(d,J=8.4 Hz,1H), 7.45(ddd,J=8.0,7.2,1.2 Hz,1H), 7.58 (ddd,J=8.0,7.2,1.2 Hz,1H), 7.64(s,1H), 7.72(dd,J=8.4,2.0 Hz,1H), 7.78(br-d,J=8.0 Hz,1H), 7.84(d,J=2.0 Hz,1H), 8.07 (br-d,J=8.0 Hz,1H).

The resulting free compound was converted into a hydrochloride in a conventional manner, and recrystallized from ethanol/ether, to give 1.38 g of the title compound as a yellow powder.
Hydrochloride:
m.p.; 125–126.5° C.
¹H-NMR(400 MHz,DMSO-d₆); δ (ppm) 1.33(t,J=7.6 Hz,3H), 3.27(q,J=7.6 Hz,2H), 3.30(br-t,2H), 3.45(br-t,2H), 3.68(br-d,2H), 3.74(s,3H), 3.78(s,3H), 3.98(br-d,2H), 6.83 (d,J=8.4 Hz,1H), 7.06(dd,J=8.0,2.0 Hz,1H), 7.09(d,J=2.0

Hz,1H), 7.29(s,1H), 7.59(br-t,1H), 7.65(br-d,1H), 7.76(br-t, 2H), 7.90(br-d,1H).

MS(FAB) m/z 378(M+H)+.

Example 15

Synthesis of 3-(3,5-dimethoxyphenyl)-1-(4-ethylpiperazin-1-yl)isoquinoline Dihydrochloride

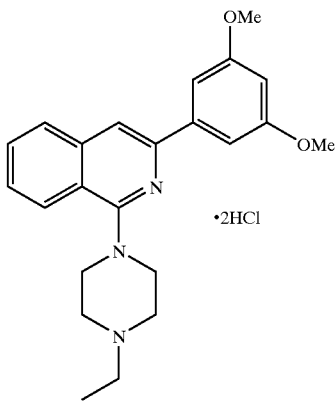

3-(3,5-Dimethoxyphenyl)isoquinolin-1-one obtained by reacting N-methyl-o-toluamide (1.49 g) and 3,5-dimethoxybenzonitrile (1.63 g) according to Example 10-1 was added to phosphorus oxychloride (10 ml), and the resulting mixture was heated at 100° C. for 3 hr. The reaction solution was evaporated, and to the resulting residue were added ethyl acetate and water. The resulting organic layer was washed with water, an aqueous solution of sodium bicarbonate and brine, and then dried over magnesium sulfate. The solvent was evaporated, and the resulting 1-chloro-3-(3,5-dimethoxyphenyl)isoquinole was reacted with N-ethylpiperazine (15 ml) at 120° C. for 4 hr. The reaction solution was evaporated, and to the resulting residue were added ethyl acetate and water. The resulting organic layer was washed with water and brine, and then dried over magnesium sulfate. The solvent was evaporated, and the reuslting residue was purified by silica gel column chromatography (methylene chloride/methanol system), to give the free compound of the title compound as a pale yellow oil.

Free compound:

$^1$H-NMR (400 MHz, CDCl$_3$); δ (ppm) 1.18 (t, J=7.2 Hz, 3H), 2.56 (q, J=7.2 Hz, 2H), 2.77 (m, 4H), 3.58 (m, 4H), 3.90 (s, 3H), 6.51 (d, J=2.4 Hz, 1H), 7.35 (br-d, 2H), 7.45 (br-t, 1H), 7.59 (br-t, 1H), 7.67 (s, 1H), 7.79 (d, J=7.6 Hz, 2H), 8.07 (d, J=7.6 Hz, 1H).

The resulting free compound was converted into a hydrochloride in a conventional manner, and recrystallized from ethanol/ether, to give 0.51 g of the title compound as a yellow powder.

Hydrochloride:

m.p.; 121–123° C.

$^1$H-NMR (400 MHz, DMSO-d$_6$); δ (ppm) 1.32 (t, J=7.2 Hz, 3H), 3.18–3.27 (m, 2H), 3.34 (q, J=7.2 Hz, 2H), 3.48–3.58 (m, 2H), 3.63 (br-d, 2H), 3.85 (s, 3H), 4.00 (br-d, 2H), 6.57 (dd, J=2.4 Hz, 1H), 7.44 (dx2, J=2.4 Hz, 2H), 7.62 (br-t, 1H), 7.62 (br-t, 1H), 8.00 (br-d, 1H), 8.12 (br-d, 1H), 8.14 (s, 1H), 11.02 (br-s, 1H).

MS(FAB) m/z 378 (M+H)+.

Example 16

Synthesis of 1-(4-ethylpiperazin-1-yl)-3-(2,4,5-trimethoxyphenyl)isoquinoline dihydrochloride

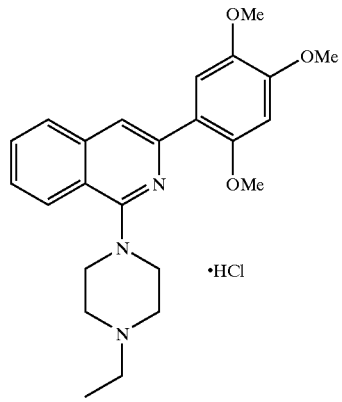

3-(2,4,5-Trimethoxyphenyl)isoquinolin-1-one obtained by reacting N-methyl-o-toluamide (1.50 g) and 2,4,5-trimethoxybenzonitrile (1.93 g) according to Example 10-1 was reacted with phosphorous oxychloride (10 ml) according to Example 10-2, to give 1-chloro-3-(2,4,5-trimethoxyphenyl)isoquinoline, which was then reacted with N-ethylpiperazine (15 ml) at 120° C. for 5 hr. The reaction solution was evaporated, and to the resulting residue were added ethyl acetate and water. The resulting organic layer was wahsed with water and brine, and then dried over magnesium sulfate. The solvent was evaporated, and the reuslting residue was purified by silica gel column chromatography (methylene chloride/methanol system), to give the free compound of the title compound as a pale yellow oil.

Free compound:

$^1$H-NMR (400 MHz, CDCl$_3$); δ (ppm) 1.17 (t, J=7.2 Hz, 3H), 2.55 (q, J=7.2 Hz, 2H), 2.76 (m, 4H), 3.55 (m, 4H), 3.88 (s, 3H), 3.91 (s, 3H), 3.94 (s, 3H), 6.65 (s, 1H), 7.43 (t, J=8.0 Hz, 1H), 7.56 (t, J=8.0 Hz, 1H), 7.77 (d, J=8.0 Hz, 1H), 7.92 (s, 1H), 8.03 (s, 1H), 8.06 (d, J=8.0 Hz, 1H).

The resulting free compound was converted into a hydrochloride in a conventional manner, and then recrystallized from ethanol/ether, to give 0.23 g of the title compound as a yellow powder.

Hydrochloride:

m.p.; 158–160° C.

$^1$H-NMR (400 MHz, DMSO-d$_6$); δ (ppm) 1.32 (t, J=7.2 Hz, 3H), 3.18–3.27 (m, 2H), 3.35 (q, J=7.2 Hz, 2H), 3.52 (br-t, 2H), 3.63 (br-d, 2H), 3.80 (s, 3H), 3.88 (s, 3H), 3.92 (s, 3H), 3.99 (br-d, 2H), 6.84 (s, 1H), 7.59 (br-t, 1H), 7.71–7.78 (m, 2H), 7.76 (s, 1H), 7.94 (d, J=8.0 Hz, 1H), 8.10 (s, 1H), 8.08–8.13 (m, 1H), 10.76 (br-s, 1H).

MS(FAB) m/z 408 (M+H)+.

Example 17

Synthesis of 1-(4-ethylpiperazin-1-yl)-3-(4-hydroxymethylphenyl)isoquinoline hydrochloride (17-1) Homophthalimide

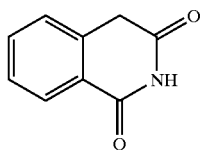

Homophthalic anhydride (20 g) and urea (60 g) were reacted at 170° C. for 1 hr. The reaction mixture was cooled, water (500 ml) was added thereto, and then the resulting precipitates were collected by filtration. The precipitate were washed with water and dried in hot air, to give 10.5 g of homophthalimide as a white powder.

(17-2) 1,3-Dichloroisoquinoline

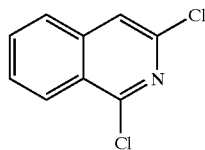

A mixture solution of homophthalimide (10.5 g) and phenylphosphonate dichloride (30 ml) was heated at 110° C. for 2 hr. After the reaction mixture was cooled, water was added thereto, and then the resulting mixture was neutralized with sodium carbonate. The resulting mixture was extracted with ethyl acetate, washed with brine, dried, and then the solvent was evaporated. The resulting residue was purified by silica gel column chromatography (methylene chloride), to give 9.30 g of the title compound as white crystals.

(17-3) 3-Chloro-1-(4-ethylpiperazin-1-yl)isoquinoline

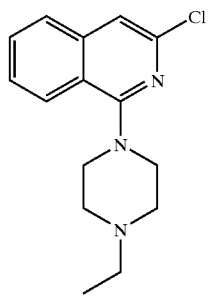

1,3-Dichloroisoquinoline (9.30 g), N-ethylpiperazine (5.90 g) and potassium carbonate (10.0 g) were reacted in dimethylformamide (70 ml) at 70° C. for 5 hr. The reaction solution was evaporated and partitioned between ethyl acetate and water. The resulting organic phase was washed with water, dried and evaporated. The resulting residue was purified by silica gel column chromatography (methylene chloride/methanol system), to give 12.80 g of the title compound as a pale brown oil.

(17-4) 3-[(1,3-Dioxolan-2-yl)phenyl]-1-(4-ethylpiperazin-1-yl)isoquinoline

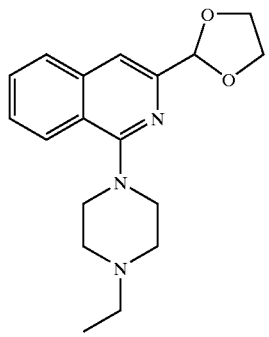

3-Chloro-1-(4-ethylpiperazin-1-yl)isoquinoline (3.5 g) and 4-(1,3,2-dioxaborynan-2-yl)-1-(1,3-dioxolan-2-yl)benzene (5.0 g) were reacted in dimethylformamide (50 ml), in the presence of cesium carbonate (7.3 g) and tetrakistriphenylphosphinepalladium (0.3 g) at 80° C. in a nitrogen stream for 12 hr. The reaction solution was evaporated, and then partitioned between ethyl acetate and water. The resulting organic layer was washed with water, dried and evaporated. The resulting residue was purified by silica gel column chromatography (methylene chloride/methanol system), to give 4.66 g of the title compound as a pale yellow oil.

(17-5) 1-(4-Ethylpiperazin-1-yl)-3-(4-formylphenyl)isoquinoline

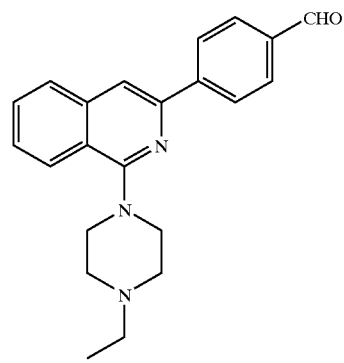

3-[(1,3-Dioxolan-2-yl)phenyl]-1-(4-ethylpiperazin-1-yl)isoquinoline (4.50 g) was dissolved in methanol (50 ml), a 1N hydrochloric acid (50 ml) was added thereto, and then the mixture was reacted at 50° C. for 1 hr. The reaction solution was evaporated, basified with sodium carbonate, and extracted with ethyl acetate. The resulting organic layer was washed with water and brine in this order, dried and concentrated. The resulting residue was purified by silica gel column chromatography (methylene chloride/methanol system), to give 3.62 g of the title compound as a pale yellow oil.

(17-6) 1-(4-Ethylpiperazin-1-yl)-3-(4-hydroxymethylphenyl)isoquinoline hydrochloride

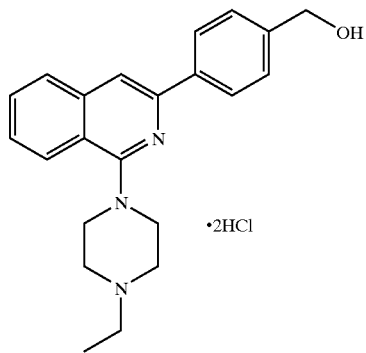

Sodium tetrahydroboride (0.20 g) was added to a solution of 1-(4-ethylpiperazin-1-yl)-3-(4-formylphenyl)isoquinoline (0.35 g) in methanol (20 ml) at 0° C. The reaction solution was stirred for 30 min and then concentrated. Water was added to the resulting residue, and then extracted with methylene chloride. The resulting product was dried and concentrated. The resulting residue was purified by NH-silica gel column chromatography (ethyl acetate), to give the free compound of the title compound as a pale yellow oil. The free form was converted into a hydrochloride in a conventional manner, to give 0.21 g of the title compound as a yellow powder.

Hydrochloride:
m.p.; 145–147° C.
$^1$H-NMR (400 MHz, DMSO-$d_6$); δ (ppm) 1.33 (t, J=7.2 Hz, 3H), 3.17–3.27 (m, 2H), 3.29–3.41 (m, 2H), 3.50–3.66 (m, 4H), 3.99 (d, J=9.2 Hz, 2H), 4.57 (s, 2H), 7.45 (d, J=8.0 Hz, 2H), 7.57–7.63 (m, 1H), 7.71–7.77 (m, 1H), 7.99 (d, J=8.0 Hz, 1H), 8.08 (s, 1H), 8.12 (d, J=8.0 Hz, 1H), 8.17 (d, J=8.0 Hz, 2H), 11.18 (m, 1H).
MS(FAB) m/z 348 (M+H)*.

Example 18

Synthesis of 3-[2-(2-hydroxyethoxy)phenyl]-1-(4-ethylpiperazin-1-yl)isoquinoline hydrochloride

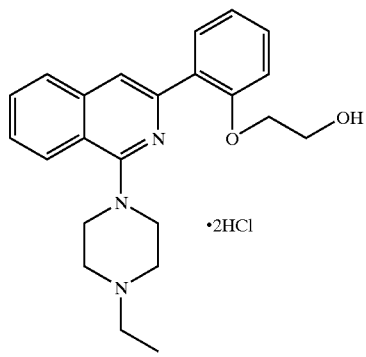

In the same manners as in Examples 161-2 and then 20, an oil was obtained from 1-bromo-2-(2-benzyloxyethoxy)benzene (886 mg) and 3-bromo-1-(4-ethylpiperazin-1-yl)isoquinoline (904 mg). Methanol (30 ml) and a palladium/carbon catalyst (200 mg) were added to the oil, which was then reacted in hydrogen atmosphere overnight at room temperature. Thereafter, the reaction solution was filtered through Celite and evaporated. The resulting residue was basified with a 1N aqueous solution of sodium hydroxide, and extracted with ethyl acetate. The resulting organic layer was washed with water, dried and concentrated. The resulting residue was purified by silica gel column chromatography, to give an oil. The oil was converted into a hydrochloride in a conventional manner, to give the hydrochloride of the title compound as yellow crystals (733 mg, yield; 89%).

Hydrochloride:
m.p.; 158–160° C.
$^1$H-NMR (400 MHz, DMSO-$d_6$); δ (ppm) 1.33 (t, J=7.2 Hz, 3H), 3.18–3.28 (m, 2H), 3.32–3.42 (m, 2H), 3.55–3.63 (m, 4H), 3.79–3.82 (m, 2H), 4.00 (d, J=14.0 Hz, 2H), 4.14–4.16 (m, 2H), 7.11 (t, J=8.4 Hz, 1H), 7.18 (d, J=8.4 Hz, 1H), 7.39 (dt, J=8.4, 1.6 Hz, 1H), 7.64 t, J=8.0 Hz, 1H), 7.78 (t, J=8.0 Hz, 1H), 7.95 (d, J=8.0 Hz, 1H), 8.05 (d, J=8.4 Hz, 1H), 8.15 (d, J=8.0 Hz, 1H), 8.29 (s, 1H).
MS(FAB) m/z 378 (M+H)*.

Free compound:
$^1$H-NMR (400 MHz, CDCl$_3$); δ (ppm) 1.16 (t, J=7.2 Hz, 3H), 2.54 (q, J=7.2 Hz, 2H), 2.74 (br, 4H), 3.53 (br, 4H), 3.92 (d, J=4.4 Hz, 2H), 4.21 (d, J=4.4 Hz, 2H), 7.03 (d, J=8.0 Hz, 1H), 7.11 (dt, J=8.0, 1.2 Hz, 1H), 7.33 (dt, J=8.0, 1.6 Hz, 1H), 7.48 (ddd, J=8.4, 8.0, 1.2 Hz, 1H), 7.59 (ddd, J=8.4, 8.0, 1.2 Hz, 1H), 7.75 (d, J=8.0 Hz, 1H), 7.81 (s, 1H), 7.91 (dd, J=8.0, 1.6 Hz, 1H), 8.10 (d, J=8.4 Hz, 1H).

Example 19

Synthesis of 1-(4-ethylpiperazin-1-yl)-3-[4-(1-hydroxypropyl)phenyl]isoquinoline hydrochloride

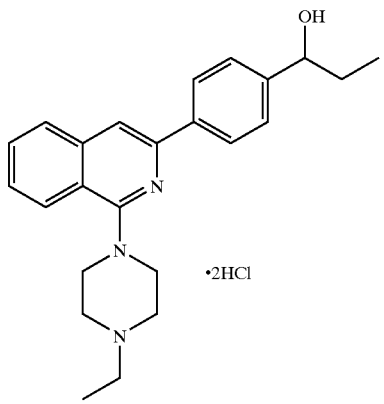

To a solution of 1-(4-ethylpiperazin-1-yl)-3-(4-formylphenyl)isoquinoline (1.20 g) obtained in Example 17-5 in tetrahydrofuran (60 ml) was added 3M ethylmagnesium bromide/diethyl ether solution (2.0 ml) at 0° C., and the mixture was stirred for 2 hr. To the resulting reaction solution were added a 2N aqueous solution of hydrochloric acid (20 ml) and ethyl acetate. The resulting aqueous layer was basified with a 2N aqueous solution of sodium hydroxide, and extracted with ethyl acetate. The resulting organic layer was washed with water and brine, dried and concentrated. The resulting residue was purified by silica gel column chromatography (methylene chloride/methanol system), to give 1.03 g of the free compound of the title compound. 0.50 g of the resulting free compound was converted into a hydrochloride in a conventional manner, to give 0.48 g of the title compound as a yellow powder.

Hydrochloride:
m.p.; 143–144° C.
$^1$H-NMR (400 MHz, DMSO-$d_6$); δ (ppm) 0.86 (t, J=7.2 Hz, 3H), 1.34 (t, J=7.2 Hz, 3H), 1.66 (m, 2H), 3.18–3.28 (m, 2H), 3.29–3.41 (m, 2H), 3.49–3.66 (m, 4H), 3.95–4.04 (m, 2H), 4.52 (t, J=6.4 Hz, 1H), 7.44 (d, J=8.4 Hz, 2H), 7.58–7.64 (m, 1H), 7.71–7.77 (m, 1H), 7.98 (d, J=8.0 Hz, 1H), 8.07 (s, 1H), 8.11 (d, J=8.4 Hz, 1H), 8.15 (d, J=8.4 Hz, 2H), 11.23 (m, 1H).

MS(FAB) m/z 376 (M+H)*.

Example 20

Synthesis of 1-(4-ethylpiperazin-1-yl)-3-[4-(3-hydroxypropyl)phenyl]isoquinoline hydrochloride

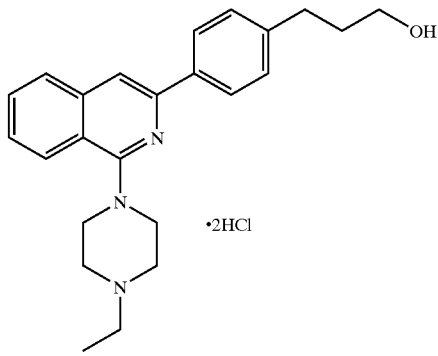

[4-(2-Ethoxycarbonylethyl)phenyl]tributylstannum (2.998 g) and 3-bromo-1-(4-ethylpiperazin-1-yl)isoquinoline (1.292 g) were reacted in the presence of tetrakistriphenylphosphine (0.185 g) in xylene (20 ml) in nitrogen atmosphere for 2 hr. After cooling, the reaction solution was filtered. The resulting filtrate was extracted with a 5N aqueous solution of hydrochloric acid. The resulting aqueous layer was basified with a 5N sodium hydroxide and extracted with ethyl acetate. The resulting organic layer was washed with water and brine, dried and concentrated. The resulting 1-(4-ethylpiperazin-1-yl)-3-[4-(2-ethoxycarbonylethyl)phenyl]isoquinoline was dissolved in tetrahydrofuran (20 ml), and then added dropwise into a suspension of lithium aluminium hydride (0.106 g). The reaction solution was stirred at room temperature for 3 hr. After cooling, water and an aqueous solution of sodium hydroxide and water were added thereto in this order, and the resulting mixture was stirred at room temperature for 1 hr. The resulting precipitates were filtered off, and the residue washed with ethyl acetate. The filtrate was concentrated, and the resulting residue was purified by silica gel column chromatography (methylene chloride/methanol system), to give 0.527 g of 1-(4-ethylpiperazin-1-yl)-3-[4-(1-hydroxypropyl)phenyl]isoquinoline as a pale yellow oil.

Free compound:
$^1$H-NMR (400 MHz, CDCl$_3$); δ (ppm) 1.18 (t, J=7.2 Hz, 3H), 1.91–1.98 (m, 2H), 2.56 (q, J=7.2 Hz, 2H), 2.76–2.79 (m, 6H), 3.59 (br-t, 4H), 3.71 (t, J=6.4 Hz, 2H), 7.31 (d, J=8.0 Hz, 2H), 7.45 (br-t, 1H), 7.58 (br-t, 1H), 7.67 (s, 1H), 7.78 (d, J=8.0 Hz, 1H), 8.07 (d, J=7.6 Hz, 1H), 8.10 (d, J=8.4 Hz, 2H).

The resulting free compound was converted into a hydrochloride in a a conventional manner, to give the title compound as a yellow powder.

Hydrochloride:
m.p.; 116–119° C.
$^1$H-NMR (400 MHz, DMSO-d$_6$); δ (ppm) 1.33 (t, J=7.2 Hz, 3H), 1.73–1.80 (m, 2H), 2.68 (t, J=7.8 Hz, 2H), 3.20–3.27 (m, 2H), 3.31–3.39 (m, 2H), 3.45 (t, J=6.6 Hz, 2H), 3.52 (br-t, 2H), 3.62 (br-d, 2H), 4.00 (br-d, 2H), 7.34 (d, J=8.0 Hz, 2H), 7.60 (br-t, 1H), 7.74 (br-t, 1H), 7.98 (d, J=8.0 Hz, 1H), 8.05 (s, 1H), 8.11 (d, J=8.4 Hz, 2H), 10.95 (br-s, 1H).

MS(FAB) m/z 376 (M+H)*.

Example 21

Synthesis of 1-(4-ethylpiperazin-1-yl)-3-[4-(1-hydroxybutyl)phenyl]isoquinoline oxalate

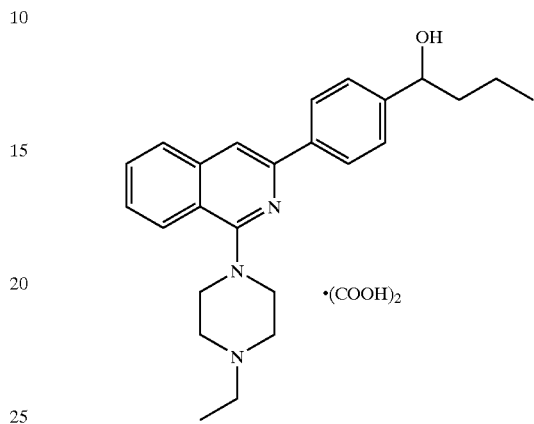

(4-Butyrylphenyl)tributylstannum (1.566 g) and 3-bromo-1-(4-ethylpiperazin-1-yl)isoquinoline (0.985 g) was reacted in the presence of tetrakistriphenylphosphine (0.138 g) in xylene (20 ml) in nitrogen atmosphere for 2 hr. After cooling, the reaction solution was filtered. The resulting filtrate was extracted with a 5N aqueous solution of hydrochloric acid. The resulting aqueous layer was basified with 5N sodium hydroxide, and then extracted with ethyl acetate. The resulting organic layer was washed with water and brine, dried and concentrated. The resulting 1-(4-ethylpiperazin-1-yl)-3-(4-butyrylphenyl)isoquinoline (0.177 g) was dissolved in methanol, and then excess amount of sodium borohydride in was added thereto little by little. After the completion of the reaction was confirmed, the solvent was evaporated. To the resulting residue was added water, and then extracted with ethyl acetate. The resulting product was washed with brine, dried over magnesium sulfate, and then the solvent was evaporated. The resulting residue was purified by silica gel column chromatography (methylene chloride/methanol system), to give 0.150 g of the title compound as a pale yellow oil.

Free compound:
$^1$H-NMR (400 MHz, CDCl$_3$); δ (ppm) 0.95 (t, J=7.2 Hz, 3H), 1.18 (t, J=7.2 Hz, 3H), 1.31–1.62 (m, 2H), 1.69–1.89 (m, 2H), 2.57 (q, J=7.2 Hz, 2H), 2.77 (br-s, 4H), 3.60 (br-s, 4H), 4.76 (t, J=6.8 Hz, 1H), 7.44–7.48 (m, 3H), 7.59 (br-t, 1H), 7.70 (s, 1H), 7.80 (d, J=7.6 Hz, 1H), 8.08 (d, J=8.0 Hz, 1H), 8.17 (d, J=8.4 Hz, 2H).

The resulting compound was converted into an oxalate in a conventional manner, to give the title compound as a white powder.

Oxalate:
m.p.; 198.5–199.5° C.
$^1$H-NMR (400 MHz, DMSO-d$_6$); δ (ppm) 0.89 (t, J=7.2 Hz, 3H), 1.26 (t, J=7.2 Hz, 3H), 1.22–1.42 (m, 2H), 1.53–1.69 (m, 2H), 3.12 (br-q, 1H), 3.36 (br-s, 4H), 3.67 (br-s, 4H), 4.59 (t, J=6.4 Hz, 1H), 7.44 (d, J=8.4 Hz, 2H), 7.60 (br-t, 1H), 7.73 (br-t, 1H), 7.98 (d, J=7.6 Hz, 1H), 8.05 (s, 1H), 8.10–8.15 (m, 3H).

MS(FAB) m/z 390 (M+H)*.

Example 22

Synthesis of 1-(4-ethylpiperazin-1-yl)-3-[4-(3-hydroxybutyl)phenyl]isoquinoline oxalate

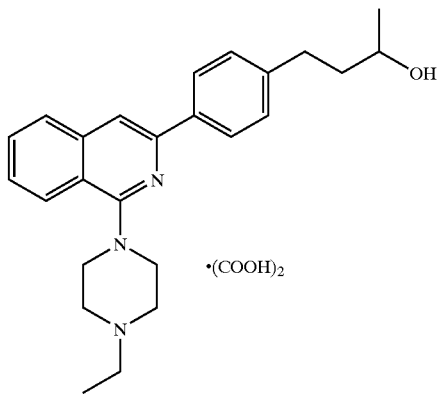

•(COOH)$_2$

[4-(3-Oxobutyl)phenyl]tributylstannum (2.457 g) and 3-bromo-1-(4-ethylpiperazin-1-yl)isoquinoline (1.405 g) were reacted in the presence of tetrakistriphenylphosphine (0.217 g) in xylene (20 ml) in nitrogen atmosphere for 2 hr. After cooling, the reaction solution was filtered. The resulting filtrate was extracted with a 5N aqueous solution of hydrochloric acid. The resulting aqueous layer was basified with 5N sodium hydroxide, and extracted with ethyl acetate. The resulting organic layer was washed with water and brine, dried and concentrated. The resulting 1-(4-ethylpiperazin-1-yl)-3-[4-(3-ethoxycarbonylpropyl)phenyl] isoquinoline was dissolved in methanol, which was then treated with excessive sodium borohydride. The reaction solution was concentrated, extracted with ethyl acetate, washed with water and brine, dried and then the solvent was removed. The resulting residue was purified by silica gel column chromatography (methylene chloride/methanol system), to give 0.346 g of the title compound as a pale yellow oil.

Free compound:

$^1$H-NMR (400 MHz, CDCl$_3$); δ (ppm) 1.18 (t, J=7.2 Hz, 3H), 1.25 (d, J=6.4 Hz, 3H), 1.79–1.85 (m, 2H), 2.56 (q, J=7.2 Hz, 2H), 2.70–2.86 (m, 6H), 3.59 (br-t, 4H), 3.87 (tq, J=6.4 Hz, 1H), 7.31 (d, J=8.0 Hz, 2H), 7.45 (br-t, 1H), 7.58 (br-t, 1H), 7.67 (s, 1H), 7.78 (J=8.0 Hz, 1H), 8.06–8.11 (m, 3H).

The resulting compound was converted into an oxalate in a conventional manner, to give the oxalate of the title compound as a white powder.

Oxalate:

m.p.; 193–194° C.

$^1$H-NMR (400 MHz, DMSO-d$_6$); δ (ppm) 1.10 (d, J=6.0 Hz, 3H), 1.26 (t, J=7.2 Hz, 3H), 1.62–1.69 (m, 2H), 2.60–2.77 (m, 2H), 3.11 (br-q, 2H), 3.35 (br-s, 4H), 3.58–3.66 (m, 5H), 7.33 (d, J=8.4 Hz, 2H), 7.59 (br-t, 1H), 7.73 (br-t, 1H), 7.97 (d, J=8.0 Hz, 1H), 8.03 (s, 1H), 8.10 (d, J=8.4 Hz, 2H).

MS(FAB) m/z 390 (M+H)*.

Example 23

Synthesis of 3-[4-(4-hydroxybutyl)phenyl]-1-(4-ethylpiperazin-1-yl)isoquinoline hydrochloride

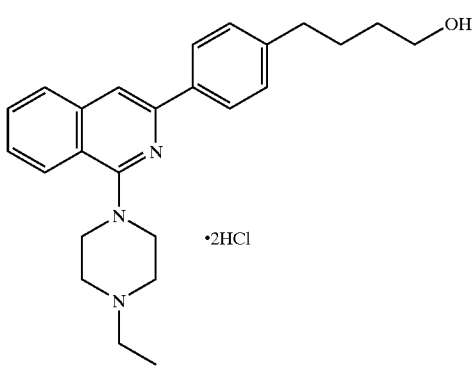

•2HCl

In the same manner as in Example 20, an oil was obtained from 1-bromo-4-(4-acetoxybutyl)benzene (1.57 g) and 3-bromo-1-(4-ethylpiperazin-1-yl)isoquinoline (1.0 g). Methanol (15 ml) and a 1N aqueous solution of sodium hydroxide (4 ml) were added thereto, and the mixture was refluxed for 3 hr. The reaction solution was partitioned between ethyl acetate and water, and the resulting organic layer was washed with water, dried and concentrated. The resulting residue was purified by silica gel column chromatography to give an oil. The oil was converted into a hydrochloride in a conventional manner, to give the hydrochloride of the title compound as yellow crystals (656 mg, yield; 66%).

Hydrochloride:

m.p.; 140–144° C.

$^1$H-NMR (400 MHz, DMSO-d$_6$); δ (ppm) 1.33 (t, J=7.2 Hz, 3H), 1.45–1.49 (m, 2H), 1.63–1.70 (m, 2H), 2.51 (br, 2H), 2.65 (t, J=7.2 Hz, 2H), 3.18–3.28 (m, 2H), 3.30–3.38 (m, 2H), 3.54 (t, J=13.2 Hz, 2H), 3.62 (d, J=10.8 Hz, 2H), 3.98 (d, J=12.4 Hz, 2H), 7.33 (d, J=8.4 Hz, 2H), 7.59 (t, J=8.0 Hz, 1H), 7.74 (t, J=8.0 Hz, 1H), 7.98 (d, J=8.0 Hz, 1H), 8.05 (s, 1H), 8.11 (d, J=8.4 Hz, 2H), 8.12 (d, J=8.0 Hz, 1H).

MS(FAB) m/z 390 (M+H)*.

Free compound:

$^1$H-NMR (400 MHz, CDCl$_3$); δ (ppm) 1.18 (t, J=7.2 Hz, 3H), 1.61–1.77 (m, 4H), 2.56 (q, J=7.2 Hz, 2H), 2.71 (t, J=7.2 Hz, 2H), 2.76 (br, 4H), 3.59 (br, 4H), 3.68 (t, J=6.4 Hz, 2H), 7.28 (d, J=8.4 Hz, 2H), 7.45 (dt, J=8.0, 1.2 Hz, 1H), 7.58 (dt, J=8.0, 1.2 Hz, 1H), 7.67 (s, 1H), 7.78 (d, J=8.0 Hz, 1H), 8.07 (d, J=8.0 Hz, 1H), 8.09 (d, J=8.4 Hz, 2H).

Example 24

Synthesis of 3-[4-(1,3-dihydroxypropyl)phenyl]-1-(4-ethylpiperazin-1-yl)isoquinoline hydrochloride

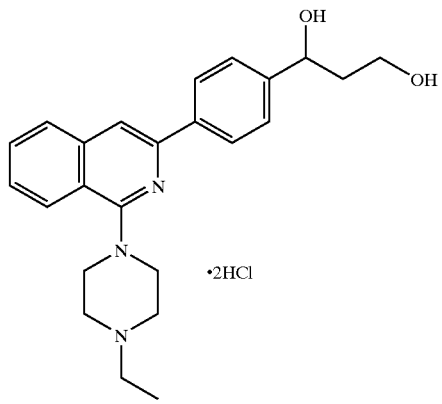

In the same manners as in Examples 161-2 and then 20, an oil was obtained from 1-bromo-4-(1,3-isopropylidenepropyl)benzene (2.21 g) and 3-bromo-1-(4-ethylpiperazin-1-yl)isoquinoline (700 mg). Tetrahydrofuran (15 ml) and 1N hydrochloric acid (2 ml) were added thereto, and the resulting mixture was reacted at room temperature for 3 hr. The reaction solution was basified with a 1N aqueous solution of sodium hydroxide and extracted with ethyl acetate. The resulting organic layer was washed with water, dried and concentrated. The resulting residue was purified by silica gel column chromatography, to give an oil. It was converted into a hydrochloride in a conventional manner, to give the hydrochloride of the title compound as yellow crystals (387 mg, yield; 44%).

Hydrochloride:

m.p.; 145–147° C.

$^1$H-NMR (400 MHz, DMSO-$d_6$); δ (ppm) 1.33 (t, J=7.2 Hz, 3H), 1.70–1.84 (m, 2H), 3.18–3.26 (m, 2H), 3.32–3.39 (m, 2H), 3.45–3.58 (m, 4H), 3.62 (d, J=6.8 Hz, 2H), 4.00 (d, J=13.2 Hz, 2H), 4.72–4.75 (m, 1H), 7.46 (d, J=8.4 Hz, 2H), 7.61 (dt, J=8.0, 1.2 Hz, 1H), 7.74 (dt, J=8.0, 1.2 Hz, 1H), 7.99 (d, J=8.0 Hz, 1H), 8.07 (s, 1H), 8.12 (d, J=8.0 Hz, 1H), 8.15 (d, J=8.4 Hz, 2H).

MS(FAB) m/z 392 (M+H)*.

Free compound:

$^1$H-NMR (400 MHz, DMSO-$d_6$); δ (ppm) 1.07 (t, J=7.2 Hz, 3H), 1.70–1.90 (m, 2H), 2.45 (q, J=7.2 Hz, 2H), 2.67 (br, 4H), 3.35–3.60 (m, 2H), 3.44 (br, 4H), 4.61 (t, J=4.8 Hz, 1H), 4.73–4.75 (m, 1H), 5.20 (d, J=4.8 Hz, 1H), 7.44 (d, J=8.4 Hz, 2H), 7.55 (t, J=8.0 Hz, 1H), 7.69 (t, J=8.0 Hz, 1H), 7.93 (d, J=8.0 Hz, 1H), 7.95 (s, 1H), 8.05 (d, J=8.0 Hz, 1H), 8.14 (d, J=8.4 Hz, 2H).

Example 25

Synthesis of 3-[4-(1,3-dihydroxy-3-methylbutyl)phenyl]-1-(4-ethylpiperazin-1-yl)isoquinoline

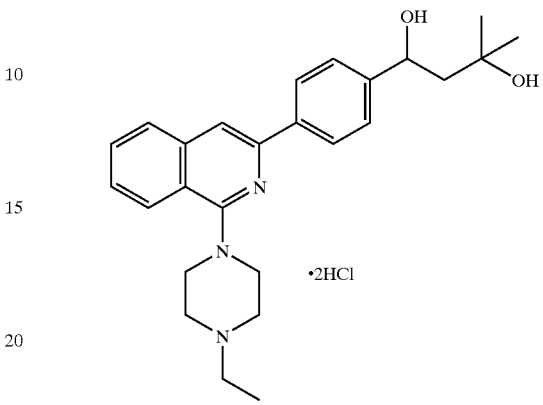

In the same manners as in Examples 161-2 and then 20, an oil was obtained from 1-bromo-4-(1,3-isopropylidene-3-methyl-butyl)benzene (1.87 g) and 3-bromo-1-(4-ethylpiperazin-1-yl)isoquinoline (413 mg). Tetrahydrofuran (10 ml) and a 1N aqueous solution of hydrochloric acid (0.5 ml) were added thereto, and the mixture was reacted at room temperature for 3 hr. The reaction solution was basified with a 1N aqueous solution of sodium hydroxide and extracted with ethyl acetate. The resulting organic layer was washed with water, dried and concentrated. The resulting residue was purified by silica gel column chromatography, to give an oil. The oil was converted into a hydrochloride in a conventional manner, to give the hydrochloride of the title compound as yellow crystals (289 mg, yield; 69%).

Hydrochloride:

m.p.; 190–192° C.

$^1$H-NMR (400 MHz, DMSO-$d_6$); δ (ppm) 1.19 (s, 3H), 1.26 (s, 3H), 1.33 (t, J=7.2 Hz, 3H), 3.22–3.26 (m, 2H), 3.37 (br, 2H), 3.50 (t, J=13.6 Hz, 2H), 3.63 (d, J=7.2 Hz, 2H), 4.00 (d, J=12.8 Hz, 2H), 4.59 (br, 2H), 4.94 (d, J=7.2 Hz, 1H), 7.47 (d, J=8.0 Hz, 2H), 7.60 (t, J=8.0 Hz, 1H), 7.74 (t, J=8.0 Hz, 1H), 7.90 (d, J=8.0 Hz, 1H), 8.07–8.16 (m, 4H).

MS(FAB) m/z 420 (M+H)*.

Free compound:

$^1$H-NMR (400 MHz, DMSO-$d_6$); δ (ppm) 1.08 (t, J=7.2 Hz, 3H), 1.19 (s, 3H), 1.26 (s, 3H), 1.65–1.80 (m, 2H), 2.65 (q, J=7.2 Hz, 2H), 2.67 (br, 4H), 3.44 (br, 4H), 4.74 (s, 1H), 4.91–4.93 (m, 1H), 5.41 (d, J=3.2 Hz, 1H), 7.44 (d, J=8.4 Hz, 2H), 7.55 (d, J=8.0 Hz, 1H), 7.69 (dt, J=8.0 Hz, 1H), 7.93 (d, J=8.0 Hz, 1H), 7.95 (s, 1H), 8.05 (d, J=8.0 Hz, 1H), 8.13 (d, J=8.4 Hz, 2H).

Example 26

Synthesis of 3-[4-(3-hydroxy-1-methoxybutyl)phenyl]-1-(4-ethylpiperazin-1-yl)isoquinoline

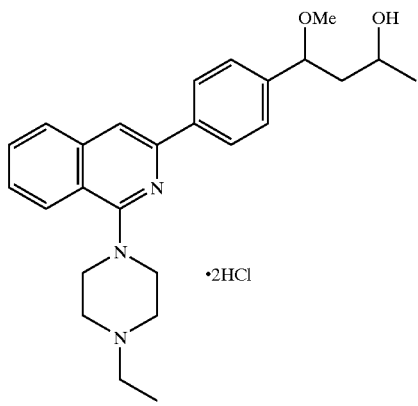

In the same manners as in Examples 161-2 and then 20, an oil was obtained from 1-bromo-4-(3-hydroxy-1-methoxybutyl)benzene (1.59 g) and 3-bromo-1-(4-ethylpiperazin-1-yl)isoquinoline (957 mg). Methanol (10 ml) and a 1N aqueous solution of sodium hydroxide (1 ml) were added thereto, and then the resulting mixture was refluxed for 3 hr. The reaction solution was partitioned between ethyl acetate and water, and the resulting organic layer was washed with water, dried and concentrated. The resulting residue was purified by silica gel column chromatography, to give an oil. The oil was converted into a hydrochloride in a conventional manner, to give the hydrochloride of the title compound as yellow crystals (196 mg, yield; 20%).

Hydrochloride:

m.p.; 171–174° C.

$^1$H-NMR (400 MHz, DMSO-$d_6$); δ (ppm) 1.06 (t, J=6.4 Hz, 3H), 1.33 (t, J=7.2 Hz, 3H), 1.52–1.60 (m, 1H), 1.91–1.98 (m, 1H), 3.12 (s, 3H), 3.21–3.26 (m, 2H), 3.34–3.39 (m, 2H), 3.39–3.51 (m, 4H), 3.63 (d, J=12.0 Hz, 2H), 4.01 (d, J=13.6 Hz, 2H), 4.35 (t, J=6.4 Hz, 2H), 7.43 (d, J=8.0 Hz, 2H), 7.62 (t, J=8.0 Hz, 1H), 7.75 (t, J=8.0 Hz, 1H), 7.99 (d, J=8.0 Hz, 1H), 8.09 (s, 1H), 8.12 (d, J=8.0 Hz, 1H), 8.18 (d, J=8.0 Hz, 2H).

MS(FAB) m/z 420 (M+H)*.

Free compound:

$^1$H-NMR (400 MHz, CDCl$_3$); δ (ppm) 1.18 (t, J=7.2 Hz, 3H), 1.71–1.76 (m, 1H), 1.92–2.00 (m, 1H), 2.56 (q, J=7.2 Hz, 2H), 2.76 (br, 4H), 3.27 (s, 3H), 3.60 (br, 4H), 3.74 (br, 1H), 4.06–4.10 (m, 2H), 4.45 (dd, J=10.0, 3.2 Hz, 1H), 7.40 (d, J=8.4 Hz, 2H), 7.47 (ddd, J=8.4, 8.0, 1.2 Hz, 1H), 7.59 (ddd, J=8.4, 8.0, 1.2 Hz, 1H), 7.70 (s, 1H), 7.80 (d, J=8.0 Hz, 1H), 8.08 (d, J=8.4 Hz, 1H), 8.17 (dd, J=8.4 Hz, 2H).

Example 27

Synthesis of 1(1-ethylpiperazin-4-yl)-3-[4-(3-hydroxy-1-fluoropropyl)phenyl]isoquinoline (27-1) Ethyl 3-(4-Bromophenyl)-3-hydroxypropionate

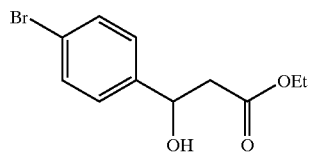

Ethyl acetate (5.8 ml) was dissolved in tetrahydrofuran (80 ml), to which was then added 1.5M lithium diisoprypylamide/cyclohexane solution (43 ml) in nitrogen atmosphere at −70° C., and then the mixture was stirred for 15 min. 4-Bromobenzaldehyde (10.151 g)/tetrahydrofuran (10 ml) solution was added to the reaction mixture, which was then stirred for 30 min. A saturated aqueous solution of ammonium chloride was added thereto, and then it was extracted with in ethyl acetate. The resulting organic layer was washed with water, dried (over MgSO$_4$) and evaporated. The resulting residue was purified by (NH) silica gel column chromatography (ethyl acetate/hexane system), to give the title compound as a yellow oil (11.906 g, yield; 80%).

$^1$H-NMR (400 MHz, CDCl$_3$); δ (ppm) 1.27 (3H, t, J=7.2 Hz), 2.68–2.71 (2H, m), 3.38 (1H, d, J=3.6 Hz), 4.19 (2H, q, J=7.2 Hz), 5.07–5.12 (1H, m), 7.26 (2H, d, J=8.8 Hz), 7.48 (2H, d, J=8.8 Hz).

(27-2) 3-(4-Bromophenyl)-3-fluoropropyl acetate

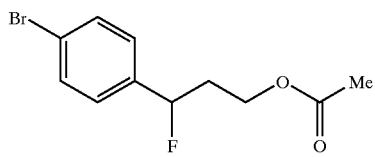

A product obtained from ethyl 3-(4-bromophenyl)-3-hydroxypropionate (7.433 g) and diethylaminosulfur trifluoride (237 ml) in the same treatment as in Example 132 was dissolved in tetrahydrofuran (60 ml). Lithium aluminium hydride (1.005 g) was added thereto under ice-cooling, and then the mixture was stirred for 20 min. To the reaction mixture were sequentially added water (1 ml), 5N sodium hydroxide (1 ml) and water (3 ml), the resulting insoluble matters were filtered off through Celite, and the resulting filtrate was evaporated. The resulting residue was dissolved in pyridine (30 ml), acetic anhydride (3.5 ml) and dimethylaminopyridine (182 mg) were added thereto, and then the mixture was stirred at room temperature for 30 min. The reaction solution was evaporated, and the resulting residue was partitioned between ethyl acetate and water. The resulting organic layer was washed with water, dried (over MgSO$_4$) and evaporated. The resulting residue was purified by silica gel column chromatography (ethyl acetate/hexane system), to give 4.542 g of the title compound as a pale yellow oil (yield; 61%).

$^1$H-NMR (400 MHz, CDCl$_3$); δ (ppm) 2.06 (3H, s), 2.06–2.31 (2H, m), 4.11–4.29 (2H, m), 5.54 (1H, ddd, J=47.6 Hz, 8.8 Hz, 4 Hz), 7.22 (2H, d, J=8.8 Hz), 7.52 (2H, d, J=8.8 Hz).

(27-3) 1-(1-Ethylpiperazin-4-yl)-3-[4-(3-hydroxy-1-fluoropropyl)phenyl]isoquinoline

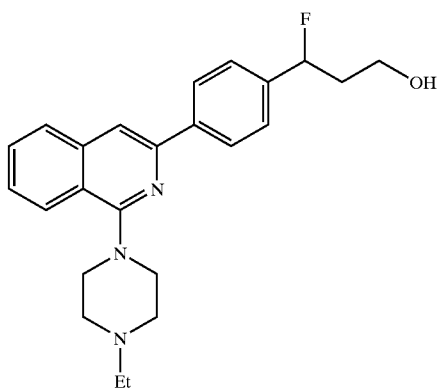

Acetate 3-(4-bromophenyl)-3-fluoropropane ester (833 mg) and bis(tributyltin) (2 ml) were treated in the same manner as in Example 161-2, and then treated with 1-(1-ethylpiperazin-4-yl)-3-bromoisoquinoline (321 mg) in the same manner as in Example 300, to give the hydrochloride of the title compound as hygroscopic yellow crystals (187 mg, yield; 40%).

Hydrochloride:

m.p.; 141–146° C.

$^1$H-NMR (400 MHz, DMSO-d$_6$); δ (ppm) 1.31 (3H, t, J=7.2 Hz), 1.70–2.20 (2H, m), 3.21 (1H, q, J=7.2 Hz), 3.22 (1H, q, J=7.2 Hz), 3.32 (1H, t, J=10.4 Hz), 3.35 (1H, t, J=10.4 Hz), 3.43–3.53 (4H, m), 3.61 (2H, d, J=10.4 Hz), 4.08 (2H, d, J=13.2 Hz), 5.70 (1H, ddd, J=48 Hz, 9.2 Hz, 4 Hz), 7.39–7.76 (4H, m), 7.95–8.24 (5H, m), 10.75–10.85 (1H, br-s).

ESI-Mass; 394 (MH*).

Example 28

Synthesis of 1-(4-ethylpiperazin-1-yl)-3-[4-(4-hydroxymethyl-3-fluoro)phenyl]isoquinoline hydrochloride (28-1) 1,3-Dibromoisoquinoline

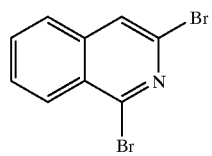

1,4-Dioxane (84 ml) was added to phosphorus oxybromide (23.5 g), and dissolved at room temperature. To the mixture was added homophthalimide (6.0 g) little by little, and then heated under reflux for 35 min. The reaction solution was cooled, dissolved in chloroform (300 ml) and methanol (50 ml), and evaporated. The resulting crystals were collected by filtration, washed with 2-propanol, dried at 50° C. for 1 hr, to give the title compound as pale brown crystals (6.1 g, yield; 57%).

(28-2) 3-Bromo-1-(4-ethylpiperazin-1-yl)isoquinoline

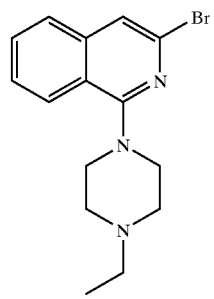

1,3-Dibromoisoquinoline (2.70 g), N-ethylpiperazine (1.16 g) and potassium carbonate (3.50 g) were reacted in DMF (30 ml) at 80° C. for 5 hr. The reaction solution was evaporated, and then partitioned between ethyl acetate and water. The resulting organic layer was washed with water, dried and evaporated. The resulting residue was purified by NH silica gel column chromatography (ethyl acetate/n-hexane system), to give the title compound (2.21 g) as a pale yellow oil.

$^1$H-NMR (400 MHz, CDCl$_3$); δ (ppm) 1.17 (t, J=7.2 Hz, 3H), 2.54 (q, J=7.2 Hz, 2H), 2.66–2.73 (m, 4H), 3.52–3.58 (m, 4H), 7.40 (s, 1H), 7.45 (dt, J=8.0, 2.0 Hz, 1H), 7.58 (dt, J=8.0, 2.0 Hz, 1H), 7.62 (dd, J=8.0, 2.0 Hz, 1H), 7.98 (dd, J=8.0, 2.0 Hz, 1H).

(28-3) 1-(4-Ethylpiperazin-1-yl)-3-[4-(3-fluoro-4-formyl)phenyl]isoquinoline

2-Fluoro-4-tributylstannylbenzaldehyde (2.20 g) produced by heating 4-bromo-2-fluorobenzaldehyde (5.0 g) and hexabutylditin (14.3 g) in xylene (50 ml) in the presence of tetrakistriphenylphosphine (0.38 g) was reacted with 3-bromo-1-(4-ethylpiperazin-1-yl)isoquinoline (1.20 g) obtained in (28-2) in the presence of tetrakistriphenylphosphine (0.3 g) in xylene in nitrogen atmosphere for 4 hr. After cooling, the reaction solution was extracted with a 2N aqueous solution of hydrochloric acid, basified with a 5N aqueous solution of sodium hydroxide, and then reverse-extracted with ethyl acetate. The resulting organic layer was washed with water and brine, dried and concentrated. The resulting residue was purified by silica gel column chromatography (methylene chloride/methanol system), to give 0.92 g of the title compound.

(28-4) 1-(4-Ethylpiperazin-1-yl)-3-[4-(4-hydroxymethyl-3-fluoro)phenyl]isoquinoline hydrochloride

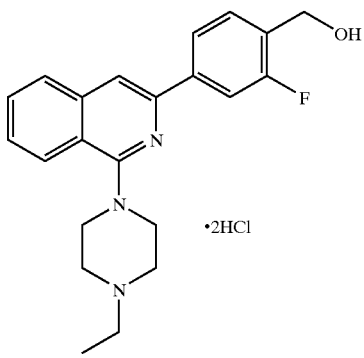

Sodium borohydride (0.10 g) was added to a solution of 1-(4-ethylpiperazin-1-yl)-3-[4-(3-fluoro-4-formyl)phenyl]isoquinoline (0.25 g) in methanol (20 ml) at 0° C. After stirring the reaction solution for 30 min, it was concentrated. To the resulting residue was added water, which was then extracted with methylene chloride, dried and concentrated. The resulting residue was purified by silica gel column chromatography (methylene chloride/methanol system), to give the free compound of the title compound as a pale yellow oil. The oil was converted into a hydrochloride in a conventional manner, to give 0.15 g of the title compound as a yellow powder.
Hydrochloride:
m.p.; 228° C. (decomp.)
$^1$H-NMR (400 MHz, DMSO-$d_6$); δ (ppm) 1.34 (t, J=7.2 Hz, 3H), 3.19–3.28 (m, 2H), 3.35 (br-q, 2H), 3.49–3.67 (m, 4H), 4.01 (br-d, 2H), 4.62 (s, 2H), 7.57–7.67 (m, 1H), 7.76 (br-t, 1H), 7.94–8.01 (m, 2H), 8.05 (dd, J=8.0, 1.6 Hz, 1H), 8.13 (d, J=8.4 Hz, 1H), 8.16 (s, 1H).
MS(FAB) m/z 366 (M+H)*.

Example 29

Synthesis of 1-(4-ethylpiperazin-1-yl)-3-[3-fluoro-4-(1-hydroxypropyl)phenyl]isoquinoline hydrochloride

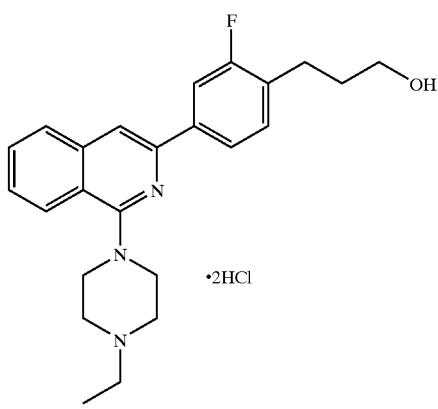

Ethyl 2-fluoro-4-tributylstannylcinnamate (1.918 g) and 3-bromo-1-(4-ethylpiperazin-1-yl)isoquinoline (1.090 g) were reacted in the presence of tetrakistriphenylphosphine (0.153 g) in xylene (20 ml) in nitrogen atmosphere for 2 hr. After cooling, the reaction solution was filtered. The resulting filtrate was extracted with a 5N aqueous solution of hydrochloric acid. The resulting aqueous layer was basified with a 5N aqueous solution of sodium hydroxide, and then extracted with ethyl acetate. The resulting organic layer was washed with water and brine, dried and concentrated. The resulting 1-(4-ethylpiperazin-1-yl)-3-[3-fluoro-4-(2-ethoxycarbonylethen-1-yl)phenyl]isoquinoline (1.222 g) was dissolved in tetrahydrofuran (10 ml), which was then added dropwise into a suspension of lithium aluminium hydride (0.211 g). The reaction solution was heated under reflux for 8 hr, and then cooled. Then, water, an aqueous solution of sodium hydroxide and water were added thereto in this order, and then stirred at room temperature for 1 hr. The resulting precipitates were filtered off, followed by washing with ethyl acetate. The filtrate was concentrated, and the resulting residue was purified by silica gel column chromatography (methylene chloride/methanol system), to give 0.226 g of 1-(4-ethylpiperazin-1-yl)-3-[3-fluoro-4-(1-hydroxypropyl)phenyl]isoquinoline as a pale yellow oil.
Free compound:
$^1$H-NMR (400 MHz, CDCl$_3$); δ (ppm) 1.18 (t, J=7.2 Hz, 3H), 1.90–1.97 (m, 2H), 2.56 (q, J=7.2 Hz, 2H), 2.76 (br-t, 4H), 2.80 (t, J=7.4 Hz, 2H), 3.59 (br-t, 4H), 3.72 (t, J=7.4 Hz, 2H), 7.16–7.19 (m, 1H), 7.47 (br-t, 1H), 7.60 (br-t, 1H), 7.66 (s, 1H), 7.79 (d, J=8.4 Hz, 1H), 7.85–7.89 (m, 2H), 8.08 (d, J=8.0 Hz, 1H).
The free compound was converted into a hydrochloride in a conventional manner, to give the title compound as a yellow powder.
Hydrochloride:
m.p.; 126–127° C. (decomp.)
$^1$H-NMR (400 MHz, DMSO-$d_6$); δ (ppm) 1.32 (t, J=7.2 Hz, 3H), 1.71–1.78 (m, 2H), 2.70 (br-t, 2H), 3.21–3.28 (m, 2H), 3.31–3.40 (m, 2H), 3.46 (t, J=6.4 Hz, 2H), 3.48 (br-t, 2H), 3.64 (br-d, 2H), 4.02 (br-d, 2H), 7.42 (dd, J=8.2, 8.2 Hz, 1H), 7.63 (br-t, 1H), 7.76 (br-t, 1H), 7.93–8.00 (m, 3H), 8.12–8.14 (m, 2H).
MS(FAB) m/z 394 (M+H)*.

Example 30

Synthesis of 3-[3-chloro-4-(3-hydroxypropyl)phenyl]-1-(4-ethylpiperazin-1-yl)isoquinoline hydrochloride

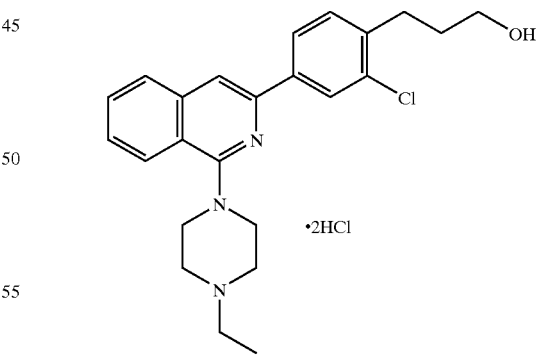

In the same manners as in Examples 161-2 and then 20, an oil was obtained from 1-bromo-3-chloro-4-ethylpropionitebenzene (1.92 g) and 3-bromo-1-(4-ethylpiperazin-1-yl)isoquinoline (1.3 g). Under ice-cooling, tetrahydrofuran (20 ml) and lithium aluminium hydride (120 mg) were added to the oil, which was then reacted at room temperature for 1 hr. Thereafter, water (0.1 ml), a 5N aqueous solution of sodium hydroxide (0.1 ml) and water (0.3 ml) were added sequentially to the resulting reaction mixture, and the mixture was stirred at room temperature for 1 hr. The resulting residue was filtered, washed with ethyl acetate, and then purified by silica gel column chromatography, to give an oil. The oil was converted into a hydrochloride in a conventional manner, give the hydrochloride of the title compound as yellow crystals (900 mg, yield; 71%).

Hydrochloride:
m.p.; 123–124° C.
$^1$H-NMR (400 MHz, DMSO-d$_6$); δ (ppm) 1.33 (t, J=7.2 Hz, 3H), 1.72–1.82 (m, 2H), 2.79 (t, J=7.6 Hz, 2H), 3.20–3.28 (m, 2H), 3.32–3.40 (m, 2H), 3.48 (t, J=6.4 Hz, 4H), 3.65 (d, J=11.6 Hz, 2H), 4.00 (d, J=13.2 Hz, 2H), 7.47 (d, J=8.0 Hz, 1H), 7.63 (t, J=8.0 Hz, 1H), 7.76 (t, J=8.0 Hz, 1H), 7.99 (d, J=8.0 Hz, 1H), 8.11 (dd, J=8.0, 1.6 Hz, 1H), 8.13 (d, J=8.0 Hz, 1H), 8.16 (s, 1H), 8.22 (d, J=1.6 Hz, 1H).
MS(FAB) m/z 410 (M+H)*.

Free compound:
$^1$H-NMR (400 MHz, CDCl$_3$); δ (ppm) 1.67 (t, J=7.2 Hz, 3H), 1.90–1.97 (m, 2H), 2.55 (q, J=7.2 Hz, 2H), 2.76 (br, 4H), 2.88 (t, J=7.6 Hz, 2H), 3.58 (br, 4H), 3.72 (t, J=6.4 Hz, 2H), 7.32 (d, J=8.0 Hz, 1H), 7.47 (t, J=8.4 Hz, 1H), 7.59 (t, J=8.4 Hz, 1H), 7.65 (s, 1H), 7.78 (d, J=8.4 Hz, 1H), 7.96 (dd, J=8.0, 2.0 Hz, 1H), 8.07 (d, J=8.4 Hz, 1H), 8.16 (d, J=2.0 Hz, 1H).

Example 31

Synthesis of 3-[3-carboxamide-4-(3-hydroxypropyl) phenyl]-1-(4-ethylpiperazin-1-yl)isoquinoline

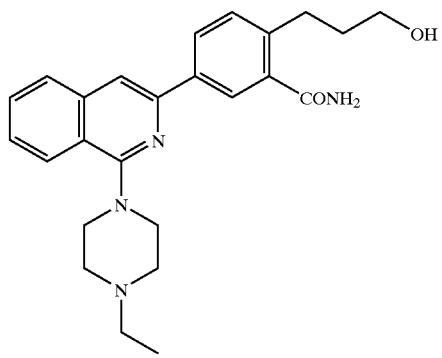

In the same manners as in Examples 161-2 and then 20, an yellow oil was obtained from 1-bromo-3-carboxamide-4-(3-acetoxypropyl)benzene (1.04 g) and 3-bromo-1-(4-ethylpiperazin-1-yl)isoquinoline (409 mg). Methanol (10 ml) and a 1N aqueous solution of sodium hydroxide solution (1 ml) were added to the oil, which was then reacted at room temperature overnight. The reaction solution was partitioned between ethyl acetate and water, and the resulting organic layer was washed with brine, dried and evaporated. Then, it was recrystallized from methanol/diethyl ether, to give the title compound as white crystals (125 mg, yield; 30%).

Free compound:
m.p.; 213–218° C. (decomp.)
$^1$H-NMR (400 MHz, DMSO-d$_6$); δ (ppm) 1.08 (t, J=7.2 Hz, 3H), 1.76 (tt, J=8.0, 7.6 Hz, 2H), 2.45 (q, J=7.2 Hz, 2H), 2.68 (br, 4H), 2.80 (t, J=8.0 Hz, 2H), 3.44 (br, 4H), 3.39–3.44 (m, 2H), 4.54 (t, J=5.2 Hz, 1H), 7.37 (d, J=8.0 Hz, 1H), 7.45 (s, 1H), 7.57 (t, J=8.4 Hz, 1H), 7.70 (t, J=8.4 Hz, 1H), 7.90 (s, 1H), 7.94 (d, J=8.4 Hz, 1H), 7.99 (s, 1H), 8.06 (d, J=8.4 Hz, 1H), 8.13 (s, 1H), 8.14 (dd, J=8.0, 2.0 Hz, 1H).
MS(FAB) m/z 419 (M+H)*.

Example 32

Synthesis of 3-[3-cyano-4-(3-hydroxypropyl) phenyl]-1-(4-ethylpiperazin-1-yl)isoquinoline hydrochloride

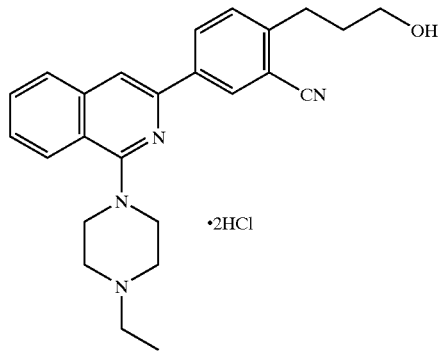

In the same manners as in Example 161-2 and then 20, a yellow oil was obtained from 5-bromo-3-carboxamide-4-(3-acetoxypropyl)benzene (1.15 g) and 3-bromo-1-(4-ethylpiperazin-1-yl)isoquinoline (442 mg). THF (5 ml), carbon tetrachloride (5 ml) and triphenylphosphine (588 mg) were added to the oil, and then it was reacted at 60° C. for 4 hr. The reaction solution was partitioned between ethyl acetate and water, and the resulting product was extracted with 2N hydrochloric acid. The resulting aqueous layer was basified with 2N sodium hydroxide, and then reverse-extracted with ethyl acetate. The resulting organic layer was washed with water, dried and evaporated. To the resulting residue were added methanol (10 ml) and a 1N aqueous solution of sodium hydroxide (1 ml), and the mixture was reacted at 50° C. for 30 min. The reaction solution was partitioned between ethyl acetate and water. The resulting organic layer was washed with brine, dried and evaporated. Thereafter, it was purified by NH-silica gel column chromatography (ethyl acetate/hexane system), to give a yellow oil (191 mg, yield; 45%). The oil was converted into a hydrochloride in a conventional manner, to give the hydrochloride of the title compound as white crystals.

Hydrochloride:
$^1$H-NMR (400 MHz, DMSO-d$_6$); δ (ppm) 1.35 (t, J=7.2 Hz, 2H), 1.78–1.85 (m, 2H), 2.89 (t, J=8.0 Hz, 2H), 3.20–3.25 (m, 2H), 3.33–3.40 (m, 2H), 3.49 (t, J=6.4 Hz, 2H), 3.55–3.65 (m, 4H), 4.02 (d, J=13.6 Hz, 2H), 7.61 (d, J=8.4 Hz, 1H), 7.65 (t, J=8.4 Hz, 1H), 7.78 (t, J=8.4 Hz, 1H), 7.99 (d, J=8.4 Hz, 1H), 8.14 (d, J=8.4 Hz, 1H), 8.22 (s, 1H), 8.45 (dd, J=8.4, 2.0 Hz, 1H), 8.54 (d, J=2.0 Hz, 1H).
MS(FAB) m/z 401 (M+H)*.

Free compound:
$^1$H-NMR (400 MHz, CDCl$_3$); δ (ppm) 1.20 (t, J=7.2 Hz, 3H), 1.96–2.05 (m, 2H), 2.59 (q, J=7.2 Hz, 2H), 2.79 (br, 4H), 3.01 (t, J=7.2 Hz, 2H), 3.61 (br, 4H), 3.75 (t, J=6.4 Hz, 2H), 7.44 (d, J=8.0 Hz, 1H), 7.51 (ddd, J=8.4, 8.0, 1.2 Hz, 1H), 7.62 (ddd, J=8.4, 8.0, 1.2 Hz, 1H), 7.68 (s, 1H), 7.81 (d, J=8.0 Hz, 1H), 8.08 (d, J=8.4 Hz, 1H), 8.29 (dd, J=8.0, 1.6 Hz, 1H), 8.43 (d, J=1.6 Hz, 1H).

Example 33

Synthesis of 1-(4-ethylpiperazin-1-yl)-3-[4-(3-hydroxypropyl)-3-methoxyphenyl]isoquinoline hydrochloride (33-1) 1-(4-Ethylpiperazin-1-yl)-3-[4-(3-acetoxypropyl)-3-methoxyphenyl]isoquinoline

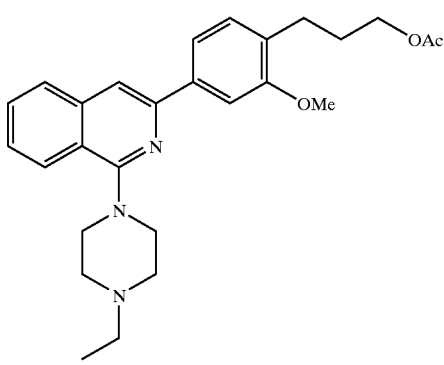

2-(3-Acetoxypropyl)-5-tributylstannylanisole (0.92 g) and 3-bromo-1-((4-ethylpiperazin-1-yl)isoquinoline (0.37 g) were reacted in the presence of tetrakistriphenylphosphine (0.3 g) in xylene in nitrogen atmosphere for 4 hr. After cooling, the reaction solution was filtered and extracted with ethyl acetate. The resulting organic layer was washed with water and brine, dried and concentrated. The resulting residue was purified by silica gel column chromatography (methylene chloride/methanol system), to give 0.28 g of the title compound.

(33-2) 1-(4-Ethylpiperazin-1-yl)-3-[4-(3-hydroxypropyl)-3-methoxyphenyl]isoquinoline hydrochloride

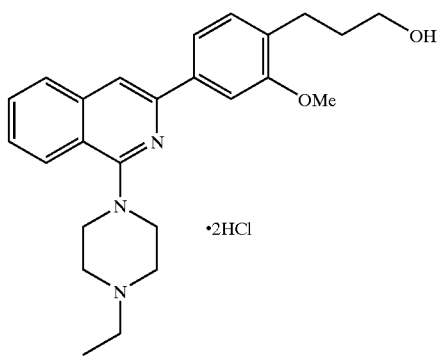

1-(4-Ethylpiperazin-1-yl)-3-[4-(3-acetoxypropyl)-3-methoxyphenyl]isoquinoline was dissolved in methanol (10 ml), a 2N aqueous solution of sodium hydroxide (2 ml) was added thereto, and then the mixture was reacted at 50° C. for 2 hr. The reaction solution was concentrated and extracted with ethyl acetate. The resulting organic layer was washed with water and brine, dried and concentrated. The resulting residue was purified by silica gel column chromatography (methylene chloride/methanol system), which was then converted into a hydrochloride in a conventional manner to give 0.18 g of the title compound as a yellow powder.

Hydrochloride:

m.p.; 123–124° C.

$^1$H-NMR (400 MHz, DMSO-$d_6$); δ (ppm) 1.32 (t, J=7.2 Hz, 3H), 1.66–1.76 (m, 2H), 2.59–2.68 (m, 2H), 3.20–3.29 (m, 2H), 3.36 (br-q, 2H), 3.41–3.55 (m, 4H), 3.64 (br-d, 2H), 3.93 (s, 3H), 4.02 (br-d, 2H), 7.26 (d, J=8.4 Hz, 1H), 7.61 (br-t, 1H), 7.76 (br-t, 1H), 7.70–7.78 (m, 2H), 7.99 (d, J=8.4 Hz, 1H), 8.09–8.14 (m, 2H).

MS(FAB) m/z 406 (M+H)*.

Free compound:

$^1$H-NMR (400 MHz, CDCl$_3$); δ (ppm) 1.17 (t, J=7.2 Hz, 3H), 1.84–1.92 (m, 2H), 2.54 (q, J=7.2 Hz, 3H), 2.73–2.81 (m, 6H), 3.58 (m, 4H), 3.63 (t, J=7.6 Hz, 3H), 3.96 (s, 3H), 7.23 (d, J=6.4 Hz, 1H), 7.45 (t, J=7.6 Hz, 1H), 7.57 (t, J=7.6 Hz, 1H), 7.65 (br-d, 1H), 7.68 (s, 1H), 7.77–7.82 (m, 2H), 8.07 (d, J=8.0 Hz, 1H).

Example 34

Synthesis of 3-[3-(3-hydroxypropyl)-4-methoxyphenyl]-1-(4-ethylpiperazin-1-yl) isoquinoline hydrochloride

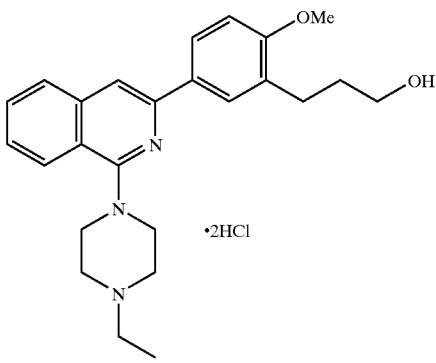

In the same manners as in Examples 161-2, and then 20, an oil was obtained from 1-bromo-3-(3-acetoxypropyl)-4-methoxybenzene (2.57 g) and 3-bromo-1-(4-ethylpiperazin-1-yl)isoquinoline (1.7 g). Methanol (10 ml) and a 1N aqueous solution of sodium hydroxide (2 ml) were added to the resulting oil, which was then heated under reflux for 3 hr. After cooling the reaction mixture, it was partitioned between ethyl acetate and water. The resulting organic layer was washed with water, dried and concentrated. The resulting residue was purified by silica gel column chromatography, to give an oil. Then, the oil was converted into a hydrochloride in a conventional manner, to give the hydrochloride of the title compound as yellow crystals (1.2 g, yield; 74%).

Hydrochloride:

m.p.; 157–160° C.

$^1$H-NMR (400 MHz, DMSO-$d_6$); δ (ppm) 1.33 (t, J=7.2 Hz, 3H), 1.72–1.79 (m, 2H), 2.67 (t, J=7.2 Hz, 2H), 3.18–3.26 (m, 2H), 3.32–3.39 (m, 2H), 3.47 (t, J=6.4 Hz, 2H), 3.53 (t, J=12.8 Hz, 2H), 3.64 (d, J=11.2 Hz, 2H), 3.86 (s, 3H), 3.99 (d, J=13.2 Hz, 2H), 7.08 (d, J=8.4 Hz, 1H), 7.57 (t, J=8.0 Hz, 1H), 7.72 (t, J=8.0 Hz, 1H), 7.95 (d, J=8.0 Hz, 1H), 7.96 (d, J=2.4 Hz, 1H), 7.99 (s, 1H), 8.04 (dd, J=8.4, 2.4 Hz, 1H), 8.09 (d, J=8.0 Hz, 1H).

MS(FAB) m/z 406 (M+H)*.

Free compound:

$^1$H-NMR (400 MHz, CDCl$_3$); δ (ppm) 1.18 (t, J=7.2 Hz, 3H), 1.93 (tt, J=7.2, 6.4 Hz, 2H), 2.56 (q, J=7.2 Hz, 2H), 2.77 (br, 4H), 2.82 (t, J=7.2 Hz, 2H), 3.58 (br, 4H), 3.66 (t, J=6.4 Hz, 2H), 3.90 (s, 3H), 6.96 (d, J=8.4 Hz, 1H), 7.43 (ddd, J=8.4, 8.0, 1.2 Hz, 1H), 7.57 (ddd, J=8.4, 8.0, 1.2 Hz, 1H), 7.62 (s, 1H), 7.77 (d, J=8.0 Hz, 1H), 7.96 (d, J=2.4 Hz, 1H), 8.03 (dd, J=8.4, 2.4 Hz, 1H), 8.06 (d, J=8.4 Hz, 1H).

Example 35

Synthesis of 3-[3-(4-hydroxybutyl)-4-methoxyphenyl]-1-(4-ethylpiperazin-1-yl)isoquinoline hydrochloride

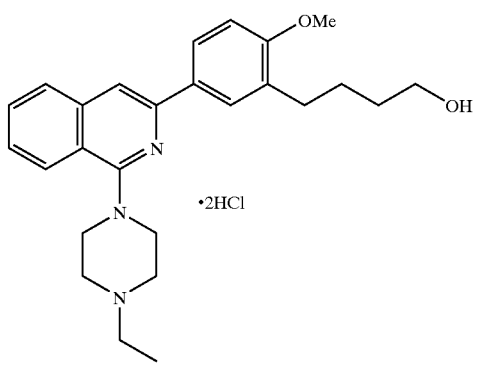

In the same manners as in Examples 161-2, and then 20, an oil was obtained from 1-bromo-3-(4-acetoxybutyl)-4-methoxybenzene (1.54 g) and 3-bromo-1-(4-ethylpiperazin-1-yl)isoquinoline (913 mg). Methanol (10 ml) and a 1N aqueous solution of sodium hydroxide (2 ml) were added to the oil, and then reacted at at room temperature for 2 hr. Then, the reaction solution was partitioned between ethyl acetate and water. The resulting organic layer was washed with water, dried and concentrated. The resulting residue was purified by silica gel column chromatography, to give an oil (805 mg, yield; 90%). The oil was converted into a hydrochloride in a conventional manner, to give the hydrochloride of the title compound as yellow crystals.

Hydrochloride:

m.p.; 128–132° C.

$^1$H-NMR (400 MHz, DMSO-d$_6$); δ (ppm) 1.31 (t, J=7.2 Hz, 3H), 1.42–1.52 (m, 2H), 1.56–1.64 (m, 2H), 2.63 (t, J=7.2 Hz, 2H), 3.16–3.24 (m, 2H), 3.28–3.38 (m, 2H), 3.41 (t, J=6.4 Hz, 2H), 3.52 (t, J=8.0 Hz, 2H), 3.62 (d, J=11.2 Hz, 1H), 3.83 (s, 3H), 3.97 (d, J=14.0 Hz, 1H), 7.06 (d, J=8.8 Hz, 1H), 7.75 (t, J=8.0 Hz, 1H), 7.70 (t, J=8.0 Hz, 1H), 7.94 (d, J=8.0 Hz, 1H), 7.94 (d, J=2.4 Hz, 1H), 7.97 (s, 1H), 8.02 (dd, J=8.8, 2.4 Hz, 1H), 8.07 (d, J=8.0 Hz, 1H).

MS(FAB) m/z 420 (M+H)*.

Free compound:

$^1$H-NMR (400 MHz, CDCl$_3$); δ (ppm) 1.18 (t, J=7.2 Hz, 3H), 1.67–1.74 (m, 4H), 2.56 (q, J=7.2 Hz, 2H), 2.72–2.77 (m, 2H), 2.76 (br, 4H), 3.58 (br, 4H), 3.68–3.71 (m, 2H), 3.87 (s, 3H), 6.93 (d, J=8.4 Hz, 1H), 7.42 (ddd, J=8.4, 8.0, 1.2 Hz, 1H), 7.56 (ddd, J=8.4, 8.0, 1.2 Hz, 1H), 7.61 (s, 1H), 7.76 (d, J=8.0 Hz, 1H), 7.93 (d, J=2.0 Hz, 1H), 8.00 (dd, J=8.4, 2.0 Hz, 1H), 8.05 (d, J=8.4 Hz, 1H).

Example 36

Synthesis of 1-(4-ethylpiperazin-1-yl)-3-[4-(2-hydroxyethoxy)phenyl]isoquinoline dihydrochloride

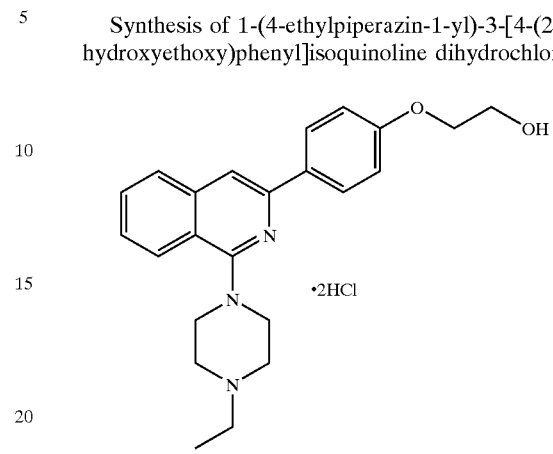

1-(4-Ethylpiperazin-1-yl)-3-(4-hydroxyphenyl)isoquinoline (1.0 g) obtained in Example 7 was dissolved in tetrahydrofuran (30 ml), followed by the addition of 60% sodium hydride (0.14 g). After the evolution of hydrogen ceased, 2-(t-butyl)dimethylsilyloxyethyl bromide (1.0 g) was added thereto, and the mixture was heated under reflux for 8 hr. The reaction solution was cooled to room temperature, and then it was partitioned between ethyl acetate and water. The resulting organic layer was washed with water, dried and evaporated. To the resulting residue was added a 2N aqueous solution of hydrochloric acid, which was then stirred at 50° C. for 30 min. The reaction solution was washed with ethyl acetate. The resulting aqueous layer was basified by adding 2N sodium hydroxide thereto, and extracted with ethyl acetate. The resulting organic layer was washed with water, dried and evaporated. The resulting residue was purified by silica gel column chromatography (methylene chloride/methanol system), to give the free compound of the title compound as a white powder. Then, the powder was converted into a hydrochloride in a conventional manner, to give 0.71 g of the title compound as a pale yellow powder.

Hydrochloride:

$^1$H-NMR (400 MHz, DMSO-d$_6$); δ (ppm) 1.33 (t, J=7.2 Hz, 3H), 3.18–3.28 (m, 2H), 3.40 (q, J=7.2 Hz, 2H), 3.50 (br-t, 2H), 3.62 (br-d, 2H), 3.97 (br-d, 2H), 6.90 (d, J=8.8 Hz, 2H), 7.55 (t, J=8.0 Hz, 1H), 7.71 (t, J=8.0 Hz, 1H), 7.93 (s, 2H), 7.91–7.96 (m, 1H), 8.04 (d, J=8.8 Hz, 2H), 8.08 (d, J=8.8 Hz, 2H), 10.92 (br-s, 1H).

Free compound:

m.p.; 127–129° C.

MS(FAB) m/z 378 (M+H)*.

Example 37

Synthesis of 3-[3,4-di(2-hydroxyethoxy)phenyl]-1-(4-ethylpiperazin-1-yl)isoquinoline hydrochloride

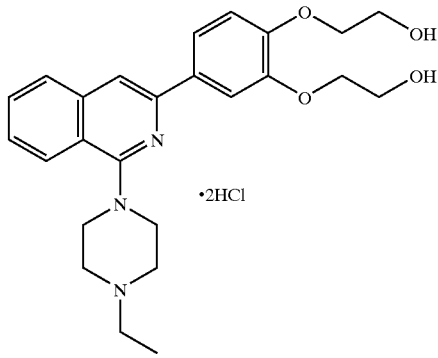

3-[3,4-Di(2-benzyloxyethoxy)phenyl]-1-(4-ethylpiperazin-1-yl)isoquinoline (2.23 g) was obtained from 3-[3,4-di(2-benzyloxyethoxy)phenyl]-1-chloroisoquinoline (1.97 g) obtained by the same treatment as in Example 20, potassium carbonate (2.5 g) and N-ethylpiperazine (5 ml). The resulting compound was converted into a hydrochloride, methanol (100 ml) and a palladium/carbon catalyst (50 mg) were added thereto, and then the mixture was reacted in hydrogen atmosphere at room temperature overnight. Subsequently, the reaction solution was filtered through Celite and evaporated. The resulting residue was basified by adding a 1N aqueous solution of sodium hydroxide thereto, and then it was extracted with ethyl acetate. The resulting organic layer was washed with brine, dried and evaporated. Then, the resulting residue was purified by silica gel column chromatography (ethyl acetate/hexane system), to give a yellow oil (686 mg, yield; 44%). The oil was converted into a hydrochloride in a conventional manner, to give the hydrochloride of the title compound as white crystals.

Hydrochloride:

m.p.; 130–132° C.

$^1$H-NMR (400 MHz, DMSO-$d_6$); δ (ppm) 1.33 (t, J=7.2 Hz, 3H), 3.20–3.28 (m, 2H), 3.32–3.40 (m, 2H), 3.51 (t, J=12.8 Hz, 2H), 3.63 (d, J=11.2 Hz, 2H), 3.74–3.78 (m, 4H), 4.00 (d, J=13.2 Hz, 2H), 4.07 (t, J=5.2 Hz, 2H), 4.14 (t, J=5.2 Hz, 2H), 7.11 (d, J=8.4 Hz, 1H), 7.58 (dt, J=8.0, 1.2 Hz, 1H), 7.73 (dt, J=8.0, 1.2 Hz, 1H), 7.76 (dd, J=8.4, 2.4 Hz, 1H), 7.81 (d, J=2.4 Hz, 1H), 7.96 (d, J=8.0 Hz, 1H), 8.04 (s, 1H), 8.09 (d, J=8.0 Hz, 1H).

MS(FAB) m/z 438 (M+H)*.

Free compound:

$^1$H-NMR (400 MHz, CDCl$_3$); δ (ppm) 1.19 (t, J=7.2 Hz, 3H), 2.57 (q, J=7.2 Hz, 2H), 2.78 (br, 4H), 3.58 (br, 4H), 3.97–4.01 (m, 4H), 4.18–4.20 (m, 2H), 4.26–4.27 (m, 2H), 7.06 (d, J=8.4 Hz, 1H), 7.47 (ddd, J=8.4, 8.0, 1.2 Hz, 1H), 7.59 (ddd, J=8.4, 8.0, 1.2 Hz, 1H), 7.63 (s, 1H), 7.78 (dd, J=8.4, 2.0 Hz, 1H), 7.79 (d, J=8.0 Hz, 1H), 7.91 (d, J=2.0 Hz, 1H), 8.08 (d, J=8.4 Hz, 1H).

Example 38

Synthesis of 3-[3,5-di(2-hydroxyethoxy)phenyl]-1-(4-ethylpiperazin-1-yl)isoquinoline hydrochloride

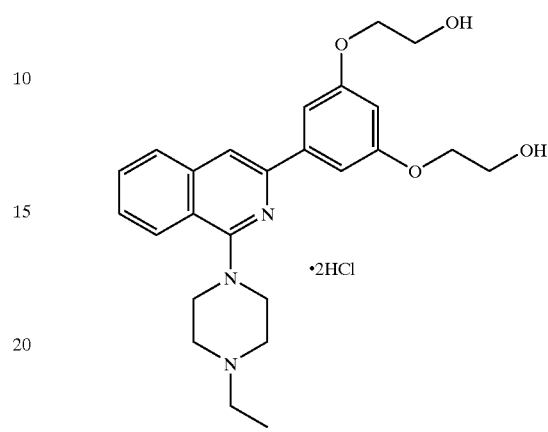

From 3-[3,5-di(2-benzyloxyethoxy)phenyl]-1-chloroisoquinoline (1.24 g) obtained by the same treatment as in Example 20, potassium carbonate (1.6 g) and N-ethylpiperazine (5 ml), 3-(3,3-dibenzyloxyethoxyphenyl)-1-(4-ethylpiperazin-1-yl)isoquinoline (1.70 g) was obtained. The resulting compound was then converted into a hydrochloride, followed by the treatment with a palladium/carbon catalyst (50 mg) added, in the same manner as in Example 18, to give the free compound of the title compound (510 mg, yield; 42%). The resulting free compound was then converted into a hydrochloride in a conventional manner, to give the hydrochloride of the title compound as yellow crystals.

Hydrochloride:

m.p.; 232–234° C.

$^1$H-NMR (400 MHz, DMSO-$d_6$); δ (ppm) 1.33 (t, J=7.2 Hz, 3H), 3.20–3.28 (m, 2H), 3.32–3.40 (m, 2H), 3.46–3.52 (m, 2H), 3.65 (d, J=11.6 Hz, 2H), 3.76 (t, J=5.2 Hz, 4H), 3.99 (d, J=13.2 Hz, 2H), 4.09 (t, J=5.2 Hz, 4H), 6.57 (t, J=2.0 Hz, 1H), 7.37 (s, 1H), 7.38 (s, 1H), 7.62 (t, J=8.0 Hz, 1H), 7.76 (t, J=8.0 Hz, 1H), 7.99 (d, J=8.0 Hz, 1H), 8.13 (d, J=8.0 Hz, 1H), 8.15 (s, 1H).

MS(FAB) m/z 438 (M+H)*.

Free compound:

$^1$H-NMR (400 MHz, CDCl$_3$); δ (ppm) 1.18 (t, J=7.2 Hz, 3H), 2.57 (q, J=7.2 Hz, 2H), 2.78 (br, 4H), 3.58 (br, 4H), 4.01 (t, J=4.8 Hz, 4H), 4.18 (t, J=4.8 Hz, 4H), 6.54 (t, J=2.0 Hz, 1H), 7.40 (d, J=2.0 Hz, 2H), 7.48 (ddd, J=8.4, 8.0, 1.2 Hz, 1H), 7.60 (ddd, J=8.4, 8.0, 1.2 Hz, 1H), 7.67 (s, 1H), 7.79 (d, J=8.0 Hz, 1H), 8.09 (d, J=8.4 Hz, 1H).

Example 39

Synthesis of 3-[3-chloro-4-(2-hydroxyethoxy)phenyl]-1-(4-ethylpiperazin-1-yl)isoquinoline hydrochloride

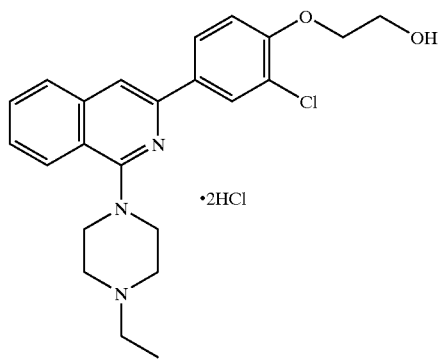

In the same manners as in Examples 161-2 and then 20, an oil was obtained from 1-bromo-3-chloro-4-(2-benzyloxyethoxy)benzene (2.52 g) and 3-bromo-1-(4-ethylpiperazin-1-yl)isoquinoline (1.3 g). Methanol (30 ml) and palladium/carbon catalyst (200 mg) were added to the oil, which was then reacted in hydrogen atmosphere at room temperature overnight. Thereafter, the reaction solution was filtered through Celite, and then evaporated. The resulting residue was basified by adding a 1N aqueous solution of sodium hydroxide thereto, which was then partitioned between ethyl acetate and water. The resulting organic layer was washed with water, dried and concentrated. The resulting residue was purified by silica gel column chromatography (hexane/ethyl acetate system), to give an oil (1.26 g, yield; 99%). The oil was then converted into a hydrochloride in a conventional manner, to give the hydrochloride of the title compound as yellow crystals.

Hydrochloride:

m.p.; 138–140° C.

$^1$H-NMR (400 MHz, DMSO-d$_6$); δ (ppm) 1.33 (t, J=7.2 Hz, 3H), 3.20–3.26 (m, 2H), 3.30–3.38 (m, 2H), 3.53 (t, J=13.6 Hz, 2H), 3.64 (d, J=11.6 Hz, 2H), 3.79 (t, J=4.8 Hz, 2H), 3.99 (d, J=13.6 Hz, 2H), 4.17 (t, J=4.8 Hz, 2H), 7.30 (d, J=8.8 Hz, 1H), 7.60 (t, J=8.0 Hz, 1H), 7.74 (t, J=8.0 Hz, 1H), 7.97 (d, J=8.0 Hz, 1H), 8.09 (s, 1H), 8.11 (d, J=8.0 Hz, 1H), 8.14 (dd, J=8.4, 2.4 Hz, 1H), 8.25 (d, J=2.4 Hz, 1H).

MS(FAB) m/z 412 (M+H)*.

Free compound:

$^1$H-NMR (400 MHz, CDCl$_3$); δ (ppm) 1.20 (t, J=7.2 Hz, 3H), 2.59 (q, J=7.2 Hz, 2H), 2.79 (br, 4H), 3.61 (br, 4H), 4.03 (t, J=4.4 Hz, 2H), 4.22 (t, J=4.4 Hz, 2H), 7.04 (d, J=8.8 Hz, 1H), 7.46 (ddd, J=8.4, 8.0, 1.2 Hz, 1H), 7.59 (ddd, J=8.4, 8.0, 1.2 Hz, 1H), 7.61 (s, 1H), 7.77 (d, J=8.0 Hz, 1H), 8.03 (dd, J=8.4, 2.4 Hz, 1H), 8.06 (d, J=8.4 Hz, 1H), 8.19 (d, J=2.4 Hz, 1H).

Example 40

Synthesis of 3-[3-methyl-4-(2-hydroxyethoxy)phenyl]-1-(4-ethylpiperazin-1-yl)isoquinoline hydrochloride

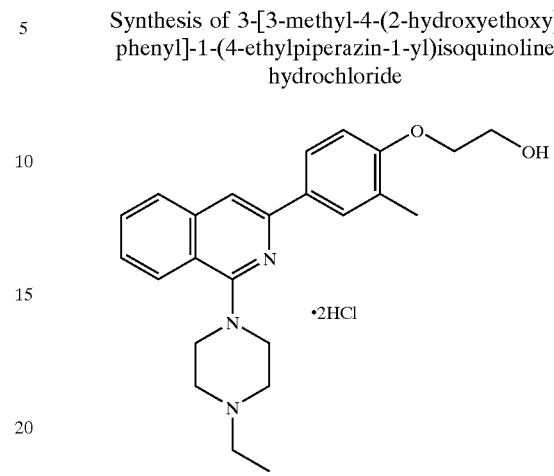

In the same manners as in Examples 161-2 and then 20, an oil was obtained from 1-bromo-3-methyl-4-(2-benzyloxyethoxy)benzene (1.48 g) and 3-bromo-1-(4-ethylpiperazin-1-yl)isoquinoline (495 mg). Methanol (30 ml) and palladium/carbon catalyst (100 mg) were added thereto, and the resulting mixture was reacted in hydrogen atmosphere at room temperature overnight. Thereafter, the reaction solution was filtered through Celite, and then evaporated. The resulting residue was basified by adding a 1N aqueous solution of sodium hydroxide thereto, and then partitioned between ethyl acetate and water. The resulting organic phase was washed with water, dried and concentrated. The resulting residue was purified by silica gel column chromatography (hexane/ethyl acetate system), to give an oil (200 mg, yield; 44%). The oil was then converted into a hydrochloride in a conventional manner, to give the hydrochloride of the title compound as yellow crystals.

Hydrochloride:

m.p.; 133–136° C.

$^1$H-NMR (400 MHz, DMSO-d$_6$); δ (ppm) 1.33 (t, J=7.2 Hz, 3H), 2.28 (s, 3H), 3.18–3.28 (m, 2H), 3.30–3.40 (m, 2H), 3.50 (t, J=12.0 Hz, 2H), 3.64 (d, J=10.8 Hz, 2H), 3.77 (t, J=4.8 Hz, 2H), 3.99 (d, J=14.0 Hz, 2H), 4.07 (t, J=5.2 Hz, 2H), 7.06 (d, J=8.8 Hz, 1H), 7.57 (t, J=8.0 Hz, 1H), 7.72 (t, J=8.0 Hz, 1H), 7.95 (d, J=8.0 Hz, 1H), 7.99–8.03 (m, 3H), 8.09 (d, J=8.0 Hz, 1H).

MS(FAB) m/z 392 (M+H)*.

Free compound:

$^1$H-NMR (400 MHz, CDCl$_3$); δ (ppm) 1.20 (t, J=7.2 Hz, 3H), 2.35 (s, 3H), 2.58 (br, 2H), 2.78 (br, 4H), 3.61 (br, 4H), 4.02 (t, J=4.4 Hz, 2H), 4.17 (t, J=4.4 Hz, 2H), 6.93 (d, J=8.4 Hz, 1H), 7.33 (t, J=8.4 Hz, 1H), 7.57 (t, J=8.4 Hz, 1H), 7.62 (s, 1H), 7.77 (d, J=8.4 Hz, 1H), 7.96 (br, 1H), 7.99 (dd, J=8.4, 2.0 Hz, 1H), 8.06 (d, J=8.4 Hz, 1H).

Example 41

Synthesis of 3-[3-isopropyl-4-(2-hydroxyethoxy)phenyl]-1-(4-ethylpiperazin-1-yl)isoquinoline hydrochloride

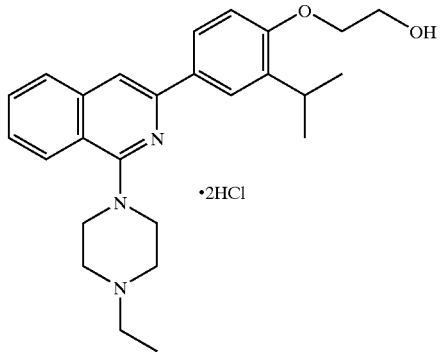

In the same manners as in Examples 161-2 and then 20, an oil was obtained form 1-bromo-3-isopropyl-4-(2-benzyloxyethoxy)benzene (3.45 g) and 3-bromo-1-(4-ethylpiperazin-1-yl)isoquinoline (1.0 g). Methanol (80 ml) and palladium/carbon catalyst (300 mg) were added thereto, which was then reacted in hydrogen atmosphere at room temperature overnight. After the reaction solution was filtered through Celite, it was evaporate. The resulting residue was basified by adding a 1N aqueous solution of sodium hydroxide thereto, which was then partitioned between ethyl acetate and water. The resulting organic layer was washed with water, dried and concentrated. The resulting residue was purified by silica gel column chromatography (hexane/ethyl acetate system), to give an oil (650 mg, yield; 40%). The oil was converted into a hydrochloride in a conventional manner, to give the hydrochloride of the title compound as yellow crystals.

Hydrochloride:

m.p.; 248–250° C. (decomp.)

$^1$H-NMR (400 MHz, DMSO-$d_6$); δ (ppm) 1.26 (s, 3H), 1.28 (s, 3H), 1.34 (t, J=7.2 Hz, 3H), 3.26–3.28 (m, 2H), 3.30–3.39 (m, 3H), 3.60 (t, J=8.8 Hz, 2H), 3.64 (d, J=11.2 Hz, 2H), 3.78 (t, J=4.8 Hz, 1H), 3.99 (d, J=13.2 Hz, 2H), 4.08 (t, J=4.8 Hz, 1H), 4.26–4.28 (m, 1H), 4.40–4.42 (m, 1H), 7.08 (t, J=8.0 Hz, 1H), 7.57 (t, J=8.0 Hz, 1H), 7.73 (t, J=8.0 Hz, 1H), 7.98 (d, J=8.0 Hz, 1H), 7.99–8.06 (m, 2H), 8.00 (s, 1H), 8.10 (d, J=8.0 Hz, 1H).

MS(FAB) m/z 420 (M+H)*.

Free compound:

$^1$H-NMR (400 MHz, CDCl$_3$); δ (ppm) 1.18 (t, J=7.2 Hz, 3H), 1.28 (d, J=7.2 Hz, 6H), 2.56 (q, J=7.2 Hz, 2H), 2.77 (br, 4H), 3.37–3.44 (m, 1H), 3.59 (br, 4H), 4.02 (t, J=4.4 Hz, 2H), 4.16 (t, J=4.4 Hz, 2H), 6.94 (d, J=8.4 Hz, 1H), 7.43 (ddd, J=8.4, 8.0, 1.2 Hz, 1H), 7.57 (ddd, J=8.4, 8.0, 1.2 Hz, 1H), 7.62 (s, 1H), 7.78 (d, J=8.0 Hz, 1H), 7.97 (dd, J=8.4, 2.4 Hz, 1H), 8.06 (d, J=8.4 Hz, 1H), 8.07 (d, J=2.4 Hz, 1H).

Example 42

Synthesis of 1-(4-ethylpiperazin-1-yl)-3-[4-(2-methoxyethoxy)phenyl]isoquinoline dihydrochloride

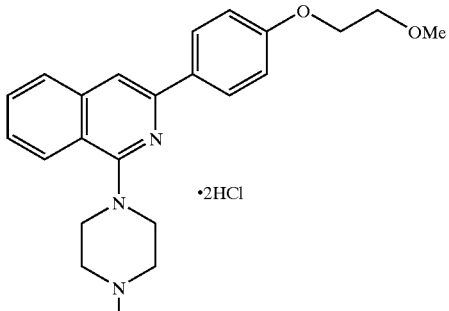

1-(4-Ethylpiperazin-1-yl)-3-(4-hydroxyphenyl)isoquinoline (0.420 g) obtained in Example 7 was dissolved in N,N-dimethylformamide (5 ml), followed by the addition of 60% sodium hydride (0.06 g). After the evolution of hydrogen was ceased, 2-methoxyethyl bromide (178 μl) was added thereto, and the mixture was stirred 50° C. for 3.5 hr. After the reaction solution was cooled to room temperature, it was partitioned between ethyl acetate and water. The resulting organic layer was washed with water, dried and evaporated. The resulting residue was purified by silica gel column chromatography (methylene chloride/methanol system), to give 1-(4-ethylpiperazin-1-yl)-3-[4-(2-methoxyethoxy)phenyl]isoquinoline as a white powder. The compound was converted into a hydrochloride in a conventional manner, to give 0.457 g of the title compound as a yellow powder.

Hydrochloride:

m.p.; 184.5–185° C. (decomp.)

$^1$H-NMR (400 MHz, DMSO-$d_6$); δ (ppm) 1.33 (t, J=7.2 Hz, 3H), 3.21–3.27 (m, 2H), 3.31–3.39 (2H, m), 3.33 (s, 3H), 3.49 (br-t, 2H), 3.63 (br-d, 2H), 3.69–3.71 (m, 2H), 3.99 (br-d, 2H), 4.16–4.18 (m, 2), 7.08 (d, J=8.8 Hz, 2H), 7.56 (br-t, 1H), 7.72 (br-t, 1H), 7.96 (b, J=8.0 Hz, 1H), 8.00 (s, 1H), 8.10 (d, J=8.4 Hz, 1H), 8.15 (d, J=7.0 Hz, 2H), 10.74 (br-s, 1H).

MS(FAB) m/z 392 (M+H)⁻.

Example 43

Synthesis of 3-[3, 4-Di(2-Methoxyethoxy)Phenyl]-1-(4-Ethylpiperazin-1-Yl)Isoquinoline Hydrochloride

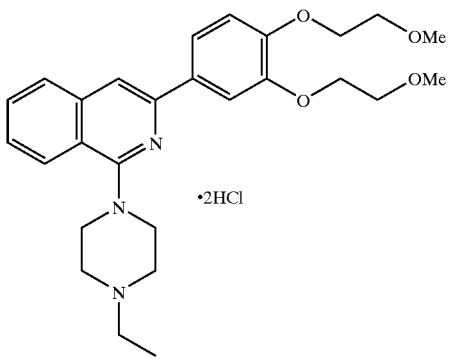

In the same manner as in Example 20, the free compound of the title compound was obtained (1.45 mg, yield; 95%)

from 3-[3,4-di(methoxyethoxy)phenyl]-1-chloroisoquinoline (1.28 g), potassium carbonate (913 mg) and ethylpiperazine (30 ml). The compound was converted into a hydrochloride in a conventional manner, to give the hydrochloride of the title compound as yellow crystals.
Hydrochloride:
m.p.; 143–144° C.
$^1$H-NMR (400 MHz, DMSO-d$_6$): δ (ppm) 1.34 (t, J=7.2 Hz, 3H), 3.20–3.26 (m, 2H), 3.30–3.40 (m, 2H), 3.34 (s, 3H), 3.36 (s, 3H), 3.54–3.63 (m, 4H), 3.69–3.71 (m, 4H), 3.99 (d, J=13.6 Hz, 2H), 4.16–4.18 (m, 2H), 4.23–4.25 (m, 2H), 7.11 (d, J=8.4 Hz, 1H), 7.58 (dt, J=8.0, 1.2 Hz, 1H), 7.73 (dt, J=8.0, 1.2 Hz, 1H), 7.78 (dd, J=8.4, 2.0 Hz, 1H), 7.80 (d, J=2.0 Hz, 1H), 7.96 (d, J=8.0 Hz, 1H), 8.04 (s, 1H), 8.10 (d, J=8.0 Hz, 1H).
MS(FAB) m/z 466 (M+H)$^+$.
Free compound:
$^1$H-NMR (400 MHz, CDCl$_3$); δ (ppm) 1.17 (t, J=7.2 Hz, 3H), 2.55 (q, J=7.2 Hz, 2H), 2.75 (br, 4H), 3.47 (s, 3H), 3.55 (s, 3H), 3.57 (br, 4H), 3.79–3.84 (m, 4H), 4.21–4.24 (m, 2H), 4.28–4.30 (m, 2H), 7.01 (d, J=8.4 Hz, 1H), 7.43 (dt, J=8.0, 1.2 Hz, 1H), 7.56 (dt, J=8.0, 1.2 Hz, 1H), 7.61 (s, 1H), 7.72 (dd, J=8.4, 2.0 Hz, 1H), 7.76 (d, J=8.0 Hz, 1H), 7.85 (d, J=2.0 Hz, 1H), 8.06 (d, J=8.0 Hz, 1H).

Example 44

Synthesis of 3-[4-(2-Hydroxyethoxylmethylphenyl]-1-(4-ethylpiperazin-1-Yl)Isoquinoline Hydrochloride

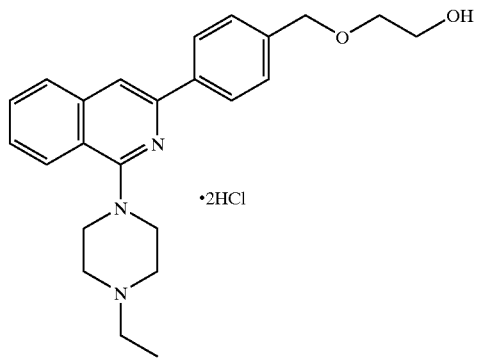

In the same manners as in Examples 161-2 and then 20, an oil was obtained from 1-bromo-4-(2-benzyloxyethy)methylbenzene (1.72 g) and 3-bromo-1-(4-ethylpiperazin-1-yl)isoquinoline (854 mg). Methanol (20 ml) and palladium/carbon catalyst (20 mg) were added thereto, which was then reacted in hydrogen atmosphere at room temperature overnight. Thereafter, the reaction solution was filtered through Celite, and then evaporated. The resulting residue was basified by adding a 1N aqueous solution of sodium hydroxide, which was then extracted with ethyl acetate. The resulting organic layer was washed with brine, dried and evaporated. Then, the resulting residue was purified by silica gel column chromatography (ethyl acetate/hexane system), to give a yellow oil (567 mg, yield; 73%). The oil was converted into a hydrochloride in a conventional manner, to give the hydrochloride of the title compound as yellow crystals.
Hydrochloride:
m.p.; 129–131° C.
$^1$H-NMR (400 MHz, DMSO-d$_6$); δ (ppm) 1.34 (t, J=7.2 Hz, 3H), 3.20–3.28 (m, 2H), 3.33–2.29 (m, 2H), 3.55–3.64 (m, 8H), 4.00 (d, J=13.6 Hz, 2H), 4.57 (s, 2H), 7.48 (d, J=8.4 Hz, 2H), 7.61 (t, J=8.0 Hz, 1H), 7.75 (t, J=8.0 Hz, 1H), 7.99 (d, J=8.0 Hz, 1H), 8.10 (s, 1H), 8.12 (d, J=8.0 Hz, 1H), 8.19 (d, J=8.4 Hz, 2H).
MS(FAB) m/z 392 (M+H)$^+$.
Free compound:
$^1$H-NMR (400 MHz, CDCl$_3$); δ (ppm) 1.18 (t, J=7.2 Hz, 3H), 2.56 (q, J=7.2 Hz, 2H), 2.77 (br, 4H), 3.60 (br, 4H), 3.64 (t, J=4.8 Hz, 2H), 3.79 (t, J=4.4 Hz, 2H), 4.63 (s, 2H), 7.44 (d, J=8.4 Hz, 2H), 7.47 (dt, J=8.4, 1.2 Hz, 1H), 7.59 (dt, J=8.4, 1.2 Hz, 1H), 7.69 (s, 1H), 7.79 (d, J=8.4 Hz, 1H), 8.08 (d, J=8.4 Hz, 1H), 8.16 (d, J=8.4 Hz, 2H).

Example 45

Synthesis of 1-(4-Ethylpiperazin-1-Yl)-3-[4-(2-Fluoroethoxy)Phenyl]Isoquinoline Dihydrochloride

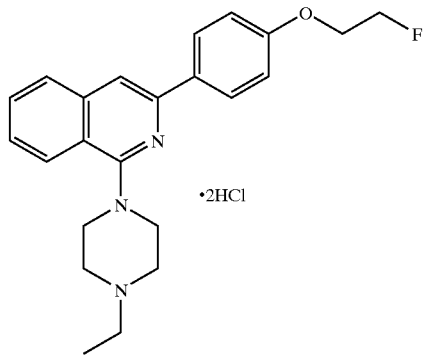

1-(4-Ethylpiperazin-1-yl)-3-(4-hydroxyphenyl)isoquinoline (0.514 g) obtained in Example 7 was dissolved in N, N-dimethylformamide (5 ml), followed by the addition of 60% sodium hydride (0.075 g). After the evolution of hydrogen was ceased, 2-fluoroethyl bromide (230 μl) was added thereto, and then heated under reflux for 8 hr. After the reaction solution was cooled to room temperature, it was partitioned between ethyl acetate and water. The resulting organic layer was washed with water, dried and evaporated. The resulting residue was purified by silica gel column chromatography (methylene chloride/methanol system), to give 0.582 g of 1-(4-ethylpiperazin-1-yl)-3-[4-(2-fluoroethoxy)phenyl]isoquinoline as a white powder. The compound was converted into a hydrochloride in a conventional manner, to give the title compound as a yellow powder.

Hydrochloride:
m.p.; 223–224° C. (decomp.)
$^1$H-NMR (400 MHz, DMSO-d$_6$); δ (ppm) 1.33 (t, J=7.4 Hz, 3H), 3.21–3.27 (m, 2H), 3.31–3.39 (m, 2H), 3.50 (br-t, 2H), 3.63 (br-d, 2H), 3.99 (br-d, 2H), 4.41 (dt, J=4.0, 30.0 Hz, 2H), 4.79 (dt, J=4.0, 48.0 Hz, 2H), 7.11 (d, J=8.8 Hz, 2H), 7.58 (br-t, 1H), 7.73 (br-t, 1H), 7.96 (d, J=8.0 Hz, 1H), 8.02 (s, 1H), 8.10 (d, J=8.4 Hz, 1H); 8.16 (d, J=8.8 Hz, 2H), 10.77 (br-s, 1H).
MS(FAB) m/z 380 (M+H)$^+$.

Example 46

Synthesis of 3-(3,4-Methylenedioxyphenyl)-1-(4-Ethylpiperazin-1-Yl)Isoquinoline Hydrochloride

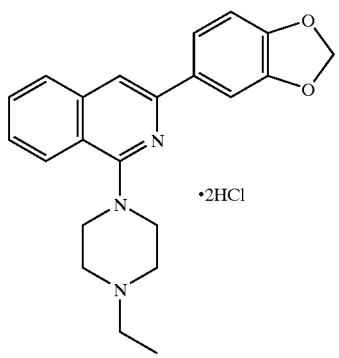

The free compound of the title compound was obtained (425 mg, yield; 94%) from 3-(3,4-methylenedioxyphenyl)-1-chloroisoquinoline (356 mg) and ethylpiperazine (10 ml) in the same manner as in Example 2. The resulting compound was converted into a hydrochloride in a conventional manner, to give the hydrochloride of the title compound as yellow crystals.

Hydrochloride:
$^{1}$H-NMR (400 MHz, DMSO-d$_6$); δ (ppm) 1.33 (t, J=7.2 Hz, 3H), 3.20–3.26 (m, 2H), 3.30–3.38 (m, 2H), 3.52 t, J=12.0 Hz, 2H), 3.62 (d, J=11.2 Hz, 2H), 3.99 (d, J=13.2 Hz, 2H), 6.10 (s, 2H), 7.06 (d, J=8.0 Hz, 1H), 7.58 (t, J=8.0 Hz, 1H), 7.73 (t, J=8.0 Hz, 1H), 7.75 (d, J=2.0 Hz, 1H), 7.77 (dd, J=8.0, 2.0 Hz, 1H), 7.95 (d, J=8.0 Hz, 1H), 8.01 (s, 1H), 8.09 (d, J=8.0 Hz, 1H).

MS(FSB) m/z 362 (M+H)$^+$.

m.p.; 223–227° C.

Free compound:
$^{1}$H-NMR (400 MHz, CDCl$_3$); δ (ppm) 1.18 (t, J=7.2 Hz, 3H), 2.55 (q, J=7.2 Hz, 2H), 2.75 (br, 4H), 3.58 (br, 4H), 6.02 (s, 2H), 6.91 (d, J=8.4 Hz, 2H), 7.44 (ddd, J=8.4, 8.0, 1.2 Hz, 1H), 7.57 (ddd, J=8.4, 8.0, 1.2 Hz, 1H), 7.58 (s, 1H), 7.69 (dd, J=8.4, 1.6 Hz, 1H), 7.71 (br, 1H), 7.76 (d, J=8.0 Hz, 1H), 8.06 (d, J=8.4 Hz, 1H).

Example 47

Synthesis of 1-(1-Ethylpiperazin-4-Yl)-3-(4-Acetonyloxyphenyl)Isoquinoline

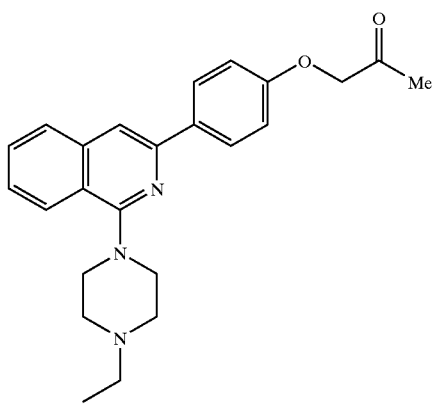

The title compound was obtained (346 mg, yield; 80%) as a yellow oil from 1-(1-ethylpiperazin-4-yl)-3-(4-hydroxyphenyl)isoquinoline (319 mg) and 1-bromo-2-propanone (100 mg), in the same manner as in Example 49.

$^{1}$H-NMR (400 MHz, CDCl$_3$); δ (ppm) 1.18 (3H, t, J=7.2 Hz), 2.31 (3H, s), 2.56 (2H, q, J=7.2 Hz), 2.76 (4H, t, J=4.4 Hz), 3.58 (4H, t, J=4.4 Hz), 4.59 (2H, s), 6.98 (2H, d, J=8.8 Hz), 7.45 (1H, ddd, J=8 Hz, 7 Hz, 1.2 Hz), 7.57 (1H, ddd, J=8 Hz, 7 Hz, 1.2 Hz), 7.61 (1H, s), 7.76 (1H, d, J=8 Hz), 8.06 (1H, d, J=8 Hz), 8.13 (2H, d, J=8.8 Hz).

ESI-Mass; 390 (MH$^+$).

Example 48

Synthesis of 3-[4-(3-Aminopropoxy)Phenyl]-1-(4-Ethylpiperazin-1-Yl)Isoquinoline Hydrochloride

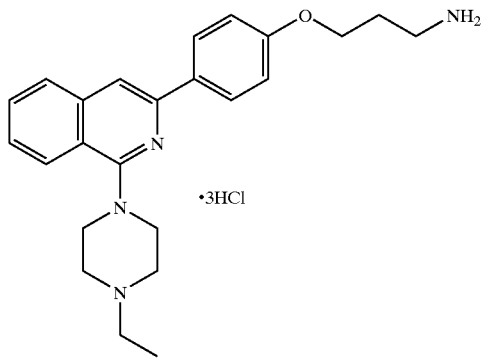

Hydrazine monohydrate (0.16 ml) and ethanol (5 ml) were added to 3-[4-(3-phthalimidepropyloxy)phenyl]-1-(4-ethylpiperazin-1-yl)isoquinoline (182 mg), and the resulting mixture was heated under reflux for 4 hr. Thereafter, the reaction solution was partitioned between chloroform and water. The resulting organic layer was washed with brine, dried and evaporated. The residue was purified by silica gel column chromatography (ethyl acetate/hexane system), to give the free compound of the title compound as a yellow oil (482 mg, yield; 48%). The free compound was converted into a hydrochloride in a conventional manner, to give the hydrochloride of the title compound as yellow crystals.

Hydrochloride:

m.p.; 173–176° C.

$^{1}$H-NMR (400 MHz, DMSO-d$_6$); δ (ppm) 1.34 (t, J=7.2 Hz, 3H), 2.04–2.12 (m, 2H), 2.94–3.00 (m, 2H), 3.18–3.26 (m, 2H), 3.32–3.38 (m, 2H), 3.52–3.63 (m, 4H), 3.97 (d, J=12.8 Hz, 2H), 4.16 (t, J=6.4 Hz, 2H), 7.09 (d, J=8.8 Hz, 2H), 7.58 (t, J=8.0 Hz, 1H), 7.73 (t, J=8.0 Hz, 1H), 7.96 (d, J=8.0 Hz, 1H), 8.01 (s, 1H), 8.10 (d, J=8.0 Hz, 1H), 8.13 (br, 2H), 8.17 (d, J=8.8 Hz, 2H).

MS(FAB) m/z 391 (M+H)$^+$.

Free compound:
$^{1}$H-NMR (400 MHz, CDCl$_3$); δ (ppm) 1.18 (t, J=7.2 Hz, 3H), 2.04 (s, 2H), 2.12–2.18 (m, 2H), 2.55 (q, J=7.2 Hz, 2H), 2.76 (br, 4H), 3.43 (t, J=6.4 Hz, 2H), 3.58 (br, 4H), 4.12 (t, J=6.0 Hz, 2H), 7.00 (d, J=8.8 Hz, 2H), 7.43 (t, J=8.0 Hz, 1H), 7.56 (t, J=8.0 Hz, 1H), 7.61 (s, 1H), 7.76 (d, J=8.0 Hz, 1H), 8.06 (d, J=8.0 Hz, 1H), 8.10 (d, J=8.8 Hz, 2H).

Example 49

Synthesis of 1-(1-Ethylpiperazin-4-Yl)-3-[4-(2-Dimethylaminoethoxy)Phenyl]Isoquinoline

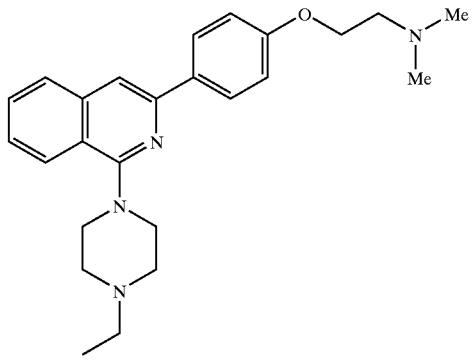

1-(1-Ethylpiperazin-4-yl)-3-(4-hydroxyphenyl)isoquinoline (500 mg) was dissolved in N,N-dimethylformamide (10 ml), followed by the addition of 60% sodium hydride (144 mg) under ice-cooling, and the resulting mixture was stirred at room temperature for 45 min. After the reaction solution was ice-cooled again, 2-dimethylaminomethyl chloride hydrochloride (259 mg) was added thereto, and the mixture was stirred at room temperature for overnight. The reaction mixture was thereafter partitioned between ethyl acetate and water. The resulting organic layer was washed with water, dried (over MgSO$_4$) and evaporated. The residue was purified by (NH) silica gel column chromatography (methylene chloride/methanol system), and the resulting product was converted into a hydrochloride in a conventional manner and recrystallized from hydrous ethanol/ether, to give the hydrochloride of the title compound as yellow crystals (595 mg, yield; 80%).

Hydrochloride:

m.p.; 153–158° C.

$^1$H-NMR (400 MHz, CDCl$_3$); δ (ppm) 1.32 (3H, t, J=7.2 Hz), 2.83 (3H, s), 2.84 (3H, s), 3.19 (2H, q, J=7.2 Hz), 3.21 (1H, q, J=7.2 Hz), 3.30 (1H, t, J=13.6 Hz), 3.33 (1H, t, J=13.6 Hz), 3.51 (1H, t, J=5.2 Hz), 3.48–3.51 (1H, m), 3.59 (2H , d, J=13.6 Hz), 3.95 (2H, d, J=13.6 Hz), 4.43 (2H, t, J=5.2 Hz), 7.13 (2H, d, J=8.8 Hz), 7.56 (1H, ddd, J=8 Hz, 7 Hz, 1.2 Hz), 7.71 (1H, ddd, J=8 Hz, 7 Hz, 1.2 Hz), 7.94 (1H, d, J=8 Hz), 8.08 (1H, d, J=8 Hz), 8.17 (2H, d, J=8.8 Hz), 10.70 (1H, br-s), 11.32 (1H, br-s).

ESI-Mass; 405 (MH$^+$).

Example 50

Synthesis of 3-[4-(3-Acetamidepropoxy)Phenyl]-1-(4-Ethylpiperazin-1-Yl)Isoquinoline Hydrochloride

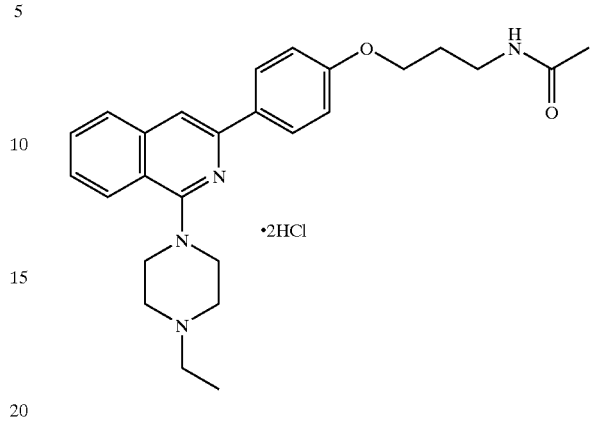

Acetic anhydride (0.06 ml), pyridine (0.07 ml) and THF (4 ml) were added to 3-[4-(3-aminopropoxy)phenyl]-1-(4-ethylpiperazin-1-yl)isoquinoline (182 mg), and the mixture was stirred at room temperature overnight. The reaction mixture was thereafter partitioned between ethyl acetate and water. The resulting organic phase was washed with brine, dried and evaporated. The resulting residue was purified by silica gel column chromatography (ethyl acetate/hexane system), to give a yellow oil (8 mg, yield; 4%). The oil was converted into a hydrochloride in a conventional manner, to give the hydrochloride of the title compound as yellow crystals.

Free compound:

$^1$H-NMR (400 MHz, CDCl$_3$); δ (ppm) 1.18 (t, J=7.2 Hz, 3H), 2.00 (s, 3H), 2.58 (q, J=7.2 Hz, 2H), 2.78 (br, 4H), 3.49 (q, J=6.0 Hz, 2H), 3.60 (br, 4H), 3.73–3.76 (m, 1H), 4.12 (t, J=6.0 Hz, 2H), 6.90 (d, J=8.8 Hz, 2H), 7.43 (dt, J=8.0, 1.2 Hz, 1H), 7.57 (dt, J=8.0, 1.2 Hz, 1H), 7.62 (s, 1H), 7.77 (d, J=8.0 Hz, 1H), 8.06 (d, J=8.0 Hz, 1H), 8.12 (d, J=8.8 Hz, 2H).

MS(FAB) m/z 433 (M+H)$^+$.

Example 51

Synthesis of 3-(4-Cyanomethoxyphenyl)-1-(4-Ethylpiperazin-1-Yl)Isoquinoline Hydrochloride

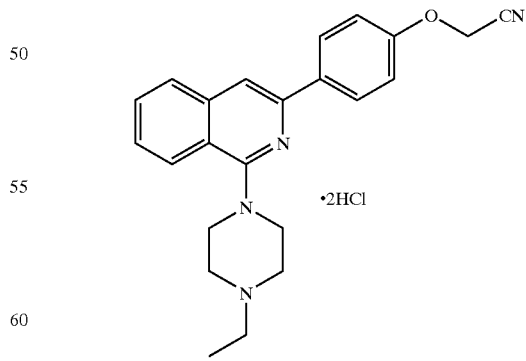

To a solution of 1-(4-ethylpiperazin-1-yl)-3-(4-hydroxyphenyl)isoquinoline (0.30 g) obtained in Example 7 in tetrahydrofuran (15 ml) was added 60% sodium hydride (36 mg) at room temperature. After the evolution of hydrogen was ceased, bromoacetonitrile (0.11 g) was added thereto, and the resulting mixture was reacted at room temperature for 12 hr. Ethyl acetate and an aqueous solution of ammonium chloride were added to the reaction solution. The resulting organic layer was then separated, washed with water, dried and concentrated. To the resulting residue, ethanol and a 2N aqueous solution of hydrochloric acid were added, reacted at 50° C. for 30 min, followed by evaporation. The resulting residue was partitioned between ethyl acetate and water. The resulting organic layer was washed with water and brine, and dried. The solvent was removed, and the resulting residue was purified by NH-silica gel column chromatography (ethyl acetate/hexane system), to give the free compound of the title compound as a pale yellow oil. The free compound was converted into a hydrochloride in a conventional manner, to give 0.17 g of the title compound as a yellow powder.

Hydrochloride:

m.p.; 123–125° C.

$^1$H-NMR (400 MHz, DMSO-d$_6$); δ (ppm) 1.34 (t, J=7.2 Hz, 3H), 3.19–3.41 (m, 4H), 3.48–3.65 (m, 4H), 4.00 (br-d, 2H), 5.27 (s, 2H), 7.22 (d, J=8.8 Hz, 2H), 7.60 (br-t, 1H), 7.74 (br-t, 1H), 7.97 (d, J=8.0 Hz, 1H), 8.06 (s, 1H), 8.11 (d, J=8.0 Hz, 1H), 8.22 (d, J=8.8 Hz, 2H), 11.11 (m, 1H).

MS(ESI) m/z 373 (M+H)$^+$.

Example 52

Synthesis of 3-[4-(2-Cyanoethoxy)Phenyl]-1-(4-Ethylpiperazin-1-Yl)Isoquinoline Hydrochloride

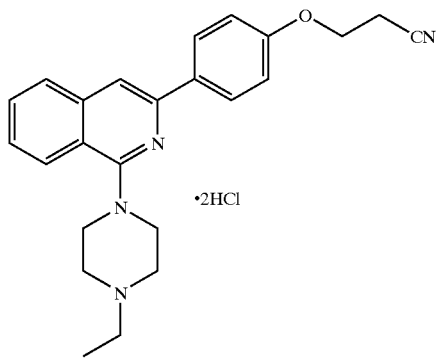

To a solution of 1-(4-ethylpiperazin-1-yl)-3-(4-hydroxyphenyl)isoquinoline (0.30 g) obtained in Example 7 in acrylonitrile (10 ml) was added hydroxylated N-benzyltrimethylammonium (0.5 g), and the resulting mixture was reacted. The reaction solution was evaporated, and the resulting residue was partitioned between ethyl acetate and water. The resulting organic layer was washed with water and brine, and dried. The solvent was remove, and the resulting residue was purified by NH-silica gel column chromatography (ethyl acetate/hexane system), to give the free compound of the title compound as a pale yellow oil. The free compound was converted into a hydrochloride in a conventional manner, to give the title compound as a yellow powder (0.24 g).

Hydrochloride:

$^1$H-NMR (400 MHz, DMSO-d$_6$); δ (ppm) 1.37 (t, J=7.2 Hz, 3H), 2.98 (t, J=5.2 Hz, 2H), 3.25–3.55 (m, 6H), 3.70 (br-d, 2H), 4.04 (br-d, 2H), 4.17 (t, J=5.2 Hz, 2H), 6.85 (d, J=8.0 Hz, 2H), 7.36 (s, 1H), 7.55 (d, J=8.0 Hz, 2H), 7.63 (br-t, 1H), 7.68 (br-d, 1H), 7.75 (br-t, 1H), 7.97 (d, J=8.0 Hz, 2H).

MS(ESI) m/z 387 (M+H)$^+$.

Example 53

Synthesis of 3-[4-(3-Cyanopropoxy)Phenyl]-1-(4-Ethylpiperazin-1-Yl)Isoquinoline Hydrochloride

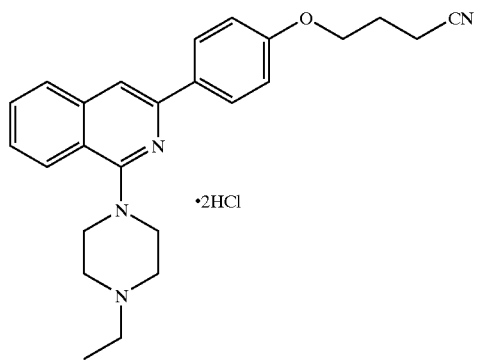

To a solution of 1-(4-ethylpiperazin-1-yl)-3-(4-hydroxyphenyl)isoquinoline (0.30 g) obtained in Example 7 in tetrahydrofuran (15 ml) was added 60% sodium hydride (36 mg) at room temperature. After the evolution of hydrogen was ceased, bromopropionitrile (0.14 g) was added thereto, and the resulting mixture was reacted at room temperature for 12 hr. Ethyl acetate and an aqueous solution of ammonium chloride were added to the reaction solution, and the resulting organic layer was then separated, washed with water, dried and concentrated. To the resulting residue were added ethanol and a 2N aqueous solution of hydrochloric acid, and the resulting mixture was reacted at 50° C. for 30 min, followed by the evaporation. The resulting residue was partitioned between ethyl acetate and water. The resulting organic layer was washed with water and brine, and dried. The solvent was removed, and the resulting residue was purified by NH-silica gel column chromatography (ethyl acetate/hexane system), to give the title compound as a pale yellow oil. The oil was converted into a hydrochloride in a conventional manner, to give 0.12 g of the title compound as a yellow powder.

Hydrochloride:

m.p.; 144–146° C., $^1$H-NMR (400 MHz, DMSO-d$_6$); δ (ppm) 1.34 (t, J=7.2 Hz, 3H), 2.02–2.11 (m, 2H), 2.70 (t, J=7.2 Hz, 2H), 3.18–3.27 (m, 2H), 3.34 (q, J=7.2 Hz, 2H), 3.50–3.65 (m, 4H), 3.98 (br-d, 2H), 4.12 (t, J=6.0 Hz, 2H), 7.09 (d, J=8.8

Hz, 2H), 7.58 (br-t, 1H), 7.73 (br-t, 1H), 7.96 (d, J=8.0 Hz, 1H), 8.01 (s, 1H), 8.10 (d, J=8.0 Hz, 1H), 8.16 (d, J=8.8 Hz, 2H), 11.22 (m, 1H).

MS(ESI) m/z 401 (M+H)$^+$.

Example 54

Synthesis of 3-[4-(3-Methylthiopropoxy)Phenyl]-1-(4-Ethylpiperazin-1-Yl)Isoquinoline Hydrochloride

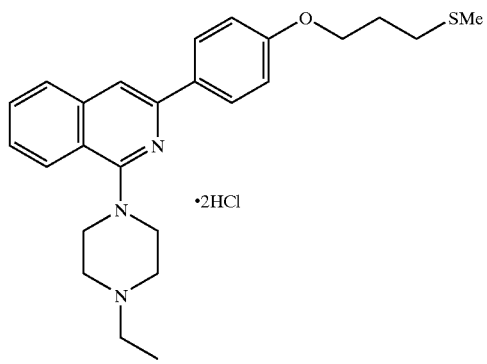

THF (6 ml), DMF (6 ml) and sodium thiomethoxide (270 mg) were added to 3-[4-(3-methanesulfonate propoxy)phenyl]-1-(4-ethylpiperazin-1-yl)isoquinoline, and then reacted at 80° C. for 10 hr. The reaction solution was partitioned between ethyl acetate and water, and the organic layer was washed with water, dried and concentrated. The resulting residue was purified by silica gel column chromatography, to give an oil (258 mg, yield; 81%). The oil was converted into a hydrochloride in a conventional manner, to give the hydrochloride of the title compound as a yellow amorphous.

Hydrochloride (amorphous):

$^1$H-NMR (400 MHz, DMSO-d$_6$); δ (ppm) 1.33 (t, J=7.2 Hz, 3H), 1.88–2.05 (m, 2H), 2.09 (s, 3H), 2.65 (t, J=7.2 Hz, 2H), 3.20–3.28 (m, 2H), 3.30–3.40 (m, 2H), 3.46–3.53 (m, 2H), 3.63 (d, J=11.2 Hz, 2H), 3.99 (d, J=13.6 Hz, 2H), 4.13 (t, J=6.4 Hz, 2H), 7.07 (d, J=8.8 Hz, 2H), 7.57 (t, J=8.4, Hz, 1H), 7.72 (t, J=8.4 Hz, 1H), 7.96 (t, J=8.4 Hz, 1H), 8.00 (s, 1H), 8.09 (d, J=8.4 Hz, 1H), 8.14 (d, J=8.8 Hz, 2H).

MS(FAB) m/z 422 (M+H)$^+$

Free compound:

$^1$H-NMR (400 MHz, CDCl$_3$); δ (ppm) 1.17 (t, J=7.2 Hz, 3H), 2.08–2.13 (m, 2H), 2.14 (s, 3H), 2.55 (q, J=7.2 Hz, 2H), 2.72 (t, J=7.2 Hz, 2H), 2.77 (br, 4H), 3.58 (br, 4H), 4.13 (t, J=6.0 Hz, 2H), 6.99 (d, J=8.8 Hz, 2H), 7.43 (ddd, J=8.4, 8.0, 1.2 Hz, 1H), 7.56 (ddd, J=8.4, 8.0, 1.2 Hz, 1H), 7.61 (s, 1H), 7.76 (d, J=8.0 Hz, 1H), 8.05 (d, J=8.4 Hz, 1H), 8.11 (d, J=8.8 Hz, 2H).

Example 55

Synthesis of 3-[4-(3-Methylsulfonpropoxy)Phenyl]-1-(4-Ethylpiperazin-1-Yl)Isoquinoline Hydorchloride

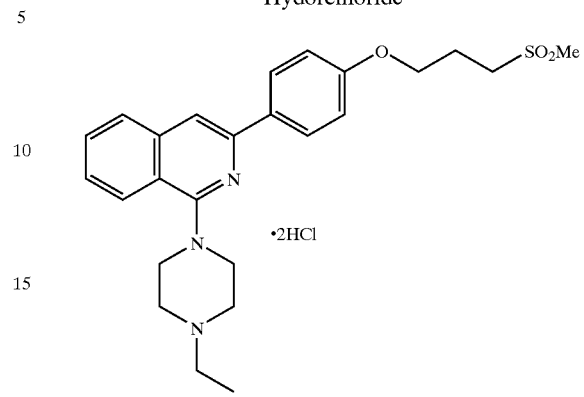

In the same manners as in Examples 161-2 and then 20, the free compound of the title compound was obtained (47 mg, yield; 31%) from 1-bromo-4-(3-methylsulfonpropoxy)benzene (855 mg) and 3-bromo-1-(4-ethylpiperazin-1-yl)isoquinoline (107 mg). The free compound was converted into a hydrochloride in a conventional manner, to give the hydrochloride of the title compound as yellow crystals.

Hydrochloride:
m.p.; 113–115° C.
$^1$-NMR (400 MHz, DMSO-d$_6$); δ (ppm) 1.33 (t, J=7.2 Hz, 3H), 2.15–2.22 (m, 2H), 3.04 (s, 3H), 3.20–3.28 (m, 2H), 3.29–3.38 (m, 4H), 3.49 (t, J=12.4 Hz,, 2H), 3.63 (d, J=12.0 Hz, 2H), 3.99 (d, J=13.6 Hz, 2H), 4.17 (t, J=6.4 Hz, 2H), 7.08 (d, J=8.8 Hz, 2H), 7.58 (t, J=8.0, Hz, 1H), 7.73 (t, J=8.0 Hz, 1H), 7.95 (d, J=8.0 Hz, 1H), 8.01 (s, 1H), 8.10 (d, J=8.0 Hz, 1H), 8.16 (d, J=8.8 Hz, 2H).
MS(FAB) m/z 454 (M+H)$^+$.
Free compound:
$^1$H-NMR (400 MHz, CDCl$_3$); δ (ppm) 1.11 (t, J=7.2 Hz, 3H), 2.25–2.35 (m, 2H), 2.50 (q, J=7.2 Hz, 2H), 2.70 (br, 4H), 2.89 (s, 3H), 3.19–3.23 (m, 2H), 3.52 (br, 4H), 4.10 (t, J=6.0 Hz, 2H), 6.90 (d, J=8.8 Hz, 2H), 7.36 (ddd, J=8.4, 8.0, 1.2 Hz, 1H), 7.50 (ddd, J=8.4, 8.0, 1.2 Hz, 1H), 7.54 (s, 1H), 7.69 (d, J=8.0 Hz, 1H), 7.98 (d, J=8.4 Hz, 1H), 8.04 (d, J=8.8 Hz, 2H).

Example 56

Synthesis of 3-{4-[2-(1-Imidazonyl)Ethoxy]phenyl}-1-(4-Ethylpiperazin-1-Yl)Isoquinoline Hydrochloride

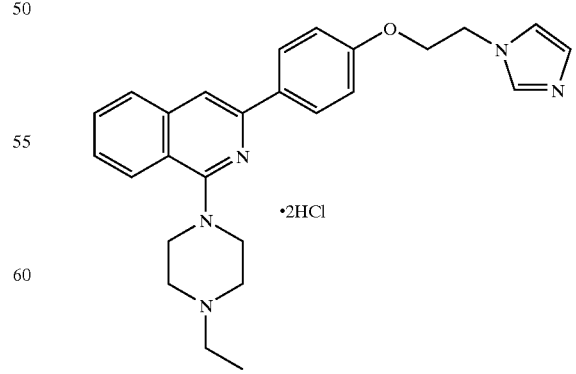

3-[4-(2-Methanesulfonate ethoxy)phenyl]-1-(4-ethylpiperazin-1-yl)isoquinoline (768 mg) was dissolved in DMF (10 ml), to which were then added 60% sodium hydride (221 m g) and imidazole (575 mg), and the resulting mixture was reacted at 60° C. overnight. The reaction solution was partitioned between ethyl acetate and water, and the resulting organic layer was washed with brine, dried and evaporated. Then, the resulting residue was purified by silica gel column chromatography (ethyl acetate/hexane system), to give a yellow oil (576 mg, yield; 80%). The oil was converted into a hydrochloride in a conventional manner, to give the hydrochloride of the title compound as yellow crystals.

Hydrochloride:
$^1$H-NMR (400 MHz, DMSO-d$_6$); δ (ppm) 1.34 (t, J=7.2 Hz, 3H), 3.18–3.26 (m, 2H), 3.30–3.40 (m, 2H), 3.53–3.62 (m, 2H), 3.94 (d, J=13.2 Hz, 2H), 4.48 (d, J=5.2 Hz, 2H), 4.67 (d, J=5.2 Hz, 1H), 7.09 (d, J=8.8 Hz, 2H), 7.58 (t, J=8.0 Hz, 1H), 7.72 (s, 1H), 7.73 (t, J=8.0 Hz, 1H), 7.89 (s, 1H), 7.96 (d, J=8.0 Hz, 1H), 8.01 (s, 1H), 8.10 (d, J=8.0 Hz, 1H), 8.16 (d, J=8.8 Hz, 2H), 9.30 (s, 1H).
MS(FAB) m/z 428 (M+H)$^+$.
m.p.; 160–162° C.

Free compound:
$^1$H-NMR (400 MHz, CDCl$_3$); δ (ppm) 1.18 (t, J=7.2 Hz, 3H), 2.55 (q, J=7.2 Hz, 2H), 2.77 (br, 4H), 3.58 (br, 4H), 4.27–4.30 (m, 2H), 4.36–4.38 (m, 2H), 4.28–4.30 (m, 2H), 6.96 (d, J=8.8 Hz, 2H), 7.07–7.09 (m, 2H), 7.44 (dt, J=8.0, 1.2 Hz, 1H), 7.57 (dt, J=8.0, 1.2 Hz, 1H), 7.61 (s, 1H), 7.62 (br, 1H), 7.77 (d, J=8.0 Hz, 1H), 8.06 (d, J=8.0 Hz, 1H), 8.11 (d, J=8.8 Hz, 2H).

Example 57

Synthesis of 3-{4-[3-(4-Pyridyl)Propoxy]Phenyl}-1-(4-Ethylpiperazin-1-Yl)Isoquinoline Hydrochloride

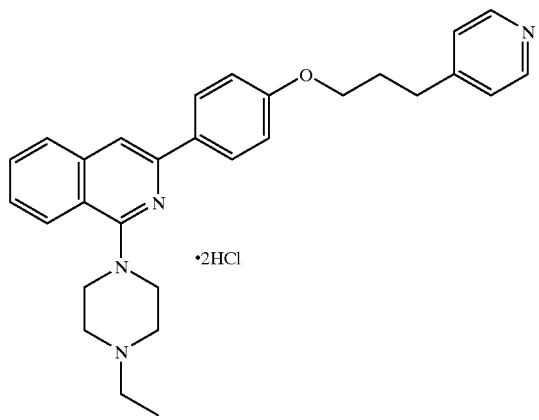

The free compound of the title compound was obtained (333 mg, yield; 76%) from 3-(4-hydroxyphenyl)-1-(4-ethylpiperazin-1-yl)isoquinoline (322 mg) and 2-(3-methanesulfonate propyl)pyridine (417 mg), in the same manner as in Example 51. The free compound was converted into a hydrochloride in a conventional manner, to give the hydrochloride of the title compound as yellow crystals.

Hydrochloride:
m.p.; 129–131° C.
$^1$H-NMR (400 MHz, DMSO-d$_6$); δ (ppm) 1.34 (t, J=7.2 Hz, 3H), 2.16–2.24 (m, 2H), 3.10 (t, J=7.2 Hz, 2H), 3.20–3.26 (m, 2H), 3.30–3.39 (m, 2H), 3.46–3.56 (m, 2H), 3.62 (d, J=11.2 Hz, 2H), 3.97 (d, J=13.2 Hz, 2H), 4.11 (t, J=6.0 Hz, 2H), 7.04 (d, J=8.8 Hz, 2H), 7.58 (t, J=8.0 Hz, 1H), 7.73 (t, J=8.0 Hz, 1H), 7.96 (d, J=8.0 Hz, 1H), 8.00 (s, 1H), 8.02 (d, J=6.8 Hz, 2H), 8.10 (d, J=8.0 Hz, 1H), 8.15 (d, J=8.8 Hz, 2H), 8.85 (d, J=6.8 Hz, 2H).
MS(FAB) m/z 453 (M+H)$^+$.

Free compound:
$^1$H-NMR (400 MHz, CDCl$_3$); δ (ppm) 1.18 (t, J=7.2 Hz, 3H), 2.11–2.18 (m, 2H), 2.56 (q, J=7.2 Hz, 2H), 2.76 (br, 4H), 2.85 (t, J=7.6 Hz, 2H), 3.58 (br, 4H), 4.03 (t, J=6.0 Hz, 2H), 6.98 (d, J=8.4 Hz, 2H), 7.16 (d, J=4.8 Hz, 2H), 7.43 (t, J=8.0 Hz, 1H), 7.57 (t, J=8.0 Hz, 1H), 7.62 (s, 1H), 7.76 (d, J =8.0 Hz, 1H), 8.06 (d, J=8.0 Hz, 1H), 8.11 (d, J=8.4 Hz, 2H), 8.51 (d, J=4.8 Hz, 1H).

Example 58

Synthesis of 3-{4-[2-(2-Methylpyridin-5-Yl)Ethoxy]Phenyl}-1-(4-Ethylpiperazin-1-Yl)Isoquinoline Hydrochloride

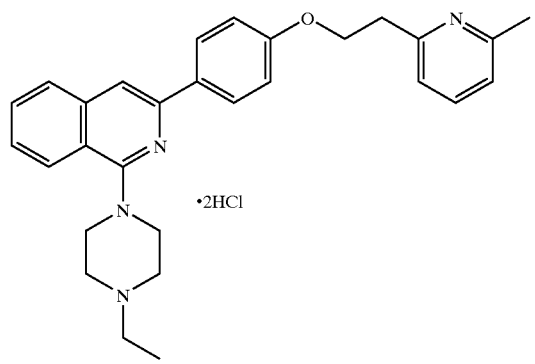

DMF (10 ml), potassium carbonate (897 mg) and 2-methyl-5-(2-methanesulfonate ethyl)pyridine (558 mg) were added to 3-(4-hydroxyphenyl)-1-(4-ethylpiperazin-1-yl)isoquinoline (432 mg), and the resulting mixture was reacted at 100° C. for 3 hr. The reaction solution was thereafter partitioned between ethyl acetate and water, and the resulting organic layer was washed with brine, dried and evaporated. The resulting residue was purified by silica gel column chromatography (ethyl acetate/hexane system), to give a yellow oil (268 mg, yield; 46%). The oil was converted into a hydrochloride in a conventional manner, to give the hydrochloride of the title compound as yellow crystals.

Hydrochloride:
m.p.; 136–138° C.
$^1$H-NMR (400 MHz, DMSO-d$_6$); δ (ppm) 1.34 (t, J=7.2 Hz, 3H), 2.81 (s, 3H), 3.18–3.26 (m, 2H), 3.30–3.38 (m, 2H), 3.53–3.62 (m, 4H), 3.95 (t, J=13.2 Hz, 4H), 4.52 (t, J=6.4 Hz, 2H), 7.09 (d, J=8.8 Hz, 2H), 7.58 (t, J=8.0 Hz, 1H), 7.73 (t, J=8.0 Hz, 1H), 7.81 (d, J=8.0 Hz, 1H), 7.90 (d, J=8.0 Hz, 1H), 7.96 (d, J=8.0 Hz, 1H), 8.01 (s, 1H), 8.10 (d, J=8.0 Hz, 1H), 8.15 (d, J=8.8 Hz, 2H), 8.44 (t, J=8.0 Hz, 1H).
MS(FAB) m/z 453 (M+H)$^+$.

Free compound:
$^1$H-NMR (400 MHz, CDCl$_3$); δ (ppm) 1.17 (t, J=7.2 Hz, 3H), 2.55 (s, 3H), 2.56 (q, J=7.2 Hz, 2H), 2.75 (br, 4H), 3.26

(t, J=6.8 Hz, 2H), 3.58 (br, 4H), 4.41 (t, J=6.8 Hz, 2H), 6.99 (d, J=8.8 Hz, 2H), 7.00–7.03 (m, 1H), 7.10 (d, J=8.0 Hz, 1H), 7.42 (ddd, J=8.4, 8.0, 1.2 Hz, 1H), 7.50 (d, J=8.0 Hz, 1H), 7.56 (ddd, J=8.4, 8.0, 1.2 Hz, 1H), 7.60 (s, 1H), 7.75 (d, J=8.0 Hz, 1H), 8.05 (d, J=8.4 Hz, 1H), 8.09 (d, J=8.8 Hz, 2H).

Example 59

Synthesis of 1-(1-Ethylpiperazin-4-Yl)-3-[4-(N-Ethylcarbamyl)Phenyl]Isoquinoline

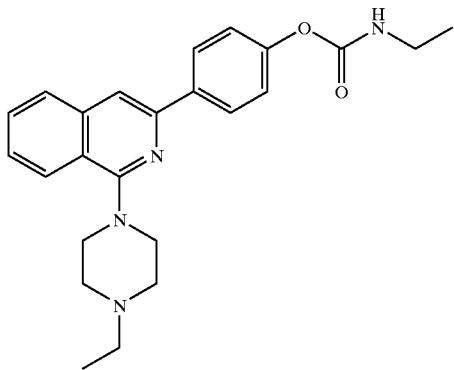

1-(1-Ethylpiperazin-4-yl)-3-(4-hydroxyphenyl)isoquinoline (333 mg) was dissolved in tetrahydrofuran (5 ml), ethyl isocyanate (800 ml) was added thereto, and then the mixture was stirred at room temperature for 3 hr. The reaction mixture was evaporated. The resulting residue was purified by silica gel column chromatography (methylene chloride/methanol system), and then recrystallized from ethyl acetate/hexane, to give the free compound of the title compound. The free compound was converted into a hydrochloride in a conventional manner, which was then recrystallized (from ethanol/isopropyl ether), to give the hydrochloride of the title compound as yellow crystals (313 mg, yield; 70%).

Hydrochloride:

m.p.; 146–150° C.

$^1$H-NMR (400 MHz, DMSO-$d_6$); δ (ppm) 1.08 (3H, t, J=7.2 Hz), 1.30 (3H, t, J=7.2 Hz), 3.05–3.14 (2H, m), 3.16–3.24 (2H, m), 3.31 (1H, t, J=11.6 Hz), 3.34 (1H, t, J=11.6 Hz), 3.49 (2H, t, J=13.2 Hz), 3.59 (2H, d, J=11.6 Hz), 3.98 (2H, d, J=13.2 Hz), 7.21 (2H, d, J=8.8 Hz), 7.58 (1H, ddd, J=8 Hz, 7 Hz, 1.2 Hz), 7.72 (1H, ddd, J=8 Hz, 7 Hz, 1.2 Hz), 7.79 (1H, t, J=5.6 Hz), 7.96 (1H, d, J=8 Hz), 8.05 (1H, s), 8.09 (1H, d, J=8 Hz), 8.17 (2H, d, J=8.8 Hz), 10.82 (1H, br-s).

ESI-Mass; 405 (MH$^+$).

Examples 60 and 61

Synthesis of (Z)-1-(4-Ethylpiperazin-1-Yl)-3-(4-Hydroxyiminomethylphenyl)Isoquinoline and (E)-1-[4-Ethylpiperazin-1-Yl)-3-(4-Hydroxyiminoimethylphenyl)Isoquinoline

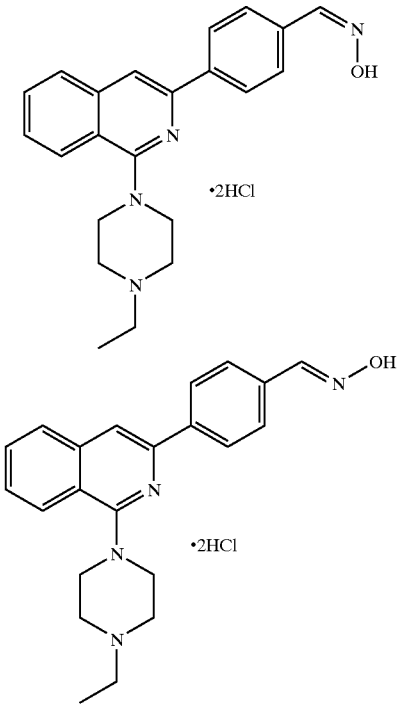

1-(4-Ethylpiperazin-1-yl)-3-(4-formylphenyl)isoquinoline (3.00 g) obtained in Example 17-5 was reacted with hydroxylamine hydrochloride (0.90 g) and sodium acetate (1.10 g) in ethanol (50 ml) at 60° C. for 2 hr. The reaction solution was evaporated, and then the resulting residue was extracted in methylene chloride, washed with brine and dried. The solvent was removed, and the resulting residue was isolated and purified by silica gel column chromatography (methylene chloride/methanol system), to give (Z)-1-(4-ethylpiperazin-1-yl)-3-(4-hydroxyiminomethylphenyl)isoquinoline (1.01 g) and (E)-1-(4-ethylpiperazin-1-yl)-3-(4-hydroxyiminomethylphenyl)isoquinoline (1.52 g), both as yellow solids. 0.30 g each of the compounds was converted into a hydrochloride in a conventional manner, to give the hydrochlorides of the title compounds as yellow powders (0.32 g and 0.35 g, respectively).

Example 60

(Z)-1-(4-Ethylpiperazin-1-Yl)-3-(4-Hydroxyiminomethylphenyl)Isoquinoline Hydrochloride m.p.; 239° C. (decomp.)

$^1$H-NMR (400 MHz, DMSO-$d_6$); δ (ppm) 1.33 (t, J=7.2 Hz, 3H), 3.18–3.28 (m, 2H), 3.29–3.41 (m, 2H), 3.50–3.66

(m, 4H), 3.98–4.06 (m, 2H), 7.60–7.66 (m, 1H), 7.74 (d, J=8.4 Hz, 2H), 7.73–7.79 (m, 1H), 8.00 (d, J=8.4 Hz, 1H), 8.13 (d, J=8.8 Hz, 1H), 8.15 (s, 1H), 8.21 (s, 1H), 8.25 (d, J=8.4 Hz, 2H), 11.13 (m, 1H).

MS(FAB) m/z 361 (M+H)+.

Example 61

(E)-1-(4-Ethylpiperazin-1-Yl)-3-(4-Hydroxyiminomethylphenyl)Isoquinoline Hydrochloride m.p.; 243° C. (decomp.)

¹H-NMR (400 MHz, DMSO-d₆); δ (ppm) 1.32 (t, J=7.2 Hz, 3H), 3.19–3.29 (m, 2H), 3.29–3.41 (m, 2H), 3.48–3.67 (m, 4H), 3.97–4.06 (m, 2H), 7.60–7.66 (m, 1H), 7.73 (d, J=8.4 Hz, 2H), 7.72–7.79 (m, 1H), 8.00 (d, J=8.4 Hz, 1H), 8.13 (d, J=8.8 Hz, 1H), 8.15 (s, 1H), 8.21 (s, 1H), 8.25 (d, J=8.4 Hz, 2H), 10.98 (m, 1H).

MS(FAB) m/z 361 (M+H)+.

Example 62

Synthesis of 3-(4-Cyanophenyl)-1-(4-Ethylpiperazin-1-Yl)Isoquinoline Hydrochloride

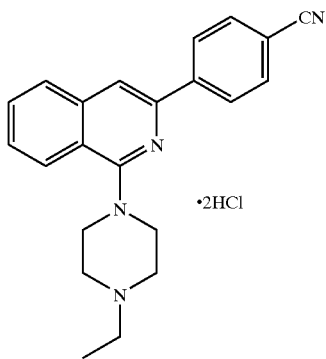

(E,Z)-1-(4-Ethylpiperazin-1-yl)-3-(4-hydroximinomethylphenyl)isoquinoline (1.92 g) obtained in Example 61 was reacted with acetic anhydride in acetic acid at 120° C. for 1.5 hr. The reaction solution was evaporated, and to the resulting residue were then added ethyl acetate and a 10% aqueous solution of potassium carbonate, and the mixture was then extracted with ethyl acetate. The resulting organic layer was washed with water and brine, dried and concentrated. The resulting residue was purified by silica gel column chromatography (methylene chloride/methanol system), to give 1.78 g of the free compound of the title compound. 0.28 g of the resulting free compound was converted into a hydrochloride in a conventional manner, to give 0.23 g of the title compound as a yellow powder.

Hydrochloride:

m.p.; 241° C. (decomp.)

¹H-NMR (400 MHz, DMSO-d₆); δ (ppm) 1.34 (t, J=7.2 Hz, 3H), 3.18–3.28 (m, 2H), 3.29–3.41 (m, 2H), 3.51–3.66 (m, 4H), 3.99–4.07 (m, 2H), 7.65–7.71 (m, 1H), 7.77–7.83 (m, 1H), 7.99 (d, J=8.8 Hz, 2H), 8.03 (d, J=8.4 Hz, 1H), 8.29 (s, 1H), 8.41 (d, J=8.8 Hz, 2H), 11.20 (m, 1H).

MS(FAB) m/z 343 (M+H)+.

Example 63

Synthesis of 1-(4-Ethylpiperazin-1-Yl)-3-(4-N-Propylaminocarbonylphenyl)Isoquinoline Hydrochloride

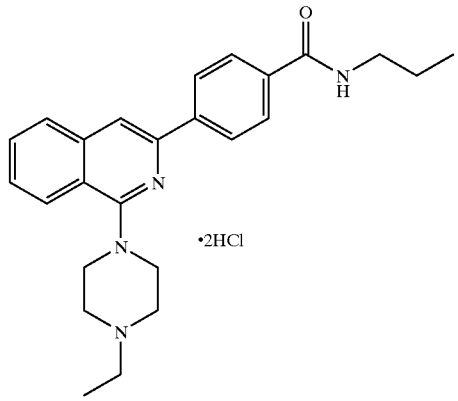

(4-N-Propylaminocarbonylphenyl)tributylstannum (1.350 g) and 3-bromo-1-(4-ethylpiperazin-1-yl) isoquinoline (0.820 g) were reacted in the presence of tetrakistriphenylphosphine (0.116 g) in xylene (20 ml) in nitrogen atmosphere overnight. After cooling, the reaction solution was filtered. The resulting filtrate was extracted with a 5N aqueous solution of hydrochloric acid. The resulting aqueous layer was basified with a 5N aqueous solution of sodium hydroxide, and then extracted with ethyl acetate. The resulting organic layer was washed with water and brine, dried and concentrated. The resulting residue was purified by silica gel column chromatography (chloroform/methanol system), to give 0.578 g of the free compound of the title compound as a pale yellow solid.

Free compound:

¹H-NMR (400 MHz, CDCl₃); δ (ppm) 1.02 (t, J=7.2 Hz, 3H), 1.18 (t, J=7.2 Hz, 3H), 1.63–1.73 (m, 2H), 2.56 (q, J=7.2 Hz, 2H), 2.77 (br-t, 2H), 3.46 (dt, J=6.0, 7.2 Hz, 2H), 3.60 (br-t, 4H), 6.19 (br-t, 1H), 7.49 (br-t, 1H), 7.61 (br-t, 1H), 7.75 (s, 1H), 7.81 (d, J=8.0 Hz, 1H), 7.86 (d, J=8.8 Hz, 2H), 8.09 (d, J=7.6 Hz, 1H), 8.24 (d, J=8.8 Hz, 2h).

The resulting free compound was converted into a hydrochloride in a conventional manner, and then recrystallized from ethanol/ether, to give the title compound as a pale yellow powder.

Hydrochloride:

m.p.; 149–150° C.

¹H-NMR (400 MHz, DMSO-d₆); δ (ppm) 0.92 (t, J=7.2 Hz, 3H), 1.33 (t, J=7.2 Hz, 3H), 1.57 (dq, J=7.2 Hz, 2H), 3.21–3.28 (m, 2H), 3.32–3.40 (m, 2H), 3.53 (br-t, 2H), 3.64 (br-d, 2H), 4.03 (br-d, 2H), 7.65 (br-t, 1H), 7.77 (br-t, 1H), 7.99 (d, J=8.4 Hz, 2H), 8.02 (d, J=7.6 Hz, 1H), 8.14 (d, J=8.4 Hz, 2H), 8.21 (s, 1H), 8.28 (d, J=8.4 Hz, 2H), 8.56 (t, J=7.2 Hz, 1H), 10.87 (br-s, 1H).

MS(FAB) m/z 403 (M+H)$^+$.

Example 64

Synthesis of 3-[4-(4-Hydroxy-1-Cyclohexen-1-Yl)Phenyl]-1-(4-Ethylpiperazin-1-Yl)Isoquinoline Hydrochloride

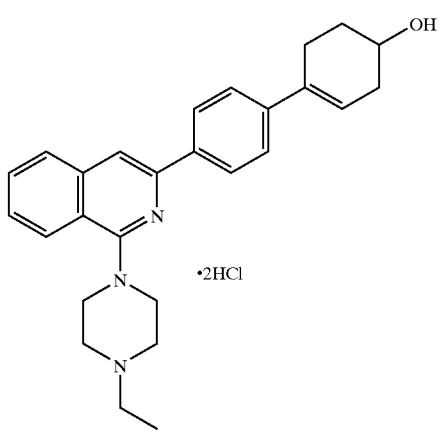

In the same manners as in Examples 161-2 and then 20, an oil was obtained from 1-bromo-4-(4-acetoxy-1-cyclohexen-1-yl)benzene (477 mg) and 3-bromo-1-(4-ethylpiperazin-1-yl)isoquinoline (200 mg). Methanol (10 ml) and a 1N aqueous solution of sodium hydroxide (1 ml) were added to the resulting oil, and then the mixture was heated under reflux for 1 hr. The reaction solution was partitioned between ethyl acetate and water, and the resulting organic layer was washed with water, dried and concentrated. The resulting residue was purified by silica gel column chromatography (hexane/ethyl acetate system), to give a colorless oil (175 mg, yield; 68%). The oil was converted into a hydrochloride in a conventional manner, to give hydrochloride of the title compound as white crystals.

Hydrochloride:

Melting point; 164–166° C.

$^1$H-NMR (400 MHz, DMSO-d$_6$); δ (ppm) 1.33 (t, J=7.2 Hz, 3H), 1.63 (br, 1H), 2.44 (br, 2H), 3.24 (t, J=6.0 Hz, 2H), 3.35–3.40 (m, 2H), 3.45–3.50 (m, 2H), 3.63 (d, J=11.6 Hz, 2H), 3.82 (br, 4H), 4.00 (d, J=14.8 Hz, 2H), 6.17 (s, 1H), 7.55 (d, J=8.4 Hz, 2H), 7.61 (t, J=8.0 Hz, 1H), 7.74 (t, J=8.0 Hz, 1H), 7.99 (d, J=8.0 Hz, 1H), 8.10 (s, 1H), 8.11 (d, J=8.0 Hz, 1H), 8.16 (d, J=8.4 Hz, 2H).

MS(FAB) m/z 414 (M+H)$^+$.

Free compound:

$^1$H-NMR (400 MHz, CDCl$_3$); δ (ppm) 1.19 (t, J=7.6 Hz, 3H), 1.86–1.89 (m, 1H), 2.05–2.10 (m, 1H), 2.24–2.31 (m, 1H), 2.55–2.66 (m, 3H), 2.57 (q, J=7.6 Hz, 2H), 2.77 (br, 4H), 3.60 (br, 4H), 4.06–4.14 (m, 1H), 6.17 (s, 1H), 7.46 (t, J=8.4 Hz, 1H), 7.50 (d, J=8.4 Hz, 2H), 7.59 (t, J=8.4 Hz, 1H), 7.76 (s, 1H), 7.79 (d, J=8.4 Hz, 1H), 8.08 (d, J=8.4 Hz, 1H), 8.14 (d, J=8.4 Hz, 2H).

Example 65

Synthesis of 3-(4-Aminophenyl)-1-(4-Ethylpiperazin-1-Yl)Isoquinoline Hydrochloride

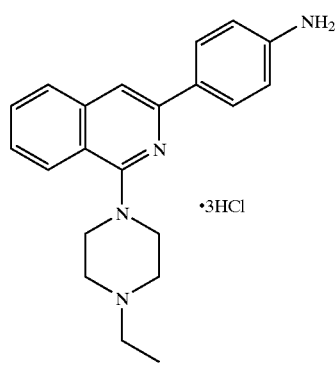

Ethanol 930 ml) and a 2N aqueous solution of hydrochloric acid (4 ml) were added to 3-(4-acetamidephenyl)-1-(4-ethylpiperazin-1-yl)isoquinoline, and the resulting mixture was stirred at 80° C. for 4 hr. The reaction solution was basified with a 1N aqueous solution of sodium hydroxide, and then extracted with ethyl acetate. The resulting organic layer was washed with water, dried and concentrated. The resulting residue was purified by silica gel column chromatography, to give an oil (71 mg, yield; 7%). The oil was converted into a hydrochloride in a conventional manner, to give the hydrochloride of the title compound as yellow crystals.

Hydrochloride:

m.p.; 267–268° C.

$^1$H-NMR (400 MHz, DMSO-d$_6$); δ (ppm) 1.35 (t, J=7.2 Hz, 3H), 3.20–3.26 3.26 (m, 2H), 3.30–3.40 (m, 2H), 3.56–3.62 (m, 4H), 4.02 (d, J=13.2 Hz, 2H), 7.54 (d, J=8.4 Hz, 2H), 7.64 (t, J=8.0, Hz, 1H), 7.77 (t, J=8.0 Hz, 1H), 8.00 (d, J=8.0 Hz, 1H), 8.13 (s, 1H), 8.14 (d, J=8.0 Hz, 1H), 8.31 (d, J=8.4 Hz, 2H).

MS(FAB) m/z 333 (M+H)$^+$.

Free compound:

$^1$H-NMR (400 MHz, CDCl$_3$); δ (ppm) 1.17 (t, J=7.2 Hz, 3H), 2.55 (q, J=7.2 Hz, 2H), 2.75 (br, 4H), 3.57 (br, 4H), 3.79 (br, 2H), 6.78 (d, J=8.4 Hz, 2H), 7.49 (t, J=8.0 Hz, 1H), 7.55 (t, J=8.0 Hz, 1H), 7.57 (s, 1H), 7.74 (d, J=8.0 Hz, 1H), 8.01 (d, J=8.4 Hz, 2H), 8.04 (d, J=8.0 Hz, 1H).

Example 66

Synthesis of 3-[4-(N,N-Dimethylamino)Phenyl]-1-(4-Ethylpiperazin-1-Yl)Isoquinoline Dihydrochloride

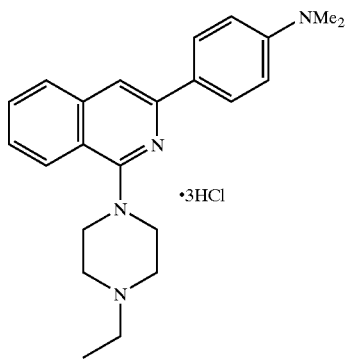

According to the method of Example 10-1, 3-[4-(N,N-dimethylamino)phenyl]isoquinolin-1-one was obtained from N-methyl-o-toluamide (4.47 g) and 4-(N,N-dimethylamino)benzonitrile.

Subsequently, the resulting 3-[4-(N,N-dimethylamino)]isoquinolin-1-one (2.834 g) was added to phosphorus oxychloride (25 ml), and the resulting mixture was heated at 110° C. for 1.5 hr. The reaction solution was evaporated, and to the resulting residue were added ethyl acetate and water. The resulting organic layer was washed with water, an aqueous solution of sodium bicarbonate and brine, and dried over magnesium sulfate. The solvent was removed, and the resulting 1-chloro-3-[4-(N,N-dimethylamino)]isoquinoline was reacted with N-ethylpiperazine (35 ml) at 120° C. for 5 hr. The reaction solution was evaporated, and the resulting residue were added ethyl acetate and water. The resulting organic layer was washed with water and brine, and dried over magnesium sulfate. The solvent was removed, and the resulting residue was purified by silica gel column chromatography (chloroform/methanol system), to give 2.687 g of the free compound of the title compound as a pale yellow oil.

Free compound:

$^1$H-NMR (400 MHz, CDCl$_3$); δ (ppm) 1.17 (t, J=7.4 Hz, 3H), 2.55 (q, J=7.4 Hz, 2H), 2.75 (br-t, 4H), 3.02 (s, 6H), 3.58 (br-t, 4H), 6.82 (d, J=8.8 Hz, 2H), 7.38 (br-t, 1H), 7.53 (br-t, 1H), 7.58 (s, 1H), 7.74 (d, J=8.4 Hz, 1H), 8.04 (d, J=8.4 Hz, 1H), 8.09 (d, J=8.8 Hz, 2H).

The resulting free compound was converted into a hydrochloride in a conventional manner, and recrystallized from ethanol/ether, to give the title compound as a yellow powder.

Hydrochloride:

m.p.; 160–162° C. (decomp.)

$^1$H-NMR (400 MHz, DMSO-d$_6$); δ (ppm) 1.34 (t, J=7.2 Hz, 3H), 3.11 (s, 6H), 3.19–3.25 (m, 2H), 3.30–3.38 (m, 2H), 3.55–3.62 (m, 4H), 4.00 (br-d, 2H), 7.54 (br-s, 2H), 7.60 (br-t, 1H), 7.75 (br-t, 1H), 7.98 (d, J=8.4 Hz, 1H), 8.07 (s, 1H), 8.11 (d, J=8.0 Hz, 1H), 8.24 (d, J=8.4 Hz, 2H), 11.31 (br-s, 1H).

MS(FAB) m/z 361 (M+H)$^+$.

Example 67

Synthesis of 3-[4-(2-Hydroxyethyl)Aminophenyl]-1-(4-Ethylpiperazin-1-Yl)Isoquinoline Hydrochloride

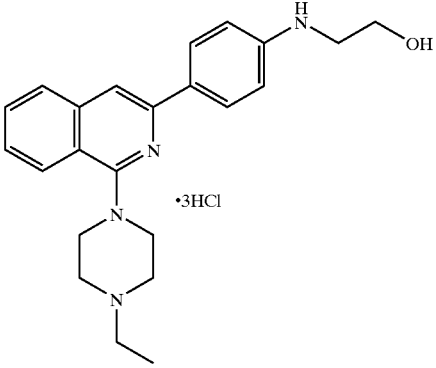

In the same manners sequentially as in Examples 161-2 and 20, an oil was obtained from 1-bromo-4-(2-acetoxyethyl)aminobenzene (905 mg) and 3-bromo-1-(4-ethylpiperazin-1-yl)isoquinoline (266 mg). Ethanol (10 ml) and a 2N aqueous solution of hydrochloric acid (1 ml) were added to the resulting oil, and then the mixture was heated under reflux for 3 hr. The reaction solution was basified with a 1N aqueous solution of sodium hydroxide, and then extracted with ethyl acetate. The resulting organic layer was washed with water, dried and concentrated. The resulting residue was purified by silica gel column chromatography, to give an oil (120 mg, yield; 38%). The oil was converted into a hydrochloride in a conventional manner, to give the hydrochloride of the title compound as a yellow amorphous.

Hydrochloride (amorphous): MS(FAB) m/z 377 (M+H)$^+$.

Free compound:

$^1$H-NMR (400 MHz, CDCl$_3$); δ (ppm) 1.18 (t, J=7.2 Hz, 3H), 2.56 (q, J=7.2 Hz, 2H), 2.76 (br, 4H), 3.39 (t, J=5.2 Hz, 2H), 3.58 (br, 4H), 3.88 (t, J=5.2 Hz, 2H), 6.75 (d, J=8.8 Hz, 2H), 7.39 (t, J=8.4 Hz, 1H), 7.44 (d, J=8.4 Hz, 1H), 7.54 (t, J=8.4 Hz, 1H), 7.57 (s, 1H), 7.73 (d, J=8.4 Hz, 1H), 8.04 (d, J=8.8 Hz, 2H).

Example 68

Synthesis of 3-(4-Acetamidephenyl)-1-(4-Ethylpiperazin-1-Yl)Isoquinoline Hydrochloride

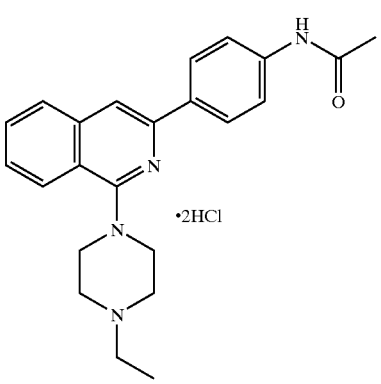

In the same manners as in Example 20, the free compound of the title compound was obtained (1.09 g, yield; 40%)

from from 1-bromo-4-acetonailide (5.07 g) and 3-bromo-1-(4-ethylpiperazin-1-yl)isoquinoline (2.3 g). The free compound was converted into a hydrochloride in a conventional manner, to give the hydrochloride of the title compound as yellow crystals.

Hydrochloride:

m.p.; 180–182° C.

MS (FAB) m/z 375 (M+H)$^+$.

Free compound:

$^1$H-NMR (400 MHz, CDCl$_3$); δ (ppm) 1.20 (t, J=7.2 Hz, 3H), 2.21 (s, 3H), 2.58 (q, J=7.2 Hz, 2H), 2.80 (br, 4H), 3.62 (br, 4H), 7.45 (t, J=8.0 Hz, 1H), 7.58 (t, J=8.0 Hz, 1H), 7.61 (d, J=8.8 Hz, 2H), 7.67 (s, 1H), 7.78 (d, J=8.0 Hz, 1H), 8.06 (d, J=8.0 Hz, 2H), 8.14 (d, J=8.8 Hz, 2H).

Example 69

Synthesis of 3-(4-Ethylcarbonylaminophenyl)-1-(4-Ethylpiperazin-1-Yl)Isoquinoline Hydrochloride

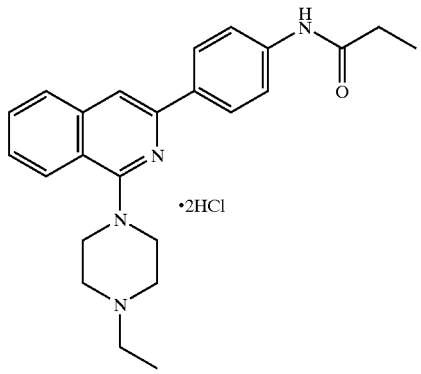

In the same manners sequentially as in Examples 161-2 and 20, the free compound of the title compound was obtained (520 mg, yield; 58%) from 1-bromo-4-ethylcarbonylaminobenzene (3.85 g) and 3-bromo-1-(4-ethylpiperazin-1-yl)isoquinoline (745 mg). The free compound was converted into a hydrochloride in a conventional manner, to give the hydrochloride of the title compound as yellow crystals.

Hydrochloride:

m.p.; 176–178° C.

$^1$H-NMR (400 MHz, DMSO-d$_6$); δ (ppm) 1.11 (t, J=7.2 Hz, 3H), 1.33 (t, J=7.2 Hz, 3H), 2.38 (q, J=7.2 Hz, 2H), 3.20–3.25 (m, 2H), 3.32–3.39 (m, 4H), 3.52 (t, J=12.4 Hz, 2H), 3.62 (d, J=11.2 Hz, 2H), 7.58 (t, J=8.0 Hz, 1H), 7.73 (t, J=8.0 Hz, 1H), 7.75 (d, J=8.8 Hz, 2H), 7.96 (d, J=8.0 Hz, 1H), 8.03 (s, 1H), 8.10 (d, J=8.0 Hz, 1H), 8.15 (d, J=8.8 Hz, 2H), 10.10 (s, 1H).

MS(FAB) m/z 389 (M+H)$^+$.

Free compound:

$^1$H-NMR (400 MHz, CDCl$_3$); δ (ppm) 1.17 (t, J=7.2 Hz, 3H), 1.27 (t, J=7.2 Hz, 3H), 2.42 (t, J=7.2 Hz, 2H), 2.55 (q, J=7.2 Hz, 2H), 2.75 (t, J=4.4 Hz, 4H), 3.58 (t, J=4.4 Hz, 4H), 7.44 (ddd, J=8.4, 8.0, 1.2 Hz, 1H), 7.57 (ddd, J=8.4, 8.0, 1.2 Hz, 1H), 7.63 (d, J=8.4 Hz, 2H), 7.65 (s, 1H), 7.76 (d, J=8.0 Hz, 1H), 8.06 (d, J=8.4 Hz, 1H), 8.14 (d, J=8.4 Hz, 2H).

Example 70

Synthesis of 3-(4-Propylcarbonylaminophenyl]-1-(4-Ethylpiperazin-1-Yl)Isoquinoline Hydrochloride

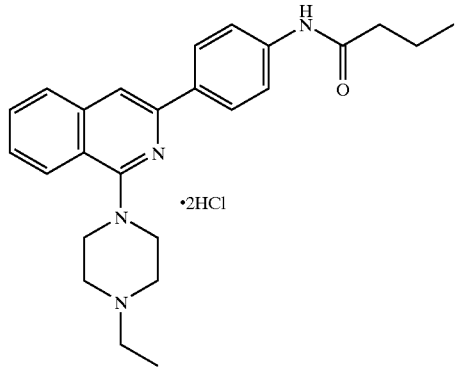

In the same manners sequentially as in Examples 161-2 and 20, the free compound of the title compound was obtained (604 mg, yield; 52%) from 1-bromo-4-propylcarbonylaminobenzene (4.13 g) and 3-bromo-1-(4-ethylpiperazin-1-yl)isoquinoline (913 mg). The free compound was converted into a hydrochloride in a conventional manner, to give the hydrochloride of the title compound as yellow crystals.

Hydrochloride:

m.p.; 170–172° C.

$^1$H-NMR (400 MHz, DMSO-d$_6$); δ (ppm) 0.94 (t, J=7.2 Hz, 3H), 1.34 (t, J=7.2 Hz, 3H), 1.59–1.79 (m, 2H), 2.35 (q, J=7.2 Hz, 2H), 3.20–3.25 (m, 2H), 3.30–3.40 (m, 4H), 3.54–3.63 (m, 4H), 4.00 (d, J=13.6 Hz, 2H), 7.59 (t, J=8.0 Hz, 1H), 7.73 (t, J=8.0 Hz, 1H), 7.78 (d, J=8.8 Hz, 2H), 7.96 (d, J=8.0 Hz, 1H), 8.02 (s, 1H), 8.10 (d, J=8.0 Hz, 1H), 8.14 (d, J=8.8 Hz, 2H), 10.40 (s, 1H).

MS(FAB) m/z 403 (M+H)$^+$.

Free compound:

$^1$H-NMR (400 MHz, CDCl$_3$); δ (ppm) 1.03 (t, J=7.2 Hz, 3H), 1.17 (t, J=7.2 Hz, 3H), 1.72–1.82 (m, 2H), 2.37 (t, J=7.2 Hz, 2H), 2.56 (q, J=7.2 Hz, 2H), 2.76 (t, J=4.0 Hz, 4H), 3.58 (t, J=4.0 Hz, 4H), 7.45 (dt, J=8.0, 1.2 Hz, 1H), 7.57 (dt, J=8.0, 1.2 Hz, 1H), 7.63 (d, J=8.4 Hz, 2H), 7.65 (s, 1H), 7.77 (d, J=8.0 Hz, 1H), 8.06 (d, J=8.0 Hz, 1H), 8.14 (d, J=8.4 Hz, 2H).

Example 71

Synthesis of 3-(4-Ethylsulfonylaminophenyl)-1-(4-Ethylpiperazin-1-Yl)Isoquinoline Hydrochloride

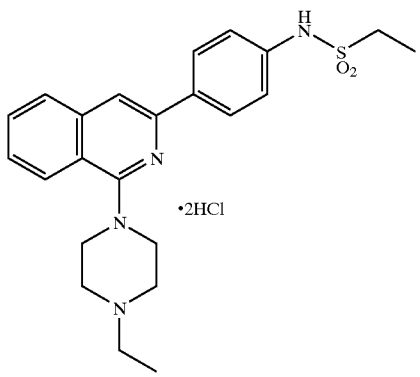

In the same manners sequentially as in Examples 161-2 and 20, the free compound of the title compound was obtained (542 mg, yield; 63%) from 1-bromo-4-ethylsulfonylaminobenzene (3.95 g) and 3-bromo-1-(4-ethylpiperazin-1-yl)isoquinoline (648 mg). The free compound was converted into a hydrochloride in a conventional manner, to give the hydrochloride of the title compound as yellow crystals.
Hydrochloride:
m.p.; 198–201° C.
$^1$H-NMR (400 MHz, DMSO-$d_6$); δ (ppm) 1.22 (t, J=7.2 Hz, 3H), 1.34 (t, J=7.2 Hz, 3H), 3.15 (q, J=7.2 Hz, 2H), 3.18–3.24 (m, 2H), 3.30–3.39 (m, 2H), 3.53–3.62 (m, 4H), 4.00 (d, J=13.6 Hz, 2H), 7.36 (d, J=8.8 Hz, 2H), 7.59 (dt, J=8.0, 1.2 Hz, 1H), 7.74 (dt, J=8.0, 1.2 Hz, 1H), 7.97 (d, J=8.0 Hz, 1H), 8.02 (s, 1H), 8.10 (d, J=8.0 Hz, 1H), 8.16 (d, J=8.8 Hz, 2H), 10.05 (s, 1H).
MS(FAB) m/z 425 (M+H)$^+$.
Free compound:
$^1$H-NMR (400 MHz, CDCl$_3$); δ (ppm) 1.18 (t, J=7.2 Hz, 3H), 1.39 (t, J=7.2 Hz, 3H), 2.56 (q, J=7.2 Hz, 2H), 2.77 (br, 4H), 3.18 (q, J=7.2 Hz, 2H), 3.58 (br, 4H), 7.32 (d, J=8.8 Hz, 2H), 7.46 (ddd, J=8.4, 8.0, 1.2 Hz, 1H), 7.59 (ddd, J=8.4, 8.0, 1.2 Hz, 1H), 7.65 (s, 1H), 7.78 (d, J=8.0 Hz, 1H), 8.07 (d, J=8.4 Hz, 1H), 8.15 (d, J=8.8 Hz, 2H).

Example 72

Synthesis of 3-(4-Propylsulfonylaminophenyl)-1-(4-Ethylpiperazin-1-Yl)Isoquinoline Hydrochloride

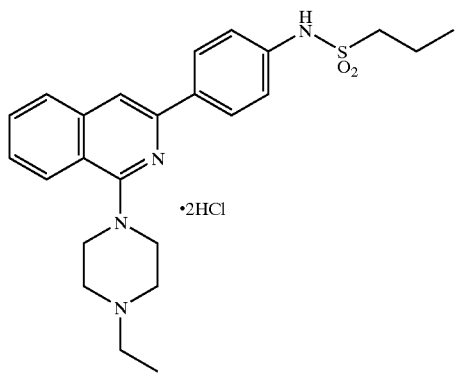

·2HCl

In the same manners sequentially as in Examples 161-2 and 20, the free compound of the title compound was obtained (1.31 g, yield; 95%) from 1-bromo-4-propylsulfonylaminobenzene (4.69 g) and 3-bromo-1-(4-ethylpiperazin-1-yl)isoquinoline (1.0 g). The free compound was converted into a hydrochloride in a conventional manner, to give the hydrochloride of the title compound as yellow crystals.
Hydrochloride:
m.p.; 163–165° C.
$^1$H-NMR (400 MHz, DMSO-$d_6$); δ (ppm) 0.95 (t, J=7.2 Hz, 3H), 1.34 (t, J=7.2 Hz, 3H), 1.66–1.76 (m, 2H), 3.11–3.15 (m, 2H), 3.20–3.25 (m, 2H), 3.30–3.40 (m, 2H), 3.51–3.62 (m, 4H), 4.00 (d, J=12.8 Hz, 2H), 7.35 (d, J=8.8 Hz, 2H), 7.60 (t, J=8.0 Hz, 1H), 7.74 (t, J=8.0 Hz, 1H), 7.96 (d, J=8.0 Hz, 1H), 8.02 (s, 1H), 8.11 (d, J=8.0 Hz, 1H), 8.16 (d, J=8.8 Hz, 2H).
MS(FAB) m/z 439 (M+H)$^+$.
Free compound:
$^1$H-NMR (400 Hz, CDCl$_3$); δ (ppm) 0.91 (t, J=7.2 Hz, 3H), 1.18 (t, J=7.2 Hz, 3H), 1.38–1.48 (m, 2H), 2.56 (q, J=7.2 Hz, 2H), 2.77 (br, 4H), 3.11–3.16 (m, 2H), 3.59 (br, 4H), 7.31 (t, J=8.8 Hz, 1H), 7.47 (ddd, J=8.4, 8.0, 1.2 Hz, 1H), 7.59 (ddd, J=8.4, 8.0, 1.2 Hz, 1H), 7.66 (s, 1H), 7.79 (d, J=8.0 Hz, 1H), 8.08 (d, J=8.4 Hz, 1H), 8.16 (d, J=8.4 Hz, 2H).

Example 73

Synthesis of 3-(4-Butylsulfonylaminophenyl)-1-(4-Ethylpiperazin-1-Yl)Isoquinoline Hydrochloride

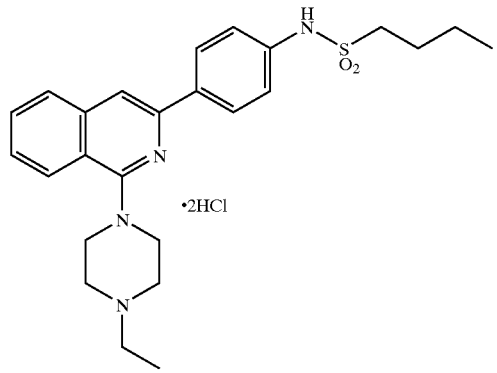

·2HCl

In the same manners sequentially as in Examples 161-2 and 20, the free compound of the title compound was obtained (828 mg, yield; 94%) from 1-bromo-4-butylsulfonylaminobenzene (3.51 g) and 3-bromo-1-(4-ethylpiperazin-1-yl)isoquinoline (602 mg). The free compound was converted into a hydrochloride in a conventional manner, to give the hydrochloride of the title compound as yellow crystals.

Hydrochloride:

m.p.; 160–163° C.

$^1$H-NMR (400 MHz, DMSO-$d_6$); δ (ppm) 0.84 (t, J=7.2 Hz, 3H), 1.32–1.39 (m, 5H), 1.64–1.70 (m, 2H), 3.13–3.17 (m, 2H), 3.22–3.24 (m, 2H), 3.33–3.38 (m, 2H), 3.53–3.62 (m, 4H), 4.00 (d, J=13.2 Hz, 2H), 7.35 (d, J=8.4 Hz, 2H), 7.60 (t, J=8.0 Hz, 1H), 7.74 (t, J=8.0 Hz, 1H), 7.97 (d, J=8.0 Hz, 1H), 8.03 (s, 1H), 8.10 (d, J=8.0 Hz, 1H), 8.17 (d, J=8.4 Hz, 2H).

MS(FAB) m/z 453 (M+H)$^+$.

Free compound:

$^1$H-NMR (400 MHz, CDCl$_3$); δ (ppm) 1.03 (t, J=7.6 Hz, 3H), 1.16–1.23 (m, 5H), 1.83–1.94 (m, 2H), 2.56 (q, J=7.2 Hz, 2H), 2.76 (br, 4H), 3.01–3.13 (m, 2H), 3.59 (br, 4H), 7.31 (d, J=8.4 Hz, 2H), 7.47 (ddd, J=8.4, 8.0, 1.2 Hz, 1H), 7.59 (ddd, J=8.4, 8.0, 1.2 Hz, 1H), 7.66 (s, 1H), 7.79 (d, J=8.0 Hz, 1H), 8.07 (d, J=8.4 Hz, 1h), 8.15 (d, J=8.4 Hz, 2H).

Example 74

Synthesis of 3-(4-Sulfonamidephenyl)-1-(4-Ethylpiperazin-1-Yl)Isoquinoline Hydrochloride

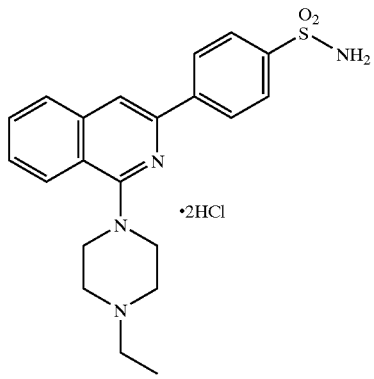

In the same manners sequentially as in Examples 161-2 and 20, the free compound of the title compound was obtained (49 mg, yield; 7%) from 1-bromo-4-benzenesulfonamide (1.55 g) and 3-bromo-1-(4-ethylpiperazin-1-yl)isoquinoline (386 mg). The free compound was converted into a hydrochloride in a conventional manner, to give the hydrochloride of the title compound as yellow crystals.

Hydrochloride:
$^1$H-NMR (400 MHz, DMSO-d$_6$); δ (ppm) 1.33 (t, J=7.2 Hz, 3H), 3.21–3.32 (m, 2H), 3.36–3.42 (m, 2H), 3.53 (t, J=6.8 Hz, 2H), 3.63 (d, J=12.0 Hz, 2H), 4.05 (d, J=13.6 Hz, 2H), 7.45 (s, 2H), 7.67 (t, J=8.0 Hz, 1H), 7.79 (t, J=8.0, Hz, 1H), 7.95 (d, J=8.4 Hz, 2H), 8.02 (d, J=8.0 Hz, 1H), 8.15 (d, J=8.0 Hz, 1H), 8.23 (s, 1H), 8.38 (d, J=8.4 Hz, 2H).

Free compound:
$^1$H-NMR (400 MHz, DMSO-d$_6$); δ (ppm) 1.08 (t, J=7.2 Hz, 3H), 2.46 (q, J=7.2 Hz, 2H), 2.68 (br, 4H), 3.47 (br, 43H), 7.42 (s, 2H), 7.62 (ddd, J=8.4, 8.0, 1.2 Hz, 1H), 7.74 (ddd, J=8.4, 8.0, 1.2 Hz, 1H), 7.94 (d, J=8.4 Hz, 2H), 7.97 (d, J=8.0 Hz, 1H), 8.09 (d, J=8.0 Hz, 1H), 8.11 (s, 1H), 8.37 (d, J=8.4 Hz, 2H).

Example 75

Synthesis of 3-[(4-Morpholinyl)Sulfonylphenyl]-1-(4-Ethylpiperazin-1-Yl)Isoquinoline Hydrochloride

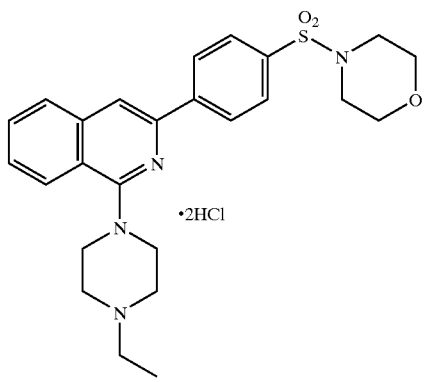

In the same manners sequentially as in Examples 161-2 and 20, the free compound of the title compound was obtained (620 mg, yield; 49%) from 4-(morpholinylsulfonyl)bromobenzene (2.63 g) and 3-bromo-1-(4-ethylpiperazin-1-yl)isoquinoline (872 mg). The free compound was converted into a hydrochloride in a conventional manner, to give the hydrochloride of the title compound as yellow crystals.

Hydrochloride:
MS (FAB) m/z 467 (M+H)$^+$.

Free compound:
$^1$H-NMR (400 MHz, CDCl$_3$); δ (ppm) 1.18 (t, J=7.2 Hz, 3H), 2.57 (q, J=7.2 Hz, 2H), 2.77 (t, J=4.4 Hz, 4H), 3.06 (t, J=4.8 Hz, 4H), 3.61 (t, J=4.4 Hz, 43H), 3.76 (t, J=4.8 Hz, 4H), 7.53 (ddd, J=8.4, 8.0, 1.2 Hz, 1H), 7.64 (ddd, J=8.4, 8.0, 1.2 Hz, 1H), 7.77 (s, 1H), 7.84 (d, J=8.8 Hz, 2H), 7.85 (d, J=8.0 Hz, 1H), 8.10 (d, J=8.4 Hz, 1H), 8.34 (d, J=8.8 Hz, 2H).

Example 76

Synthesis of 3-[(4-Thiomorpholinyl)Sulfonylphenyl]-1-(4-Ethylpiperazin-1-Yl)Isoquinoline Hydrochloride

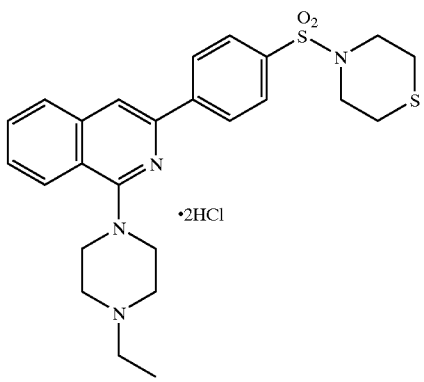

In the same manners sequentially as in Examples 161-2 and 20, the free compound of the title compound was obtained (550 mg, yield; 38%) from 4-(thiomorpholinylsulfonyl)bromobenzene (5.5 g) and 3-bromo-1-(4-ethylpiperazin-1-yl)isoquinoline (953 mg). The free compound was converted into a hydrochloride in a conventional manner, to give the hydrochloride of the title compound as yellow crystals.

Hydrochloride:
m.p.; 268–270° C. (decomp.)
$^1$H-NMR (400 MHz, DMSO-d$_6$); δ (ppm) 1.34 (t, J=7.2 Hz, 3H), 2.69 (t, J=4.8 Hz, 4H), 3.18–3.20 (m, 6H), 3.32–3.40 (m, 2H), 3.55–3.64 (m, 4H), 4.03 (d, J=13.6 Hz, 2H), 7.68 (t, J=8.0 Hz, 1H), 7.80 (t, J=8.0, Hz, 1H), 7.88 (d, J=8.8 Hz, 2H) 8.05 (d, J=8.0 Hz, 1H), 8.16 (d, J=8.0 Hz, 1H), 8.28 (s, 1H), 8.46 (d, J=8.8 Hz, 2H).

MS(FAB) m/z 483 (M+H)$^+$

Free compound:
$^1$H-NMR (400 MHz, CDCl$_3$); δ (ppm) 1.19 (t, J=7.2 Hz, 3H), 2.58 (q, J=7.2 Hz, 2H), 2.72–2.74 (m, 2H), 2.79 (br, 4H), 3.38–3.41 (m, 2H), 3.62 (br, 4H), 7.53 (dt, J=8.0, 1.2 Hz, 1H), 7.64 (dt, J=8.0, 1.2 Hz, 1H), 7.70 (s, 1H), 7.82 (d, J=8.8 Hz, 2H), 7.83 (d, J=8.0 Hz, 1H), 8.10 (d, J=8.0 Hz, 1H), 8.32 (d, J=8.8 Hz, 2H).

Example 77

Synthesis of 3-[(1,1-Dioxythiomorpholinyl)Sulfonylphenyl]-1-(4-Ethylpiperazin-1-Yl)Isoquinoline Hydrochloride

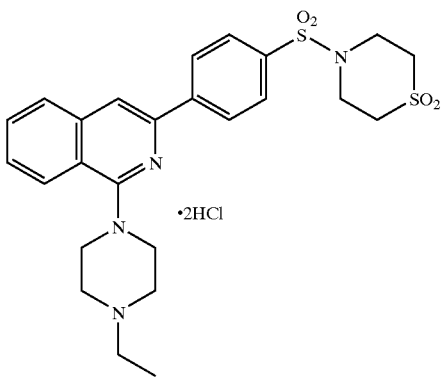

In the same manners sequentially as in Examples 161-2 and 20, the free compound of the title compound was obtained (673 mg, yield; 52%) from 1-bromo-4-(1,1-dioxythiomorpholinyl)sulfonylbenzene (3.59 g) and 3-bromo-1-(4-ethylpiperazin-1-yl)isoquinoline (811 mg). The free compound was converted into a hydrochloride in a conventional manner, to give the hydrochloride of the title compound as yellow crystals.

Hydrochloride:

m.p.; 198–200° C.

$^1$H-NMR (400 MHz, DMSO-$d_6$); δ (ppm) 1.34 (t, J=7.2 Hz, 3H), 3.22–3.25 (m, 2H), 3.29–3.40 (m, 6H), 3.51–3.55 (m, 6H), 3.61 (t, J=11.6 Hz, 2H), 4.04 (d, J=13.6 Hz, 2H), 7.69 (dt, J=8.0, 1.2 Hz, 1H), 7.81 (dt, J=8.0, 1.2 Hz, 1H), 7.95 (d, J=8.4 Hz, 2H), 8.05 (d, J=8.0 Hz, 1H), 8.16 (d, J=8.0 Hz, 1H), 8.30 (s, 1H), 8.49 (d, J=8.4 Hz, 2H).

MS(FAB) m/z 515 (M+H)$^+$.

Free compound:

$^1$H-NMR (400 MHz, DMSO-$d_6$); δ (ppm) 1.10 (br-t, 3H), 2.66 (br, 2H), 3.29–3.31 (m, 4H), 3.34 (br, 4H), 3.49 (br, 8H), 7.64 (t, J=8.0 Hz, 1H), 7.76 (t, J=8.0 Hz, 1H), 7.94 (d, J=8.8 Hz, 2H), 8.00 (d, J=8.0 Hz, 1H), 8.10 (d, J=8.0 Hz, 1H), 8.19 (s, 1H), 8.48 (d, J=8.8 Hz, 2H).

Example 78

Synthesis of 3-(4-Ethylsulfonylaminomethylphenyl)-1-(4-Ethylpiperazin-1-Yl)Isoquinoline Hydrochloride

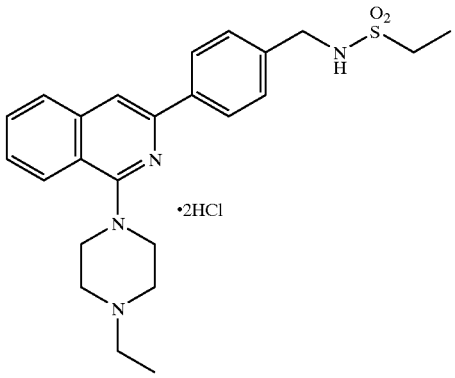

In the same manners sequentially as in Examples 161-2 and 20, the free compound of the title compound was obtained (655 mg, yield; 49%) from 1-bromo-4-ethylsulfonylaminobenzene (2.73 g) and 3-bromo-1-(4-ethylpiperazin-1-yl)isoquinoline (975 mg). The free compound was converted into a hydrochloride in a conventional manner, to give the hydrochloride of the title compound as yellow crystals.

Hydrochloride:

MS (FAB) m/s 439 (M+H)$^+$.

Free compound:

$^1$H-NMR (400 MHz, CDCl$_3$); δ (ppm) 1.18 (t, J=7.6 Hz, 3H), 1.35 (t, J=7.2 Hz, 3H), 2.56 (q, J=7.2 Hz, 2H), 2.77 (br, 4H), 3.00 (q, J=7.6 Hz, 2H), 3.59 (br, 4H), 4.37 (d, J=6.0 Hz, 2H), 4.59 (br, 1H), 7.45 (d, J=8.4 Hz, 2H), 7.48 (t, J=8.4 Hz, 1H), 7.60 (t, J=8.4 Hz, 1H), 7.70 (s, 1H), 7.80 (d, J=8.4 Hz, 1H), 8.09 (d, J=8.4 Hz, 1H), 8.18 (d, J=8.4 Hz, 2H).

Example 79

Synthesis of 3-(4-Ethylsulfonylaminoethylphenyl)-1-(4-Ethylpiperazin-1-Yl)Isoquinoline Hydrochloride

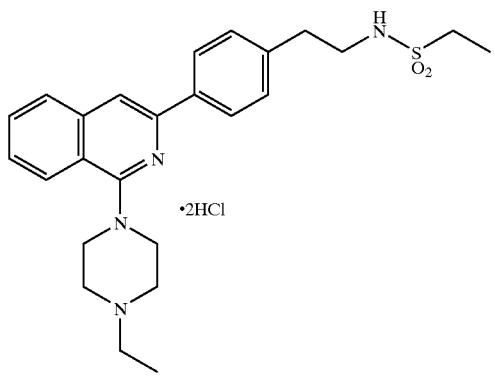

In the same manners sequentially as in Examples 161-2 and 20, the free compound of the title compound was obtained (1.22 g, yield; 76%) from 1-bromo-4-ethylsulfonylaminoethylbenzene (3.54 g) and 3-bromo-1-(4-ethylpiperazin-1-yl)isoquinoline (1.14 g). The free compound was converted into a hydrochloride in a conventional manner, to give the hydrochloride of the title compound as yellow crystals.

Hydrochloride:

m.p.; 194–197° C.

$^1$H-NMR (400 MHz, DMSO-d$_6$); δ (ppm) 1.16 (t, J=7.2 Hz, 3H), 1.34 (t, J=7.2 Hz, 3H), 2.84 (t, J=7.2 Hz, 2H), 2.97 (q, J=7.2 Hz, 2H), 3.19–3.24 (m, 4H), 3.33–3.39 (m, 2H), 3.56–3.63 (m, 4H), 4.00 (d, J=13.2 Hz, 2H), 7.38 (d, J=8.4 Hz, 2H), 7.61 (dt, J=8.0, 1.2 Hz, 1H), 7.75 (dt, J=8.0, 1.2 Hz, 1H), 7.99 (d, J=8.0 Hz, 1H), 8.07 (s, 1H), 8.11 (d, J=8.0 Hz, 1H), 8.13 (d, J=8.4 Hz, 2H).

MS(FAB) m/z 453 (M+H)$^+$.

Free compound:

$^1$H-NMR (400 MHz, CDCl$_3$); δ (ppm) 1.17 (t, J=7.2 Hz, 3H), 1.28 (t, J=7.6 Hz, 3H), 2.55 (q, J=7.2 Hz, 2H), 2.76 (br, 4H), 2.92 (t, J=6.4 Hz, 2H), 2.96 (q, J=7.6 Hz 3.59 (br, 4H), 4.36 (t, J=6.4 Hz, 1H), 7.30 (d, J=8.4 Hz, 2H), 7.46 (ddd, J=8.4, 8.0, 1.2 Hz, 1H), 7.58 (ddd, J=8.4, 8.0, 1.2 Hz, 1H), 7.67 (s, 1H), 7.78 (d, J=8.0 Hz, 1H), 8.07 (d, J=8.4 Hz, 1H), 8.12 (d, J=8.4 Hz, 2H).

Example 80

Synthesis of 3-(4-Ethylaminosulfonylmethylphenyl)-1-(4-Ethylpiperazin-1-Yl)Isoquinoline Hydrochloride

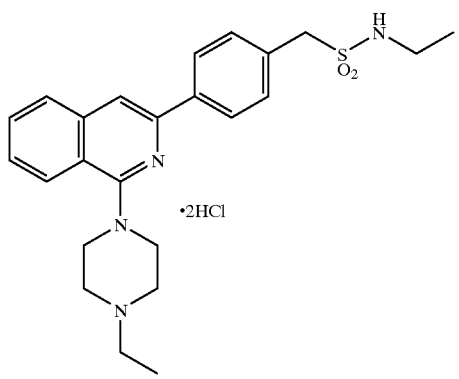

In the same manners sequentially as in Examples 161-2 and 20, the free compound of the title compound was obtained (449 mg, yield; 60%) from 1-bromo-4-ethylaminosulfonylmethylbenzene (1.28 g) and 3-bromo-1-(4-ethylpiperazin-1-yl)isoquinoline (550 mg). The free compound was converted into a hydrochloride in a conventional manner, to give the hydrochloride of the title compound as yellow crystals.

Hydrochloride:

m.p.; 154–156° C.

$^1$H-NMR (400 MHz, DMSO-d$_6$); δ (ppm) 1.03 (t, J=7.2 Hz, 3H), 1.31 (t, J=7.2 Hz, 3H), 2.90–3.00 (m, 2H), 3.18–3.25 (m, 2H), 3.30–3.40 (m, 2H), 3.49–3.62 (m, 4H), 3.99 (d, J=13.6 Hz, 2H), 4.37 (s, 2H), 7.09 (br, 1H), 7.48 (d, J=8.4 Hz, 2H), 7.60 (t, J=8.0 Hz, 1H), 7.74 (t, J=8.0 Hz, 1H), 7.98 (d, J=8.0 Hz, 1H), 8.10 (s, 1H), 8.11 (d, j=8.0 Hz, 1H), 8.18 (d, J=8.4 Hz, 2H).

MS(FAB) m/z 439 (M+H)$^+$.

Free compound:

$^1$H-NMR (440 HMz, CDCl$_3$); δ (ppm) 1.14–1.20 (m, 6H), 2.57 (q, J=7.2 Hz, 2H), 2.78 (br, 4H), 3.10 (dd, J=7.2, 6.0 Hz, 2H), 3.60 (br, 4H), 4.07 (t, J=6.0 Hz, 1H), 4.31 (s, 2H), 7.48 (ddd, J=8.4, 8.0, 1.2 Hz, 1H), 7.49 (d, J=8.4 Hz, 2H), 7.60 (ddd, J=8.4, 8.0, 1.2 Hz, 1H), 7.71 (s, 1H), 7.80 (d, J=8.0 Hz, 1H), 8.08 (d, J=8.4 Hz, 1H), 8.19 (d, J=8.4 Hz, 2H).

Example 81

Synthesis of 3-(4-Propylaminosulfonylmethylphenyl)-1-(4-Ethylpiperazin-1-Yl)Isoquinoline Hydrochloride

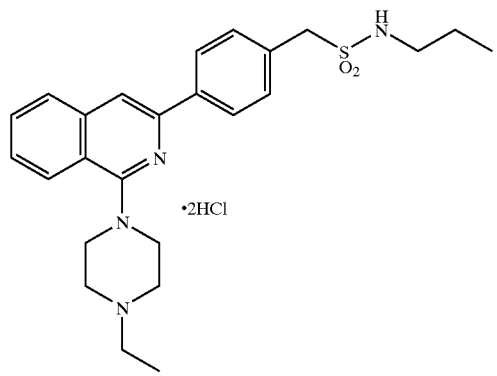

In the same manners sequentially as in Examples 161-2 and 20, the free compound of the title compound was obtained (307 mg, yield; 28%) from 1-bromo-4-propylaminosulfonylmethylbenzene (1.62 g) and 3-bromo-1-(4-ethylpiperazin-1-yl)isoquinoline (766 mg). The free compound was converted into a hydrochloride in a conventional manner, to give the hydrochloride of the title compound as yellow crystals.

Hydrochloride:

m.p.: 194–197° C.

$^1$H-NMR (400 MHz,DMSO-d$_6$); δ (ppm) 0.83(t,J=7.2 Hz,3H), 1.31(t,J=7.2 Hz,3H), 1.38–1.48(m,2H), 2.86–2.90 (m,2H), 3.18–3.25(m,2H), 3.31–3.37(m,2H), 3.50–3.61(m, 4H), 3.97–4.02(m,2H), 4.37(s,2H), 7.11(br,1H), 7.48(d,J= 8.0 Hz,2H), 7.60(t,J=8.0 Hz,1H), 7.74(t,J=8.0 Hz,1H), 7.98 (d,J=8.0 Hz,1H), 8.09(s,1H), 8.10(d,J=8.0 Hz,1H), 8.18(d, J=8.0 Hz,2H).

MS(FAB) m/z 453(M+H)$^+$.

Free compound:

$^1$H-NMR (400 MHz,CDCl$_3$); δ (ppm) 0.91(t,J=7.2 Hz,3H), 1.19(t,J=7.2 Hz,3H), 1.54(q,J=7.2 Hz,2H), 2.58(q, J=7.2 Hz,2H), 2.79(br,4H), 3.02(q,J=7.2 Hz,2H), 3.62(br, 4H), 4.08(t,J=6.0 Hz,1H), 4.32(s,2H), 7.48(ddd,J=8.4,8.0, 1.2 Hz,1H), 7.49(d,J=8.4 Hz,2H), 7.61(ddd,J=8.4,8.0,1.2 Hz,1H), 7.71(s,1H), 7.80(d,J=8.0 Hz,1H), 8.08(d,J=8.4 Hz,1H), 8.19(d,J=8.4 Hz,2H).

Example 82

Synthesis of 3-[4-(N,N-diethylamino)sulfonylmethylphenyl]-1-(4-ethylpiperazin-1-yl)isoquinoline Hydrochloride

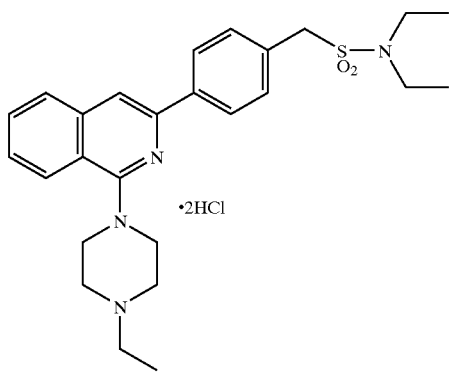

In the same manners sequentially as in Examples 161-2 and 20, the free compound of the title compound was obtained (101 mg, yield: 17%) from 1-bromo-4-N,N-diethylaminosulfonylmethylbenzene (819 mg) and 3-bromo-1-(4-ethylpiperazin-1-yl)isoquinoline (530 mg). The free compound was converted into a hydrochloride in a conventional manner, to give the hydrochloride of the title compound as yellow crystals.

Hydrochloride:

$^1$H-NMR (400 MHz,DMSO-$d_6$); δ (ppm) 1.04(t,J=7.2 Hz,6H), 1.31(t,J=7.2 Hz,3H), 3.10(q,J=7.2 Hz,4H), 3.18–3.25(m,2H), 3.30–3.38(m,2H), 3.51–3.61(m,4H), 4.00 (d,J=13.2 Hz,2H), 4.43(s,2H), 7.50(d,J=8.4 Hz,2H), 7.60(t, J=8.0 Hz,1H), 7.74(t,J=8.0 Hz,1H), 7.98(d,J=8.0 Hz,1H), 8.10(d,J=8.0 Hz,1H), 8.11(s,1H), 8.20(d,J=8.4 Hz,2H).

MS(FAB) m/z 456(M+H)$^+$.

Free compound:

$^1$H-NMR (400 MHz,CDCl$_3$); δ (ppm) 1.12(t,J=7.2 Hz,6H), 1.19(t,J=7.2 Hz,3H), 2.58(q,J=7.2 Hz,2H), 2.78(br, 4H), 3.13(q,J=7.2 Hz,4H), 3.61(br,4H), 4.27(s,2H), 7.46–7.50(m,1H), 7.48(d,J=8.0 Hz,2H), 7.06(t,J=8.0 Hz,1H), 7.72(s,1H), 7.80(d,J=8.0 Hz,1H), 8.08(d,J=8.0 Hz,1H), 8.19(d,J=8.0 Hz,2H).

Example 83

Synthesis of 3-[4-(Tetrahydropyran-4-yl)phenyl]-1-(4-ethylpiperazin-1-yl)isoquinoline Hydrochloride

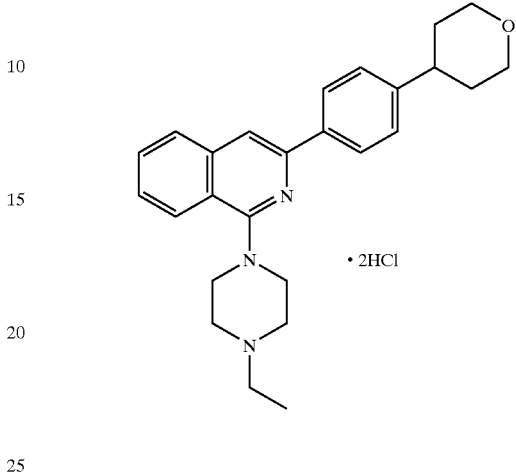

Methanol (80 ml) and platinum oxide (100 mg) were added to 3-[4-(5,6-dihydro-2H-pyran-4-yl)phenyl]-1-(4-ethylpiperazin-1-yl)isoquinoline (2.3 g), and the mixture was reacted at room temperature for 2 hr. The reaction solution was filtered through Celite, and then evaporated. The resulting residue was basified with a 1N aqueous solution of sodium hydroxide, and then partitioned between ethyl acetate and water. The resulting organic layer was washed with water, dried and concentrated. Then, the resulting residue was purified by silica gel column chromatography (hexane/ethyl acetate system), to give an oil (905 mg, yield: 47%). The oil was converted into a hydrochloride in a conventional manner, to give the hydrochloride of the title compound as yellow crystals.

Hydrochloride:

m.p.: 148–150° C.

$^1$H-NMR (400 MHz,DMSO-$d_6$); δ (ppm) 1.33(t,J=7.2 Hz,3H), 1.70–1.76(m,4H), 2.85(br,1H), 3.20–3.28(m,2H), 3.30–3.38(m,2H), 3.44–3.56(m,4H), 3.63(d,J=11.6 Hz,2H), 3.95–4.01(m,4H), 7.40(d,J=8.4 Hz,2H), 7.60(t,J=8.4 Hz,1H), 7.74(t,J=8.4 Hz,1H), 7.99(d,J=8.4 Hz,1H), 8.06(s, 1H), 8.11(d,J=8.4 Hz,1H), 8.14(d,J=8.4 Hz,2H).

MS(FAB) m/z 402(M+H)$^+$.

Free compound:

$^1$H-NMR (400 MHz,CDCl$_3$); δ (ppm) 1.18(t,J=7.2 Hz,3H), 1.69–1.93(m,4H), 2.55(q,J=7.2 Hz,2H), 2.76(br, 4H), 2.75–2.88(m,1H), 3.53–3.59(m,2H), 3.59(br,4H), 4.09–4.13(m,2H), 7.33(d,J=8.4 Hz,2H), 7.45(ddd,J=8.4,8.0, 1.2 Hz,1H), 7.58(ddd,J=8.4,8.0,1.2 Hz,1H), 7.67(s,1H), 7.78 (d,J=8.0 Hz,1H), 8.07(d,J=8.4 Hz,1H), 8.12(d,J=8.4 Hz,2H).

Example 84

Synthesis of 3-[4-(5,6-Dihydro-2H-pyran-4-yl)phenyl]-1-(4-ethylpiperazin-1-yl)isoquinoline Hydrochloride

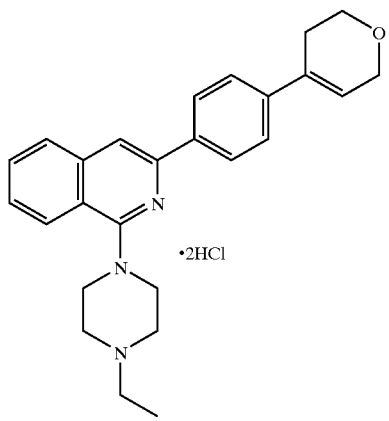

In the same manners sequentially as in Examples 161-2 and 20, the free compound of the title compound was obtained (443 mg, yield: 58%) from 1-bromo-(5,6-dihydro-2H-pyran-4-yl)benzene (2.3 g) and 3-bromo-1-(4-ethylpiperazin-1-yl)isoquinoline (800 mg). The free compound was converted into a hydrochloride in a conventional manner, to give the hydrochloride of the title compound as yellow crystals.

Hydrochloride:

m.p.: 170–172° C.

$^1$H-NMR (400 MHz,DMSO-$d_6$); δ (ppm) 1.33(t,J=7.2 Hz,3H), 3.20–3.38(m,2H), 3.32–3.40(m,2H), 3.54(t,J=13.6 Hz,4H), 3.63(d,J=12.0 Hz,2H), 3.86(t,J=5.6 Hz,2H), 4.01(d,J=14.0 Hz,2H), 4.27(br,2H), 6.38(br,1H), 7.60(d,J=8.8 Hz,2H), 7.61(t,J=8.0 Hz,1H), 7.76(t,J=8.0 Hz,1H), 7.99(d,J=8.0 Hz,1H), 8.11(s,1H), 8.13(d,J=8.0 Hz,1H), 8.20(d,J=8.8 Hz,2H).

MS(FAB) m/z 400(M+H)$^+$.

Free compound:

$^1$H-NMR (400 MHz,CDCl$_3$); δ (ppm) 1.17(t,J=7.2 Hz,3H), 2.52–2.58(m,2H), 2.54(q,J=7.2 Hz,2H), 2.75(br,4H), 3.59(br,4H), 3.95(t,J=5.6 Hz,2H), 4.35(t,J=2.8 Hz,2H), 6.30(br,1H), 7.45(ddd,J=8.4,8.0,1.2 Hz,1H), 7.48(d,J=8.8 Hz,2H), 7.57(ddd,J=8.4,8.0,1.2 Hz,1H), 7.68(s,1H), 7.77(d,J=8.0 Hz,1H), 8.07(d,J=8.0 Hz,1H), 8.14(d,J=8.8 Hz,2H).

Example 85

Synthesis of 3-(4-Ethylcarbonylaminomethylphenyl)-1-(4-ethylpiperazin-1-yl)isoquinoline Hydrochloride

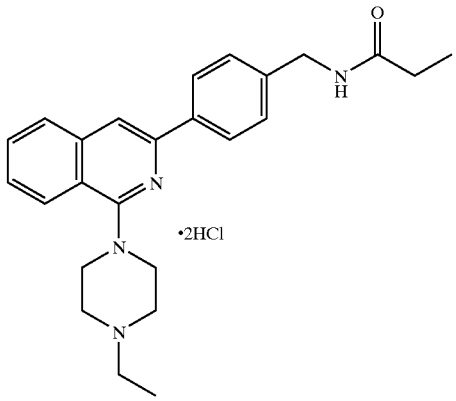

In the same manners sequentially as in Examples 161-2 and 20, the free compound of the title compound was obtained (608 mg, yield: 59%) from 1-bromo-4-ethylcarbonylaminomethylbenzene (2.31 g) and 3-bromo-1-(4-ethylpiperazin-1-yl)isoquinoline (808 mg). The free compound was converted into a hydrochloride in a conventional manner, to give the hydrochloride of the title compound as yellow crystals.

Hydrochloride:

m.p.: 171–174° C.

$^1$H-NMR (400 MHz,DMSO-$d_6$); δ (ppm) 1.05(t,J=7.6 Hz,3H), 1.33(t,J=7.2 Hz,3H), 2.17(q,J=7.6 Hz,2H), 3.15–3.28(m,2H), 3.30–3.38(m,2H), 3.53(t,J=12.8 Hz,2H), 3.61(d,J=11.2 Hz,2H), 3.99(d,J=12.8 Hz,2H), 4.32(d,J=6.0 Hz,2H), 7.38(d,J=8.4 Hz,2H), 7.61(t,J=8.0 Hz,1H), 7.74(t,J=8.0 Hz,1H), 7.99(d,J=8.0 Hz,1H), 8.07(s,1H), 8.11(d,J=8.0 Hz,1H), 8.15(d,J=8.4 Hz,2H), 8.37(t,J=6.0 Hz,1H).

MS(FAB) m/z 403 (M+H)$^+$.

Example 86

Synthesis of 3-(4-Propylcarbonylaminomethylphenyl)-1-(4-ethylpiperazin-1-yl)isoquinoline Hydrochloride

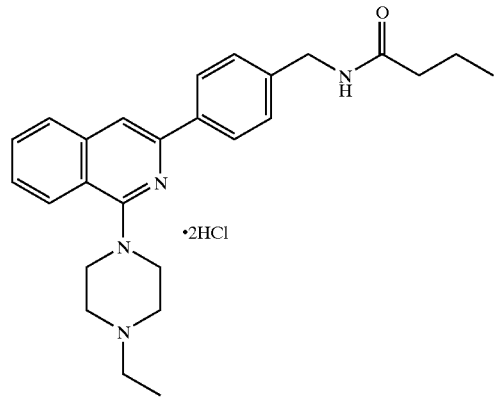

In the same manners sequentially as in Examples 161-2 and 20, the free compound of the title compound was obtained (777 mg, yield: 52%) from 1-bromo-4-propylcarbonylaminomethylbenzene (2.34 g) and 3-bromo-1-(4-ethylpiperazin-1-yl)isoquinoline (1.14 mg). The free compound was converted into a hydrochloride in a conventional manner, to give the hydrochloride of the title compound as yellow crystals.

Hydrochloride:

m.p.: 126–128° C.

¹H-NMR (400 MHz,DMSO-d₆); δ (ppm) 0.88(t,J=7.2 Hz,3H), 1.33(t,J=7.2 Hz,3H), 1.57(q,J=7.2 Hz,2H), 2.15(t, J=7.2 Hz,2H), 3.18–3.26(m,2H), 3.30–3.40(m,2H), 3.52–3.63(m,4H), 4.00(d,J=13.6 Hz,2H), 4.33(d,J=6.0 Hz,2H), 7.38(d,J=8.4 Hz,2H), 7.61(t,J=8.0 Hz,1H), 7.74(t, J=8.0 Hz,1H), 7.98(d,J=8.0 Hz,1H), 8.07(s,1H), 8.11(d,J= 8.0 Hz,1H), 8.12(d,J=8.4 Hz,2H), 8.40(t,J=6.0 Hz,1H).

MS(FAB) /mz 417 (M+H)⁺.

Free compound:

¹H-NMR (400 MHz,CDCl₃); δ (ppm) 0.98(t,J=7.2 Hz,3H), 1.18(t,J=7.2 Hz,3H), 1.67–1.76(m,2H), 2.22(t,J= 7.2 Hz,2H), 2.55(q,J=7.2 Hz,2H), 2.76(br,4H), 3.59(br,4H), 4.50(d,J=5.6 Hz,2H), 5.75(br,1H), 7.37(d,J=8.4 Hz,2H), 7.46(t,J=8.0 Hz,1H), 7.59(t,J=8.0 Hz,1H), 7.68(s,1H), 7.79 (d,J=8.0 Hz,1H), 8.08(d,J=8.0 Hz,1H), 8.14(d,J=8.4 Hz,2H).

Example 87

Synthesis of 3-(4-Ethylaminocarbonylmethylphenyl)-1-(4-ethylpiperazin-1-yl)isoquinoline Hydrochloride

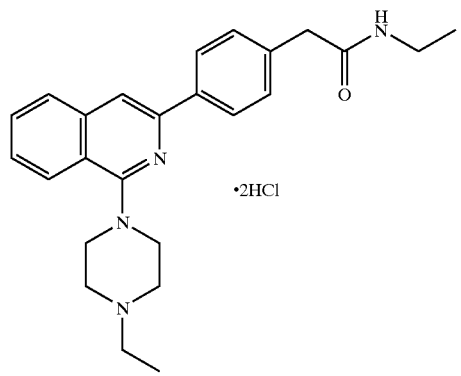

·2HCl

In the same manners sequentially as in Examples 161-2 and 20, the free compound of the title compound was obtained (587 mg, yield: 56%) from 1-bromo-4-ethylaminocarbonylmethylbenzene (1.29 g) and 3-bromo-1-(4-ethylpiperazin-1-yl)isoquinoline (830 mg). The free compound was converted into a hydrochloride in a conventional manner, to give the hydrochloride of the title compound as yellow crystals.

Hydrochloride:

m.p.: 143–145° C.

¹H-NMR (400 MHz,DMSO-d₆); δ (ppm) 1.03(t,J=7.2 Hz,3H), 1.33(t,J=7.2 Hz,3H), 3.06–3.12(m,2H), 3.18–3.26 (m,2H), 3.30–3.38(m,2H), 3.46(s,2H), 3.52–3.63(m,4H), 4.00(d,J=13.2 Hz,2H), 7.39(d,J=8.4 Hz,2H), 7.60(dt,J=8.0, 1.2 Hz,1H), 7.74(dt,J=8.0,1.2 Hz,1H), 7.98(d,J=8.0 Hz,1H), 8.07(s,1H), 8.11(d,J=8.0 Hz,1H), 8.12(d,J=8.4 Hz,2H).

MS(FAB) m/z 403(M+H)⁺.

Free compound:

¹H-NMR (400 MHz,CDCl₃); δ (ppm) 1.61(t,J=7.2 Hz,3H), 1.18(t,J=7.2 Hz,3H), 2.56(q,J=7.2 Hz,2H), 2.78(br, 4H), 3.23–3.29(m,2H), 3.60(br,4H), 3.64(s,2H), 5.40(br, 1H), 7.35(d,J=8.4 Hz,2H), 7.45(t,J=8.0 Hz,1H), 7.60(t,J=8.0 Hz,1H), 7.70(s,1H), 7.80(d,J=8.0 Hz,1H), 8.09(d,J=8.0 Hz,1H), 8.17(d,J=8.4 Hz,2H).

Example 88

Synthesis of 3-(4-Propylaminocarbonylmethylphenyl)-1-(4-ethylpiperazin-1-yl)isoquinoline Hydrochloride

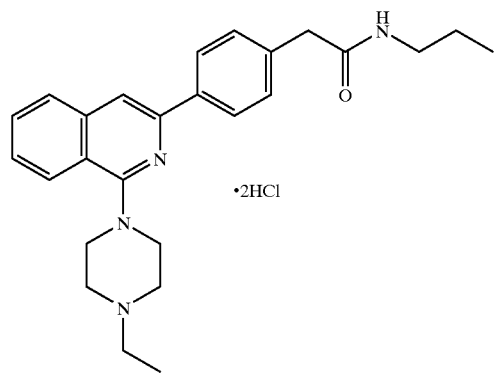

·2HCl

In the same manners sequentially as in Examples 161-2 and 20, the free compound of the title compound was obtained (517 mg, yield: 56%) from 1-bromo-4-propylaminocarbonylmethylbenzene (2.01 g) and 3-bromo-1-(4-ethylpiperazin-1-yl)isoquinoline (706 mg). The free compound was converted into a hydrochloride in a conventional manner, to give the hydrochloride of the title compound as yellow crystals.

Hydrochloride:

m.p.: 138–141° C.

¹H-NMR (400 MHz,DMSO-d₆); δ (ppm) 0.84(t,J=7.2 Hz,3H), 1.33(t,J=7.2 Hz,3H), 1.40–1.45(m,2H), 3.03(q,J= 7.2 Hz,2H), 3.22(t,J=7.2 Hz,2H), 3.30–3.40(m,2H), 3.47(s, 2H), 3.52–3.63(m,4H), 4.01(d,J=13.2 Hz,2H), 7.39(d,J=8.0 Hz,2H), 7.61(t,J=8.0 Hz,1H), 7.74(t,J=8.0 Hz,1H), 7.98(d, J=8.0 Hz,1H), 8.07(s,1H), 8.11(d,J=8.0 Hz,1H), 8.12(d,J= 8.0 Hz,2H).

MS(FAB) m/z 417 (M+H)⁺.

Free compound:

¹H-NMR (400 MHz,CDCl₃); δ (ppm) 0.84(t,J=7.2 Hz,3H), 1.18(t,J=7.2 Hz,3H), 1.40–1.50(m,2H), 2.56(q,J=

7.2 Hz,2H), 2.77(br,4H), 3.18(q,J=6.4 Hz,2H), 3.59(br,4H), 3.65(s,2H), 5.42(br,1H), 7.36(d,J=8.4 Hz,2H), 7.48(t,J=8.0 Hz,1H), 7.60(t,J=8.0 Hz,1H), 7.70(s,1H), 7.80(d,J=8.0 Hz,1H), 8.09(d,J=8.0 Hz,1H), 8.17(d,J=8.4 Hz,2H).

Example 89

Synthesis of 3-(4-Butylaminocarbonylmethylphenyl)-1-(4-ethylpiperazin-1-yl)isoquinoline Hydrochloride

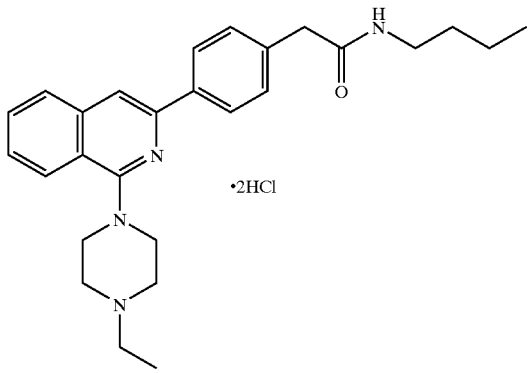

In the same manners sequentially as in Examples 161-2 and 20, the free compound of the title compound was obtained (615 mg, yield: 67%) from 1-bromo-4-butylaminocarbonylmethylbenzene (1.75 g) and 3-bromo-1-(4-ethylpiperazin-1-yl)isoquinoline (679 mg). The free compound was converted into a hydrochloride in a conventional manner, to give the hydrochloride of the title compound as yellow crystals.

Hydrochloride:

m.p.: 133–136° C.

$^1$H-NMR (400 MHz,DMSO-$d_6$); δ (ppm) 0.87(t,J=7.2 Hz,3H), 1.27–1.42(m,7H), 3.06(q,J=6.4 Hz,2H), 3.18–3.26 (m,2H), 3.30–3.38(m,2H), 3.47(s,2H), 3.51–3.63(m,4H), 4.00(d,J=13.6 Hz,2H), 7.39(d,J=8.4 Hz,2H), 7.61(t,J=8.0 Hz,1H), 7.74(t,J=8.0 Hz,1H), 7.95(d,J=8.0 Hz,1H), 8.06(s,1H), 8.11(d,J=8.0 Hz,1H), 8.12(d,J=8.4 Hz,2H).

MS(FAB) m/z 431(M+H)$^+$.

Free compound:

$^1$H-NMR (400 MHz,CDCl$_3$); δ (ppm) 0.88(t,J=7.2 Hz,3H), 1.18(t,J=7.2 Hz,3H), 1.32–1.42(m,2H), 1.37–1.44 (m,2H), 2.56(q,J=7.2 Hz,2H), 2.76(br,4H), 3.21(q,J=6.4 Hz,2H), 3.59(br,4H), 3.64(s,2H), 5.39(br,1H), 7.35(d,J=8.4 Hz,2H), 7.48(t,J=8.0 Hz,1H), 7.60(t,J=8.0 Hz,1H), 7.71(s,1H), 7.80(d,J=8.0 Hz,1H), 8.09(d,J=8.0 Hz,1H), 8.17(d,J=8.4 Hz,2H).

Example 90

Synthesis of 3-(4-Methylsulfonylmethylphenyl)-1-(4-ethylpiperazin-1-yl)isoquinoline Hydrochloride

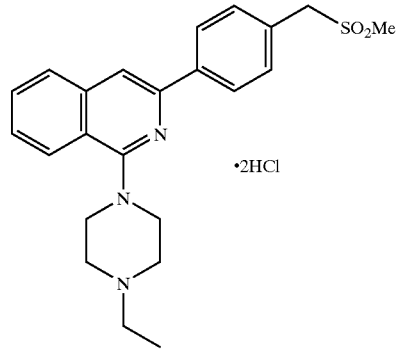

In the same manners sequentially as in Examples 161-2 and 20, the free compound of the title compound was obtained (430 mg, yield: 49%) from 1-bromo-4-methylsulfonylmethylbenzene (1.26 g) and 3-bromo-1-(4-ethylpiperazin-1-yl)isoquinoline (685 mg). The free compound was converted into a hydrochloride in a conventional manner, to give the hydrochloride of the title compound as yellow crystals.

Hydrochloride:

m.p.: 260–262° C.

$^1$H-NMR (400 MHz,DMSO-$d_6$); δ (ppm) 1.34(t,J=7.2 Hz,3H), 2.95(s,3H), 3.18–3.28(m,2H), 3.30–3.38(m,2H), 3.55–3.63(m,4H), 4.02(d,J=13.6 Hz,2H), 4.57(s,2H), 7.55 (d,J=8.4 Hz,2H), 7.63(t,J=8.0 Hz,1H), 7.76(t,J=8.0 Hz,1H), 8.00(d,J=8.0 Hz,1H), 8.13(d,J=8.0 Hz,1H), 8.13(s,1H), 8.23 (d,J=8.4 Hz,2H).

MS(FAB) m/z 410(M+H)$^+$.

Free compound:

$^1$H-NMR (400 MHz,CDCl$_3$); δ (ppm) 1.18(t,J=7.2 Hz,3H), 2.56(q,J=7.2 Hz,2H), 2.77(br,4H), 2.79(s,2H), 3.59 (br,4H), 4.32(s,2H), 7.49(ddd,J=8.4,8.0,1.2 Hz,1H), 7.51(d, J=8.4 Hz,2H), 7.61(ddd,J=8.4,8.0,1.2 Hz,1H), 7.72(s,1H), 7.81(d,J=8.0 Hz,1H), 8.09(d,J=8.4 Hz,1H), 8.22(d,J=8.0 Hz,2H).

Example 91

Synthesis of 3-(3-Chloro-4-ethylsulfonylaminomethylphenyl)-1-(4-ethylpiperazin-1-yl)isoquinoline Hydrochloride

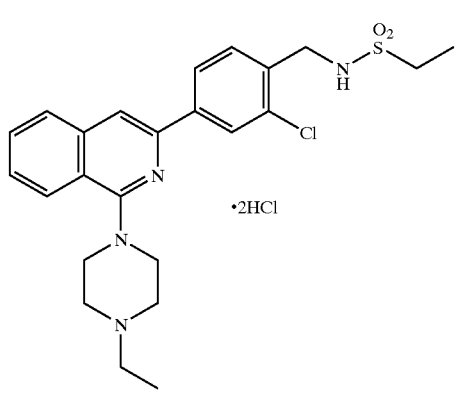

In the same manners sequentially as in Examples 161-2 and 20, the free compound of the title compound was obtained (101 mg, yield: 17%) from 3-chloro-4-ethylsulfonylaminomethylbromobenzene (819 mg) and 3-bromo-1-(4-ethylpiperazin-1-yl)isoquinoline (530 mg). The free compound was converted into a hydrochloride in a conventional manner, to give the hydrochloride of the title compound as yellow crystals.

Hydrochloride:
m.p.: 278–280° C. (decomp.)
$^1$H-NMR (400 MHz,DMSO-$d_6$); δ (ppm) 1.20(t,J=7.2 Hz,3H), 1.31(t,J=7.2 Hz,3H), 3.04(q,J=7.2 Hz,2H), 3.18–3.25(m,2H), 3.28–3.37(m,2H), 3.51(t,J=12.8 Hz,2H), 3.62(d,J=11.6 Hz,2H), 3.97–4.03(m,2H), 4.29(d,J=6.0 Hz,2H), 7.62(t,J=8.0 Hz,1H), 7.66(d,J=8.0 Hz,1H), 7.75(t,J=8.0 Hz,1H), 7.99(d,J=8.0 Hz,1H), 8.12(d,J=8.0 Hz,1H), 8.18(dd,J=8.0,1.6 Hz,1H), 8.18(s,1H), 8.24(d,J=1.6 Hz,1H).
MS(FAB) m/z 473(M+H)$^+$.

Free compound:
$^1$H-NMR (400 MHz,CDCl$_3$); δ (ppm) 1.18(t,J=7.2 Hz,3H), 1.30(t,J=7.6 Hz,3H), 2.56(q,J=7.2 Hz,2H), 2.77(br,4H), 2.93(q,J=7.6 Hz,2H), 3.59(br,4H), 4.45(d,J=6.4 Hz,2H), 4.88(br,1H), 7.50 (ddd,J=8.4,8.0,1.2 Hz,1H), 7.52 (d,J=8.0 Hz,1H), 7.61(ddd,J=8.4,8.0,1.2 Hz,1H), 7.68(s,1H), 7.80(d,J=8.4 Hz,1H), 8.05(dd,J=8.0,1.6 Hz,1H), 8.08 (d,J=8.4 Hz,1H), 8.23(d,J=1.6 Hz,1H).

Example 92

Synthesis of 3-(3-Chloro-4-propylsulfonylaminomethylphenyl)-1-(4-ethylpiperazin-1-yl)isoquinoline Hydrochloride

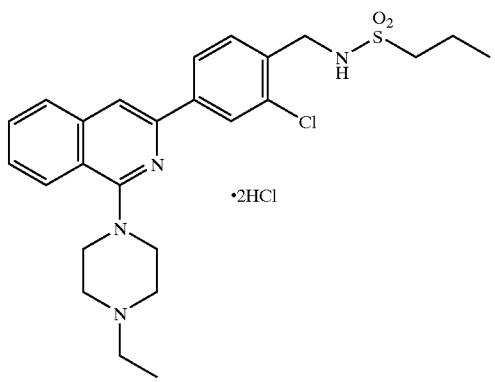

In the same manners sequentially as in Examples 161-2 and 20, the free compound of the title compound was obtained (365 mg, yield: 39%) from 3-chloro-4-propylsulfonylaminomethylbromobenzene (1.58 g) and 3-bromo-1-(4-ethylpiperazin-1-yl)isoquinoline (825 mg). The free compound was converted into a hydrochloride in a conventional manner, to give the hydrochloride of the title compound as yellow crystals.

Hydrochloride:
m.p.: 253–255° C. (decomp.)
$^1$H-NMR (400 MHz,DMSO-$d_6$); δ (ppm) 0.94(t,J=7.6 Hz,3H), 1.31(t,J=7.2 Hz,3H), 1.62–1.74(m,2H), 2.98–3.02 (m,2H), 3.18–3.25(m,2H), 3.30–3.38(m,2H), 3.50(t,J=12.8 Hz,2H), 3.62(d,J=11.6 Hz,2H), 3.99(d,J=13.2 Hz,2H), 4.28 (d,J=6.0 Hz,2H), 7.62(t,J=8.0 Hz,1H), 7.65(d,J=8.0 Hz,1H), 7.75(t,J=8.0 Hz,1H), 7.99(d,J=8.0 Hz,1H), 8.12(d,J=8.0 Hz,1H), 8.18(dd,J=8.0,2.0 Hz,1H), 8.18(s,1H), 8.24(d,J=2.0 Hz,1H).

MS(FAB) m/z 488(M+H)$^+$.

Free compound:
$^1$H-NMR (400 MHz,CDCl$_3$); δ (ppm) 0.96(t,J=7.6 Hz,3H), 1.19(t,J=7.2 Hz,3H), 1.76–1.81(m,2H), 2.57(q,J=7.2 Hz,2H), 2.77(br,4H), 2.87–2.91(m,2H), 3.59(br,4H), 4.45(d,J=6.4 Hz,2H), 4.82(t,J=6.4 Hz,1H), 7.50(t,J=8.4 Hz,1H), 7.52(d,J=8.0 Hz,1H), 7.61(t,J=8.4 Hz,1H), 7.68(s,1H), 7.80(d,J=8.4 Hz,1H), 8.05(dd,J=8.0,1.6 Hz,1H), 8.08 (d,J=8.4 Hz,1H), 8.23(d,J=1.6 Hz,1H).

Example 93

Synthesis of 3-(4-Morpholinylmethylphenyl)-1-(4-ethylpiperazin-1-yl)isoquinoline Hydrochloride

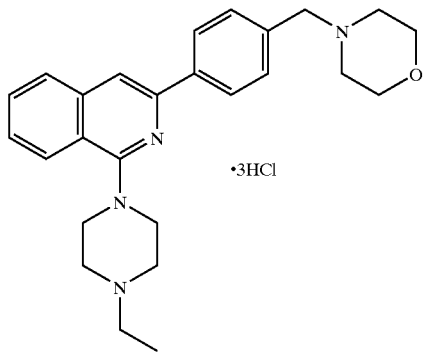

In the same manners sequentially as in Examples 161-2 and 20, the free compound of the title compound was obtained (472 mg, yield: 71%) from 4-morpholinylmethyl-bromobenzene (1.02 g) and 3-bromo-1-(4-ethylpiperazin-1-yl)isoquinoline (651 mg). The free compound was converted into a hydrochloride in a conventional manner, to give the hydrochloride of the title compound as a yellow amorphous.

Hydrochloride (amorphous):
MS(FAB) m/z 417(M+H)$^+$.

Free compound:
$^1$H-NMR (400 MHz,CDCl$_3$); δ (ppm) 1.18(t,J=7.2 Hz,3H), 2.49(t,J=4.8 Hz,4H), 2.54(q,J=7.2 Hz,2H), 2.77(br,4H), 3.56(s,2H), 3.60(br,4H), 3.73(t,J=4.8 Hz,4H), 7.42(d,J=8.4 Hz,2H), 7.46(dt,J=8.0,1.2 Hz,1H), 7.59(dt,J=8.0,1.2 Hz,1H), 7.69(s,1H), 7.79(d,J=8.0 Hz,1H), 8.08(d,J=8.0 Hz,1H), 8.12(d,J=8.4 Hz,2H).

Example 94

Synthesis of 3-(4-Thiomorpholinylmethylphenyl)-1-(4-ethylpiperazin-1-yl)isoquinoline Hydrochloride

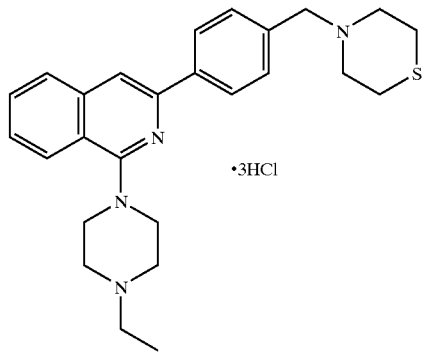

In the same manners sequentially as in Examples 161-2 and 20, the free compound of the title compound was obtained (273 mg, 22%) from 4-thiomorpholinylmethyl-bromobenzene (1.08 g) and 3-bromo-1-(4-ethylpiperazin-1-yl)isoquinoline (882 mg). The free compound was converted into a hydrochloride in a conventional manner, to give the hydrochloride of the title compound as yellow crystals.

Hydrochloride:

m.p.: 193–197° C.

$^1$H-NMR (400 MHz,DMSO-$d_6$); δ (ppm) 1.34(t,J=7.2 Hz,3H), 2.81(d,J=14.4 Hz,2H), 3.08–3.16(m,2H), 3.21–3.38 (m,6H), 3.53–3.65(m,6H), 4.01(d,J=12.8 Hz,2H), 4.40(d,J= 5.2 Hz,2H), 7.64(t,J=8.0 Hz,1H), 7.77(t,J=8.0 Hz,1H), 7.79 (d,J=8.4 Hz,2H), 8.01(d,J=8.0 Hz,1H), 8.14(t,J=8.0 Hz,1H), 8.17(s,1H), 8.28(d,J=8.4 Hz,2H).

MS(FAB) m/z 433(M+H)$^+$.

Free compound:

$^1$H-NMR (400 MHz,CDCl$_3$); δ (ppm) 1.17(t,J=7.2 Hz,3H), 2.56(t,J=7.2 Hz,4H), 2.68–2.77(m,10H), 3.58(s, 2H), 3.68(br,4H), 7.40(d,J=8.0 Hz,2H), 7.46(ddd,J=8.4,8.0, 1.2 Hz,1H), 7.59(ddd,J=8.4,8.0,1.2 Hz,1H), 7.69(s,1H), 7.79 (d,J=8.0 Hz,1H), 8.07(d,J=8.4 Hz,1H), 8.12(d,J=8.0 Hz,2H).

Example 95

Synthesis of 3-[4-(3-Oxazolidinone)phenyl]-1-(4-ethylpiperazin-1-yl)isoquinoline Hydrochloride

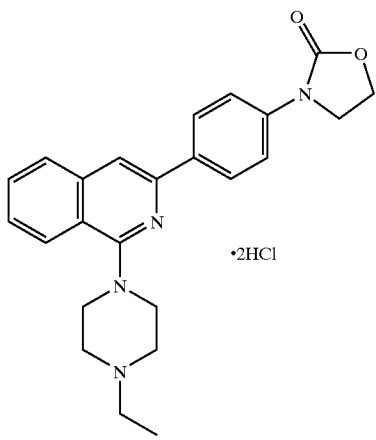

In the same manners sequentially as in Examples 161-2 and 20, the free compound of the title compound was obtained (1.0 g, yield: 71%) was obtained from 1-bromo-4-(3-oxazolidinone)benzene (2.29 g) and 3-bromo-1-(4-ethylpiperazin-1-yl)isoquinoline (1.19 g). The free compound was converted into a hydrochloride in a conventional manner, to give the hydrochloride of the title compound as yellow crystals.

Hydrochloride:

m.p.: 171–174° C.

$^1$H-NMR (400 MHz,DMSO-$d_6$); δ (ppm) 1.33(t,J=7.2 Hz,3H), 3.20–3.28(m,2H), 3.32–3.39(m,2H), 3.54(t,J=12.8 Hz,2H), 3.62(d,J=10.8 Hz,2H), 4.02(d,J=13.6 Hz,2H), 4.14 (t,J=8.0 Hz,2H), 4.46–4.50(m,2H), 7.60(t,J=8.0 Hz,1H), 7.71(d,J=8.8 Hz,2H), 7.74(t,J=8.0 Hz,1H), 7.98(d,J=8.0 Hz,1H), 8.08(s,1H), 8.11(d,J=8.0 Hz,1H), 8.24(d,J=8.8 Hz,2H).

MS(FAB) m/z 403(M+H)$^+$.

Free compound:

$^1$H-NMR (400 MHz,CDCl$_3$); δ (ppm) 1.19(t,J=7.2 Hz,3H), 2.58(q,J=7.2 Hz,2H), 2.79(br,4H), 3.61(br,4H), 4.04–4.08(m,2H), 4.44–4.48(m,2H), 7.44(ddd,J=8.4,8.0,1.2 Hz,1H), 7.57(ddd,J=8.4,8.0,1.2 Hz,1H), 7.61(d,J=8.8 Hz,2H), 7.65(s,1H), 7.76(d,J=8.0 Hz,1H), 8.04(d,J=8.0 Hz,1H), 8.16(d,J=8.8 Hz,2H).

Example 96

Synthesis of 3-[4-(4,4-Ethylenedioxypiperidin-1-yl) phenyl]-1-(4-ethylpiperazin-1-yl)isoquinoline

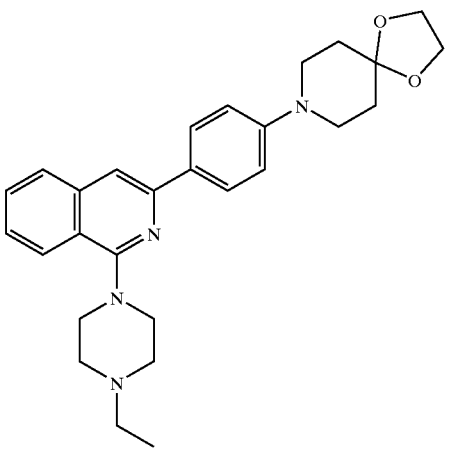

3-Bromo-1-(4-ethylpiperazin-1-yl)isoquinoline (1.72 g) and 4-(4,4-ethylenedioxypiperidin-1-yl) phenyltributylstannum (3.12 g) were reacted in the presence of tetrakistriphenylphosphine dichloride (0.5 g) in xylene (50 ml) at 140° C. for 5 hr. The reaction solution was concentrated, and ethyl acetate and an aqueous saturated solution of sodium bicarbonate were added to the resulting residue, for partitioning. The resulting organic layer was washed with water and brine, dried over magnesium sulfate and evaporated. The resulting residue was purified by silica gel column chromatography (methylene chloride/methanol system), to give 1.27 g of title compound as a white powder.

Free compound:

m.p.: 118° C.

$^1$H-NMR (400 MHz,CDCl$_3$); δ (ppm) 1.18(t,J=7.2 Hz,3H), 1.87(br-t,4H), 2.55(q,J=7.2 Hz,2H), 2.75(br-s,4H), 3.42(m,4H), 3.58(br-s,4H), 4.01(s,4H), 7.03(d,J=8.8 Hz,2H), 7.41(br-t,1H), 7.55(br-t,1H), 7.60(s,1H), 7.75(d,J= 8.0 Hz,1H), 8.05(d,J=8.0 Hz,1H), 8.08(dd,J=8.8 Hz,2H).

Example 97

Synthesis of 1-(4-Ethylpiperazin-1-yl)-3-[4-(4-hydroxypiperidin-1-yl)phenyl]isoquinoline Trihydrochloride

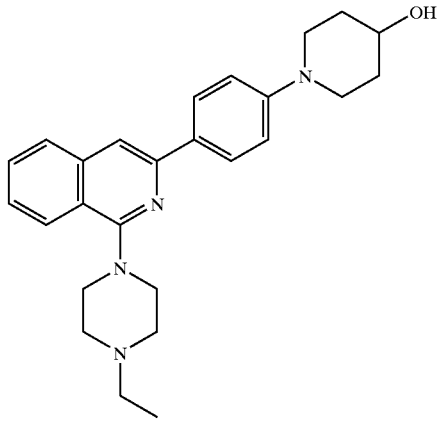

3-[4-(4,4-Ethylenedioxypiperidin-1-yl)phenyl]-1-(4-ethylpiperazin-1-yl)isoquinoline (290 mg) obtained in Example 96 was treated with camphorsulfonic acid and methanol. Then, a 2N aqueous solution of hydrochloric acid (50 ml) was added thereto, and the mixture was reacted for 1 hr. The reaction solution was basified and extracted with ethyl acetate. The resulting organic layer was washed with water and brine, and dried over magnesium sulfate. The solvent was evaporated, the resulting residue was dissolved in methanol (20 ml), and then it was reacted with sodium borohydride (54 mg). The reaction solution was evaporated, and the resulting residue was purified by silica gel column chromatography (methylene chloride/methanol system), to give 119 mg of the free compound of the title compound as a white solid.

Free compound:

$^1$H-NMR (400 MHz,CDCl$_3$); δ (ppm) 1.18(t,J=7.2 Hz,3H), 1.71(m,2H), 2.04(m,2H), 2.55(q,J=7.2 Hz,2H), 2.76(br-s,4H), 3.00(ddd,J=12.8,10.0,3.0 Hz,2H), 3.56(br-s, 4H), 3.67(dt,J=12.8,4.4 Hz,2H), 3.88(m,1H), 7.02(d,J=8.8 Hz,2H), 7.41(br-t,1H), 7.55(br-t,1H), 7.60(s,1H), 7.75(d,J= 8.0 Hz,1H), 8.05(d,J=8.0 Hz,1H), 8.08(d,J=8.8 Hz,2H).

The resulting free compound was converted into a hydrochloride in a conventional manner, and recrystallized from ethanol/ether, to give 148 mg of the title compound as a white powder.

Hydrochloride:

m.p.: 178° C.

MS(FAB) m/z 417(M+H)$^+$.

Example 98

Synthesis of 1-(4-Ethylpiperazin-1-yl)-3-[4-(4-methoxypiperidin-1-yl)phenyl]isoquinoline Trihydrochloride

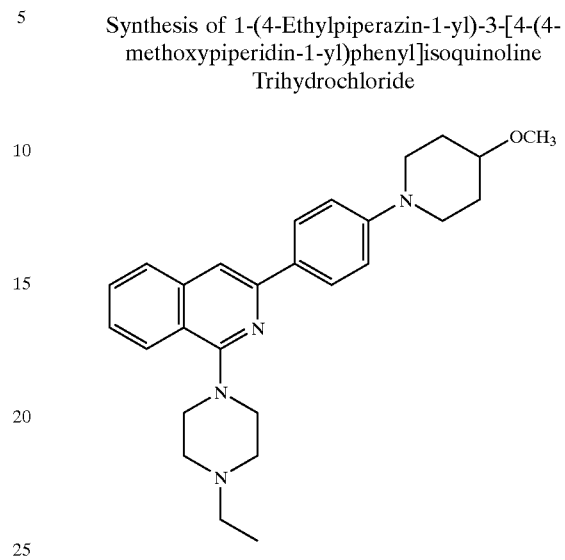

3-Bromo-1-(4-ethylpiperazin-1-yl)isoquinoline (0.79 g) and 4-(4-methoxypiperidin-1-yl)phenyltributylstannum (1.30 g) were reacted in the presence of tetrakistriphenylphosphine dichloride (0.30 g) in xylene (30 ml) at 140° C. for 5 hr. The reaction solution was concentrated, and ethyl acetate and an aqueous solution of saturated sodium bicarbonate were added to the resulting residue, for partitioning. The resulting organic layer was washed with water and brine, dried over magnesium sulfate, and the solvent was evaporated. The resulting residue was purified by silica gel column chromatography (methylene chloride/methanol system), to give 0.17 g of the free compound of the title compound as a yellow solid.

Free compound:

$^1$H-NMR (400 MHz,CDCl$_3$); δ (ppm) 1.18(t,J=7.2 Hz,3H), 1.72(m,2H), 2.03(m,2H), 2.55(q,J=7.2 Hz,2H), 2.76(br-s,4H), 3.00(ddd,J=12.8,10.0,3.0 Hz,2H), 0.40(s, 3H), 3.48(m,1H), 3.59(br-s,4H), 7.02(d,J=8.8 Hz,2H), 7.41 (br-t,1H), 7.55(br-t,1H), 7.61(s,1H), 7.75(d,J=8.0 Hz,1H), 8.05(d,J=8.0 Hz,1H), 8.08(d,J=8.8 Hz,2H).

The resulting free compound was converted into a hydrochloride in a conventional manner, and recrystallized from ethanol/ether, to give 0.24 g of the title compound as a yellow powder.

Hydrochloride:

m.p.: 165° C.

MS(FAB) m/z 431(M+H)$^+$.

Example 99

Synthesis of 3-[2-(4-Acetylpiperazin-1-yl)pyridin-5-yl]-1-(4-ethylpiperazin-1-yl)isoquinoline Trihydrochloride

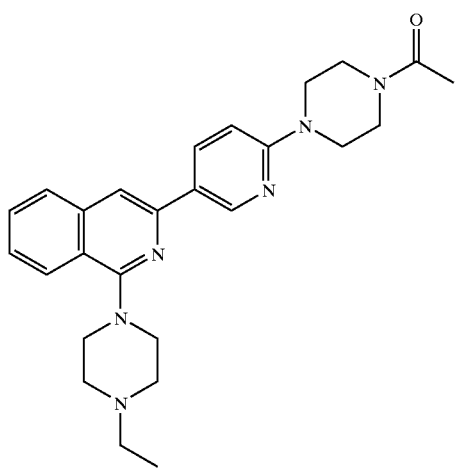

3-Bromo-1-(4-ethylpiperazin-1-yl)isoquinoline (0.53 g) and [2-(4-acetylpiperazin-1-yl)pyridin-5-yl]tributylstannum (0.91 g) were reacted in the presence of tetrakistriphenylphosphine dichloride (0.30 g) in xylene (30 ml) at 140° C. for 5 hr. The reaction solution was concentrated. Ethyl acetate and an aqueous solution of saturated sodium bicarbonate were added to the resulting residue, for partitioning. The resulting organic layer was washed with water and brine, dried over magnesium sulfate, and the solvent was evaporated. The resulting residue was purified by silica gel column chromatography (methylene chloride/methanol system), to give 0.67 g of the free compound of the title compound as a white powder.

Free compound:

$^1$H-NMR (400 MHz,CDCl$_3$); δ (ppm) 1.21(t,J=7.2 Hz,3H), 2.16(s,3H), 2.81(br-s,4H), 3.56–3.66(m,8H), 3.73 (m,2H), 3.78(m,2H), 6.75(d,J=8.8 Hz,2H), 7.44(br-t,1H), 7.56(s,1H), 7.57(br-t,1H), 7.76(d,J=8.0 Hz,1H), 8.04(d,J=8.0 Hz,1H), 8.28(dd,J=8.8,2.4 Hz,1H), 9.01(d,J=2.4 Hz,1H).

The resulting free compound was converted into a hydrochloride in a conventional manner, and recrystallized from ethanol/ether, to give 0.72 g of the title compound as a yellow powder.

Hydrochloride:

m.p.: 206° C.

$^1$H-NMR (400 MHz,DMSO-d$_6$); δ (ppm) 1.33(t,J=7.2 Hz,3H), 2.08(s,3H), 3.23(m,2H), 3.37(m,2H), 3.54(br-t,2H), 3.61–3.69(m,6H), 3.77(br,2H), 3.86(br,2H), 3.98(br-d,2H), 7.42(m,1H), 7.63(br-t,1H), 7.77(br-t,1H), 7.97(br-d,1H), 8.11–8.16(m,2H), 8.65(m,1H), 8.79(br,1H).

Example 100

Synthesis of 3-[4-(4-Acetylpiperazin-1-yl)phenyl]-1-(4-ethylpiperazin-1-yl)isoquinoline Trihydrochloride

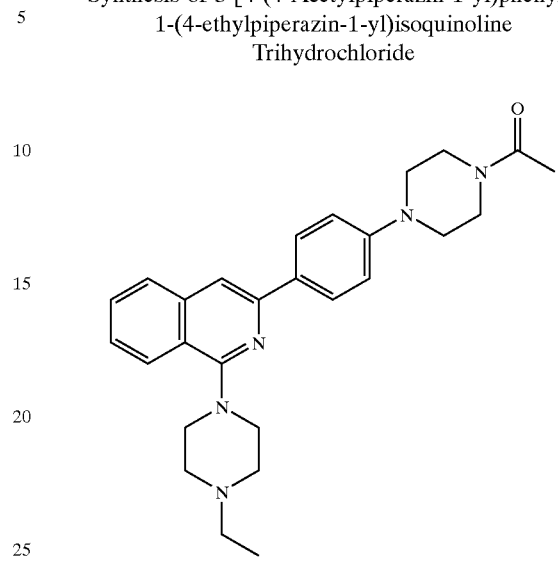

3-Bromo-1-(4-ethylpiperazin-1-yl)isoquinoline (0.27 g) and [4-(4-acetylpiperidin-1-yl)phenyl]tributylstannum (0.90 g) were reacted in the presence of tetrakistriphenylphosphine dichloride (0.30 g) in xylene (30 ml) at 140° C. for 5 hr. The reaction solution was concentrated. Ethyl acetate and an aqueous solution of saturated sodium bicarbonate were added to the resulting residue, for partitioning. The resulting organic layer was washed with water and brine, dried over magnesium sulfate, and the solvent was evaporated. The resulting residue was purified by silica gel column chromatography (methylene chloride/methanol system), to give 0.12 g of the free compound of the title compound as a white solid.

Free compound:

$^1$H-NMR (400 MHz,CDCl$_3$); δ (ppm) 1.21(t,J=7.2 Hz,3H), 2.16(s,3H), 2.60(q,J=7.2 Hz,2H), 2.81(br-s,4H), 3.26(m,4H), 3.62(br-s,4H), 3.65(m,2H), 3.81(m,2H), 7.02 (d,J=8.8 Hz,2H), 7.43(br-t,1H), 7.58(br-t,1H), 7.62(s,1H), 7.77(d,J=8.4 Hz,1H), 8.05(d,J=8.4 Hz,1H), 8.11(d,J=8.88 Hz,2H).

The resulting free compound form was converted into a hydrochloride in a conventional manner, recrystallized from ethanol/ether, to give 0.16 g of the title compound as a yellow powder.

Hydrochloride:

$^1$H-NMR (400 MHz,DMSO-d$_6$); δ (ppm) 1.33(t,J=7.2 Hz,3H), 2.07(s,3H), 3.22–3.28(m,4H), 3.51(br-t,2H), 3.60–3.68(m,4H), 3.98(br-d,2H), 7.17(m,1H), 7.56(br-t, 1H), 7.71(br-t,1H), 7.94(br-d,1H), 7.94(br-d,1H), 7.98(br-s, 1H), 8.07–8.13(m,2H).

MS(FAB) m/z 431 (M+H)$^+$.

Example 101

Synthesis of 3-(2-Methoxybenzyl)-1-(4-ethylpiperazin-1-yl)isoquinoline Oxalate

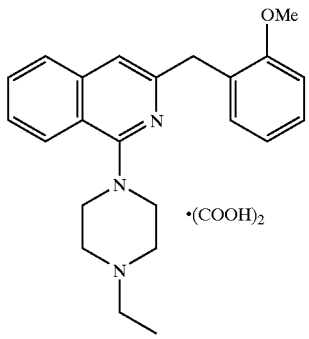

Potassium hydroxide (117 mg) and hydrazine monohydrate (2 ml) were added to a solution of 3-(2-methoxyphenylcarbonyl)-1-(4-ethylpiperazin-1-yl)isoquinoline (261 mg) in ethylene glycol (6 ml), and the resulting mixture was reacted at 140° C. overnight. Water and ethyl acetate were added to the reaction solution, for partitioning. The resulting organic layer was washed with brine, dried and evaporated. The resulting residue was then purified by NH-silica gel column chromatography (ethyl acetate/hexane system), to give a yellow oil (185 mg, yield: 73%). The resulting oil was converted into an oxalate in a conventional manner, to give the oxalate of the title compound as white crystals.

Oxalate:
m.p.: 194–197° C.
$^1$H-NMR (400 MHz,DMSO-d$_6$); δ (ppm) 1.25(br,3H), 3.14(br,2H), 3.35(br,4H), 3.60(br,4H), 3.78(s,3H), 4.08(s,2H), 6.89(br,1H), 7.00(d,J=8.0 Hz,1H), 7.09(s,1H), 7.17(d,J=8.0 Hz,1H), 7.23(br,1H), 7.54(br,1H), 7.66(br,1H), 7.78 (d,J=8.0 Hz,1H), 8.05(d,J=8.0 Hz,1H).
MS(FAB) m/z 374 (M+H)$^+$.

Free compound:
$^1$H-NMR (400 MHz,CDCl$_3$); δ (ppm) 1.16(t,J=7.2 Hz,3H), 2.53(q,J=7.2 Hz,2H), 2.70(br,4H), 3.47(br,4H), 3.82(s,3H), 4.16(s,2H), 6.87–6.91(m,2H), 6.94(s,1H), 7.19–7.24(m,2H), 7.38(dt,J=8.0,0.8 Hz,1H), 7.49(dt,J=8.0, 0.8 Hz,1H), 7.60(d,J=8.0 Hz,1H), 8.01(d,J=8.0 Hz,1H).

Example 102

Synthesis of 3-[α-Methyl-(4-methoxybenzyl)]-1-(4-ethylpiperazin-1-yl)isoquinoline Oxalate

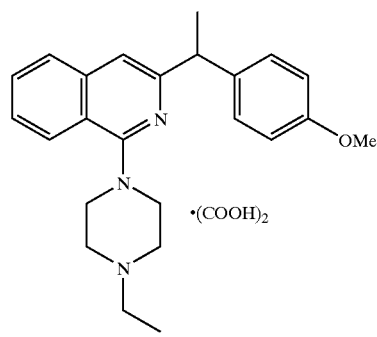

3-[1-(4-Methoxyphenyl)ethen-1-yl]-1-(4-ethylpiperazin-1-yl)isoquinoline obtained in Example 217 was converted into the hydrochloride. To the hydrochloride (145 mg) were added methanol (15 ml) and palladium/carbon catalyst (10 mg), and the resulting mixture was reacted in hydrogen atmosphere at room temperature overnight. The reaction solution was filtered through Celite, and then evaporated. The resulting residue was basified by adding a 1N aqueous solution of sodium hydroxide thereto, which was then extracted with ethyl acetate. The resulting organic layer was washed with brine, dried and evaporated. Then, the residue was purified by NH-silica gel column chromatography (ethyl acetate/hexane system), to give a yellow oil (140 mg, yield: 96%). The oil was converted into an oxalate in a conventional manner, to give the oxalate of the title compound as white crystals.

Oxalate:
m.p.: 86–88° C.
$^1$H-NMR (400 MHz,DMSO-d$_6$); δ (ppm) 1.25(t,J=7.2 Hz,3H), 1.64(d,J=6.8 Hz,3H), 3.13(br,2H), 3.35(br,4H), 3.60(br,4H), 3.70(s,3H), 4.22(q,J=6.8 Hz,1H), 6.84(d,J=8.4 Hz,2H), 7.29(s,1H), 7.30(d,J=8.4 Hz,2H), 7.54(t,J=8.0 Hz,1H), 7.67(t,J=8.0 Hz,1H), 7.82(d,J=8.0 Hz,1H), 8.04 (t,J=8.0 Hz,1H).
MS(FAB) m/z 376(M+H)$^+$.

Free compound:
$^1$H-NMR (400 MHz,CDCl$_3$); δ (ppm) 1.16(t,J=7.6 Hz,3H), 1.70(d,J=7.2 Hz,3H), 2.54(q,J=7.6 Hz,2H), 2.71(br, 4H), 3.48(br,4H), 3.77(s,3H), 4.18(q,J=7.2 Hz,1H), 6.82(d, J=8.8 Hz,2H), 7.00(s,1H), 7.36(d,J=8.8 Hz,2H), 7.39(ddd, J=8.4,8.0,1.2 Hz,1H), 7.50(ddd,J=8.4,8.0,1.2 Hz,1H), 7.62 (d,J=8.0 Hz,1H), 8.00 (d,J=8.4 Hz,1H).

Example 103

Synthesis of 3-[α-Hydroxy-(2-methoxybenzyl)]-1-(4-ethylpiperazin-1-yl)isoquinoline Oxalate

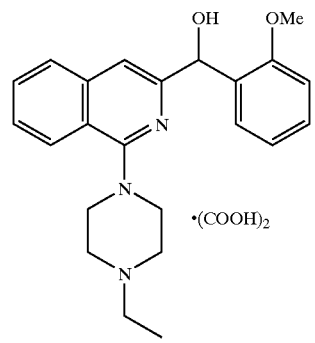

In the same manner as in Example 104, the free compound of the title compound was obtained (1.13 g, yield: 91%) from o-anisaldehyde (0.8 ml) and 3-bromo-1-(4-ethylpiperazin-1-yl)isoquinoline (1.05 g). The resulting free compound was converted into an oxalate in a conventional manner, to give the oxalate of the title compound as white crystals.

Oxalate:
m.p.: 100–103° C.
$^1$H-NMR (400 MHz,DMSO-d$_6$); δ (ppm) 1.20(t,J=7.2 Hz,3H), 3.00(br,2H), 3.20(br,4H), 3.56(br,4H), 3.60(br,1H), 3.78(s,3H), 6.09(s,1H), 6.89(t,J=7.2 Hz,1H), 6.97(d,J=7.2 Hz,1H), 7.21(d,J=7.6,2.0 Hz,1H), 7.33(dd,J=7.6,2.0 Hz,1H), 7.47(s,1H), 7.55(t,J=8.0 Hz,1H), 7.68(t,J=8.0 Hz,1H), 7.90 (d,J=8.0 Hz,1H), 8.03(d,J=8.0 Hz,1H).

MS(FAB) m/z 378(M+H)+.

Free compound:

¹H-NMR (400 MHz,CDCl₃); δ (ppm) 1.17(t,J=7.2 Hz,3H), 2.55(q,J=7.2 Hz,2H), 2.73(br,4H), 3.54(br,4H), 3.89(s,3H), 5.24(d,J=5.6 Hz,1H), 6.23(d,J=5.6 Hz,1H), 6.89–6.94(m,2H), 7.14(s,1H), 7.23(dt,J=7.2,1.6 Hz,1H), 7.40(dd,J=7.2,1.6 Hz,1H), 7.43(ddd,J=8.4,8.0,1.2 Hz,1H), 7.54(ddd,J=8.4,8.0,1.2 Hz,1H), 7.64(d,J=8.0 Hz,1H), 8.04 (d,J=8.0 Hz,1H).

Example 104

Synthesis of 3-[α-Hydroxy-(4-methoxybenzyl)]-1-(4-ethylpiperazin-1-yl)isoquinoline Oxalate

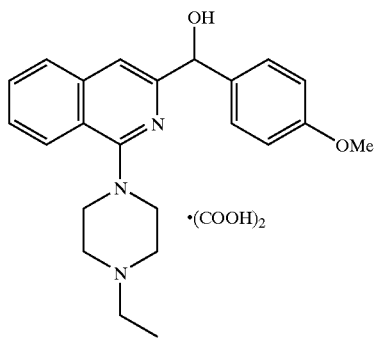

To a solution of 3-bromo-1-(4-ethylpiperazin-1-yl)isoquinoline (1.08 g) in tetrahydrofuran (20 ml) was added 1.7 M t-butyl lithium (3.0 ml) at −78° C., and the mixture was stirred for 15 min. Thereafter, p-anisaldehyde (0.82 ml) was added at −78° C., and the mixture was stirred for 15 min. The reaction solution was poured into an aqueous solution of saturated ammonium chloride, and then extracted with ethyl acetate. The resulting organic layer was washed with water and brine, dried and evaporated. Then, the residue was purified by NH-silica gel column chromatography (ethyl acetate/hexane system), to give a yellow oil (1.23 g, yield: 97%). The oil was converted into an oxalate in a conventional manner, to give the oxalate of the title compound as white crystals.

Oxalate:

m.p.: 95–97° C.

¹H-NMR (400 MHz,DMSO-d₆); δ (ppm) 1.21(t,J=7.2 Hz,3H), 3.02(br,2H), 3.23(br,4H), 3.46(br,4H), 3.60(t,J=6.8 Hz,1H), 3.70(s,3H), 5.69(s,1H), 6.84(d,J=8.8 Hz,2H), 7.36 (d,J=8.8 Hz,2H), 7.55(t,J=8.0 Hz,1H), 7.58(s,1H), 7.69(t,J= 8.0 Hz,1H), 7.91(d,J=8.0 Hz,1H), 8.03(d,J=8.0 Hz,1H).

MS(FAB) m/z 378(M+H)+.

Free compound:

¹H-NMR (400 MHz,CDCl₃); δ (ppm) 1.18(t,J=7.2 Hz,3H), 2.55(q,J=7.2 Hz,2H), 2.74(br,4H), 3.55(br,4H), 3.80(s,3H), 5.18(d,J=4.8 Hz,1H), 5.72(d,J=4.8 Hz,1H), 6.87 (d,J=8.8 Hz,2H), 7.00(s,1H), 7.35(d,J=8.8 Hz,2H), 7.45 (ddd,J=8.4,8.0,1.2 Hz,1H), 7.50(ddd,J=8.4,8.0,1.2 Hz,1H), 7.63(d,J=8.0 Hz,1H). 8.05 (d,J=8.4 Hz, 1H).

Example 105

Synthesis of 1-[α-Methyl-α-hydroxy-(4-methoxybenzyl)]-1-(4-ethylpiperazin-1-yl)isoquinoline Oxalate

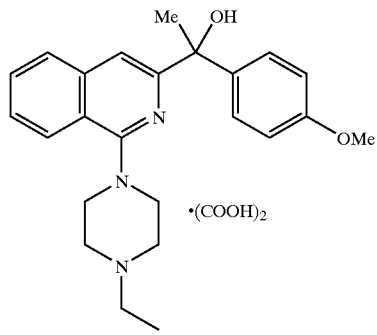

To a solution of 3-(4-methoxyphenylcarbonyl)-1-(4-ethylpiperazin-1-yl)isoquinoline (667 mg) in tetrahydrofuran (10 ml) was added a 3.0 M solution of methylmagnesium bromide in diethyl ether (1.8 ml) at 0° C. The mixture was reacted at 0° C. for further 10 min, and then the reaction solution was poured into an aqueous solution of saturated ammonium chloride, and was then extracted with ethyl acetate. The resulting organic layer was washed with water and brine, dried and evaporated. Then the resulting residue was purified by NH-silica gel column chromatography (ethyl acetate/hexane system), to give a yellow oil (643 mg, yield: 92%). The oil was converted into an oxalate in a conventional manner, to give the oxalate of the title compound as white crystals.

Oxalate:

m.p.: 179–181° C.

¹H-NMR (400 MHz,DMSO-d₆); δ (ppm) 1.20(t,J=7.6 Hz,3H), 1.90(s,3H), 2.99(br,2H), 3.19(br,4H), 3.52(br,4H), 3.69(s,3H), 6.81(d,J=8.8 Hz,2H), 7.48(d,J=8.8 Hz,2H), 7.54 (t,J=8.0 Hz,1H), 7.66(s,1H), 7.67(t,J=8.0 Hz,1H), 7.90(d,J= 8.0 Hz,1H), 8.02(d,J=8.0 Hz,1H).

MS(FAB) m/z 392(M+H)+.

Free compound:

¹H-NMR (400 MHz,CDCl₃); δ (ppm) 1.16(t,J=7.2 Hz,3H), 1.95(s,3H), 2.53(q,J=7.2 Hz,2H), 2.71(br,4H), 3.50 (br,4H), 3.78(s,3H), 5.59(s,1H), 6.82(d,J=8.8 Hz,2H), 7.15 (s,1H), 7.43(d,J=8.8 Hz,2H), 7.45(ddd,J=8.4,8.0,1.2 Hz,1H), 7.57(ddd,J=8.4,8.0,1.2 Hz,1H), 7.69(d,J=8.0 Hz,1H), 8.04(d,J=8.4 Hz,1H).

Example 106

Synthesis of 1-(1-Ethylpiperazin-4-yl)-3-(4-methoxyphenethyl)isoquinoline (106-1) 4-Methoxyphenethyl bromide

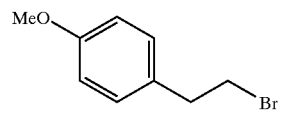

4-Methoxyphenethyl alcohol (50 g) and triphenylphosphine (103 g) were dissolved in methylene chloride (600 ml), followed by the addition of N-bromosuccinimide (70 g) in small portions under ice-cooling, and the resulting mixture was stirred at room temperature for 30 min. The reaction mixture was evaporated, and to the resulting residue was added hexane. The insoluble matters were filtered off, while the resulting filtrate was evaporated, to give the title compound as a colorless oil (50.32 g, yield: 71%).

$^1$H-NMR (400 MHz,CDCl$_3$); δ (ppm) 3.10(2H,t,J=7.6 Hz), 3.53(2H,t,J=7.6 Hz), 3.80(3H,s), 6.86(2H,d,J=8.8 Hz), 7.13(2H,d,J=8.8 Hz).

(106-2) 1-(1-Ethylpiperazin-4-yl)-3-(4-methoxyphenethyl)isoquinoline

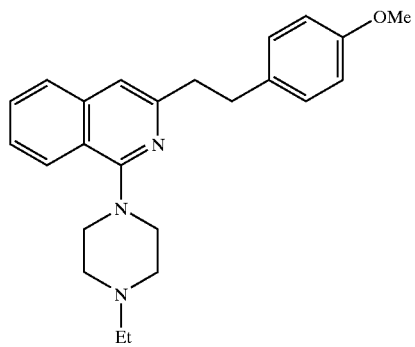

Grignard reagent was prepared from magnesium (735 mg) and 4-methoxyphenethyl bromide (4.302 g) in a conventional manner. It was added dropwise into a solution of 1-(1-ethylpiperazin-4-yl)-3-bromoisoquinoline (961 mg) and [1,3-bis(diphenylphosphino)propane]nickel (II) chloride (49 mg) in tetrahydrofuran (15 ml), in nitrogen atmosphere under ice-cooling. After stirring the resulting mixture for 10 min, it was further stirred at room temperature for 3.5 hr. To the resulting mixture was added 1N hydrochloric acid (10 ml), followed by stirring for 10 min. Then, the mixture was basified with a 5N sodium hydroxide. The insoluble matters were filtered off through Celite, and then the resulting filtrate was evaporated with ethyl acetate. The resulting organic layer was washed with water, dried (over MgSO$_4$), evaporated and purified by (NH) silica gel column chromatography (ethyl acetate/hexane system). The resulting product was converted into a hydrochloride in a conventional manner, recrystallized from ethanol/isopropyl ether, to give the hydrochloride of the title compound as pale yellow crystals (346 mg, yield: 27%).

Hydrochloride:

m.p.: 224–227° C.

$^1$H-NMR (400 MHz,DMSO-d$_6$); δ (ppm) 1.32(3H,t,J=7.2 Hz), 2.95–3.00(2H,m), 3.07–3.11(2H,m), 3.18(1H,q,J=7.2 Hz), 3.20(1H,q,J=7.2 Hz), 3.31(1H,t,J=10.4 Hz), 3.34(1H, t,J=10.4 Hz), 3.59(2H,d,J=10.4 Hz), 3.60(2H,t,J=12.8 Hz), 3.08(3H,s), 3.95(2H,d,J=12.8 Hz), 6.80(2H,d,J=8.8 Hz), 7.14(2H,d,J=8.8 Hz), 7.32(1H,s), 7.59(1H,dd,J=8 Hz,7 Hz), 7.74(1H,dd,J=8 Hz,7 Hz,), 7.84(1H,d,J=8 Hz), 8.09(1H,d, J=8 Hz), 11.43(1H,br-s).

ESI-Mass; 376(MH$^+$).

Example 107

Synthesis of 1-(1-Ethylpiperazin-4-yl)-3-[2-(2-hydroxyethoxy)phenethyl]isoquinoline

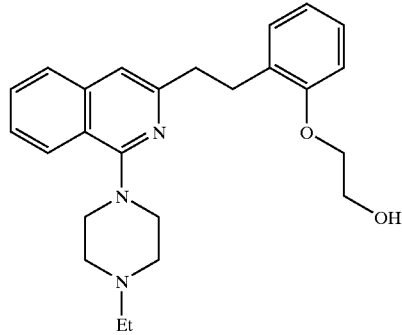

In the same manner as in Example 110, the oxalate of the title compound was obtained as a brown amorphous (209 mg, yield: 36%) from 1-(1-ethylpiperazin-4-yl)-3-[2-(2-hydroxyethoxy)phenylethynyl]isoquinoline (453 mg).

Oxalate:

$^1$H-NMR (400 MHz,DMSO-d$_6$); δ (ppm) 1.23(3H,t,J=7.2 Hz), 3.02(4H,s), 3.10(2H,q,J=7.2 Hz), 3.26–3.36(4H,m), 3.46–3.62(4H,m), 3.73(2H,t,J=5 Hz), 3.98(2H,t,J=5 Hz), 6.77(1H,ddd,J=7.6 Hz,7.4 Hz, 1.2 Hz), 6.92(1H,dd,J=8 Hz,1.2 Hz), 7.07(1H,dd,J=7.4 Hz,1.6 Hz), 7.10(1H,ddd,J=8 Hz,7.6 Hz,1.6 Hz), 7.23(1H,s), 7.51(1H,ddd,J=8 Hz,7 Hz,1.2 Hz), 7.64(1H,ddd,J=8 Hz,7 Hz,1.2 Hz), 7.7(1H,dd, J=8 Hz,1.2 Hz), 8.03(1H,dd,J=8 Hz,1.2 Hz).

ESI-Mass; 406(MH$^+$).

Example 108

Synthesis of 1-(1-Ethylpiperazin-4-yl)-3-[3-(2-hydroxyethoxy)phenethyl]isoquinoline

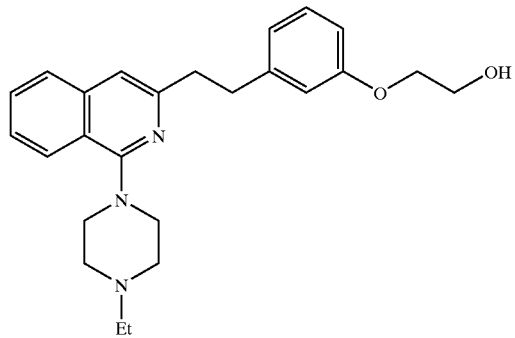

In the same manner as in Example 110, the oxalate of the title compound was obtained as a colorless amorphous (218 mg, yield: 36%) from 1-(1-ethylpiperazin-4-yl)-3-[3-(2-hydroxyethoxy)phenylethynyl]isoquinoline (454 mg).

Oxalate:

$^1$H-NMR (400 MHz,DMSO-d$_6$); δ (ppm) 1.23(3H,t,J=7.2 Hz), 3.00–3.04(4H,m), 3.09(2H,q,J=7.2 Hz), 3.26–3.57(4H, m), 3.46–3.52(4H,m), 3.65(2H,t,J=5 Hz), 3.89(2H,t,J=5 Hz), 6.70(1H,dd,J=8 Hz,2.5 Hz), 6.76(1H,d,J=7.6 Hz), 6.77 (1H,d,J=2.5 Hz), 7.12(1H,dd,J=8 Hz,7.6 Hz), 7.25(1H,s), 7.52(1H,ddd,J=8 Hz,7 Hz,1.2 Hz), 7.65(1H,ddd,J=8 Hz,7

Hz,1.2 Hz), 7.78(1H,d,J=8 Hz), 8.04(1H,d,8 Hz), 11.10(1H, br-s).

ESI-Mass; 406(MH+).

Example 109

Synthesis of 1-(1-Ethylpiperazin-4-yl)-3-[4-(2-hydroxyethoxy)phenethyl]isoquinoline

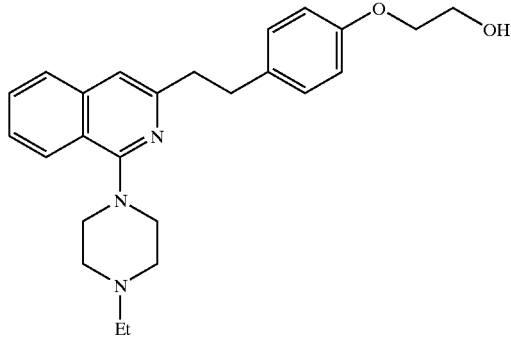

1-(1-Ethylpiperazin-4-yl)-3-[trans-4-(2-hydroxyethoxy) styryl]isoquinoline (722 mg) was dissolved in ethanol (16 ml), to which was then added Lindlar catalyst (1.4 g). Then, the resulting mixture was stirred in hydrogen atmosphere for 2 days. After the catalyst was filtered off, the resulting solution was evaporated and purified by (NH) silica gel column chromatography (ethyl acetate/hexane system). The resulting product was converted into an oxalate in a conventional manner, to give the oxalate of the title compound as a pale brown amorphous (118 mg, yield: 11%).

Oxalate:

$^1$H-NMR (400 MHz,DMSO-$d_6$); δ (ppm) 1.23(3H,t,J=7.2 Hz), 2.99(2H,t,J=3.2 Hz), 3.00(2H,t,J=3.2 Hz), 3.10(2H,q, J=7.2 Hz), 3.24–3.36(4H,m), 3.46–3.60(4H,m), 3.66(2H,t, J=5 Hz), 3.89(2H,t,J=5 Hz), 6.78(2H,d,J=8.8 Hz), 7.09(2H, d,J=8.8 Hz), 7.23(1H,s), 7.52(1H,ddd,J=8 Hz,7 Hz,1.2 Hz), 7.64(1H,ddd,J=8 Hz,7 Hz,1.2 Hz), 7.78(1H,d,J=8 Hz), 8.04 (1H,d,J=8 Hz). FAB-Mass; 406(MH+).

Example 110

Synthesis of 1-(1-Ethylpiperazin-4-yl)-3-[3-[2-(2-hydroxyethoxy)phenyl]propyl]isoquinoline

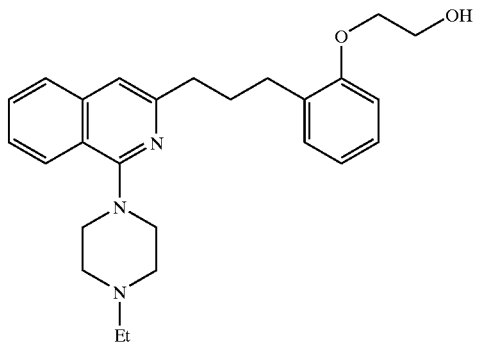

1-(1-Ethylpiperazin-4-yl)-3-[3-[2-(2-hydroxyethoxy) phenyl]propyl]isoquinoline (619 mg) was converted into a hydrochloride, and then dissolved in ethanol (20 ml), to which was then added 10% palladium-carbon catalyst (1.25 g). The resulting mixture was stirred in hydrogen atmosphere overnight. After the catalyst was filtered off, the resulting solution was evaporated. The reaction mixture was partitioned between ethyl acetate and 1N sodium hydroxide. The resulting organic layer was washed with water, dried (over MgSO$_4$), evaporated, and then purified by (NH)silica gel column chromatography (ethyl acetate/hexane system). The resulting product was converted into an oxalate in a conventional manner, to give the oxalate of the title compound as a pale brown amorphous (200 mg, yield: 27%).

Oxalate:

$^1$H-NMR (400 MHz,DMSO-$d_6$); δ (ppm) 1.23(3H,t,J=7.2 Hz), 1.99(2H,qui,J=7.6 Hz), 2.64(2H,t,J=7.6 Hz), 2.76(2H, t,J=7.6 Hz), 3.08(2H,q,J=7.2 Hz), 3.26–3.34(4H,m), 3.42–3.60(4H,m), 3.68(2H,t,J=5.2 Hz), 3.96(2H,t,J=5.2 Hz), 6.84(1H,ddd,J=7.6 Hz,7.4 Hz, 1.2 Hz), 6.91(1H,dd,J=8 Hz,1.2 Hz), 7.12(1H,ddd,J=8 Hz,7.6 Hz,1.2 Hz), 7.13(1H, dd,J=7.4 Hz,1.6 Hz), 7.26(1H,s), 7.51(1H,ddd,J=8 Hz,7 Hz,1.2 Hz), 7.65(1H,ddd,J=8 Hz,7 Hz,1.2 Hz), 7.81(1H,d, J=8 Hz), 8.03(1H,d,J=8 Hz).

ESI-Mass; 420(MH+).

Example 111

Synthesis of 3-(2-Methoxyphenylcarbonyl)-1-(4-ethylpiperazin-1-yl)isoquinoline Oxalate

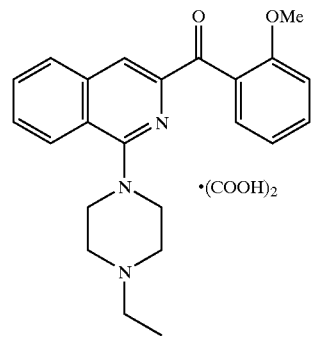

In the same manner as in Example 112, the free compound of the title compound was obtained (600 mg, yield: 60%) from 3-[α-hydroxy-(2-methoxybenzyl)]-1-(4-ethylpiperazin-1-yl)isoquinoline (1.0 g) and manganese dioxide (1.2 g).

The resulting free compound was converted into an oxalate in a conventional manner, to give the oxalate of the title compound as white crystals.

Oxalate:

m.p.: 153–156° C.

$^1$H-NMR (400 MHz,DMSO-$d_6$); δ (ppm) 1.20(t,J=7.2 Hz,3H), 3.04(q,J=7.2 Hz,2H), 3.22(br,4H), 3.42(br,4H), 3.63(s,3H), 7.08(t,J=8.0 Hz,1H), 7.14(d,J=8.0 Hz,1H), 7.43 (dd,J=7.6,1.6 Hz,1H), 7.54(dd,J=7.6,1.6 Hz,1H), 7.78(t,J= 7.6 Hz,1H), 7.84(t,J=7.6 Hz,1H), 8.16(d,J=7.6 Hz,1H), 8.19 (d,J=7.6 Hz,1H).

MS(FAB) m/z 376(M+H)+.

Free compound:

$^1$H-NMR (400 MHz,CDCl$_3$); δ (ppm) 1.12(t,J=7.2 Hz,3H), 2.48(q,J=7.2 Hz,2H), 2.62(br,4H), 3.36(br,4H), 3.69(s,3H), 6.96(d,J=8.4 Hz,1H), 7.03(dt,J=7.6,0.8 Hz,1H), 7.45(ddd,J=8.4,7.6,1.6 Hz,1H), 7.55(dd,J=7.6,1.6 Hz,1H), 7.61(ddd,J=8.4,8.0,1.2 Hz,1H), 7.66(ddd,J=8.4,8.0,1.2 Hz,1H), 7.92(d,J=8.0 Hz,1H), 8.06(s,1H), 8.09(d,J=8.4 Hz,1H).

Example 112

Synthesis of 3-(4-Methoxyphenylcarbonyl)-1-(4-ethylpiperazin-1-yl)isoquinoline Oxalate

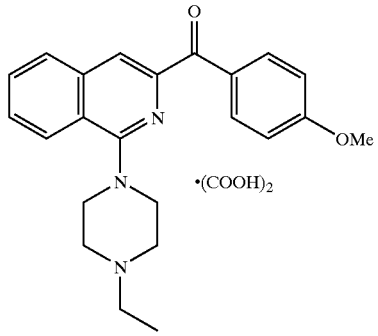

3-[α-Hydroxy-(4-methoxybenzyl)]-1-(4-ethylpiperazin-1-yl)isoquinoline (1.1 g) was dissolved in a mixture solution of benzene (20 ml) and methylene chloride (20 ml), followed by the addition of manganese dioxide (1.3 g). After the mixture was reacted under stirring at room temperature overnight, it was filtered and evaporated. The resulting crystals were washed with diethyl ether, to give the free compound of the title compound as a white solid (765 mg, yield: 70%). The resulting free compound was converted into an oxalate in a conventional manner, to give the oxalate of the title compound as white crystals.

Oxalate:

m.p.: 176–179° C.

$^1$H-NMR (400 MHz,DMSO-d$_6$); δ (ppm) 1.21(t,J=7.2 Hz,3H), 3.01(br,2H), 3.24(br,2H), 3.59(br,6H), 3.87(s,3H), 7.08(d,J=8.8 Hz,2H), 7.79(t,J=8.0 Hz,1H), 7.84(t,J=8.0 Hz,1H), 8.11(d,J=8.8 Hz,2H), 8.13(s,1H), 8.17(d,J=8.0 Hz,1H), 8.21(d,J=8.0 Hz,1H).

MS(FAB) m/z 376(M+H)$^+$.

Free compound:

$^1$H-NMR (400 MHz,CDCl$_3$); δ (ppm) 1.16(t,J=7.6 Hz,3H), 2.54(q,J=7.6 Hz,2H), 2.73(br,4H), 3.51(br,4H), 3.91(s,3H), 6.96(d,J=8.8 Hz,2H), 7.62(ddd,J=8.4,8.0,1.2 Hz,1H), 7.68(ddd,J=8.4,8.0,1.2 Hz,1H), 7.92(d,J=8.0 Hz,1H), 8.06(s,1H), 8.14(d,J=8.4 Hz,1H), 8.29(d,J=8.8 Hz,2H).

Example 113

Synthesis of 3-(4-Methoxyindan-1-yl)-1-(4-ethylpiperazin-1-yl)isoquinoline Hydrochloride

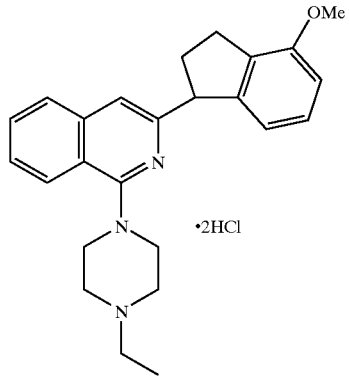

In the same manner as in Example 104, a yellow compound was obtained (440 mg, yield: 98%) from 5-methoxy-1-indanone (608 mg) and 3-bromo-1-(4-ethylpiperazin-1-yl)isoquinoline (800 mg). The resulting compound was converted into a hydrochloride in a conventional manner, to give the title compound as white crystals.

Hydrochloride:

m.p.: 108–110° C.

$^1$H-NMR (400 MHz,DMSO-d$_6$); δ (ppm) 1.29(t,J=7.2 Hz,3H), 2.39–2.46(m,1H), 2.48–2.82(m,1H), 2.83–2.89(m,1H), 2.99–3.07(m,1H), 3.14–3.24(m,4H), 3.40–3.58(m,4H), 3.76–3.90(m,2H), 3.80(s,3H), 4.58(t,J=7.2 Hz,1H), 6.67(d,J=8.0 Hz,1H), 6.79(d,J=8.0 Hz,1H), 7.10(t,J=8.0 Hz,1H), 7.30(s,1H), 7.58(t,J=8.4 Hz,1H), 7.71(t,J=8.4 Hz,1H), 7.86 (d,J=8.4 Hz,1H), 8.07(d,J=8.4 Hz,1H).

MS(FAB) m/z 388(M+H)$^+$.

Free compound:

$^1$H-NMR (400 MHz,CDCl$_3$); δ (ppm) 1.15(t,J=7.2 Hz,3H), 2.17–2.61(m,2H), 2.51(q,J=7.2 Hz,2H), 2.68(br,4H), 2.88–2.96(m,1H), 3.08–3.15(m,1H), 3.44(br,4H), 3.86 (s,3H), 4.54(t,J=7.2 Hz,1H), 6.70(d,J=7.6 Hz,1H), 6.79(d,J=7.6 Hz,1H), 7.02(s,1H), 7.10(t,J=7.6 Hz,1H), 7.40(ddd,J=8.4,8.0,1.2 Hz,1H), 7.52(ddd,J=8.4,8.0,1.2 Hz,1H), 7.64(d,J=8.0 Hz,1H), 8.02(d,J=8.4 Hz,1H).

Example 114

Synthesis of 3-(6-Methoxyindan-1-yl)-1-(4-ethylpiperazin-1-yl)isoquinoline Oxalate

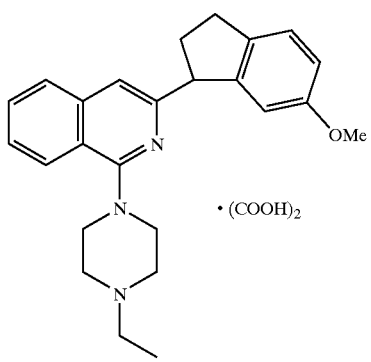

In the same manner as in Example 104, an oil was obtained from 6-methoxy-1-indanone (713 mg) and 3-bromo-1-(4-ethylpiperazin-1-yl)isoquinoline (937 mg). Methanol (20 ml) and platinum oxide (20 mg) were added to the oil (387 mg), and the mixture was reacted in hydrogen atmosphere overnight. The resulting reaction solution was filtered through Celite, and then evaporated. The resulting residue was purified by NH-silica gel column chromatography, to give a yellow oil (307 mg, yield: 79%). The oil was converted into an oxalate in a conventional manner, to give the oxalate of the title compound as white crystals.

Oxalate:

m.p.: 122–124° C.

$^1$H-NMR (400 MHz,DMSO-$d_6$); δ (ppm) 1.22(t,J=7.2 Hz,3H), 2.34–2.42(m,1H), 2.44–2.54(m,1H), 2.82–2.93(m, 1H), 3.02–3.10(m,4H), 3.30(br,4H), 3.53(br,5H), 3.64(s, 3H), 4.48(t,J=7.2 Hz,1H), 6.64(d,J=2.4 Hz,1H), 6.74(dd,J= 8.0,2.4 Hz,1H), 7.19(d,J=8.0 Hz,1H), 7.32 (s,1H), 7.56(t,J= 8.0 Hz,1H), 7.69(t,J=8.0 Hz,1H), 7.86(d,J=8.0 Hz,1H), 8.06 (d,J=8.0 Hz,1H).

MS(FAB) m/z 388(M+H)$^+$.

Free compound:

$^1$H-NMR (400 MHz,CDCl$_3$); δ (ppm) 1.15(t,J=7.2 Hz,3H), 2.41–2.61(m,2H), 2.52 (q,J=7.2 Hz,2H), 2.69(br, 4H), 2.86–2.93(m,1H), 3.12–3.04(m,1H), 3.45(br,4H), 3.71 (s,3H), 4.49(t,J=7.2 Hz,1H), 6.72(d,J=2.4 Hz,1H), 6.73(dd, J=8.0,2.4 Hz,1H), 7.03(s,1H), 7.18(d,J=8.0 Hz,1H), 7.41 (ddd,J=8.4,8.0,1.2 Hz,1H), 7.53(ddd,J=8.4,8.0,1.2 Hz,1H), 7.64(d,J=8.0 Hz,1H), 8.03(d,J=8.4 Hz,1H).

Example 115

Synthesis of 3-[4-(2-Hydroxyethoxy)indan-1-yl)-1-(4-ethylpiperazin-1-yl)isoquinoline Hydrochloride

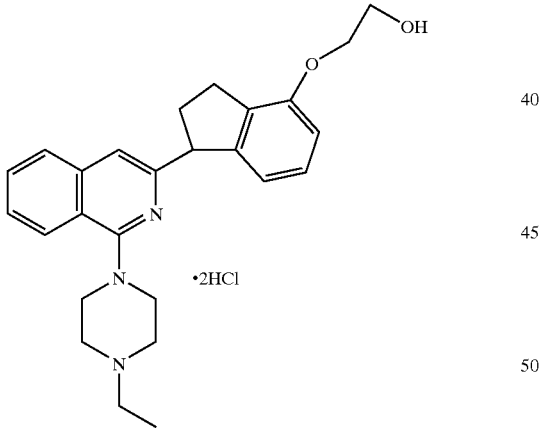

In the same manner as in Example 104, an oil was obtained from 5-(2-t-butyldimethylsilyloxyethoxy)-1-indanone (1.1 g) and 3-bromo-1-(4-ethylpiperazin-1-yl) isoquinoline (800 mg). To a solution of the oil in tetrahydrofuran (10 ml) was added a 1.0 M solution of tetrabutylammonium fluoride in tetrahydrofuran (6 ml), and the mixture was stirred at room temperature for 30 min. The reaction mixture was partitioned between ethyl acetate and water. The resulting organic layer was washed with water, dried and concentrated. The resulting residue was purified by silica gel column chromatography (hexane/ethyl acetate system), to give the free compound of the title compound as a colorless oil (394 mg, yield: 36%). The free compound was converted into a hydrochloride in a conventional manner, to give the hydrochloride of the title compound as a white amorphous.

Hydrochloride (amorphous):

$^1$H-NMR (400 MHz,CDCl$_3$); δ (ppm) 1.28(t,J=7.2 Hz,3H), 2.38–2.41(m,1H), 2.45–2.50(m,1H), 2.83–2.93(m, 1H), 3.00–3.11(m,1H), 3.14–3.30(m,4H), 3.45–3.60(m,4H), 3.76(t,J=4.8 Hz,2H), 3.82–3.91(m,1H), 4.03(br,2H), 4.58(t, J=7.2 Hz,2H), 6.66(d,J=8.0 Hz,1H), 6.78(t,J=8.0 Hz,1H), 7.08(t,J=8.0 Hz,1H), 7.28(s,1H), 7.58(t,J=8.0 Hz,1H), 7.71 (t,J=8.0 Hz,1H), 7.86(d,J=8.0 Hz,1H), 8.07(d,J=8.0 Hz,1H).

MS(FAB) m/z 418(M+H)$^+$.

Free compound:

$^1$H-NMR (400 MHz,CDCl$_3$); δ (ppm) 1.45(t,J=7.2 Hz,3H), 2.43–2.61(m,2H), 2.53 (q,J=7.2 Hz,2H), 2.69(br, 4H), 2.89–2.97(m,1H), 3.09–3.17(m,1H), 3.44(br,4H), 3.99 (t,J=4.0 Hz,2H), 4.13–4.16(m,2H), 4.54(t,J=7.6 Hz,1H), 6.71(d,J=7.6 Hz,1H), 6.81(d,J=7.6 Hz,1H), 7.03(s,1H), 7.09 (t,J=7.6 Hz,1H), 7.41(ddd,J=8.4,8.0,1.2 Hz,1H), 7.53(ddd, J=8.4,8.0,1.2 Hz,1H), 7.64(d,J=8.0 Hz,1H), 8.03(d,J=8.4 Hz,1H).

Example 116

Synthesis of 3-(8-Methoxy-1,2-dihydronaphthalen-4-yl)-1-(4-ethylpiperazin-1-yl)isoquinoline Oxalate

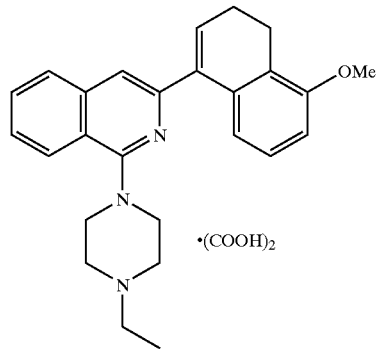

In the same manner as in Example 104, a brown oil was obtained (97 mg, yield: 93%) from 5-methoxy-1-tetralone (711 mg) and 3-bromo-1-(4-ethylpiperazin-1-yl) isoquinoline (860 mg). The resulting oil was converted into an oxalate in a conventional manner, to give the oxalate of the title compound as white crystals.

Oxalate:

m.p.: 136–139° C.

$^1$H-NMR (400 MHz,DMSO-$d_6$); δ (ppm) 1.22(t,J=7.2 Hz,3H), 2.36(br,2H), 2.77(t,J=8.0 Hz,2H), 3.06(br,2H), 3.28 (br,4H), 3.52(br,4H), 3.83(s,3H), 6.52(t,J=4.4 Hz,1H), 6.79 (d,J=8.0 Hz,1H), 6.93(d,J=8.0 Hz,1H), 7.11(t,J=8.0 Hz,1H), 7.53(s,1H), 7.61(t,J=8.0 Hz,1H), 7.72(t,J=8.4 Hz,1H), 7.93 (d,J=8.4 Hz,1H), 8.12(d,J=8.4 Hz,1H).

MS(FAB) m/z 400(M+H)$^+$.

Free compound:

$^1$H-NMR (400 MHz,CDCl$_3$); δ (ppm) 1.16(t,J=7.2 Hz,3H), 2.40–2.45(m,2H), 2.54(q,J=7.2 Hz,2H), 2.73(br, 4H), 2.88(t,J=8.0 Hz,2H), 3.52(br,4H), 3.88(s,3H), 6.60(t, J=4.4 Hz,1H), 6.82(d,J=8.0 Hz,1H), 6.99(d,J=8.0 Hz,1H), 7.09(t,J=8.0 Hz,1H), 7.35(s,1H), 7.46(dt,J=8.4,1.2 Hz,1H), 7.57(dt,J=8.4,1.2 Hz,1H), 7.71(d,J=8.4 Hz,1H), 8.08(d,J= 8.4 Hz,1H).

Example 117

Synthesis of 3-(7-Methoxy-1,2-dihydronaphthalen-4-yl)-1-(4-ethylpiperazin-1-yl)isoquinoline Oxalate

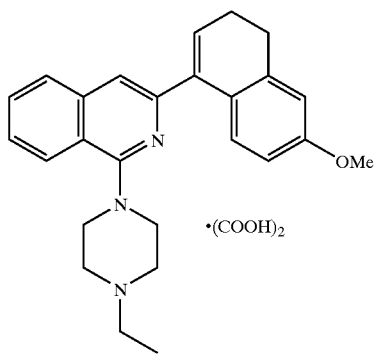

To a solution of 3-bromo-1-(4-ethylpiperazin-1-yl)isoquinoline (860 mg) in tetrahydrofuran (10 ml) was added 2.5 M n-butyl lithium (1.3 ml) at −78° C. Thereafter, the mixture was raised to −40° C., to which was then added 6-methoxy-1-tetralone (711 mg), and then the mixture was stirred at −40° C. for 20 min. The reaction solution was poured into an aqueous solution of saturated ammonium chloride and extracted with ethyl acetate. The resulting organic layer was washed with water and brine, dried and evaporated. Then, to the resulting residue were added methanol (10 ml) and 5N hydrochloric acid (1 ml), and the mixture was heated under reflux for 1 hr. The reaction solution was basified by adding a 2N aqueous solution of sodium hydroxide thereto, which was then partitioned between ethyl acetate and water. The resulting organic layer was washed with water, dried and evaporated. The resulting residue was purified by silica gel column chromatography (hexane/ethyl acetate system), to give free compound of the title compound as a colorless oil (410 mg, yield: 86%). The free compound was converted into an oxalate in a conventional manner, to give the oxalate of the title compound as white crystals.

Oxalate:

m.p.: 112–114° C.

$^1$H-NMR (400 MHz, DMSO-$d_6$); δ (ppm) 1.24(br,3H), 2.39(br,2H), 2.51(br,2H), 2.78(br,2H), 3.13(br,2H), 3.33(br,2H), 3.76(br,4H), 6.40(s,1H), 6.71(d,J=8.4 Hz,1H), 6.87(s,1H), 7.14(d,J=8.4 Hz,1H), 7.57(s,1H), 7.62(t,J=8.0 Hz,1H), 7.73(t,J=8.0 Hz,1H), 7.94(d,J=8.0 Hz,1H), 8.12(d,J=8.0 Hz,1H).

MS(FAB) m/z 400(M+H)$^+$.

Free compound:

$^1$H-NMR (400 MHz,CDCl$_3$); δ (ppm) 1.16(t,J=7.2 Hz,3H), 2.42–2.47(m,2H), 2.54(q,J=7.2 Hz,2H), 2.73(br,4H), 2.85(t,J=7.6 Hz,2H), 3.51(br,4H), 3.82(s,3H), 6.47(t, J=4.8 Hz,1H), 6.67(dd,J=8.8,2.8 Hz,1H), 6.79(d,J=2.8 Hz,1H). 7.32(d,J=8.8 Hz,1H), 7.44(s,1H), 7.46 (ddd, J=8.4, 8.0, 1.2 Hz, 1H), 7.57 (ddd, J=8.4, 8.0, 1.2 Hz, 1H), 7.71 (d, J=8.0 Hz, 1H), 8.08 (d, J=8.4 Hz, 1H).

Example 118

Synthesis of 3-(6-Methoxy-1,2-Dihydronaphthalen-4-yl)-1-(4-Ethylpiperazin-1-yl)Isoquinoline Oxalate

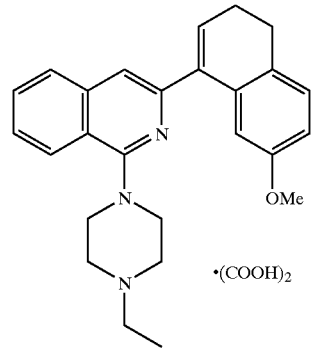

In the same manner as in Example 104, the free compound of the title compound was obtained as a colorless oil (97 mg, yield; 98%) from 7-methoxy-1-tetralone and 3-bromo-1-(4-ethylpiperazin-1-yl)isoquinoline. The free compound was converted into an oxalate in a conventional manner, to give the oxalate of the title compound as white crystals.

Oxalate:

m.p.; 150–153° C.

$^1$H-NMR (400 Hz, DMSO-$d_6$); δ (ppm) 1.24 (t, J=7.2 Hz, 3H), 2.38 (br, 2H), 2.74 (t, J=7.6 Hz, 2H), 3.11 (br, 2H), 3.35 (br, 4H), 3.55 (br, 4H), 3.63 (s, 3H), 6.55 (t, J=4.4 Hz, 1H), 6.78–6.79 (m, 2H), 7.18 (d, J=8.4 Hz, 1H), 7.59 (s, 1H), 7.62 (t, J=8.0 Hz, 1H), 7.73 (t, J=8.0 Hz, 1H), 7.96 (d, J=8.0 Hz, 1H), 8.13 (d, J=8.0 Hz, 1H).

MS(FAB) m/z 400 (M+H)$^+$.

Free compound:

$^1$H-NMR (400 MHz, CDCl$_3$); δ (ppm) 1.16 (t, J=7.2 Hz, 3H), 2.42–2.47 (m, 2H), 2.54 (q, J=7.2 Hz, 2H), 2.73 (br, 4H), 2.80 (t, J=8.0 Hz, 2H), 3.52 (br, 4H), 3.70 (s, 3H), 6.60 (t, J=4.8 Hz, 1H), 6.73 (dd, J=8.0, 2.8 Hz, 1H), 6.96 (d, J=2.8 Hz, 1H), 7.13 (d, J=8.0 Hz, 1H), 7.38 (s, 1H), 7.46 (ddd, J=8.4, 8.0, 1.2 Hz, 1H), 7.57 (ddd, J=8.4, 8.0, 1.2 Hz, 1H), 7.72 (d, J=8.0 Hz, 1H), 8.08 (d, J=8.4 Hz, 1H).

Example 119

Synthesis of 3-(5-Methoxy-1,2,3,4-Tetrahydronaphthalen-1-yl)-1-(4Ethylpiperazin-1-yl) Isoquinoline Oxalate

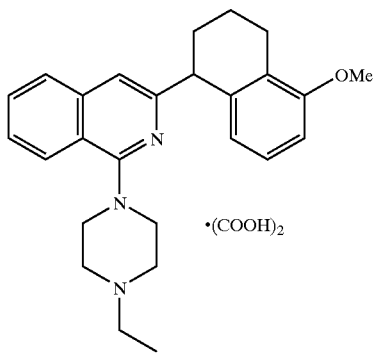

In the same manner as in Example 18, the free compound of the title compound was obtained as a colorless oil (218 mg, yield; 83%) from 3-(8-methoxy-1,2-dihydronaphthalen-4-yl)-1-(4-ethylpiperazin-1-yl)isoquinoline (273 mg) and palladium/carbon catalyst (20 mg). The free compound was converted into an oxalate in a conventional manner, to give the oxalate of the title compound as white crystals.

Oxalate:

m.p.; 133–136° C.

$^1$H-NMR (400 Hz, DMSO-d$_6$); δ (ppm) 1.23 (t, J=7.2 Hz, 3H), 1.65–1.80 (m, 3H), 2.00 (br, 1H), 2.15 (br, 1H), 2.55–2.72 (m, 2H), 3.11 (d, J=5.6 Hz, 2H), 3.32 (br, 2H), 3.54 (br, 1H), 3.60 (br, 2H), 3.80 (s, 3H), 3.93 (br, 2H), 4.24 (t, J=5.6 Hz, 1H), 6.52 (d, J=8.0 Hz, 1H), 6.79 (d, J=8.0 Hz, 1H), 6.95 (s, 1H), 7.04 (t, J=8.0 Hz, 1H), 7.55 (t, J=8.0 Hz, 1H), 7.66 (t, J=8.0 Hz, 1H), 7.78 (d, J=8.0 Hz, 1H), 8.06 (d, J=8.0 Hz, 1H).

MS(FAB) m/z 402 (M+H)$^+$.

Free compound:

$^1$H-NMR (400 MHz, CDCl$_3$); δ (ppm) 1.16 (t, J=7.6 Hz, 3H), 1.68–1.75 (m, 2H), 2.01–2.09 (m, 1H), 2.23–2.29 (m, 1H), 2.53 (q, J=7.6 Hz, 2H), 2.62–2.84 (m, 2H), 2.70 (br, 4H), 3.47 (br, 4H), 3.87 (s, 3H), 4.29 (t, J=5.6 Hz, 1H), 6.67 (d, J=8.0 Hz, 1H), 6.70 (s, 1H), 6.72 (d, J=8.0 Hz, 1H), 7.06 (t, J=8.0 Hz, 1H), 7.40 (ddd, J=8.4, 8.0, 1.2 Hz, 1H), 7.49 (ddd, J=8.4, 8.0, 1.2 Hz, 1H), 7.56 (d, J=8.0 Hz, 1H), 8.03 (d, J=8.4 Hz, 1H).

Example 120

Synthesis of 3-(6-Methoxy-1,2,3,4-Tetrahydronaphthalen-1-yl)-1-(4-Ethylpiperazin-1-yl)Isoquinoline Oxalate

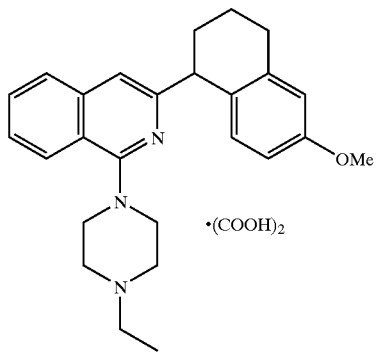

Methanol (30 ml) and platinum oxide (30 mg) were added to 3-(6-methoxy-1,2-dihydronapthalen-1-yl)-1-(4-ethylpiperazin-1-yl)isoquinoline (347 mg), and the mixture was reacted in hydrogen atmosphere for 6 hr. The resulting reaction solution was filtered through Celite, and then evaporated. The resulting residue was purified by NH-silica gel column chromatography, to give the free compound of the title compound as an oil (189 mg, yield; 54%). The resulting free compound was converted into an oxalate in a conventional manner, to give the oxalate of the title compound as white crystals.

Oxalate:

m.p.; 170–173° C.

$^1$H-NMR (400 MHz, DMSO-d$_6$); δ (ppm) 1.21 (br, 3H), 1.60–1.80 (m, 2H), 1.95–2.20 (m, 2H), 2.81 (br, 2H), 3.04 (br, 2H), 3.23 (br, 4H), 3.49 (br, 4H), 3.72 (s, 3H), 4.19 (br, 1H), 6.64 (d, J=8.4 Hz, 1H), 6.73 (s, 1H), 6.82 (d, J=8.4 Hz, 1H), 6.96 (s, 1H), 7.55 (t, J=8.0 Hz, 1H), 7.65 (t, J=8.0 Hz, 1H), 7.78 (d, J=8.0 Hz, 1H), 8.05 (d, J=8.0 Hz, 1H).

MS(FAB) m/z 402 (M+H)$^+$.

Free compound:

$^1$H-NMR (400 MHz, CDCl$_3$); δ (ppm) 1.16 (t, J=7.2 Hz, 3H), 2.05–2.14 (m, 3H), 2.18–2.26 (m, 1H), 2.51 (q, J=7.2 Hz, 2H), 2.71 (br, 4H), 2.71–2.89 (m, 2H), 3.47 (br, 4H), 3.81 (s, 3H), 4.25 (t, J=5.6 Hz, 1H), 6.66 (dd, J=8.4, 2.8 Hz, 1H), 6.70 (d, J=2.8 Hz, 1H), 6.72 (s, 1H), 6.94 (d, J=8.4 Hz, 1H), 7.40 (ddd, J=8.4, 8.0, 1.2 Hz, 1H), 7.50 (ddd, J=8.4, 8.0, 1.2 Hz, 1H), 7.57 (d, J=8.0 Hz, 1H), 8.03 (d, J=8.4 Hz, 1H).

Example 121

Synthesis of 3-(7-Methoxy-1,2,3,4-Tetrahydronaphthalen-1-yl)-1-(4-Ethylpiperazin-1-yl)Isoquinoline Oxalate

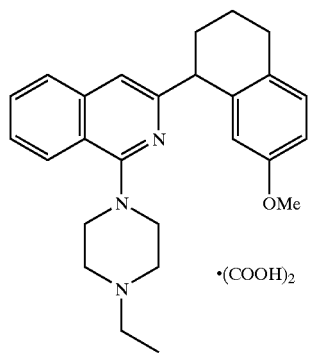

In the same manner as in Example 18, the free compound of the title compound was obtained as a colorless oil (239 mg, yield; 61%) from 3-(6-methoxy-1,2-dihydronaphthalen-4-yl)-1-(4-ethylpiperazin-1-yl)isoquinoline (405 mg) and palladium/carbon catalyst (30 mg). The free compound was converted into an oxalate in a conventional manner, to give the oxalate of the title compound as white crystals.

Oxalate:

m.p.; 110–112° C.

$^1$H-NMR (400 MHz, DMSO-d$_6$); δ (ppm) 1.21 (br, 3H), 1.73 (br, 2H), 2.02 (br, 1H), 2.12 (br, 1H), 2.73 (br, 2H), 3.09 (br, 2H), 3.29 (br, 4H), 3.50 (br, 4H), 3.58 (s, 3H), 4.21 (br, 1H), 6.43 (s, 1H), 6.72 (d, J=8.4 Hz, 1H), 6.97 (s, 1H), 7.06 (d, J=8.4 Hz, 1H), 7.53 (t, J=8.0 Hz, 1H), 7.64 (t, J=8.0 Hz, 1H), 7.77 (d, J=8.0 Hz, 1H), 8.04 (d, J=8.0 Hz, 1H).

MS(FAB) m/z 402 (M+H)$^+$.

Free compound:

$^1$H-NMR (400 MHz, CDCl$_3$); δ (ppm) 1.16 (t, J=7.2 Hz, 3H), 1.66–1.81 (m, 2H), 2.05–2.13 (m, 1H), 2.21–2.28 (m, 1H), 2.52 (q, J=7.2 Hz, 2H), 2.71 (br, 4H), 2.71–2.85 (m, 2H), 3.47 (br, 4H), 3.67 (s, 3H), 4.27 (t, J=6.0 Hz, 1H), 6.58 (d, J=2.4 Hz, 1H), 6.74 (s, 1H), 6.75 (dd, J=8.8, 2.4 Hz, 1H), 7.08 (d, J=8.4 Hz, 1H), 7.41 (dt, J=8.4, 1.2 Hz, 1H), 7.51 (dt, J=8.4, 1.2 Hz, 1H), 7.59 (d, J=8.4 Hz, 1H), 8.03 (d, J=8.4 Hz, 1H).

Example 122

Synthesis of 3-(3-Hydroxymethylchroman-6-yl)-1-(4-Ethylpiperazin-1-yl)Isoquinoline Hydrochloride

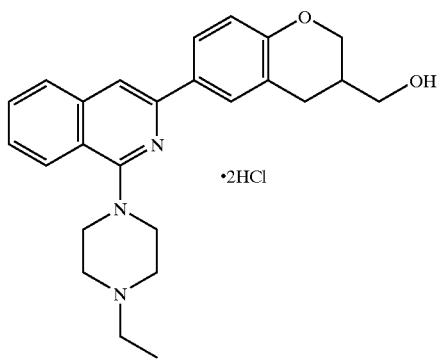

In the same manners sequentially as in Examples 161-2 and 20, an oil was obtained from 6-bromo-3-acetoxymethylchroman (4.67 g) and 3-bromo-1-(4-ethylpiperazin-1-yl)isoquinoline (2.2 g). To the resulting oil were added methanol (20 ml) and a 1 N aqueous solution of sodium hydroxide (2 ml), and then reacted at 50° C. for 2 hr. The reaction solution was partitioned between ethyl acetate and water. The resulting organic layer was washed with water, dried and concentrated. The resulting residue was purified by silica gel column chromatography, to give the free compound of the title compound as an oil. The free compound was converted into a hydrochloride in a conventional manner, to give the hydrochloride of the title compound as yellow crystals (1.93 g, yield; 91%).

Hydrochloride:

m.p.; 168–172° C.

$^1$H-NMR (400 MHz, DMSO-$d_6$); δ (ppm) 1.34 (t, J=7.2 Hz, 3H), 2.13 (br, 1H), 2.63 (dd, J=16.4, 4.8 Hz, 1H), 2.89 (dd, J=16.4, 5.2 Hz, 1H), 3.19–3.26 (m, 2H), 3.33–3.43 (m, 3H), 3.48–3.60 (m, 3H), 3.62 (d, J=11.6 Hz, 2H), 3.90–3.98 (m, 3H), 4.31 (dd, J=11.2, 2.0 Hz, 1H), 6.87 (d, J=9.2 Hz, 1H), 7.56 (t, J=8.0 Hz, 1H), 7.71 (t, J=8.0 Hz, 1H), 7.91–7.96 (m, 4H), 8.09 (d, J=8.0 Hz, 1H).

MS(FAB) m/z 404 (M+H)$^+$.

Free compound:

$^1$H-NMR (400 MHz, CDCl$_3$); δ (ppm) 1.18 (t, J=7.2 Hz, 3H), 2.30–2.36 (m, 1H), 2.56 (q, J=7.2 Hz, 2H), 2.66–2.73 (m, 1H), 2.76 (br, 4H), 2.98 (dd, J=16.4, 1.2 Hz, 1H), 3.57 (br, 4H), 3.78–3.69 (m, 2H), 4.05–4.13 (m, 1H), 4.33–4.37 (m, 1H), 6.89 (d, J=8.0 Hz, 1H), 7.42 (ddd, J=8.4, 8.0, 1.2 Hz, 1H), 7.56 (ddd, J=8.4, 8.0, 1.2 Hz, 1H), 7.59 (s, 1H), 7.75 (d, J=8.0 Hz, 1H), 7.88 (dd, J=8.0, 2.0 Hz, 1H), 7.89 (s, 1H), 8.05 (d, J=8.4 Hz, 1H).

Example 123

Synthesis of 1-(4-Ethylpiperazin-1-yl)-3-(2-Pyridyl) Isoquinoline Dihydrochloride or Compound Identified by the Following Analytical Data and Synthetic Procedures

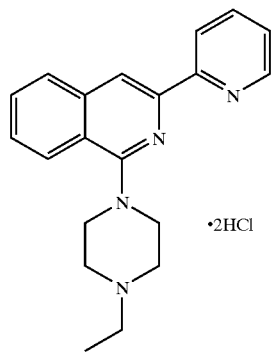

3-(2-Pyridyl)isoquinolin-1-one obtained by reacting N-methyl-o-toluamide (2.28 g) and 2-cyanopyridine (1.59 g) according to Example 10-1 was added to phosphorus oxychloride (10 ml), and the mixture was stirred at 100° C. for 3 hr. The reaction solution was evaporated, and then ethyl acetate and water were added to the resulting residue. The resulting organic layer was washed with water, an aqueous solution of sodium bicarbonate and brine, and dried over magnesium sulfate. The solvent was evaporated, and the resulting 1-chloro-3-(2-pyridyl)isoquinoline was reacted with N-ethylpiperazine (15 ml) at 110° C. for 12 hr. The reaction solution was evaporated, and then ethyl acetate and water were added to the resulting residue. The resulting organic layer was washed with water and brine, and dried over magnesium sulfate. The solvent was evaporated, and the resulting residue was purified by silica gel column chromatography (methylene chloride/methanol system), to give the free compound of the title compound as a pale yellow oil.

Free compound:

$^1$H-NMR (400 MHz, CDCl$_3$); δ (ppm) 1.10 (t, J=8.0 Hz, 3H), 2.57 (q, J=8.0 Hz, 2H), 2.78 (m, 4H), 3.58 (m, 4H), 7.27 (m, 1H), 7.50 (t, J=9.2 Hz, 1H), 7.61 (t, J=9.2 Hz, 1H), 7.81 (t, J=9.2 Hz, 1H), 7.89 (d, J=9.2 Hz, 1H), 8.10 (d, J=9.2 Hz, 1H), 8.40 (s, 1H), 8.52 (d, J=9.2 Hz, 1H), 8.67 (d, J=4.5 Hz, 1H).

The resulting free compound was converted into a hydrochloride in a conventional manner, and recrystallized from ethanol/ether, to give 0.31 g of the title compound as a yellow powder.

Hydrochloride:

m.p.; 160–162° C.

$^1$H-NMR (400 MHz, CDCl$_3$); δ (ppm) 1.34 (t, J=7.2 Hz, 3H), 3.19–3.28 (m, 2H), 3.31–3.43 (m, 2H), 3.55–3.70 (m, 4H), 4.14 (br-d, 2H), 7.71–7.79 (m, 2H), 7.84 (t, J=8.0 Hz, 1H), 8.10 (d, J=8.0 Hz, 1H), 8.20 (d, J=8.0 Hz, 1H), 8.30–8.39 (m, 1H), 8.63 (s, 1H), 8.66 (d, J=8.0 Hz, 1H), 8.85 (br-d, 1H), 11.26 (br-s, 1H).

MS(FAB) m/z 319 (M+H)$^+$.

Example 124

Synthesis of 1-(1-Ethylpiperazin-4-yl)-3-[5-(2-Hydroxyethoxy)Pyridin-2-yl]Isoquinoline

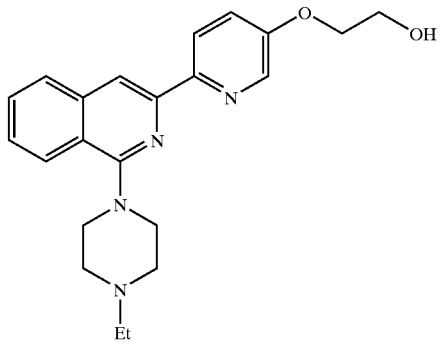

In the same manner as in Example 127-1, 5-(2-acetoxyethoxy)-2-tributylstannylpyridine was obtained as a colorless solid (3.362 g) from a mixture (4.015 g) of 2-iodo-3-hydroxypyridine and 4-iodo-3-hydroxypyridine, 2-bromoethyl acetate (4.551 g) and bis(tributyltin) (13.6 ml). The resulting compound and 1-(1-ethylpiperazin-4-yl)-3-bromoisoquinoline (452 mg) were treated in the same manner as in Example 300, to give the hydrochloride of the title compound as yellow crystals (recrystallized from ethanol/isopropyl ether) (189 mg, yield; 29%).

Hydrochloride:

m.p.; 110–115° C.

$^1$H-NMR (400 MHz, DMSO-$d_6$); δ (ppm) 1.30 (3H, t, J=7.2 Hz), 3.20 (1H, q, J=7.2 Hz), 3.22 (1H, q, J=7.2 Hz), 3.30–3.40 (2H, m), 3.48–3.60 (4H, m), 3.80–3.90 (2H, m), 4.17 (2H, d, J=13.2 Hz), 4.30–4.40 (2H, m), 7.75 (1H, dd, J=8 Hz, 7 Hz), 7.76–7.88 (1H, m), 7.84 (1H, dd, J=8H, 7 Hz), 8.07 (1H, d, J=8 Hz), 8.19 (1H, d, J=8 Hz), 8.16–8.30 (1H, m), 8.44–8.60 (2H, m).

ESI-Mass; 379 (MH$^+$).

Example 125

Synthesis of 1-(1-Ethylpiperazin-4-yl)-3-[2-(2-Hydroxyethoxy)Pyridin-5-yl]Isoquinoline (125-1) 2-(2-Benzyloxyethoxy)-5-bromopyridine

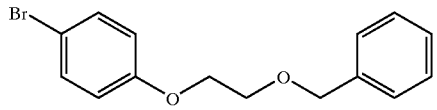

In the same manner as in Example 126-1, 2.705 g of the title compound was obtained as a yellow oil from 2-benzyloxyethanol (15.219 g) and 2,5-dibromopyridine (2.369 g). $^1$H-NMR (400 MHz, CDCl$_3$); δ (ppm) 3.81 (2H, t, J=4.8 Hz), 4.46 (2H, t, J=4.8 Hz), 4.61 (2H, s), 6.72 (1H, d, J=8.8 Hz), 7.27–7.36 (5H, m), 7.64 (1H, dd, J=8.8 Hz, 2.4 Hz), 8.16 (1H, d, J=2.4 Hz).

(125-2) 1-(1-Ethylpiperazin-4-yl)-3-[2-(2-hydroxyethoxy)pyridin-5-yl]isoquinoline

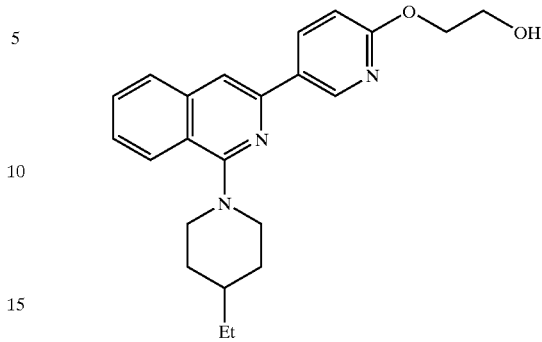

According to Example 167-2, 2-(2-benzyloxyethoxy)-5-bromopyridine (1.233 g) and 1-(1-ethylpiperazin-4-yl)-3-bromoisoquinoline (480 mg) were treated, which were continuously treated in the same manner as in Example 167-3, to give the hydrochloride of the title compound. The resulting hydrochloride was recrystallized from ethanol/isopropyl ether, to give the title compound as pale yellow crystals (186 mg, yield; 27%).

Hydrochloride:

m.p.; 137–142° C.

$^1$H-NMR (400 MHz, DMSO-$d_6$); δ (ppm) 1.31 (3H, t, J=7.2 Hz), 3.16–3.24 (2H, m), 3.30 (1H, t, J=10.4 Hz), 3.33 (1H, t, J=10.4 Hz), 3.54 (2H, t, J=13.6 Hz), 3.58 (2H, d, J=10.4 Hz), 3.73 (2H, t, J=5.2 Hz), 3.99 (2H, d, J=13.6 Hz), 4.33 (2H, t, J=5.2 Hz), 6.96 (1H, d, J=8.8 Hz), 7.58 (1H, ddd, J=8 Hz, 7 Hz, 1.2 Hz), 7.73 (1H, ddd, J=8 Hz, 7 Hz, 1.2 Hz), 7.93 (1H, d, J=8 Hz), 8.04 (1H, s), 8.09 (1H, d, J=8 Hz), 8.46 (1H, dd, J=8.8 Hz, 2.8 Hz), 8.96 (1H, d, J=2.8 Hz), 11.15 (1H, br-s).

ESI-Mass; 379 (MH$^+$).

Example 126

Synthesis of 1-(1-Ethylpiperazin-4-yl)-3-[2-(2-Methoxyethoxy)Pyridin-5-yl]Isoquinoline (126-1) 2-(2-Methoxyethoxy)-5-bromopyridine

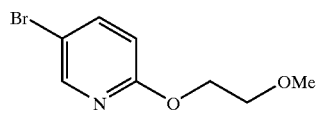

2-Methoxyethanol (7.9 mg) was dissolved in N,N-dimethylformamide (50 ml), followed the by addition of 60% sodium hydride (4 g) under ice-cooling, and the mixture was stirred for 20 min. Thereafter, it was stirred at 90° C. for further 30 min. To the reaction mixture was added dropwise 2,5-dibromopyridine (2.369 g)/N,N-dimethylformamide (20 ml) solution, and the mixture was stirred overnight. The reaction mixture was partitioned between ethyl acetate and water. The resulting organic layer was washed with water, dried (over MgSO$_4$) and evaporated. The resulting residue was purified by silica gel column chromatography (ethyl acetate/hexane system), to give the title compound as a colorless oil (1.122 g, yield; 48%).

$^1$H-NMR (400 MHz, CDCl$_3$); δ (ppm) 3.43 (3H, s), 3.73 (2H, t, J=4.6 Hz), 4.44 (2H, t, 4.6 Hz), 6.72 (1H, dd, J=8.8 Hz, 0.8 Hz), 7.64 (1H, dd, J=8.8 Hz, 2.4 Hz), 8.17 (1H, dd, J=2.4 Hz, 0.8 Hz).

(126-2) 1-(1-Ethylpiperazin-4-yl)-3-[2-(2-methoxyethoxy)pyridin-5-yl]isoquinoline

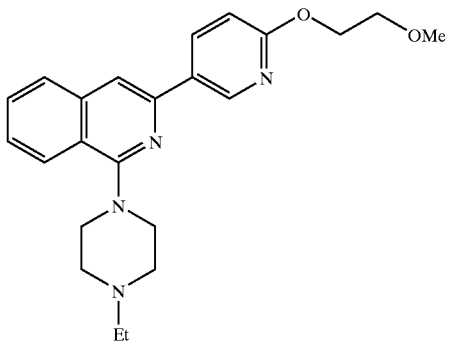

In the same manner as in Example 167-2, the hydrochloride of the title compound was obtained as yellow crystals (371 mg, yield; 53%) from 2-(2-methoxyethoxy)-5-bromopyridine (928 mg) and 1-(1-ethylpiperazin-4-yl)-3-bromoisoquinoline (480 mg).
Hydrochloride:
m.p.; 115–120° C.
$^1$H-NMR (400 MHz, DMSO-d$_6$); δ (ppm) 1.33 (3H, t, J=7.2 Hz), 3.18–3.65 (2H, m), 3.70 (2H, t, J=4.6 Hz), 4.02 (2H, d, J=13.6 Hz), 4.45 (2H, t, J=4.6 Hz), 6.99 (1H, d, J=8.4 Hz), 7.61 (1H, dd, J=8.4 Hz, 7 Hz), 7.75 (1H, dd, J=8.4 Hz, 7 Hz), 7.96 (1H, d, J=8.4 Hz), 8.07 (1H, s), 8.12 (1H, d, J=8.4 Hz), 8.48 (1H, dd, J=8.4 Hz, 2.8 Hz), 8.99 (1H, s, J=2.8 Hz).
ESI-Mass; 393 (MH$^+$).

Example 127

Synthesis of 1-(1-Ethylpiperazin-4-yl)-3-[5-(2-Methoxyethoxy)Pyridin-2-yl]Isoquinoline
(127-1) 5-Methoxyethoxy-2-tributylstannylpyridine

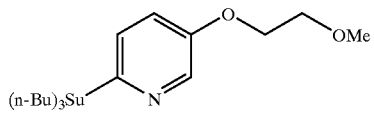

3-Hydroxypyridine (20.077 g) was dissolved in methanol (350 ml), sodium iodide (31.565 g) and sodium hydroxide (8.545 g) were added thereto, 5% sodium hypochlorite (314 mg) was added thereto under ice-cooling, and then the mixture was stirred for 5 hr. 10% sodium thiosulfate solution (200 ml) was added to the reaction mixture, which was then neutralized with 5 N hydrochloric acid and extracted with ethyl acetate. The resulting organic layer was washed with water, dried (over MgSO$_4$) and evaporated. The resulting residue was purified by silica gel column chromatography (ethyl acetate/hexane system), to give a mixture of 2-iodo-3-hydroxypyridine and 4-iodo-3-hydroxypyridine (7:3) as a yellow solid (12.544 g). The resulting mixture (2.97 g) was dissolved in N,N-dimethylformamide (40 ml), followed by the addition of 2-bromoethyl methyl ether (3.822 g) and potassium carbonate (3.704 g), and the mixture was stirred at 80° C. overnight. The resulting insoluble matters were filtered off. The resulting reaction mixture was partitioned between ethyl acetate and water. The resulting organic layer was washed with water, dried (over MgSO$_4$) and evaporated. The resulting residue and bis(tributyltin) (5 ml) were treated in the same manner as in Example 161-2, to give 1.142 g of the title compound as a colorless oil.

$^1$H-NMR (400 MHz, CDCl$_3$); δ (ppm) 0.87 (9H, t, J=7.4 Hz), 1.11–1.16 (6H, m), 1.29–1.37 (6H, m), 1.50–1.61 (6H, m), 3.43 (3H, s), 3.74 (2H, t, J=5 Hz), 4.06 (2H, t, J=5 Hz), 6.97 (1H, dd, J=8.4 Hz, 1.2 Hz), 7.08 (1H, dd, J=8.4 Hz, 4.8 Hz), 8.37 (1H, dd, J=4.8 Hz, 1.2 Hz).
(127-2) 1-(1-Ethylpiperazin-4-yl)-3-[5-(2-methoxyethoxy)pyridin-2-yl]isoquinoline

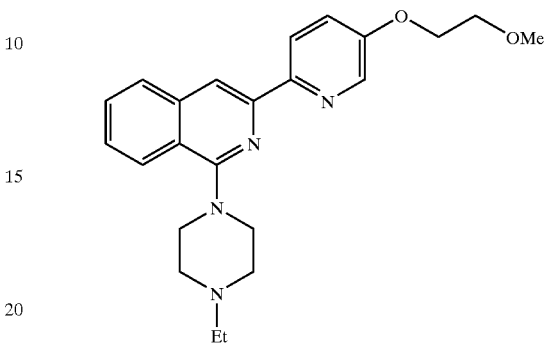

In the same manner as in Example 161-3, the hydrochloride of the title compound was obtained as yellow crystals (recrystallized form ethanol/isopropyl ether) (225 mg, yield; 36%) from 5-(2-methoxyethoxy)-2-tributylstannylpyridine (1.142 g) and 1-(1-ethylpiperazin-4-yl)-3-bromoisoquinoline (448 mg).
Hydrochloride:
m.p.; 116–119° C.
$^1$H-NMR (400 MHz, DMSO-d$_6$); δ (ppm) 1.31 (3H, t, J=7.2 Hz), 3.15–3.25 (2H, m), 3.30–3.40 (2H, m), 3.37 (3H, s), 3.54–3.62 (4H, m), 3.80–3.85 (2H, m), 4.20 (2H, d, J=14 Hz), 4.45–4.52 (2H, m), 7.77 (1H, dd, J=8 Hz, 7 Hz), 7.86 (1H, dd, J=8 Hz, 7 Hz), 7.88–7.96 (1H, m), 8.03 (1H, d, J=8 Hz), 8.20 (1H, d, J=8 Hz), 8.24–8.36 (1H, m), 8.50–8.60 (2H, m).
ESI-Mass; 393 (MH$^+$).

Example 128

Synthesis of 3-(2-propylcarbonylaminopyridin-5-yl)-1-(4-ethylpiperazin-1-yl)isoquinoline hydrochloride

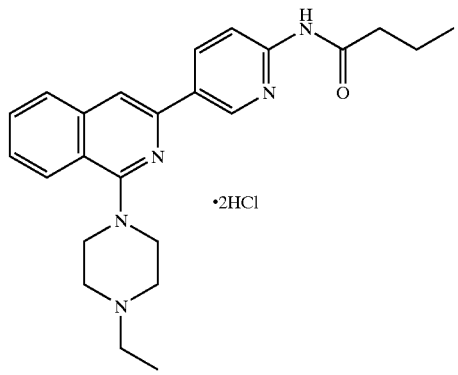

In the same manners sequentially as in Examples 161-2 and 20, the free compound of the title compound (338 mg, yield; 40%) from 5-bromo-2-propylcarbonylaminopyridine (3.11 g) and 3-bromo-1-(4-ethylpiperazin-1-yl)isoquinoline (514 mg). The resulting free compound was converted into a hydrochloride in a conventional manner, to give the hydrochloride of the title compound as yellow crystals.

Hydrochloride:

m.p.; 168–171° C.

$^1$H-NMR (400 MHz, DMSO-d$_6$); δ (ppm) 0.94 (t, J=7.2 Hz, 3H), 1.35 (t, J=7.2 Hz, 3H), 1.66 (q, J=7.2 Hz, 2H), 2.47 (t, J=7.2 Hz, 2H), 3.18–3.26 (m, 2H), 3.30–3.40 (m, 2H), 3.54–3.63 (m, 4H), 4.02 (d, J=14.0 Hz, 2H), 7.64 (t, J=8.0 Hz, 1H), 7.78 (t, J=8.0 Hz, 1H), 7.99 (d, J=8.0 Hz, 1H), 8.13, (d, J=8.8 Hz, 1H), 8.16 (s, 1H), 8.16 (d, J=8.0 Hz, 1H), 8.69 (dd, J=8.8, 2.4 Hz, 1H), 9.14 (d, J=2.4 Hz, 1H).

MS(FAB) m/z 404 (M+H)$^+$.

Free compound:

$^1$H-NMR (400 MHz, CDCl$_3$); δ (ppm) 1.04 (t, J=7.2 Hz, 3H), 1.17 (t, J=7.2 Hz, 3H), 1.76–1.85 (m, 2H), 2.42 (t, J=7.2 Hz, 2H), 2.60 (q, J=7.2 Hz, 2H), 2.76 (br, 4H), 3.56 (br, 4H), 7.48 (ddd, J=8.4, 8.0, 1.2 Hz, 1H), 7.61 (ddd, J=8.4, 8.0, 1.2 Hz, 1H), 7.65 (s, 1H), 7.79 (d, J=8.4 Hz, 1H), 8.07 (d, J=8.4 Hz, 1H), 8.31 (d, J=8.8 Hz, 1H), 8.44 (dd, J=8.8, 2.4 Hz, 1H), 9.06 (br, 1H).

Example 129

Synthesis of 3-[(2-Methylsulfonylpyridin)-5-yl]-1-(4-Ethylpiperazin-1-yl)Isoquinoline Hydrochloride

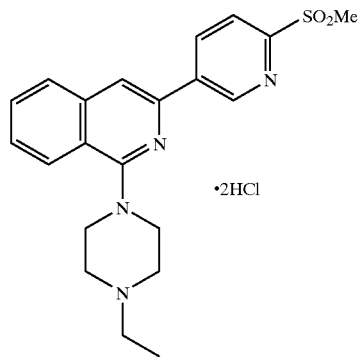

In the same manners sequentially as in Examples 161-2 and 20, the free compound of the title compound (609 mg, yield; 82%) from 5-bromo-2-methylsulfonylpyridine (1.72 g) and 3-bromo-1-(4-ethylpiperazin-1-yl)isoquinoline (582 mg). The free compound was converted into a hydrochloride in a conventional manner, to give the hydrochloride of the title compound as yellow crystals.

Hydrochloride:

m.p.; 248–250° C.

$^1$H-NMR (400 MHz, DMSO-d$_6$); δ (ppm) 1.34 (t, J=7.2 Hz, 3H), 3.20–3.26 (m, 2H), 3.35 (s, 3H), 3.30–3.40 (m, 2H), 3.56–3.63 (m, 4H), 4.00 (d, J=14.0 Hz, 2H), 7.71 (t, J=8.0 Hz, 1H), 7.82 (t, J=8.0 Hz, 1H), 8.05 (d, J=8.0 Hz, 1H), 8.17 (d, J=8.0 Hz, 1H), 8.18 (d, J=8.0 Hz, 1H), 8.37 (s, 1H), 8.86 (dd, J=8.0, 2.4 Hz, 1H), 9.57 (d, J=2.4 Hz, 1H).

MS(FAB) m/z 397 (M+H)$^+$.

Free compound:

$^1$H-NMR (400 MHz, CDCl$_3$); δ (ppm) 1.18 (t, J=7.2 Hz, 3H), 2.56 (q, J=7.2 Hz, 2H), 2.76 (t, J=4.8 Hz, 4H), 3.28 (s, 3H), 3.61 (t, J=4.8 Hz, 4H), 7.56 (t, J=8.0 Hz, 1H), 7.67 (t, J=8.0 Hz, 1H), 7.79 (s, 1H), 7.85 (d, J=8.0 Hz, 1H), 8.11 (d, J=8.0 Hz, 1H), 8.17 (d, J=8.0 Hz, 1H), 8.67 (dd, J=8.0, 2.0 Hz, 1H), 9.48 (d, J=2.0 Hz, 1H).

Example 130

Synthesis of 3-[(2-Ethylsulfonylpyridin)-5-yl]-1-(4-Ethylpiperazin-1-yl)Isoquinoline Hydrochloride

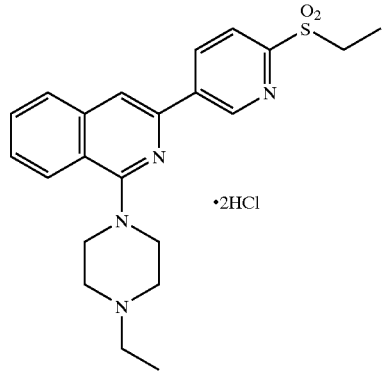

In the same manners sequentially as in Examples 161-2 and 20, the free compound of the title compound was obtained (710 mg, yield; 96%) from 5-bromo-2-ethylsulfonylpyridine (1.77 g) and 3-bromo-1-(4-ethylpiperazin-1-yl)isoquinoline (579 mg). The free compound was converted into a hydrochloride in a conventional manner, to give the hydrochloride of the title compound as yellow crystals.

Hydrochloride:

m.p.; 155–159° C.

$^1$H-MNR (400 MHz, DMSO-d$_6$); δ (ppm) 1.18 (t, J=7.2 Hz, 3H), 1.35 (t, J=7.2 Hz, 3H), 3.19–3.26 (m, 2H), 3.32–3.40 (m, 2H), 3.50 (q, J=7.2 Hz, 2H), 3.59–3.66 (m, 4H), 4.07 (d, J–13.2 Hz, 2H), 7.71 (t, J=8.0 Hz, 1H), 7.83 (t, J=8.0 Hz, 1H), 8.04 (d, J=8.0 Hz, 1H), 8.17 (d, J=8.0 Hz, 1H), 8.19 (d, J=8.4 Hz, 1H), 8.38 (s, 1H), 8.87 (dd, J=8.4, 2.0 Hz, 1H), 9.58 (d, J=2.0 Hz, 1H).

MS(FAB) m/z 411 (M+H)$^+$.

Free compound:

$^1$H-NMR (400 MHz, CDCl$_3$); δ (ppm) 1.18 (t, J=7.2 Hz, 3H), 1.34 (t, J=7.6 Hz, 3H), 2.56 (q, J=7.2 Hz, 2H), 2.76 (t, J=4.8 Hz, 4H), 3.45 (q, J=7.6 Hz, 2H), 3.61 (t, J=4.8 Hz, 4H), 7.56 (ddd, J=8.4, 8.0, 1.2 Hz, 2H), 7.66 (ddd, J=8.4, 8.0, 1.2 Hz, 1H), 7.79 (s, 1H), 7.85 (d, J=8.0 Hz, 1H), 8.11 (d, J=8.4 Hz, 1H), 8.17 (d, J=8.4 Hz, 1H), 8.67 (dd, J=8.4, 2.0 Hz, 1H), 9.49 (d, J=2.0 Hz, 1H).

Example 131

Synthesis of 1-(1-Ethylpiperazin-4-yl)-3-(2-Butylpyridin-5-yl)Isoquinoline

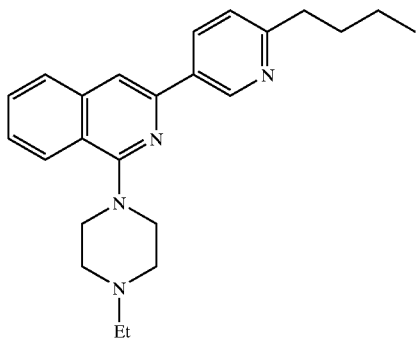

1-(1-Ethylpiperazin-4-yl)-3-[2-(1-butyn-1-yl)pyridin-5-yl]isoquinoline (148 mg) was dissolved in ethanol (20 ml), followed by the addition of platinum oxide (15 mg), and the mixture was stirred in hydrogen atmosphere at room temperature overnight. After the platinum oxide was filtered off, the resulting solution was evaporated, and the resulting residue was purified by (NH) silica gel column chromatography (ethyl acetate/hexane system). Continuously, the resulting product was converted into an oxalate in a conventional manner, to give the oxalate of the title compound as a pale brown amorphous (98 mg, yield; 50%).

Oxalate:

$^1$H-NMR (400 MHz, DMSO-$d_6$); δ (ppm) 0.90 (3H, t, J=7.2 Hz), 1.24 (3H, t, J=7.2 Hz), 1.27–1.38 (2H, m), 1.64–1.72 (2H, m), 2.78 (2H, t, J=7.6 Hz), 3.12 (2H, q, J=7.2 Hz), 3.32–3.42 (4H, brs), 7.36 (1H, d, J=8 Hz), 7.61 (1H, ddd, J=8 Hz, 7 Hz, 1.2 Hz), 7.74 (1H, ddd, J=8 Hz, 7 Hz, 1.2 Hz), 7.96 (1H, d, J=8 Hz), 8.10 (1H, s), 8.11 (1H, d, J=8 Hz), 8.40 (1H, dd, J=8 Hz, 2.4 Hz), 9.25 (1H, d, J=2.4 Hz).

ESI-Mass; 375 (MH$^+$).

Example 132

Synthesis of 1-(1-Ethylpiperazin-4-yl)-3-[5-(3-Fluoropropyl)Pyridin-2-yl)Isoquinoline

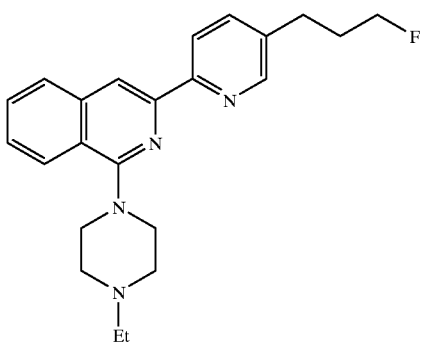

Diethylaminosulfur trifluoride (237 ml) was dissolved in methylene chloride (2 ml), followed by the addition of 1-(1-ethylpiperazin-4-yl)-3-[5-(3-hydroxypropyl)pyridin-2-yl]isoquinoline (160 mg)/methylene chloride (2 ml) solution in nitrogen atmosphere at −70° C. After the cooling bath was removed, subsequently, the resulting mixture was stirred for 2 hr. The reaction solution was diluted with methylene chloride, washed subsequently with an aqueous solution of saturated sodium bicarbonate and brine, dried (over MgSO$_4$) and evaporated. The resulting residue was purified by (NH) silica gel column chromatography (ethyl acetate/hexane system), to give the oxalate of the title compound as a yellow amorphous (60 mg, yield; 31%).

Oxalate:

$^1$H-NMR (400 MHz, DMSO-$d_6$); δ (ppm) 1.26 (3H, t, J=7.2 Hz), 1.94–2.10 (2H, m), 2.76 (2H, t, J=7.6 Hz), 3.17 (2H, q, J=7.2 Hz), 3.35–3.48 (4H, m), 3.60–3.80 (4H, m), 4.43 (1H, t, J=6 Hz), 4.55 (1H, t, J=6 Hz), 7.62 (1H, ddd, J=8 Hz, 7 Hz, 1.2 Hz), 7.73 (1H, ddd, J=8 Hz, 7 Hz, 1.2 Hz), 7.82 (1H, dd, J=8 Hz, 2.4 Hz), 8.07 (1H, d, J=8 Hz), 8.13 (1H, d, J=8 Hz), 8.34 (1H, d, J=8 Hz), 8.45 (1H, s), 8.55 (1H, d, J=2.4 Hz).

ESI-Mass; 379 (MH$^+$).

Example 133

Synthesis of 1-(1-Ethylpiperazin-4-yl)-3-[2-(3-Fluoropropyl)Pyridin-5-yl]Isoquinoline

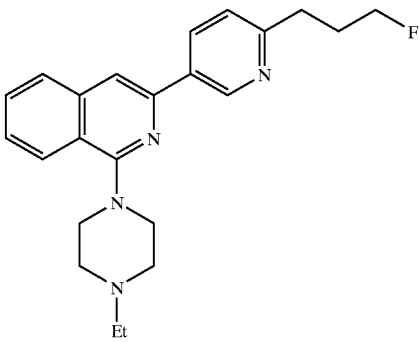

Diethylaminosulfur trifluoride (53 ml) and pyridine hydrogen fluoride (320 ml) were dissolved in methylene chloride (3 ml), followed by the addition of 1-(1-ethylpiperazin-4-yl)-3-[5-(3-hydroxypropyl)pyridin-2-yl] isoquinoline (152 mg)/methylene chloride (2 ml) solution in nitrogen atmosphere at −70° C. After the cooling bath was removed, subsequently, the resulting mixture was stirred for 2 hr. The reaction solution was diluted with methylene chloride, washed sequentially with an aqueous solution of sodium bicarbonate and brine, dried (over MgSO$_4$) and evaporated. The resulting residue was purified by (NH) silica gel column chromatography (ethyl acetate/hexane system), to give the title compound as a yellow oil (6 mg, yield; 5%).

Free compound:

$^1$H-NMR (400 MHz, CDCl$_3$); δ (ppm) 1.18 (3H, t, J=7.2 Hz), 2.15–2.28 (2H, m), 2.56 (2H, q, J=7.2 Hz), 2.76 (4H, t, J=4.4 Hz), 2.99 (2H, t, J=7.6 Hz), 3.60 (4H, t, J=6.4 Hz), 4.48 (1H, t, J=6.4 Hz), 4.60 (1H, t, J=6.4 Hz), 7.28 (1H, d, J=8 Hz), 7.49 (1H, dd, J=8 Hz, 7 Hz), 7.61 (1H, dd, J=8 Hz, 7 Hz), 7.68 (1H, s), 7.81 (1H, d, J=8 Hz), 8.09 (1H, d, J=8 Hz), 8.35 (1H, dd, J=8 Hz, 2.4 Hz), 9.30 (1H, d, J=2.4 Hz).

ESI-Mass; 379 (MH$^+$).

Example 134

Synthesis of 1-(1-Ethylpiperazin-4-yl)-3-[5-(3-Hydroxypropyl)Pyridin-2-yl]Isoquinoline (134-1) 3-(3-Benzyloxypropyl)pyridine

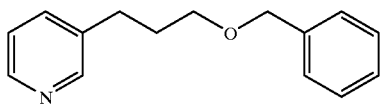

In the same manner as in Example 167-1, the title compound was obtained as a brown oil (34.28 g, yield; 83%) from 3-pyridinepropanol (24.882 g) and benzyl bromide (26 ml). $^1$H-NMR (400 MHz, CDCl$_3$); δ (ppm) 1.90–1.97 (2H, m), 2.73 (2H, t, J=7.8 Hz), 3.48 (2H, t, J=6.4 Hz), 4.50 (2H, s), 7.18 (1H, dd, J=8 Hz, 4.8 Hz), 7.27–7.37 (5H, m), 7.48 (1H, ddd, J=8 Hz, 2.4 Hz, 1.6 Hz), 8.43 (1H, dd, J=4.8 Hz, 1.6 Hz), 8.45 (1H, d, J=2.4 Hz).

155

(134-2) 3-(3-Benzyloxypropyl)pyridine N-oxide

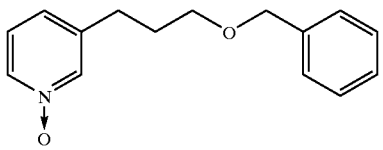

3-(3-Benzyloxypropyl)pyridine (34.28 g) was dissolved in acetic acid (260 ml), followed by the addition of a 30% aqueous solution of hydrogen peroxide (52 ml), and the mixture was stirred at 50° C. overnight. After cooling as it was, water (52 ml) was added to the reaction solution, which was then evaporated. The resulting residue was dissolved in chloroform, washed with water, dried (over MgSO$_4$) and evaporated. The resulting residue was purified by silica gel column chromatography (methylene chloride/methanol system), to give the title compound as a yellow oil (30.23 g, yield; 88%).

$^1$H-NMR (400 MHz, CDCl$_3$); δ (ppm) 1.87–1.95 (2H, m), 2.70 (2H, t, J=7.8 Hz), 3.47 (2H, t, J=6 Hz), 4.50 (2H, s), 7.08 (1H, d, J=8 Hz), 7.16 (1H, dd, J=8 Hz, 6.4 Hz), 7.28–7.39 (5H, m), 8.05–8.10 (2H, m).

(134-3) 1-(1-Ethylpiperazin-4-yl)-[5-(3-benzyloxypropyl) pyridin-2-yl]isoquinoline

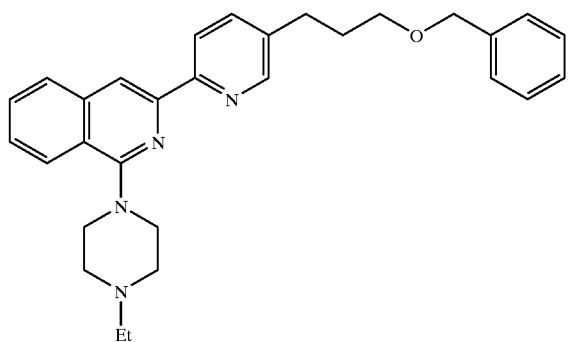

3-(3-Benzyloxypropyl)pyridine N-oxide (4.546 g) was dissolved in methylene chloride, phosphorus oxybromide (11.47 g) was added thereto under ice-cooling, and the mixture was stirred for 2 hr. Then, it was further stirred at room temperature for 2 hr. The reaction mixture was poured into warm water, and then it was neutralized by adding sodium bicarbonate thereto. The mixture was extracted with ethyl acetate. The resulting organic layer was washed with water, dried (over MgSO$_4$) and evaporated. The resulting residue was purified by silica gel column chromatography (ethyl acetate/hexane system), to give a mixture of 2-bromo-5-(3-benzyloxypropyl)pyridine and 2-bromo-3-(3-benzyloxypropyl)pyridine (1:1) as a brown oil (2.203 g). The resulting mixture (1.111 g) and 1-(1-ethylpiperazin-4-yl)-3-bromoisoquinoline (662 mg) were treated in the same manner as in Example 167-2, to give the title compound as a yellow oil (326 mg, yield; 33%).

$^1$H-NMR (400 MHz, CDCl$_3$); δ (ppm) 1.18 (3H, t, J=7.2 Hz), 1.94–2.02 (2H, m), 2.56 (2H, q, J=7.2 Hz), 2.77 (4H, t, J=4 Hz), 2.80 (2H, t, J=7.2 Hz), 2.80 (2H, t, J=7.2 Hz), 3.52 (2H, t, J=6 Hz), 3.59 (4H, t, J=4 Hz), 4.52 (2H, s), 7.27–7.37 (5H, m), 7.49 (1H, ddd, J=8 Hz, 7 Hz, 1.2 Hz), 7.60 (1H, ddd, J=8 Hz, 7 Hz, 1.2 Hz), 7.62 (1H, dd, J=8.4 Hz, 2.4 Hz), 7.88 (1H, d, J=8 Hz), 8.10 (1H, d, J=8 Hz), 8.36 (1H, s), 8.43 (1H, dd, J=8.4 Hz), 8.52 (1H, d, J=2.4 Hz).

156

(134-4) 1-(1-Ethylpiperazin-4-yl)-3-[5-(3-hydroxypropyl) pyridin-2-yl]isoquinoline

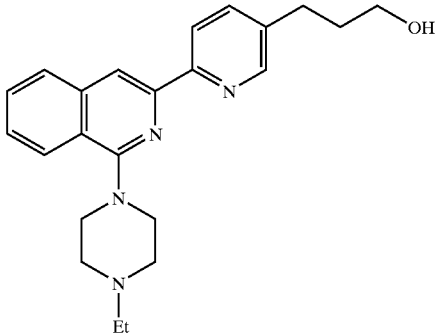

In the same manner as in Example 167-3, the oxalate of the title compound was obtained as a yellow amorphous (150 mg, yield; 43%) from 1-(1-ethylpiperazin-4-yl)-3-[5-(3-benzyloxypropyl)pyridin-2-yl]isoquinoline (326 mg).

Oxalate:

$^1$H-NMR (400 MHz, DMSO-d$_6$); δ (ppm) 1.24 (3H, t, J=7.2 Hz), 1.72–1.80 (2H, m), 2.69 (2H, t, J=7.8 Hz), 3.11 (2H, q, J=7.2 Hz), 3.30–3.40 (4H, m), 3.44 (2H, t, J=6.2 Hz), 7.62 (1H, ddd, J=8 Hz, 7 Hz, 1.2 Hz), 7.73 (1H, ddd, J=8 Hz, 7 Hz, 1.2 Hz), 7.78 (1H, dd, J=8.4 Hz, 2.4 Hz), 8.06 (1H, d, J=8 Hz), 8.12 (1H, d, J=8.4 Hz), 8.33 (1H, d, J=8 Hz), 8.43 (1H, s), 8.53 (1H, d, J=2.4 Hz).

ESI-Mass; 377 (MH$^+$).

Example 135

Synthesis of 1-(1-Ethylpiperazin-4-yl)-3-[2-(3-Hydroxypropyl)Pyridin-5-yl]Isoquinoline (135-1) 5-Bromo-2-[3-(t-butyldimethylsilyloxy]propyl] pyridine

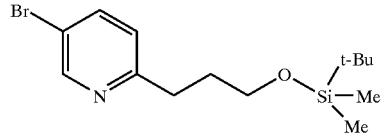

From 5-bromo-2-pyridinepropanol (4.266 g) synthesized according to J. O. C., 53, 386, 1988, the title compound was obtained as a colorless oil in the same manner as in Example 163-1 (6.297 g, yield; 97%).

$^1$H-NMR (400 MHz, CDCl$_3$); δ (ppm) 0.04 (6H, s), 0.90 (9H, s), 1.89–1.97 (2H, m), 2.82 (2H, t, J=7.8 Hz), 3.65 (2H, t, J=6.2 Hz), 7.07 (1H, dd, J=8 Hz, 2.4 Hz), 8.57 (1H, d, J=2.4 Hz).

(135-2) 1-(1-Ethylpiperazin-4-yl)-3-[2-(3-hydroxypropyl)pyridin-5-yl]isoquinoline

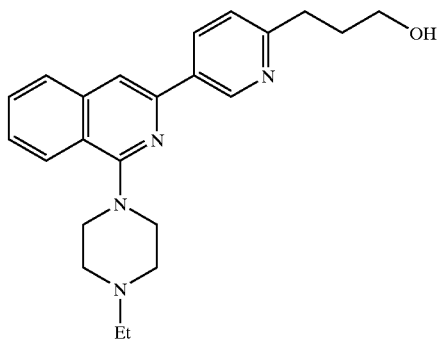

In the same manner as in Example 167-2, the free compound of the title compound was obtained as a yellow solid (1.288 g, yield; 94%) from 5-bromo-2-[3-(t-butyl)dimethylsilyloxypropyl]pyridine (2.973 g) and 1-(1-ethylpiperazin-4-yl)-3-bromoisoquinoline (1.158 g). A part (150 mg) of the resulting free compound was converted into an oxalate in a conventional manner, to give the oxalate of the title compound as a pale yellow amorphous (80 mg, yield; 43%).
Oxalate:
$^1$H-NMR (400 MHz, DMSO-d$_6$); δ (ppm) 1.25 (3H, t, J=7.2 Hz), 1.80–1.84 (2H, m), 2.81 (2H, t, J=7.6 Hz), 3.15 (2H, q, J=7.2 Hz), 3.34–3.46 (4H, m), 3.45 (2H, t, J=6.4 Hz), 3.60–3.80 (4H, m), 7.61 (1H, ddd, J=8 Hz, 7 Hz, 1.2 Hz), 7.74 (1H, ddd, J=8 Hz, 7 Hz, 1.2 Hz), 7.96 (1H, d, J=8 Hz), 8.11 (1H, s), 8.11 (1H, d, J=8 Hz), 8.40 (1H, dd, J=8 Hz, 2.4 Hz), 9.26 (1H, d, J=2.4 Hz).
ESI-Mass; 377 (MH$^+$).

Example 136

Synthesis of 1-(1-Ethylpiperazin-4-yl)-3-[2-(3-Hydroxybutyl)Pyridin-5-yl]Isoquinoline

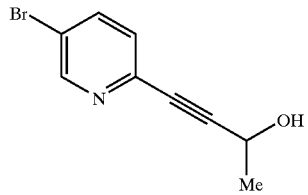

In the same manner as in Example 139-1, the title compound was obtained as a brown solid (15.895 g, yield; 88%) from 2,5-dibromopyridine (18.951 g) and 3-butyn-2-ol (6.3 ml).
$^1$H-NMR (400 MHz, CDCl$_3$); δ (ppm) 1.57 (3H, d, J=6.8 Hz), 4.77 (1H, m), 7.31 (1H, d, J=7.8 Hz), 7.79 (1H, dd, J=7.8 Hz, 2.4 Hz), 8.63 (1H, d, J=2.4 Hz).
(136-2) 5-Bromo-2-(3-hydroxybutyl)pyridine

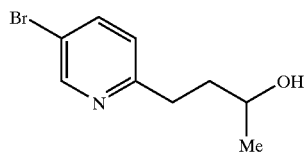

In the same manner as in Example 139-2, the title compound was obtained as a yellow oil (2.783 g, yield; 60%) from 5-bromo-2-(3-hydroxy-1-butyryl)pyridine (4.521 g).

$^1$H-NMR (400 MHz, CDCl$_3$); δ (ppm) 1.23 (3H, d, J=6 Hz), 1.78–1.93 (2H, m), 2.91 (2H, t, J=7.8 Hz), 3.23 (1H, br-s), 3.78–3.88 (1H, m), 7.09 (1H, d, J=8.4 Hz), 7.73 (1H, dd, J=8.4 Hz, 2.4 Hz), 8.55 (1H, d, J=2.4 Hz).

(136-3) 5-Bromo-2-[3-(t-butyldimethylsilyloxy)butyl]pyridine

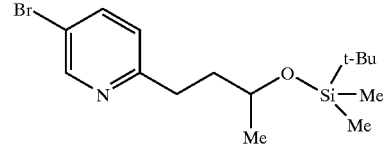

In the same manner as in Example 163-1, the title compound was obtained as a colorless oil (3.75 g, yield; 95%) from 5-bromo-2-(3-hydroxybutyl)pyridine (2.647 g).

$^1$H-NMR (400 MHz, CDCl$_3$); δ (ppm) 0.04 (6H, s), 0.88 (9H, s), 1.16 (3H, d, J=6 Hz), 1.77–1.83 (2H, m), 2.67–2.87 (2H, m), 3.56–3.58 (1H, m), 7.04 (1H, d, J=8.4 Hz), 7.69 (1H, J=8.4 Hz, 2.4 Hz), 8.55 (1H, d, J=2.4 Hz).

(136-4) 1-(1-Ethylpiperazin-4-yl)-3-[2-(3-hydroxybutyl)pyridin-5-yl]isoquinoline

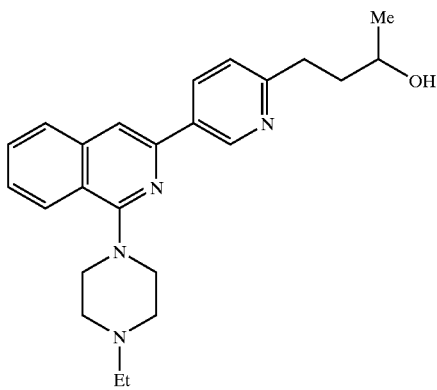

In the same manner as in Example 167-2, the oxalate of the title compound was obtained as a yellow amorphous (420 mg, yield; 56%) from 5-bromo-2-[3-(t-butyl)dimethylsilyloxybutyl]pyridine (2.066 g) and 1-(1-ethylpiperazin-4-yl)-3-bromoisoquinoline (491 mg).

Oxalate:

$^1$H-NMR (400 MHz, DMSO-d$_6$); δ (ppm) 1.09 (3H, d, J=6 Hz), 1.24 (3H, t, J=7.2 Hz), 1.70–1.78 (2H, m), 2.74–2.90 (2H, m), 3.13 (2H, q, J=7.2 Hz), 3.37 (4H, br-s), 3.60–3.76 (6H, m), 7.37 (2H, d, J=8.4 Hz), 7.61 (1H, ddd, J=8 Hz, 7 Hz, 1.2 Hz), 7.74 (1H, ddd, J=8 Hz, 7 Hz, 1.2 Hz), 7.96 (1H, d, J=8 Hz), 8.10 (1H, s), 8.11 (1H, d, J=8 Hz), 8.39 (1H, dd, J=8.4 Hz, 2.4 Hz), 9.25 (1H, d, J=2.4 Hz).

ESI-Mass; 391 (MH$^+$).

Example 137

Synthesis of 1-(1-Ethylpiperazin-4-yl)-3-[2-(4-Hydroxybutyl)Pyridin-5-yl]Isoquinoline (137-1) 5-Bromo-2-(4-hydroxy-1-butynyl)pyridine

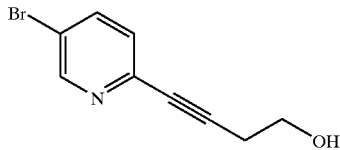

In the same manner as in Example 139-1, the title compound was obtained as a brown solid (6.6 g, yield; 48%) from 2,5-dibromopyridine (14.213 g) and 3-butyn-1-ol (4.5 ml).

$^1$H-NMR (400 MHz, CDCl$_3$); δ (ppm) 2.72 (2H, t, J=6.4 Hz), 3.85 (1H, t, J=6.4 Hz), 3.86 (1H, t, J=6.4 Hz), 7.29 (1H, d, J=8.4 Hz), 7.77 (1H, dd, J=8.4 Hz, 2.4 Hz), 8.60 (1H, d, J=2.4 Hz).

(137-2) 5-Bromo-2-(4-hydroxybutyl)pyridine

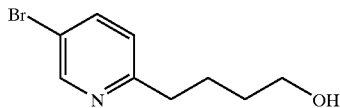

In the same manner as in Example 139-2, the title compound was obtained as a yellow oil (3.397 g, yield; 74%) from 5-bromo-2-(4-hydroxy-1-butynyl)pyridin (4.522 g).

$^1$H-NMR (400 MHz, CDCl$_3$); δ (ppm) 1.61–1.67 (2H, m), 1.77–1.85 (3H, m), 2.80 (2H, t, J=7.6 Hz), 3.68 (2H, m), 7.07 (1H, d, J=8 Hz), 7.72 (1H, dd, J=8 Hz, 2.4 Hz), 8.57 (1H, d, J=2.4 Hz).

(137-3) 5-Bromo-2-[4-(t-butyldimethylsilyloxy)butyl]pyridine

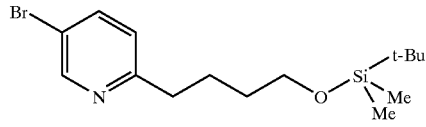

In the same manner as in Example 163-1, the title compound was obtained as a colorless oil (2.484 g, yield; 87%) from 5-bromo-2-(4-hydroxybutyl)pyridine (1.905 g).

$^1$H-NMR (400 MHz, CDCl$_3$); δ (ppm) 0.04 (6H, s), 0.88 (9H, s), 1.52–1.60 (2H, m), 1.72–1.79 (2H, m), 2.76 (2H, t, J=7.6 Hz), 3.63 (2H, t, J=6.6 Hz), 7.06 (1H, d, J=8 Hz), 7.70 (1H, dd, J=8 Hz, 2.4 Hz), 8.57 (1H, d, J=2.4 Hz).

(137-4) Synthesis of 1-(1-ethylpiperazin-4-yl)-3-[2-(4-hydroxybutyl)pyridin-5-yl]isoquinoline

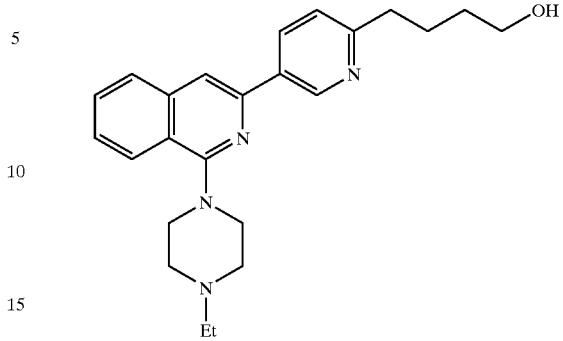

In the same manner as in Example 167-2, the oxalate of the title compound was obtained as a yellow amorphous (420 mg, yield; 64%) from 5-bromo-2-[4-(t-butyl)dimethylsilyloxybutyl]pyridine (2.484 g) and 1-(1-ethylpiperazin-4-yl)-3-bromoisoquinoline (435 mg).

Oxalate:
$^1$H-NMR (400 MHz, DMSO-d$_6$); δ (ppm) 1.25 (3H, t, J=7.2 Hz), 1.42–1.49 (2H, m), 1.68–1.76 (2H, m), 2.78 (2H, t, J=7.6 Hz), 3.15 (2H, q, J=7.2 Hz), 3.36–3.44 (4H, br-s), 3.41 (2H, t, J=6.2 Hz), 7.36 (1H, d, J=8 Hz), 7.61 (1H, dd, J=8 Hz, 7 Hz), 7.74 (1H, dd, J=8 Hz, 7 Hz), 7.96 (1H, d, J=8 Hz), 8.11 (1H, d, J=8 Hz), 8.40 (1H, dd, J=8 Hz, 2.4 Hz), 9.26 (1H, d, J=2.4 Hz).

ESI-Mass; 391 (MH$^+$).

Example 138

Synthesis of 1-(1-Ethylpiperazin-4-yl)-3-[2-(3-Hydroxy-3-Methylbutyl)Pyridin-5-yl]Isoquinoline Oxalate (138-1) 5-Bromo-2-(3-methyl-3-hydroxy-1-butynyl)pyridine

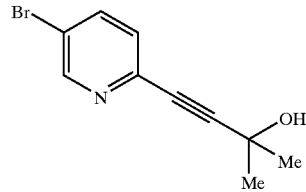

In the same manner as in Example 139-1, the title compound was obtained as a yellowish brown solid (17.91 g, yield; 94%) from 2,5-dibromopyridine (18.951 g) and 2-methyl-3-butyn-2-ol (6.3 ml).

$^1$H-NMR (400 MHz, CDCl$_3$); δ (ppm) 1.64 (6H, s), 2.16 (1H, br-s), 7.31 (1H, d, J=8.4 Hz), 7.78 (1H, dd, J=8.4 Hz, 2.4 Hz), 8.63 (1H, d, J=2.4 Hz).

(138-2) 5-Bromo-2-(3-methylbutane-3-hydroxybutyl)pyridine

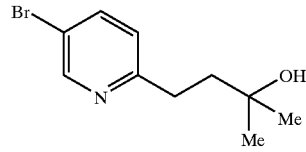

In the same manner as in Example 139-2, the title compound was obtained as a yellow oil (1.366 g, yield;

28%) from 5-bromo-2-(3-methyl-3-hydroxy-1-butynyl) pyridine (4.802 g).

$^1$H-NMR (400 MHz, CDCl$_3$); δ (ppm) 1.29 (6H, s), 1.73 (1H, s), 1.90 (2H, t, J=7.8 Hz), 7.09 (1H, d, J=8.4 Hz), 7.71 (1H, dd, J=8.4 Hz, 2.4 Hz), 8.55 (1H, d, J=2.4 Hz).

(138-3) 5-Bromo-2-[3-(t-butyldimethylsilyloxy)-3-methylbutyl]pyridine

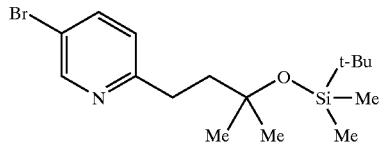

5-Bromo-2-(3-methylbutane-3-hydroxybutyl)pyridine (1.359 g) was dissolved in methylene chloride (20 ml), followed by the sequential addition of 2,6-lutidine (2.5 ml) and t-butyldimethylsilyltrifluoromethanesulfonic acid (1.7 ml) in nitrogen atmosphere under ice-cooling, and the mixture was stirred overnight. The reaction mixture was washed with water, dried (over MgSO$_4$) and evaporated. The resulting residue was was purified by silica gel column chromatography (ethyl acetate/hexane system), to give the title compound as a colorless oil (1.724 g, yield; 86%).

$^1$H-NMR (400 MHz, CDCl$_3$); δ (ppm) 0.10 (6H, s), 0.88 (9H, s), 1.27 (6H, s), 1.78–1.83 (2H, m), 2.82–2.87 (2H, m), 7.06 (1H, d, J=8.4 Hz), 7.69 (1H, dd, J=8.4 Hz, 2.4 Hz), 8.56 (1H, d, J=2.4 Hz).

(138-4) 1-(1-Ethylpiperazin-4-yl)-3-[2-(3-hydroxy-3-methylbutyl)pyridin-5-yl]isoquinoline oxalate

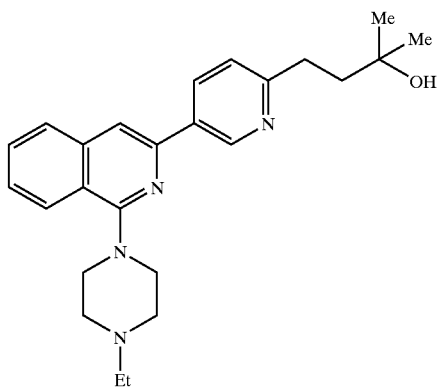

In the same manner as in Example 167-2, the oxalate of the title compound was obtained as a yellow amorphous (132 mg, yield; 30%) from 5-bromo-2-[3-(t-butyl) dimethylsilyloxy-3-methylbutyl]pyridine (1.724 g) and 1-(1-ethylpiperazin-4-yl)-3-bromoisoquinoline (324 mg). Oxalate:

$^1$H-NMR (400 MHz, DMSO-d$_6$); δ (ppm) 1.15 (6H, s), 1.25 (3H, t, J=7.2 Hz), 1.74–1.79 (2H, m), 2.80–2.85 (2H, m), 3.13 (2H, q, J=7.2 Hz), 3.32–3.42 (4H, br-s), 3.58–3.78 (4H, br-s), 7.37 (1H, d, J=8 Hz), 7.61 (1H, dd, J=8 Hz), 7.74 (1H, dd, J=8 Hz, 7 Hz), 7.96 (1H, d, J=8 Hz), 8.10 (1H, s), 8.11 (1H, d, J=8 Hz), 8.40 (1H, dd, J=8 Hz, 2.4 Hz), 9.25 (1H, d, J=2.4 Hz).

ESI-Mass; 405 (MH$_+$).

Example 139

Synthesis of 1-(1-Ethylpiperazin-4-yl)-3-[2-(3-Methoxypropyl)Pyridin-5-yl]Isoquinoline Oxalate (139-1) 5-Bromo-2-(3-methoxypropynyl)pyridine

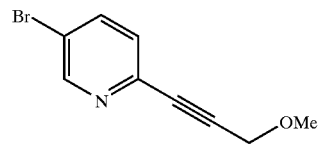

2,5-Dibromopyridine (16.582 g) was dissolved in triethylamine (200 ml), followed by the addition of methyl propargyl ether (5.9 ml), copper iodide (267 mg) and bis(triphenylphosphine)palladium (II) chloride (46 mg). The resulting mixture was stirred in nitrogen atmosphere at room temperature for 1 hr. Subsequently, it was stirred at room temperature for further 3 hr. After the resulting insoluble matters were filtered off, the resulting solution was evaporated. The resulting residue was purified by silica gel column chromatography (ethyl acetate/hexane system), to give the title compound as a brown solid (12.411 g, yield; 79%).

$^1$H-NMR (400 MHz, CDCl$_3$); δ (ppm) 3.47 (3H, d, J=0.8 Hz), 4.34 (2H, s), 7.34 (1H, d, J=8 Hz), 7.79 (1H, ddd, J=8 Hz, 2.4 Hz, 0.8 Hz), 8.64 (1H, d, J=2.4 Hz).

(139-2) 5-Bromo-2-(3-methoxypropyl)pyridine

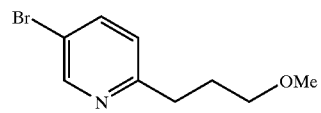

5-Bromo-2-(3-methoxypropynyl)pyridine (5.652 g) was dissolved in ethanol (150 ml), followed by the addition of triethylamine (2.5 ml) and platinum oxide (230 mg), and the resulting mixture was stirred in hydrogen atmosphere at room temperature for 5 hr. After the platinum oxide was filtered off, the resulting mixture was evaporated and partitioned between ethyl acetate and water. The resulting organic layer was washed with water, dried (over MgSO$_4$) and evaporated. The resulting residue was purified by silica gel column chromatography (ethyl acetate/hexane system), to give the title compound as a yellow oil (3.991 g, yield; 68%(.

$^1$H-NMR (400 MHz, CDCl$_3$); δ (ppm) 1.95–2.03 (2H, m), 2.82 (2H, t, J=7.6 Hz), 3.34 (3H, s), 3.41 (2H, t, J=6.4 Hz), 7.07 (1H, d, J=8 Hz), 7.71 (1H, dd, J=8 Hz, 2.4 Hz), 8.58 (1H, d, J=2.4 Hz).

(139-3) Synthesis of 1-(1-ethylpiperazin-4-yl)-3-[2-(3-methoxypropyl)pyridin-5-yl]isoquinoline oxalate

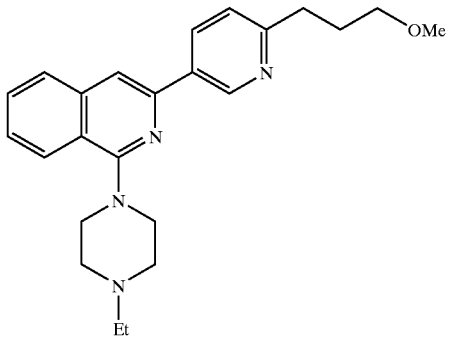

In the same manner as in Example 167-2, the oxalate of the title compound was obtained as a yellow amorphous (982 mg, yield; 74%) from 5-bromo-2-(3-methoxypropyl)pyridine (2.301 g) and 1-(1-ethylpiperazin-4-yl)-3-bromoisoquinoline (865 mg).
Oxalate:
$^1$H-NMR (400 MHz, DMSO-$d_6$); δ (ppm) 1.24 (3H, t, J=7.2 Hz), 1.88–1.97 (2H, m), 2.81 (2H, t, J=7.6 Hz), 3.13 (2H, q, J=7.2 Hz), 3.23 (3H, s), 3.32–3.42 (6H, m), 3.60–3.80 (4H, m), 7.37 (1H, d, J=8 Hz), 7.61 (1H, ddd, J=8 Hz, 7 Hz, 1.2 Hz), 7.74 (1H, ddd, J=8 Hz, 7 Hz, 1.2 Hz), 7.96 (1H, d, J=8 Hz), 8.11 (1H, d, J=8 Hz), 8.11 (1H, s), 8.40 (1H, dd, J=8 Hz, 2.4 Hz), 9.27 (1H, d, J=2.4 Hz).
ESI-Mass; 391 (MH$^+$).

Example 140

Synthesis of 1-(1-Ethylpiperazin-4-yl)-3-[3-(3-Methoxypropyl)Pyridin-5-yl]Isoquinoline Oxalate
(140-1) 5-Bromo-3-(3-methoxypropynyl)pyridine

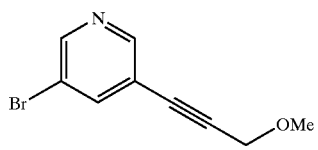

In the same manner as in Example 139-1, the title compound was obtained as a yellowish orange solid (7.216 g, yield; 64%) from 3,5-dibromopyridine (11.854 g) and methyl propargyl ether (4.2 ml).
$^1$H-NMR (400 MHz, CDCl$_3$); δ (ppm) 3.46 (3H, s), 4.33 (2H, s), 7.89 (1H, t, J=2 Hz), 8.58 (1H, d, J=2 Hz), 8.61 (1H, d, J=2 Hz).
(140-2) 5-Bromo-3-(3-methoxypropyl)pyridine

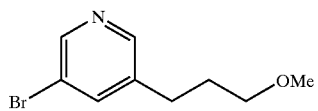

In the same manner as in Example 139-2, the title compound was obtained as a pale yellow oil (3.62 g, yield; 79%) from 5-bromo-3-(3-methoxypropynyl)pyridine (4.521 g).
$^1$H-NMR (400 MHz, CDCl$_3$); δ (ppm) 1.85–1.92 (2H, m), 2.70 (2H, t, J=7.8 Hz), 3.35 (3H, s), 3.38 (2H, t, J=6.2 Hz), 7.67 (1H, t, J=2 Hz), 8.37 (1H, d, J=2 Hz), 8.51 (1H, d, J=2 Hz).

(140-3) 1-(1-Ethylpiperazin-4-yl)-3-[3-(3-methoxypropyl)pyridin-5-yl]isoquinoline oxalate

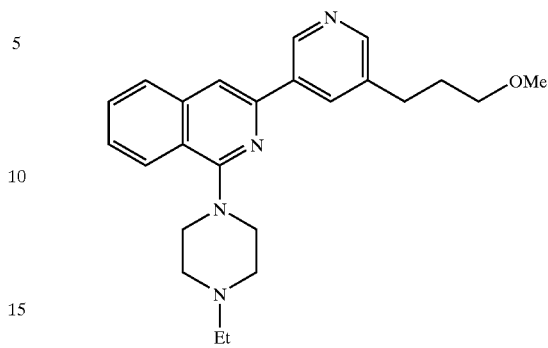

In the same manner as in Example 167-2, the oxalate of the title compound was obtained as a yellow amorphous (324 mg, yield; 64%) from 5-bromo-3-(3-methoxypropyl)pyridine (1.151 g) and 1-(1-ethylpiperazin-4-yl)-3-bromoisoquinoline (345 mg).
Oxalate:
$^1$H-NMR (400 MHz, DMSO-$d_6$); δ (ppm) 1.25 (3H, t, J=7.2 Hz), 1.84–1.92 (2H, m), 2.73 (2H, t, J=7.6 Hz), 3.16 (2H, q, J=7.2 Hz), 3.25 (3H, s), 3.36 (2H, t, 6.4 Hz), 3.38–3.48 (4H, m), 3.60–3.80 (4H, m), 7.63 (1H, ddd, J=8.4 Hz, 7 Hz, 1.2 Hz), 7.76 (1H, ddd, J=8.4 Hz, 7 Hz, 1.2 Hz), 7.98 (1H, d, J=8.4 Hz), 8.12 (1H, d, J=8.4 Hz), 8.17 (1H, m), 8.33 (1H, t, J=2.4 Hz), 8.43 (1H, t, J=2.4 Hz), 8.45 (1H, d, J=2.4 Hz), 9.21 (1H, d, J=2.4 Hz).
ESI-Mass; 391 (MH$^+$).

Example 141

Synthesis of 1-(1-Ethylpiperazin-4-yl)-3-[5-(3-Methoxypropyl)Pyridin-2-yl]Isoquinoline Oxalate
(141-1) 3-(3-Methoxypropyl)pyridine

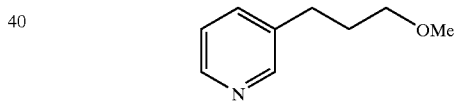

In the same manner as in Example 167-1, the title compound was obtained as a yellow oil (5.494 g, yield; 72%) from 3-pyridinepropanol (6.452 g) and methyl iodide (3.4 ml). $^1$H-NMR (400 MHz, CDCl$_3$); δ (ppm) 1.86–1.93 (2H, m), 2.70 (2H, t, J=7.8 Hz), 3.35 (3H, s), 3.39 (2H, t, J=6.2 Hz), 7.21 (1H, dd, J=8 Hz, 4.8 Hz), 7.51 (1H, dt, J=8 Hz, 1.6 Hz), 8.45 (1H, dd, J=4.8 Hz, 1.6 Hz), 8.46 (1H, d, J=1.6 Hz).
(141-2) 3-(3-Methoxypropyl)pyridine N-oxide

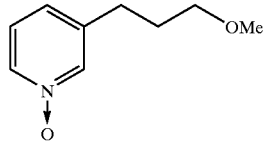

3-(3-Methoxypropyl)pyridine (5.551 g) was dissolved in methylene chloride (60 ml), followed by the addition of 70% m-perbenzoic acid (10.86 g) and stirring under ice-cooling for 90 min. The reaction mixture was washed sequentially with a 10% aqueous solution of sodium sulfite and an aqueous solution of saturated sodium bicarbonate, dried (over MgSO₄) and evaporated. The resulting residue was purified by silica gel column chromatography (ethyl acetate/methanol system), to give the title compound as a yellow oil (5.901 g, yield; 95%).

¹H-NMR (400 MHz, CDCl₃); δ (ppm) 1.85–1.92 (2H, m), 2.69 (2H, t, J=7.6 Hz), 3.35 (3H, s), 3.39 (2H, t, J=6.2 Hz), 7.14 (1H, d, J=7.2 Hz), 7.21 (1H, dd, J=7.2 Hz, 6.8 Hz), 8.08–8.12 (2H, m).

(141-3) 1-(1-Ethylpiperazin-4-yl)-3-[5-(3-methoxypropyl)pyridin-2-yl]isoquinoline oxalate

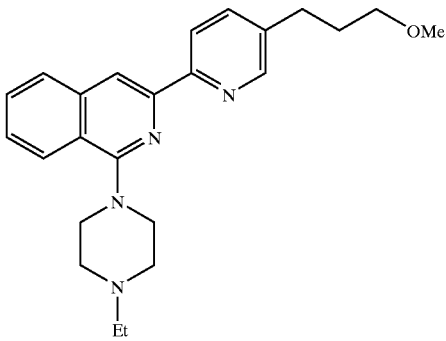

In the same manner as in Example 134-3, the oxalate of the title compound was obtained as a brown amorphous (120 mg, yield; 9%) from 3-(3-methoxypropyl)pyridine N-oxide (5.901 g) and 1-(1-ethylpiperazin-4-yl)-3-bromoisoquinoline (694 mg).

Oxalate:
¹H-NMR (400 MHz, DMSO-d₆); δ (ppm) 1.25 (3H, t, J=7.2 Hz), 1.80–1.88 (2H, m), 2.69 (2H, t, J=7.2 Hz), 3.15 (2H, q, J=7.2 Hz), 3.24 (3H, s), 3.34 (2H, t, J=6.2 Hz), 3.34–3.46 (4H, m), 3.58–3.80 (4H, m), 7.26 (1H, ddd, J=8 Hz, 7 Hz, 1.2 Hz), 7.74 (1H, ddd, J=8 Hz, 7 Hz, 1.2 Hz), 7.78 (1H, dd, J=8.4 Hz, 2.4 Hz,), 8.07 (1H, d, J=8 Hz), 8.13 (1H, d, J=8 Hz), 8.33 (1H, d, J=8.4 Hz), 8.44 (1H, s), 8.53 (1H, d, J=2.4 Hz).

ESI-Mass; 391 (MH⁺).

Example 142

Synthesis of 1-(1-Ethylpiperazin-4-yl)-3-[2-(3-Ethoxypropyl)Pyridin-5-yl]Isoquinoline Oxalate (142-1) 5-Bromo-2-(3-hydroxy-1-propenyl)pyridine

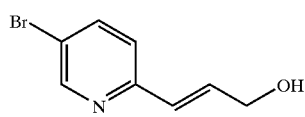

3-(5-Bromo-2-pyridinyl)-3-propyn-1-ol (10.602 g) synthesized according to J. O. C., 53, 386, 1988 was dissolved in tetrahydrofuran (100 ml), to which were then added lithium aluminum hydride (1.06 g) in several portions under ice-cooling, and then the mixture was stirred for 10 min. Water (1.1 ml), 5 N sodium hydroxide (1.1 ml) and water (3.3 ml) were sequentially added to the reaction mixture, and the resulting insoluble matters were filtered off through Celite. The resulting filtrate was evaporated, and the resulting residue was purified by silica gel column chromatography (ethyl acetate/hexane system), to give the title compound as a colorless solid (3.718 g, yield; 34%).

¹H-NMR (400 MHz, CDCl₃); δ (ppm) 2.66 (1H, br-s), 4.38 (2H, br-s), 6.68 (1H, dt, J=15.6 Hz), 7.18 (1H, d, 8.4 Hz), 7.74 (1H, dd, J=8.4 Hz, 2.4 Hz), 8.58 (1H, d, J=2.4 Hz).

(142-2) 5-Bromo-2-(3-ethoxy-1-propenyl)pyridine

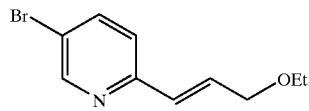

5-Bromo-2-(3-hydroxy-1-propenyl)pyridine (3.718 g) was dissolved in tetrahydrofuran (60 ml), followed by the sequential addition of triethylamine (7.1 ml) and methanesulfonyl chloride (1.6 ml) under ice-cooling, and the resulting mixture was stirred as it was, for 25 min. After the resulting insoluble matters were filtered off, the mixture was evaporated. The resulting residue was dissolved in ethanol (60 ml), followed by the addition of sodium ethoxide (1.388 g)/ethanol (25 ml) solution under ice-cooling, and the mixture was stirred at room temperature for 3.5 hr. The reaction mixture was evaporated, and the resulting residue was partitioned between ethyl acetate and water. The resulting organic layer was washed with water, dried (over MgSO₄) and evaporated. The resulting residue was purified by silica gel column chromatography (ethyl acetate/hexane system), to give the title compound as a yellow oil (2.607 mg, yield; 65%).

¹H-NMR (400 MHz, CDCl₃); δ (ppm) 1.25 (3H, t, J=7.2 Hz), 3.56 (2H, q, J=7.2 Hz), 4.17 (2H, dd, J=5.2 Hz, 1.6 Hz), 6.65 (1H, dt, J=15.8 Hz, 1.6 Hz), 6.79 (1H, dt, J=15.8 Hz, 5.2 Hz), 7.16 (1H, d, J=8.4 Hz), 7.71 (1H, dd, J=8.4 Hz, 2.4 Hz), 8.58 (1H, d, J=2.4 Hz).

(142-3) 5-Bromo-2-(3-ethoxypropyl)pyridine

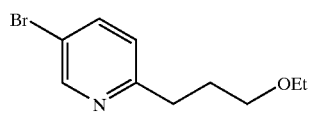

The title compound was obtained as a brown oil (2.286 g, yield; 74%) from 5-bromo-2-(3-ethoxy-1-propenyl)pyridine (3.079 g) in the same manner as in Example 139-2.

¹H-NMR (400 MHz, CDCl₃); δ (ppm) 1.19 (3H, t, J=7.2 Hz), 1.96–2.03 (2H, m), 2.83 (2H, t, J=7.8 Hz), 3.45 (2H, t, J=6 Hz), 3.47 (2H, q, J=7.2 Hz), 7.08 (1H, d, J=8.4 Hz), 7.70 (1H, dd, J=8.4 Hz, 2.4 Hz), 8.58 (1H, d, J=2.4 Hz).

(142-4) 1-(1-Ethylpiperazin-4-yl)-3-[2-(3-ethoxypropyl)pyridin-5-yl]isoquinoline oxalate

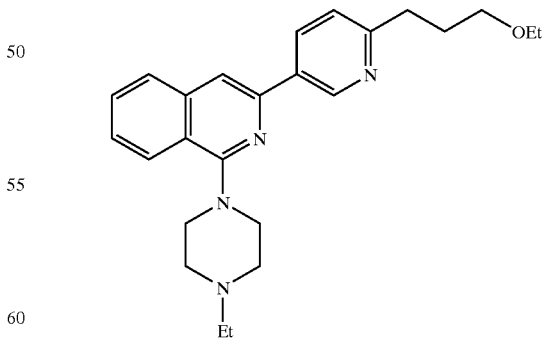

In the same manner as in Example 167-2, the oxalate of the title compound was obtained as a pale yellow amorphous (472 mg, yield; 91%) from 5-bromo-2-(3-ethoxypropyl)pyridine (1.465 g) and 1-(1-ethylpiperazin-4-yl)-3-bromoisoquinoline (348 mg).

Oxalate:

¹H-NMR (400 MHz, DMSO-d₆); δ (ppm) 1.10 (3H, t, J=7.2 Hz), 1.25 (3H, t, J=7.2 Hz), 1.88–1.96 (2H, m), 2.82 (2H, t, J=7.6 Hz), 3.13 (2H, q, J=7.2 Hz), 3.36–3.43 (8H, m), 3.58–3.80 (4H, br-s), 7.37 (1H, d, J=8 Hz), 7.61 (1H, ddd, J=8 Hz, 7 Hz, 1.2 Hz), 7.74 (1H, ddd, J=8 Hz, 7 Hz, 1.2 Hz), 7.96 (1H, d, J=8 Hz), 8.11 (1H, s), 8.11 (1H, d, J=8 Hz), 8.41 (1H, dd, J=8 Hz, 2.4 Hz), 9.27 (1H, d, J=2.4 Hz).

ESI-Mass; 405 (MH⁺).

Example 143

Synthesis of 1-(1-Ethylpiperazin-4-yl)-3-[2-[3-(2-Propoxy)Propyl]Pyridin-5-yl]Isoquinoline Oxalate (143-1) 5-Bromo-2-[3-(2-propoxy)-1-propenyl]pyridine

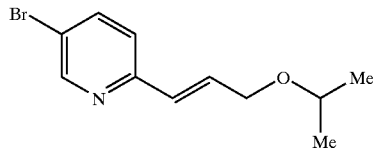

5-Bromo-2-(3-hydroxy-1-propenyl)pyridine (8.891 g) was dissolved in tetrahydrofuran (200 ml), followed by the sequential addition of triethylamine (17.6 ml) and methanesulfonyl chloride (3.9 ml) under ice-cooling, and the mixture was stirred for 20 min. After the resulting insoluble matters were filtered off, the solution was evaporated. The resulting residue was dissolved in 2-propanol (100 ml), sodium 2-propanoxide/2-propanol solution prepared from 60% sodium hydride (2 g) and 2-propanol (70 ml) was added thereto under ice-cooling, and the resulting mixture was stirred, as it was, at room temperature for 30 min. After the resulting insoluble matters were filtered off from the reaction mixture, the resulting solution was evaporated and partitioned between ethyl acetate and water. The resulting organic layer was washed with water, dried (over MgSO₄) and evaporated. The resulting residue was purified by silica gel column chromatography (ethyl acetate/hexane system), to give the title compound as a brown oil (3.519 g, yield; 33%).

¹H-NMR (400 MHz, CDCl₃); δ (ppm) 1.22 (6H, d, J=6 Hz), 3.69 (1H, sept, J=6 Hz), 4.18 (2H, dd, J=5.2 Hz, 1.6 Hz), 6.66 (1H, dd, J=15.8 Hz, 1.6 Hz), 6.79 (1H, dd, J=15.8 Hz, 5.2 Hz), 7.19 (1H, d, J=8.4 Hz), 7.73 (1H, dd, J=8.4 Hz, 2.4 Hz), 8.59 (1H, d, J=2.4 Hz).

(143-2) 5-Bromo-2-[3-(2-propoxy)propyl]pyridine

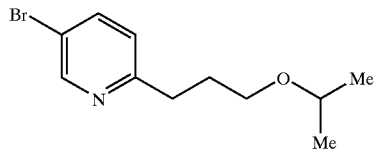

In the same manner as in Example 139-2, the title compound was obtained as a yellow oil (2.859 g, yield; 81%) from 5-bromo-2-[3-(2-propoxy)-1-propenyl)pyridine (3.519 g).

¹H-NMR (400 MHz, CDCl₃); δ (ppm) 1.14 (6H, d, J=6 Hz), 1.94–2.01 (2H, m), 2.83 (2H, t, J=7.8 Hz), 3.43 (2H, t, J=6 Hz), 3.54 (1H, sept, J=6 Hz), 7.08 (1H, d, J=8.4 Hz), 7.70 (1H, dd, J=8.4 Hz, 2.4 Hz), 8.57 (1H, d, 2.4 Hz).

(143-3) 1-(1-Ethylpiperazin-4-yl)-3-[2-(3-(2-propoxy)propyl]pyridin-5-yl]isoquinoline oxalate

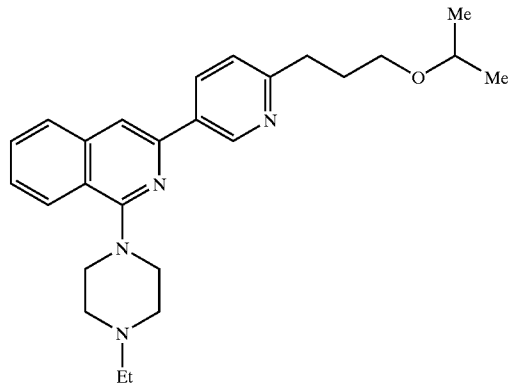

In the same manner as in Example 167-2, the oxalate of the title compound was obtained as a pale yellow amorphous (418 mg. yield; 73%) from 5-bromo-2-[3-(2-propoxy)propyl]pyridine (1.291 g) and 1-(1-ethylpiperazin-4-yl)-3-bromoisoquinoline (348 mg).

Oxalate:

¹H-NMR (400 MHz, DMSO-d₆); δ (ppm) 1.07 (3H, t, J=6 Hz), 1.25 (3H, t, J=7.2 Hz), 1.86–1.96 (2H, m), 2.82 (2H, t, J=7.6 Hz), 3.14 (2H, q, J=7.2 Hz), 3.33–3.43 (4H, m), 3.38 (2H, t, J=6.4 Hz), 3.50 (1H, qui, J=6 Hz), 7.37 (1H, d, J=8 Hz), 7.61 (1H, ddd, J=8 Hz, 7 Hz, 1.2 Hz), 7.74 (1H, ddd, J=8 Hz, 7 Hz, 1.2 Hz), 7.96 (1H, d, J=8 Hz), 8.11 (1H, s), 8.11 (1H, d, J=8 Hz), 8.41 (1H, dd, J=8 Hz, 2.4 Hz), 9.27 (1H, d, 2.4 Hz).

ESI-Mass; 419 (MH⁺).

Example 144

Synthesis of 1-(1-Ethylpiperazin-4-yl)-3-[2-(3-Methoxybutyl)Pyridin-5-yl]Isoquinoline Oxalate (144-1) 5-Bromo-2-(3-methoxy-1-butynyl)pyridine

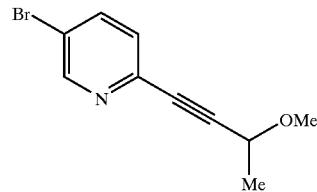

5-Bromo-2-(3-hydroxy-1-butynyl)pyridine (5.426 g) was dissolved in tetrahydrofuran (60 ml), followed by the sequential addition of triethylamine (10 ml) and methanesulfonyl chloride (2.2 ml) under ice-cooling, and the resulting mixture was stirred for 1 hr. The reaction mixture was partitioned between ethyl acetate and water. The organic layer was washed with water, dried (over MgSO₄) and evaporated. The resulting residue was dissolved in methanol (16 ml), and under ice-cooling, 28% sodium methoxide/methanol solution (4.6 ml) was added thereto and the resulting mixture was stirred at room temperature overnight. The reaction mixture was evaporated and partitioned between ethyl acetate and water. The resulting organic layer was washed with water, dried (over MgSO₄) and evaporated. The resulting residue was purified by silica gel column chromatography (ethyl acetate/hexane system), to give the title compound as a brown oil (1.968 g, yield; 34%).

¹H-NMR (400 MHz, CDCl₃); δ (ppm) 1.54 (3H, d, J=6.4 Hz), 3.85 (1H, t, J=6.4 Hz), 3.86 (1H, t, J=6.4 Hz), 7.33 (1H, dd, J=8.4 Hz, 0.8 Hz), 7.79 (1H, dd, J=8.4 Hz, 2.4 Hz), 8.64 (1H, dd, J=2.4 Hz, 0.8 Hz).

(1.44-2) 5-Bromo-2-(3-methoxybutyl)pyridine

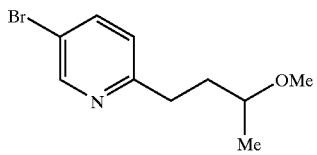

In the same manner as in Example 139-2, the title compound was obtained as a brown oil (1.125 g, yield; 56%) from 5-bromo-2-(3-methoxy-1-butynyl)pyridine (1.968 g).

¹H-NMR (400 MHz, CDCl₃); δ (ppm) 1.17 (3H, d, J=6.4 Hz), 1.83–1.90 (2H, m), 3.32 (4H, s), 7.07 (1H, d, J=8.4 Hz), 7.70 (1H, dd, J=8.4 Hz, 2.4 Hz), 8.57 (1H, d, J=2.4 Hz).

(144-3) 1-(1-Ethylpiperazin-4-yl)-3-[2-(3-methoxybutyl)pyridin-5-yl]isoquinoline oxalate

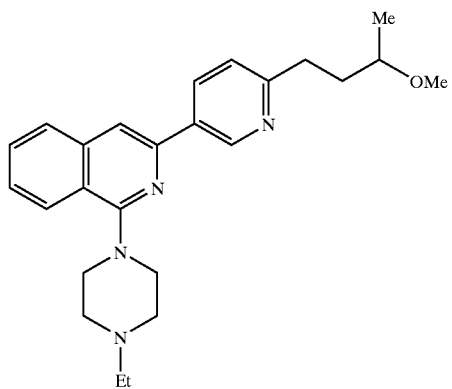

In the same manner as in Example 167-2, the oxalate of the title compound was obtained as a yellowish brown amorphous (352 mg, yield; 58%) from 5-bromo-2-(3-methoxybutyl)pyridine (1.125 g) and 1-(1-ethylpiperazin-4-yl)-3-bromoisoquinoline (377 mg).

Oxalate:

¹H-NMR (400 MHz, DMSO-d₆); δ (ppm) 1.11 (3H, d, J=6.4 Hz), 1.24 (3H, t, J=7.2 Hz), 1.75–1.90 (2H, m), 2.74–2.87 (2H, m), 3.13 (2H, q, J=7.2 Hz), 3.22 (3H, s), 3.26–3.34 (1H, m), 3.32–3.42 (4H, br-s), 7.37 (1H, d, J=8 Hz), 7.61 (1H, dd, J=8 Hz, 7 Hz), 7.74 (1H, dd, J=8 Hz, 7 Hz), 7.96 (1H, d, J=8 Hz), 8.11 (1H, s), 8.12 (1H, d, J=8 Hz), 8.41 (1H, dd, J=8 Hz, 2.4 Hz), 9.26 (1H, d, J=2.4 Hz).

ESI-Mass; 405 (MH⁺).

Example 145

Synthesis of 1-(1-Ethylpiperazin-4-yl)-3-{2-[2-(2-Hydroxy-2-Cyclohexyl)Ethynyl]Pyridin-4-yl}Isoquinoline Oxalate (145-1) 5-Bromo-2-[2-(1-hydroxycyclohexyl)ethynyl]pyridine

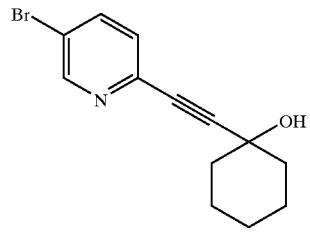

In the same manner as in Example 139-1, the title compound was obtained as a pale brown solid (14.305 g, yield; 85%) from 2,5-dibromopyridine (14.213 g) and 1-ethynylcyclopentanol (7.451 g).

¹H-NMR (400 MHz, CDCl₃); δ (ppm) 1.25–1.36 (1H, m), 1.52–1.80 (6H, m), 2.00–2.06 (2H, m), 2.40–2.45 (1H, m), 7.31 (1H, d, J=8.4 Hz), 7.78 (1H, dd, J=8.4 Hz, 2.4 Hz), 8.63 (1H, d, J=2.4 Hz).

(145-2) 5-Bromo-2-[2-[1-(tert-butyldimethylsilyloxy)cyclohexyl]ethynyl]pyridine

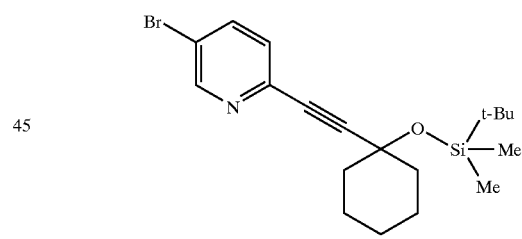

In the same manner as in Example 138-3, the title compound was obtained as a pale yellow oil (4 g, yield; 100%) from 5-bromo-2-[2-(1-hydroxycyclohexyl)ethynyl]pyridine (2.802 g).

¹H-NMR (400 MHz, CDCl₃); δ (ppm) 0.21 (6H, s), 0.90 (9H, s), 1.32–1.94 (10H, m), 7.28 (1H, d, J=8.4 Hz), 7.77 (1H, dd, J=8.4 Hz, 2.4 Hz), 8.64 (1H, d, J=2.4 Hz).

(145-3) 1-(1-Ethylpiperazin-4-yl)-3-[2-[2-[2-(t-butyldimethylsilyloxy)-2-cyclohexyl]ethynyl]pyridin-4-yl]isoquinoline or compound identified by the following analytical data and synthetic procedures

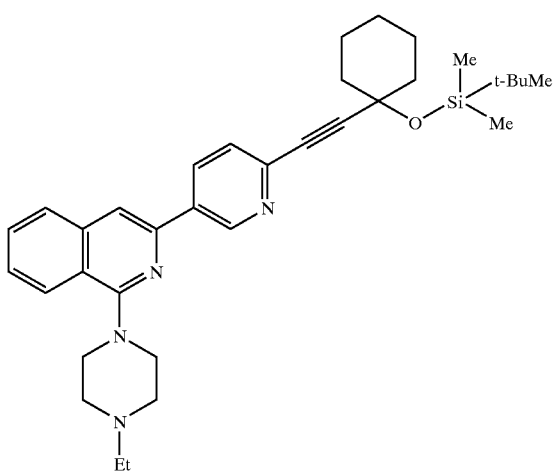

In the same manner as in Example 167-2, the title compound was obtained as a yellow oil (156 mg, yield; 21%) from 5-bromo-2-[2-[1-t-butyldimethylsilyloxy)cyclohexyl]ethynyl]pyridine (4 g) and 1-(1-ethylpiperazin-4-yl)-3-bromoisoquinoline (446 mg).

$^1$H-NMR (400 MHz, CDCl$_3$); δ (ppm) 0.26 (6H, s), 0.92 (9H, s), 1.14 (3H, t, J=7.2 Hz), 1.05–1.75 (10H, m), 2.55 (2H, q, J=7.2 Hz), 2.74 (4H, t, J=4.4 Hz), 3.59 (4H, t, J=4.4 Hz), 7.49 (1H, dd, J=8.4 Hz, 0.8 Hz), 7.50 ((1H, ddd, J=8 Hz, 7 Hz, 1.2 Hz), 7.61 (1H, ddd, J=8 Hz, 7 Hz, 1.2 Hz), 7.69 (1H, s), 7.80 (1H, d, J=8 Hz), 8.07 (1H, d, J=8 Hz), 8.40 (1H, dd, J=8.4 Hz, 2.4 Hz), 9.35 (1H, dd, J=2.4 Hz, 0.8 Hz).

(145-4) 1-(1-Ethylpiperazin-4-yl)-3-[2-[2-(2-hydroxy-2-cyclohexyl)ethynyl]pyridin-4-yl]isoquinoline oxalate or compound identified by the following analytical data and synthetic procedures

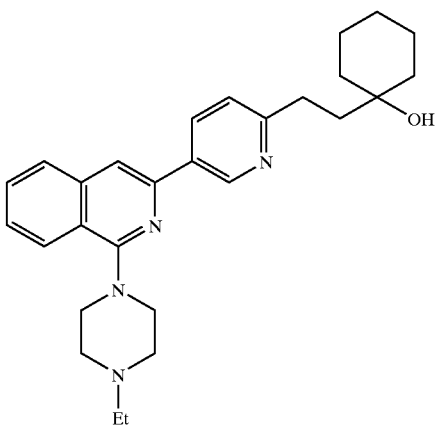

1-(1-Ethylpiperazin-4-yl)-3-[2-{2-(1-(t-butyldimethylsilyloxy)-2-cyclohexyl]ethynyl}pyridin-4-yl]]isoquinoline (156 mg) was dissolved in tetrahydrofuran (10 ml), followed by the addition of 1M tetrabutylammonium fluoride/tetrahydrofuran solution (0.6 ml), and the resulting mixture was stirred at room temperature for 30 min. The reaction mixture was partitioned between ethyl acetate and water. The resulting organic layer was washed with water, dried (over MgSO$_4$) and evaporated. The resulting residue was then treated in the same manner as in Example 131, to give the oxalate of the title compound as a yellow amorphous (110 mg, yield; 67%).

Oxalate:
$^1$H-NMR (400 MHz, DMSO-d$_6$); δ (ppm) 1.23 (3H, t, J=7.2 Hz), 1.28–1.64 (8H, m), 1.71–1.78 (2H, m), 2.79–2.86 (2H, m), 3.06 (2H, q, J=7.2 Hz), 3.26–3.36 (4H, br-s), 3.38–3.76 (4H, br-s), 7.36 (1H, d, J=8 Hz), 7.60 (1H, ddd, J=8 Hz, 7 Hz, 1.2 Hz), 7.74 (1H, ddd, J=8 Hz, 7 Hz, 1.2 Hz), 7.69 (1H, s), 8.10 (1H, dd, J=8 Hz, 2.4 Hz), 9.24 (1H, d, J=2.4 Hz).

ESI-Mass; 445 (MH$^+$).

Example 146

Synthesis of 1-(1-ethylpiperazin-4-yl)-3-[2-(1-butyn-1-yl)pyridin-5-yl]isoquinoline (146-1) 5-Bromo-2-(1-butynyl)pyridine

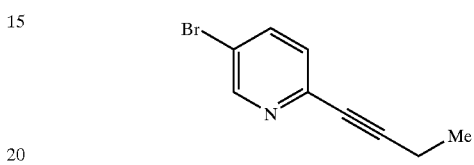

In the same manner as in Example 139-1, the title compound was obtained as a brown solid (13.113 g, yield; 60%) from 2,5-dibromopyridine (24.7 g) and 1-butyne (5.63 g).

$^1$H-NMR (400 MHz, CDCl$_3$); δ (ppm) 1.26 (3H, t, J=7.6 Hz), 2.44 (2H, q, J=7.6 Hz), 7.74 (1H, dd, J=8.4 Hz, 2.4 Hz), 8.59 (1H, d, J=2.4 Hz).

(146-2) 2-(1-Butynyl)-5-tributylstannylpyridine

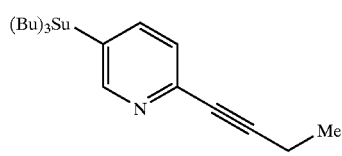

In the same manner as in Example 161-2, the title compound was obtained as a pale green oil (1.331 g, yield; 25%) from 5-bromo-2-(1-butynyl)pyridine (2.521 g).

$^1$H-NMR (400 MHz, CDCl$_3$); δ (ppm) 0.88 (9H, t, J=7.6 Hz), 1.06–1.11 (6H, m), 1.26 (3H, t, J=7.6 Hz), 7.30 (1H, dd, J=7.4 Hz, 1.2 Hz), 7.67 (1H, dd, J=7.4 Hz, 1.2 Hz), 8.53 (1H, t, J=1.2 Hz).

(146-3) 1-(1-Ethylpiperazin-4-yl)-3-[2-(1-butynyl)pyridin-5-yl]isoquinoline

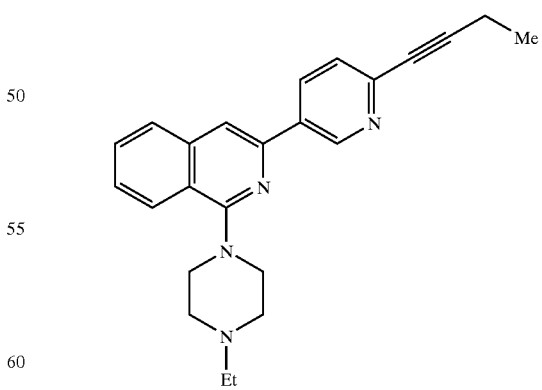

In the same manner as in Example 161-2, the title compound was obtained as a yellow amorphous (155 mg, yield; 27%) from 2-(1-butynyl)-5-tributylstannylpyridine (1.331 g) and 1-(1-ethylpiperazin-4-yl)-3-bromoisoquinoline (466 mg).

Free compound:

¹H-NMR (400 MHz, CDCl₃); δ (ppm) 1.18 (3H, t, J=7.2 Hz), 1.29 (3H, t, J=7.2 Hz), 2.50 (2H, q, J=7.2 Hz), 2.56 (2H, q, J=7.2 Hz), 2.75 (4H, t, J=4.4 Hz), 3.59 (4H, t, J=4.4 Hz), 7.46 (1H, d, J=8 Hz), 7.50 (1H, ddd, J=8 Hz, 7 Hz, 1.2 Hz), 7.62 (1H, ddd, J=8 Hz, 7 Hz, 1.2 Hz), 7.71 (1H, s), 7.82 (1H, d, J=8 Hz), 8.09 (1H, d, J=8 Hz), 8.40 (1H, dd, J=8 Hz, 2.4 Hz), 9.29 (1H, d, J=2.4 Hz).

ESI-Mass; 371 (MH⁺).

Example 147

Synthesis of 1-(4-ethylpiperazin-1-yl)-3-[2-(morpholin-4-yl)pyridin-5-yl]isoquinoline trihydrochloride

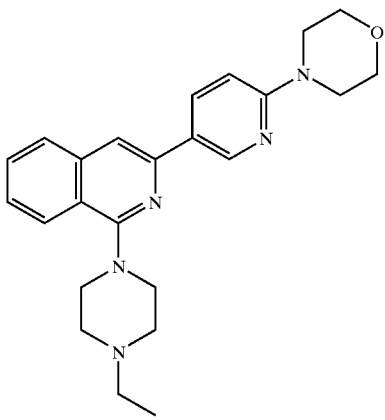

3-Bromo-1-(4-ethylpiperazin-1-yl)isoquinoline (1.27 g) and [2-(morpholin-4-yl)pyridin-5-yl]tributylstannum (3.03 g) were reacted in the presence of tetrakistriphenylphosphine dichloride (0.50 g) in xylene (50 ml) at 140° C. for 5 hr. The reaction solution was concentrated. Ethyl acetate and an aqueous solution of saturated sodium bicarbonate were added to the resulting residue, and then it was partitioned. The resulting organic layer was washed with water and brine, and then dried over magnesium sulfate. The solvent was evaporated, and the resulting residue was purified by silica gel column chromatography (methylene chloride/methanol system), to give 0.39 g of the free compound of the title compound as a pale yellow oil.

Free compound:

¹H-NMR (400 MHz, CDCl₃); δ (ppm) 1.17 (t, J=7.2 Hz, 3H), 2.55 (q, J=7.2 Hz, 2H), 2.75 (br-t, 4H), 3.54 (m, 4H), 3.59 (br-t, 4H), 3.85 (m, 4H), 6.72 (d, J=8.8 Hz, 1H), 7.42 (br-t, 1H), 7.55 (s, 1H), 7.56 (br-t, 1H), 7.75 (d, J=8.0 Hz, 1H), 8.04 (d, J=8.0 Hz, 1H), 8.27 (dd, J=8.4, 2.4 Hz, 1H), 9.02 (d, J=2.4 Hz, 1H).

The resulting free compound was converted into a hydrochloride in a conventional manner, and recrystallized from ethanol/ether, to give 0.51 g of the title compound as a white powder.

Hydrochloride:

m.p.; 186° C.

¹H-NMR (400 MHz, DMSO-d₆); δ (ppm) 1.33 (t, J=7.2 Hz, 3H), 3.23 (m, 2H), 3.36 (m, 2H), 3.51 (br-t, 2H), 3.63 (br-d, 2H), 3.68 (m, 4H), 3.77 (m, 4H), 4.00 (br-d, 2H), 7.26 (m, 1H), 7.61 (br-t, 1H), 7.75 (br-t, 1H), 7.95 (br-d, 1H), 8.08 (s, 1H), 8.11 (br-d, 1H), 8.54 (m, 1H), 8.86 (br-s, 1H).

MS(FAB) m/z 404 (M+H)⁻.

Example 148

Synthesis of 1-(4-ethylpiperazin-1-yl)-3-[5-(morpholin-4-yl)pyridin-2-yl]isoquinoline trihydrochloride

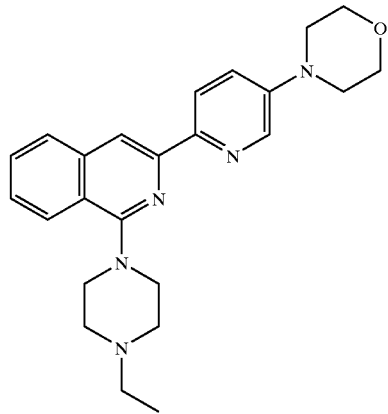

3-(5-Bromopyridin-2-yl)-1-(4-ethylpiperazin-1-yl)isoquinoline (0.21 g) and morpholine (0.12 ml) were reacted in the presence of tetrakistriphenylphosphine dichloride (0.30 g) in xylene (30 ml) at 140° C. for 5 hr. The reaction solution was concentrated. Ethyl acetate and an aqueous solution of saturated sodium bicarbonate were added to the resulting residue, and partitioned. The resulting organic layer was washed with water and brine, and then dried over magnesium sulfate. The solvent was evaporated, and the resulting residue was purified by silica gel column chromatography (methylene chloride/methanol system), to give 47 mg of the free compound of the title compound as a colorless oil.

Free compound:

¹H-NMR (400 MHz, CDCl₃); δ (ppm) 1.20 (t, J=7.2 Hz, 3H), 2.58 (q, J=7.2 Hz, 2H), 2.79 (br-s, 4H), 3.27 (m, 4H), 3.59 (br-s, 4H), 3.91 (m, 4H), 7.30 (dd, J=2.8 Hz, 1H), 7.46 (br-t, 1H), 7.58 (br-t, 1H), 7.85 (d, J=8.0 Hz, 1H), 8.07 (d, J=8.0 Hz, 1H), 8.26 (s, 1H), 8.37 (d, J=2.8 Hz, 1H), 8.41 (d, J=8.8 Hz, 1H).

The resulting free compound was converted into a hydrochloride in a conventional manner, and recrystallized from ethanol/ether, to give 52 mg of the free compound of the title compound as a white powder.

Hydrochloride:

¹H-NMR (400 MHz, DMSO-d₆); δ (ppm) 1.34 (t, J=7.2 Hz, 3H), 3.24 (m, 2H), 3.32–3.42 (m, 6H), 3.50–3.65 (m, 4H), 3.81 (m, 4H), 4.13 (br-d, 2H), 7.69 (br-t, 1H), 7.81 (br-t, 1H), 7.94 (br, 1H), 8.04 (br-d, 1H), 8.16 (br-d, 1H), 8.36 (br-d, 1H), 8.45 (br-s, 1H), 8.48 (br-d, 1H).

MS(FAB) m/z 404 (M+H)⁺.

Example 149

Synthesis of 3-[2-(2,6-dimethylmorpholin-4-yl)pyridin-5-yl]-1-(4-ethylpiperazin-1-yl)isoquinoline trihydrochloride

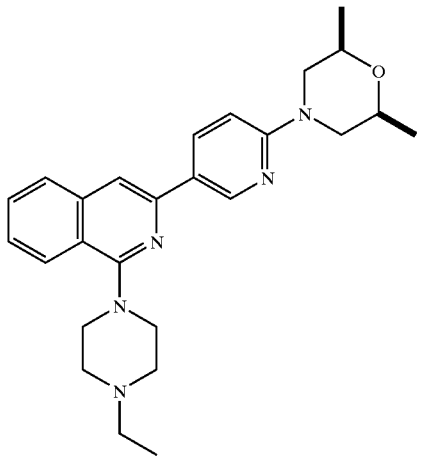

3-Bromo-1-(4-ethylpiperazin-1-yl)isoquinoline (2.00 g) and [2-(2,6-dimethylmorpholin-4-yl)pyridin-5-yl]tributylstannum (5.70 g) were reacted in the presence of tetrakistriphenylphosphine dichloride (0.50 g) in xylene (70 ml) at 140° C. for 5 hr. The reaction solution was concentrated. Ethyl acetate and an aqueous solution of saturated sodium bicarbonate were added to the resulting residue, for partitioning. The resulting organic layer was washed with water and brine, and then dried over magnesium sulfate. The solvent was evaporated, and the resulting residue was purified by silica gel column chromatography (methylene chloride/methanol system), to give 0.76 g of the free compound of the title compound as a colorless oil.

Free compound:

$^1$H-NMR (400 MHz, CDCl$_3$); δ (ppm) 1.18 (t, J=7.2 Hz, 3H), 1.30 (d, J=6.0 Hz, 6H), 2.57 (q, J=7.2 Hz, 2H), 2.60 (dd, J=13.0, 10.4 Hz, 6H), 2.76 (br-t, 4H), 3.60 (br-t, 4H), 3.76 (ddd, J=10.4, 6.0, 2.0 Hz, 2H), 4.14 (dd, J=13.0, 2.0, 2H), 6.72 (d, J=8.8 Hz, 1H), 7.42 (br-t, 1H), 7.55 (s, 1H), 7.57 (br-t, 1H), 7.76 (d, J=8.0 Hz, 1H), 8.04 (d, J=8.0, 1.0 Hz, 1H), 8.26 (dd, J=8.0, 2.4 Hz, 1H), 9.02 (d, J=2.4 Hz, 1H).

The resulting free compound was converted into a hydrochloride in a conventional manner, and recrystallized from ethanol/ether, to give 1.08 g of the hydrochloride of the title compound as a white powder.

Hydrochloride:

m.p.; 180° C.

$^1$H-NMR (400 MHz, DMSO-d$_6$); δ (ppm) 1.19 (d, J=5.6 Hz, 6H), 1.32 (t, J=7.2 Hz, 3H), 2.62–2.68 (m, 2H), 3.24 (m, 2H), 3.37 (m, 2H), 3.48 (br-t, 2H), 3.60–3.70 (m, 4H), 4.01 (br-d, 2H), 4.29 (br-d, 2H), 7.24 (m, 1H), 7.60 (br-t, 1H), 7.55 (br-t, 1H), 7.75 (br-t, 1H), 7.95 (br-d, 1H), 8.05 (br-s, 1H), 8.11 (br-d, 1H), 8.49 (m, 1H), 8.86 (br-s, 1H).

MS(FAB) m/z 432 (M+H)$^+$.

Example 150

Synthesis of 1-(4-ethylpiperazin-1-yl)-3-[2-(thiomorpholin-4-yl)pyridin-5-yl]isoquinoline trihydrochloride

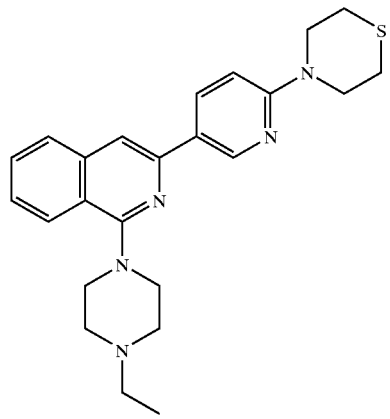

3-Bromo-1-(4-ethylpiperazin-1-yl)isoquinoline (0.69 g) and [2-(thiomorpholin-4-yl)pyridin-5-yl]tributylstannum (1.62 g) were reacted in the presence of tetrakistriphenylphosphine dichloride (0.50 g) in xylene (50 ml) at 140° C. for 5 hr. The reaction solution was concentrated. Ethyl acetate and an aqueous solution of saturated sodium bicarbonate were added to the resulting residue, for partitioning. The resulting organic layer was washed with water and brine, and then dried over magnesium sulfate. The solvent was evaporated, and the resulting residue was purified by silica gel column chromatography (methylene chloride/methanol system), to give 0.66 g of the free compound of the title compound as a white amorphous.

Free compound:

$^1$H-NMR (400 MHz, CDCl$_3$); δ (ppm) 1.24 (br-s, 3H), 2.64 (br-s, 2H), 2.70 (m, 4H), 2.80 (br, 4H), 3.67 (br, 4H), 4.04 (m, 4H), 6.42 (d, J=8.8 Hz, 2H), 7.43 (br-t, 1H), 7.56 (br-t, 1H), 7.76 (d, J=8.0 Hz, 1H), 8.03 (d, J=8.0 Hz, 1H), 8.24 (dd, J=8.8, 2.4 Hz, 1H), 9.00 (d, J=2.4 Hz, 1H).

The resulting free compound (0.20 g) was converted into a hydrochloride in a conventional manner, and recrystallized from ethanol/ether, to give 0.26 g of the hydrochloride of the title compound as a pale yellow powder.

Hydrochloride:

m.p.; 210° C.

$^1$H-NMR (400 MHz, DMSO-d$_6$); δ (ppm) 1.33 (t, J=7.2 Hz, 3H), 2.75 (br-s, 4H), 3.20–3.27 (m, 2H), 3.47–3.56 (m, 2H), 3.60–3.66 (br-d, 2H), 3.97–4.02 (br-d, 2H), 4.10 (br-s, 4H), 7.37 (m, 1H), 7.62 (br-t, 1H), 7.77 (br-t, 1H), 7.96 (br-d, 1H), 8.09–8.14 (m, 1H), 8.58 (m, 1H), 8.80 (m, 1H), 10.9 (m, 1H).

MS(FAB) m/z 420 (M+H)$^+$.

Example 151

Synthesis of 1-(4-ethylpiperazin-1-yl)-3-[2-(S-oxythiomorpholin-4-yl)pyridin-5-yl]isoquinoline trihydrochloride

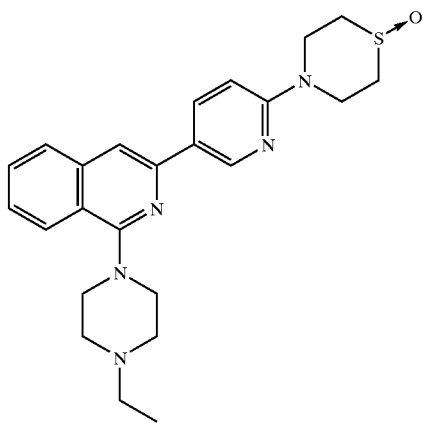

1-(4-Ethylpiperazin-1-yl)-3-[2-(thiomorpholin-4-yl)pyridin-5-yl]isoquinoline (0.10 g) obtained in Example 150 was dissolved in dichloromethane (10 ml), and the resulting solution was reacted with 3-chloroperbenzoic acid (56 mg) under ice-cooling for 1 hr. The reaction solution was partitioned between ethyl acetate and an aqueous solution of saturated sodium bicarbonate. The resulting organic layer was washed with water and brine, and then dried over magnesium sulfate. The solvent was evaporated, and the resulting residue was purified by silica gel column chromatography (methylene chloride/methanol system), to give 28 mg of the free compound of the title compound as a colorless oil.

Free compound:

$^1$H-NMR (400 MHz, CDCl$_3$); δ (ppm) 1.22 (t, J=7.2 Hz, 3H), 2.63 (q, J=7.2 Hz, 2H), 2.79–2.88 (m, 8H), 3.65 (br-s, 4H), 4.22 (m, 4H), 6.82 (d, J=8.8 Hz, 2H), 7.45 (br-t, 1H), 7.58 (br-t, 1H), 7.76 (d, J=8.0 Hz, 1H), 8.03 (d, J=8.0 Hz, 1H), 8.28 (dd, J=8.8, 2.4 Hz, 1H), 9.01 (d, J=2.4 Hz, 1H).

The resulting free compound was converted into a hydrochloride in a conventional manner, and recrystallized from ethanol/ether, to give 40 mg of the hydrochloride of the title compound as a yellow powder.

Hydrochloride:

m.p.; 170° C.

MS(FAB) m/z 436 (M+H)$^+$.

Example 152

Synthesis of 1-(4-ethylpiperazin-1-yl)-3-[2-(4-hydroxypiperidin-1-yl)pyridin-5-yl]isoquinoline trihydrochloride

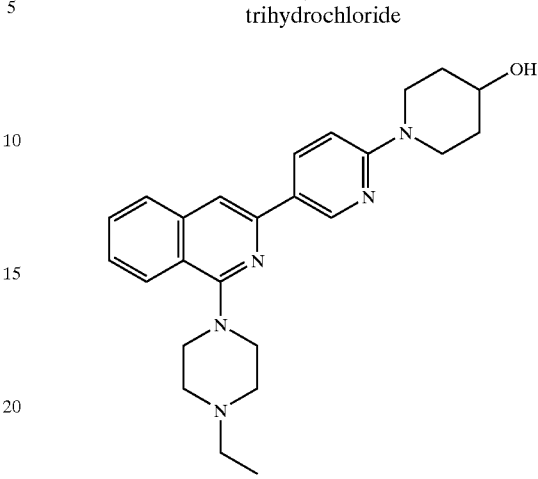

3-Bromo-1-(4-ethylpiperazin-1-yl)isoquinoline (1.16 g) and {2-[4-(t-butyldimethyloxy)piperidin-1-yl]pyridin-5-yl}tributylstannum (1.37 g) was reacted in the presence of tetrakistriphenylphosphine dichloride (0.30 g) in xylene (30 ml) at 140° C. for 5 hr. The reaction solution was concentrated. A 2N aqueous solution of hydrochloric acid was added to the resulting residue, and then reacted at 50° C. for 1 hr. The reaction solution was basified with a 2N aqueous solution of sodium hydroxide, and then it was extracted with ethyl acetate. The resulting organic layer was washed with water and brine, and dried over magnesium sulfate. The solvent was evaporated, and the resulting residue was purified by silica gel column chromatography (methylene chloride/methanol system), to give 0.26 g of the free compound of the title compound as a colorless amorphous.

Free compound:

$^1$H-NMR (400 MHz, CDCl$_3$); δ (ppm) 1.18 (t, J=7.2 Hz, 3H), 1.33 (dd, J=12.0, 4.0 Hz, 2H), 1.43 (dt, J=0.8, 6.0 Hz, 1H), 1.86 (br-d, J=12 Hz, 2H), 2.56 (q, J=7.2 Hz, 2H), 2.76 (br-s, 4H), 2.92 (dt, 2.4, 12.8 Hz, 2H), 3.55 (t, J=6 Hz, 2H), 3.59 (br-s, 4H), 4.44 (br-d, J=12.8, 2H), 6.76 (d, J=8.8 Hz, 1H), 7.42 (br-t, 1H), 7.54 (s, 1H), 7.75 (d, J=8.0 Hz, 1H), 8.04 (d, J=8.0 Hz, 1H), 8.23 (dd, J=8.8, 2.4 Hz, 1H), 9.01 (d, J=2.4 Hz, 1H).

The resulting free compound was converted into a hydrochloride in a conventional manner, and recrystallized from ethanol/ether, to give 0.30 g of the hydrochloride of the title compound as a yellow powder.

Hydrochloride:

m.p.; 188° C.

$^1$H-NMR (400 MHz, DMSO-d$_6$); δ (ppm) 1.27 (br-d, J=13.4 Hz, 3H), 1.34 (t, J=7.2 Hz, 3H), 1.73–1.86 (m, 1H), 1.83 (br-d, J=13.4, 2H), 3.23 (m, 2H), 3.31 (m, 2H), 3.32–3.37 (m, 2H), 3.42–3.56 (m, 4H), 3.98 (br-d, 2H), 4.41 (br-d, 2H), 7.52 (br-d, 1H), 7.64 (br-t, J=7.6 Hz, 1H), 7.78 (br-t, J=7.6 Hz, 1H), 7.97 (br-d, J=7.6 Hz, 1H), 8.11–8.15 (m, 1H), 8.13 (s, 1H), 8.65 (br-d, J=7.6 Hz, 1H), 8.68 (br-s, 1H), 11.14 (br-s, 1H).

MS(FAB) m/z 432 (M+H)$^+$.

Example 153

Synthesis of 1-(4-ethylpiperazin-1-yl)-3-[2-(4-methoxypiperidin-1-yl)pyridin-5-yl]isoquinoline trihydrochloride

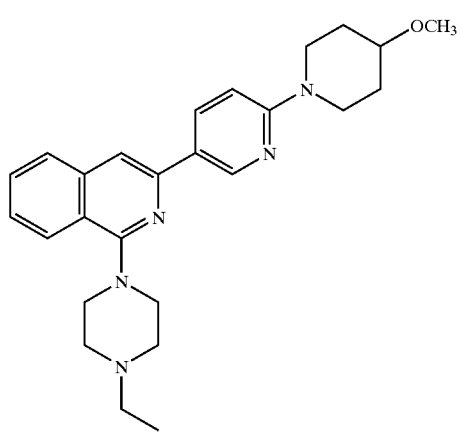

3-Bromo-1-(4-ethylpiperazin-1-yl)isoquinoline (0.83 g) and [2-(4-methoxypiperidin-1-yl)pyridin-5-yl] tributylstannum (0.94 g) were reacted in the presence of tetrakistriphenylphosphine dichloride (0.40 g) in xylene (30 ml) at 140° C. for 5 hr. The reaction solution was concentrated and partitioned between ethyl acetate and water. The resulting organic layer was washed with water and brine, and then dried over magnesium sulfate. The solvent was evaporated, and the resulting residue was purified by silica gel column chromatography (methylene chloride/methanol system), to give 0.61 g of the free compound of the title compound as a pale yellow oil.

Free compound:

$^1$H-NMR (400 MHz, CDCl$_3$); δ (ppm) 1.18 (t, J=7.2 Hz, 3H), 1.65 (m, 2H), 2.56 (q, J=7.2 Hz, 2H), 2.76 (br-s, 4H), 3.31 (ddd, J=13.2, 9.6, 3.6 Hz, 2H), 3.40 (s, 3H), 3.59 (br-s, 4H), 4.06 (m, 2H), 6.77 (d, J=8.8 Hz, 1H), 7.42 (br-t, 1H), 7.54 (s, 1H), 7.76 (d, J=8.0 Hz, 1H), 8.04 (d, J=8.0 Hz, 1H), 8.23 (dd, J=8.8, 2.4 Hz, 1H), 9.01 (d, J=2.4 Hz, 1H).

The resulting free compound was converted into a hydrochloride in a conventional manner, and recrystallized from ethanol/ether, to give 0.62 g of the hydrochloride of the title compound as a white powder.

Hydrochloride:

m.p.; 170° C.

$^1$H-NMR (400 MHz, DMSO-d$_6$); δ (ppm) 1.35 (t, J=7.2 Hz, 3H), 1.58–1.68 (m, 2H), 1.95–2.04 (m, 2H), 3.23 (m, 2H), 3.31 (s, 3H), 3.38 (m, 2H), 3.51–3.59 (m, 5H), 3.64 (m, 2H), 3.97 (br-d, 2H), 4.02 (m, 2H), 7.54 (br-d, 1H), 7.64 (br-t, 1H), 7.78 (br-t, 1H), 7.97 (br-d, 1H), 8.11–8.15 (m, 2H), 8.65–8.70 (m, 2H), 11.34 (br-s, 1H).

MS(FAB) m/z 432 (M+H)$^+$.

Example 154

Synthesis of 1-(4-ethylpiperazin-1-yl)-3-[2-(4-hydroxymethylpiperidin-1-yl)pyridin-5-yl] isoquinoline trihydrochloride

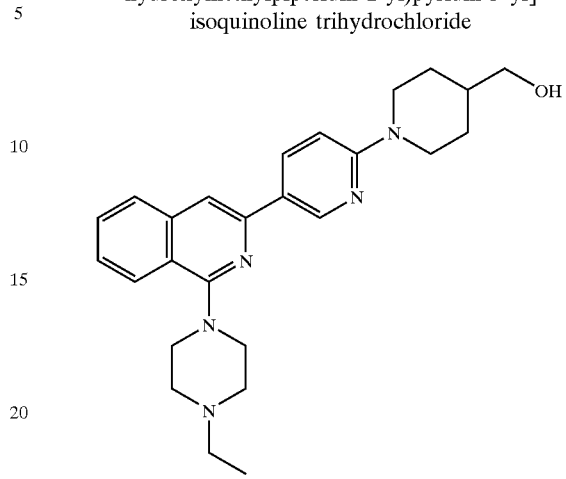

3-Bromo-1-(4-ethylpiperazin-1-yl)isoquinoline (1.35 g) and [2-(4-ethoxycarbonylpiperidin-1-yl)pyridin-5-yl] tributylstannum (1.71 g) were reacted in the presence of tetrakistriphenylphosphine dichloride (0.40 g) in xylene (50 ml) at 140° C. for 5 hr. The reaction solution was concentrated and partitioned between ethyl acetate and water. The resulting organic layer was washed with water and brine, and then dried over magnesium sulfate. The solvent was evaporated. The resulting residue in a pale yellow oil was dissolved in tetrahydrofuran (30 ml) and reacted with lithium aluminium hydride (1.9 ml, 1M-THF solution). Water (0.07 ml), a 5N aqueous solution of sodium hydroxide (0.07 ml) and water (0.21 ml) were added to the reaction solution in this order, which was stirred at room temperature for 1 hr. The reaction solution was filtered, and the resulting insoluble matters were washed with ethyl acetate, while the resulting filtrate was concentrated. The resulting residue was purified by silica gel column chromatography (methylene chloride/methanol system), to give 0.78 g of the free compound of the title compound as a pale yellow oil.

Free compound:

$^1$H-NMR (400 MHz, CDCl$_3$); δ (ppm) 1.18 (t, J=7.2 Hz, 3H), 1.33 (dd, J=12.0, 4.0 Hz, 2H), 1.43 (dt, J=0.8, 6.0 Hz, 1H), 1.86 (br-d, J=12, 2H), 2.56 (q, J=7.2 Hz, 2H), 2.76 (br-s, 4H), 2.92 (dt, 2.4, 12.8 Hz, 2H), 3.55 (t, J=6 Hz, 2H), 3.59 (br-s, 4H), 4.44 (br-d, J=12.8, 2H), 6.76 (d, J=8.8 Hz, 1H), 7.42 (br-t, 1H), 7.54 (s, 1H), 7.75 (d, J=8.0 Hz, 1H), 8.04 (d, J=8.0 Hz, 1H), 8.23 (dd, J=8.8, 2.4 Hz, 1H), 9.01 (d, J=2.4 Hz, 2H).

The resulting free compound was converted into a hydrochloride in a conventional manner, and recrystallized from ethanol/ether, to give 0.45 g of the hydrochloride of the title compound as a white powder.

Hydrochloride:

m.p.; 188° C.

$^1$H-NMR (400 MHz, DMSO-d$_6$); δ (ppm) 1.27 (br-d, J=13.4 Hz, 3H), 1.34 (t, J=7.2 Hz, 3H), 1.73–1.86 (m, 1H), 1.83 (br-d, J=13.4, 2H), 3.23 (m, 2H), 3.31 (m, 2H), 3.32–3.37 (m, 2H), 3.42–3.56 (m, 4H), 3.98 (br-d, 2H), 4.41 (br-d, 2H), 7.52 (br-d, 1H), 7.64 (br-t, J=7.6 Hz, 1H), 7.78

(br-t, J=7.6 Hz, 1H), 7.97 (br-d, J=7.6 Hz, 1H), 8.11–8.15 (m, 1H), 8.13 (s, 1H), 8.65 (br-d, J=7.6 Hz, 1H), 8.68 (br-s, 1H), 11.14 (br-s, 1H).

MS(FAB) m/z 432 (M+H)$^+$.

Example 155

Synthesis of 3-[2-(5,6-dihydro-2H-pyran-4-yl)pyridin-5-yl]-1-(4-ethylpiperazin-1-yl)isoquinoline oxalate

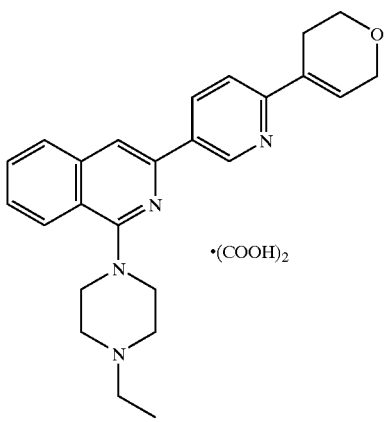

In the same manners sequentially as in Examples 161-2 and 20, a yellow oil was obtained (127 mg, yield; 90%) from 5-bromo-2-(5,6-dihydro-2H-pyran-4-yl)pyridine (432 mg) and 3-bromo-1-(4-ethylpiperazin-1-yl)isoquinoline (111 mg). The resulting compound was converted into a oxalate in a conventional manner, to give the oxalate of the title compound as white crystals.

Oxalate:

m.p.; 156–159° C.

$^1$H-NMR (400 MHz, DMSO-d$_6$); δ (ppm) 1.23 (br, 3H), 2.51 (br, 2H), 3.06 (br, 2H), 3.32 (br, 4H), 3.67 (br, 4H), 3.84 (br, 2H), 4.26 (br, 2H), 6.47 (s, 1H), 7.63 (br, 1H), 7.96 (d, J=8.0 Hz, 1H), 8.06–8.13 (m, 2H), 8.38 (d, J=8.0 Hz, 1H), 8.45 (s, 1H), 8.78 (s, 1H).

MS(FAB) m/z 401 (M+H)$^+$.

Free compound:

$^1$H-NMR (400 MHz, CDCl$_3$); δ (ppm) 1.16 (t, J=7.2 Hz, 3H), 2.54 (q, J=7.2 Hz, 2H), 2.88 (t, J=8.0 Hz, 1H), 2.73 (br, 4H), 3.52 (br, 4H), 3.99 (t, J=5.6 Hz, 2H), 4.38 (q, J=2.8 Hz, 2H), 6.28 (br, 1H), 7.49 (t, J=8.0 Hz, 1H), 7.61 (t, J=8.0 Hz, 1H), 7.80 (dd, J=8.4, 2.4 Hz, 1H), 7.89 (d, J=8.0 Hz, 1H), 8.10 (d, J=8.0 Hz, 1H), 8.38 (s, 1H), 8.49 (d, J=8.4 Hz, 1H), 8.74 (d, J=2.4 Hz, 1H).

Example 156

Synthesis of 3-[2-(tetrahydropyran-4-yl)pyridin-5-yl]-1-(4-ethylpiperazin-1-yl)isoquinoline oxalate In the same manners sequentially as in Examples 161-2 and 20, an oil was obtained from 5-bromo-2-(tetrahydropyran-4-yl)pyridine (745 mg) and 3-bromo-1-(4-ethylpiperazin-1-yl)isoquinoline (300 mg). Methanol (10 ml) and palladium-carbon catalyst (25 mg) were added to the oil (387 mg), and then reacted in hydrogen atmosphere overnight. The resulting reaction solution was filtered through Celite, and then evaporated. The resulting residue was basified by adding a 1N aqueous solution of sodium hydroxide thereto, and then it was partitioned between ethyl acetate and water. The resulting organic layer was washe with water, dried and concentrated. The resulting residue was purified by silica gel column chromatography (hexane/ethyl acetate system), to give a yellow oil (260 mg, yield; 69%). The resulting oil was converted into an oxalate in a conventional manner, to give the oxalate of the title compound as white crystals.

Oxalate:

m.p.; 158–160° C.

$^1$H-NMR (400 MHz, DMSO-d$_6$); δ (ppm) 1.27 (t, J=7.2 Hz, 3H), 1.76 (br, 4H), 2.92 (br, 1H), 3.19 (br, 2H), 3.30–3.85 (m, 10H), 3.99 (d, J=11.2 Hz, 2H), 7.65 (t, J=8.0 Hz, 1H), 7.76 (t, J=8.0 Hz, 1H), 7.86 (dd, J=8.4, 2.0 Hz, 1H), 8.09 (d, J=8.0 Hz, 1H), 8.14 (d, J=8.4 Hz, 1H), 8.37 (d, J=8.0 Hz, 1H), 8.46 (s, 1H), 8.61 (d, J=2.0 Hz, 1H).

MS(FAB) m/z 403 (M+H)$^+$.

Free compound:

$^1$H-NMR (400 MHz, CDCl$_3$); δ (ppm) 1.19 (t, J=6.8 Hz, 3H), 1.82–1.92 (m, 4H), 2.57 (q, J=6.8 Hz, 2H), 2.78 (br, 4H), 2.78–2.98 (m, 1H), 3.55–3.59 (m, 6H), 4.11–4.14 (m, 2H), 7.50 (t, J=8.4 Hz, 1H), 7.61 (t, J=8.4 Hz, 1H), 7.68 (dd, J=8.4, 2.4 Hz, 1H), 7.89 (d, J=8.4 Hz, 1H), 8.11 (d, J=8.4 Hz, 1H), 8.36 (s, 1H), 8.48 (d, J=8.4 Hz, 1H), 8.57 (d, J=2.4 Hz, 1H).

Example 157

Synthesis of 3-[4-[3-(3-pyridyl)propoxy]phenyl]-1-(4-ethylpiperazin-1-yl)isoquinoline hydrochloride

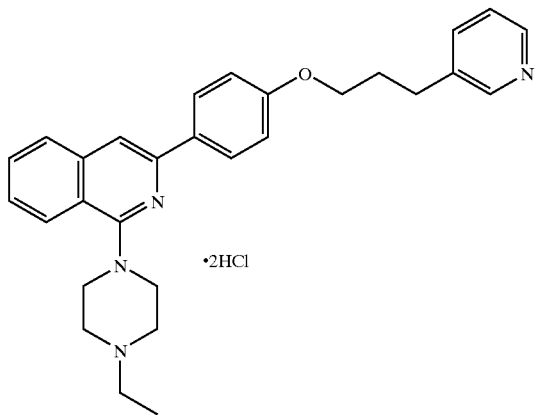

·2HCl

In the same manner as in Examples 51, the free compound of the title compound was obtained (62 mg, yield; 23%) from 3-(4-hydroxyphenyl)-1-(4-ethylpiperazin-1-yl) isoquinoline (201 mg) and 3-(3-methanesulfonate propyl) pyridine (194 mg). The resulting free compound was converted into a hydrochloride in a conventional manner, to give the hydrochloride of the title compound as yellow crystals.
Free compound:
$^1$H-NMR (400 MHz, CDCl$_3$); δ (ppm) 1.19 (t, J=7.2 Hz, 3H), 2.10–2.18 (m, 2H), 2.57 (q, J=7.2 Hz, 2H), 2.78 (br, 4H), 2.85 (t, J=7.6 Hz, 2H), 3.60 (br, 4H), 4.04 (t, J=6.0 Hz, 2H), 6.98 (d, J=8.8 Hz, 2H), 7.22 (dd, J=7.6, 4.4 Hz, 1H), 7.43 (dt, J=8.0, 1.2 Hz, 1H), 7.53–7.56 (m, 1H), 7.56 (dt, J=8.0, 1.2 Hz, 1H), 7.62 (s, 1H), 7.76 (d, J=8.0 Hz, 1H), 8.05 (d, J=8.0 Hz, 1H), 8.11 (d, J=8.8 Hz, 2H), 8.46 (dd, J=4.4, 1.6 Hz, 1H), 8.51 (d, J=2.0 Hz, 1H).
MS(FAB) m/z 453 (M+H)$^+$.

Example 158

Synthesis of 1-(1-ethylpiperazin-4-yl)-3-(1-phenylpiperazin-4-yl)isoquinoline

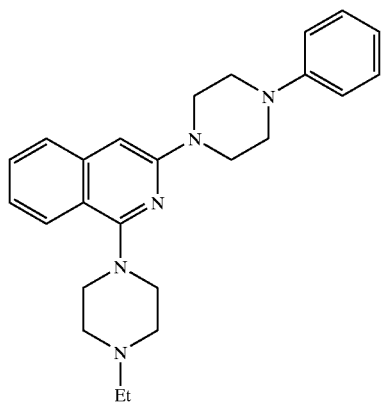

1-(1-Ethylpiperazin-4-yl)-3-bromoisoquinoline (631 mg) was dissolved in dioxane (15 ml), followed by the addition of 1-phenylpiperazine (331 mg), tris(dibenzylideneacetone) (chloroform)dipalladium (0) (10 mg), tri-o-tolylphosphine (12 mg) and t-butoxysodium (231 mg), and the resulting mixture was stirred in nitrogen atmosphere at 100° C. overnight. The reaction mixture was partitioned between ethyl acetate and water. The resulting organic layer was washed with water, dried (over MgSO$_4$), evaporated, and then purified by (NH) silica gel column chromatography (ethyl acetate/hexane system). The resulting product was converted into an oxalate in a conventional manner, to give the oxalate of the title compound as a gray amorphous (196 mg, yield; 20%).

Oxalate:
$^1$H-NMR (400 MHz, DMSO-d$_6$); δ (ppm) 1.22 (3H, t, J=7.2 Hz), 3.08 (2H, q, J=7.2 Hz), 3.24–3.32 (8H, m), 3.46–3.62 (4H, m), 3.63 (4H, t, J=4.4 Hz), 6.67 (1H, s), 6.80 (2H, d, J=8.8 Hz), 7.21 (1H, ddd, J=8 Hz, 7 Hz, 1.2 Hz), 7.23 (1H, dd, J=8.8 Hz, 7.2 Hz), 7.49 (1H, ddd, J=8 Hz, 7 Hz, 1.2 Hz), 7.63 (1H, d, J=8 Hz), 7.87 (1H, d, J=8 Hz).

ESI-Mass; 402 (MH$^+$).

Example 159

Synthesis of 1-(1-ethylpiperazin-4-yl)-3-[1-(2-pyridyl)piperazin-4-yl]isoquinoline

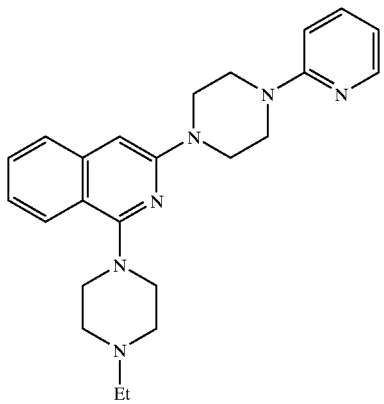

In the same manner as in Example 158, the oxalate of the title compound was obtained as a pale amorphous (533 mg, yield; 42%) from 1-(1-ethylpiperazin-4-yl)-3-bromoisoquinoline (760 mg) and 1-(2-pyridyl)piperazine (1.162 mg).

Oxalate:
$^1$H-NMR (400 MHz, DMSO-d$_6$); δ (ppm) 1.23 (3H, t, J=7.2 Hz), 3.10 (2H, q, J=7.2 Hz), 3.26–3.36 (4H, m), 3.46–3.64 (4H, m), 3.57–3.66 (8H, m), 6.65 (1H, ddd, J=7 Hz, 5 Hz, 0.8 Hz), 6.66 (1H, s), 6.89 (1H, d, J=8.8 Hz), 7.21 (1H, ddd, J=8 Hz, 7 Hz, 1.2 Hz), 7.48 (1H, ddd, J=8 Hz, 7 Hz, 1.2 Hz), 7.55 (1H, ddd, J=8.8 Hz, 7 Hz, 2 Hz), 7.61 (1H, d, J=8 Hz), 7.87 (1H, d, J=8 Hz), 8.13 (1H, ddd, J=5 Hz, 2 Hz, 0.8 Hz).

ESI-Mass; 403 (MH$^+$).

Example 160

Synthesis of 3-[4-(4-morpholinyl)phenyl]-1-(4-ethylpiperazin-1-yl)isoquinoline dihydrochloride

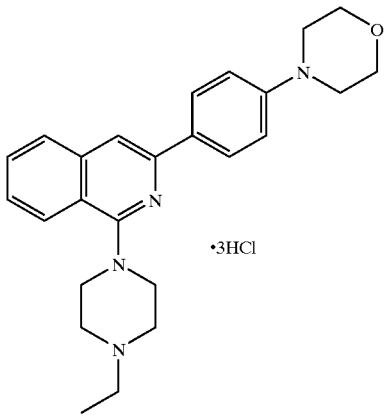

4-(4-Morpholinyl)benzonitrile obtained by reacting 4-fluorobenzonitrile (10.89 g) and morpholine (7.84 g) in the presence of potassium carbonate (12.42 g) in dimethyl sulfoxide (45 ml) was reacted with N-methyl-o-toluamide (8.019 g) according to Example 10-1, to give 6.840 g of 3-[4-(4-morpholinyl)phenyl]isoquinolin-1-one.

The resulting 3-[4-(4-morpholinyl)phenyl]isoquinolin-1-one (1.523 g) was reacted in the same manner as in Example 66, and then purified by silica gel column chromatography (chloroform/methanol system), to give 1.623 g of the free compound of the title compound as a pale yellow oil.

Free compound:

$^1$H-NMR (400 MHz, CDCl$_3$); δ (ppm) 1.17 (t, J=7.2 Hz, 3H), 2.55 (q, J=7.2 Hz, 2H), 2.75 (br-t, 4H), 3.23 (t, J=4.8 Hz, 4H), 3.58 (br-t, 4H), 3.88 (t, J=4.8 Hz, 4H), 6.99 (d, J=9.0 Hz, 2H), 7.41 (br-t, 1H), 7.55 (br-t, 1H), 7.60 (s, 1H), 7.75 (d, J=8.0 Hz, 1H), 8.05 (d, J=8.4 Hz, 1H), 8.11 (d, J=9.0 Hz, 2H).

The resulting free compound was converted into a hydrochloride in a conventional manner, and recrystallized from ethanol/ether, to give the hydrochloride of the title compound as a yellow powder.

Hydrochloride:

m.p.; 242–245° C. (decomp.)

$^1$H-NMR (400 MHz, DMSO-d$_6$); δ (ppm) 1.33 (t, J=7.2 Hz, 3H), 3.19–3.28 (m, 6H), 3.30–3.38 (m, 2H), 3.45 (br-t, 2H), 3.62 (br-d, 2H), 3.82 (br-t, 4H), 3.98 (br-d, 2H), 7.19 (d, J=8.6 Hz, 2H), 7.56 (br-t, 1H), 7.71 (br-t, 1H), 7.95 (d, J=7.6 Hz, 1H), 7.98 (s, 1H), 8.09 (d, J=8.4 Hz, 1H), 8.12 (d, J=8.6 Hz, 2H), 11.13 (br-s, 1H).

MS(FAB) m/z 403 (M+H)$^+$.

Example 161

Synthesis of 1-(1-ethylpiperazin-4-yl)-3-(2-hydroxymethylthiophen-4-yl)isoquinoline dihydrochloride (161-1) 2-(4-Bromothiophen-2-yl)-1,3-dioxolane

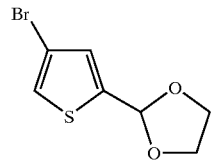

4-Bromo-2-thiophenecarboxyaldehyde (50 g) was dissolved in toluene (500 ml), followed by the addition of ethylene glycol (81 g) and p-toluenesulfonic acid (572 mg). The resulting mixture was heated under reflux overnight with a Dean-Stark apparatus. After cooling as it was, the reaction mixture was washed sequentially with an aqueous solution of saturated sodium bicarbonate and brine, dried (over MgSO$_4$) and evaporated. The resulting residue was purified by silica gel column chromatography (ethyl acetate/hexane system), to give the title compound as a yellow oil (55 g, yield; 89%).

$^1$H-NMR (400 MHz, CDCl$_3$); δ (ppm) 4.00–4.13 (4H, m), 6.06 (1H, s), 7.08 (1H, d, J=1.2 Hz), 7.21 (1H, d, J=1.2 Hz).

(161-2) 4-Tributylstannyl-2-thiophenecarboxyaldehyde

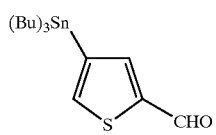

2-(4-Bromothiophen-2-yl)-1,3-dioxolane (2.351 g) was dissolved in xylene (30 ml), followed by the addition of bis(tributyltin) (5.1 ml) and tetrakis(triphenylphosphine) palladium (116 mg). The resulting mixture was heated under stirring in nitrogen atmosphere at 120° C. for 1 hr. After the resulting insoluble matters were filtered off, the resulting solution was evaporated, and then purified by silica gel column chromatography (ethyl acetate/hexane system), to give the title compound as a pale yellow oil (1.165 g, yield; 29%).

$^1$H-NMR (400 MHz, CDCl$_3$); δ (ppm) 0.90 (9H, t, J=7.2 Hz), 1.07–1.12 (6H, m), 1.28–1.38 (6H, m), 1.50–1.58 (6H, m), 7.72 (1H, d, J=1.2 Hz), 7.79 (1H, d, J=1.2 Hz), 7.79 (1H, d, J=1.2 Hz), 9.99 (1H, d, J=1.2 Hz).

(161-3) 1-(1-Ethylpiperazin-4-yl)-3-(2-formylthiophen-4-yl)isoquinoline

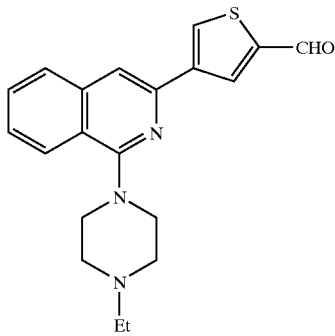

1-(1-Ethylpiperazin-4-yl)-3-bromoisoquinoline (356 mg) was dissolved in xylene (30 ml), followed by the addition of 4-tributylstannyl-2-thiophenecarboxyaldehyde (1.165 g) and tetrakis(triphenylphosphine)palladium (35 mg). The resulting mixture was heated under stirring in nitrogen atmosphere at 120° C. overnight. Then, it was diluted with ethyl acetate and extracted with 2N hydrochloric acid. The resulting aqueous layer was washed with ethyl acetate, basified with 8N sodium hydroxide, and then extracted with ethyl acetate. The resulting organic layer was washed with water, dried (over MgSO$_4$) and evaporated. The resulting product was purified by silica gel column chromatography (ethyl acetate/hexane system), to give the title compound as a yellow oil (265 mg, yield; 73%).

$^1$H-NMR (400 MHz, CDCl$_3$); δ (ppm) 1.18 (3H, t, J=7.2 Hz), 2.56 (2H, q, J=7.2 Hz), 2.76 (4H, t, J=4.4 Hz), 3.57 (4H, t, J=4.4 Hz), 7.48 (1H, ddd, J=8 Hz, 7 Hz, 1.2 Hz), 7.55 ((H, ddd, J=8 Hz, 7 Hz, 1.2 Hz), 7.77 (1H, d, J=8 Hz), 8.07 (1H, d, J=8 Hz), 8.37 (2H, s), 10.00 (1H, s).

(161-4) 1-(1-Ethylpiperazin-4-yl)-3-(2-hydroxymethylthiophen-4-yl)isoquinoline dihydrochloride

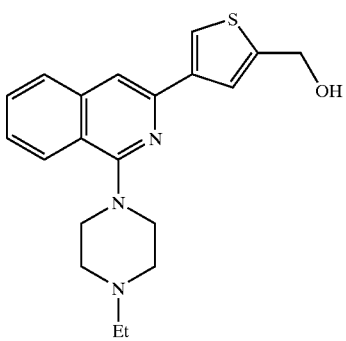

1-(1-Ethylpiperazin-4-yl)-3-(2-formylthiophen-4-yl) isoquinoline (141 mg) was dissolved in ethanol (10 ml), followed by the addition of sodium borohydride (8 mg) under ice-cooling, and the resulting mixture was stirred at room temperature for 30 min. The reaction mixture was partitioned between ethyl acetate and water. The resulting organic layer was washed with water, dried (over MgSO$_4$) and evaporated. The resulting residue was converted into a hydrochloride in a conventional manner, and then recrystallized from ethanol/isopropyl ether, to give the hydrochloride of the title compound as yellow crystals (130 mg, yield; 75%).

Hydrochloride:
m.p.; 170° c. (decomp.)
$^1$H-NMR (400 MHz, DMSO-d$_6$); δ (ppm) 1.30 (3H, t, J=7.2 Hz), 3.15–3.22 (2H, m), 3.29 (1H, t, J=11 Hz), 3.32 (1H, t, J=11 Hz), 3.49 (2H, t, J=13.4 Hz), 3.57 (2H, d, J=11 Hz), 3.94 (2H, d, J=13.4 Hz), 4.66 (2H, s), 7.55 (1H, ddd, J=8 Hz, 7 Hz, 1.2 Hz), 7.62 (1H, d, J=1.6 Hz), 7.69 (1H, ddd, J=8 Hz, 7 Hz, 1.2 Hz), 7.86 (1H, s), 7.89 (1H, d, J=8 Hz), 8.02 (1H, d, J=1.6 Hz), 8.05 (1H, d, J=8 Hz).
ESI-Mass; 354 (MH$^+$).

Example 162

Synthesis of 1-(1-ethylpiperazin-4-yl)-3-(2-hydroxymethylthiophen-5-yl)isoquinoline dihydrochloride (162-1) 2-(5-Bromothiophen-2-yl)-1,3-dioxolane

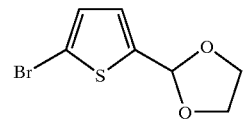

In the same manner as in Example 161-1, the title compound was obtained as a brown oil (57.2 g, yield; 93%) from 5-bromo-2-thiophenecarboxaldehyde (50 g).
$^1$H-NMR (400 MHz, CDCl$_3$); δ (ppm) 3.96–4.13 (4H, m), 6.01 (1H, s), 6.90 (1H, d, J=3.6 Hz), 6.93 (1H, d, J=3.6 Hz).

(162-2) [5-(1,3-Dioxan-2-yl)thiophen-2-yl]-1,3,2-dioxaborylate

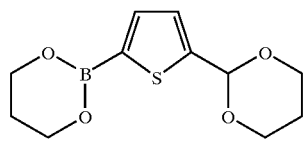

2-(5-Bromothiophen-2-yl)-1,3-dioxolane (2.351 g) was dissolved in tetrahydrofuran (10 ml), to which was then added 2.5 M n-butyl lithium/hexane solution (4 ml) in nitrogen atmosphere at −78° C., and the mixture was stirred for 30 min. Then, trimethoxyborane (1.3 ml) was added thereto, and the mixture was stirred for 30 min, and then it was stirred at room temperature for 30 min. 2N Hydrochloric acid (10 ml) was added to the reaction mixture, and then the mixture was stirred for 30 min. Thereafter, the resulting mixture was extracted with ether. The resulting organic layer was evaporated. The resulting residue was dissolved in ether, followed by the addition of trimethylene glycol (529 mg). The resulting mixture was stirred at room temperature for 90 min, and then evaporated. The resulting residue was dissolved in toluene, followed by the addition of trimethylene glycol (3.517 g) and p-toluenesulfonic acid (9 mg), and the resulting mixture was heated under reflux with a Dean-Stark apparatus for 3 hr. After cooling as it was, the reaction mixture was washed with water, dried (over MgSO$_4$) and evaporated, to give the title compound as a pale yellow oil (1.516 g, yield; 60%).

$^1$H-NMR (400 MHz, CDCl$_3$); δ (ppm) 1.40–1.46 (1H, m), 2.00–2.08 (2H, m), 2.15–2.28 (1H, m), 3.93–4.00 (2H, m), 4.13 (4H, t, J=5 Hz), 4.20–4.28 (2H, m), 5.74 (1H, s), 7.15 (1H, d, J=3.6 Hz), 7.40 (1H, d, J=3.6 Hz).

(162-3) 1-(1-Ethylpiperazin-4-yl)-3-(2-formylthiophen-4-yl)isoquinoline

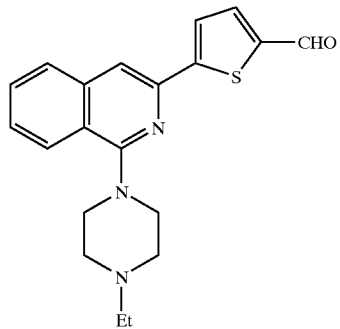

1-(1-Ethylpiperazin-4-yl)-3-bromoisoquinoline (480 mg) was dissolved in N,N-dimethylformamide (12 ml), followed by the addition of [5-(1,3-dioxan-2-yl)thiophen-2-yl]-1,3,2-dioxaborate (643 mg), tetrakis(triphenylphosphine) palladium (23 mg) and cesium carbonate (977 mg), and the resulting mixture was heated under stirring in nitrogen atmosphere at 100° C. overnight. The reaction mixture was partitioned between ethyl acetate and water. The resulting organic layer was washed with water, dried (over MgSO$_4$) and evaporated. The resulting product was purified by silica gel column chromatography (toluene/acetone system), and then dissolved in tetrahydrofuran (10 ml). 1N Hydrochloric acid (10 ml) was added thereto, and the mixture was stirred for 1 hr. The reaction solution was basified by adding 5N sodium hydroxide thereto, followed by the extraction with ethyl acetate. The resulting organic layer was washed with water, dried (over MgSO$_4$) and evaporated, to give the title compound as a brown solid (494 mg, yield; 93%).

$^1$H-NMR (400 MHz, CDCl$_3$); δ (ppm) 1.17 (3H, t, J=7.2 Hz), 2.54 (2H, q, J=7.2 Hz), 2.73 (4H, t, J=4.8 Hz), 3.62 (4H, t, J=4.8 Hz), 7.50 (1H, ddd, J=8 Hz, 7 Hz, 1.2 Hz), 7.62 (1H, ddd, J=8 Hz, 7 Hz, 1.2 Hz), 7.66 (1H, s), 7.70 (1H, d, J=4 Hz), 7.77 (1H, d, J=4 Hz), 7.79 (1H, d, J=8 Hz), 8.06 (1H, d, J=8 Hz), 9.92 (1H, s).

(162-4) 1-(1-Ethylpiperazin-4-yl)-3-(2-hydroxymethylthiophen-5-yl)isoquinoline dihydrochloride

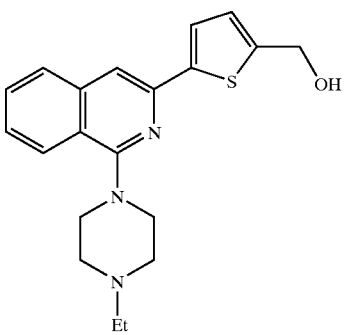

In the same manner as in Example 161-4, the hydrochloride of the title compound was obtained as a yellow crystals (130 mg, yield; 75%) from 1-(1-ethylpiperazin-4-yl)-3-[2-(2-hydroxyethyl)thiophen-5-yl]isoquinoline dihydrochloride (163-1) 2-[2-(t-Butyldimethylsilyloxy)ethyl]thiophene

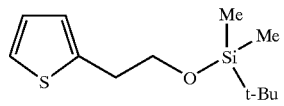

2-(2-Thienyl)ethanol (2.6 g) was dissolved in N,N-dimethylformamide (20 ml), followed by the addition of t-butyldimethylsilyl chloride (3.667 g) and imidazole (1.634 g), and the mixture was stirred at room temperature overnight. The reaction mixture was partitioned between ethyl acetate and water. The resulting organic layer was washed with water, dried (over MgSO$_4$) and evaporated. The resulting residue was purified by silica gel column chromatography (ethyl acetate/hexane system), to give the title compound as a colorless oil (4.87 g, yield; 100%).

$^1$H-NMR (400 MHz, CDCl$_3$); δ (ppm) 0.03 (6H, s), 0.89 (9H, s), 3.04 (2H, t, J=6.8 Hz), 3.82 (2H, t, J=6.8 Hz). 6.83 (1H, dd, J=3.6 Hz, 1 Hz), 6.93 (1H, dd, J=5 Hz, 3.6 Hz), 7.13 (1H, dd, J=5 Hz, 1 Hz).

(163-2) 1-(1-Ethylpiperazin-4-yl)-3-[2-(2-hydroxyethyl)thiophen-5-yl]isoquinoline dihydrochloride

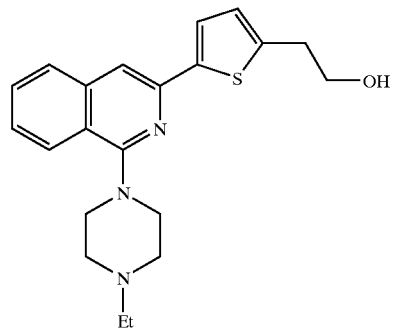

In the same manner as in Example 167-2, the hydrochloride of the title compound was obtained as yellow brown crystals (722 mg, yield; 64%) from 2-[2-(t-butyldimetylsilyloxy)ethyl]thiophene (2.435 g) and 1-(1-ethylpiperazin-4-yl)-3-bromoisoquinoline (809 mg).

Hydrochloride:

m.p.; 129–134° C.

$^1$H-NMR (400 MHz, DMSO-d$_6$); δ (ppm) 1.30 (3H, t, J=7.2 Hz), 2.93 (2H, t, J=6.4 Hz), 3.15–3.24 (2H, m), 3.28 (1H, t, J=11.6 Hz), 3.31 (1H, t, J=11.6 Hz), 3.45 (2H, t, J=13.2 Hz), 3.59 (2H, d, J=11.6 Hz), 3.63 (2H, t, J=6.4 Hz), 3.91 (2H, d, J=13.2 Hz), 6.90 (1H, d, J=3.6 Hz), 7.52 (1H, ddd, J=8 Hz, 7 Hz, 1.2 Hz), 7.58 (1H, d, J=3.6 Hz), 7.68 (1H, ddd, J=8 Hz, 7 Hz, 1.2 Hz), 7.85 (1H, s), 7.88 (1H, d, J=8 Hz), 8.04 (1H, d, J=8 Hz), 10.75 (1H, br-s).

ESI-Mass; 368 (MH$^+$).

Example 164

Synthesis of 1-(1-ethylpiperazin-4-yl)-3-[2-(1-hydroxypropyl)thiophen-4-yl]isoquinoline hydrochloride

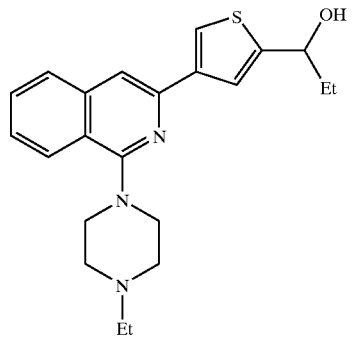

In the same manner as in Example 160, the hydrochloride of the title compound was obtained as a brown amorphous (226 mg, yield; 73%) from 1-(1-ethylpiperazin-4-yl)-3-(2-formylthiophen-4-yl)isoquinoline (233 mg) and 3M ethylmagnesium bromide (0.7 ml).

Hydrochloride:

$^1$H-NMR (400 MHz, DMSO-d$_6$); δ (ppm) 0.89 (3H, t, J=7.4 Hz), 1.22 (3H, t, J=7.2 Hz), 1.70–1.78 (2H, m), 2.97–3.07 (2H, br-s), 3.18–3.32 (4H, br-s), 3.47–3.72 (4H, br-s), 4.72 (1H, t, J=6.4 Hz), 7.54 (1H, dd, J=8 Hz, 7 Hz), 7.58 (1H, s), 7.69 (1H, dd, J=8 Hz, 7 Hz), 7.84 (1H, s), 7.88 (1H, d, J=8 Hz), 7.98 (1H, s), 8.05 (1H, d, J=8 Hz).

ESI-Mass; 382 (MH$^+$).

Example 165

Synthesis of 1-(1-Ethylpiperazin-4-yl)-3-[2-(1-hydroxypropyl)thiophen-5-yl]isoquinoline hydrochloride

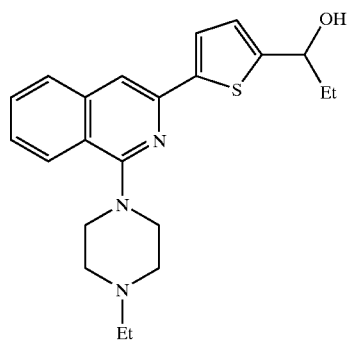

In the same manner as in Example 260, the hydrochloride of the title compound was obtained as a brown amorphous (197 mg, yield; 79%) from 1-(1-ethylpiperazin-4-yl)-3-(2-fomylthiophen-5-yl)isoquinoline (181 mg) and 3M ethylmagnesium bromide (0.7 ml).

Hydrochloride:

$^1$H-NMR (400 MHz, DMSO-d$_6$); δ (ppm) 0.88 (3H, t, J=7.4 Hz), 1.19 (3H, t, J=7.2 Hz), 1.68–1.74 (2H, m), 2.90–3.02 (2H, br-s), 3.10–3.27 (4H, br-s), 3.45–3.62 (4H, br-s), 4.68 (1H, t, J=6.4 Hz), 6.94 (1H, d, J=3.6 Hz), 7.52 (1H, ddd, J=8 Hz, 7 Hz, 1.2 Hz), 7.59 (1H, d, J=3.6 Hz), 7.68 (1H, ddd, J=8 Hz, 7 Hz, 1.2 Hz), 7.84 (1H, s), 7.87 (1H, d, J=8 Hz), 8.03 (1H, d, J=8 Hz).

ESI-Mass; 382 (MH$^+$).

Example 166

Synthesis of 3-[2-(tetrahydropyran-4-yl]thiophen-5-yl]-1-(4-ethylpiperazin-1-yl)isoquinoline hydrochloride

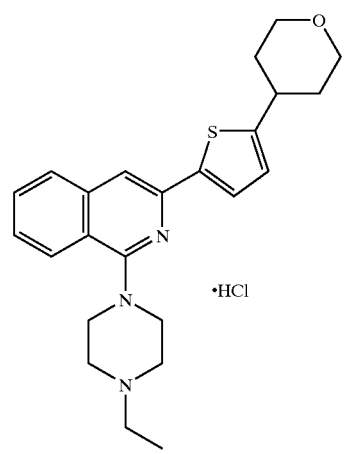

In the same manners sequentially as in Examples 161-2 and 20, a yellow compound was obtained (330 mg, yield; 86%) from 4-bromo-2-(tetrahydropyran-4-yl)thiophene (700 mg) and 3-bromo-1-(4-ethylpiperazin-1-yl) isoquinoline (300 mg). The resulting compound was converted into a hydrochloride in a conventional manner, to give the hydrochloride of the title compound as yellow crystals.

Hydrochloride:

m.p.; 251–253° C.

$^1$H-NMR (400 MHz, DMSO-d$_6$); δ (ppm) 1.33 (t, J=7.2 Hz, 3H), 1.62–1.74 (m, 2H), 1.94 (br, 1H), 3.06–3.16 (m, 2H), 3.18–3.26 (m, 2H), 3.30–3.38 (m, 2H), 3.42–3.52 (m, 4H), 3.61 (d, J=11.6 Hz, 2H), 3.94 (d, J=14.0 Hz, 4H), 6.96 (d, J=4.0 Hz, 1H), 7.56 (t, J=8.0 Hz, 1H), 7.64 (t, J=4.0 Hz, 1H), 7.72 (d, J=8.0 Hz, 1H), 7.89 (s, 1H), 7.91 (d, J=8.0 Hz, 1H), 8.07 (d, J=8.0 Hz, 1H).

MS(FAB) m/z 408(M+H)$^+$.

Free compound:

$^1$H-NMR (400 MHz, CDCl$_3$); δ (ppm) 1.17 (t, J=7.2 Hz, 3H), 1.83–2.05 (m, 4H), 2.55 (q, J=7.2 Hz, 2H), 2.74 (t, J=4.4 Hz, 4H), 3.05–3.10 (m, 1H), 3.51–3.58 (m, 6H), 4.06–4.09 (m, 2H), 6.83 (dd, J=3.6, 0.4 Hz, 1H), 7.40 (ddd, J=8.4, 8.0, 1.2 Hz, 1H), 7.48 (d, J=3.6 Hz, 1H), 7.49 (s, 1H), 7.55 (ddd, J=8.4, 8.0, 1.2 Hz, 1H), 7.72 (d, J=8.0 Hz, 1H), 8.02 (d, J=8.0 Hz, 1H).

Example 167

Synthesis of 1-(1-ethylpiperazin-4-yl)-3-[4-methyl-5-(2-hydroxyethyl)thiazol-2-yl]isoquinoline dihydrochloride (167-1) 4-Methyl-5-(2-benzyloxyethyl)thiazole

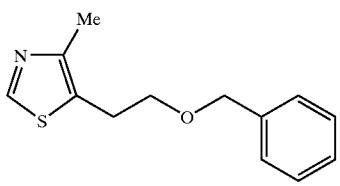

2-(4-Methyl-5-thiazolyl)ethanol (25.71 g) was dissolved in tetrahydrofuran (200 ml), followed by the addition of 60% sodium hydride (7.185 g) under ice-cooling. The resulting mixture was stirred at room temperature for 1 hr. Thereafter, the it was ice-cooled again, followed by the addition of benzyl bromide (21.4 ml) and tetrabutylammonium bromide (665 mg). The resulting mixture was stirred at room temperature overnight. The reaction mixture was partitioned between ethyl acetate and water. The resulting organic layer was washed with water, dried (over $MgSO_4$) and evaporated. The resulting residue was purified by silica gel column chromatography (ethyl acetate/hexane system), to give the title compound as a yellow oil (39.059 g, yield; 93%).

$^1$H-NMR (400 MHz, $CDCl_3$); δ (ppm) 2.40 (3H, s), 3.06 (2H, t, J=6.6 Hz), 3.66 (2H, t, J=6.6 Hz), 4.54 (1H, s), 7.26–7.37 (5H, m), 8.57 (1H, s).

(167-2) 1-(1-Ethylpiperazin-4-yl)-3-[4-methyl-5-(2-benzyloxyethyl)thiazol-2-yl]isoquinoline

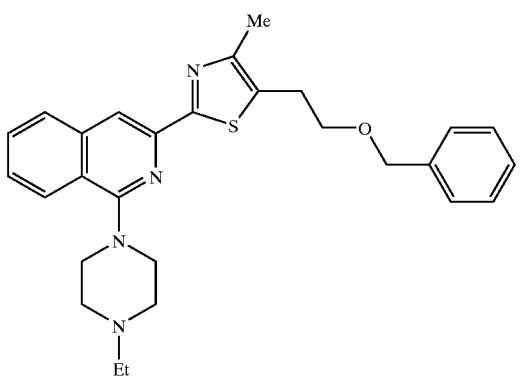

4-Methyl-5-(2-benzyloxyethyl)thiazole (2.333 g) was dissolved in tetrahydrofuran (20 ml), followed by the addition of 2.5 M n-butyl lithium (4 ml) in nitrogen atmosphere at −78° C., and the resulting mixture was stirred for 50 min. Tributyltin chloride (2.8 ml) was added thereto, and the mixture was stirred for 1 hr. Sequentially, it was stirred at room temperature for 30 min. The reaction mixture was partitioned between ethyl acetate and water. The resulting organic layer was washed with water, dried (over $MgSO_4$) and evaporated. The resulting residue was dissolved in xylene (30 ml), followed by the addition of 1-(1-ethylpiperazin-4-yl)-3-bromoisoquinoline (506 mg) and tetrakis(triphenylphosphine)palladium (121 mg), and the resulting mixture was heated under stirring in nitrogen atmosphere at 120° C. overnight. The reaction solution was diluted with ethyl acetate and extracted with 2N hydrochloric acid. The resulting aqueous layer was washed with ethyl acetate, basified with 8N sodium hydroxide, and then extracted with ethyl acetate. The resulting organic layer was washed with water, dried (over $MgSO_4$) and evaporated. The resulting residue was purified by silica gel column chromatography (ethyl acetate/acetone system), to give the title compound as a yellow oil (512 mg, yield; 69%).

$^1$H-NMR (400 MHz, $CDCl_3$); δ (ppm) 1.17 (3H, t, J=7.2 Hz), 2.44 (3H, s), 2.54 (2H, q, J=7.2 Hz), 2.74 (4H, t, J=4.4 Hz), 3.10 (2H, t, J=6.6 Hz), 3.57 (4H, t, J=4.4 Hz), 3.57 (4H, t, J=4.4 Hz), 3.72 (2H, t, J=6.6 Hz), 4.57 (2H, s), 7.26–7.38 (5H, m), 7.47 (1H, ddd, J=8 Hz, 7 Hz, 1.2 Hz), 7.58 (1H, ddd, J=8 Hz, 7 Hz, 1.2 Hz), 7.82 (1H, dd, J=8 Hz, 1.2 Hz), 8.04 (1H, s), 8.05 (1H, dd, J=8 Hz, 1.2 Hz).

(167-3) 1-(1-Ethylpiperazin-4-yl)-3-[4-methyl-5-(2-hydroxyethyl)thiazol-2-yl]isoquinoline dihydrochloride

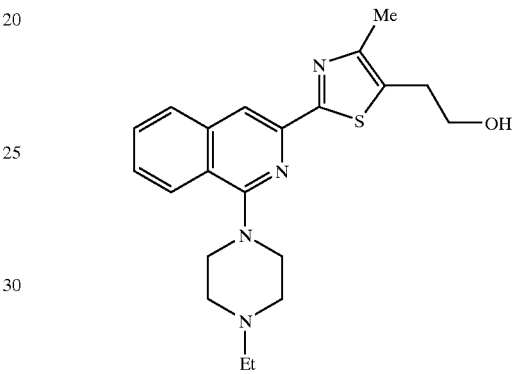

1-(1-Ethylpiperazin-4-yl)-3-[4-methyl-5-(2-benzyloxyethyl)thiazol-2-yl]isoquinoline (512 mg) was converted into a hydrochloride, which was then dissolved in ethanol (7 ml), followed by the addition of palladium hydroxide (222 mg), and the mixture was stirred in hydrogen atmosphere at room temperature for 3 days. After palladium hydroxide was filtered off, the resulting residue was purified by silica gel column chromatography (methylene chloride/methanol system). The resulting product was converted into a hydrochloride in a conventional manner, and then recrystallized from ethanol/isopropyl ether, to give the hydrochloride of the title compound as pale yellow crystals (129 mg, yield; 27%).

Hydrochloride:

m.p.; 149–154° C.

$^1$H-NMR (400 MHz, DMSO-$d_6$); δ (ppm) 1.30 (3H, t, J=7.2 Hz), 2.35 (3H, s), 2.91 (2H, t, J=6.4 Hz), 3.15–3.24 (2H, m), 3.30 (1H, t, J=11.6 Hz), 3.33 (1H, t, J=11.6 Hz), 3.47 (2H, t, J=13.2 Hz), 3.60 (2H, d, J=11.6 Hz), 3.60 (2H, t, J=6.4 Hz), 3.93 (2H, d, J=13.2 Hz), 7.62 (1H, ddd, J=8 Hz, 7 Hz, 1.2 Hz), 7.74 (1H, ddd, J=8 Hz, 7 Hz, 1.2 Hz), 8.06 (1H, d, J=8 Hz), 8.10 (1H, d, J=8 Hz), 8.14 (1H, s), 10.92 (1H, br-s).

ESI-Mass; 383 ($MH^+$).

Example 168

Synthesis of 1-(1-ethylpiperazin-4-yl)-3-(2-hydroxymethylthiazol-5-yl)isoquinoline dihydrochloride (168-1) 2-(1,3-Dioxan-2-yl)thiazole

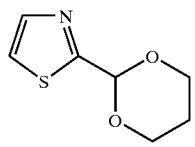

2-Thiazolecarboxaldehyde (1 g) was dissolved in toluene (50 ml), followed by the addition of trimethylene glycol (3.36 g) and p-toluenesulfonic acid (17 mg). The resulting mixture was heated under reflux with a Dean-Stark apparatus for 4 hr. After cooling as it was, the reaction mixture was washed sequentially with an aqueous solution of saturated sodium bicarbonate and brine, dried (over MgSO$_4$) and evaporated. The resulting residue was purified by silica gel column chromatography (ethyl acetate/hexane system), to give the title compound as a brown solid (1.104 g, yield; 73%).

$^1$H-NMR (400 MHz, CDCl$_3$); δ (ppm) 1.45–1.53 (1H, m), 2.20–2.34 (1H, m), 4.00–4.08 (2H, m), 4.26–4.34 (2H, m), 5.91 (1H, s), 7.38 (1H, d, J=3.2 Hz), 8.01 (1H, d, J=3.2 Hz).

(168-2) 1-(1-Ethylpiperazin-4-yl)-3-[2-(1,3-dioxan-2-yl)thiazol-5-yl]isoquinoline

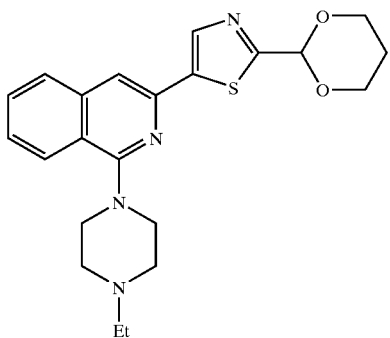

In the same manner as in Example 167-2, the title compound was obtained as a yellow oil (231 mg, yield; 35%) from 2-(1,3-dioxan-2-yl)thiazole (1.104 g) and 1-(1-ethylpiperazin-4-yl)-3-bromoisoquinoline (538 mg).

$^1$H-NMR (400 MHz, CDCl$_3$); δ (ppm) 1.17 (3H, t, J=7.2 Hz), 1.47–1.53 (1H, m), 2.50–2.56 (1H, m), 2.54 (2H, q, J=7.2 Hz), 2.72 (4H, t, J=4.8 Hz), 3.57 (4H, t, J=4.8 Hz), 4.02–4.10 (2H, m), 4.30–4.36 (2H, m), 5.80 (2H, s), 7.46 (1H, ddd, J=8 Hz, 7 Hz, 1.2 Hz), 7.57 (1H, s), 7.59 (1H, ddd, J=8 Hz, 7 Hz, 1.2 Hz), 7.74 (1H, d, J=8 Hz), 8.03 (1H, d, J=8 Hz), 8.25 (1H, s).

(168-3) 1-(1-Ethylpiperazin-4-yl)-3-(2-formylthiazol-5-yl)isoquinoline

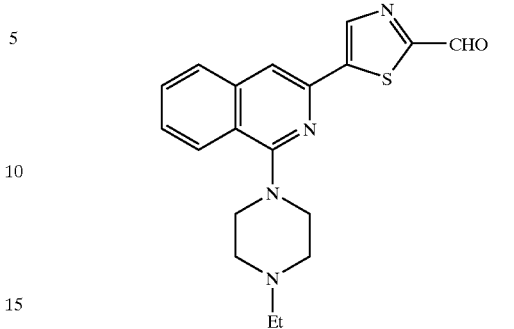

1-(1-Ethylpiperazin-4-yl)-3-[2-(1,3-dioxan-2-yl)thiazol-5-yl]isoquinoline (205 mg) was dissolved in tetrahydrofuran (4 ml), followed by the addition of 1N hydrochloric acid (3 ml), and the resulting mixture was stirred at room temperature for 8 hr. The reaction solution was basified by adding 8N sodium hydroxide thereto, and then extracted with in ethyl acetate. The resulting organic layer was washed with water, dried (over MgSO$_4$) and evaporated, to give the title compound as a colorless oil (155 mg, yield; 80%).

$^1$H-NMR (400 MHz, CDCl$_3$); δ (ppm) 1.18 (3H, t, J=7.2 Hz), 2.55 (2H, q, J=7.2 Hz), 2.74 (4H, t, J=4.8 Hz), 3.60 (4H, t, J=4.8 Hz), 7.53 (1H, ddd, J=8 Hz, 7 Hz, 1.2 Hz), 7.65 (1H, ddd, J=8 Hz, 7 Hz, 1.2 Hz), 7.69 (1H, s), 7.81 (1H, d, J=8 Hz), 8.06 (1H, d, J=8 Hz), 8.56 (1H, s), 9.99 (1H, s).

(168-4) 1-(1-Ethylpiperazin-4-yl)-3-(2-hydroxymethylthiazol-5-yl)isoquinoline dihydrochloride

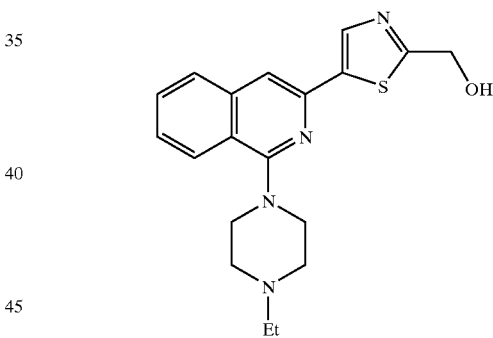

In the same manner as in Example 161, the hydrochloride of the title compound as a yellow amorphous (79 mg, yield; 82%) from 1-(1-ethylpiperazin-4-yl)-3-(2-formylthiazol-5-yl)isoquinoline (205 mg).

Hydrochloride:
$^1$H-NMR (400 MHz, DMSO-d$_6$); δ (ppm) 1.30 (3H, t, J=7.2 Hz), 3.15–3.23 (2H, m), 3.28 (1H, t, J=11.6 Hz), 3.31 (1H, t, J=11.6 Hz), 3.49 (2H, t, J=13.2 Hz), 3.58 (2H, d, J=11.6 Hz), 3.94 (2H, d, J=13.2 Hz), 4.73 (2H, s), 7.58 (1H, ddd, J=8 Hz, 7 Hz, 1.2 Hz), 7.73 (1H, ddd, J=8 Hz, 7 Hz, 1.2 Hz), 7.90 (1H, d, J=8 Hz), 7.98 (1H, s), 8.07 (1H, d, J=8 Hz), 8.35 (1H, d, J=2 Hz), 11.00 (1H, br-s).

ESI-Mass; 355 (MH$^+$).

Example 169

Synthesis of 1-(1-ethylpiperazin-4-yl)-3-[1-(2-hydroxyethyl)pyrazol-3-yl]isoquinoline dihydrochloride (169-1) 1-(1-Ethylpiperazin-4-yl)-3-[1-(2-benzyloxyethyl)pyrazol-3-yl]isoquinoline

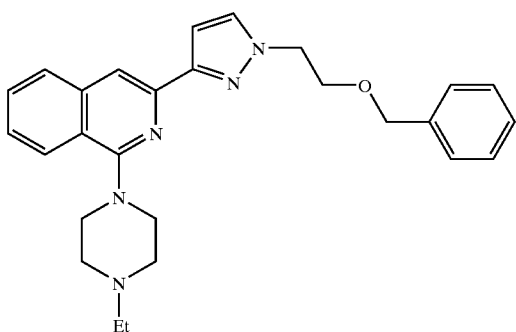

In the same manner as in Example 167-2, the title compound was obtained as a yellow oil (386 mg, yield; 87%) from 1-(2-benzyloxyethyl)-3-bromopyrazole (1.144 g) described in Production Example 42 of JP-A 9-984331 and 1-(1-ethylpiperazin-4-yl)-3-bromoisoquinoline (320 mg).

$^1$H-NMR (400 MHz, CDCl$_3$); δ (ppm) 1.17 (3H, t, J=7.2 Hz), 2.55 (2H, q, J=7.2 Hz), 2.74 (4H, t, J=4.4 Hz), 3.53 (4H, t, J=4.4 Hz), 3.89 (2H, t, J=5.4 Hz), 4.38 (2H, t, J=5.4 Hz), 4.51 (2H, s), 7.24–7.36 (5H, m), 7.38 (1H, s), 7.40 (1H, ddd, J=8 Hz, 7 Hz, 1.2 Hz), 7.55 (1H, ddd, J=8 Hz, 7 Hz, 1.2 Hz), 7.70 (1H, d, J=8 Hz), 8.03 (1H, d, J=8 Hz), 8.04 (1H, s), 8.08 (1H, s).

(169-2) 1-(1-Ethylpiperazin-4-yl)-3-[1-(2-hydroxyethyl)pyrazol-3-yl]isoquinoline dihydrochloride

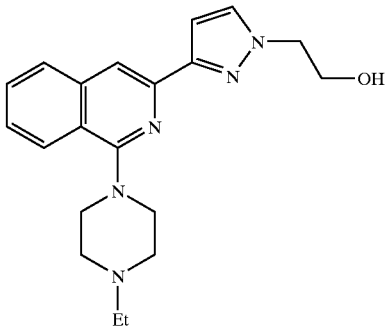

In the same manner as in Example 167, the hydrochloride of the title compound was obtained as pale yellow crystals (340 mg, yield; 92%) from 1-(1-ethylpiperazin-4-yl)-3-[1-(2-benzyloxyethyl)pyrazol-3-yl]isoquinoline (386 mg).

Hydrochloride:

m.p.; 134–140° C.

$^1$H-NMR (400 MHz, DMSO-d$_6$); δ (ppm) 1.31 (3H, t, J=7.2 Hz), 3.14–3.25 (2H, m), 3.29 (1H, t, J=11.2 Hz), 3.32 (1H, t, J=11.2 Hz), 3.49 (2H, t, J=13.2 Hz), 3.57 (2H, d, J=11.2 Hz), 3.76 (2H, t, J=5.6 Hz), 3.91 (2H, d, J=13.2 Hz), 4.19 (2H, t, J=5.6 Hz), 7.50 (1H, dd, J=8 Hz, 7 Hz), 7.67 (1H, dd, J=8 Hz, 7 Hz), 7.70 (1H, s), 7.83 (1H, d, J=8 Hz), 8.03 (1H, d, J=8 Hz), 8.04 (1H, s), 8.26 (1H, s).

ESI-Mass; 352 (MH$^+$).

Example 170

Synthesis of 1-(1-ethylpiperazin-4-yl)-3-[(1-hydroxypropyl)thiazol-5-yl]isoquinoline dihydrochloride

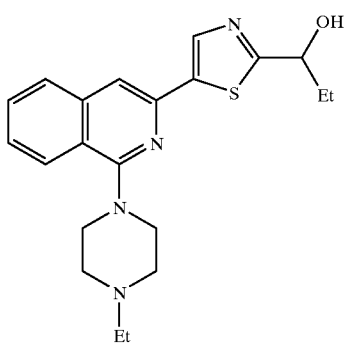

1-(1-Ethylpiperazin-4-yl)-3-(2-formylthiazol-5-yl)isoquinoline (205 mg) was dissolved in tetrahydrofuran (2 ml), 1M ethylmagnesium bromide/tetrahydrofuran solution (0.26 ml) was added thereto under ice-cooling. The resulting mixture was stirred overnight. An aqueous solution of saturated ammonium chloride was added to the reaction solution, which was then extracted with ethyl acetate. The resulting organic layer was washed with water, dried (over MgSO$_4$) and evaporated. The resulting residue was purified by silica gel column chromatography (toluene/acetone system). The resulting product was converted into a hydrochloride in a conventional manner, and then solidified by adding ether thereto, to give the hydrochloride of the title compound as a brown amorphous (20 mg, yield; 23%).

Hydrochloride:

$^1$H-NMR (400 MHz, DMSO-d$_6$); δ (ppm) 0.91 (3H, t, J=7.6 Hz), 1.29 (3H, t, J=7.2 Hz), 1.68–1.92 (2H, m), 3.15–3.23 (2H, m), 3.28 (1H, t, J=11.6 Hz), 3.31 (1H, t, J=11.6 Hz), 3.48 (2H, t, J=13.6 Hz), 3.58 (2H, d, J=11.6 Hz), 3.94 (2H, d, J=13.6 Hz), 4.71–4.75 (1H, m), 7.58 (1H, ddd, J=8 Hz, 7 Hz, 1.2 Hz), 7.73 (1H, ddd, J=8 Hz, 7 Hz, 1.2 Hz), 7.90 (1H, d, J=8 Hz), 7.97 (1H, s), 8.07 (1H, d, J=8 Hz), 8.33 (1H, s), 10.95 (1H, br-s).

ESI-Mass; 383 (MH$^+$).

Example 171

Synthesis of 1-(1-ethylpiperazin-4-yl)-3-[2-(3-hydroxypropyl)thiazol-5-yl]isoquinoline oxalate

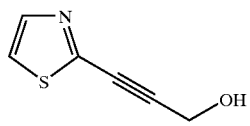

In the same manner as in Example 139-1, the title compound was obtained as a brown oil (8.596 g, yield; 75%) from 2-bromothiazole (13.547 g) and propargyl alcohol (5 ml).

¹H-NMR (400 MHz, CDCl₃); δ (ppm) 4.55 (2H, s), 7.36 (1H, d, J=3.4 Hz), 7.81 (1H, d, J=3.4 Hz).

(171-2) 2-(3-Hydroxypropyl)thiazole

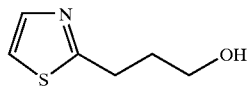

In the same manner as in Example 139-2, the title compound was obtained as a yellow oil (2.173 g, yield; 24%) from 2-(3-hydroxy-1-propynyl)thiazole (8.594 g).

¹H-NMR (400 MHz, CDCl₃); δ (ppm) 2.02–2.09 (2H, m), 3.18 (2H, t, J=7 Hz), 3.44 (1H, br-s), 3.74 (2H, t, J=6 Hz), 7.20 (1H, d, J=3.4 Hz), 7.67 (1H, d, J=3.4 Hz).

(171-3) 2-[3-(t-Butyldimethylsilyloxy)propyl]thiazole

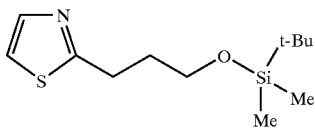

In the same manner as in Example 163-1, the title compound was obtained as a colorless oil (3.792 g, yield; 98%) from 2-(3-hydroxypropyl)thiazole (2.173 g).

¹H-NMR (400 MHz, CDCl₃); δ (ppm) 0.05 (6H, s), 0.90 (9H, s), 1.99–2.06 (2H, m), 3.11 (2H, t, J=7.6 Hz), 3.70 (2H, t, J=6 Hz), 7.19 (1H, d, J=3.6 Hz), 7.67 (1H, d, J=3.6 Hz).

(171-4) 1-(1-Ethylpiperazin-4-yl)-3-[2-(3-hydroxypropyl)thiazol-5-yl]isoquinoline oxalate

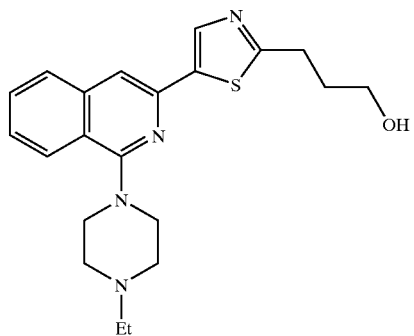

In the same manner as in Example 167-2, the oxalate of the title compound was obtained as a pale yellow amorphous (221 mg, yield; 25%) from 2-[3-(t-butyldimethylsilyloxy)propyl]thiazole (3.792 g) and 1-(1-ethylpiperazin-4-yl)-3-bromoisoquinoline (631 mg).

Oxalate:

¹H-NMR (400 MHz, CDCl₃); δ (ppm) 1.23 (3H, t, J=7.2 Hz), 1.84–1.93 (2H, m), 3.02 (2H, t, J=7.6 Hz), 3.10 (2H, q, J=7.2 Hz), 3.28–3.38 (4H, m), 3.48 (2H, t, J=6.4 Hz), 3.54–3.70 (4H, m), 7.58 (1H, dd, J=8 Hz, 7 Hz), 7.90 (1H, d, J=8 Hz), 7.94 (1H, s), 8.07 (1H, d, 8 Hz), 8.29 (1H, s).

ESI-Mass; 383 (MH⁺).

Example 172

Synthesis of 1-(1-ethylpiperazin-4-yl)-3-[2-(3-methoxypropyl)thiazol-5-yl]isoquinoline oxalate

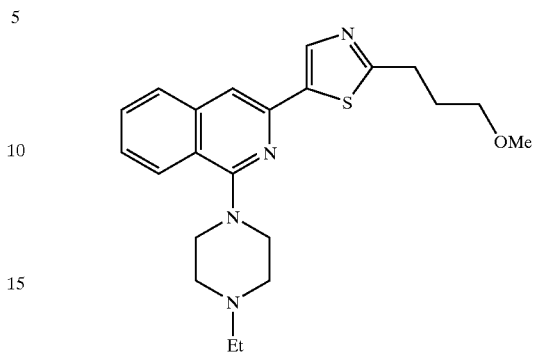

1-(1-Ethylpiperazin-4-yl)-3-[2-(3-hydroxypropyl)thiazol-5-yl]isoquinoline (95 mg) was dissolved in tetrahydrofuran (1 ml), followed by the addition of 60% sodium hydride (10 ml) under ice-cooling. The resulting mixture was stirred at room temperature for 40 min. The reaction solution was ice-cooled again, followed by the addition of methyl iodide (17 ml), and the resulting mixture was stirred at room temperature overnight. The reaction mixture was partitioned between ethyl acetate and water. The resulting organic layer was washed with water, dried (over MgSO₄) and evaporated. The resulting residue was purified by (NH) silica gel column chromatography (ethyl acetate/hexane system). Then, the resulting product was converted into an oxalate in a conventional manner, to give the oxalate of the title compound as a colorless amorphous (12 mg, yield; 10%).

Oxalate:

¹H-NMR (400 MHz, DMSO-d₆); δ (ppm) 1.22 (3H, t, J=7.2 Hz), 1.93–2.00 (2H, m), 3.02 (2H, t, J=7.6 Hz), 3.07 (2H, q, J=7.2 Hz), 3.24 (3H, s), 3.25–3.36 (4H, br-s), 3.39 (2H, t, J=6.4 Hz), 7.58 (1H, ddd, J=8 Hz, 7 Hz, 1.2 Hz), 7.73 (1H, ddd, J=8 Hz, 7 Hz, 1.2 Hz), 7.91 (1H, d, J=8 Hz), 7.94 (1H, s), 8.07 (1H, d, J=8 Hz), 8.30 (1H, s).

ESI-Mass; 397 (MH⁺).

Example 173

Synthesis of 1-(1-ethylpiperazin-4-yl)-3-[2-(4-morpholinyl)-5-thiazolyl]isoquinoline dihydrochloride (173-1) 2-(4-Morpholinyl)thiazole

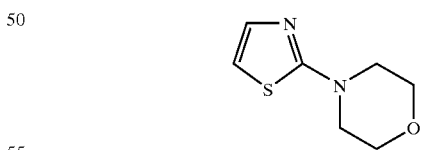

2-Bromothiazole (4.592 g) was added to morpholine (24 ml), and the mixture was stirred at 100° C. for 4 hr. The reaction mixture was partitioned between ethyl acetate and water. The resulting organic layer was washed with water, dried (over MgSO₄) and evaporated. The resulting residue was purified by silica gel column chromatography (ethyl acetate/hexane system), to give the title compound as a pale yellow oil (4.531 g, yield; 95%).

¹H-NMR (400 MHz, CDCl₃); δ (ppm) 3.47 (4H, t, J=4.8 Hz), 3.83 (4H, t, J=4.8 Hz), 3.61 (2H, d, J=3.8 Hz), 7.22 (2H, d, J=3.8 Hz).

(173-2) 1-(1-Ethylpiperazin-4-yl)-3-[2-(4-morpholinyl)-5-thiazolyl]isoquinoline dihydrochloride

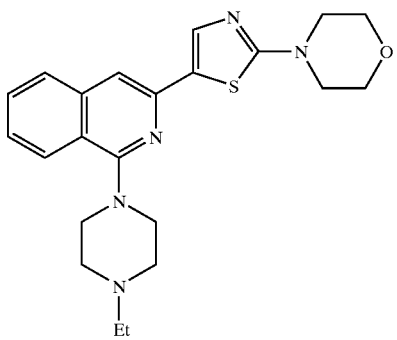

In the same manner as in Example 167-2, the hydrochloride of the title compound was obtained as colorless crystals (recrystallized in ethanol/isopropyl ether) (728 mg, yield; 97%) from 2-(4-morpholinyl)thiazole (1.702 g) and 1-(1-ethylpiperazin-4-yl)-3-bromoisoquinoline (543 mg).

Hydrochloride:

m.p.; 265° (decomp.)

$^1$H-NMR (400 MHz, DMSO-$d_6$); δ (ppm 1.31 (3H, t, J=7.2 Hz), 3.18 (1H, q, J=7.2 Hz), 3.20 (1H, q, J=7.2 Hz), 3.28 (1H, t, J=11.2 Hz), 3.31 (1H, t, J=11.2 Hz), 3.46 (2H, t, J=13.2 Hz), 3.56 (4H, t, J=4.8 Hz), 3.57 (2H, d, J=11.2 Hz), 3.75 (4H, t, J=4.8 Hz), 3.89 (2H, d, J=13.2 Hz), 7.55 (1H, ddd, J=8 Hz, 7 Hz, 1.2 Hz), 7.71 (1H, ddd, J=8 Hz, 7 Hz, 1.2 Hz), 7.84 (1H, dd, J=8 Hz, 1.2 Hz), 7.89 (1H, s), 8.04 (1H, s), 8.05 (1H, dd, J=8 Hz, 1.2 Hz), 11.40 (1H, br-s).

ESI-Mass; (410 (MH$^+$).

Example 174

Synthesis of 3-(2-Propylcarbonylaminopyrimidin-5-Yl)-1-(4-Ethylpiperazin-1-Yl)Isoquinoline Hydrochlroide

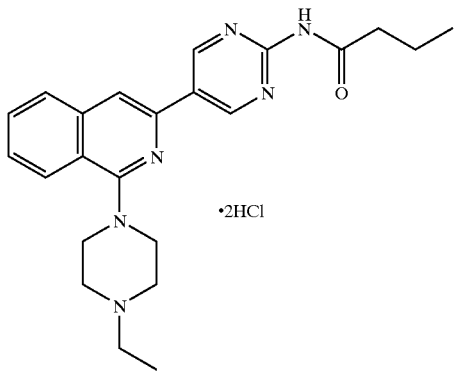

In the same manners sequentially as in Examples 161-2 and 20, the free compound of the title compound was obtained (60 mg, yield; 13%) from 5-bromo-2-propylcarbonylaminopyridine (2.73 g) and 3-bromo-1-(4-ethylpiperazin-1-yl)isoquinoline (363 mg). The resulting free compound was converted into a hydrochloride in a conventional manner, to give the hydrochloride of the title compound as yellow crystals.

Hydrochloride:

m.p.; 216–219° C.

MS(FAB) m/z 405 (M+H)$^+$.

Free compound:

$^1$H-NMR (400 MHz, CDCl$_3$); δ (ppm) 1.06 (t, J=7.2 Hz, 3H), 1.17 (t, J=7.6 Hz, 3H), 1.77–1.86 (m, 2H), 2.55 (q, J=7.2 Hz, 2H), 2.74 (br, 6H), 3.60 (br, 4H), 7.51 (d, J=8.0, 1.2 Hz, 1H), 7.63 (dt, J=8.0, 1.2 Hz, 1H), 7.63 (s, 1H), 7.81 (d, J=8.0 Hz, 1H), 8.08 (d, J=8.0 Hz, 1H), 9.12 (s, 2H).

Example 175

Synthesis of 3-[2-(5,6-Dihydro-2H-Pyran-4-Yl) Thiophen-4-Yl)-1-(4-Ethylpiperazin-1-Yl) Isoquinoline Hydrochloride

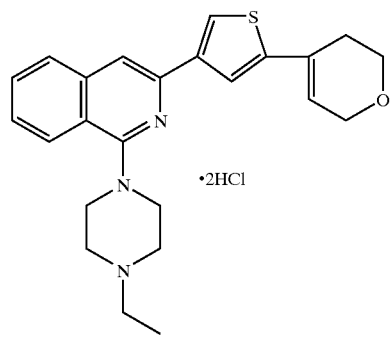

In the same manners sequentially as in Examples 161-2 and 20, a yellow compound was obtained (310 mg, yield; 82%) from 4-bromo-2-(5,6-dihydro-2H-pyran-4-yl) thiophene (650 mg) and 3-bromo-1-(4-ethylpiperazin-1-yl) isoquinoline (300 mg). The resulting compound was converted into a hydrochloride in a conventional manner, to give the hydrochloride of the title compound as yellow crystals.

Hydrochloride:

m.p.; 190–193° C.

$^1$H-NMR (400 MHz, DMSO-$d_6$); δ (ppm) 1.32 (t, J=7.2 Hz, 3H), 3.20–3.28 (m, 2H), 3.30–3.38 (m, 2H), 3.45–3.52 (m, 2H), 3.59–3.63 (m, 2H), 3.83–3.87 (m, 2H), 3.96–4.02 (m, 4H), 4.23 (d, J=2.8 Hz, 2H), 6.23 (s, 1H), 7.59 (t, J=8.0 Hz, 1H), 7.74 (t, J=8.0 Hz, 1H), 7.78 (s, 1H), 7.91 (d, J=8.0 Hz, 1H), 7.95 (s, 1H), 8.05 (s, 1H), 8.09 (d, J=8.0 Hz, 1H).

MS(FAB) m/z 406 (M+H)$^+$.

Free compound:

$^1$H-NMR (400 MHz, CDCl$_3$); δ (ppm) 1.17 (t, J=7.2 Hz, 3H), 2.25 (q, J=7.2 Hz, 2H), 2.62–2.63 (m, 2H), 2.75 (br, 4H), 3.56 (br, 4H), 3.94–3.97 (m, 2H), 4.32–4.34 (m, 2H), 6.17 (br, 1H), 7.44 (t, J=8.4 Hz, 1H), 7.50 (s, 1H), 7.57 (t, J=8.4 Hz, 1H), 7.58 (s, 1H), 7.75 (d, J=8.4 Hz, 1H), 7.84 (s, 1H), 8.05 (d, J=8.4 Hz, 1H).

Example 176

Synthesis of 3-[2-(5,6-Dihydro-2H-Pyran-4-Yl)Thiophen-5-Yl]-1-[4-Ethylpiperazin-1-Yl)Isoquinoline Hydrochloride

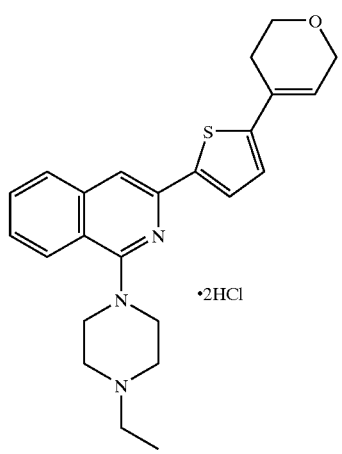

In the same manners sequentially as in Examples 161-2 and 20, a yellow compound was obtained (120 mg, yield; 32%) from 5-bromo-2-(5,6-dihydro-2H-pyran-4-yl)thiophene (632 mg) and 3-bromo-1-(4-ethylpiperazin-1-yl)isoquinoline (300 mg). The resulting compound was converted into a hydrochloride in a conventional manner, to give the hydrochloride of the title compound as yellow crystals.

Hydrochloride:

m.p.; 256–258° C.

$^1$H-NMR (400 MHz, DMSO-d$_6$); δ (ppm) 1.32 (t, J=7.2 Hz, 3H), 3.23 (br, 2H), 3.33 (br, 4H), 3.48 (br, 2H), 3.61 (br, 2H), 3.83 (t, J=6.4 Hz, 2H), 3.96 (d, J=13.2 Hz, 2H), 4.23 (br, 2H), 6.25 (br, 1H), 7.16 (d, J=3.6 Hz, 1H), 7.57 (t, J=8.0 Hz, 1H), 7.71 (d, J=3.6 Hz, 1H), 7.73 (t, J=8.0 Hz, 1H), 7.92 (d, J=8.0 Hz, 1H), 7.92 (d, J=8.0 Hz, 1H), 7.95 (s, 1H), 8.08 (d, J=8.0 Hz, 1H).

MS(FAB) m/z 406 (M+H)$^+$.

Free compound:

$^1$H-NMR (400 MHz, CDCl$_3$); δ (ppm) 1.17 (t, J=7.2 Hz, 3H), 2.52–2.57 (m, 2H), 2.54 (q, J=7.2 Hz, 2H), 2.74 (br, 4H), 3.57 (br, 4H), 3.94 (t, J=5.6 Hz, 2H), 4.40 (q, J=2.8 Hz, 2H), 6.21 (br, 1H), 6.99 (d, J=3.6 Hz, 1H), 7.42 (ddd, J=8.4, 8.0, 1.2 Hz, 1H), 7.52 (s, 1H), 7.53 (d, J=3.6 Hz, 1H), 7.56 (ddd, J=8.4, 8.0, 1.2 Hz, 1H), 7.72 (d, J=8.0 Hz, 1H), 8.03 (d, J=8.4 Hz, 1H).

Example 177

Synthesis of 1-(1-Ethylpiperazin-4-Yl)-3-(Phenylethynyl)Isoquinoline Dihydrochloride

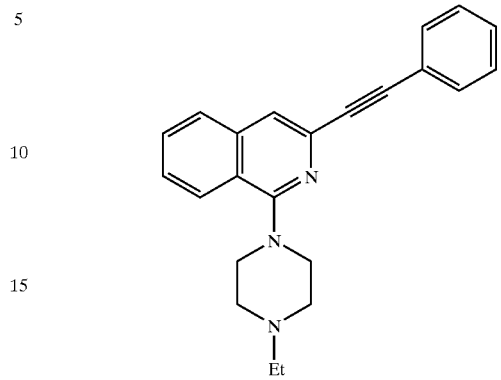

1-(1-Ethylpiperazin-4-yl)-3-bromoisoquinoline (357 mg) was dissolved in triethylamine (6 ml), followed by the addition of phenylacetylene (132 ml), copper iodide (4 mg) and bis(triphenylphosphine)palladium (II) chloride (14 mg), and the resulting mixture was stirred in nitrogen atmosphere at room temperature overnight, and then stirred at 50° C. for 6 hr. The reaction mixture was partitioned between ethyl acetate and water. The resulting organic layer was washed with water, dried (over MgSO$_4$) and evaporated. The resulting residue was purified by (NH) silica gel column chromatography (ethyl acetate/hexane system). The resulting product was converted into a hydrochloride in a conventional manner, and then recrystallized from ethanol/isopropyl ether, to give the hydrochloride of the title compound as yellow crystals (270 mg, yield; 58%).

Hydrochloride:

m.p.; 133–136° C.

$^1$H-NMR (400 MHz, DMSO-d$_6$); δ (ppm) 1.31 (3H, t, J=7.2 Hz), 3.19 (1H, q, J=7.2 Hz), 3.20 (1H, q, J=7.2 Hz), 3.29 (1H, t, J=11.2 Hz), 3.32 (1H, t, J=11.2 Hz), 3.49 (2H, t, J=13.6 Hz), 3.57 (2H, d, J=11.2 Hz), 3.85 (2H, d, J=13.6 Hz), 7.42–7.47 (3H, m), 7.59–7.63 (2H, m), 7.66 (1H, ddd, J=8 Hz, 7 Hz, 1.2 Hz), 7.77 (1H, ddd, J=8 Hz, 7 Hz, 1.2 Hz), 7.83 (1H, s), 7.95 (1H, d, J=8 Hz), 8.12 (1H, d, J=8 Hz), 11.35 (1H, br-s).

ESI-Mass; 342 (MH$^+$.

Example 178

Synthesis of 1-(1-Ethylpiperazin-4-Yl)-3-(4-Methoxyphenyl)Ethynylisoquinoline Dihydrochloride

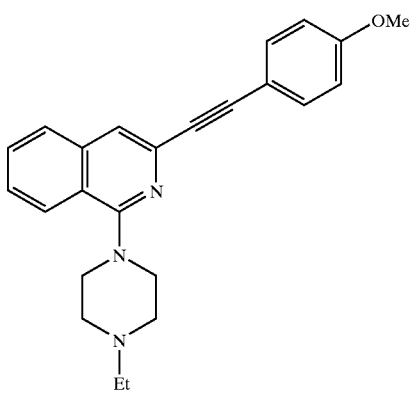

In the same manner as in Example 177, the hydrochloride of the title compound was obtained as yellow crystals (recrystallized from ethanol/isopropyl ether) 437 mg, yield; 77%) from 4-metehoxyphenylacetylene (185 mg) and 1-(1-ethylpiperazin-4-yl)-3-bromoisoquinoline (370 mg).

Hydrochloride:

m.p.; 230° C. (decomp.)

$^1$H-NMR (400 MHz, DMSO-d$_6$); δ (ppm) 1.30 (3H, t, J=7.2 Hz), 3.20 (1H, q, J=7.2 Hz), 3.22 (1H, q, J=7.2 Hz), 3.29 (1H, t, J=11.6 Hz), 3.32 (1H, t, J=11.6 Hz), 3.42 (2H, t, J=12.8 Hz), 3.58 (2H, d, J=11.6 Hz), 3.80 (3H, s), 3.86 (2H, d, J=12.8 Hz), 7.00 (2H, d, J=8.8 Hz), 7.55 (2H, d, J=8.8 Hz), 7.65 (1H, ddd, J=8 Hz, 7 Hz, 1.2 Hz), 7.76 (1H, ddd, J=8 Hz, 7 Hz, 1.2 Hz), 7.78 (1H, s), 7.93 (1H, d, J=8 Hz), 8.11 (1H, d, J=8 Hz).

ESI-Mass; 372 (MH$^+$).

Example 179

Synthesis of 1-(1-Ethylpiperazin-4-Yl)-3-(2-Pyridyl) Ethynylisoquinoline Oxalate

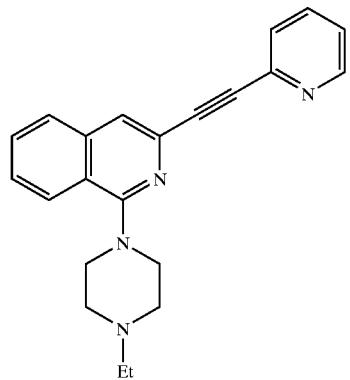

In the same manner as in Example 177, the oxalate of the title compound was obtained as a yellow amorphous (437 mg, yield; 77%) from 2-ethynylpyridine (157 mg) and 1-(1-ethylpiperazin-4-yl)-3-bromoisoquinoline (425 mg).

Hydrochloride:

m.p.; 148–154° C.

$^1$H-NMR 400 MHz, DMSO-d$_6$); δ (ppm) 1.23 (3H, t, J=7.2H), 3.10 (2H, q, J=7.2 Hz), 3.27–3.38 (4H, br-s), 3.50–3.66 (4H, br-s), 7.44 (1H, ddd, J=7.8 Hz, 4.8 Hz, 1.2 Hz), 7.68 (1H, ddd, J=8 Hz, 7 Hz, 1.2 Hz), 7.70 (1H, ddd, J=7.8 Hz, 1.2 Hz, 0.8 Hz), 7.78 (1H, ddd, J=8 Hz, 7 Hz, 1.2 Hz), 7.7 (1H, ddd, J=7.8 Hz, 7.8H, 1.6 Hz), 7.96 (1H , d, J=8 Hz), 8.10 (1H, d, J=8 Hz), 8.63 (1H, ddd, J=4.8 Hz, 1.6 Hz, 0.8 Hz).

ESI-Mass; 343 (MH$^+$).

Example 180

Synthesis of 3-[3-(4-Morpholinyl)-1-Propynyl]-1-(4-Ethylpiperazin-1-Yl)Isoquinoline Oxalate

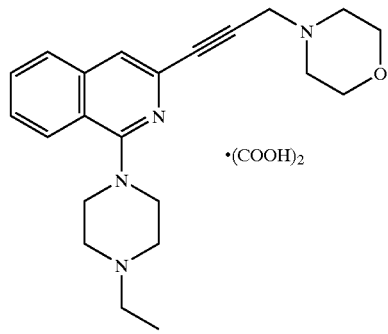

In the same manner as in Example 177, the free compound of the title compound was obtained (485 mg, yield; 77%) from 4-propargyl morpholine (819 mg) and 3-bromo-1-(4-ethylpiperazin-1-yl)isoquinoline (552 mg). The resulting free compound was converted into an oxalate in a conventional manner, to give the oxalate of the title compound as yellow crystals.

Oxalate:
m.p.; 231–233° C.
$^1$H-NMR (400 MHz, DMSO-d$_6$); δ (ppm) 1.28 (t, J=7.2 Hz, 3H), 2.66 (t, J=4.8 Hz, 2H), 3.23 (q, J=7.2 Hz, 2H), 3.46 (br, 6H), 3.66–3.69 (m, 8H), 7.66 (ddd, J=8.4, 8.0, 1.2 Hz, 1H), 7.73 (s, 1H), 7.77 (ddd, J=8.4, 8.0, 1.2 Hz, 1H), 7.94 (d, J=8.0 Hz, 1H), 8.12 (d, J=8.4 Hz, 1H).
MS(FAB) m/z 365 (M+H)$^+$.
Free compound:
$^1$H-NMR (400 MHz, CDCl$_3$); δ (ppm) 1.15–1.18 (m, 3H), 2.57 (br, 2H), 2.69 (t, J=4.8 Hz, 4H), 2.74 (br, 4H), 3.51 (t, J=4.8 Hz, 4H), 3.59 (s, 2H), 3.79 (t, J=4.8 Hz, 4H), 7.45 (s, 1H), 7.49 (ddd, J=8.4, 8.0, 1.2 Hz, 1H), 7.60 (ddd, J=8.4, 8.0, 1.2 Hz, 1H), 7.68 (d, J=8.0 Hz, 1H), 8.03 (d, J=8.4 Hz, 1H).

Example 181

Synthesis of 1-(1-Ethylpiperazin-4-Yl)-3-(3-Phenyl-1-Propynyl)Isoquinoline Oxalate

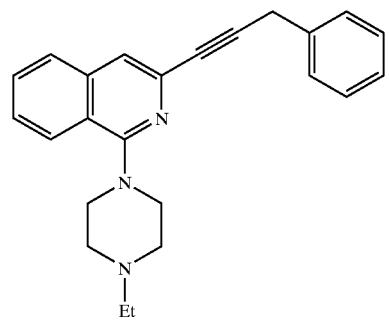

In the same manner as in Example 177, the oxalate of the title compound was obtained as brown crystals (recrystallized from ethanol/isopropyl ether) 468 mg, yield; 73%) from 3-phenyl-1-propyne (268 mg) and 1-(1-ethylpiperazin-4-yl)-3-bromoisoquinoline (493 mg).

Oxalate:

m.p.; 180–183° C.

$^1$H-NMR (400 MHz, DMSO-d$_6$); δ (ppm) 1.22 (3H, t, J=7.2 Hz), 3.09 (2H, q, J=7.2 Hz), 3.26–3.36 (4H, m), 3.46–3.58 (4H, m), 3.94 (2H, s), 7.23–7.29 (1H, m), 7.33–7.44 (4H, m), 7.62 (1H, ddd, J=8 Hz, 7 Hz, 1.2 Hz), 7.67 (1H, s), 7.73 (1H, ddd, J=8 Hz, 7 Hz, 1.2 Hz), 7.88 (1H, d, J=8 Hz), 8.07 (1H, d, J=8 Hz).

ESI-Mass; 356 (MH$^+$).

Example 182

Synthesis of 1-(1-Ethylpiperazin-4-Yl)-3-[4-Phenyl-1-Butynyl)Isoquinoline Dihydrochloride

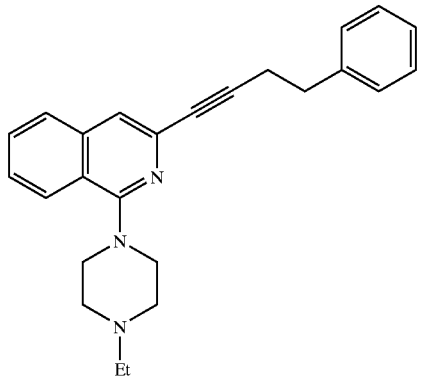

In the same manner as in Example 177, the hydrochloride of the title compound was obtained as brown crystals (recrystallized from ethanol/isopropyl ether) (468 mg, yield; 73%) from 4-phenyl-1-butyne (302 mg) and 1-(1-ethylpiperazin-4-yl)-3-bromoisoquinoline (474 mg).

Hydrochloride:

m.p.; 120–128° C.

$^1$H-NMR (400 MHz, DMSO-d$_6$); δ (ppm) 1.30 (3H, t, J=7.2 Hz), 2.75 (3H, t, J=7.4 Hz), 2.88 (2H, t, J=7.4 Hz), 3.18 (1H, q, J=7.2 Hz), 3.20 (1H, q, J=7.2 Hz), 3.26 (1H, t, J=11.6 Hz), 3.29 (1H, t, J=11.6 Hz), 3.40 (2H, t, J=13.2 Hz), 3.56 (2H, d, J=11.6 Hz), 3.81 (2H, d, J=13.2 Hz), 7.19–7.23 (1H, m), 7.28–7.34 (4H, m), 7.56 (1H, s), 7.61 (1H, ddd, J=8 Hz, 7 Hz, 1.2 Hz), 7.72 (1H, ddd, J=8 Hz, 7 Hz, 1.2 Hz), 7.88 (11H, d, J=8 Hz), 8.07 (1H, d, J=8 Hz), 11.00 (1H, br-s).

ESI-MASS; 370 (MH$^+$).

Example 183

Synthesis of 1-(1-Ethylpiperazin-4-Yl]-3-[4-(2-Hydroxyethoxy)Phenylethynyl]Isoquinoline Dihydrochloride

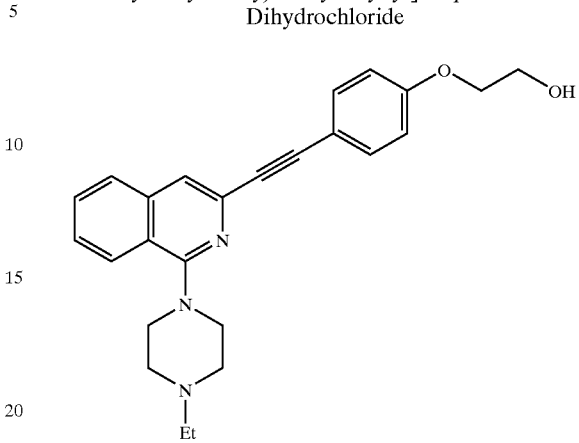

4-Iodophenol (11.041 g) was dissolved in N,N-dimethylformamide (100 ml), followed by the addition of 60% sodium hydride (2.2 g) under ice-cooling, and the mixture was stirred at room temperature for 30 min. Subsequently, the mixture was ice-cooled again, followed by the addition of (2-bromoethoxy)-t-butyldimethylsilane (13.158 g), and the mixture was stirred at room temperature for 2 hr. Then the mixture was stirred at 80° C. for further 2 hr. The reaction mixture was partitioned between ethyl acetate and water. The resulting organic layer was washed with water, dried (over MgSO$_4$) and evaporated. The resulting residue and (trimethylsilyl)acetylene (6 g) were treated in the same manner as in Example 139-1. The reaction mixture was partitioned between ethyl acetate and water. The resulting organic layer was washed with water, dried (over MgSO$_4$) and evaporated. The resulting residue was dissolved in tetrahydrofuran (50 ml), followed by the addition of 5N hydrochloric acid (25 ml), and the resulting mixture was stirred for 30 min. Then, it was extracted with ethyl acetate and evaporated. The resulting residue was dissolved in methanol (15 ml), followed by the addition of 1N sodium hydroxide (5 ml), and the mixture was stirred at room temperature for 2 hr. The resulting mixture was evaporated, and the resulting residue was partitioned between ethyl acetate and water. The resulting organic layer was washed with water, dried (over MgSO$_4$) and evaporated. From the product obtained by the same treatment as in Example 177 and 1-(1-ethylpiperazin-4-yl)-3-bromoisoquinoline (419 mg), the hydrochloride of the title compound was obtained as yellow crystals (recrystallized in ethanol/isopropyl ether) (328 mg, yield; 54%).

Hydrochloride:

m.p.; 205–208° C.

$^1$H-NMR (400 MHz, DMSO-d$_6$); δ (ppm) 1.31 (3H, t, J=7.2 Hz), 3.19 (1H, q, J=7.2 Hz), 3.21 (1H, q, J=7.2 Hz), 3.29 (1H, t, J=10.8 Hz), 3.32 (1H, t, J=10.8 Hz), 3.45 (2H, t, J=13.6 Hz), 3.58 (2H, d, J=10.8 Hz), 3.71 (2H, t, J=4.8 Hz), 3.85 (2H, d, J=13.6 Hz), 4.03 (2H, t, J=4.8 Hz), 7.00 (2H, d, J=8.8 Hz), 7.54 (2H, d, J=8.8 Hz), 7.65 (1H, ddd, J=8 Hz, 7 Hz, 1.2 Hz), 7.76 (1H, ddd, J=8 Hz, 7 Hz, 1.2 Hz), 7.78 (1H, s), 7.93 (1H, d, J=8 Hz), 8.11 (1H, d, J=8 Hz), 11.02 (1H, br-s).

ESI-Mass; 402 (MH$^+$).

Example 184

Synthesis of 1-(1-Ethylpiperazin-4-Yl)-3-Benzoylethynylisoquinoline Oxalate

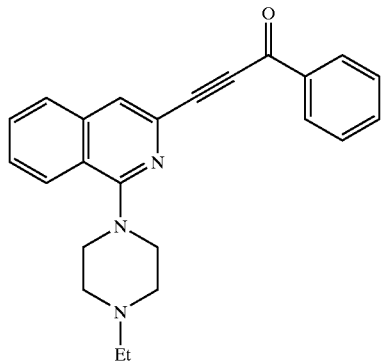

1-(1-Ethylpiperazin-4-yl)-3-(3-hydroxy-3-phenyl-1-propynyl)isoquinoline (400 mg) was dissolved in chloroform (30 ml), followed by the addition of manganese dioxide (4.038 g), and the resulting mixture was stirred at room temperature for 1 hr. After the manganese dioxide was filtered off, the resulting solution was evaporated, and the resulting residue was purified by silica gel column chromatography (ethyl acetate/acetone system). The resulting product was converted into an oxalate in a conventional manner, and then recrystallized from ethanol, to give the oxalate of the title compound as brown crystals (358 mg, yield; 73%).
Oxalate:
m.p.; 161–163° C.
$^1$H-NMR (400 MHz, DMSO-d$_6$); δ (ppm) 1.23 (3H, t, J=7.2 Hz), 3.07 (2H, q, J=7.2 Hz), 3.25–3.35 (4H, m), 3.54–3.68 (4H, m), 7.63–7.68 (2H, m), 7.74–7.87 (3H, m), 8.06 (1H, d, J=8 Hz), 8.16 (1H, d, J=8 Hz), 8.19–8.22 (3H, m).
ESI-Mass; 370 (MH$^+$).

Example 185

Synthesis of 1-(1-Ethylpiperazin-4-Yl)-3-(2,4-Dimethoxyphenylethynyl)Isoquinoline Dihydrochloride

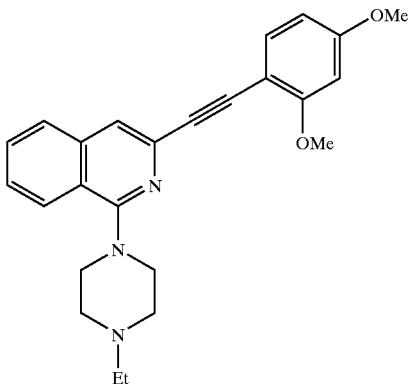

1-Bromo-2,4-dimethoxybenzene (2.18 g) was dissolved in triethylamine (20 ml), followed by the addition of (trimethylsilyl)acetylene (1.092 g), copper iodide (38 mg) and bis(triphenylphosphine)palladium (II) chloride (140 mg), and the resulting mixture was stirred in nitrogen atmosphere at 50° C. overnight. The resulting insoluble matters were filtered off from the reaction mixture, which was then evaporated. The resulting residue was dissolved in methanol (50 ml), followed by the addition of 1N sodium hydroxide (20 ml), and the mixture was stirred at room temperature for 1 hr. Subsequently, it was evaporated. The resulting residue was partitioned between ethyl acetate and water. The resulting organic layer was washed with water, dried (over MgSO$_4$) and evaporated. Then, the resulting residue was dissolved in triethylamine (15 ml), followed by the addition of 1-(1-ethylpiperazin-4-yl)-3-bromoisoquinoline (415 mg), cooper iodide (5 mg) and bis(triphenylphosphine)palladium (II) chloride (18 mg), and the resulting mixture was stirred in nitrogen atmosphere at 50° C. overnight. The resulting insoluble matters were filtered off from the reaction mixture, which was then evaporated. They acetate was added to the resulting residue, and then the mixture was extracted with 2N hydrochloric acid. The resulting aqueous layer was basified with 8N sodium hydroxide and extracted with ethyl acetate. The resulting organic layer was washed with water, dried (over MgSO$_4$) and evaporated. The resulting residue was purified by (NH) silica gel column chromatography (ethyl acetate/hexane system). The resulting product was converted into a hydrochloride in a conventional manner, and then recrystallized (from ethanol/isopropyl ether), to give the hydrochloride of the title compound as yellow crystals (161 mg, yield; 31%).
Hydrochloride:
m.p.; 123–129° C.
$^1$H-NMR (400 MHz, DMSO-d$_6$); δ (ppm) 1.30 (3H, t, J=7.2 Hz), 3.20 (1H, q, J=7.2 Hz), 3.22 (1H, q, J=7.2 Hz), 3.29 (1H, t, J=10.8 Hz), 3.32 (1H, t, J=10.8 Hz), 3.42 (2H, t, J=12.8 Hz), 3.58 (2H, d, J=10.8 Hz), 3.81 (3H, s), 3.82 (2H, d, J=12.8 Hz), 3.86 (3H, s), 6.58 (1H, dd, J=8.4 Hz, 2.4 Hz), 7.45 (1H, d, J=8.4 Hz), 7.63 (1H, ddd, J=8 Hz, 7 Hz, 1.2 Hz), 7.73 (1H, s), 7.75 (1H, ddd, J=8 Hz, 7 Hz, 1.2 Hz), 7.93 (1H, d, J=8 Hz), 8.10 (1H, d, J=8 Hz), 10.90 (1H, br-s).
ESI-Mass; 420 (MH$^+$).

Example 186

Synthesis of 1-(1-Ethylpiperazin-4-Yl)-3-[3-(3-Methoxypropyl)-5-Pyridyl]Ethynylisoquinoline

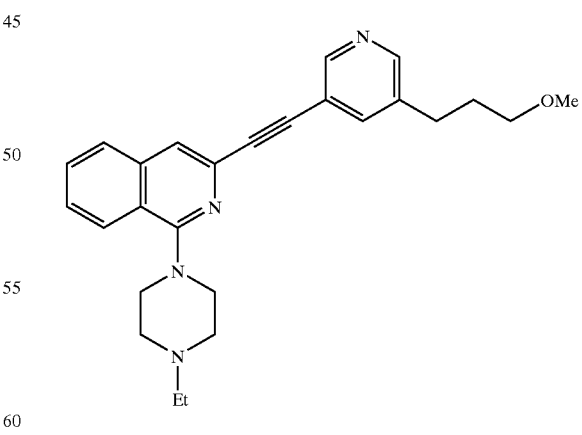

In the same manner as in Example 185, the hydrochloride of the title compound was obtained as pale yellow crystals (recrystallized from ethanol/isopropyl ether) (361; mg, yield; 50%) from 5-bromo-3-(3-methoxypropyl)pyridine (470 mg), (trimethylsilyl)acetylene (390 mg) and 1-(1-ethylpiperazin-4-yl)-3-bromoisoquinoline (345 mg).

Hydrochloride:

m.p.; 135–140° C.

$^1$H-NMR (400 MHz, DMSO-d$_6$); δ (ppm) 1.32 (3H, t, J=7.2 Hz), 1.84–1.92 (2H, m), 2.79 (2H, t, J=7.8 Hz), 3.18 (1H, q, J=7.2 Hz), 3.20 (1H, q, J=7.2 Hz), 3.22 (3H, s), 3.29 (1H, t, J=11.6 Hz), 3.32 (1H, t, J=11.6 Hz), 3.33 (2H, t, J=6.2 Hz), 3.51 (2H, t, J=13.2 Hz), 3.57 (2H, d, J=11.6 Hz), 3.84 (2H, d, J=13.2 Hz), 7.71 (1H, ddd, J=8 Hz, 7 Hz, 1.2 Hz), 7.80 (1H, ddd, J=8 Hz, 7 Hz, 1.2 Hz), 7.92 (1H, s), 7.99 (1H, d, J=8 Hz), 8:15 (1H, d, J=8 Hz), 8.47 (1H, t, J=2 Hz), 8.73 (1H, d, J=2 Hz), 8.97 (1H, d, J'2 Hz), 11.60 (1H, br-s).

ESI-Mass; 415 (MH$^+$).

Example 187

Synthesis of 1-(1-Ethylpiperazin-4-Yl)-3-[2-(2-Hydroxyethoxylphenyl]Ethynylisoquinoline Oxalate

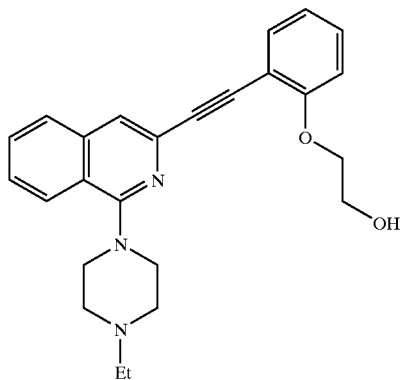

In the same manner as in Example 185, the oxalate of the title compound was obtained as a pale yellow amorphous (330 mg, yield; 54%) from 2-iodophenol (1.089 g), (2-bromoethoxy)-t-butyldimethylsilane (1.302 g), (trimethylsilyl)acetylene (579 mg) and 1-(1-ethylpiperazin-4-yl)-3-bromoisoquinoline (408 mg).

Oxalate:

$^1$H-NMR (400 MHz, DMSO-d$_6$); δ (ppm) 1.24 (3H, t, J=7.2 Hz), 3.11 (3H, q, J=7.2 Hz), 3.30–3.38 (4H, m), 3.33–3.48 (1H, m), 3.50–3.66 (4H, m), 3.78 (2H, t, J=5.2 Hz), 4.12 (2H, t, J=5.2 Hz), 6.98 (1H, ddd, J=7.6 Hz, 7.6 Hz, 1.6 Hz), 7.65 (1H, ddd, J=8 Hz, 7 Hz, 1.2 Hz), 7.75 (1H, s), 7.76 (1H, ddd, J=8 Hz, 7 Hz, 1.2 Hz), 7.93 (1H, d, J=8 Hz), 8.11 (1H, d, J=8 Hz).

ESI-Mass; 402 (MH$^+$).

Example 188

Synthesis of 1-(1-Ethylpiperazin-4-Yl)-3-[3-(2-Hydroxyethoxy)-2-Pyridyl]Ethynylisoquinoline

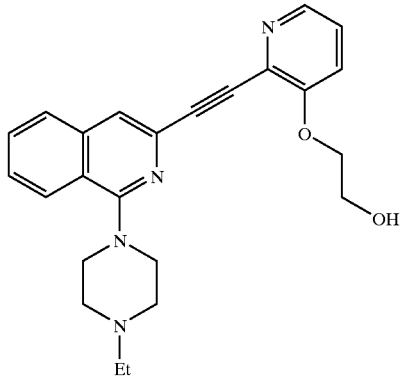

In the same manner as in example 185, the hydrochloride of the title compound was obtained as yellow crystals (261 mg, yield; 38%) from 2-bromo-3-hydroxypyridine (2.095 g), (2-bromoethoxy)-t-butyldimethylsilane (3.425 g), (trimethylsilyl)acetylene (613 mg) and 1-(1-ethylpiperazin-4-yl)-3-bromoisoquinoline (410 mg).

Hydrochloride:
  m.p.; 153–159° C.
  $^1$H-NMR (400 MHz, DMSO-d$_6$); δ (ppm) 1.31 (3H, t, J=7.2 Hz), 3.18 (1H, q, J=7.2 Hz), 3.20 (1H, q, J=7.2 Hz), 3.29 (1H, t, J=10.2 Hz), 3.32 (1H, t, J=10.2 Hz), 3.51 (2H, t, J=13.2 Hz), 3.58 (2H, d, J=10.2 Hz), 3.80 (1H, t, J=5 Hz), 3.90 (2H, d, J=13.2 Hz), 4.23 (1H, t, J=5 Hz), 7.55 (1H, dd, J=8.4 Hz, 1.6 Hz), 7.89 (1H, s), 7.99 (1H, d, J=8 Hz), 8.13 (1H, d, J=8 Hz). 8.26 (1H, dd, J=4.6 Hz, 1.6 Hz), 7.89 (1H, s), 7.99 (1H, d, J=8 Hz), 8.13 (1H, d, J=8 Hz), 8.26 (1H, dd, J=4.6 Hz, 1.6 Hz), 7.89 (1H, s), 7.99 (1H, d, J=8 Hz), 8.13 (1H, d, J=8 Hz), 8.26 (1H, dd, J=4.6 Hz, 1.6 Hz), 11.55 (1H, br-s).
  ESI-Mass; 403 (MH$^+$).

Example 189

Synthesis of 1-(1-Ethylpiperazin-4-Yl)-3-(Trans-2-Phenylethenyl)Isoquinoline Dihydrochloride

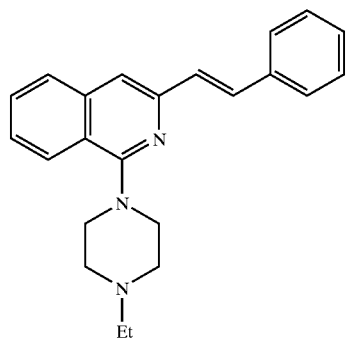

1-(1-Ethylpiperazin-4-yl)-3-bromoisoquinoline (702 mg) was dissolved in N,N-dimethylformamide (15 ml), followed by the addition of styrene (369 mg), palladium (II) acetate (49 mg), tri-o-tolylphosphine (134 mg) and triethylamine (5 ml), and the resulting mixture was stirred in nitrogen atmosphere at 100° C. overnight. After the insoluble matters were filtered off, the resulting filtrate was evaporated. The resulting residue was purified by (NH) silica gel column chromatography (ethyl acetate/hexane system). The resulting product was converted into a hydrochloride in a conventional manner, and recrystallized from ethanol/isopropyl ether, to give the hydrochloride of the title compound as pale brown crystals (412 mg, yield; 45%).

Hydrochloride:

m.p.; 222–225° C.

$^1$H-NMR (400 MHz, DMSO-$d_6$); δ (ppm) 1.32 (3H, t, J=7.2 Hz), 3.21 (1H, q, J=7.2 Hz), 3.23 (1H, q, J=7.2 Hz), 3.33 (1H, t, J=11.2 Hz), 3.55 (1H, t, J=11.2 Hz), 3.49 (2H, t, J=13.6 Hz), 3.60 (2H, d, J=11.2 Hz), 3.96 (2H, d, J=13.6 Hz), 7.27–7.32 (1H, m), 7.35 (1H, d, J=15.6 Hz), 7.40 (2H, t, J=7.6 Hz), 7.50 (1H, s), 7.57 (1H, ddd, J=8 Hz, 7 Hz, 1.2 Hz), 7.65 (2H, d, J=7.6 Hz), 7.68 (1H, d, J=15.6 Hz), 7.70 (1H, ddd, J=8 Hz, 7 Hz, 1.2 Hz), 7.89 (1H, d, J=8 Hz), 10.59 (1H, br-s).

ESI-Mass; 344 (MH$^+$).

Example 190

Synthesis of 1-(1-Ethylpiperazin-4-Yl)-3-[Trans-2-(4-Methoxyphenyl)Ethenyl]Isoquinoline Dihydrochloride

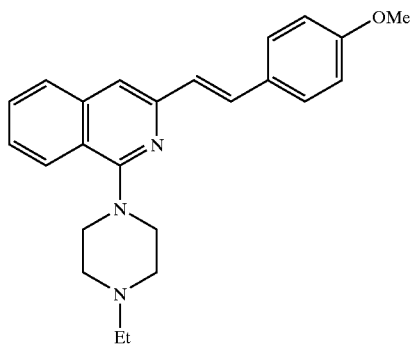

In the same manner as in Example 189, the hydrochloride of the title compound was obtained as yellow crystals (450 mg, yield; 53%) from 1-(1-ethylpiperazin-4-yl)-3-bromoisoquinoline (595 mg) and 4-methoxystyrene (382 mg).

Hydrochloride:

m.p.; 227° C. (decomp.)

$^1$H-NMR (400 MHz, DMSO-$d_6$); δ (ppm) 1.32 (3H, t, J=7.2 Hz), 3.20 (1H, q, J=7.2 Hz), 3.22 (1H, q, J=7.2 Hz), 3.31 (1H, t, J=11.6 Hz), 3.34 (1H, t, J=11.6 Hz), 3.60 (2H, d, J=11.6 Hz), 3.78 (3H, s), 3.95 (2H, d, J=13.6 Hz), 6.96 (2H, d, J=8.8 Hz), 7.20 (1H, d, J=15.6 Hz), 7.45 (1H, s), 7.54 (1H, ddd, J=8 Hz, 7 Hz, 1.2 Hz), 7.59 (2H, d, J=8.8 Hz), 7.63 (1H, d, J=15.6 Hz), 7.69 (1H, ddd, J=8 Hz, 7 Hz, 1.2 Hz), 7.86 (1H, dd, J=8 Hz, 1.2 Hz), 8.06 (1H, dd, J=8 Hz, 1.2 Hz), 11.05 (1H, br-s).

ESI-Mass; 374 (MH$^+$).

Example 191

Synthesis of 1-(1-Ethylpiperazin-4-Yl)-3-[Cis-2-(4-Methoxyphenyl)Ethenyl]Isoquinoline Oxalate

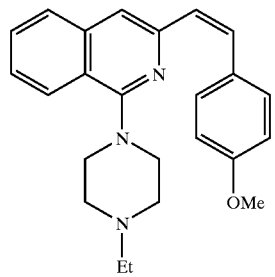

1-(1-Ethylpiperazin-4-yl)-3-(4-methoxyphenylethynyl) isoquinoline (226 mg) was dissolved in ethanol (10 ml), followed by the addition of Lindlar catalyst (45 mg), and the resulting mixture was stirred in hydrogen atmosphere at room temperature for 25 min. After the catalyst was filtered off, the mixture was evaporated and partitioned between ethyl acetate and 1N sodium hydroxide. The resulting organic layer was washed with water, dried (over MgSO$_4$), evaporated, and then purified by (NH) silica gel column chromatography (ethyl acetate/hexane system). The resulting product was converted into an oxalate in a conventional manner to give the oxalate of the title compound as a yellow amorphous (137 mg, yield; 49%).

Oxalate:

$^1$H-NMR (400 MHz, DMSO-$d_6$); δ (ppm) 1.02 (3H, t, J=7.2 Hz), 2.83 (2H, q, J=7.2 Hz), 2.94–3.04 (4H, m), 3.14–3.28 (4H, m), 3.58 (3H, s), 6.40 (1H, d, J=12.4 Hz), 6.48 (1H, d, J=12.4 Hz), 6.68 (1H, d, J=8.8 Hz), 7.21 (2H, d, J=8.8 Hz), 7.22 (1H, s), 7.39 (1H, ddd, J=8 Hz, 7 Hz, 1.2 Hz), 7.50 (1H, ddd, J=8 Hz, 7 Hz, 1.2 Hz), 7.63 (1H, d, J=8 Hz), 7.87 (1H, d, J=8 Hz).

ESI-Mass; 374 (MH$^+$).

Example 192

Synthesis of 1-(1-Ethylpiperazin-4-Yl)-3-(Cis-1-Methyl-2-Phenylethenyl) Isoquinoline Oxalate

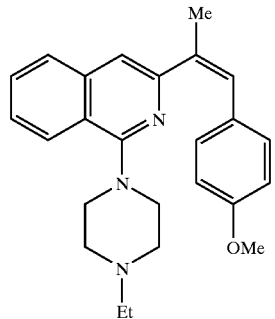

In the same manner as in Example 189, the oxalate of the title compound was obtained as a yellow amorphous (465 mg, yield; 53%) from 1-(1-ethylpiperazin-4-yl)-3-bromoisoquinoline (617 mg) and cis-β-methylstyrene (451 mg).

Oxalate:

$^1$H-NMR (400 MHz, DMSO-$d_6$); δ (ppm) 1.14 (3H, t, J=7.2 Hz), 2.25 (3H, s), 3.01 (2H, q, J=7.2 Hz), 3.12–3.22

(4H, m), 3.30–3.44 (4H, m), 6.64 (1H, s), 6.93 (2H, d, J=7.6 Hz), 7.04–7.12 (3H, m), 7.29 (1H, s), 7.5 (1H, ddd, J=8 Hz, 7 Hz, 1.2 Hz), 7.64 (1H, ddd, J=8 Hz, 7 Hz, 1.2 Hz), 7.76 (1H , d, J=8 Hz), 8.03 (1H, d, J=8 Hz).

ESI-Mass; 358 (MH$^+$).

Example 193

Synthesis of 1-(1-Ethylpiperazin-4-Yl)-3-(Trans-1-Methyl-2-Phenylethenyl)Isoquinoline

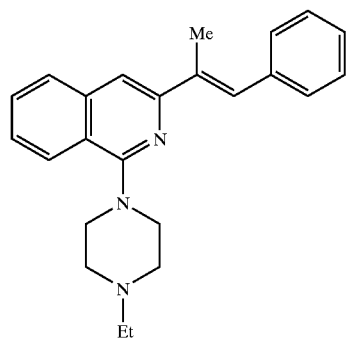

In the same manner as in Example 189, the oxalate of the title compound was obtained as a yellow amorphous (576 mg, yield; 68%) from 1-(1-ethylpiperazin-4-yl)-3-bromoisoquinoline (607 mg) and trans-β-methylstyrene (453 mg).

Oxalate:
$^1$H-NMR (400 MHz, DMSO-d$_6$); δ (ppm) 1.24 (3H, t, J=7.2 Hz), 2.31 (3H, s), 3.12 (2H, q, J=7.2 Hz), 3.30–3.40 (4H, m), 3.54–3.70 (4H, m), 7.25–7.32 (1H, m), 7.39–7.45 (4H, m), 7.57 (1H, ddd, J=8 Hz, 7 Hz, 1.2 Hz), 7.69 (1H, s), 7.70 (1H, ddd, J=8 Hz, 7 Hz, 1.2 Hz), 7.82 (1H, s), 7.95 (1H, dd, J=8 Hz, 1.2 Hz), 8.08 (1H, dd, J=8 Hz, 1.2 Hz).

ESI-Mass; 358 (MH$^+$).

Example 194

Synthesis of 1-(1-Ethylpiperazin-4-Yl)-3-[trans-2-(2-Hydroxyethoxyphenyl)Ethenyl]Isoquinoline Oxalate

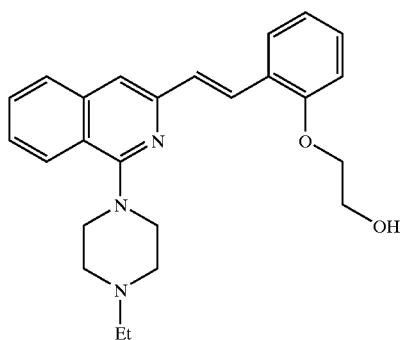

The product obtained from 1-(1-ethylpiperazin-4-yl)-3-bromoisoquinoline (700 mg) and 2-vinylphenoxyacetate n-butyl ester (486 mg) by the same treatment as in Example 189 was dissolved in tetrahydrofuran (6 ml), followed by the addition of lithium aluminium hydride (83 mg) under ice-cooling, and stirring for 5 min. To the reaction mixture was sequentially added water (85 ml), 5N sodium hydroxide (85 ml) and water (255 ml), the resulting insoluble matters were filtered off through Celite, and the resulting solution was evaporated. The resulting residue was purified by (NH) silica gel column chromatography (ethyl acetate/hexane system), and then converted into an oxalate in a conventional manner, to give the oxalate of the title compound as a yellow amorphous (248 mg, yield; 23%).

Oxalate:

$^1$H-NMR (400 MHz, DMSO-d$_6$); δ (ppm) 1.25 (3H, t, J=7.2 Hz), 3.13 (2H, q, J=7.2 Hz), 3.30–3.42 (4H, m), 3.60–3.80 (4H, m), 3.82 (2H, t, J=5 Hz), 4.08 (2H, t, J=5 Hz), 6.98 (1H, dd, J=7.6 Hz, 7.6 Hz), 7.05 (1H, d, J=8.2 Hz), 7.26 (1H, ddd, J=8.2 Hz, 7.6 Hz, 1.6 Hz), 7.34 (1H, d, J=16 Hz), 7.42 (1H , s), 7.54 (1H, ddd, J=8 Hz, 7 Hz, 1.2 Hz), 7.68 (1H, ddd, J=8 Hz, 7 Hz, 1.2 Hz), 7.69 (1H, dd, J=7.6 Hz, 1.6 Hz), 7.87 (1H, d, J=8 Hz), 8.06 (1H, d, J=16 Hz), 8.06 (1H , d, J=8 Hz).

ESI-Mass; 404 (MH$^+$).

Example 195

Synthesis of 1-(1-Ethylpiperazin-4-Yl)-3-[Trans-2-(2-Methoxyphenyl)Ethenyl]Isoquinoline Oxalate

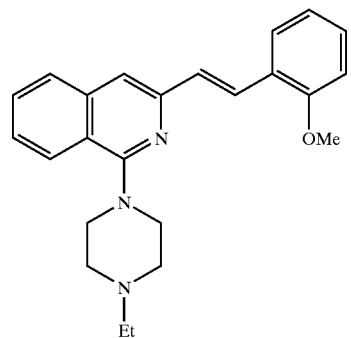

In the same manner as in Example 189, the oxalate of the title compound obtained as a yellow amorphous (224 mg, yield; 31%) from 1-(1-ethylpiperazin-4-yl)-3-bromoisoquinoline (507 mg) and 2-methoxystyrene (425 mg).

Oxalate:

$^1$H-NMR (400 MHz, DMSO-d$_6$); δ (ppm) 1.26 (3H, t, J=7.2 Hz), 3.16 (2H, q, J=7.2 Hz), 3.36–3.46 (4H, m), 3.54–3.72 (4H, m), 3.87 (3H, s), 6.98 (1H, t, J=7.6 Hz), 7.06 (1H, d, J=8.2 Hz), 7.29 (1H, ddd, J=8.2 Hz, 7.6 Hz, 1.6 Hz), 7.30 (1H, d, 16 Hz). 7.47 (1H, s), 7.55 (1H, ddd, J=8 Hz, 7 Hz, 1.2 Hz), 7.68 (1H, ddd, J=8 Hz, 7 Hz, 1.2 Hz), 7.69 (1H, dd, J=7.6 Hz, 1.6 Hz), 7.88 (1H, d, J=8 Hz), 7.96 (1H, d, J=16 Hz), 8.07 (1H, d, J=8 Hz). FAB-Mass; 376 (MH$^+$).

Example 196

Synthesis of 1-(1-Ethylpiperazin-4-Yl)-3-(Trans-2-Methyl-2-Phenylethen-1-Yl)Isoquinoline Oxalate

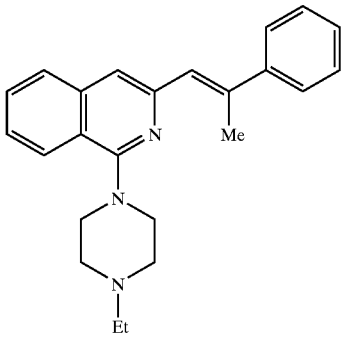

In the same manner as in Example 189, the oxalate of the title compound was obtained as a yellow amorphous (371 mg, yield; 44%) from 1-(1-ethylpiperazin-4-yl)-3-bromoisoquinoline (584 mg) and α-methylstyrene (425 mg). Oxalate:

$^1$H-NMR (400 MHz, DMSO-d$_6$); δ (ppm) 1.23 (3H, t, J=7.2 Hz), 2.68 (3H, d, J=1.2 Hz), 3.08 (2H, q, J=7.2 Hz), 3.28–3.38 (4H, m), 3.50–3.64 (4H, m), 6.87 (1H, d, J=1.2 Hz), 7.28–7.34 (1H, m), 7.40 (2H, t, J=7.6 Hz), 7.52 (1H, s), 7.54–7.62 (3H, m), 7.69 (1H, ddd, J=8 Hz, 7 Hz, 1.2 Hz), 7.86 (1H, d, J=8 Hz), 8.08 (1H, d, J=8 Hz). FAB-Mass; 368 (MH$^+$).

Example 197

Synthesis of 1-(1-Ethylpiperazin-4-Yl)-3-[Trans-2-(2-Fluorophenyl)Ethenyl]isoquinoline Oxalate

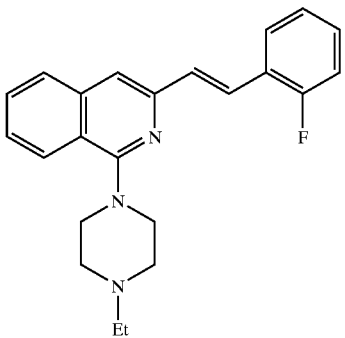

In the same manner as in Example 189, the oxalate of the title compound was obtained as a yellow amorphous (563 mg, yield; 71%) from 1-(1-ethylpiperazin-4-yl)-3-bromoisoquinoline (542 mg) and 2-fluorostyrene (415 mg). Oxalate:

$^1$H-NMR (400 MHz, DMSO-d$_6$); δ (ppm) 1.24 (3H, t, J=7.2 Hz), 3.09 (2H, q, J=7.2 Hz), 3.25–3.40 (4H, m), 3.50–3.70 (4H, m), 7.22–7.28 (2H, m), 7.31–7.38 (1H, m), 7.42 (1H, d, J=15.6 Hz), 7.53 (1H, s), 7.58 (1H, ddd, J=8 Hz, 7 Hz, 1.2 Hz), 7.71 (1H, ddd, J=8 Hz, 7 Hz, 1.2 Hz), 7.81 (1H, d, J=15.6 Hz), 7.82–7.87 (1H, m), 7.90 (1H, dd, J=8 Hz, 1.2 Hz), 8.08 (1H, dd, J=8 Hz, 1.2 Hz). FAB-Mass; 362 (MH$^+$).

Example 198

Synthesis of 1-(1-Ethylpiperazin-4-Yl)-3-[(E)-4-(2-Hydroxyethoxy)Styryl]Isoquinoline Oxalate (198-1) 2-(4-Vinylphenoxy)ethanol

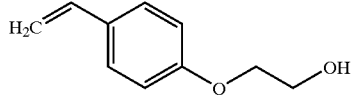

4-Hydroxybenzaldehyde (3.664 g) was dissolved in N,N-dimethylformamide (60 ml), followed by the addition of 60% sodium hydride (1.44 g) under ice-cooling. The resulting mixture was stirred at room temperature for 40 min. To the mixture was added (2-bromoethoxy)-t-butyldimethylsilane (8.612 g), and the resulting mixture was stirred at 100° C. for 30 min. After the mixture was cooled as it was, it was partitioned between ethyl acetate and water. The resulting organic layer was washed with water, dried (over MgSO$_4$) and evaporated. The resulting residue was dissolved in N,N-dimethylformamide (70 ml), followed by the addition of (ethyl)triphenylphosphonium bromide (13.218 g) and 60% sodium hydride (1.623 g) under ice-cooling, and the resulting mixture was stirred at room temperature for 2 hr. Water was added to the reaction mixture, extracted with hexane extraction, and then the resulting organic layer was evaporated. The resulting residue was dissolved in tetrahydrofuran (50 ml), followed by the addition of 2N hydrochloric acid (20 ml) and stirring for 1 hr. The reaction mixture was extracted with ethyl acetate, and the resulting organic layer was washed with water, dried (over MgSO$_4$) and evaporated. The resulting residue was purified by silica gel column chromatography (ethyl acetate/hexane system), to give the title compound as a colorless solid (3.025 g, yield; 60%).

$^1$H-NMR (400 MHz, CDCl$_3$); δ (ppm) 2.09 (1H, s), 3.97 (2H, t, J=4.6 Hz), 4.09 (2H, t, J=4.6 Hz), 5.14 (1H, dd, J=10.8 Hz, 0.8 Hz), 5.62 (1H, dd, J=17.6 Hz, 0.8 Hz), 6.68 (1H, dd, J=17.6 Hz, 10.8 Hz), 6.83 (1H, ddd, J=8 Hz, 2.4 Hz, 0.8 Hz), 6.97 (1H, dd, J=2.4 Hz, 1.6 Hz), 7.03 (1H, ddd, J=8 Hz, 1.6 Hz, 0.8 Hz), 7.25 (1H, t, J=8 Hz).

(198-2) 1-(1-Ethylpiperazin-4-yl)-3-[(E)-4-(2-hydroxyethoxy)styryl]isoquinoline oxalate

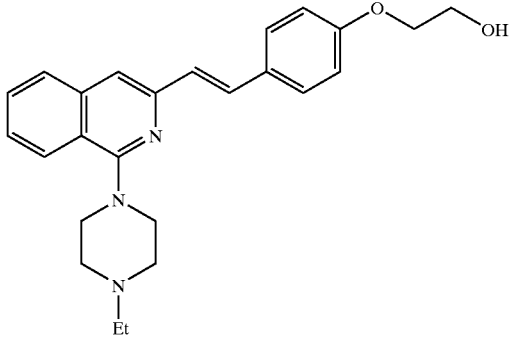

In the same manner as in Example 189, the oxalate of the title compound was obtained as a yellow amorphous (788 mg, yield; 89%) from 1-(1-ethylpiperazin-4-yl)-3-bromoisoquinoline (580 mg) and 2-(4-vinylphenoxy)ethanol (534 mg). Oxalate:

$^1$H-NMR (400 MHz, DMSO-d$_6$); δ (ppm) 1.25 (3H, t, J=7.2 Hz), 3.13 (2H, q, J=7.2 Hz), 3.30–3.42 (4H, m), 3.54–3.72 (4H, m), 3.71 (2H, t, J=5 Hz), 4.01 (2H, t, J=5 Hz), 6.96 (2H, d, J=8.8 Hz), 7.18 (1H, d, J=15.6 Hz), 7.42 (1H, s), 7.54 (1H, ddd, J=8 Hz, 7 Hz, 1.2 Hz), 7.57 (2H, d, J=8.8 Hz), 7.62 (1H, d, J=15.6 Hz), 7.68 (1H, ddd, J=8 Hz, 7 Hz, 1.2 Hz), 7.85 (1H, d, J=8 Hz), 8.06 (1H, d, J=8 Hz). FAB-Mass; 404 (MH$^+$).

Hz), 6.87 (1H, dd, J=8 Hz, 2.4 Hz), 7.20 (1H, d, J=7.6 Hz), 7.22 (1H, d, J=2.4 Hz), 7.29 (1H, dd, J=8 Hz, 7.6 Hz), 7.35 (1H, d, J=15.6 Hz), 7.48 (1H, s), 7.56 (1H, ddd, J=8 Hz, 7 Hz, 1.2 Hz), 7.64 (1H, d, J=15.6 Hz), 7.70 (1H, ddd, J=8 Hz, 7 Hz, 1.2 Hz), 7.87 (1H, d, J=8 Hz), 8.07 (1H, d, J=8 Hz). FAB-Mass; 404 (MH$^+$).

Example 199

Synthesis of 1-(1-Ethylpiperazin-4-Yl)-3-(Trans-2-(3-(2-Hydroxyethoxy)Phenyl]Ethenyl]isoquinoline Oxalate (199-1) 2-(3-Vinylphenoxy]ethanol

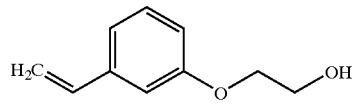

In the same manner as in Example 198-1, the title compound was obtained as a colorless oil (2.931 g, yield; 60%) from 3-hydroxybenzaldehyde (3.664 g), (2-bromoethoxy)-t-butyldimethylsilane (8.612 g) and (ethyl)triphenylphosphonium bromide (13.240 g).

$^1$H-NMR (400 MHz, CDCl$_3$); δ (ppm) 2.00–2.03 (1H, m), 3.95–4.00 (2H, m), 4.11 (2H, t, J=4.6 Hz), 5.26 (1H, dd, J=10.8 Hz, 0.8 Hz), 5.74 (1H, dd, J=17.6 Hz, 0.8 Hz), 6.68 (1H, dd, J=17.6 Hz, 10.8 Hz), 6.83 (1H, ddd, J=8 Hz, 2.4 Hz, 0.8 Hz), 6.97 (1H, dd, J=2.4 Hz, 1.6 Hz), 7.03 (1H, ddd, J=8 Hz, 1.6 Hz, 0.8 Hz), 7.25 (1H, t, J=8 Hz).

(199-2) 1-(1-Ethylpiperazin-4-yl)-3-[trans-2-[3-(2-hydroxyethoxy)phenyl]ethenyl]isoquinoline oxalate

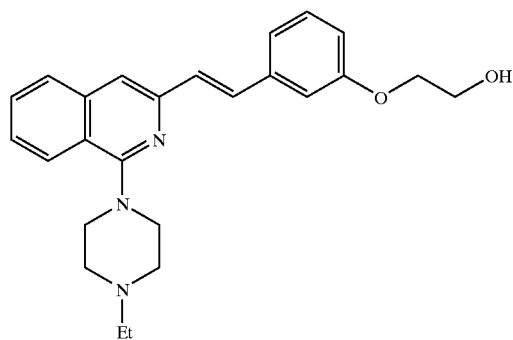

In the same manner as in Example 189, the oxalate of the title compound was obtained as a yellow amorphous (571 mg, yield; 71%) from 1-(1-ethylpiperazin-4-yl)-3-bromoisoquinoline (560 mg) and 2-(3-vinylphenoxy) ethanol (504 mg).

Oxalate:

$^1$H-NMR (400 MHz, DMSO-d$_6$); δ (ppm) 1.25 (3H, t, J=7.2 Hz), 3.15 (2H, q, J=7.2 Hz), 3.32–3.44 (4H, m), 3.52–3.74 (4H, m), 3.73 (2H, t, J=5 Hz), 4.04 (2H, t, J=5

Example 200

Synthesis of 3-[(E)-2-[2-(4-Morpholinyl)Pyridin-5-Yl]Ethenyl]-1-(4-Ethylpiperazin-1-Yl)Isoquinoline Hydrochloride

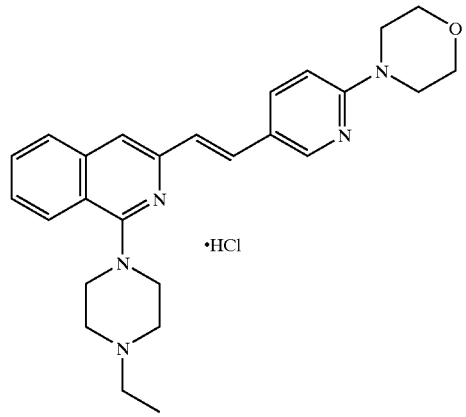

In the same manner as in Example 189, the free compound of the title compound was obtained (1.06 g, yield; 95%) from 2-(4-morpholinyl)-5-vinylpyridine (1.0 g) and 3-bromo-1-(4-ethylpiperazin-1-yl)isoquinoline (832 mg). The resulting free compound was converted into a hydrochloride in a conventional manner, to give the hydrochloride of the title compound as yellow crystals.

Hydrochloride:

m.p.; 190–194° C.

$^1$H-NMR (400 MHz, DMSO-d$_6$); δ (ppm) 1.35 (t, J=7.2 Hz, 3H), 3.18–3.26 (m, 2H), 3.30–3.39 (m, 2H), 3.52–3.62 (m, 4H), 3.78 (br, 8H), 3.99 (d, J=13.2 Hz, 2H), 7.44 (d, J=16.0 Hz, 1H), 7.46 (d, J=9.6 Hz, 1H), 7.49 (s, 1H), 7.60 (t, J=8.0 Hz, 1H), 7.68 (d, J=16.0 Hz, 1H), 7.73 (t, J=8.0 Hz, 1H), 7.91 (d, J=8.0 Hz, 1H), 8.09 (d, J=8.0 Hz, 1H), 8.28 (d, J=2.0 Hz, 1H), 8.47 (d, J=9.6 Hz, 1H).

MS(FAB) m/z 422 (M+H)$^+$.

Free compound:

$^1$H-NMR (400 MHz, CDCl$_3$); δ (ppm) 1.18 (t, J=7.2 Hz, 3H), 2.56 (q, J=7.2 Hz, 2H), 2.76 (br, 4H), 3.56 (t, J=4.8 Hz, 8H), 3.84 (t, J=4.8 Hz, 4H), 6.66 (d, J=8.8 Hz, 1H), 7.02 (d, J=15.6 Hz, 1H), 7.16 (s, 1H), 7.42 (ddd, J=8.4, 8.0, 1.2 Hz, 1H), 7.55 (ddd, J=8.4, 8.0, 1.2 Hz, 1H), 7.67 (d, J=8.0 Hz, 1H), 7.68 (d, J=15.6 Hz, 1H), 7.80 (dd, J=8.8, 2.4 Hz, 1H), 8.04 (d, J=8.4 Hz, 1H), 8.37 (d, J=2.4 Hz, 1H).

Example 201

Synthesis of 3-[(E)-2-(4-Methylsulfonylphenyl)Ethenyl]-1-(4-Ethylpiperazin-1-Yl)Isoquinoline Hydrochloride

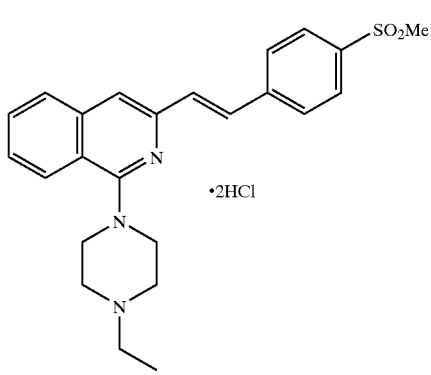

In the same manner as in Example 189, the free compound of the title compound was obtained (646 mg, yield; 70%) from 4-methylsulfonylvinylbenzene (638 mg) and 3-bromo-1-(4-ethylpiperazin-1-yl)isoquinoline (700 mg). The resulting free compound was converted into a hydrochloride in a conventional manner, to give the hydrochloride of the title compound as yellow crystals.

Hydrochloride:

m.p.; 170–174° C.

$^1$H-NMR (400 MHz, DMSO-$d_6$); δ (ppm) 1.34 (t, J=7.2 Hz, 3H), 3.17–3.25 (m, 2H), 3.25 (s, 3H), 3.32–3.39 (m, 2H), 3.50–3.57 (m, 2H), 3.63 (d, J=11.6 Hz, 2H), 4.01 (d, J=13.6 Hz, 2H), 7.59 (d, J=15.6 Hz, 1H), 7.60 (s, 1H), 7.62 (t, J=8.0 Hz, 1H), 7.75 (t, J=8.0 Hz, 1H), 7.77 (d, J=15.6 Hz, 1H), 7.94 (br, 4H), 7.95 (d, J=8.0 Hz, 1H), 8.11 (d, J=8.0 Hz, 1H).

MS(FAB) m/z 422 (M+H)$^+$.

Free compound:

$^1$H-NMR (400 MHz, CDCl$_3$); δ (ppm) 1.19 (t, J=7.2 Hz, 3H), 2.57 (q, J=7.2 Hz, 2H), 2.77 (br, 4H), 3.08 (s, 3H), 3.58 (br, 4H), 7.25 (s, 1H), 7.30 (d, J=15.6 Hz, 1H), 7.48 (ddd, J=8.4, 8.0, 1.2 Hz, 1H), 7.59 (ddd, J=8.4, 8.0, 1.2 Hz, 1H), 7.74 (d, J=8.0 Hz, 1H), 7.75 (d, J=8.4 Hz, 2H), 7.81 (d, J=15.6 Hz, 1H), 7.93 (d, J=8.4 Hz, 2H), 8.07 (d, J=8.4 Hz, 1H).

Example 202

Synthesis of 3-[(E)-2-(2-Methylsulfonylphenyl)Ethenyl]-1-(4-Ethylpiperazin-1-Yl)Isoquinoline Hydrochloride

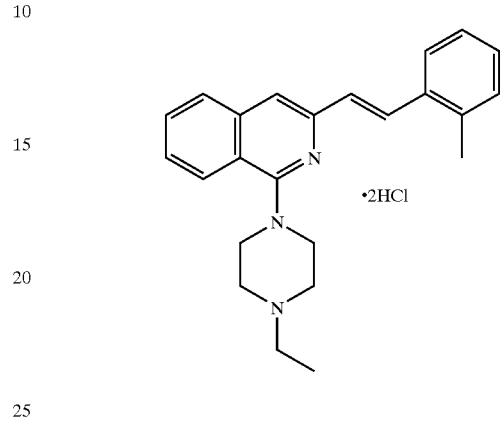

In the same manner as in Example 189, the free compound of the title compound was obtained (599 mg, yield; 84%) from 2-methylsulfonylvinylbenzene (500 mg) and 3-bromo-1-(4-ethylpiperazin-1-yl)isoquinoline (549 mg). The resulting free compound was converted into a hydrochloride in a conventional manner, to give the hydrochloride of the title compound as yellow crystals.

Hydrochloride:

m.p.; 146–149° C.

$^1$H-NMR (400 MHz, DMSO-$d_6$); δ (ppm) 1.33 (t, J=7.2 Hz, 3H), 3.18–3.25 (m, 2H), 3.30 (s, 3H), 3.33–3.45 (m, 2H), 3.58–3.67 (m, 4H), 4.02–4.07 (m, 2H), 7.50 (d, J=15.6 Hz, 1H), 7.56 (s, 1H), 7.58 (dd, J=8.0, 1.2 Hz, 1H), 7.60 (t, J=8.0 Hz, 1H), 7.62 (t, J=8.0 Hz, 1H), 7.75 (t, J=8.0 Hz, 1H), 7.79 (t, J=8.0 Hz, 1H), 7.95 (d, J=8.0 Hz, 1H), 8.00 (dd, J=80, 1.2 Hz, 1H), 8.11 (d, J=8.0 Hz, 1H), 8.66 (d, J=15.6 Hz, 1H).

MS(FAB) m/z 422 (M+H)$^+$.

Free compound:

$^1$H-NMR (400 MHz, CDCl$_3$); δ (ppm) 1.18 (t, J=7.2 Hz, 3H), 2.55 (q, J=7.2 Hz, 2H), 2.56 (br, 4H), 3.15 (s, 3H), 3.63 (br, 4H), 7.19 (d, J=15.6 Hz, 1H), 7.26 (s, 1H), 7.43–7.57 (m, 2H), 7.60 (ddd, J=8.4, 8.0, 1.2 Hz, 1H), 7.64 (ddd, J=8.4, 8.0, 1.2 Hz, 1H), 7.74 (d, J=8.0 Hz, 1H), 7.87 (d, J=7.2 Hz, 1H), 8.06 (d, J=8.4 Hz, 1H), 8.12 (d, J=8.0, 1.2 Hz, 1H), 8.74 (d, J=15.6 Hz, 1H).

Example 203

Synthesis of 3-[(E)-2-(4-Methylsulfonylmethylphenyl)Ethenyl]-1-(4-Ethylpiperazin-1-Yl)Isoquinoline Oxalate

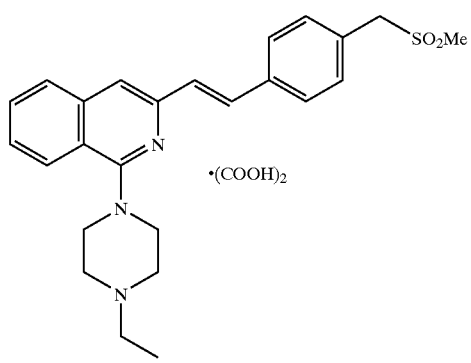

In the same manner as in Example 189, the free compound of the title compound was obtained (496 mg, yield; 78%) from 4-methylsulfonylmethylstyrene (432 mg) and 3-bromo-1-(4-ethylpiperazin-1-yl)isoquinoline (470 mg). The resulting free compound was converted into an oxalate in a conventional manner, to give the oxalate of the title compound as yellow crystals.

Oxalate:

m.p.; 245–247° C.

$^1$H-NMR (400 MHz, DMSO-$d_3$); δ (ppm) 1.28 (t, J=7.2 Hz, 3H), 2.93 (s, 3H), 3.18 (q, J=7.2 Hz, 2H), 3.42 (br, 4H), 3.67 (br, 4H), 4.52 (s, 2H), 7.40 (d, J=15.6 Hz, 1H), 7.44 (d, J=8.4 Hz, 2H), 7.52 (s, 1H), 7.59 (t, J=8.0 Hz, 1H), 7.70 (d, J=8.4 Hz, 2N), 7.71 (d, J=15.6 Hz, 1H), 7.72 (t, J=8.0 Hz, 1H), 7.91 (d, J=8.0 Hz, 1H), 8.10 (d, J=8.0 Hz, 1H).

MS(FAB) m/z 436 (M+H)$^+$.

Free compound:

$^1$H-NMR (400 MHz, CDCl$_3$); δ (ppm) 1.19 (t, J=7.2 Hz, 3H), 2.58 (q, J=7.2 Hz, 2H), 2.78 (br, 7H), 3.58 (br, 4H), 4.27 (s, 2H), 7.20 (d, J=15.6 Hz, 1H), 7.22 (s, 1H), 7.41 (d, J=8.4 Hz, 2H), 7.45 (ddd, J=8.4, 8.0, 1.2 Hz, 1H), 7.58 (ddd, J=8.4, 8.0, 1.2 Hz, 1H), 7.63 (d, J=8.4 Hz, 2H), 7.72 (d, J=8.0 Hz, 1H), 7.78 (d, J=15.6 Hz, 1H), 8.06 (d, J=8.4 Hz, 1H).

Example 204

Synthesis of 3-{(E)-2-[3-(4-Morpholinyl)Phenyl]Ethenyl}-1-(4-Ethylpiperazin-1-Yl)Isoquinoline Oxalate

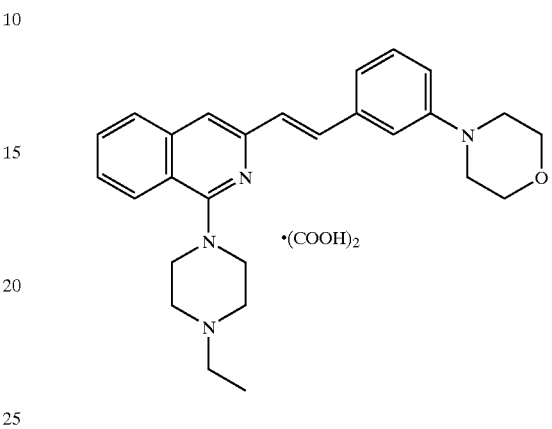

In the same manner as in Example 189, the free compound of the title compound was obtained (600 mg, yield; 95%) from 3-(4-morpholinyl)styrene (417 mg) and 3-bromo-1-(4-ethylpiperazin-1-yl)isoquinoline (470 mg). The resulting free compound was converted into an oxalate in a conventional manner, to give the oxalate of the title compound as yellow crystals.

Oxalate:

m.p.; 180–182° C.

$^1$H-NMR (400 MHz, DMSO-$d_6$); δ (ppm) 1.28 (t, J=7.2 Hz, 3H), 3.18 (br, 6H), 3.43 (br, 4H), 3.66 (br, 4H), 3.77 (t, J=4.8 Hz, 4H), 6.91 (dd, J=8.0, 2.0 Hz, 1H), 7.12 (d, J=8.0 Hz, 1H), 7.21 (br, 1H), 7.26 (t, J=8.0 Hz, 1H), 7.36 (d, J=16.0 Hz, 1H), 7.49 (s, 1H), 7.58 (t, J=8.0 Hz, 1H), 7.65 (d, J=16.0 Hz, 1H), 7.72 (t, J=8.0 Hz, 1H), 7.89 (d, J=8.0 Hz, 1H), 8.09 (d, J=8.0 Hz, 1H).

MS(FAB) m/z 429 (M+H)$^+$.

Free compound:

$^1$H-NMR (400 MHz, CDCl$_3$); δ (ppm) 1.17 (t, J=7.2 Hz, 3H), 2.55 (q, J=7.2 Hz, 2H), 2.76 (br, 4H), 3.22 (t, J=4.8 Hz, 4H), 3.56 (br, 4H), 3.89 (t, J=4.8 Hz, 4H), 6.84 (dd, J=7.6, 1.2 Hz, 1H), 7.12–7.17 (m, 2H), 7.15 (d, J=16.0 Hz, 1H), 7.19 (s, 1H), 7.28 (dt, J=7.6 Hz, 1H), 7.42 (t, J=8.0 Hz, 2H), 7.55 (t, J=8.0 Hz, 1H), 7.70 (d, J=8.0 Hz, 1H), 7.74 (d, J=16.0 Hz, 1H), 8.04 (d, J=8.0 Hz, 1H).

Example 205

Synthesis of 3-{(E)-2-[4-(4-Morpholinyl)Phenyl]Ethenyl}-1-(4-Ethylpiperazin-1-Yl)Isoquinoline Oxalate

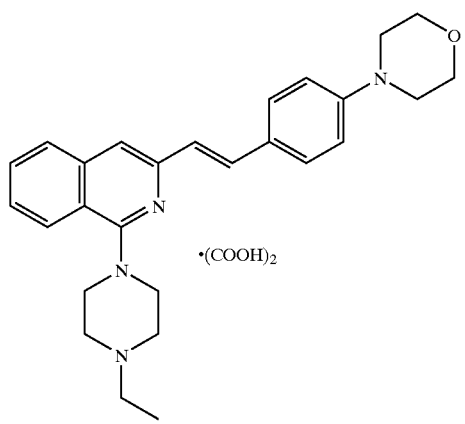

In the same manner as in Example 189, the free compound of the title compound was obtained (157 mg, yield; 36%) from 4-(4-morpholinyl)styrene (284 mg) and 3-bromo-1-(4-ethylpiperazin-1-yl)isoquinoline (320 mg). The resulting free compound was converted into an oxalate in a conventional manner, to give the oxalate of the title compound as yellow crystals.

Oxalate:

m.p.; 248–250° C.

$^1$H-NMR (400 MHz, DMSO-d$_6$); δ (ppm) 1.29 (t, J=7.2 Hz, 2H), 3.18 (br, 4H), 3.24 (q, J=7.6 Hz, 2H), 3.48 (br, 6H), 3.75 (br, 6H), 6.98 (d, J=8.8 Hz, 2H), 7.15 (d, J=16.0 Hz, 1H), 7.43 (s, 1H), 7.53 (d, J=8.8 Hz, 2H), 7.55 (t, J=8.0 Hz, 1H), 7.61 (d, J=16.0 Hz, 1H), 7.69 (t, J=8.0 Hz, 1H), 7.86 (d, J=8.0 Hz, 1H), 8.07 (d, J=8.0 Hz, 1H).

MS(FAB) m/z 429 (M+H)$^+$.

Free compound:

$^1$H-NMR (400 MHz, CDCl$_3$); δ (ppm) 1.18 (t, J=7.6 Hz, 3H), 2.56 (q, J=7.6 Hz, 2H), 2.56 (br, 4H), 3.21 (t, J=4.8 Hz, 4H), 3.56 (br, 4H), 3.87 (t, J=4.8 Hz, 4H) 6.90 (d, J=8.8 Hz, 2H), 7.05 (d, J=15.6 Hz, 1H), 7.15 (s, 1H), 7.40 (ddd, J=8.4, 8.0, 1.2 Hz, 1H), 7.52 (d, J=8.8 Hz, 2H), 7.54 (ddd, J=8.4, 8.0, 1.2 Hz, 1H), 7.68 (d, J=8.0 Hz, 1H), 7.73 (d, J=15.6 Hz, 1H), 8.03 (d, J=8.4 Hz, 1H).

Example 206

Synthesis of 3-{(E)-2-Methyl-2-[4-(4-Morpholinyl)Phenyl]Ethenyl}-1-(4-Ethylpiperazin-1-Yl)Isoquinoline Oxalate

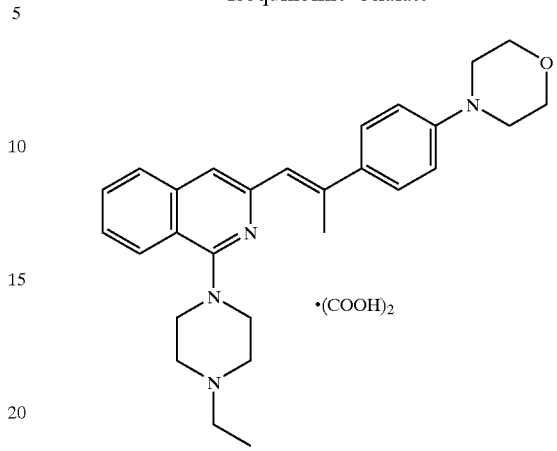

In the same manner as in Example 189, the free compound of the title compound was obtained (475 mg, yield; 66%) from 4-(4-morpholinyl)-α-methylstyrene (500 mg) and 3-bromo-1-(4-ethylpiperazin-1-yl)isoquinoline (523 mg). The resulting free compound was converted into an oxalate in a conventional manner, to give the oxalate of the title compound as yellow crystals.

Oxalate:

m.p.; 266–267° C.

$^1$H-NMR (400 MHz, MSO-d$_6$); δ (ppm) 1.27 (t, J=7.2 Hz, 3H), 2.66 (s, 3H), 3.16 (br, 6H), 3.41 (br, 6H), 3.76 (br, 6H), 6.84 (s, 1H), 6.98 (d, J=8.8 Hz, 2H), 7.50 (s, 1H), 7.51 (d, J=8.8 Hz, 2H), 7.56 (t, J=8.0 Hz, 1H), 7.70 (t, J=8.0 Hz, 1H), 7.87 (d, J=8.0 Hz, 1H), 8.08 (d, J=8.0 Hz, 1H).

MS(FAB) m/z 443 (M+H)$^+$.

Free compound:

$^1$H-NMR (400 MHz, CDCl$_3$); δ (ppm) 1.17 (t, J=7.2 Hz, 3H), 2.56 (q J=7.2 Hz, 2H), 2.73 (s, 3H), 2.76 (br, 4H), 3.21 (t, J=4.8 Hz, 4H), 3.52 (br, 4H), 3.88 (t, J=4.8 Hz, 4H), 6.79 (s, 1H), 6.92 (d, J=8.8 Hz, 2H), 7.21 (s, 1H), 7.42 (ddd, J=8.4, 8.0, 1.2 Hz, 1H), 7.52 (d, J=8.8 Hz, 2H), 7.55 (ddd, J=8.4, 8.0, 1.2 Hz, 1H), 7.70 (t, J=8.0 Hz, 1H), 8.05 (d, J=8.4 Hz, 1H).

Example 207

Synthesis of 3-{(E)-2-Methyl-2-[3-(4-Morpholinyl)Phenyl]Ethenyl}-1-(4-Ethylpiperazin-1-Yl)Isoquinoline Oxalate

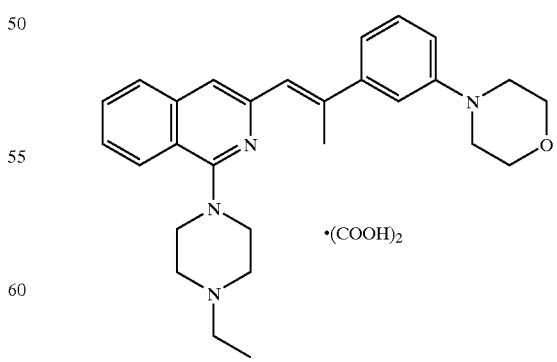

In the same manner as in Example 189, the free compound of the title compound was obtained (332 mg, yield;

35%) from 3-(4-morpholinyl)-α-methylstyrene (658 mg) and 3-bromo-1-(4-ethylpiperazin-1-yl)isoquinoline (691 mg). The resulting free compound was converted into an oxalate in a conventional manner, to give the oxalate of the title compound as yellow crystals.

Oxalate:
m.p.; 190–192° C.
$^1$H-NMR (400 MHz, DMSO-d$_6$); δ (ppm) 1.28 (t, J=7.2 Hz, 3H), 2.67 (s, 3H), 3.17 (t, J=4.8 Hz, 6H), 3.21 (q, J=7.2 Hz, 2H), 3.47 (br, 6H), 3.77 (t, J=4.8 Hz, 4H), 6.87 (s, 1H), 6.92 (dd, J=8.0, 2.0 Hz, 1H), 7.04 (d, J=8.0 Hz, 1H), 7.11 (br, 1H), 7.26 (t, J=8.0 Hz, 1H), 7.55 (s, 1H), 7.59 (t, J=8.0 Hz, 1H), 7.72 (t, J=8.0 Hz, 1H), 7.89 (d, J=8.0 Hz, 1H), 8.10 (d, J=8.0 Hz, 1H).
MS(FAB) m/z 443 (M+H)$^+$.

Free compound:
$^1$H-NMR (400 MHz, CDCl$_3$); δ (ppm) 1.17 (t, J=7.2 Hz, 3H), 2.56 (q, J=7.2 Hz, 2H), 2.74 (s, 3H), 2.75 (br, 4H), 3.22 (t, J=4.8 Hz, 4H), 3.52 (br, 4H), 3.89 (t, J=4.8 Hz, 4H), 6.79 (s, 1H), 6.86 (dd, J=8.0, 2.4 Hz, 1H), 7.09 (d, J=8.0 Hz, 1H), 7.10 (s, 1H), 7.22 (s, 1H), 7.29 (t, J=8.0 Hz, 1H), 7.44 (t, J=7.6 Hz, 1H), 7.56 (t, J=7.6 Hz, 1H), 7.70 (d, J=7.6 Hz, 1H), 8.05 (d, J=7.6 Hz, 1H).

Example 208

Synthesis of 3-[(E)-2-Methoxymethyl-2-Phenylethenyl]-1-(4-Ethylpiperazin-1-Yl) Isoquinoline Oxalate

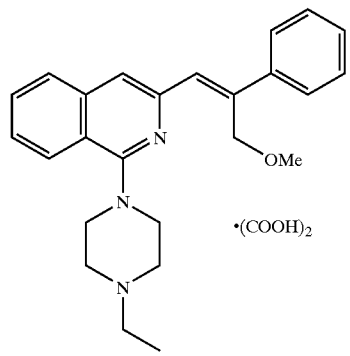

In the same manner as in Example 189, the free compound of the title compound (492 mg, yield; 71%) from α-methoxymethylstyrene (403 mg) and 3-bromo-1-(4-ethylpiperazin-1-yl)isoquinoline (580 m g). The resulting free compound was converted into an oxalate in a conventional manner, to give the oxalate of the title compound as yellow crystals.

Oxalate:
m.p.; 180–182° C.
$^1$H-NMR (400 MHz, DMSO-d$_6$); δ (ppm) 1.23 (t, J=7.2 Hz, 3H), 3.05 (br, 2H), 3.25 (br, 4H), 3.49 (br, 4H), 3.75 (s, 3H), 3.95 (s, 2H), 6.91 (s, 1H), 7.10 (t, J=7.6 Hz, 1H), 7.15 (s, 1H), 7.23 (t, J=7.6 Hz, 2H), 7.42 (d, J=7.6 Hz, 2H), 7.50 (t, J=8.0 Hz, 1H), 7.62 (t, J=8.0 Hz, 1H), 7.76 (d, J=8.0 Hz, 1H), 8.01 (d, J=8.0 Hz, 1H).
MS(FAB) m/z 388 (M+H)$^+$.

Free compound:
$^1$H-NMR (400 MHz, CDCl$_3$); δ (ppm) 1.16 (t, J=7.2 Hz, 3H), 2.53 (q, J=7.2 Hz, 2H), 2.70 (br, 4H), 3.45 (br, 4H), 3.75 (s, 3H), 4.04 (s, 2H), 6.65 (s, 1H), 7.08 (s, 1H), 7.12 (dt, J=7.6, 1.2 Hz, 1H), 7.22 (t, J=7.6 Hz, 1H), 7.36 (ddd, J=8.4, 8.0, 1.2 Hz, 1H), 7.42 (dd, J=7.6, 1.2 Hz, 2H), 7.49 (ddd, J=8.4, 8.0, 1.2 Hz, 1H), 7.59 (d, J=8.0 Hz, 1H), 7.99 (d, J=8.4 Hz, 1H).

Example 209

Synthesis of 1-(1-Ethylpiperazin-4-Yl)-3-[Trans-2-(2-Pyridyl)Ethenyl]Isoquinoline Trihydrochloride

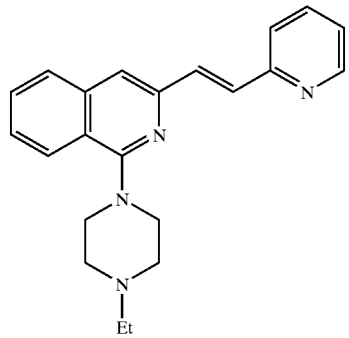

In the same manner as in Example 189, the hydrochloride of the title compound was obtained as yellow crystals (789 mg, yield; 77%) from 1-(1-ethylpiperazin-4-yl)-3-bromoisoquinoline (714 mg) and 2-vinylpyridine (469 mg).

Hydrochloride:
m.p.; 220° C. (decomp.)
$^1$H-NMR (400 MHz, DMSO-d$_6$); δ (ppm) 1.33 (3H, t, J=7.2 Hz), 3.20 (1H, q, J=7.2 Hz), 3.22 (1H, q, J=7.2 Hz), 3.32 (1H, t, J=11.2 Hz), 3.35 (1H, t, J=11.2 Hz), 3.56 (2H, t, J=13.6 Hz), 3.58 (2H, d, J=11.2 Hz), 4.00 (2H, d, J=13.6 Hz), 7.58–7.67 (3H, m), 7.73–7.77 (1H, m), 7.88–8.01 (2H, m), 7.95 (1H, d, J=15.6 Hz), 8.10–8.15 (2H, m), 8.18–8.25 (1H, m), 8.70 (1H, d, J=4.4 Hz), 11.06 (1H, br-s).
ESI-Mass; 345 (MH$^+$).

Example 210

Synthesis of 1-(1-Ethylpiperazin-4-Yl)-3-[Trans-2-(4-Pyridyl)Ethenyl]Isoquinoline

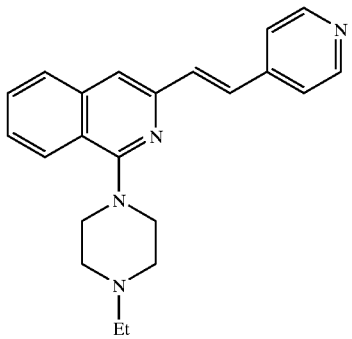

In the same manner as in Example 189, the oxalate of the title compound as a yellow amorphous (468 mg, yield; 79%) from 1-(1-ethylpiperazin-4-yl)-3-bromoisoquinoline (435 mg) and 4-vinylpyridine (286 mg).

Oxalate:
$^1$H-NMR (400 MHz, DMSO-d$_6$); δ (ppm) 1.26 (3H, t, J=7.2 Hz), 3.17 (2H, q, J=7.2 Hz), 3.36–3.46 (1H, m), 3.58–3.76 (1H, m), 7.56–7.63 (7H, m), 7.73 (1H, ddd, J=8

Hz, 7 Hz, 1.2 Hz), 7.92 (1H, d, J=8 Hz), 8.10 (1H, d, J=8 Hz), 8.56 (2H, dd, J=6 Hz, 1.6 Hz).

ESI-Mass; 345 (MH$^+$).

Example 211

Synthesis of 1-(1-Ethylpiperazin-4-Yl)-3-[3-(2-Methoxy)Phenyl-2-Propenyl]Isoquinoline Oxalate

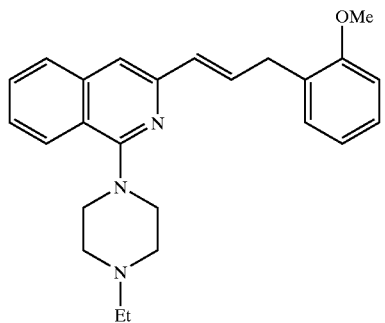

2-Allylphenol (444 mg) was dissolved in N,N-dimethylformamide (5 ml), followed by the addition of 60% sodium hybride (157 mg). The resulting mixture was stirred at room temperature for 20 min. Methyl iodide (250 ml) was added thereto, and the mixture was stirred at room temperature overnight. The reaction mixture was partitioned between ethyl acetate and water. The resulting organic layer was washed with water, dried (over MgSO$_4$) and evaporated. The resulting residue and 1-(1-ethylpiperazin-4-yl)-3-bromoisoquinoline (563 mg) were treated in the same manner as in Example 189, to give the oxalate of the title compound as a pale red amorphous (400 mg, yield; 44%).

Oxalate:

$^1$H-NMR (400 MHz, DMSO-d$_6$); δ (ppm) 1.21 (3H, t, J=7.2 Hz), 3.05 (2H, q, J=7.2 Hz), 3.20–3.36 (4H, m), 3.52 (2H, d, J=2.4 Hz), 3.80 (3H, s), 6.47 (1H, d, J=15.2 Hz), 6.87–6.94 (2H, m), 6.99 (1H, d, J=8.4 Hz), 7.16–7.24 (2H, m), 7.27 (1H, s), 7.51 (1H, ddd, J=8 Hz, 7 Hz, 1.2 Hz), 7.65 (1H, ddd, J=8 Hz, 7 Hz, 1.2 Hz), 7.81 (1H, d, J=8 Hz), 8.02 (1H, d, J=8 Hz). FAB-Mass; 388 (MH$^+$).

Example 212

Synthesis of 1-(1-Ethylpiperazin-4-Yl)-3-[3-(2-Hydroxyethoxy)Phenyl-1-Propenyl]Isoquinoline Oxalate (212-1) 2-(2-Allylphenoxy)ethanol

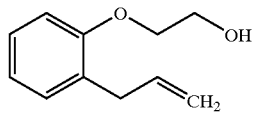

2-Allylphenol (5.066 g) was dissolved in N,N-dimethylformamide (70 ml), followed by the addition of methyl 2-bromoacetate (6.931 g) and potassium carbonate (7.88 g), and the resulting mixture was stirred at 100° C. overnight. The reaction mixture was partitioned between ethyl acetate and water. The organic layer was washed with water, dried (over MgSO$_4$) and evaporated. The resulting residue was dissolved in tetrahydrofuran (40 ml), followed by the addition of lithium aluminium hydride (1.442 g) in small portions under ice-cooling. The resulting mixture was stirred for 5 min. To the reaction mixture were sequentially added water (1.5 ml), 5N sodium hydroxide (1.5 ml) and water (4.5 ml), and the resulting insoluble matters were filtered off through Celite. The resulting filtrate was partitioned between ethyl acetate and water. The organic layer was washed with water, dried (over MgSO$_4$) and evaporated. The resulting residue was purified by (NH) silica gel column chromatography (ethyl acetate/hexane system), to give the title compound as a colorless oil (5.248 mg, yield; 76%).

$^1$H-NMR (400 MHz, CDCl$_3$); δ (ppm) 3.41 (2H, d, J=6.4 Hz), 3.93–3.98 (2H, m), 4.09 (2H, t, J=4.4 Hz), 5.00–5.07 (2H, m), 5.94–6.05 (1H, m), 6.85 (1H, dd, J=7.6 Hz, 1.6 Hz), 6.93 (1H, td, J=7.6 Hz, 1.6 Hz), 7.16 (1H, dd, J=7.6 Hz, 1.6 Hz), 7.20 (1H, td, J=7.6 Hz, 1.6 Hz).

(212-2) 1-(1-Ethylpiperazin-4-yl)-3-[3-(2-hydroxyethoxy)phenyl-1-propenyl]isoquinoline oxalate

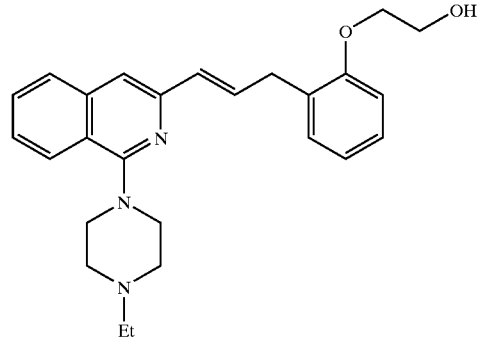

In the same manner as in Example 189, the oxalate of the title compound was obtained as a pale yellow amorphous (313 mg, yield; 38%) from 1-(1-ethylpiperazin-4-yl)-3-bromoisoquinoline (528 mg) and 2-(2-allylphenoxy)ethanol (570 mg).

Oxalate:

$^1$H-NMR (400 MHz, DMSO-d$_6$); δ (ppm) 1.20 (3H, t, J=7.2 Hz), 3.02 (2H, q, J=7.2 Hz), 3.16–3.30 (4H, m), 3.42–3.60 (4H, m), 3.55 (2H, d, J=7.2 Hz), 3.75 (2H, t, J=5 Hz), 4.01 (2H, t, J=5 Hz), 6.53 (1H, d, J=15.2 Hz), 6.88 (1H, td, J=7.6 Hz, 1 Hz), 6.94 (1H, dt, 15.2 Hz, 7.2 Hz), 6.97 (1H, dd, J=8.2 Hz, 1 Hz), 7.18 (1H, ddd, J=8 Hz, 7 Hz, 1.2 Hz), 7.65 (1H, ddd, J=8 Hz, 7 Hz, 1.2 Hz), 7.81 (1H, d, J=8 Hz), 8.02 (1H, d, J=8 Hz).

ESI-Mass; 418 (MH$^+$).

Example 213

Synthesis of 3-{(E)-2-[2-(4-Morpholinyl)Pyridin-5-Yl]Ethenyl}-1-(4-Ethylpiperazin-1-Yl)Isoquinoline Oxalate

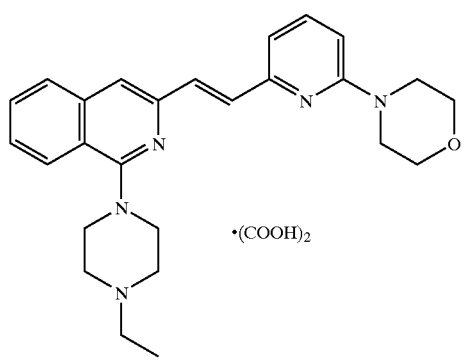

In the same manner as in Example 189, the free compound of the title compound was obtained (750 mg, yield; 94%) from 2-(4-morpholinyl)-5-vinylpyridine (708 mg) and 3-bromo-1-(4-ethylpiperazin-1-yl)isoquinoline (595 mg). The resulting free compound was converted into an oxalate in a conventional manner, to give the oxalate of the title compound as yellow crystals.

Oxalate:

m.p.; 124–128° C.

$^1$H-NMR (400 MHz, DMSO-$d_6$); δ (ppm) 1.28 (t, J=7.2 Hz, 3H), 3.19 (br, 2H), 3.43 (br, 4H), 3.54 (t, J=4.8 Hz, 6H), 3.75 (t, J=4.8 Hz, 6H), 6.79 (d, J=8.4 Hz, 1H), 6.89 (d, J=7.2 Hz, 1H), 7.56 (d, J=15.2 Hz, 1H), 7.57–7.64 (m, 3H), 7.65 (d, J=15.2 Hz, 1H), 7.73 (t, J=8.0 Hz, 1H), 7.90 (d, J=8.0 Hz, 1H), 8.10 (d, J=8.0 Hz, 1H).

MS(FAB) m/z 430 (M+H)$^+$.

Free compound:

$^1$H-NMR (400 MHz, CDCl$_3$); δ (ppm) 1.18 (t, J=7.2 Hz, 3H), 2.55 (q, J=7.2 Hz, 2H), 2.76 (br, 4H), 3.57 (br, 4H), 3.62 (t, J=4.8 Hz, 4H), 3.88 (t, J=4.8 Hz, 4H), 6.54 (d, J=8.4 Hz, 1H), 6.81 (d, J=6.8 Hz, 1H), 7.27 (s, 1H), 7.44 (ddd, J=8.4, 8.0, 1.2 Hz, 1H), 7.50 (dd, J=8.4, 6.8 Hz, 1H), 7.55 (ddd, J=8.4, 8.0, 1.2 Hz, 1H), 7.67 (br, 1H), 7.71 (d, J=8.0 Hz, 1H), 8.05 (d, J=8.4 Hz, 1H).

Example 214

Synthesis of 3-{(E)-2-[3-(4-Morpholinyl)Pyridazin-6-Yl]Ethenyl}-1-(4-Ethylpiperazin-1-Yl) Isoquinoline Oxalate

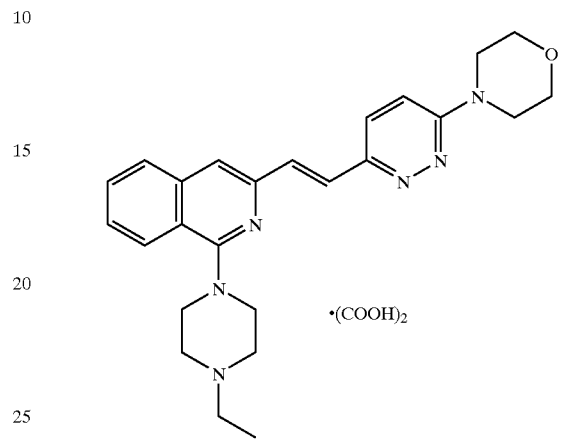

In the same manner as in Example 189, the free compound of the title compound was obtained (560 mg, yield; 87%) from 3-(4-morpholinyl)-6-vinylpyridazine (567 mg) and 3-bromo-1-(4-ethylpiperazin-1-yl)isoquinoline (476 mg). The resulting free compound was converted into an oxalate in a conventional manner, to give the oxalate of the title compound as yellow crystals.

Oxalate:

m.p.; 88–90° C.

$^1$H-NMR (400 MHz, DMSO-$d_6$); δ (ppm) 1.30 (t, J=7.2 Hz, 3H), 3.28 (q, J=7.2 Hz, 2H), 3.40 (br, 2H), 3.62 (t, J=4.8 Hz, 6H), 3.75 (t, J=4.8 Hz, 6H), 4.02 (br, 2H), 7.36 (d, J=9.6 Hz, 1H), 7.55 (s, 1H), 7.56 (d, J=16.0 Hz, 1H), 7.62 (t, J=8.0 Hz, 1H), 7.74 (t, J=8.0 Hz, 1H), 7.82 (d, J=16.0 Hz, 1H), 7.93 (d, J=9.6 Hz, 1H), 7.94 (d, J=8.0 Hz, 1H), 8.12 (d, J=8.0 Hz, 1H).

MS(FAB) m/z 431(M+H)$^+$.

Free compound:

$^1$-NMR(400 MHz,CDCl$_3$); δ (ppm) 1.17(t, J=7.2 Hz, 3H), 2.55(q, J=7.2 Hz, 2H), 2.75(br, 4H), 3.58(br, 4H), 3.67(t=4.8 Hz, 4H), 3.86(t, J=4.8 Hz, 4H), 6.89(d, J=9.6 Hz, 1H), 7.23(s, 1H), 7.45(t, J=8.0 Hz, 1H), 7.49(d, J=15.6 Hz, 1H), 7.51(d, J=9.6 Hz, 1H), 7.57(d, J=8.0 Hz, 1H), 7.72(d, J=8.0 Hz, 1H), 7.91(d, J=15.6 Hz, 1H), 8.05(d, J=8.0 Hz, 1H).

Example 215

Synthesis of 3{(E)-2-[4-(4-morpholinyl)pyrimidin-6-yl]ethenyl}-1-(4-ethylpiperazin-1-yl)isoquinoline oxalate

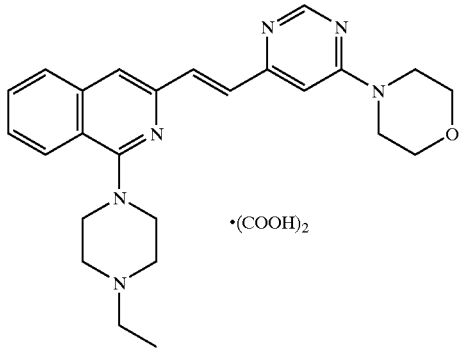

In the same manner as in Example 189, the free compound of the title compound was obtained (380 mg, yield: 70%) from 4-(4-morpholinyl)-6-vinylpyrimidine (360 mg) and 3-bromo-1-(4-ethylpiperazin-1-yl)isoquinoline (400 mg). The resulting free compound was converted into an oxalate in a conventional manner, to give the oxalate of the title compound as yellow crystals.

Oxalate:
m.p.; 130–134° C.
$^1$H-NMR(400 MHz, DMSO-$d_6$); δ (ppm) 1.31(t,J=7.2 Hz,3H), 3.29(q,J=7.2 Hz,2H), 3.39(br,2H), 3.74(br,10H), 4.03(br,2H), 7.19(s, 1H), 7.56(d,J=16.0 Hz,1H), 7.64(s,1H), 7.66(t,J=8.0 Hz,1H), 7.78(t,J=8.0 Hz,1H), 7.93(d,J=16.0 Hz,1H), 7.98(d,J=8.0 Hz,1H), 8.14(d,J=8.0 Hz,1H), 8.62(s, 1H).
MS(FAB m/z 431 (M+H)$^+$.

Free compound:
$^1$H-NMR(400 MHz,CDCl$_3$); δ (ppm) 1.18(t,J=7.2 Hz,3 H), 2.56(q,J=7.2 Hz,2H), 2.76(br,4H), 3.58(br,4H), 3.69(t, J=4 Hz,4H), 3.82(t,J=4.8 Hz,4H), 6.60(s,1H), 7.29(s,1H), 7.48(ddd,J=8.4,8.0,1.2 Hz,1H), 7.60(d,J=14.8 Hz,1H), 7.59 (ddd,J=8.4,8.0,1.2 Hz,1H), 7.74(d,J=8.0 Hz,1H), 7.84(d,J=14.8 Hz,1H), 8.06(d,J=8.4 Hz,1H), 8.64(s,1H).

Example 216

Synthesis of 3-{(E)-2-[2-(4-morpholinyl)pyrazin-6-yl]ethenyl}-1-(4-ethylpiperazin-1-yl)isoquinoline oxalate

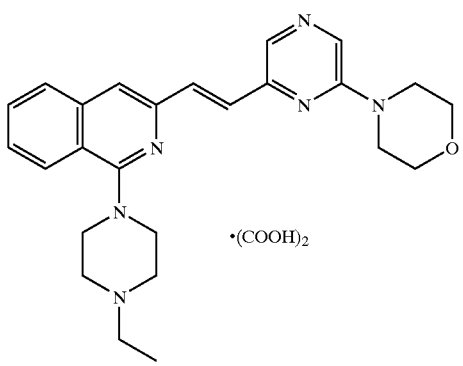

In the same manner as in Example 189, the free compound of the title compound was obtained (295 mg, yield; 69%) from 2-(4-morpholinyl)-6-vinylpyrazine (287 mg) and 3-bromo-1-(4-ethylpiperazin-1-yl)isoquinoline (320 mg). The resulting free compound was converted into an oxalate in a conventional manner, to give the oxalate of the title compound as yellow crystals.

Oxalate:
m.p.; 173–175° C.
$^1$H-NMR(400 MHz,DMSO-$d_6$); δ (ppm) 1.29(t,J=7.2 Hz,3H), 3.25(q,J=7.2 Hz,2H), 3.49(br,4H), 3.64(br,6H), 3.77(br,6H), 7.60(d,J=15.2 Hz,1H), 7.62(t,J=8.0 Hz,1H), 7.65(s,1H), 7.75(t,J=8.0 Hz,1H), 7.75(d,J=15.2 Hz,1H), 7.93(d,J=8.0 Hz,1H), 8.08(s,1H), 8.12(d,J=8.0 Hz,1H), 8.25 (s,1H).
MS(FAB) m/z 431 (M+H)$^+$.

Free compound:
$^1$H-NMR(400 MHz,CDCl$_3$); δ (ppm) 1.18(t,J=7.2 Hz,3H), 2.56(q,J=7.2 Hz,2H), 2.77(br,4H), 3.58(br,4H), 3.66(t,J=4.8 Hz,4H), 3.89(t,J=4.8 Hz,4H), 7.29(s,1H), 7.47 (dt,J=8.0,1.2 Hz,2H), 7.58(dt,J=8.0,1.2 Hz,1H), 7.69(s,1H), 7.70(s,1H), 7.72(d,J=8.0 Hz,1H), 8.01(s,1H), 8.02(s,1H), 8.06(d,J=8.0 Hz,1H).

Example 217

Synthesis of 3-[1-(4-methoxyphenyl)ethenyl]-1-(4-ethylpiperazin-1-yl)isoquinoline oxalate

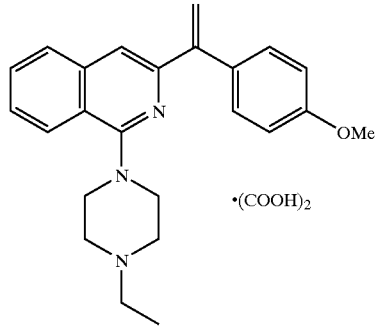

A 5N aqueous solution of hydrochloric acid (2 ml) was added to 3-[α-methyl-α-hydroxy-(4-methoxy)]-1-(4-ethylpiperazin-1-yl)isoquinoline (600 mg)/ethanol (10 ml) solution, and the resulting mixture was reacted with heating under reflux for 1 hr. The reaction solution was evaporated, and then basified with a 1N aqueous solution of sodium hydroxide and extracted with ethyl acetate. The resulting organic layer was washed with brine, dried and evaporated. The resulting residue was purified by NH-silica gel column chromatography (ethyl acetate/hexane system), to give a yellow oil (352 mg, yield; 62%). The resulting oil was converted into an oxalate in a conventional manner, to give the oxalate of the title compound as white crystals.

Oxalate:
m.p.;106–108° C.
$^1$H-NMR (400 MHz,DMSO-$d_6$); δ (ppm) 1.23(t,J=7.2 Hz,3H), 3.05(br,2H), 3.27(br,4H), 3.60(br,4H), 3.80(s,3H), 5.46(s,1H), 6.14(s,1H), 6.98(d,J=8.8 Hz,2H), 7.27(s,1H), 7.34(d,J=8.8 Hz,2H), 7.60(t,J=8.0 Hz,1H), 7.68(d,J=8.0 Hz,1H), 7.86(d,J=8.0 Hz,1H), 8.10(d,J=8.0 Hz,1H).
MS(FAB) m/z 362(M+H)$^+$.

Free compound:
$^1$H-NMR(400 MHz,CDCl$_3$); δ (ppm) 1.17(t,J=7.2 Hz,3H), 2.55(q,J=7.2 Hz,2H), 2.74(br,4H), 3.54(br,4H), 3.86(s,3H), 5.44(d,J=2.4 Hz,1H), 6.33(d,J=2.4 Hz,1H), 6.93 (d,J=8.8 Hz,2H), 7.09(s,1H), 7.38(d,J=8.8 Hz,2H), 7.44

(ddd,J=8.4,8.0,1.2 Hz,1H), 7.52(ddd,J=8.4,8.0,1.2 Hz,1H), 7.61(d,J=8.0 Hz,1H), 8.06(d,J=8.0 Hz,1H).

Example 218

Synthesis of 1-(ethylpiperazin-4-yl)-N-phenyl-3-isoquinolinecarboxamide dihydrochloride

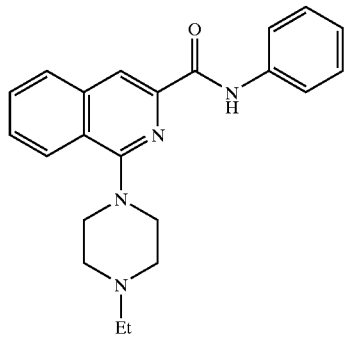

Isocarbostyryl-3-carboxylic acid (366 mg) synthesized according to Nippon Kagaku Zasshi (the Japanese Chemical Journal), 81 (6), 106, 1960 was added to phosphorous oxychloride (4 ml), which was then stirred at 110° C. for 20 min. The reaction solution was evaporated, and the resulting residue was dissolved in toluene (5 ml). A solution mixture of aniline (2 ml)/toluene (3 ml) was added thereto, and the mixture was stirred for 15 min. The reaction mixture was partitioned between ethyl acetate and 1N hydrochloric acid. The organic layer was washed with water, dried (over MgSO$_4$) and evaporated. 1-Ethylpiperadine (5 ml) was added to the resulting residue, which was then stirred at 120° C. for 30 min. The reaction solution was evaporated, and then partitioned between ethyl acetate and water. The organic layer was washed with water, dried (over MgSO$_4$) and evaporated, and the resulting residue was purified by silica gel column chromatography (ethyl acetate/acetone system). The resulting product was converted into a hydrochloride in a conventional manner, to give the hydrochloride of the title (504 mg, yield; 63%) as colorless crystals.

Hydrochloride:

m.p.; 260° C. (decomp.)

$^1$H-NMR(400 MHz,DMSO-d$_6$); δ (ppm) 1.32(3H,t,J=7.2 Hz) 3.21(1H,q,J=7.2 Hz), 3.23(1H,q,J=7.2 Hz), 3.33(1H,t, J=11.6 Hz), 3.36(1H,t,J=11.6 Hz), 3.54–3.62(4H, m), 4.18 (2H,d,J=14 Hz), 7.14(1H,tt,J=7.6 Hz,0.8 Hz), 7.40(2H,dd, J=7.6 Hz,7.6 Hz), 7.75(1H,ddd,J=8 Hz,7 Hz,1.2 Hz), 7.82 (2H,dd,J=7.6 Hz,0.8 Hz), 7.83(1H,ddd,J=8 Hz,7 Hz,1.2 Hz), 8.17(1H,d,J=8 Hz), 8.19(1H,d,J=8 Hz), 8.27(1H,s), 10.20 (1H,s), 11.00(1H,br-s).

ESI-Mass: 361(MH$^+$).

Example 219

Synthesis of 1-(1-ethylpiperazin-4-yl)-3-(4-methoxyanilinomethyl)isoquinoline oxalate (219-1) 1-Ethylpiperazin-4-yl)-3-N-(4-methoxyphenyl)isoquinolinecarboximide

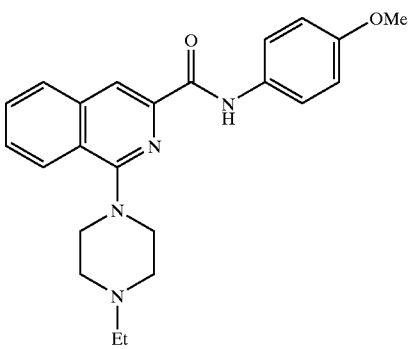

In the same manner as in Example 218, 793 mg of the title compound was obtained as a brown oil from isocarbostyryl-3-carboxylic acid (741 mg) and p-anisidine (916 mg).

$^1$H-NMR(400 MHz, CDCl$_3$); δ (ppm) 1.19(3H,t,J=7.2 Hz), 2.57(2H,q,J=7.2 Hz), 2.78(4H,t,J=4.4 Hz), 3.54(4H,t, J=4.4 Hz), 3.82(3H,s),6.94(2H,d,J=8.8 Hz), 7.60(1H,ddd, J=8 Hz,7 Hz,1.2 Hz), 7.67(1H,ddd,J=8 Hz,7 Hz,1.2 Hz), 7.70(2H,d,J=8.8 Hz), 7.91(1H,dd,J=8 Hz,1.2 Hz), 8.14(1H, dd,J=8 Hz,1.2 Hz), 8.27 (1H,s), 10.03(1H,s).

(219-2) 1-(1-Ethylpiperazine-4-yl)-3-(4-methoxyanilinomethyl)isoquinoline oxalate

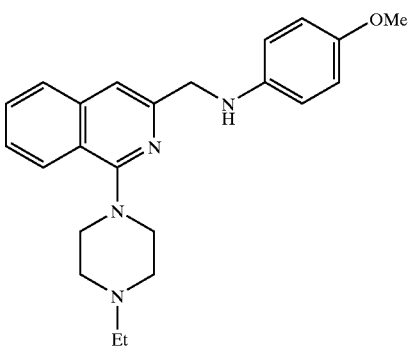

1-(1-Ethylpiperazin-4-yl)-3-N-(4-methoxyphenyl)isoquinolinecarboxamide (793 mg) was dissolved in tetrahydrofuran (15 ml), followed by the addition of lithium aluminum hydride (456 mg), and the mixture was stirred at 40° C. overnight. Water (0.5 ml), 1N sodium hydroxide (0.5 ml) and water (1.5 ml) were sequentially added thereto, and the resulting insoluble matters were filtered off through Celite. The resulting filtrate was partitioned between ethyl acetate and water. The resulting organic layer was washed with water, dried (over MgSO$_4$) and evaporated. The resulting residue was purified by (NH) silica gel column chromatography (ethyl acetate/hexane system). The resulting product was converted into an oxalate in a conventional manner, to give the title compound as a dark yellow amorphous (43 mg, yield; 5%).

$^1$H-NMR(400 MHz,DMSO-d$_6$); δ (ppm) 1.24(3H,t,J=7.2 Hz), 3.12(2H,q,J=7.2 Hz), 3.25–3.42(4H,m), 3.59(2H,s), 3.46–3.84(4H,m), 3.78(3H,s), 6.55(1H,d,J=9.2 Hz), 6.67 (1H,d,J=9.2 Hz), 6.94–7.02(2H,m), 7.37(1H,d,J=9.2 Hz), 7.64–7.84 (2H,m), 8.04–8.20(2H,m).

ESI-Mass; 377 MH$^+$)

Example 220

Synthesis of 1-(1-ethylpiperazin-4-yl)-3-(4-methoxybenzylamino)isoquinoline oxalate

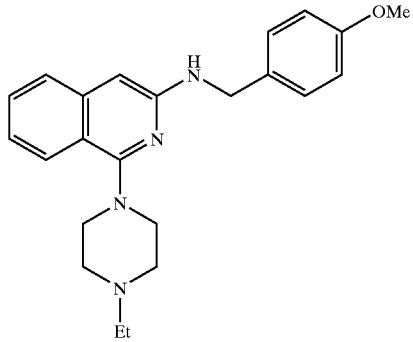

In the same manner as in Example 158, the oxalate of the title compound was obtained was obtained as a pale yellow amorphous (164 mg, yield; 42%) from 1-(1-ethylpiperazin-4-yl)-3-bromoisoquinoline (760 mg) and 4-methoxybenzylamine (449 mg).

Oxalate:

$^1$H-NMR (400 MHz,DMSO-d$_6$); δ (ppm) 1.16(3H,t,J=7.2 Hz), 2.52(1H,t,J=4.8 Hz), 2.88(2H,q,J=7.2 Hz), 3.00–3.12 (4H,m), 3.38–3.46(4H,m), 3.69(3H,s), 4.36(2H,d,J=4.8 Hz), 6.18 (1H,s), (6.85(2H,d,J=8.8 Hz), 7.05(1H,ddd,J=8 Hz,7 Hz,1.2 Hz), 7.27(2H,d,J=8.8 Hz), 7.35(1H,ddd,J=8 Hz,7 Hz,1.2 Hz), 7.40(1H,d,J=8 Hz), 7.76(1H,d,J=8 Hz). FAB-Mass; 377 (MH$^{30}$).

Example 221

Synthesis of 1-(1-ethylpiperazin-4-yl)-4-methoxy-3-(4-methoxyphenyl)isoquinoline dihydrochloride (221-1) 3-(4-Methoxyphenzylidine)phthalide

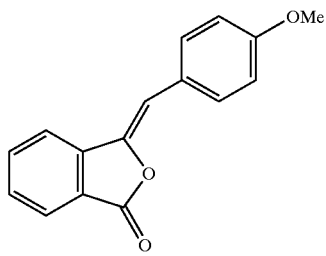

A mixture of phthalic anhydride (100 g), 4-methoxyphenylacetic acid (110.897 g) and sodium acetate (2.6 g) was melted at 200–220° C. for 6 hr. After the mixture was cooled to 90–95° C. as it stands, ethanol (600 ml) was added thereto and the insoluble matters were collected by filtration, to give the title compound as a yellow solid (83.016 g, yield; 49%).

$^1$H-NMR(400 MHz,CDCl$_3$); δ (ppm) 3.86(3H,s), 6.40 (1H,s), 6.95(2H,d,J=8.8 Hz), 7.52(1H,ddd,J=8 Hz,7 Hz,1.2 Hz), 7.71(1H,ddd,J=8 Hz,7 Hz,1.2 Hz), 7.75(1H,dt,J=8 Hz,1.2 Hz), 7.82(2H,d,J=8.8 Hz), 7.94(1H,dt,J=8 Hz,1.2 Hz).

(221-2) 3-Hydroxy-3-(4-methoxyphenzyl)phthalimidine

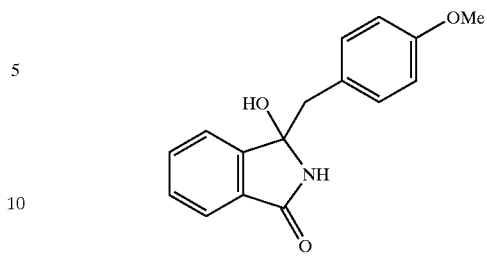

3-(4-Methoxybenzylidene)phthalide (15.168 g) was dissolved in ethanol (35 ml), followed by the addition of a 29% aqueous solution of ammonia (35 ml). The resulting mixture was stirred at 80° C. for 1 hr. The reaction solution was evaporated, followed by the addition of ether and the resulting precipitates were collected by filtration, to give the title compound as a yellow solid (16.202 g, yield: 100%).

$^1$H-NMR(400 MHz,CDCl$_3$); δ (ppm) 3.05(1H,d,J=13.8 Hz), 3.33(1H,d,J=13.8 Hz). 3.76(3H,s), 6.58(1H,br-s). 6.78 (2H,d,J=8.8 Hz), 7.211(2H,d,J=8.8 Hz), 7.41(1H,t,J=7.6 Hz), 7.48(1H,d,J=7.6 Hz), 7.53–7.59(2H,m).

(221-3-) (E)-3-(α-Bromo-4-methoxybenzylidene)phthalimidine

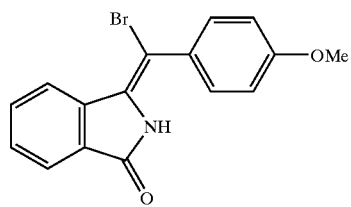

2-Hydroxy-3-(4-methoxybenzyl)phthalimidine (16.192 g) was dissolved in benzene (400 ml), N-bromosuccinide (14.523 ) g) was added thereto and the resulting mixture was heated under reflux for 2 hr. The reaction mixture was cooled, the resulting precipitates were filtered off. Then, the filtrate was washed with water, dried (over MgSO$_4$), evaporated, and the resulting residue was recrystallized from ethanol/hexane, to give the title compound as pale yellow crystals (11.074 g, yield; 57%).

$^1$H-NMR(400 MHz); δ (ppm) 3.90(3H,s), 6.74(1H,dt,J= 7.6 Hz,0.8 Hz), 7.00(2H,d,J=8.8 Hz), 7.30(1H,td, J=7.6 Hz,0.8 Hz), 7.42(1H,td,J=6.7 Hz,0.8 Hz), 7.43(2H,d,J=8.8 Hz), 7.83(1H,dt,J=7.6 Hz,0.8 Hz), 7.88(1H, br-s).

(221-4) 4-Methoxy-3-(4-methoxyphenyl)isoquinolin-1-(2H)-one

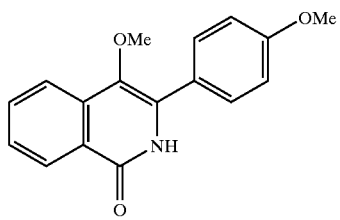

(E)-3-(α-Bromo-α-4-methyoxybenzylidene)phthalimidine (4.031 g) and potassium hydroxide (1.6 g) were added to methanol (20 ml), and the resulting mixture was heated at 200–220° C. for 1 hr. After cooling as it was, the reaction solution was evaporated, and the resulting residue was partitioned between ethyl acetate and water. The resulting organic layer was washed with water, dried (MgSO$_4$) and evaporated. Ether was added thereto, and the resulting insoluble matters were collected by filtration, to give the title compound as a pale yellow solid (1.786 g, yield: 52%).

$^1$H-NMR(400 MHz,CDCl$_3$); δ (ppm) 3.54(3H,s), 3.89 (3H,s), 7.04(2H,d,8.8 Hz), 7.53(1H,ddd,J=8 Hz,7 Hz,1.2 Hz), 7.62(1H,dd,J=8 Hz,1.2 Hz), 7.76(1H,ddd,J=8 Hz,7 Hz,1.2 Hz), 7.89(1H,dd,J=8 Hz,1.2 Hz), 8.41(1H,dd,J=8 Hz,1.2 Hz), 8.50(1H,br-s).

(221-5) 1-(1-Ethylpiperazin-4-yl)-4-methoxy-3-(4-methoxyphenyl)-isoquinoline dihydrochloride

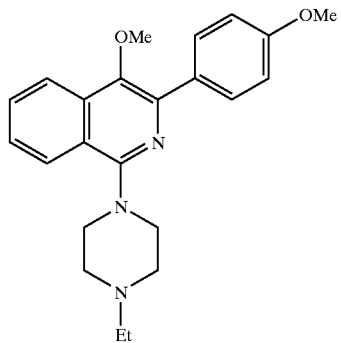

4-Methoxy-3-(4-methoxyphenyl)isoquinolin-1-(2H)-one (1.263 g) was treated in the same manner as in Example 252-4, to give the hydrochloride of the title compound as colorless crystals (recrystallized from ethanol/isopropyl ether) (632 mg, yield; 31%).

Hydrochloride:

m.p.; 227–235° C.

$^1$H-NMR(400 MHz,DMSO-d$_6$); δ (ppm) 1.30(3H,t,J=7.2 Hz), 3.20(1H,q,J=7.2 Hz), 3.22(1H,q,J=7.2 Hz), 3.26–3.38 (2H,m), 3.44(2H,t,J=13.2 Hz), 3.59(2H,d,J=11.2 Hz), 3.63 (3H,s), 3.82(3H,s),3.85(2H,d,J=13.2 Hz), 7.06(2H,d,J=8.8 Hz), 7.67(1H,ddd,J=8 Hz,7 Hz,1.2 Hz), 7.80(1H,ddd,J=8 Hz,7 Hz,1.2 Hz), 8.11(1H,d,J=8 Hz), 8.12(1H,d,J=8 Hz), 8.13(2H,d,J=8.8 Hz), 10.80–10.90(1H,br-s).

ESI-Mass; 378(MH$^+$).

Example 222

Synthesis of 1-(1-ethylpiperazin-4-yl)-5-methyl-3-(4-methoxyphenyl)isoquinoline dihydrochloride (221-1) (2,3-Dimethyl-N-methylbenzamide

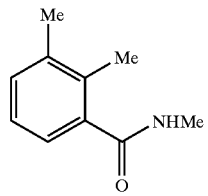

In the same manner as in Example 225-1, the title compound was obtained as a colorless solid (10.99 g, yield; 100%) from 2,3-dimethylbenzoic acid (10.068 g).

$^1$H-NMR(400 MHz,CDCl$_3$); δ (ppm) 2.38(3H,s), 2.30 (3H,s), 2.99(3H,d,J=4.8 Hz), 5.76(1H, br-s), 7.09(1H,t,J=7.4 Hz), 7.15(1H,d,J=7.4 Hz), 7.18(1H,d,J=7.4 Hz).

(222-2) 5-Methyl-3-(4-methoxyphenyl)isoquinoline-1-(2H)-one

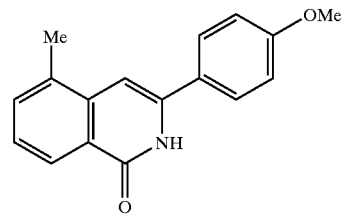

In the same manner as in Example 10-1, the title compound was obtained as a pale yellow solid (3.456 g, yield; 42%) from 2,5-dimethyl-N-methylbenzamide (5.008 g) and anisonitrile (4.128 g).

$^1$H-NMR(400 MHz,CDCl$_3$); δ (ppm) 2.59(3H,s), 3.89 (3H,s), 6.80(1H,s), 7.05(2H,d,J=8.8 Hz), 7.36(1H,t,J=7.6 Hz), 7.50(1H,d,J=7.6 Hz), 7.67(2H,d,J=8.8 Hz), 8.28(1H,d, J=7.6 Hz), 9.75(1H,s).

(222-3) 1-(1-Ethylpiperazin-4-yl)-5-methyl-3-(4-methoxyphenyl)isoquinoline dihydrochloride

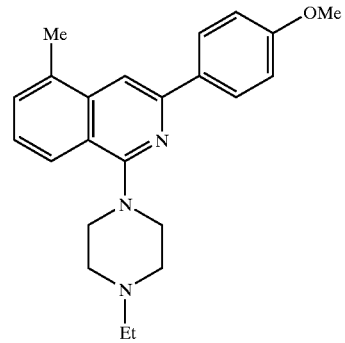

In the same manner as in Example 252-3, 5-methyl-3-(4-methoxyphenyl)isoquinoline-1-(2H)-one (1.003 mg) was treated, to give the hydrochloride of the title compound as yellow crystals (recrystallized in ethanol/isopropyl ether) (721 mg, yield; 45%).

Hydrochloride:

m.p.; 249–253° C.

$^1$H-NMR(400 MHz,DMSO-d$_4$); δ (ppm) 1.31(3H,t,J=7.2 Hz), 2.68(3H,s), 3.18(1H,q,J=7.2 Hz), 3.20(1H,q,J=7.2 Hz), 3.30(1H,t,J=10.6 Hz), 3.33(1H,t,J=10.6 Hz), 3.49(2H,t,J= 13.2 Hz), 3.59(2H,d,J=10.6 Hz), 3.81(3H,s), 3.92(2H,d,J= 13.2 Hz) 7.05(2H,d,J=8.8 Hz), 7.43(1H,t,J=7.6 Hz), 7.54 (1H,d,J=7.6 Hz), 7.92(1H,d,J=7.6 Hz), 7.93(1H,s), 8.18(2H, d,J=8.8 Hz), 10.06(1H,br-s).

ESI-Mass: 362(MH$^+$).

Example 223

Synthesis of 1-(4-ethylpiperazin-1-yl)-3-[4-(2-hydroxyethoxy)phenyl]-6-fluoroisoquinoline dihydrochloride

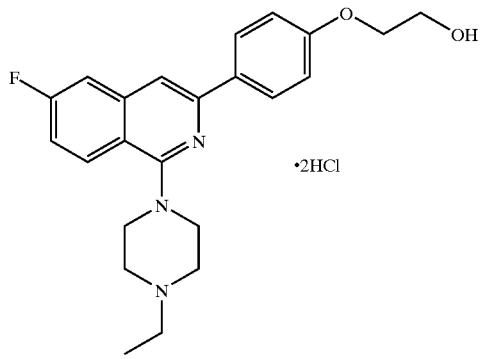

From starting materials 4-(2-benzyloxyethoxy)-1-ethynylbenzene (7.64 g) and 2-bromo-4-fluorobenzalhyde (4.38 g), 3-[4-(2-benzyloxyethoxy)phenyl]-1-(4-ethylpiperazin-1-yl)-6-fluoroisoquinoline was obtained according to Example 231. The resulting compound was hydrogenized in methanol in the presence of 10% palladium-carbon, for debenzylation. The catalyst was filtered off, the resulting solution was washed with methanol, and then 0.90 g of the title compound was obtained directly as a hydrochloride.

Hydrochloride:
m.p.; 152–170° C.
$^1$H-NMR(400 MHz,DMSO-d$_6$); δ (ppm) 1.31(t,J=7.2 Hz,3H), 3.14–3.24(m,2H), 3.25–3.36(m,2H), 3.47–3.62(m, 4H), 3.70–3.76(m,2H), 3.88–3.97(m,2H), 4.01–4.07(m,2H), 7.06(d,J=9.0 Hz,2H), 7.38–7.45(m,1H), 7.66–7.72(m,1H), 7.96(s,1H), 8.10(d,J=9.0 Hz,2H), 8.13–8.18(m,1H), 11.16–11.27(br,1H).
MS(FAB) m/z 396.00(M+H)$^+$.

Example 224

Synthesis of 1-(1-ethylpiperazin-4-yl)-6-fluoro-3-(4-methoxyphenyl)isoquinoline dihydrochloride (224-1) 2-Bromo-4-fluorobenzaldehyde

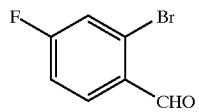

2-Bromo-4-fluorotoluene (10.215 g) was dissolved in ethyl acetate (100 ml), N-bromosuccinimide (11.3 g) and 70% benzoyl peroxide (200 mg) were added thereto, and the resulting mixture was stirred under heating at 80° C. for 1 hr. After the reaction solution was cooled, the resulting insoluble matters were filtered off. The resulting filtrate was washed with an aqueous solution of saturated sodium bicarbonate, dried (over MgSO$_4$) and evaporated. The resulting residue was dissolved in acetic acid (30 ml), water (30 ml) and hexamethylene tetramine (15.14 g) were added thereto, and the resulting mixture was heated under stirring at 100° C. for 1 hr. To the mixture was added 38% hydrochloric acid (20 ml), which was then stirred for 1 hr, and then it was cooled as it was, and extracted with ethyl acetate. The resulting organic phase was washed with an aqueous solution of saturated sodium bicarbonate, dried (over MgSO$_4$) and evaporated. The resulting residue was purified by silica gel column chromatography (ethyl acetate/hexane system), to give the title compound as a colorless solid (4.376 g, yield; 41%).

$^1$H-NMR(400 MHz,CDCl$_3$); δ (ppm) 7.14–7.19(1H,m), 7.40(1H,dd,J=8.4 Hz,2.4 Hz), 7.97(1H,dd,J=8.4 Hz,6 Hz), 10.30(1H,s).

(224-2) 6-Fluoro-3-(4-methoxyphenyl)isoquinoline-2-oxide

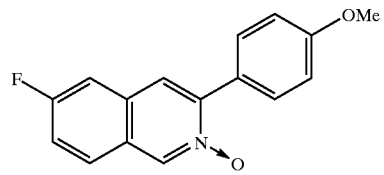

2-Bromo-4-fluorobenzaldehyde (1.003 g) and 4-methoxyphenylacetylene (714 mg) were treated in the same manners as in Examples 177, 251-3 and 251-4 in this order, to give the title compound as a dark green solid (467 mg, yield; 35%).

$^1$H-NMR(400 MHz,CDCl$_3$); δ (ppm) 3.88(3H,s), 7.03 (2H,d,J=8.8 Hz), 7.33–7.43(2H,m), 7.71–7.75(2H,m), 2H,d, J=8.8 Hz), 8.89(1H,s).

(224-3) (1-(1-Ethylpiperazin-4-yl)-6-fluoro-3-(4-methoxyphenyl)isoquinoline dihydrochloride

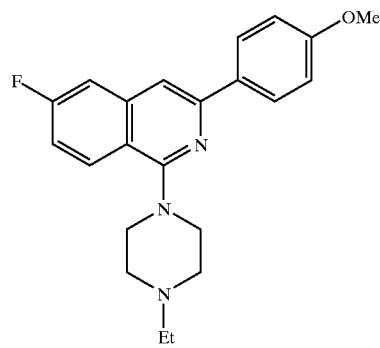

In the same manner as in Example 251, the hydrochloride of the title compound was obtained as yellow crystals (187 mg, yield; 24%) from 6-fluoro-3-(4-methoxyphenyl)isoquinoline-2-oxide (467 mg).

Hydrochloride:

m.p.; 131–135° C.

$^1$H-NMR(400 MHz,DMSO-d$_6$); δ (ppm) 1.30(3H,t,J=7.2 Hz), 3.20(1H,q,J=7.2 Hz), 3.22(1H,q,J=7.2 Hz), 3.30(1H,t, J=12 Hz), 3.33(1H,t,J=12 Hz), 3.49(2H,t,J=14 Hz), 3.60(2H, d,J=12 Hz), 3.81(3H,s), 3.95(2H,d,J=14 Hz), 7.06(2H,d,J= 8.8 Hz), 7.42(1H,td,J=9.2 Hz,2.8 Hz), 7.70(1H,dd,J=9.8 Hz,2.8 Hz), 7.97(1H,s), 8.11(2H,d,J=8.8 Hz), 8.16(1H,dd, J=9.2 Hz,5.6 Hz), 10.77(1H,br-s).

ESI-Mass; 366(MH$^+$).

Example 225

Synthesis of 1-(1-ethylpiperazin-4-yl)-6-methyl-3-(4-methoxyphenyl)isoquinoline dihydrochloride (225-1) 2,4-Dimethyl-N-methylbenzamide

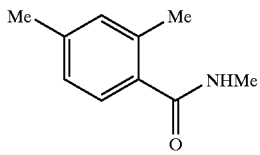

2,4-Dimethylbenzoic acid (11.877 g) was added to thionyl chloride (30 ml), and the resulting mixture was stirred under heating for 45 min. The reaction solution was evaporated, and then dissolved in tetrahydrofuran (50 ml). To the mixture was added dropwise 40% methylamine/methanol solution (100 ml) under ice-cooling, and then it was stirred for 20 min. The resulting reaction solution was evaporated, and then partitioned between ethyl acetate and water. The resulting organic layer was washed with water, dried (over MgSO$_4$) and evaporated, to give the title compound as a colorless solid (12.281 g, yield; 95%).

$^1$H-NMR(400 MHz,CDCl$_3$); δ (ppm) 2.32(3H,s), 2.42 (3H,s), 2.99(3H,d,J=5.6 Hz), 5.74(1H,br-s), 6.99(1H,d,J=8.4 Hz), 7.03(1H,s), 7.25(1H,d,J=8.4 Hz).

(225-2) 6-Methyl-3-(4-methoxyphenyl)isoquinoline-1-(2H)-one

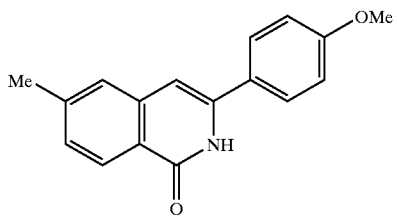

In the same manner as in Example 10-1, the title compound was obtained as a pale yellow solid (3.140 g, yield; 39%) from 2,4dimethyl-N-methylbenzamide (5.008 g) and anisonitrile (4.128 g).

$^1$H-NMR(400 MHz,CDCl$_3$); δ (ppm) 2.49(3H,s), 3.88 (3H,s), 6.64(1H,s), 7.02(2H,d,J=8.8 Hz), 7.27(1H,d,J=8 Hz), 7.35(1H,s), 7.65(2H,d,J=8.8 Hz), 8.27(1H,d,J=8 Hz), 9.84(1H,br-s).

(225-3) 1-(1-Ethylpiperazin-4-yl)-6-methyl-3-(4-methoxyphenyl)isoquinoline dihydrochloride

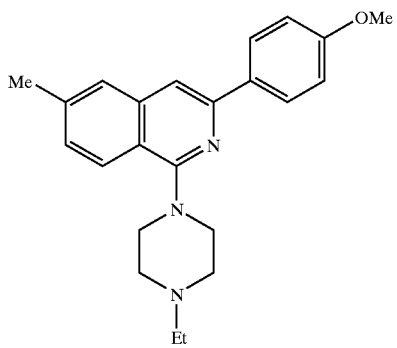

6-Methyl-3-(4-methoxyphenyl)isoquinoline-1-(2H)-one (1.024 mg) was treated in the same manner as in Example 252-3, to give the hydrochloride of the title compound as yellow crystals (recrystallized in ethanol/isopropyl ether) (1.084 g, yield; 64%).

Hydrochloride:
  m.p.; 219–221° C.
  $^1$H-NMR (400 MHz, DMSO-d$_6$); δ (ppm) 1.31(3H,t,J=7.2 Hz), 2.49(3H, s), 3.19(1H,q,J=7.2 Hz), 3.21(1H,q,J=7.2 Hz), 3.29(1H,t,J=10.4 Hz), 3.32(1H,t,J=10.4 Hz), 3.50(2H,t,J=13.6 Hz), 3.59(2H,d,J=10.4 Hz), 3.80(3H,s), 3.94(2H,d,J=13.6 Hz), 7.04(2H,d,J=8.8 Hz), 7.38(1H,dd,J=8.8 Hz,1.6 Hz), 7.70(1H, s), 7.86(1H,s), 7.97(1H,d,J=8.8 Hz), 8.11(2H, d,J=8.8 Hz), 11.05(1H,br-s).
  ESI:Mass; 326(MH$^+$).

Example 226

Synthesis of 1-(4-ethylpiperazin-1-yl)-6-methoxy-3-(4-triflouromethylphenyl)isoquinoline dihydrochloride

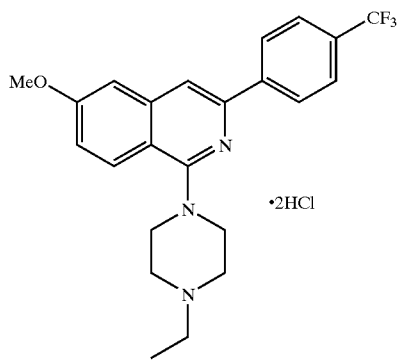

6-Methoxy-3-(4-trifluoromethylphenyl)isoquinoline-1-one obtained by reacting N-methyl-4-methoxy-2-methylbenzamide (1.0 g) and 4-trifluoromethylbenzonitrile (0.96 g) according to Example 10-1 was reacted with phosphorus oxychloride (10 ml) according to Example 10-2, to give 1-chloro-6-methoxy-3-(4-trifluoromethylphenyl) isoquinoline dihydrochloride.

Subsequently, the resulting compound was reacted with N-ethylpiperazine (15 ml) at 100° C. for 6 hr. The reaction solution was evaporated, and to the resulting residue were added ethyl acetate and water. The resulting organic layer was washed with water and brine, and dried over magnesium sulfate. The solvent was evaporated, and the resulting residue was purified by silica gel column chromatography (methylene chloride/methanol system), to give the free compound of the title compound as a pale yellow oil.

Free compound:
  $^1$H-NMR(400 MHz,CDCl$_3$); δ (ppm) 1.18(t,J=8.0 Hz,3H), 2.57(q,J=8.0 Hz, 2H), 2.76(m, 4H), 3.56(m,4H), 3.95(s,3H), 7.08–7.14(m, 2H), 7.65(s,1H), 7.71(d,J=8.4 H,2H), 7.99(d,J=8.0 Hz,1H), 8.25(d,J=8.4 Hz,1H).

The resulting free compound was converted into a hydrochloride in a conventional manner, and recrystallized from ethanol/ether, to give 0.20 g of the title compound as a yellow powder.

Hydrochloride:
  m.p.; 232–233° C.
  $^1$H-NMR(400 MHz,DMSO-d$_6$); δ (ppm) 1.32(t,J=7.2 Hz,3H), 3.20–3.28(m,2H), 3.29–3.41(m,2H), 3.41–3.52(m, 2H), 3.58–3.82(m,2H), 3.94(s,3H), 3.93–4.01(m,2H), 7.27 (dd,J=9.2,2.4 Hz,1H), 7.45(d,J=2.4 Hz,1H), 7.88(d,J=8.0

Hz,1H), 8.07(d,J=9.2 Hz,1H), 8.16(s,1H), 8.39(d,J=8.0 Hz,1H).

MS(FAB) m/z 386(M+H)+.

Example 227

Synthesis of 1-(4-ethylpiperazin-1-yl)-6-methoxy-3-(4-methoxyphenyl)isoquinoline dihydrochloride

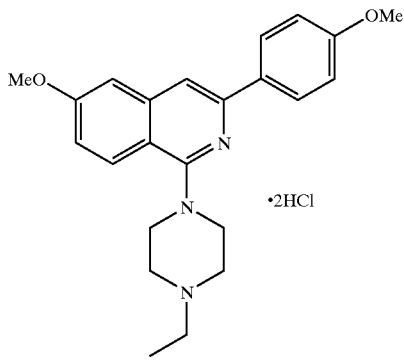

6-Methoxy-3-(4-methoxyphenyl)isoquinolin-1-one (0.40 g) obtained by reacting N-methyl-4-methoxy-2-methylbenzamide (1.0 g) and 4-methoxybenzonitrile (0.75 g) according to Example 10-1 was reacted with phosphorus oxychloride (10 ml) according to Example 10-2, to give 1-chloro-6-methoxy-3-(4-methoxyphenyl)isoquinoline.

Subsequently, the resulting compound was reacted with N-ethylpiperazine (10 ml) at 120° C. for 5 hr. The reaction solution was evaporated, and to the resulting residue were added ethyl acetate and water. The resulting organic layer was washed with water and brine, and dried over magnesium sulfate. The solvent was evaporated, and the resulting residue was purified by silica gel column chromatography (methylene chloride/methanol system), to give the free compound of the title compound was obtained as a pale yellow oil.

Free compound:

$^1$H-NMR(400 MHz,CDCl$_3$); δ (ppm) 1.17(t,J=8.0 Hz,3H), 2.56(q,J=8.0 Hz,2H), 2.76(m,4H), 3.56(m,4H), 3.86(s,3H), 3.92(s,3H), 6.99(t,J=9.2 Hz,2H), 7.32(m,2H), 7.54(s,1H), 7.95(d,J=9.4 Hz,1H), 8.10(d,J=9.2 Hz,2H).

The resulting free compound was converted into a hydrochloride in a conventional manner, and recrystallized from ethanol/ether, to give 86 mg of the title compound as a yellow powder.

Hydrochloride:

m.p.;218–220° C.

$^1$H-NMR(400 MHz,DMSO-d$_6$); δ (ppm) 1.32(t,J=7.2 Hz,3H), 3.19–3.28(m,2H), 3.28–3.39(m,2H), 3.40–3.51(m, 2H), 3.54–3.70(m,2H), 3.83(s,3H), 3.92(s,3H), 3.90–3.98 (m,2H), 7.07(d,J=9.0 Hz,2H), 7.17(dd,J=8.8,2.4 Hz,1H), 7.36(d,J=2.4 Hz,1H), 7.91(s,1H), 8.00(d,J=8.8 Hz,1H), 8.12 (d,J=9.0 Hz,2H), 10.58(br-s,1H).

MS(FAB) m/z 378(M+H)+.

Example 228

Synthesis of 1-(1-ethylpiperazin-4-yl)-7-methyl-3-(4-methoxyphenyl)isoquinoline dihydrochloride (228-1) 2,5-Dimethyl-N-methylbenzamide

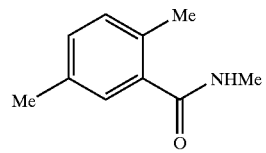

In the same manner as in Example 225-1, the title compound was obtained as a colorless solid (9.656 g, yield; 88%) from 2,5-dimethylbenzoic acid (10.083 g).

$^1$H-NMR (400 MHz,CDCl$_3$); δ (ppm) 2.31(3H,s), 2.39 (3H,s), 2.99(3H,d,4.8 Hz), 5.72(1H,br-s), 7.10(2H,s), 7.26 (1H,s).

(228-2) 7-Methyl-3-(4-methoxyphenyl)isoquinoline-1-(2H)-one

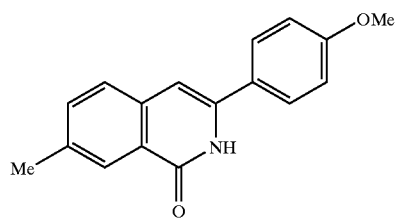

In the same manner as in Example 10-1, the title compound was obtained as a pale yellow solid (1.053 g, yield; 13%) from 2,5-dimethyl-N-methylbenzamide (5.002 g) and anisonitrile (4.128 g).

$^1$H-NMR(400 MHz,CDCl$_3$); δ (ppm) 2.50(3H,s), 3.88 (3H,s), 6.68(1H,s), 7.02(2H,d,J=8.8 Hz), 7.49(1H,d,J=1.2 Hz), 8.20(1H,s), 9.41(1H,br-s).

(228-3) 1-(1-Ethylpiperazin-4-yl)-7-methyl-3-(4-methoxyphenyl)isoquinoline dihydrochloride

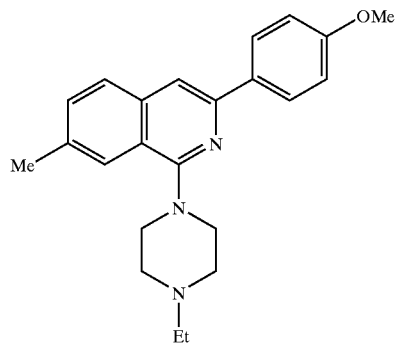

7-Methyl-3-(4-methoxyphenyl)isoquinoline-1-(2H)-one (0.153 mg) was treated in the same manner as in Example 252-3, to give the hydrochloride of the title compound as yellow crystals (recrystallized in ethanol/isopropyl ether) (1.085 g, yield; 63%).

Hydrochloride:

m.p.; 243–246° C.

$^1$H-NMR(400 MHz, DMSO-d$_6$); δ (ppm) 1.32(3H,t,J=7.2 Hz), 2.51(3H,s), 3.20(1H,q,J=7.2 Hz), 3.22(1H,q,J=7.2 Hz), 3.32(1H,t,J=11.6 Hz), 3.35(1H,t,J=11.6 Hz), 3.49(2H,t,J= 13.6 Hz), 3.60(2H,d,J=11.6 Hz), 3.93(2H,d,J=13.6 Hz), 3.80

(3H,s), 7.04(2H,d,J=8.8 Hz), 7.55(1H,dd,J=8.4 Hz,1.2 Hz), 7.83(1H,d,J=1.24 Hz), 7.84(1H,d,J=8.4 Hz), 7.94(1H,s), 8.11(2H,d,J=8.8 Hz), 11.00(1H,br-s).

ESI-Mass; 362(MH+).

Example 229

Synthesis of 1-(4-ethylpiperazin-1-yl)-7-fluoro-3-(4-methoxyphenyl)isoquinoline dihydrochloride

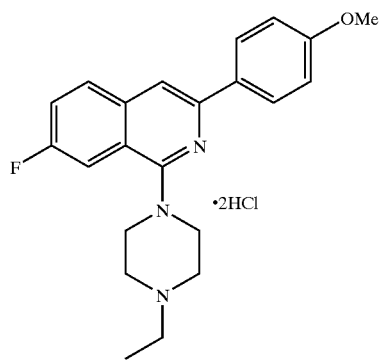

From starting materials 4-ethynylanisole (12.5 g) and 2-bromo-5-fluorobenzaldehyde (2.15 g), 2.67 g of the free compound of the title compound was obtained according to Example 231.

Free compound:

$^1$H-NMR (400 MHz,CDCl$_3$); δ (ppm) 1.18(t,J=7.20 Hz,3H), 2.56(q,J=7.20 Hz,2H), 2.80–2.70(br,4H), 3.57–3.50 (br,4H), 3.87(s,3H), 7.00(d,J=8.80 Hz,2H), 7.38–7.33(m, 1H), 7.61(s,1H), 7.69–7.66 (m, 1H), 7.79–7.775(m,1H), 8.10(d,J=8.8 Hz,2H).

The resulting free compound was converted into a hydrochloride in a conventional manner, and recrystallized from ethanol/ether, to give the title compound as a yellow powder.

Hydrochloride:

m.p.; 220–225° C.

$^1$H-NMR(400 MHz, DMSO-d$_6$); δ (ppm) 3.60–3.20(m, 8H), 3.81(s,3H), 3.94–3.90(m,2H), 7.06(d,J=9.00 Hz,2H), 7.68–7.62(m,1H), 7.82–7.76(m,1H), 8.07–8.01(m,2H), 8.12 (d,J=9.00 Hz,2H).

MS(FAB) m/z 366.00(M+H)+.

Example 230

Synthesis of 1-(4-ethylpiperazin-1-yl)-3-[4-(2-hydroxyethoxy)phenyl]-7-fluoroisoquinoline dihydrochloride

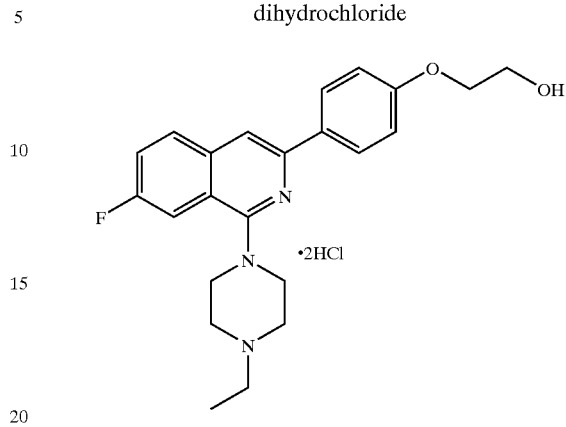

1-(4-Ethylpiperazin-1-yl)-7-fluoro-3-(4-methoxyphenyl) isoquinoline obtained in Example 229 was converted into the free compound of the title compound in the same manners as in Examples 7 and 36.

Free compound:
$^1$H-NMR(400 MHz,CDCl$_3$); δ (ppm) 1.18(t,J=7.2 Hz, 3H), 2.57(q,J=7.2 Hz,2H), 2.82–2.70(m,4H), 3.58–3.48(m, 4H), 4.03–3.98(m,2H), 4.18–4.14(m,2H), 7.02(d,J=8.8 Hz,2H), 7.39–7.33(m,1H), 7.62(s,1H), 7.69–7.65(m,1H), 7.80–7.75(m,1H), 8.10(d,J=8.8 Hz,2H).

The resulting free compound was converted into a hydrochloride in a conventional manner, and recrystallized from ethanol/ether, to give 0.57 g of the title compound as a yellow powder.
Hydrochloride:
m.p.; 225–229° C.
$^1$H-NMR (400 MHz,DMSO-d$_6$); δ (ppm) 1.31(t,J=7.3 Hz,3H), 3.29–3.17(m, 2H), 3.64–3.30(m,6H), 3.76–3.71(m, 2H), 3.96–3.87(m,2H), 4.06–4.01(m,2H), 7.06(d,J=9.00 Hz,2H), 7.68–7.62(m, 1H), 7.81–7.76(m,1H), 8.07–8.01(m, 2H), 8.11(d,J=9.00 Hz,2H), 10.79–10.66(m,1H).
MS(FAB) m/z 396.00(M+H)+.

Example 231

Synthesis of 1-(4-ethylpiperazin-1-yl)-7-methoxy-3-phenylisoquinoline dihydrochloride (231-1) 2-(2-Phenylethynyl)-5-methoxybenzaldehyde

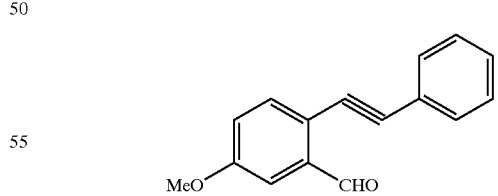

Phenylacetylene (2.04 g) and 2-bromo-5-methoxybenzaldehyde (2.15 g) was reacted in dimethylformamide (10 ml) in the presence of dichloro-bis-triphenylphosphine palladium (0.3 g), cuprous iodide (0.15 g) and triethylamine (2 ml) is nitrogen atmosphere at 50° C. for 6 hr. The resulting solution was evaporated, and to the resulting residue were added ethyl acetate and water. The resulting organic layer was washed with water and brine, and dried over magnesium sulfate. The solvent was evaporated, and the resulting residue was purified by silica gel column chromatography (ethyl acetate/hexane system), to give the hydrochloride of the title compound as a pale yellow oil (0.48 g, yield; 20%).

(231-2) 7-Methoxy-3-phenylisoquinoline-2-oxide

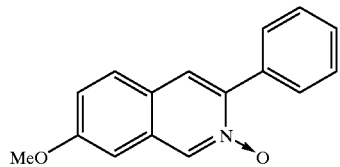

2-(2-Phenylethynyl)-5-methoxybenzaldehyde (0.48 g) was reacted with hydroxylamine hydrochloride (0.17 g) and sodium acetate (0.21 g) in ethanol (10 ml) at 60° C. for 2 hr. Potassium carbonate (0.3 g) and water (1 ml) were added to the reaction mixture, and it was heated under reflux for 12 hr. The reaction solution was evaporated. The resulting residue was extracted with methylene chloride, and then washed with brine and dried. The solvent was removed, and the resulting residue was purified by silica gel column chromatography (methylene chloride/methanol system), to give 0.30 g of the title compound as a yellowish brown amorphous.

(231-3) 1-Chloro-7-methoxy-3-phenylisoquinoline

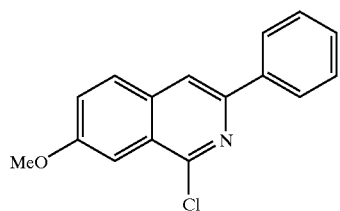

7-Methoxy-3-phenylisoquinoline-2-oxide (0.30 g) was reacted with phosphorus oxychloride (3 ml) at 110° C. for 2 hr.

The reaction solution was evaporated, and to the resulting residue were added ethyl acetate and an aqueous solution of saturated sodium bicarbonate. The resulting organic layer was washed with water and brine, and dried over magnesium sulfate. The solvent was evaporated, and the resulting residue was purified by silica gel column chromatography (ethyl acetate/hexane system), to give 0.20 g of the title compound was obtained as a white solid.

(231-4) 1-(4-Ethylpiperazin-1-yl)-7-methoxy-3-phenylisoquinoline dihydrochloride

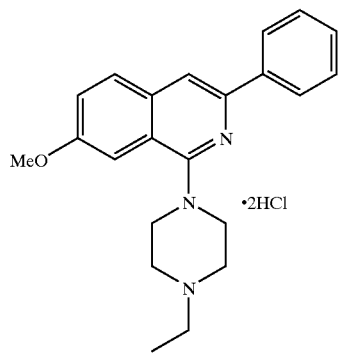

1-Chloro-7-methoxy-3-phenylisoquinoline (0.20 g) was reacted with N-ethylpiperazine (3 ml) and potassium carbonate (0.2 g) at 120° C. for 5 hr. To the reaction solution were added ethyl acetate and water, and it was extracted with ethyl acetate. The resulting organic layer was washed with water and brine, and dried over magnesium sulfate. The solvent was evaporated, and the resulting residue was purified by silica gel column chromatography (methylene chloride/methanol system, to give 0.18 g of the free compound of the title compound as a pale yellow oil.

Free compound:

$^1$H-NMR (400 MHz,CDCl$_3$); δ (ppm) 1.17(t,J=7.2 Hz,3H), 2.56(q,J=7.2 Hz,2H), 2.77(m,4H), 3.56(m,4H), 3.95(s,3H), 7.23–7.29(m,1H), 7.32–7.40(m,1H), 7.42–7.48 (m,2H), 7.68(s,1H), 7.73(d,J=7.6 Hz,1H), 8.15(br-d,1H).

The resulting free compound was converted into a hydrochloride in a conventional manner, and then recrystallized from ethanol/ether, to give 0.18 g of the title compound as a yellow powder.

Hydrochloride:

m.p.; 130–132° C.

$^1$H-NMR(400 MHz,DMSO-d$_6$); δ (ppm) 1.32(t,J=7.2 Hz,3H), 3.19–3.28(m,2H), 3.36(q,J=7.2 Hz,2H), 3.51(br-t, 2H), 3.62(br-d,2H), 3.96(s,3H), 3.93–4.01(m,2H), 7.33(d,J= 2.4 Hz,1H), 7.37–7.43(m,1H), 7.44(dd,J=9.0,2.4 Hz,1H), 7.48–7.53(m,2H), 7.96(d,J=9.0 Hz,1H), 8.08(s,1H), 8.16–8.20(m,1H), 10.96(br-s,1H).

MS(FAB) m/z 348(M+H)$^+$.

Example 232

Synthesis of 1-(4-ethylpiperazin-1-yl)-7-methoxy-3-(2-methoxyphenyl)isoquinoline dihydrochloride (232-1) 2-Ethynylanisole

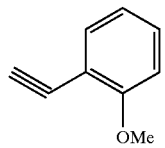

2-Iodoanisole (10.5 g) and trimethylsilylacetylene (10.3 g) were reacted in dimethylformamide (50 ml), in the presence of dichloro-bis-triphenylphosphine palladium (1.0 g), cuprous iodide (0.5 g) and triethylamine (15 ml) in nitrogen atmosphere at 50° C. for 12 hr. The resulting reaction solution was evaporated, and to the resulting residue was added ethyl acetate and water. The resulting organic layer was washed with water and brine, and dried over magnesium sulfate. The solvent was evaporated, and the resulting residue was dissolved in methanol (100 ml), a 5N aqueous solution of sodium hydroxide (20 ml) was added thereto, and then reacted at 60° C. for 1 hr. The reaction solution was evaporated, and to the resulting residue was added ether and water. The resulting ether layer was washed with water and brine, and dried over magnesium sulfate. The solvent was evaporated, and the resulting residue was purified by silica gel column chromatography (ethyl acetate/hexane system), to give the title compound as a pale yellow oil (3.02 g, yield; 51%).

(232-2) 2-[2-Methoxyphenyl)ethynyl]-5-methoxybenzaldehyde

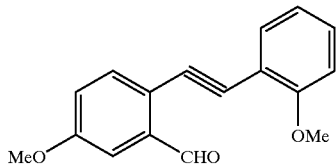

The resulting 2-ethynylanisole (0.79 g) and 2-bromo-5-methoxybenzaldehyde (1.14 g) was reacted in dimethylformamide (50 ml) in the presence of dichloro-bis-triphenylphosphine palladium (1.0 g), cuprous iodide (0.5 g) and triethylamine (15 ml), in nitrogen atmosphere at 50° C. for 6 hr. The resulting reaction solution was evaporated, and to the resulting residue were added ethyl acetate and water. The resulting organic layer was washed with water and brine, and dried over magnesium sulfate. The solvent was evaporated, and the resulting residue was purified by silica gel column chromatography (ethyl acetate/hexane system), to give 0.95 g of the title compound as a pale yellow oil.

(232-3) 7-Methoxy-3-(2-methoxyphenyl)isoquinoline-2-oxide

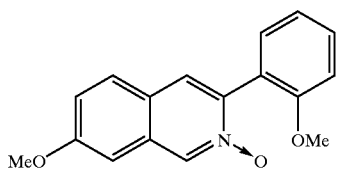

2-[2-(2-Methoxyphenyl)-ethynyl]-5-methoxybenzaldehyde (0.95 g), hydroxylamine hydrochloride (0.25 g) and sodium acetate (0.32 g) were reacted in ethanol (20 ml) at 60° C. for 2 hr. Potassium carbonate (0.6 g) and water (2 ml) were added to the reaction mixture, and the mixture was heated under reflux for 12 hr. The reaction solution was evaporated, and then the resulting residue was extracted with methylene chloride, washed with brine and dried. The solvent was removed, and the resulting residue was purified by silica gel column chromatography (methylene chloride/methanol system), to give 0.60 g of the title compound as a yellowish brown amorphous.

(232-4) 1-Chloro-7-methoxy-3-(2-methoxyphenyl)isoquinoline

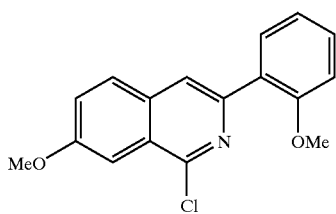

7-Methoxy-3-(2-methoxyphenyl)isoquinoline-2-oxide (0.60 g) and phosphorous oxychloride (5 ml) were reacted at 110° C. for 2 hr. The reaction solution was concentrated, and to the resulting residue were added ethyl acetate and an aqueous saturated sodium bicarbonate. The resulting organic layer was washed with water and brine, and dried over magnesium sulfate. The solvent was evaporated, and the resulting residue was purified by silica gel column chromatography (ethyl acetate/hexane system), to give 0.56 g of the title compound as a white solid.

(232-5) 1-(4-Ethylpiperazin-1-yl)-7-methoxy-3-(2-methoxyphenyl)isoquinoline dihydrochloride

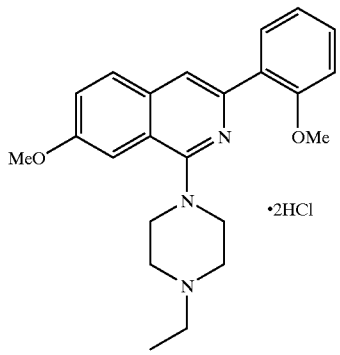

1-Chloro-7-methoxy-3-(2-methoxyphenyl)isoquinoline (0.56 g) (was reacted with N-ethylpiperazine (5 ml) and potassium carbonate (0.5 g) at 120° C. for 5 hr. To the resulting reaction solution were added ethyl acetate and water, and then it was extracted with ethyl acetate. The resulting organic layer was washed with water and brine, and dried over magnesium sulfate. The solvent was evaporated, and the resulting residue was purified by silica gel column chromatography (methylene chloride/methanol system), to give 0.43 g of the free compound of the title compound as a pale yellow oil.

Free compound:
$^1$H-NMR(400 MHz,CDCl$_3$); δ (ppm) 1.16(t,J=7.2 Hz,3H), 2.56(q,J=7.2 Hz, 2H), 2.76(m,4H), 3.52(m,4H), 3.92(s,3H), 3.94(s,3H), 7.02(d,J=8.0 Hz,1H), 7.09(t,J=8.0 Hz,1H), 7.22–7.27(m,1H), 7.30(br-t,1H), 7.38(br-s,1H), 7.71(d,J=8.8 Hz,1H), 7.97(s,1H), 8.12(br-d,1H).

The resulting free compound was converted into a hydrochloride in a conventional manner, and then recrystallized from ethanol/ether, to give 0.32 g of the title compound as a yellow powder.

Hydrochloride:
m.p.; 178–179° C.
$^1$H-NMR(400 MHz,DMSO-d$_6$); δ (ppm) 1.33(t,J=7.2 Hz,3H), 3.18–3.28(m,2H), 3.36(q,J=7.2 Hz,2H), 3.43–3.54 (m,2H), 3.61(br-d,2H), 3.78–4.00(m,2H), 3.90(s,3H), 3.95 (s,3H), 7.10(br-t,1H), 7.17(d,J=8.0 Hz,1H), 7.34(d,J=2.4 Hz,1H), 7.40(br-t,1H), 7.43(dd,J=8.8,2.4 Hz,1H), 7.93(d,J= 8.8 Hz,1H), 7.99(dd,J=7.6,1.6 Hz,1H), 10.89(br-s,1H)
MS(FAB) m/z 378(M+H)$^+$.

Example 233

Synthesis of 1-(1-ethylpiperazin-4-yl)-8-fluoro-3-(4-methoxyphenyl)isoquinoline dihydrochloride (233-1) 2-Fluoro-6-iodobenzaldehyde

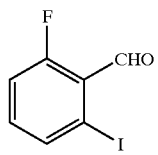

2-Fluoro-6-iodobenzonitrile (10.274 g) was dissolved in Toluene (100 ml), followed by the dropwise addition of 1.5M diisobutylaluminum hydride/toluene solution (31 ml) in nitrogen atmosphere at −70° C., and the mixture was stirred for 25 min. Subsequently, it was stirred at room temperature for further 45 min. To the mixture was added 5% sulfuric acid and it was stirred for 1 hr. Sequentially, the resulting solution was extracted with ethyl acetate, and the resulting organic layer was washed with water, dried (over MgSO$_4$) and evaporated. The resulting residue was purified by silica gel column chromatography (ethyl acetate/hexane system), to give the title compound as yellow oil (8.683 g, yield; 83%).

$^1$H-NMR(400 MHz,CDCl$_3$); δ (ppm) 7.15–7.26 (2H,m), 7.82(1H,d,J=7.6 Hz), 10.15(1H,s).

(233-2) 1-(1-Ethylpiperazin-4-yl)-8-fluoro-3-(4-methoxyphenyl)isoquinoline dihydrochloride

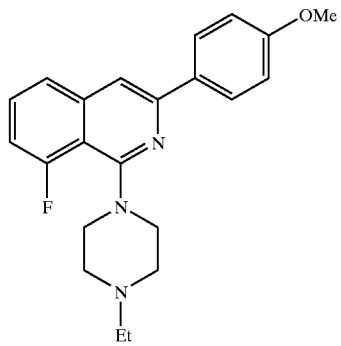

2-Fluoro-6-iodobenzalhyde (7.012 g) and 4-methoxyphenylacetylene (4.756 g) were treated in the same manner as in Example 139-1, and then the resulting product was treated in the same manner as in Example 251-3 and continuously in the same manner as in Example 251-4, to give 8-fluoro-3-(4-methoxyphenyl)isoquinoline-2-oxide as a grayish black solid (4.556 g). A part (234 mg) of the solid was treated in the same manner as in Example 251-5, to give the hydrochloride of the title compound as yellow crystals (217 mg, yield; 29%).

Hydrochloride:

m.p.; 222–227° C.

$^1$H-NMR(400 MHz,DMSO-d$_6$); δ (ppm) 1.30(3H,t,J=7.2 Hz), 3.13–3.24(4H,m), 3.45(2H,t,J=14 Hz), 3.60(2H,d,J= 11.6 Hz), 3.93(2H,d,J=14 Hz), 7.06(2H,d,J=8.8 Hz), 7.32 (1H,ddd,J=12.8 Hz,7.9 Hz,1 Hz), 7.68(1H,ddd,J=8.2 Hz,7.9 Hz,4.8 Hz), 7.76(1H,dd,J=8.2 Hz,1 Hz), 7.98(1H,d,J=2.4 Hz), 8.14(2H,d,J=8.8 Hz), 11.00–11.10(1H,br-s). FAB-Mass; 366(MH$^+$).

Example 234

Synthesis of 1-(1-ethylpiperazin-4-yl)-8-fluoro-3-[4-(2-hydroxyethoxy)phenyl]isoquinoline dihydrochloride (234-1) 1-(1-Ethylpiperazin-4-yl)-8-fluoro-3-(4-hydroxyphenyl)isoquinoline

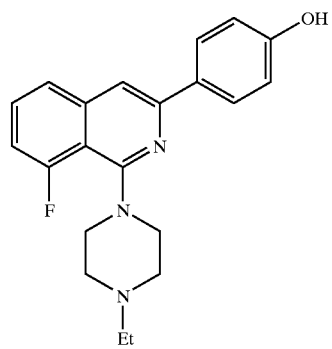

In the same manner as in Example 3-1, the title compound was obtained as a yellow solid (1.636 g, yield; 75% from 1-(1-ethylpiperazin-4-yl)-8-fluoro-3-(4-methoxyphenyl) isoquinoline (2.285 g).

$^1$H-NMR(400 MHz,CDCl$_3$); δ (ppm) 1.22(3H,t,J=7.2 Hz), 2.61(2H,q,J=7.2 Hz), 2.82(4H,br-s), 3.54)4H,br-s), 6.94(2H,d,J=8.8 Hz), 7.05(1H,ddd,J=12.5 Hz,7.6 Hz,1.2 Hz), 7.48(1H,td,J=7.6 Hz,4.8 Hz), 7.52(1H,dd,J=7.6 Hz,1.2 Hz), 7.54(1H,s), 8.07(2H,d,J=8.8 Hz).

(234-2) 1-(1-Ethylpiperazin-4-yl)-8-fluoro-3-[4-(2-acetoxyethoxy)phenyl]isoquinoline

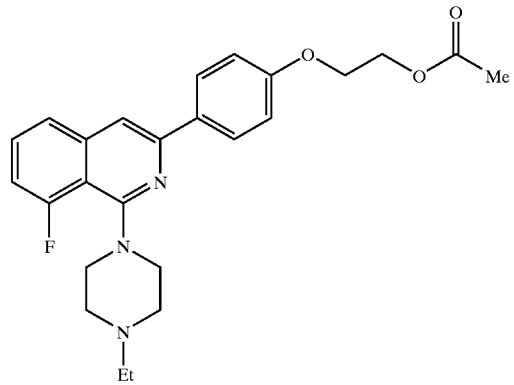

In the same manner as in Example 300-2, the title compound was obtained as a colorless oil (327 mg, yield; 50%) from 1-(1-ethylpiperazin-4-yl)-8-fluoro-3-(4-hydroxyphenyl)isoquinoline (527 mg) and 2-bromoethyl acetate (188 ml).

$^1$H-NMR(400 MHz,CDCl$_3$); δ (ppm) 1.16(3H,t,J=7.2 Hz), 2.12(3H,s), 2.53(2H,q,J=7.2 Hz), 2.71(4H,br-s), 3.53 (4H,br-s), 4.23(2H,t,J=4.8 Hz), 4.45(2H,t,J=4.8 Hz), 7.00 (2H,d,J=8.8 Hz), 7.04(1H,ddd,J=12.5 Hz,7.6 Hz,1.2 Hz), 7.46(1H,td,J=7.6 Hz,4.8 Hz), 7.51(1H,dd,J=7.6 Hz,1.2 Hz), 7.52(1H,s), 8.10(2H,d,J=8.8 Hz).

(234-3) 1-(1-Ethylpiperazin-4-yl)-8-fluoro-3-[4-(2-hydroxyethoxy)phenyl)isoquinoline dihydrochloride

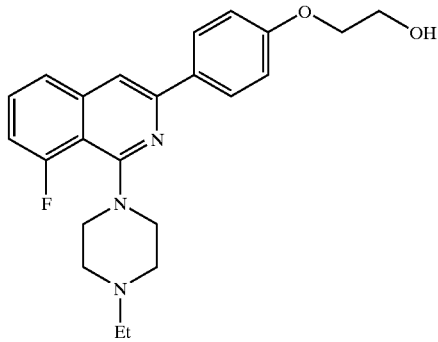

1-(1-Ethylpiperazin-4-yl)-8-fluoro-3-[4-(2-acetoxyethoxy)phenyl]isoquinoline (527 mg) was dissolved in ethanol (16 ml), followed by the addition of 2N sodium hydroxide (8 ml), and the mixture was stirred at room temperature overnight. The reaction mixture was evaporated, and then it was partitioned between ethyl acetate and water. The resulting organic layer was washed with water, dried (over MgSO$_4$) and evaporated. The resulting residue was purified by (NH) silica gel column chromatography (ethyl acetate/hexane system). Then, the resulting product was converted into a hydrochloride in a conventional manner, and then recrystallized from ethanol/isopropyl ether, to give the hydrochloride of the title compound as yellow crystals (343 mg, yield 97%).
Hydrochloride:
m.p.; 215–219° C.
$^1$H-NMR(400 MHz,DMSO-d$_6$); δ (ppm) 1.30(3H,t,J=7.2 Hz), 3.13–3.25(4H,m), 3.43(2H,t,J=13.6 Hz), 3.60(2H,d,J= 11.6 Hz), 3.73(2H,t,J=5 Hz), 3.93(2H,d,J=13.6 Hz), 4.04 (2H,t,J=5 Hz), 7.06(2H,d,J=8.8 Hz), 7.31(1H,ddd,J=12.8 Hz,1 Hz), 7.67(1H,ddd,J=8.2 Hz,7.9 Hz,4.8 Hz), 7.75(1H, dd,J=8.2 Hz,1 Hz), 7.98(1H,d,J=2 Hz), 8.13(2H,d,J=8.8 Hz), 10.85–10.95(1H,br-s). FAB-Mass; 396(MH$^+$).

Example 235

Synthesis of 1-(1-ethylpiperazin-4-yl)-8-methoxy-3-(4-methoxyphenyl)isoquinoline dihydrochloride
(235-1) 8-Methoxy-3-(4-methoxyphenyl)isoquinoline-1-(2H)-one

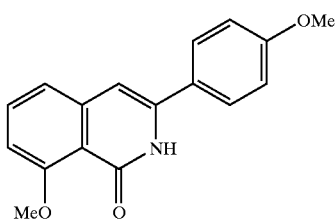

Ethyl 2-methoxy-6-methylbenzoate (5.011 g) was dissolved in tetrahydrofuran (20 ml), followed by the addition of 1.5M lithium diisopropylamide/cyclohexane solution (19 ml) in nitrogen atmosphere at −70° C. The resulting mixture was stirred for 45 min. Anisonitrile (3.462 g)/tetrahydrofuran (10 ml) solution was added to the reaction mixture. The cooling bath was removed, and then the mixture was stirred for 100 min. An aqueous solution of saturated ammonium chloride and ethyl acetate were added to the reaction solution, and the mixture was stirred for 30 min. The resulting insoluble matters were collected by filtration, and then washed with ethyl acetate and water, to give the title compound as a pale yellow solid (991 mg, yield; 13%).
$^1$H-NMR(400 MHz,CDCl$_3$); δ (ppm) 3.87(3H,s), 4.02 (3H,s), 6.58(1H,s), 6.93(1H,d,J=7.6 Hz), 7.01(2H,d,J=8.8 Hz), 7.11(1H,d,J=7.6 Hz), 7.52–7.58(3H,m), 8.58(1H,br-s).
(235-2) 1-(1-Ethylpiperazin-4-yl)-8-methoxy-3-(4-methoxyphenyl)isoquinoline dihydrochloride

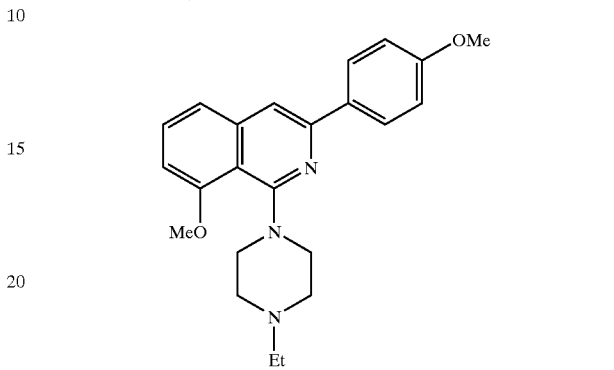

8-Methoxy-3-(4-methoxyphenyl)isoquinolin-1-(2H)-one (991 mg) was treated in the same manner as in Example 252-3, to give the hydrochloride of the title compound as colorless crystals (recrystallized from 10% hydrous ethanol/isopropyl ether) (1.115 g, yield; 71%).
Hydrochloride:
m.p.; 237–241° C.
$^1$H-NMR (400 MHz,CDCl$_3$); δ (ppm) 1.30(3H,t,J=7.2 Hz), 3.12–3.36(6H,m), 3.59(2H,d,J=10.4 Hz), 3.91(2H,d,J= 12.4 Hz), 7.02(1H,d,J=8 Hz), 7.04(2H,d,J=8.8 Hz), 7.44(1H, d,J=8 Hz), 7.58(1H,t,J=8 Hz), 7.82(1H,s), 8.11(2H,d,J=8.8 Hz), 10.67(1H,br-s).
ESI-Mass; 378 (MH$^+$).

Example 236

Synthesis of 1-(1-propylpiperazin-4-yl)-3-(4-methoxyphenyl)isoquinoline dihydrochloride
(236.1) 1-(4-Formylpiperazinyl)-3-(4-methoxyphenyl)isoquinoline

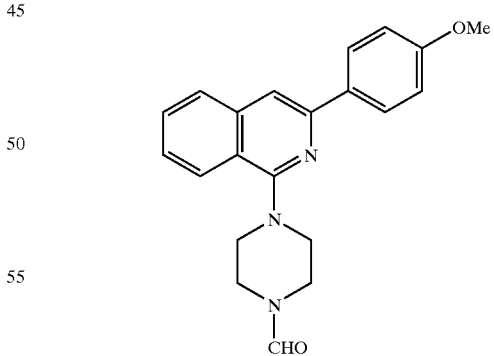

In the same manner as in Example 322, the title compound was obtained as a yellow amorphous (4.797 g, yield; 86%) from 1-chloro-3-(4-methoxyphenyl)isoquinoline (4.316 g) and 1-piperazinecarboxyaldehyde (4.6 ml).
$^1$H-NMR(400 MHz,CDCl$_3$); δ (ppm) 3.47–3.50(2H,m), 7.48(1H,ddd,J=8 Hz,7 Hz,1.2 Hz), 7.61(1H,ddd,J=8 Hz,7 Hz,1.2 Hz), 7.68(1H,s), 7.80(1H,d,J=8 Hz), 8.10(2H,d,J=8.8 Hz), 8.16(1H,s).

(236-2) 1-Piperazinyl-3-(4-methoxyphenyl)isoquinoline

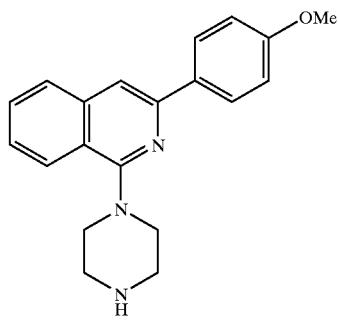

1-(4-Formylpiperazinyl)-3-(4-methoxyphenyl)isoquinoline (4.797 g) was dissolved in ethanol (85 ml), followed by the addition of 2N sodium hydroxide (35 ml), and the mixture was heated under reflux for 4 hr. The reaction mixture was evaporated, water and added thereto, and extracted with chloroform. The resulting organic layer was washed with water, dried (over MgSO$_4$) and evaporated. The resulting residue was purified by (NH) silica gel column chromatography (ethyl acetate/hexane system), to give the title compound as a colorless solid (2.720 g, yield; 63%).

$^1$H-NMR(400 MHz,CDCl$_2$); δ (ppm) 3.16–3.19(4H,m), 3.47–3.51(4H,m), 3.88(3H,s), 7.01(2H,d,J=8.8 Hz), 7.44 (1H,ddd,J=8 Hz,7 Hz,1.2 Hz), 7.57(1H,ddd,J=8 Hz,7 Hz,1.2 Hz), 7.77(1H,d,J=8 Hz), 8.07(1H,d,J=8 Hz), 8.12(2H,d,J=8.8 Hz).

(236-3) 1-(1-Propylpiperazin-4-yl)-3-(4-methoxyphenyl)isoquinoline dihydrochloride

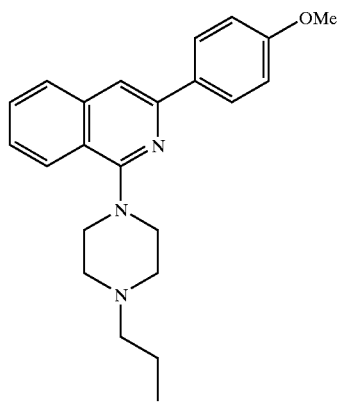

1-Piperazinyl-3-(4-methoxyphenyl)isoquinoline (319 mg) was dissolved in N,N-dimethylformamide (3 ml), followed by the addition of 1-bromopropane (91 ml) and triethylamine (167 ml), and the mixture was stirred at 50° C. overnight. The reaction mixture was partitioned between ethyl acetate and water. The resulting organic layer was washed with water, dried (over MgSO$_1$) and evaporated. The resulting residue was purified by silica gel column chromatography (methylene chloride/methanol system). Then, the resulting product was converted into a hydrochloride in a conventional manner and recrystallized from ethanol/isopropyl ether, to give the hydrochloride of the title compound as yellow crystals (380 mg, yield; 90%).
Hydrochloride:
m.p.; 220–226° C.
$^1$H-NMR(400 MHz,DMSO-d$_6$); δ (ppm) 0.93(3H,t,J=7.2 Hz), 1.72–1.82(2H, m), 3.07–3.13(2H,m), 3.32(1H,t,J=11 Hz). 3.35(1H,t,J=11 Hz), 3.52(2H,t,J=14 Hz), 3.60(2H,d,J=11 Hz), 3.81(3H,s), 3.95(2H,d,J=14 Hz), 7.05(2H,d,J=8.8 Hz), 7.55(1H,ddd,J=8 Hz,1.2 Hz), 7.70(1H,ddd,J=8 Hz,7 Hz,1.2 Hz), 7.93(1H,d,J=8 Hz), 7.97(1H,s), 8.07(1H,d,J=8 Hz). 8.13(2H,d,J=8.8 Hz), 10.93(1H,br-s).

ESI-Mass; 362(MH$^+$).

Example 237

Synthesis of 1-(1-propylpiperazin-4-yl)-3-[4-(2-hydroxyethoxy)phenyl]isoquinoline dihydrochloride (237-1) 1-(1-Propylpiperazin-4-yl)-3-(4-hydroxyphenyl)isoquinoline

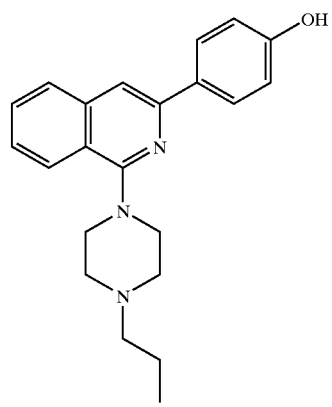

In the same manner as in Example 3-1, the title compound was obtained as a pale brown solid (853 mg, yield; 78%) from 1(1-propylpiperazin-4-yl)-3-(4-methoxyphenyl)isoquinoline (1.147 g).

$^1$H-NMR(400 MHz,CDCl$_3$); δ (ppm) 0.97(3H,t,J=7.6 Hz), 1.56–1.66(2H,m), 2.43–2.48(2H,m), 2.77(4H,t, J=4.4 Hz), 3.57(4H,t,J=4.4 Hz), 6.93(2H,d,J=8.8 Hz), 7.43(1H, ddd,J=8 Hz,7 Hz,1.2 Hz), 7.57(1H,ddd,J=8 Hz,7 Hz,1.2 Hz), 7.61(1H,s), 7.76(1H,d,J=8 Hz), 8.08(2H,d,J=8.8 Hz).

(237-2) 1-(1-Propylpiperazin-4-yl)-3-[4-(2-hydroxyethoxy)phenyl]isoquinoline dihydrochloride

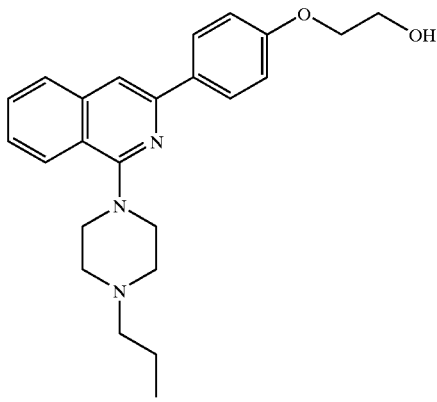

1-(1-Propylpiperazin-4-yl)-3-(4-hydroxyphenyl)isoquinoine (853 mg) was dissolved in N,N-dimethylformamide (12 ml), followed by the addition of 60% sodium hydride (120 mg) under ice-cooling, and the mixture was stirred at room temperature for 1 hr. The reaction solution was ice-cooled again, followed by the addition of (2-bromoethoxy)-t-butyldimethylsilane (718 mg), and the mixture was stirred overnight. The reaction mixture was partitioned between ethyl acetate and water. The resulting organic layer was washed with water, dried (over MgSO$_4$) and evaporated. The resulting residue was dissolved in tetrahydrofuran (10 ml). To the mixture, 0.1M tetrabutylammonium fluoride/tetrahydrofuran solution (2.8 ml) was added under ice-cooling. The resulting mixture was stirred, as it was, at room temperature for 1 hr. The reaction mixture was evaporated, and then purified by silica gel column chromatography (methylene chloride/methanol system). Sequentially, the resulting product was converted into a hydrochloride in a conventional manner, and then recrystallized from ethanol/isopropyl ether, to give the hydrochloride of the title compound as yellow crystals (485 mg, yield; 40%)

Hydrochloride:

m.p.; 220–225° C.

$^1$H-NMR(400 MHz,DMSO-d$_6$); δ (ppm) 0.93(3H,t,J=7.6 Hz), 1.72–1.82(2H,m), 3.07–3.15(2H,m), 3.33(1H,t,J=10.6 Hz), 3.36(1H,t,J=10.6 Hz), 3.51(2H,t,J=13.6 Hz), 3.60(2H, d=10.6 Hz), 3.73(2H,t,J=5 Hz), 3.95(2H,d,J=13.6 Hz), 4.04 (2H,t,J=5 Hz), 7.05(2H,d,J=8.8 Hz), 7.55(1H,ddd,J=8.4 Hz,7 Hz,1.2 Hz), 7.70(1H,ddd,J=8.4 Hz,7 Hz,1.2 Hz), 7.93 (1H,d,J=8.4 Hz), 7.97(1H,s), 8.07(1H,d,J=8.4 Hz), 8.12(2H, d,J=8.8 Hz), 10.88 (1H,br-s).

ESI-Mass; 392(MH$^+$).

Example 238

Synthesis of 1-(1-isopropylpiperazin-4-yl)-3-(4-methoxyphenyl)isoquinoline dihydrochloride

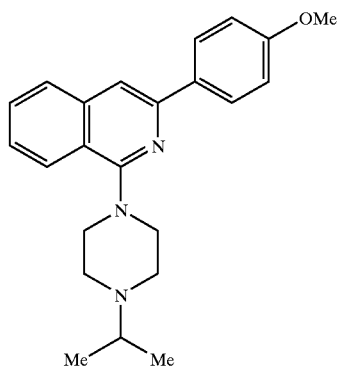

In the same manner as in Example 236, the hydrochloride of the title compound was obtained as pale brown crystals (recrystalized from ethanol/isopropyl ether) (189 mg, yield; 80%) from 1-piperazinyl-3-(4-methoxyphenyl)isoquinoline (160 mg) and 2-bromopropane (470 ml).

Hydrochloride:

m.p.; 220° C. (decomp.)

$^1$H-NMR(400 MHz,DMSO-d$_6$); δ (ppm) 1.35(6H,d,J=6.8 Hz), 3.36(1H,t,J=10 Hz), 3.39(1H,t,J=10 Hz), 3.48–3.64 (5H,m), 3.94(2H,d,J=13.6 Hz), 7.04(2H,d,J=8.8 Hz), 7.54 (1H,ddd,J=8 Hz,7 Hz,1.2 Hz), 7.69(1H,ddd,J=8 Hz,7 Hz,1.2 Hz), 7.92(1H,d,J=8 Hz), 7.97(1H,s), 8.11(1H,d,J=8 Hz). 8.13(2H,d,J=8.8 Hz), 11.14(1H,br-s).

ESI-Mass; 362(MH$^+$).

Example 239

Synthesis of 1-(1-cyclopropylpiperaziin-4-yl)-3-(4-methoxyphenyl)isoquinoline dihydrochloride

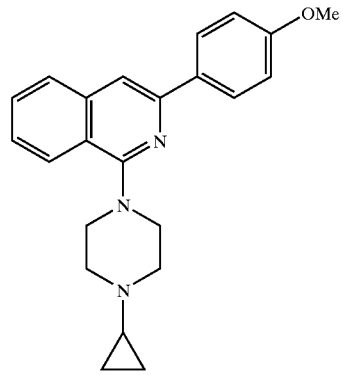

1-Chloro-3-(4-methoxyphenyl)isoquinoline (514 mg), and 1-cyclopropylpiperazine hydrochloride salt (378 mg) described in JP-A 62-129273 were dissolved in dimethyl sulfoxide (7 ml, followed by the addition of potassium carbonate (788 mg), and the resulting mixture was stirred at 100° C. overnight. The reaction mixture was partitioned between ethyl acetate and water. The resulting organic layer was washed with water, dried (over MgSO$_4$) and evaporated. The resulting residue was purified by silica gel column chromatography (methylene chloride/methanol system). The resulting product was converted into a hydrochloride in a conventional manner, and then recrystallized from ethanol/ isopropyl ether, to give the hydrochloride of the title compound as yellow crystals (136 mg, yield; 16%).

Hydrochloride:

m.p.; 138–143° C.

$^1$H-NMR(400 MHz,DMSO-d$_6$); δ (ppm) 0.80–0.88(4H, br-q), 1.18–1.22(4H,br-q), 2.93–3.02(1H,m), 3.48–3.63(6H, m), 3.80(3H,s), 3.92–3.98(2H,d,J=9.6 Hz), 7.04(2H,d,J=8.8 Hz), 7.55(1H,ddd,J=8 Hz,7 Hz,1.2 Hz), 7.69(1H,ddd,J=8 Hz,7 Hz,1.2 Hz), 7.93(1H,d,J=8 Hz), 7.97(1H,s), 8.07(1H, d,J=8 Hz), 8.13(2H,d,J=8.8 Hz), 11.08(1H,br-s).

ESI-Mass; 360(MH$^+$).

Example 240

Synthesis of 1-(1-allylpiperazin-4-yl)-3-(4-methoxyphenyl)isoquinoline dihydrochloride

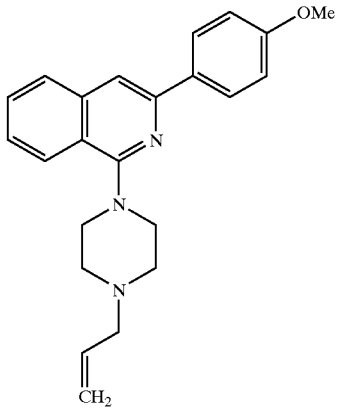

In the same manner as in Example 236, the hydrochloride of the title compound was obtained as yellow crystals (recrystalized from ethanol) (364 mg, yield; 80%) form 1-piperazinyl-3-(4-methoxyphenyl)isoquinoline (319 mg) and allyl bromide (87 ml).

Hydrochloride:
m.p.; 111–116° C.

$^1$H-NMR(400 MHz,DMSO-d$_6$); δ (ppm) 3.28–3.38(2H, m), 3.45–3.58(4H,m, 3.81(3H,s), 3.82–3.88(2H,br-t), 3.96 (2H,d,J=14 Hz), 5.50–5.60(2H,m), 6.00–6.12(1H,m), 7.05 (2H,d,J=8.8 Hz), 7.55(1H,ddd,J=8 Hz,7 Hz,1,2 Hz), 7.70 (1H,ddd,J=8 Hz,7 Hz,1.2 Hz), 7.93(1H,d,J=8.8 Hz), 7.97 (1H,s), 8.07(1H,d,J=8 Hz), 8.13(2H,d,J=8.8 Hz), 11.31(1H, br-s).

ESI-Mass; 360(MH$^+$).

Example 241

Synthesis of 1-[1-(2-fluoroethyl)piperazin-4-yl]-3-(4-methoxyphenyl)isoquinoline Dihydrochloride

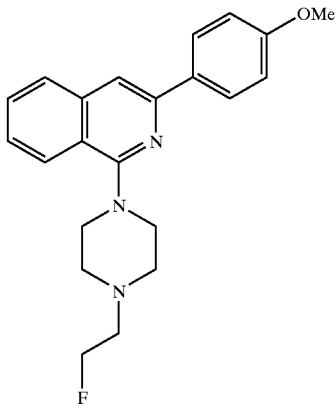

In the same manner as in Example 236, the hydrochloride of the title compound was obtained as yellow crystals (recrystallized from ethanol) (355 mg, yield; 80%) from 1-piperazinyl-3-(4-methoxyphenyl)isoquinoline (319 mg) and 1-bromo-2-fluoroethane (74 ml).

Hydrochloride:
m.p.; 120–124° C.

$^1$H-NMR(400 MHz,DMSO-d$_6$); δ (ppm) 3.44–3.68(8H, m), 3.81(3H,s), 3.98(2H,d,J=12 Hz), 4.91(1H,t,J=4.2 Hz), 5.02(1H,t,J=4.2 Hz), 7.05(2H,d,J=8.8 Hz), 7.55(1H,dd,J=8 Hz,7 Hz,1.2 Hz), 7.70(1H,ddd,J=8 Hz,7 Hz,1.2 Hz), 7.93 (1H,d,J=8 Hz), 7.98(1H,s), 8.08(1H,d,J=8 Hz), 8.13(2H,d, J=8 Hz), 11.35(1H,br-s).

ESI-Mass; 362(MH$^+$).

Example 242

Synthesis of 1-[4-(2-hydroxyethyl)piperazin-1-yl]-3-(4-methoxyphenyl)isoquinoline Dihydrochloride

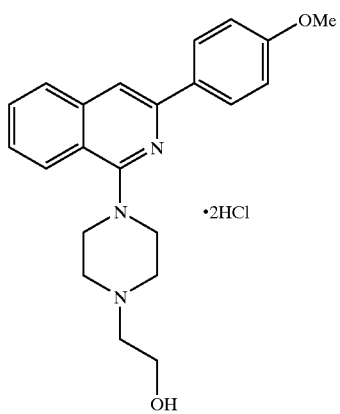

A mixture of 1-chloro-3-(4-methoxyphenyl)isoquinoline (0.79 g) obtained in Example 10-2, 1-(2-hydroxyethyl) piperazine (0.6 g), and potassium carbonate (0.83 g) was reacted in dimethylformamide (10 ml) at 100° C. for 6 hr. The reaction mixture solution was evaporated. Ethyl acetate and water were added to the resulting residue. The resulting organic layer was washed with water and brine, and dried over magnesium sulfate. The solvent was evaporated, and the resulting residue was purified by silica gel column chromatography (methylene chloride/methanol system), to give the free compound of the title compound as a pale yellow oil.

Free compound:

$^1$H-NMR(400 MHz,CDCl$_3$); δ (ppm) 3.87(s,3H), 7.02(d, J=8.4 Hz,2H), 7.61(br-t,1H), 7.71(br-t,1H), 7.84(d,J=8.0 Hz,1H), 7.92(s,1H), 8.07(d,J=8.4 Hz,2H), 8.32(d,J=8.0 Hz,1H).

The resulting free compound was converted into a hydrochloride in a conventional manner, and recrystallized from ethanol/ether, to give 0.48 g of the title compound as a yellow powder.

Hydrochloride:
m.p.; 163–165° C.

$^1$H-NMR(400 MHz,DMSO-d$_6$): δ (ppm) 3.27(m,2H), 3.42(t,J=11.0 Hz,2H), 3.53(t,J=11.0 Hz,2H), 3.65(d,J=11.0 Hz,2H), 3.80(s,3H), 3.82(m,2H), 3.94(d,J=11.0 Hz,2H), 7.05(d,J=8.4 Hz,2H), 7.55(t,J=8.0 Hz,1H), 7.70(t,J=8.0 Hz,1H), 7.92(d,J=8.0 Hz,1H), 7.97(s,1H), 8.06(t,J=8.0 Hz,1H), 8.13(d,J=8.4 Hz,2H), 10.68(m,1H).

MS(FAB) m/z 364(M+H)$^+$.

Example 243

Synthesis of 3-(4-ethylsulfonylaminomethylphenyl)-1-[4-(2-hydroxyethyl)piperazin-1-yl]isoquinoline Hydrochloride

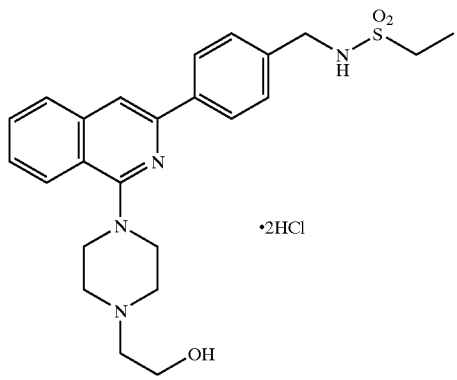

The free compound of the title compound was obtained (118 mg, yield; 62%) from 1-chloro-3-(4-ethylsulfonylaminomethylphenyl)isoquinoline (152 mg) and 4-hydroxyethylpiperazine (1 ml) in the same manner as in Example 10. The resulting free compound was converted into a hydrochloride in a conventional manner, to give the hydrochloride of the title compound as yellow crystals.
Hydrochloride:
  m.p.; 171–174° C.
  $^1$H-NMR(400 MHz,DMSO-d$_6$); δ (ppm) 1.20(t,J=7.2 Hz,3H), 2.99(q,J=7.6 Hz,2H), 3.30–3.34(m,2H), 3.43–3.52 (m,2H), 3.56–3.66(m,2H), 3.70(d,J=11.2 Hz,2H), 3.87–3.90 (m,2H), 4.01(d,J=12.8 Hz,2H), 4.23(d,J=6.0 Hz,2H), 7.50 (d,J=8.4 Hz,2H), 7.62(t,J=8.0 Hz,1H), 7.73(br,1H), 7.56(t, J=8.0 Hz,1H), 8.00(d,J=8.0 Hz,1H), 8.11(s,1H), 8.13(d,J= 8.0 Hz,1H), 8.20(d,J=8.4 Hz,2H).
  MS(FAB) m/z 455(M+H)$^+$.
Free compound:
  $^1$H-NMR(400 MHz,CDCl$_3$); δ (ppm) 1.34(t,J=7.6 Hz,3H), 2.69(t,J=5.2 Hz,2H), 2.82(br,4H), 2.99(q,J=7.2 Hz,2H), 3.56(br,4H), 3.69(t,J=5.2 Hz,2H), 4.36(d,J=4.4 Hz,2H), 4.74(br,1H), 7.44(d,J=8.4 Hz,2H), 7.48(ddd,J=8.4, 8.0,1.2 Hz,1H), 7.60(ddd,J=8.4,8.0,1.2 Hz,1H), 7.70(s,1H), 7.79(d,J=8.0 Hz,1H), 8.07(d,J=8.4 Hz,1H), 8.16(d,J=8.4 Hz,2H).

Example 244

Synthesis of 8-(4-ethylpiperazin-1-yl)-6-(4-methoxyphenyl)pyrido[2,3-c]pyridine Hydrochloride (244-1) 2-Cyano-3-(4-methoxyphenyl)ethynylpyridine

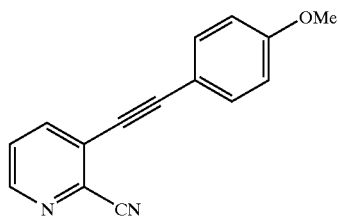

A mixture of 3-bromo-2-cyanopyridine (3.63 g, 19.8 mmol), 4-ethynylanisole (3.15 g, 1.2 equivalents), dichlorobis(triphenylphosphine)palladium (II) (0.28 g, 0.02 equivalent), copper (I) iodide (0.14 g), triethylamine (60 ml) and dry pyridine (6 ml) was heated under reflux in nitrogen atmosphere for 12.5 hr. After the mixture was cooled as it was, ethyl acetate and a 10% aqueous solution of sodium carbonate were added thereto. The resulting mixture was stirred, and the resulting insoluble matters were filtered off. The organic layer was separated and washed with water/ brine (1:1(v/v)) and brine in this order, and then dried over magnesium sulfate. The solvent was evaporated, and the resulting residue was purified by silica gel column chromatography (n-hexane/ethyl acetate/chloroform/methanol system). The resulting product was recrystallized from chloroform/n-hexane, to give the title compound as a pale yellow powder (3.53 g, yield; 81%).

$^1$H-NMR(400 MHz,CDCl$_3$); δ (ppm) 3.85(s,3H), 3.92(d, J=9.0 Hz,2H), 7.47(dd,J=4.8,8.0 Hz,1H), 7.57(d,J=9.0 Hz,2H), 7.90(dd,J=1.6,8.0 Hz,1H), 8.60(dd,J=1.6,4.8 Hz,1H).

(244-2) 6-(4-Methoxyphenyl)-7,8-dihydropyrido[2,3-c]pyridine-8-one

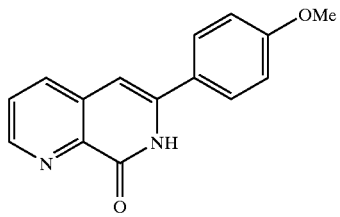

Polyphosphoric acid (45 g) was added to 2-cyano-3-(4-methoxyphenyl)ethynylpyridine (3.07 g, 13.1 mmol), which was then stirred at 110–120° C. for 15 min. After cooling as it was, ice was added thereto and the mixture was stirred. Ethyl acetate and sodium carbonate were added thereto, and the pH of the aqueous layer was adjusted to about pH 8. The organic layer was separated and washed with brine, and then dried over magnesium sulfate. The solvent was evaporated, to give 2.43 g of a pale brown powder.

Sodium acetate of 5.88 g was added to the resulting pale brown powder, which was then stirred in a sealed tube at 120° C. for 13 hr. After cooled as it was, water was added thereto, and then it was extracted with chloroform. The organic layer was separated and washed with brine, and then dried over magnesium sulfate. The solvent was evaporated, and the resulting residue was purified by silica gel column chromatography (chloroform/methanol system). The resulting product was reprecipitated with chloroform/n-hexane, to give the title compound as a pale brown powder (0.71 g, yield; 21%).

$^1$H-NMR(400 MHz,DMSO-d$_6$); δ (ppm) 3.83(s,3H), 6.83 (s,1H), 7.06(d,J=8.8 Hz,2H), 7.67(dd,J=4.2,8.2 Hz,1H), 7.77(d,J=8.8 Hz,2H), 8.11(dd,J=1.6,8.2 Hz,1H), 8.72(dd,J= 1.6,4.2 Hz,1H), 11.71(s,1H).

(244-3) 8-(4-Ethylpiperazin-1-yl)-6-(4-methoxyphenyl)pyrido[2,3-c]pyridine hydrochloride

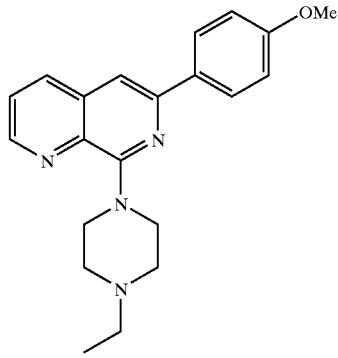

Phosphorus oxychloride (20 ml) was added to 6-(4-methoxyphenyl)-7,8-dihydropyrido[2,3-c]pyridin-8-one (0.70 g, 2.77 mmol), and the mixture was heated under reflux for 1.5 hr. After cooling as it was, excess phosphorus oxychloride was evaporated. To the resulting residue was added N-ethylpiperazine (35 ml), and the mixture was stirred in nitrogen atmosphere at 100° C. for 2 hr. After cooling as it was, the reaction solution was evaporated. The resulting residue was dissolved in ethyl acetate, washed sequentially with a 10% aqueous solution of sodium carbonate, water and brine, and dried over magnesium sulfate. Then, the solvent was evaporated, and the resulting residue was purified by NH-silica gel column chromatography (n-hexene/ethyl acetate system), to give the title compound as pale brown crystals (0.98 g, yield; quantitative).

The resulting compound was converted into a hydrochloride in a conventional manner, and recrystallized from ethanol/diisopropyl ether, to give 0.98 g of the hydrochloride of the title compound.
Hydrochloride:
$^1$H-NMR (400 MHz,DMSO-$d_6$); δ (ppm) 1.31(t,J=7.2 Hz,3H), 3.16–3.28(m,4H), 3.55–3.65(m,4H), 3.83(s,3H), 5.15(br-d,2H), 7.07(d,J=9.0 Hz,2H), 7.70(dd,J=4.2,8.4 Hz,1H), 7.85(s,1H), 8.14(d,J=9.0 Hz,2H), 8.32(dd,J=1.6,8.4 Hz,1H), 8.33(dd,J=1.6,4.2 Hz,1H), 10.73(br-s,1H).
MS(FAB) m/z 349(M+H)$^+$.
Free compound:
$^1$H-NMR(400 MHz,CDCl$_3$); δ (ppm) 1.17(t,J=7.2 Hz,3H), 2.53(q,J=7.2 Hz,2H), 2.74(br-t,4H), 3.88(s,3H), 4.15(br-t,4H), 7.01(d,J=8.8 Hz,2H), 7.42(s,1H), 7.44(dd,J=4.0,8.0 Hz,1H), 8.02(dd,J=1.6,8.0 Hz,1H), 8.11(d,J=8.8 Hz,2H), 8.75(dd,J=1.6,4.0 Hz,1H).

Example 245

Synthesis of 8-(1-ethylpiperazin-4-yl)-6-[4-(2-hydroxyethoxy)phenyl]-1,7-naphthyridine Dihydrochloride (245-1) 6,8-Dibromo-1,7-napthyridine

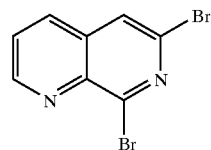

To 6-amino-8-bromo-1,7-naphthyridine (6.554 g) synthesized according to Tetrahedron Letters, 12, 1233, 1966 was added 48% hydrobromic acid (55 ml). Sodium nitrite (4.141 g) was added thereto in small portions under ice-cooling, and the mixture was stirred overnight. The reaction mixture was basified by adding 5N sodium hydroxide thereto, and it was extracted with ethyl acetate. The resulting organic layer was washed with water, dried (over MgSO$_4$) and evaporated. The resulting residue was purified by silica gel column chromatography (ethyl acetate/hexane system), to give the title compound as a yellowish orange solid (2.856 g, yield; 34%).
$^1$H-NMR(400 MHz,CDCl$_3$); δ (ppm) 7.70(1H,dd,J=8.4 Hz,4 Hz), 8.12(1H,dd,J=8.4 Hz,1.6 Hz), 9.15(1H,dd,J=4 Hz,1.6 Hz).

(245-2) 6-Bromo-8-(1-ethylpiperazin-4-yl)-1,7-napthyridine

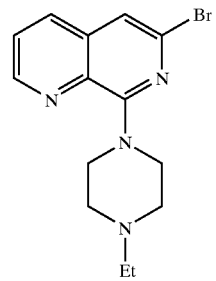

6,8-Dibromo-1,7-naphthyridine (3.464 g) was added to 1-ethylpiperazine (10 ml), and the resulting mixture was stirred at 100° C. for 15 min. The reaction mixture was evaporated, and then partitioned between ethyl acetate and water. The resulting organic layer was washed with water, dried (over MgSO$_4$) and evaporated. The resulting residue was purified by (NH) silica gel column chromatography (ethyl acetate/hexane system), to give the title compound as a yellowish orange solid (3.780 g, yield; 98%).
$^1$H-NMR(400 MHz,CDCl$_3$); δ (ppm) 1.15(3H,t,J=7.2 Hz), 2.50(2H,q,J=7.2 Hz), 2.67(4H,t,J=5 Hz), 4.19(4H,t,J=5 Hz), 7.14(1H,s), 7.45(1H,dd,J=8.4 Hz,4 Hz), 7.88(1H,dd,J=8.4 Hz,1.6 Hz), 8.75(1H,dd,J=4 Hz,1.6 Hz).

(245-3) 8-(1-Ethylpiperazin-4-yl)-6-[4-(2-hydroxyethoxy)phenyl]-1,7-naphthyridine dihydrochloride

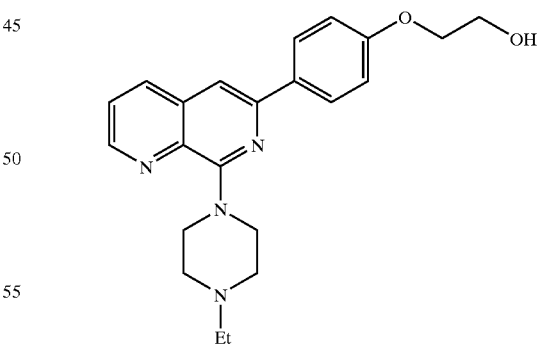

In the same manner as in Example 300, the hydrochloride of the title compound was obtained as yellow crystals (374 mg, yield; 67%) from 6-bromo-8-(1-ethylpiperazin-4-yl)-1,7-naphthyridine (385 mg) and 4-tributylstannylphenoxyethyl acetate (684 mg).
Hydrochloride:
m.p.; 137–143° C.
$^1$H-NMR(400 MHz,DMSO-$d_6$); δ (ppm) 1.29(3H,t,J=7.2 Hz), 3.10–3.26(4H,m), 3.57–3.65(4H,m), 3.73(2H,t,J=5

Hz), 4.04(2H,t,J=4 Hz), 5.09–5.12(2H,m), 7.05(2H,d,J=8.8 Hz), 7.68(1H,dd,J=8.4 Hz,4.4 Hz), 7.83(1H,s), 8.11(2H,d, J=8.8 Hz), 8.30(1H,dd,J=8.4 Hz,1.6 Hz), 8.81(1H,dd,J=4.4 Hz,1.6 Hz), 11.05–11.15(1H,br-s).

ESI-Mass; 379(MH$^+$).

Example 246

Synthesis of 8-(1-ethylpiperazin-4-yl)-6-{4-[(S)-2-hydroxypropoxy}phenyl]-1,7-naphthyridine Dihydrochloride

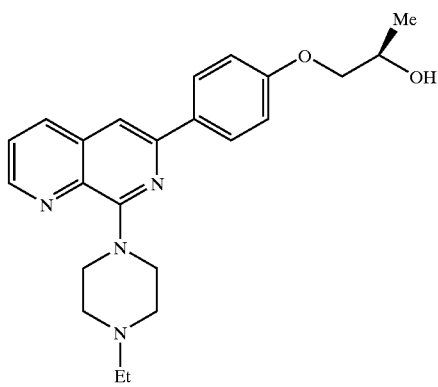

In the same manner as in Example 300, the hydrochloride of the title compound was obtained as a pale yellow amorphous (459 mg, yield; 77%) from 6-bromo-8-(1-ethylpiperazin-4-yl)-1,7-naphthyridine (418 mg) and 2-(4-tributylstannylphenoxy)-(S)-1-methylethyl acetate (1.136 mg).

Hydrochloride:

m.p.; 136–140° C.

$^1$H-NMR(400 MHz,DMSO-d$_6$); δ (ppm) 1.16(3H,d,J=6.4 Hz), 1.29(3H,t,J=7.2 Hz), 3.16(1H,q,J=7.2 Hz), 3.18(1H,q, J=7.2 Hz), 3.20(1H,t,J=10.8 Hz), 3.23(1H,t,J=10.8 Hz), 3.58 (2H,t,J=13.6 Hz), 3.62(1H,q,J=10.8 Hz), 3.82–3.91(2H,m), 3.93–4.00(1H,m), 5.11(2H,d,J=13.6 Hz), 7.05(2H,d,J=8.8 Hz), 7.68(1H,dd,J=8.4 Hz,4.4 Hz), 7.83(1H,s), 8.11(2H,d, J=8.8 Hz), 8.30(1H,dd,J=8.4 Hz,1.6 Hz), 8.81(1H,dd,4.4 Hz,1.6 Hz), 10.85–10.95(1H,br-s).

ESI-Mass; 393(MH$^+$).

Example 247

Synthesis of 8-(1-ethylpiperazin-4-yl)-6-[4-(3-hydroxypropyl)phenyl]-1,7-naphthyridine Dihydrochloride

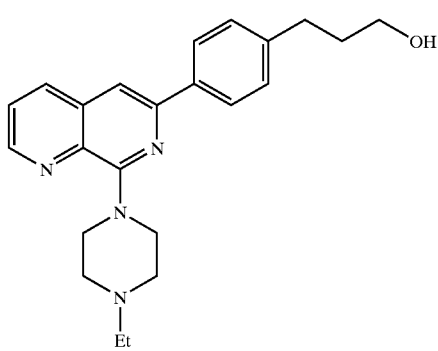

In the same manner as in Example 167-2, the hydrochloride of the title compound was obtained as yellow crystals (recrystallized from ethanol/isopropyl ether) (352 mg, yield; 62%) from 4-[3-(t-butyldimethylsilyloxy)propyl]-1-bromobenzene (2.035 g) and 6-bromo-8-(1-ethylpiperazin-4-yl)-1,7-naphthyridine (418 mg).

Hydrochloride:

m.p.; 119–122° C.

$^1$H-NMR(400 MHz,DMSO-d$_6$); δ (ppm) 1.29(3H,t,J=7.2 Hz), 1.70–1.78(2H,m), 2.66(2H,t,J=7.6 Hz), 3.16(1H,q,J=7.2 Hz), 3.18(1H,q,J=7.2 Hz), 3.20(1H,t,J=12.4 Hz), 3.23 (1H,t,J=12.4 Hz), 3.43(2H,t,J=6.4 Hz), 3.56(2H,t,J=13.6 Hz), 3.62(2H,d,J=12.4 Hz), 7.31(2H,d,J=8.8 Hz), 7.70(1H, dd,J=8.4 Hz,4 Hz), 7.89(1H,s), 8.08(2H,d,J=8.8 Hz), 8.33 (1H,dd,J=8.4 Hz,1.6 Hz), 8.83(1H,dd,J=4 Hz,1.6 Hz), 10.65–10.75(1H,br-s).

ESI-Mass; 377(MH$^+$).

Example 248

Synthesis of 8-(1-ethylpiperazin-4-yl)-6-[4-(3-hydroxybutyl)phenyl]-1,7-naphthyridine Dihydrochloride

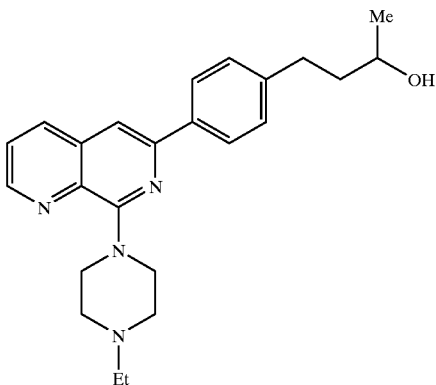

In the same manner as in Example 161-3, the hydrochloride of the title compound was obtained as yellow crystals (recrystallized from ethanol/isopropyl ether) (346 mg, yield; 54%) from 4-[3-(t-butyldimethylsilyloxy)butyl]-1-bromobenzene (2.237 g) and 6-bromo-8-(1-ethylpiperazin-4-yl)-1,7-naphthyridine (418 mg).

Hydrochloride:

m.p.; 118–121° C.

$^1$H-NMR(400 MHz,DMSO-d$_6$); δ (ppm) 1.08(3H,d,J=6.4 Hz), 1.29(3H,t,J=7.2 Hz), 1.60–1.67(2H,m), 2.58–2.75(2H, m), 3.15(1H,q,J=7.2 Hz), 3.17(1H,q,J=7.2 Hz), 3.19(1H,t, J=10.8 Hz), 3.22(1H,t,J=10.8 Hz), 3.55–3.64(5H,m), 5.13 (2H,d,J=13.6 Hz), 7.31(2H,d,J=8.8 Hz), 7.70(1H,dd,J=8.4 Hz,4.4 Hz), 7.88(1H,s), 8.07(2H,d,J=8.8 Hz), 8.33(1H,dd, J=8.4 Hz,1.6 Hz), 8.83(1H,dd,J=4.4 Hz,1.6 Hz), 11.00–11.10(1H,br-s).

ESI-Mass; 391(MH$^+$).

Example 249

Synthesis of 8-(1-ethylpiperazin-4-yl)-6-[4-(3-hydroxy-1-fluoropropyl)phenyl]-1,7-naphthyridine Dihydrochloride

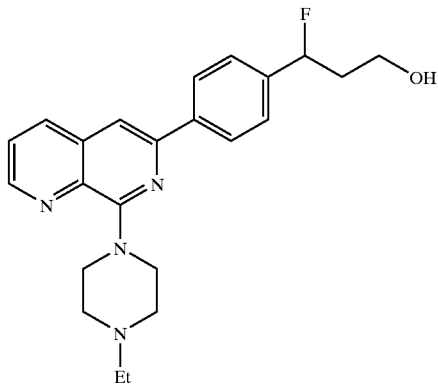

In the same manner as in Example 27, the hydrochloride of the title compound was obtained as yellow hygroscopic crystals (135 mg, yield; 30%) from 6-bromo-8-(1-ethylpiperazin-4-yl)-1,7-naphthyridine (321 mg).
Hydrochloride:
m.p.; 123–125° C.
$^1$H-NMR(400 MHz,DMSO-d$_6$); δ (ppm) 1.29(3H,t,J=7.2 Hz), 1.70–2.20(2H,m), 3.13–3.27(4H,m), 3.45–3.65(5H,m), 5.15(2H,d,J=13.6 Hz), 5.65(1H,ddd,J=48 Hz,9.2 Hz,4 Hz), 7.50(2H,d,J=8.8 Hz), 7.72(1H,dd,J=8.2 Hz,4.4 Hz), 7.96 (1H,s), 8.20(2H,d,J=8.8 Hz), 8.35(1H,dd,J=8.2 Hz,1.6 Hz), 8.86(1H,dd,J=4.4 Hz,1.6 Hz), 10.75–10.85(1H,br-s).
ESI-Mass; 395(MH$^+$).

Example 250

Synthesis of 8-(1-ethylpiperazin-4-yl)-6-[4-(2-hydroxy-2-methylpropoxy)phenyl]-1,7-naphthyridine Dihydrochloride (250-1) 8-(1-Ethylpiperazin-4-yl)-6-[(4-ethoxycarbonylmethoxy)phenyl]-1,7-naphthyridine

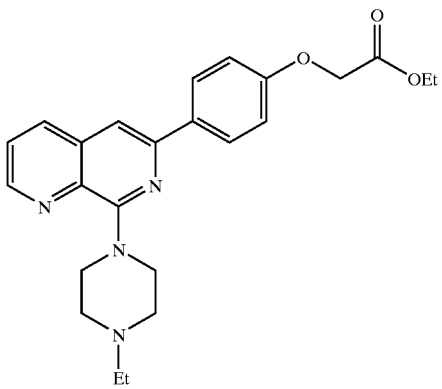

In the same manner as in Example 161-3, the title compound was obtained as a yellow oil (362 mg, yield; 72%) from 6-bromo-8-(1-ethylpiperazin-4-yl)-1,7-naphthyridine (403 mg) and ethyl 2-(4-tributylstannylphenoxy)acetate (1.374 g).
$^1$H-NMR(400 MHz,CDCl$_3$); δ (ppm) 1.17(3H,t,J=7.2 Hz), 1.32(3H,t,J=7.2 Hz), 2.53(2H,q,J=7.2 Hz), 2.74(4H,t, J=5 Hz), 4.15(4H,t,J=5 Hz), 4.29(2H,q,J=7.2 Hz), 4.68(2H, s), 7.01(2H,d,J=8.8 Hz), 7.42(1H,s), 7.44(1H,dd,J=8.4 Hz,4 Hz), 8.01(1H,dd,J=8.4 Hz,1.6 Hz), 8.75(1H,dd,J=4 Hz,1.6 Hz).

(250-2) 8-(1-Ethylpiperazin-4-yl)-6-[4-(2-hydroxy-2-methylpropoxy)phenyl]-1,7-naphthyridine dihydrochloride or compound identified by the following analysis data and synthetic procedure

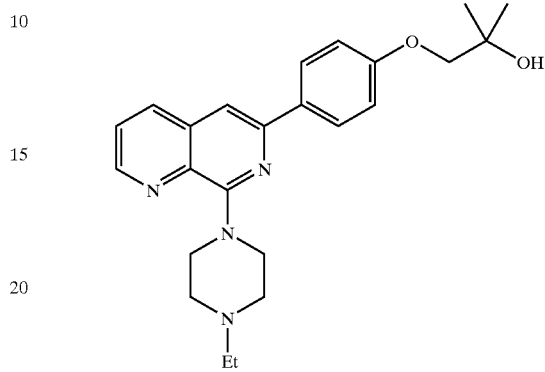

In the same manner as in Example 260, the hydrochloride of the title compound was obtained as a yellow solid (348 mg, yield; 75%) from 8-(1-ethylpiperazin-4-yl)-6-[(4-ethoxycarbonylmethoxy)phenyl]-1,7-naphthyridine (362 mg) and a 3M solution of magnesium bromide/ether (1.5 ml).
Hydrochloride:
m.p.; 127–132° C.
$^1$H-NMR(400 MHz,DMSO-d$_6$); δ (ppm) 1.21(6H,s), 1.30 (3H,t,J=7.2 Hz), 3.15(1H,q,J=7.2 Hz), 3.17(1H,q,J=7.2 Hz), 3.18(1H,t,J=12 Hz), 3.22(1H,t,J=12 Hz), 3.60(2H,t,J=14.4 Hz), 3.61(2H,d,J=12 Hz), 3.77(2H,s), 5.10(2H,d,J=14.4 Hz), 7.05(2H,d,J=8.8 Hz), 7.68(1H,dd,J=8.4 Hz,4 Hz), 7.83 (1H,s), 8.11(2H,d,J=8.8 Hz), 8.30(1H,dd,J=8.4 Hz,1.6 Hz), 8.81(1H,dd,J=4 Hz,1.6 Hz), 11.05–11.15 (1H,br-s).
ESI-Mass; 407(MH$^+$).

Example 251

Synthesis of 1-(1-ethylpiperazin-4-yl)-3-(4-methoxyphenyl)-2,6-naphthyridine Dihydrochloride (251-1) 3-Bromo-4-pyridinecarboxaldehyde

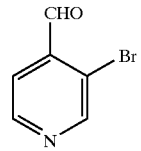

3-Bromopyridine (1.582 g) was dissolved in tetrahydrofuran (20 ml), followed by the addition of a 1.5M solution of lithium diisopropylamide/cyclohexane (7.3 ml) in nitrogen atmosphere at −70° C., and the resulting mixture was stirred for 5 min. Continuously, 4-formylmorpholine (3 ml) was added thereto and stirred for 20 min, followed by the further stirring at room temperature for 30 min. An aqueous solution of saturated ammonium chloride was added to the reaction mixture, and then it was extracted with ethyl acetate. The resulting organic layer was washed with water, dried (over MgSO$_4$) and evaporated. The resulting residue was purified by silica gel column chromatography (ethyl acetate/hexane system), to give the title compound as a colorless solid (749 mg, yield; 40%).

¹H-NMR(400 MHz, CDCl₃); δ (ppm) 7.70(1H,d,J=4.6 Hz), 8.91(1H,s), 10.36(1H,s).

(251-2) 3-(4-Methoxyphenylethynyl)-4-pyridinecarboxaldehyde

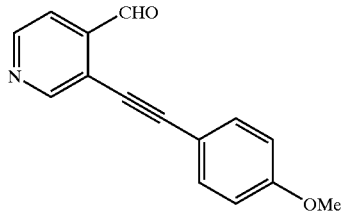

In the same manner as in Example 177, the title compound was obtained as a pale yellow solid (4.965 g, yield; 82%) from 3-bromo-4-pyridinecarboxaldehyde (4.755 g) and 4-methoxyphenylacetylene (3.742 g).

¹H-NMR(400 MHz,CDCl₃); δ (ppm) 3.86(3H,s), 6.93 (2H,d,J=8.8 Hz), 7.70(1H,dd,J=5.2 Hz,0.8 Hz), 8.70(1H,dd, J=5.2 Hz,0.8 Hz), 8.94(1H,d,J=0.8 Hz), 10.62(1H,s).

(251-3) 3-(4-Methoxyphenylethynyl)-4-pyridine aldoxime

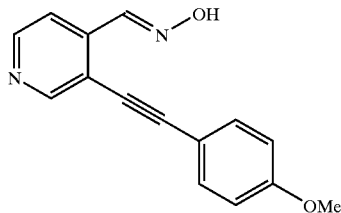

3-(4-Methoxyphenylethynyl)-4-pyridinecarboxaldehyde (4.965 g) was dissolved in ethanol (70 ml), a solution of hydroxylamine hydrochloride (2.179 g) and sodium acetate (3.429 g) in water (18 ml) was added thereto, and then the mixture was stirred at 70° C. overnight. After cooling as it was, the reaction mixture was evaporated and partitioned between ethyl acetate and water. The resulting organic layer was washed with water, dried (over MgSO₄) and evaporated. The resulting residue was purified by silica gel column chromatography (ethyl acetate/hexane system), to give the title compound as a yellow solid (4.724 g, yield; 96%).

¹H-NMR(400 MHz,CDCl₃); δ (ppm) 3.85(3H,s), 6.92 (2H,d,J=8.8 Hz), 7.51(2H,d,J=8.8 Hz), 7.73(1H,dd,J=5.2 Hz,0.8 Hz), 7.97(1H,s), 8.50(1H,dd,J=5.2 Hz,0.8 Hz), 8.62 (1H,s), 8.78(1H,d,J=0.8 Hz).

(251-4) 3-(4-Methoxyphenyl)-2,6-naphthyridine-2-oxide

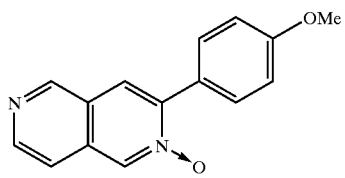

3-(4-Methoxyphenylethynyl)-4-pyridine aldoxime (4.724 g) was dissolved in ethanol (100 ml), followed by the addition of potassium carbonate (2.768 g)/water (30 ml) solution, and the mixture was stirred at 70° C. for 50 min. After cooling as it was, the resulting insoluble matters were collected by filtration, and then washed with water and ethanol, to give the title compound as a dark green solid (3.757 g, yield; 75%).

¹H-NMR(400 MHz,CDCl₃); δ (ppm) 3.89(3H,s), 7.04 (2H,d,J=8.8 Hz), 7.50(1H,dd,J=6.2 Hz,0.8 Hz), 7.77(2H,d, J=8.8 Hz), 7.88(1H,s), 8.61(1H,d,J=6.2 Hz), 8.85(1H,s), 8.78(1H,d,J=0.8 Hz).

(251-5) 1-(1-Ethylpiperazin-4-yl)-3-(4-methoxyphenyl)-2,6-naphthyridine dihydrochloride

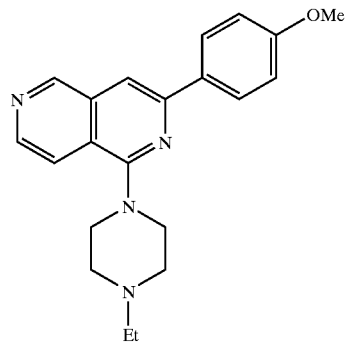

3-(4-Methoxyphenyl)-2,6-naphthyridine-2-oxide (234 mg) was dissolved in phosphorus oxychloride (6 ml), and the resulting mixture was heated under stirring at 110° C. for 20 min. After cooling as it was, the reaction solution was evaporated. To the resulting residue was added 1-ethylpiperazine (20 ml), which was then heated under stirring at 160° C. for 45 min. The reaction mixture was evaporated, and the resulting residue was partitioned between ethyl acetate and water. The resulting organic layer was washed with water, dried (over MgSO₄) and evaporated. The resulting residue was purified by (NH) silica gel column chromatography (ethyl acetate/hexane system), and then the resulting product was converted into a hydrochloride in a conventional manner, and recrystallized from ethanol/isopropyl ether, to give the hydrochloride of the title compound as yellow crystals (91 mg, yield; 22%).

Hydrochloride:

m.p.; 157–160° C.

¹H-NMR(400 MHz,CDCl₃); δ (ppm) 1.31(3H,t,J=7.2 Hz), 3.19(1H,q,J=7.2 Hz), 3.21(1H,q,J=7.2 Hz), 3.29(1H,t, J=10.3 Hz), 3.32(1H,t,J=10.3 Hz), 3.59(2H,d,J=10.3 Hz), 3.61(2H,t,J=12.8 Hz), 4.09(2H,d,J=12.8 Hz), 7.09(2H,d,J= 8.8 Hz), 8.10(1H,d,J=6 Hz), 8.16(2H,d,J=8.8 Hz), 8.19(1H, s), 8.61(1H,d,J=6 Hz), 9.49(1H,s), 11.20(1H,br-s).

ESI-Mass; 349(MH⁺).

Example 252

Synthesis of 5-(1-ethylpiperazin-4-yl)-7-(4-methoxyphenyl)-1,6-naphthyridine Dihydrochloride (252-1) 2-Methyl-N-methylnicotinamide

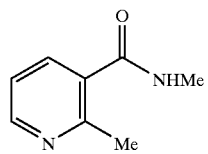

To ethyl 2-methylnicotinate (24.2 g) was added a solution of 40% methylamine in methanol (150 ml), which was then heated in a sealed tube at 50° C. overnight. The reaction mixture was evaporated, to give the title compound as a pale yellow solid (20.781 g, yield; 95%).

¹H-NMR(400 MHz,CDCl₃); δ (ppm) 3.27(3H,s), 4.08 (3H,s), 7.48(1H,dd,J=7.8 Hz,4.8 Hz), 8.16(1H,dd,J=7.8 Hz,1.6 Hz), 8.87(1H,dd,J=4.8 Hz,1.6 Hz).

(252-2) 2-[2-(4-Methoxyphenyl)-2-hydroxyethenyl]-N-methylnicotinamide

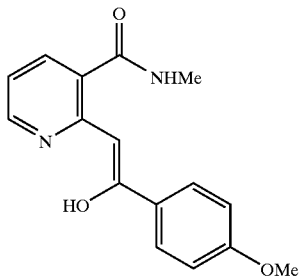

2-Methyl-N-methylnicotinamide (4.505 g) was dissolved in tetrahydrofuran (150 ml), followed by the dropwise addition of a solution of 1.5M lithium diisopropylamide in cyclohexane (40 ml) in nitrogen atmosphere at −30 to −20° C., and the mixture was stirred for 50 min. After cooling to −78° C., 4-methoxybenzonitrile (3.995 g)/tetrahydrofuran solution (20 ml) was added dropwise thereinto. After the mixture was stirred for 1 hr as it was, the cooling bath was removed, and then it was stirred overnight. An aqueous solution of saturated ammonium chloride was added thereto, and then the mixture was extracted with ethyl acetate. The resulting organic layer was washed with water, dried (over MgSO$_4$) and evaporated. A small amount of ethyl acetate was added to the resulting residue, and then the resulting insoluble matters were collected by filtration, to give 5.395 g of the title compound as a yellow solid.

$^1$H-NMR(400 MHz,DMSO-d$_6$); δ (ppm) 2.75(3H,d,J=4.8 Hz), 3.79(3H,s), 5.62(1H,s), 6.90(1H,dd,J=7.6 Hz,4.8 Hz), 7.01(2H,d,J=8.8 Hz), 7.52(2H,d,J=8.8 Hz), 7.53(1H,dd,J=7.6 Hz,2 Hz), 8.27(1H,q,J=4.8 Hz), 8.42(1H,dd,J=4.8 Hz,2 Hz).

(252-3) 7-(4-Methoxyphenyl)-1,6-naphthyridin-5-(6H)-one

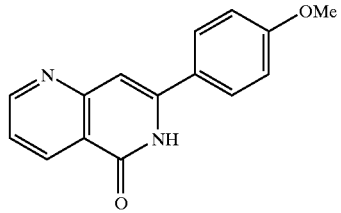

2-[2-(4-Methoxyphenyl)-2-hydroxyethenyl]-N-methylnicotinamide (2.509 g) was added to a 29% aqueous solution of ammonia (100 ml) and dioxane (50 ml), which was then heated in a sealed tube at 170° C. overnight. After cooling as it was, the resulting insoluble matters were collected by filtration, to give the title compound as a dark green solid (1.694 g, yield; 73%).

$^1$H-NMR(400 MHz,DMSO-d$_6$); δ (ppm) 3.83(3H,s), 6.87 (1H,s), 7.07(2H,d,J=8.8 Hz), 7.46(1H,dd,J=8 Hz,4 Hz), 7.81 (2H,d,J=8.8 Hz), 8.45(2H,d,J=8.8 Hz), 8.45(1H,dd,J=8 Hz,1.6 Hz), 8.91(1H,dd,J=4.4 Hz,1.6 Hz).

(252-4) 5-(1-Ethylpiperazin-4-yl)-7-(4-methoxyphenyl)-1,6-naphthyridine dihydrochloride

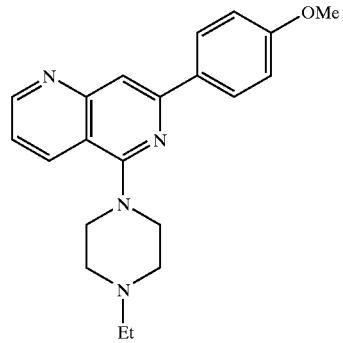

Phosphorus oxychloride (10 ml) was added to 7-(4-methoxyphenyl)-1,6-naphthyridin-5-(6H)-one (1.505 g), and the resulting mixture was heated under stirring at 100° C. for 6 hr. After cooling as it was, the reaction mixture was evaporated, followed by the addition of 1-ethylpiperazine (10 ml). The resulting mixture was heated under stirring at 150° C. overnight, and then evaporated. The resulting residue was purified by silica gel column chromatography (methylene chloride/methanol system), and then the resulting product was converted into a hydrochloride in a conventional manner, and recrystallized from ethanol/isopropyl ether, to give the hydrochloride of the title compound as yellow crystals (1.974 g, yield; 78%).
Hydrochloride:
m.p.; 242–245° C.
$^1$H-NMR(400 MHz,DMSO-d$_6$); δ (ppm) 1.30(3H,t,J=7.2 Hz), 3.14–3.35(4H,m), 3.54–3.68(4H,m), 3.82(3H,s), 4.08 (2H,d,J=14 Hz), 7.08(2H,d,J=8.8 Hz), 7.66(1H,dd,J=8.4 Hz,4.2 Hz), 8.00(1H,s), 8.17(2H,d,J=8.8 Hz), 8.71(1H,dd, J=8.4 Hz,1.6 Hz), 9.09(1H,dd,J=4.2 Hz,1.6 Hz), 11.28(1H, br-s).
ESI-Mass; 349(MH$^+$).

Example 253

Synthesis of 5-[4-(2-hydroxyethoxy)phenyl]-7-(4-methylpiperazin-1-yl)thieno[2,3-c]pyridine Hydrochloride

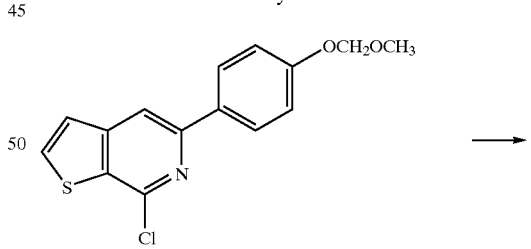

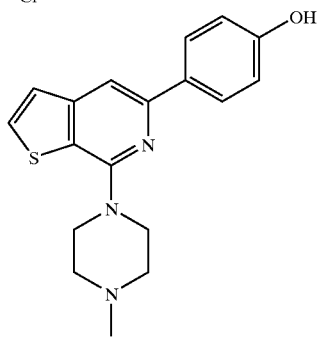

-continued

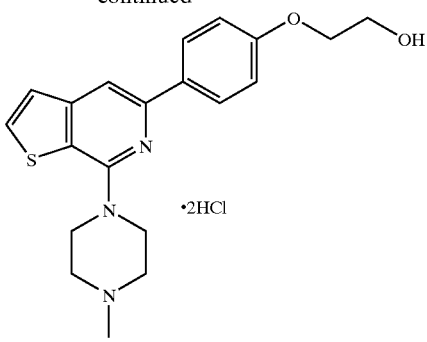

An oil (794 mg) was obtained from 7-chloro-5-(4-methoxymethoxyphenyl)thieno[2,3-c]pyridine (432 mg) obtained by the same treatment as in Example 18 and N-methylpiperazine (8 ml). To the resulting oil was added 5N hydrochloric acid/ethanol (6 ml), and the mixture was heated under reflux for 3 hr. The reaction solution was cooled and subsequently neutralized with a 5N aqueous solution of sodium hydroxide, and then extracted with chloroform. The resulting organic layer was washed with water, dried and evaporated, to give 5-(4-hydroxyphenyl)-7-(4-methylpiperazin-1-yl)thieno[2,3-c]pyridine (433 mg). To a solution of the resulting compound in dimethylformamide (6 ml) were added 60% sodium hydride (212 mg) and 2-bromoethoxy t-butyldimethylsilane (1.7 ml), and the mixutre was reacted at 80° C. for 3 hr. The reaction solution was poured into an aqueous solution of saturated ammonium chloride, and then extracted with ethyl acetate. The resulting organic layer was washed with water and brine, dried and evaporated. Sequentially, to the resulting residue were added tetrahydrofuran (10 ml) and 1.0M tetrabutylammonium fluoride/tetrahydrofuran solution (10 ml), and the mixture was stirred at room temperature for 30 min. The reaction solution was partitioned between ethyl acetate and water. The resulting organic layer was washed with water, dried and evaporated. The resulting residue was purified by NH-silica gel column chromatography (hexane/ethyl acetate system), to give a yellow oil (210 mg, yield; 43%). The resulting oil was converted into a hydrochloride in a conventional manner, to give the hydrochloride of the title compound as yellow crystals.

Hydrochloride:

m.p.; 141–143° C.

$^1$H-NMR(400 MHz,DMSO-d$_6$); δ (ppm) 2.83(d,J=4.8 Hz,3H), 3.14–3.29(m,2H), 3.49–3.58(m,4H), 3.75(t,J=4.8 Hz,2H), 4.05(t,J=4.8 Hz,2H), 4.40(d,J=14.0 Hz,2H), 7.05(d,J=8.8 Hz,2H), 7.54(d,J=5.6 Hz,1H), 7.97(s,1H), 8.06(d,J=5.6 Hz,1H), 8.08(d,J=8.8 Hz,2H).

MS(FAB) m/z 370(M+H)$^+$.

Free compound:

$^1$H-NMR(400 MHz,CDCl$_3$); δ (ppm) 2.39(s,3H), 2.65(t, J=4.8 Hz,4H), 3.83(t,J=4.8 Hz,4H), 3.99(t,J=4.4 Hz,2H), 4.15(t,J=4.4 Hz,2H), 7.00(d,J=8.8 Hz,2H), 7.33(d,J=5.6 Hz,1H), 7.55(d,J=5.6 Hz,1H), 7.62(s,1H), 8.05(d,J=8.8 Hz,2H).

Example 254

Synthesis of 7-(1-ethylpiperazin-4-yl)-5-[4-(1-hydroxypentyl)phenyl]thieno[2,3-c]pyridine Dihydrochloride

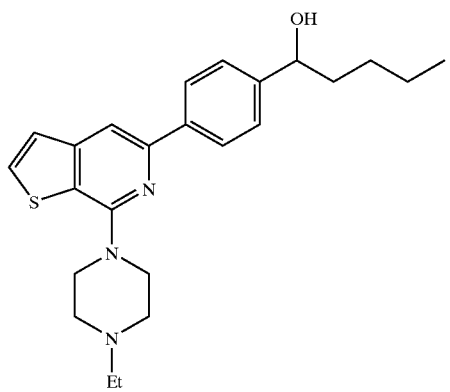

7-(1-Ethylpiperazin-4-yl)-5-(4-pentanoylphenyl)thieno[2,3-c]pyridine (206 mg) was dissolved in tetrahydrofuran (12 ml), followed by the addition of lithium aluminum hydride (20 mg) under ice-cooling, and the mixture was stirred for 15 min. To the reaction mixture were sequentially added water (20 ml), 5N sodium hydroxide (20 ml) and water (60 ml). The resulting insoluble matters were filtered off through Celite, and then the resulting filtrate was evaporated. The resulting residue was purified by (NH) silica gel column chromatography (ethyl acetate/hexane system). The resulting product was converted into a hydrochloride in a conventional manner, to give the hydrochloride the title compound as a yellow amorphous (196 mg, yield; 80%).

Hydrochloride:

$^1$H-NMR(400 MHz,DMSO-d$_6$): δ (ppm) 0.83(3H,t,J=7 Hz), 1.08–1.30(4H,m), 1.29(3H,t,J=7.2 Hz), 1.52–1.68(2H, m), 3.12–3.22(4H,m), 3.54–3.63(4H,m), 4.40(2H,d,J=14 Hz), 4.54(1H,t,J=6.4 Hz), 7.40(2H,d,J=8 Hz), 7.55(1H,d,J=5.4 Hz), 8.00(1H,s), 8.05(2H,d,J=8 Hz), 8.06(1H,d,J=5.4 Hz), 11.10–11.20(1H,br-s).

ESI-Mass; 410(MH$^+$).

Example 255

Synthesis of 7-(1-ethylpiperazin-4-yl)-5-[4-(1-hydroxy-3-methylbutyl)phenyl]thieno[2,3-c]pyridine Dihydrochloride

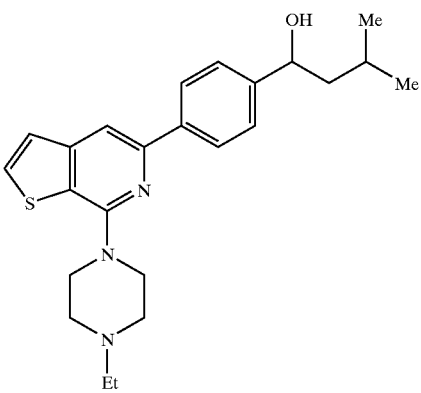

In the same manner as in Example 254, the hydrochloride of the titled compound was obtained as a yellow amorphous (149 mg, yield; 60%) from 7-(1-ethylpiperazin-4-yl)-5-(4-isopentanoylphenyl)thieno[2,3-c]pyridine (212 mg).
Hydrochloride:

$^1$H-NMR(400 MHz,DMSO-d$_6$); δ (ppm) 0.89(3H,d,J=6.4 Hz), 0.90(3H,d,J=6.4 Hz), 1.29(3H,t,J=7.2 Hz), 1.32–1.40 (1H,m), 1.53–1.70(2H,m), 3.13–3.22(4H,m), 3.54–3.63(4H,m), 4.40(2H,d,J=14 Hz), 4.60(1H,dd,J=8.6 Hz,5 Hz), 7.41 (2H,d,J=8.4 Hz), 7.55(1H,d,J=5.4 Hz), 8.00(1H,s), 8.05(2H,d,J=8.4 Hz), 8.06(1H,d,J=5.4 Hz), 11.10–11.20(1H,br-s).

ESI-Mass; 410(MH$^+$).

Example 256

Synthesis of 7-(1-ethylpiperazin-4-yl)-5-[4-(3-hydroxy-1-fluoropropyl)phenyl]thieno[2,3-c]pyridine Dihydrochloride

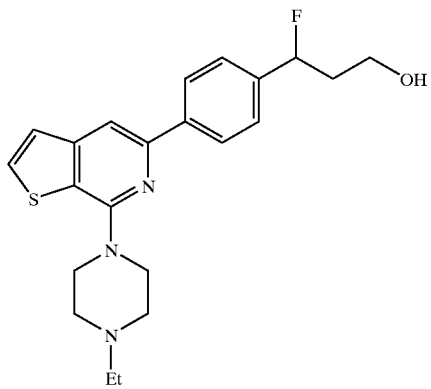

In the same manner as in Example 27, the hydrochloride of the title compound was obtained as a hygroscopic yellow amorphous (101 mg, yield; 20%) from 7-(1-ethylpiperazin-4-yl)-5-bromothieno[2,3-c]pyridine (330 mg).

$^1$H-NMR(400 MHz,DMSO-d$_6$); δ (ppm) 1.29(3H,t,J=7.2 Hz), 1.65–2.20(2H,m), 3.10–3.24(4H,m), 3.30–3.65(6H,m), 4.42(2H,d,J=13.6 Hz), 5.70(1H,ddd,J=48 Hz,9.2 Hz,4 Hz), 7.48(2H,d,J=8.8 Hz), 7.56(1H,d,J=5.6 Hz), 8.05(1H,s), 8.08 (1H,d,J=5.6 Hz), 8.15(2H,d,J=8.8 Hz), 11.05–11.15(1H,br-s).

ESI-Mass; 400(MH$^+$).

Example 257

Synthesis of 5-[4-(3-hydroxypropyl)-3-chlorophenyl]-7-(4-ethylpiperazin-1-yl)thieno[2,3-c]pyridine Oxalate

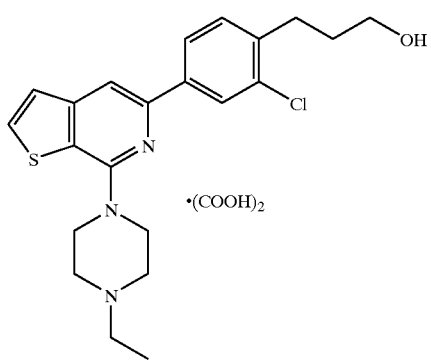

In the same manners sequentially as in Examples 161-2 and 20, an oil was obtained from 1-bromo-4-(3-acetoxypropyl)-3-chlorobenzene (948 mg) and 5-bromo-7-(4-ethylpiperazin-1-yl)thieno[2,3-c]pyridine (243 mg). To the resulting oil were added tetrahydrofuran (10 ml) and 1.0 M lithium aluminum hydride/tetrahydrofuran solution (0.8 ml) under ice-cooling, and the mixture was reacted under ice-cooling for 1 hr. Subsequently, water (0.03 ml), a 5N aqueous solution of sodium hydroxide (0.03 ml) and water (0.09 ml) were sequentially added to the resulting mixture, and then the mixture was stirred at room temperature for 1 hr. The resulting residue was filtered, washed with ethyl acetate, and then purified by silica gel column chromatography (hexane/ethyl acetate system), to give a colorless oil. The resulting oil was converted into an oxalate in a conventional manner, to give the oxalate of the title compound as white crystals (205 mg, yield; 60%).

Oxalate:

m.p.; 114–116° C.

$^1$H-NMR(400 MHz,DMSO-d$_6$); δ (ppm) 1.22(t,J=7.2 Hz,3H), 1.76(t,J=7.6 Hz,2H), 2.78(t,J=7.6 Hz,2H), 2.99(q, J=7.2 Hz,2H), 3.20(br,4H), 3.48(t,J=7.6 Hz,2H), 3.89(br, 4H), 7.44(d,J=8.0 Hz,1H), 7.55(d,J=5.2 Hz,1H), 8.02(d,J= 8.0 Hz,1H), 8.05(s,1H), 8.08(d,J=5.2 Hz,1H), 8.14(s,1H).

MS(FAB) m/z 416(M+H)$^+$.

Free compound:

$^1$H-NMR(400 MHz,CDCl$_3$); δ (ppm) 1.16(t,J=7.2 Hz,3H), 1.91–1.98(m,2H), 2.52(q,J=7.2 Hz,2H), 2.69(t,J= 4.8 Hz,4H), 2.88(t,J=7.6 Hz,2H), 3.73(t,J=7.6 Hz,2H), 3.85 (t,J=4.8 Hz,4H), 7.31(d,J=8.0 Hz,1H), 7.34(d,J=5.6 Hz,1H), 7.58(d,J=5.6 Hz,1H), 7.64(s,1H), 7.90(dd,J=8.0,2.0 Hz,1H), 8.09(d,J=2.0 Hz,1H).

Example 258

Synthesis of 7-(1-ethylpiperazin-4-yl)-5-[3-(2-hydroxyethoxy)phenyl]thieno[2,3-c]pyridine Dihydrochloride (258-1) 3-Bromophenoxyethyl acetate

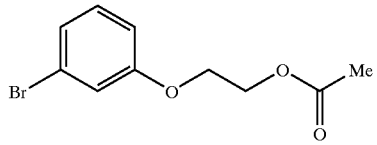

In the same manner as in Example 300-2, the titled compound was obtained as a colorless oil (11.213 g, yield; 74%) from 3-bromophenol (10.062 g) and 2-bromoethyl acetate (24.4 g).

$^1$H-NMR(400 MHz,CDCl$_3$): δ (ppm) 2.10(3H,s), 4.15 (2H,t,J=4.6 Hz), 4.41(2H,t,J=4.6 Hz), 6.85(1H,ddd,J=8 Hz,2.4 Hz,1.2 Hz), 7.07–7.12(2H,m), 7.15(1H,t,J=8 Hz).

(258-2) 7-(1-Ethylpiperazin-4-yl)-5-[3-(2-hydroxyethoxy)phenyl]thieno[2,3-c]pyridine dihydrochloride

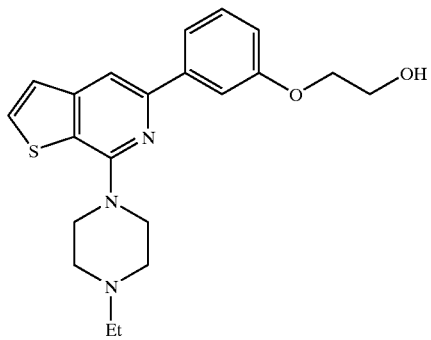

In the same manner as in Example 161-1, 3-tributylstannylphenoxyethyl acetate of was obtained as a colorless oil (2.255 g) from 3-bromophenoxyethyl acetate (3.454 g) and bis(tributyltin) (5.1 ml). A part (394 mg) of the resulting compound and 7-(1-ethylpiperazin-4-yl)-5-bromothieno[2,3-c]pyridine (137 mg) were treated in the same manner as in Example 300-4, to give the hydrochloride of the title compound as pale yellow crystals (34 mg, yield; 18%).
Hydrochloride:
m.p.; 132–135° C.
$^1$H-NMR(400 MHz,DMSO-$d_6$); δ (ppm) 1.29(3H,t,J=7.2 Hz), 3.13–3.22(4H,m), 3.58(2H,t,J=14.4 Hz), 3.62(2H,d,J=11.2 Hz), 3.74(2H,t,J=5.2 Hz), 4.07(2H,t,J=5.2 Hz), 4.40 (2H,d,J=14.4 Hz), 6.97(1H,ddd,J=8 Hz,2.6 Hz,1.6 Hz), 7.37 (1H,t,J=8 Hz), 7.55(1H,d,J=5.6 Hz), 7.68(1H,dd,J=2.6 Hz,1 Hz), 7.69(1H,ddd,J=8 Hz,1.6 Hz,1 Hz), 8.05(1H,s), 8.06 (1H,d,J=5.6 Hz), 11.15–11.25(1H,br-s). FAB-Mass; 384 (MH$^+$).

Example 259

Synthesis of 7-(4-ethylpiperazin-1-yl)-5-(4-hydroxyethoxyphenyl)thieno[2,3-c]pyridine Hydrochloride (259-1) 3-Bromo-2-thiophenecarboxaldehyde

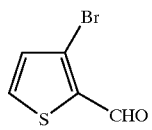

Methyl 3-amino-2-thiophenecarboxylate (23.5 g) was converted into methyl 3-bromo-2-thiophenecarboxylate (20.8 g) by Sandmeyer's method, and the resulting ester was reduced with lithium aluminum hydride (2.8 g). Continuously, the resulting compound was oxidized with activated manganese dioxide (30.0 g), to give 14.5 g of the title compound.

(259-2) 1-[(1,3-Dioxolan-2-yl)methoxy]-4-iodobenzene

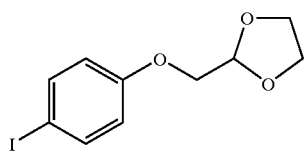

A suspension of 65% sodium hydride (9.3 g)/dimethylformamide (100 ml) was ice-cooled, followed by the addition of 4-iodophenol (50.5 g)/dimethylformamide (200 ml) solution, and the mixture was stirred for 3 hr. To the mixture solution was added (1,3-dioxolan-2-yl)methyl bromide (46.0 g), and the mixture was reacted at 60° C. for 1 day. The reaction solution was poured into water, and extracted with ethyl acetate. The resulting organic layer was washed with water and brine, and then dried (over magnesium sulfate). The solvent was removed, and the resulting residue was purified by NH silica gel column chromatography (chloroform), and then recrystallized from ethyl acetate/hexane, to give 32.7 g of the title compound as pale yellow prisms.

(259-3) 1-[(1,3-Dioxolan-2-yl)methyloxy]-4-ethynylbenzene

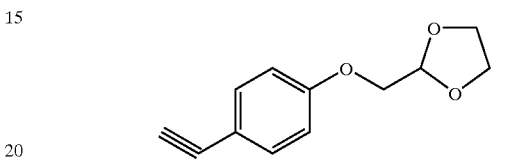

1-[(1,3-Dioxolan-2-yl)methyloxy]-4-iodobenzene (36.3 g) and trimethylsilylacetylene (50.0 g) were reacted in the presence of bistriphenylphosphinepalladium dichloride (2.50 g) and cuprous iodide (1.25 g), in triethylamine (140 ml) and pyridine (70 ml) at 60° C. for 2 hr. The reaction solution was partitioned between ethyl acetate and water. The resulting organic layer was washed with water, dried and concentrated. The resulting residue was dissolved in methanol and treated with 2N sodium hydroxide, to give 20.1 g of the title compound.

(259-4) 3-[2-(4-Methoxyphenyl)ethynyl]-2-thiophenecarboxyaldehyde

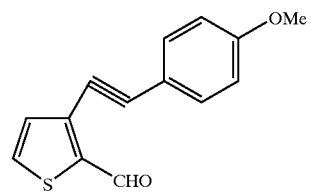

3-Bromo-2-thiophenecarboxyaldehyde (7.5 g) and 1-[(1,3-dioxolan-2-yl)methyloxy]-4-ethynylbenzene (7.8 g) were reacted in dimethylformamide (25 ml), in the presence of bistriphenylphosphinepalladium dichloride (0.48 g), cuprous iodide (0.13 g) and triethylamine (25 ml) at 60° C. for 12 hr. The reaction solution was evaporated, extracted with ethyl acetate, washed with water and dried. The solvent was removed, and the resulting residue was purified by silica gel column chromatography (ethyl acetate/hexane system), to give 7.2 g of the title compound as a pale yellow oil.

(259-5) 5-(4-Methoxyphenyl)thieno[2,3-c]pyridine-6-oxide

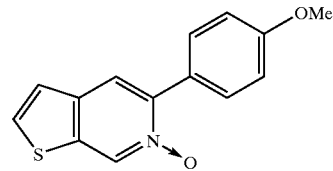

3-[2-(4-Methoxyphenyl)ethynyl]-2-thiophenecarboxaldehyde (7.2 g), hydroxylamine hydrochloride (2.4 g) and sodium acetate (3.3 g) were reacted in ethanol (100 ml) at 60° C. for 2 hr. Then the resulting solution was concentrated. Potassium carbonate (3.0 g), water (10 ml) and 1-butanol (50 ml) were added to the resulting residue, and the mixture was reacted at 100° C. for 3 days. The reaction solution was evaporated, extracted with methylene chloride, washed with brine and dried. The solvent was removed, and the resulting residue was purified by silica gel column chromatography (methylene chloride/methanol system), to give 3.04 g of the title compound as a white amorphous.

(259-6) 7-(4-Ethylpiperazin-1-yl)-5-(4-methoxyphenyl)thieno[2,3-c]pyridine

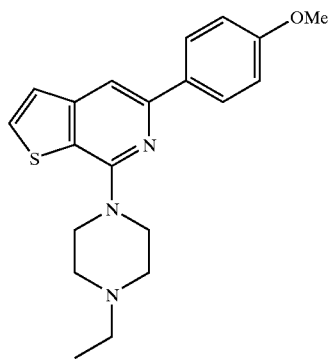

5-(4-Methoxyphenyl)thieno[2,3-c]pyridine-6-oxide (3.0 g) was reacted with phosphorus oxychloride (15 ml) at 100° C. for 3 hr. The reaction mixture was poured into ice-water, neutralized with sodium carbonate and extracted with ethyl acetate. The organic layer was washed with water and brine and dried. The extract was filtered through silica gel, and the column was washed with ethyl acetate. The filtrates were combined and concentrated. The resulting 7-chloro-5-(4-methoxyphenyl)thieno[2,3-c]pyridine (2.1 g) was reacted reacted in N-ethylpiperazine (5 ml) and dimethyl sulfoxide (20 ml) with potassium carbonate (5.0 g) at 100° C. for 1 day. The reaction solution was evaporated, and the resulting residue was partitioned between ethyl acetate and water and extracted with ethyl acetate. The organic layer was washed with water and dried. Then, the solvent was removed, and the resulting residue was purified by silica gel column chromatography (methylene chloride/methanol system), to give 0.93 g of the title compound of as a pale brown oil.

(259-7) 7-(4-Ethylpiperazin-4-yl)-5-(4-hydroxyphenyl)thieno[2,3-c]pyridine

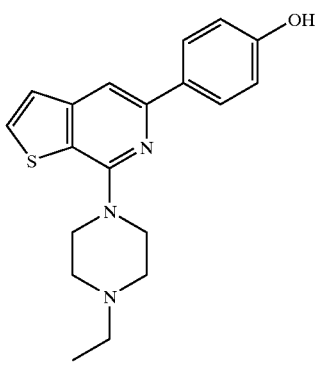

7-(4-Ethylpiperazin-1-yl)-5-(4-methoxyphenyl)thieno[2,3-c]pyridine (0.43 g) was reacted with 48% hydrbromic acid (10 ml) at 120° C. for 2 hr. The reaction solution was cooled, and then neutralized with 5N sodium hydroxide and extracted with chlororform. The resulting organic layer was washed with water, dried and concentrated. The resulting pale brown solid was washed with hexane/ethyl acetate (20:1), to give 0.13 g of the title compound.

(259-8) 7-(4-Ethylpiperazin-1-yl)-5-(4-(2-hydroxyethoxy)phenyl)thieno[2,3-c]pyridine

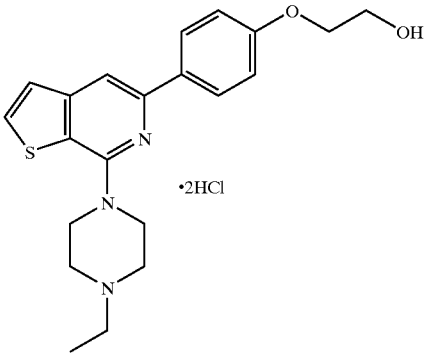

To 7-(4-ethylpiperazin-1-yl)-5-(4-hydroxyphenyl)thieno[2,3-c]pyridine (130 mg)/dimethylformamide (10 ml) solution was added 60% sodium hydride (23 mg) at room temperature. After the evolution of hydrogen was ceased, dimethyl-(t-butyl)silyloxyethyl bromide (100 mg) was added thereto, and the mixture was reacted at room temperature for 12 hr. Ethyl acetate and an aqueous solution of ammonium chloride were added to the reaction solution. The organic phase was separated, washed with water, dried and concentrated. To the resulting residue were added ethanol (20 ml) and a 2N aqueous solution of hydrochloric acid (10 ml), and the mixture was reacted at 50° C. for 30 min, followed by the evaporation. The resulting residue was partitioned between ethyl acetate and water. The organic layer was washed with water and brine, and dried. The solvent was removed, and then resulting residue was purified by NH-silica gel column chromatography (ethyl acetate), to give 73 mg of the title compound as a pale yellow oil.

The resulting compound was converted into a hydrochloride in a conventional manner, to give 77 mg of the title compound as a yellow powder.

Hydrochloride:

$^1$H-NMR(400 MHz,DMSO-d$_6$); δ (ppm) 1.28(t,J=7.2 Hz,3H), 3.14–3.25(m,4H), 3.54(br-t,2H), 3.63(br-d,2H), 3.73(m,2H), 3.90–4.18(m,2H), 4.41(br-d,2H), 7.03(d,J=8.4 Hz,2H), 7.54(d,J=5.6 Hz,1H), 7.97(s,1H), 8.03–8.10(m,2H). m.p.; 135–136° C.

MS(FAB) m/z 384(M+H)$^+$.

Example 260

Synthesis of 7-(1-ethylpiperazin-4-yl)-5-[4-(2-hydroxy-3-methylpropyl)phenyl]thieno[2,3-c]pyridine Dihydrochloride

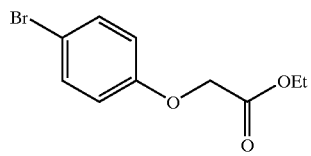

In the same manner as in Example 300-2, the titled compound was obtained as a colorless solid (41.938 g, yield; 92%) from 2-bromophenol (30.121 g) and ethyl bromoacetate (40.304 g).

¹H-NMR(400 MHz,CDCl₃); δ (ppm) 1.30(3H,t,J=7.2 Hz), 4.27(2H,q,J=7.2 Hz), 4.59(2H,s), 6.80(2H,d,J=8.8 Hz), 7.39(2H,d,J=8.8 Hz).

(260-2) 7-(1-Ethylpiperazin-4-yl)-5-[(4-ethoxycarbonylmethoxy)phenyl]thieno[2,3-c]pyridine

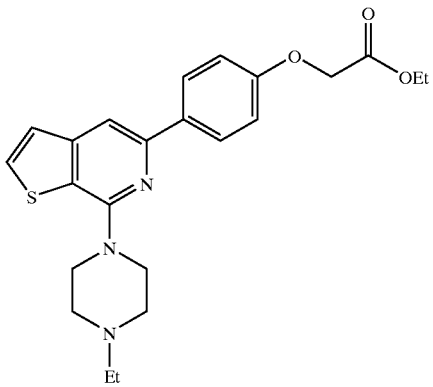

In the same manner as in Example 161-2, ethyl (4-tributylstannylphenoxy)acetate was obtained as a colorless oil (5.594 g) from ethyl (4-bromophenoxy)acetate (9.069 g) and bis(tributyltin) (18 ml). The resulting compound and 7-(1-ethylpiperazin-4-yl)-5-bromothieno[2,3-c]pyridine (368 mg) were treated in the same manner as in Example 161-3, to give the title compound as a colorless oil (339 mg, yield; 73%).

¹H-NMR(400 MHz,CDCl₃); δ (ppm) 1.16(3H,t,J=7.2 Hz), 1.31(3H,t,J=7.2 Hz), 2.51(2H,q,J=7.2 Hz), 2.68(4H,t,J=5 Hz), 3.84(4H,t,J=5 Hz), 4.29(2H,q,J=7.2 Hz), 4.70(2H,s), 6.99(2H,d,J=8.8 Hz), 7.32(1H,d,J=5.2 Hz), 7.54(1H,d,J=5.2 Hz), 7.60(1H,s), 8.05(2H,d,J=8.8 Hz).

(260-3) 7-(1-Ethylpiperazin-4-yl)-5-[4-(2-hydroxy-2-methylpropoxy)phenyl]thieno[2,3-c]pyridine dihydrochloride or compound identified by the following analysis data and synthetic procedures

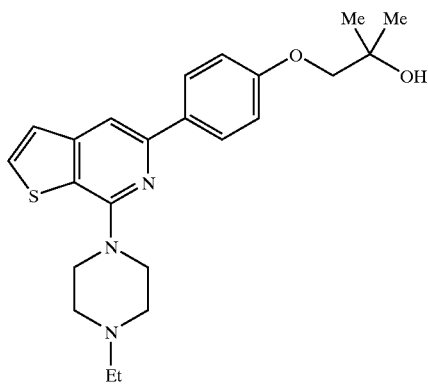

7-(1-Ethylpiperazin-4-yl)-5-[(4-ethoxycarbonylmethoxy)phenyl]thieno[2,3-c]pyridine (339 mg) was dissolved in tetrahydrofuran (12 ml), followed by the addition of 3M methylmagnesium bromide/ether solution (1.3 ml) under ice-cooing, and the mixture was stirred for 1 hr. An aqueous saturated ammonium chloride was added to the reaction mixture, and then extracted with ethyl acetate. The resulting organic layer was washed with water, dried (over MgSO₄) and evaporated. The resulting residue was purified by (NH) silica gel column chromatography (ethyl acetate/hexane system). Then, the resulting product was converted into a hydrochloride in a conventional manner, and then recrystallized from ethanol/isopropyl ether, to give the hydrochloride of the title compound as a pale yellow solid (326 mg, yield; 88%).

Hydrochloride:
m.p.; 137–139° C.
¹H-NMR(400 MHz,DMSO-d₆); δ (ppm) 1.21(6H,s), 1.29 (3H,t,J=7.2 Hz), 3.13–3.23(4H,m), 3.53(2H,t,J=13.6 Hz), 3.63(2H,d,J=11.6 Hz), 3.76(2H,s), 4.39(2H,d,J=13.6 Hz), 7.03(2H,d,J=8.8 Hz), 7.52(1H,d,J=5.6 Hz), 7.95(1H,s), 8.04 (1H,d,J=5.6 Hz), 8.06(2H,d,J=8.8 Hz), 10.90(1H,br-s). FAB-Mass; 412(MH)⁺.

Example 261

Synthesis of 5-[3-(3-hydroxypropyl)-4-methoxyphenyl]-7-(4-ethylpiperazin-1-yl)thieno[2,3-c]pyridine Oxalate

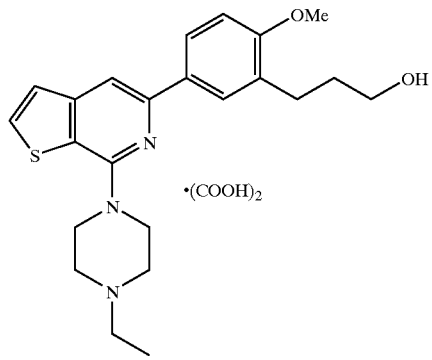

In the same manners sequentially as in Examples 161-2 and 20, an oil was obtained prepared from 1-bromo-3-(3-acetoxypropyl)-4-methoxybenzene (2.57 g) and 5-bromo-7-(4-ethylpiperazin-1-yl)thieno[2,3-c]pyridine (1.7 g). To the resulting oil were added methanol (9 ml) and a 1N aqueous solution of sodium hydroxide (1 ml), and the mixture was heated under reflux for 1 hr. The reaction solution was partitioned between ethyl acetate and water. The resulting organic layer was washed with water, dried and concentrated. The resulting residue was purified by silica gel column chromatography (hexane/ethyl acetate system), to give a colorless oil (188 mg, yield; 64%). The resulting oil was converted into an oxalate in a conventional manner, to give the oxalate of the title compound as white crystals.

Oxalate:
m.p.; 98–102° C.
¹H-NMR(400 MHz,DMSO-d₆); δ (ppm) 1.21(t,J=7.2 Hz,3H), 1.65–1.78(m,4H), 2.66(t,J=7.2 Hz,2H), 2.97(q,J=7.2 Hz,2H), 3.72(br,4H), 3.46(t,J=6.8 Hz,2H), 3.59–3.62(m, 2H), 3.84(s,3H), 7.05(d,J=8.4 Hz,1H), 7.53(d,J=5.2 Hz,1H), 7.89(br,1H), 7.92(s,1H), 7.96(d,J=8.4 Hz,1H), 8.03(d,J=5.2 Hz,1H).
MS(FAB) m/z 412(M+H)⁺.

Free compound:
¹H-NMR(400 MHz,CDCl₃); δ (ppm) 1.16(t,J=7.6 Hz,3H), 1.88–1.94(m,2H), 2.51(q,J=7.6 Hz,2H), 2.69(t,J=4.8 Hz,4 H), 2.81(t,J=7.2 Hz,2H), 3.65(t,J=6.0 Hz,2H), 3.84(t,J=4.8 Hz,4H), 3.88(s,3H), 6.94(d,J=8.8 Hz,1H), 7.32 (d,J=5.6 Hz,1H), 7.54(d,J=5.6 Hz,1H), 7.61(s,1H), 7.87(d, J=2.4 Hz,1H), 7.94(dd,J=8.8,2.0 Hz,1H).

Example 262

Synthesis of 5-[4-(3-hydroxypropyl)-3-cyanophenyl]-7-(4-ethylpiperazin-1-yl)thieno[2,3-c]pyridine Oxalate

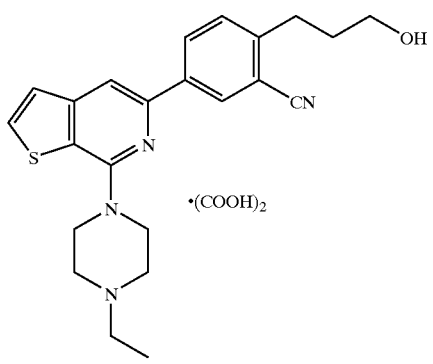

In the same manners sequentially as in Example 161-2 and 20, a yellow oil was obtained from 1-bromo-4-(3-acetoxypropyl)-3-cyanobenzene (610 mg) and 5-bromo-7-(4-ethylpiperazin-1-yl)thieno[2,3-c]pyridine (164 mg). To the resulting oil were added THF (5 ml), carbon tetrachloride (5 ml) and triphenylphosphine (630 mg), and the mixture was reacted at 60° C. for 2 hr. The reaction solution was partitioned between ethyl acetate and water, and the resulting organic layer was extracted with 2N hydrochloric acid. The aqueous layer was basified with 2N sodium hydroxide, and then back-extracted with ethyl acetate. The resulting organic layer was washed with water, dried and evaporated. To the resulting residue were added methanol (10 ml) and a 1N aqueous solution of sodium hydroxide (1 ml), and the mixture was reacted at 50° C. for 30 min. The reaction solution was partitioned between ethyl acetate and water. The resulting organic layer was washed with brine, dried and evaporated. The resulting residue was purified by NH-silica gel column chromatography (ethyl acetate/hexane system), to give a yellow oil (75 mg, yield; 38%). The resulting oil was converted into an oxalate in a conventional manner, to give the oxalate of the title compound as white crystals.

Oxalate:

m.p.; 132–134° C.

$^1$H-NMR(400 MHz,DMSO-$d_6$); δ (ppm) 1.23(t,J=7.2 Hz,3H), 1.76–1.84(m,2H), 2.88(t,J=7.6 Hz,2H), 3.06(q,J=7.2 Hz,2H), 3.27(br,4H), 3.48(t,J=5.2 Hz,2H), 3.92(br,4H), 7.56(d,J=5.6 Hz,1H), 7.60(d,J=8.4 Hz,1H), 8.10(d,J=5.6 Hz,1H), 8.13(s,1H), 8.38(dd,J=8.4,1.6 Hz,1H), 8.49(d,J=1.6 Hz,1H).

MS(FAB) m/z 407(M+H)$^+$.

Free compound:

$^1$H-NMR(400 MHz,CDCl$_3$); δ (ppm) 1.17(t,J=7.6 Hz,3H), 1.95–2.05(m,2H), 2.53(q,J=7.6 Hz,2H), 2.70(t,J=4.8 Hz,4H), 3.00(t,J=7.6 Hz,2H), 3.75(t,J=6.4 Hz,2H), 3.87 (t,J=4.8 Hz,4H), 7.37(d,J=5.6 Hz,1H), 7.43(d,J=8.0 Hz,1H), 7.61(d,J=5.6 Hz,1H), 7.65(s,1H), 8.22(dd,J=8.0,2.0 Hz,1H), 8.37(d,J=2.0 Hz,1H).

Example 263

Synthesis of 5-[2-(4-morpholinyl)pyridin-5-yl]-7-(4-ethylpiperazin-1-yl)thieno[2,3-c]pyridine Hydrochloride

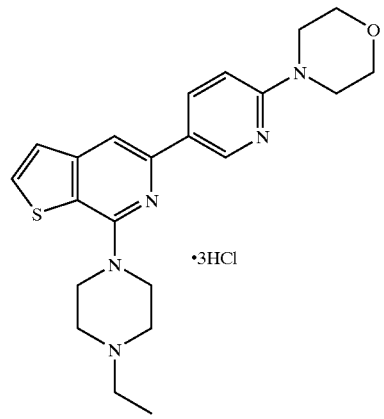

In the same manners sequentially as in Examples 161-2 and 20, an oil was obtained (209 mg, yield; 83%) from 5-bromo-2-(4-morpholinyl)pyridine (756 mg) and 5-bromo-7-(4-ethylpiperazin-1-yl)thieno[2,3-c]pyridine (200 mg). The resulting oil was converted into an oxalate in a conventional manner, to give the oxalate of the title compound as white crystals.

Oxalate:

m.p.; 182–185° C.

$^1$H-NMR(400 MHz,DMSO-$d_6$); δ (ppm) 1.32(t,J=7.2 Hz,3H), 3.15–3.27(m,4H), 3.58–3.66(m,4H), 3.76–3.79(m, 8H), 4.44(d,J=14.0 Hz,2H), 7.45(d,J=9.6 Hz,1H), 7.56(d,J=5.6 Hz,1H), 8.11(s,1H), 8.13(d,J=5.6 Hz,1H), 8.67(d,J=9.6 Hz,1H), 8.69(s,1H).

MS(FAB) m/z 410(M+H)$^+$.

Free compound:

$^1$H-NMR(400 MHz,CDCl$_3$): δ (ppm) 1.16(t,J=7.6 Hz,3H), 2.51(q,J=7.6 Hz,2H), 2.68(t,J=5.2 Hz,4H), 3.58(t, J=5.2 Hz,4H), 3.85(t,J=5.2 Hz,8H), 6.72(d,J=8.8 Hz,1H), 7.33(d,J=5.6 Hz,1H), 7.56(d,J=5.6 Hz,1H), 7.57(s,1H), 8.21 (dd,J=8.8,2.4 Hz,1H), 8.97(d,J=2.4 Hz,1H).

Example 264

Synthesis of 5-[2-(4-thiomorpholinyl)pyridin-5-yl]-7-(4-ethylpiperazine-1-yl)thieno[2,3-c]pyridine Hydrochloride

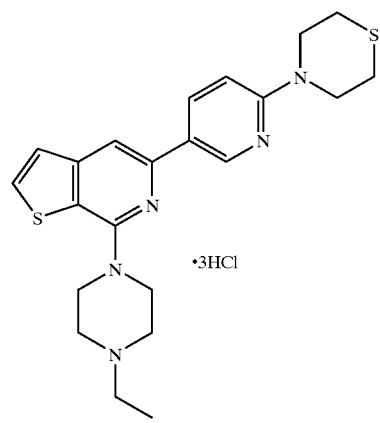

In the same manners sequentially as in Examples 161-2 and 20, a colorless oil was obtained (240 mg, yield; 92%)

from 5-bromo-2-(4-thiomorpholinyl)pyridine (848 mg) and 5-bromo-7-(4-ethylpiperazin-1-yl)thieno[2,3-c]pyridine (200 mg). The resulting oil was converted into a hydrochloride in a conventional manner, to give the hydrochloride of the title compound as yellow crystals.

Hydrochloride:

m.p.; 201–203° C.

$^1$H-NMR(400 MHz,DMSO-$d_6$); δ (ppm) 1.31(t,J=7.2 Hz,3H), 2.75(br,4H), 3.16–3.26(m,4H), 3.55–3.66(m,4H), 4.10(br,4H), 4.42(d,J=14.0 Hz,2H), 7.36(br,1H), 7.56(d,J=5.6 Hz,1H), 8.07(s,1H), 8.11(d,J=5.6 Hz,1H), 8.54(br,1H), 8.73(s,1H).

MS(FAB) m/z 426(M+H)$^+$.

Free compound:

$^1$H-NMR(400 MHz,CDCl$_3$); δ (ppm) 1.16(t,J=7.6 Hz,3H), 2.53(q,J=7.6 Hz,2H), 2.66–2.72(m,4H), 2.69(t,J=4.8 Hz,4H), 3.84(t,J=4.8 Hz,4H), 4.02–4.04(m,4H), 6.70(d, J=8.8 Hz,1H), 7.32(d,J=5.6 Hz,1H), 7.55(d,J=5.6 Hz,1H), 7.55(s,1H), 8.18(dd,J=8.8,2.4 Hz,1H), 8.95(d,J=2.4 Hz,1H).

Example 265

Synthesis of 5-[2-(4-hydroxypiperidin-1-yl)pyridin-5-yl]-7-(4-ethylpiperazin-1-yl)thieno[2,3-c]pyridine Hydrochloride

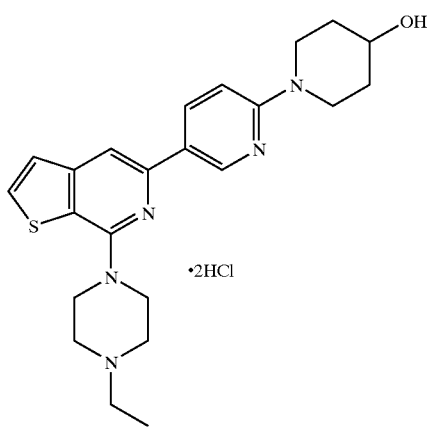

In the same manners sequentially as in Examples 161-2 and 20, an oil was obtained from 5-bromo-2-(4-hydroxypiperidin-1-yl)pyridine (554 mg) and 5-bromo-7-(4-ethylpiperazin-1-yl)thieno[2,3-c]pyridine (200 mg). To the resulting oil were added methanol (10 ml) and a 1N aqueous solution of sodium hydroxide (1 ml), and the mixture was heated under reflux for 1 hr. The reaction solution was partitioned between ethyl acetate and water. The resulting organic layer was washed with water, dried and concentrated. The resulting residue was purified by silica gel column chromatography (hexane/ethyl acetate system), to give a colorless oil (224 mg, yield; 86%). The resulting oil was converted into an oxalate in a conventional manner, to give the oxalate of the title compound as white crystals.

Oxalate:

m.p.; 208–210° C.

$^1$H-NMR(400 MHz,DMSO-$d_6$); δ (ppm) 1.25(t,J=7.2 Hz,3H), 1.36–1.42(m,2H), 1.76–1.82(m,2H), 3.11–3.19(m, 4H), 3.34(br,4H), 3.70–3.78(m,1H), 3.92(br,4H), 4.09(d,J=13.6 Hz,2H), 6.93(d,J=8.8 Hz,1H), 7.51(d,J=5.2 Hz,1H), 7.90(s,1H), 8.04(d,J=5.2 Hz,1H), 8.20(d,J=8.9 Hz,1H), 8.89 (s,1H).

MS(FAB) m/z 424(M+H)$^+$.

Free compound:

$^1$H-NMR(400 MHz,CDCl$_3$); δ (ppm) 1.16(t,J=7.2 Hz,3H), 1.58–1.64(m,2H), 1.99–2.05(m,2H), 2.51(q,J=7.2 Hz,2H), 2.68(t,J=4.8 Hz,4H), 3.24(dt,J=9.6,3.2 Hz,2H), 3.85(t,J=4.8 Hz,4H), 3.92–3.95(m,1H), 4.12–4.18(m,2H), 6.76(d,J=8.8 Hz,1H), 7.32(d,J=5.6 Hz,1H), 7.55(d,J=5.6 Hz,1H), 7.55(s,1H), 8.18(dd,J=8.8,2.4 Hz,1H), 8.95(d,J=2 Hz,1H).

Example 266

Synthesis of 5-[4-(5,6-dihydro-2H-pyran-4-yl)phenyl]-7-(4-ethylpiperazin-1-yl)thieno[2,3-c]pyridine Hydrochloride

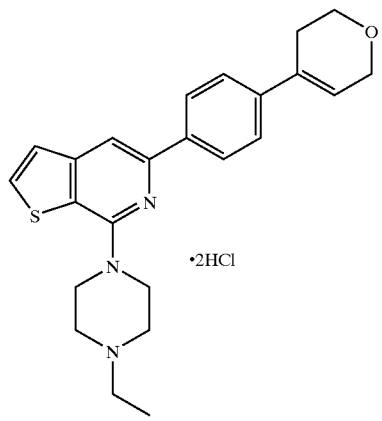

In the same manners sequentially as in Example 161-2 and 20, a colorless oil was obtained (222 mg, yield; 89%) from 1-bromo-4-(5,6-dihydro-2H-pyran-4-yl)benzene (690 mg) and 3-bromo-1-(4-ethylpiperazin-1-yl)isoquinoline (200 mg). The resulting oil was converted into a hydrochloride in a conventional manner, to give the hydrochloride of the title compound as yellow crystals.

Hydrochloride:

m.p.; 176–179° C.

$^1$H-NMR(400 MHz,DMSO-$d_6$); δ (ppm) 1.31(t,J=7.2 Hz,3H), 3.20(br,4H), 3.57–3.70(m,4H), 3.85(t,J=5.2 Hz,4H), 4.26(br,2H), 4.42(d,J=13.2 Hz,2H), 6.37(s,1H), 7.56(d,J=8.4 Hz,2H), 7.57(d,J=5.6 Hz,1H), 8.06(s,1H), 8.09 (d,J=5.6 Hz,1H), 8.13(d,J=8.4 Hz,2H).

MS(FAB) m/z 406(M+H)$^+$.

Free compound:

$^1$H-NMR(400 MHz,CDCl$_3$); δ (ppm) 1.17(t,J=7.6 Hz,3H), 2.52(q,J=7.6 Hz,2H), 2.57–2.59(m,2H), 2.69(t,J=5.2 Hz,4H), 3.86(t,J=5.2 Hz,4H), 3.97(t,J=5.6 Hz,2H), 4.36 (q,J=2.8 Hz,2H), 6.21(br,1H), 7.35(d,J=5.6 Hz,1H), 7.49(d, J=8.4 Hz,2H), 7.57(d,J=5.6 Hz,1H), 7.69(s,1H), 8.08(d,J=8.4 Hz,2H).

Example 267

Synthesis of 5-[2-(2-methoxyethoxy-2-methyl)pyridin-5-yl]-7-(4-ethylpiperazin-1-yl)thieno[2,3-c]pyridine Hydrochloride

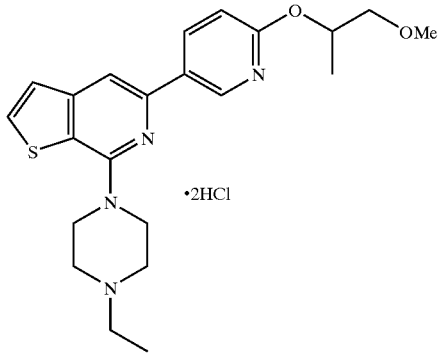

In the same manners sequentially as in Examples 161-2 and 20, a colorless oil was obtained (193 mg, yield; 85%) from 5-bromo-2-(2-methoxyethoxy-2-methyl)pyridine (563 mg) and 5-bromo-7-(4-ethylpiperazin-1-yl)thieno[2,3-c]pyridine (180 mg). The resulting oil was converted into a hydrochloride in a conventional manner, to give the hydrochloride of the title compound as yellow crystals.

Hydrochloride:
m.p.; 112–114° C.
$^1$H-NMR(400 MHz,DMSO-d$_6$); δ (ppm) 1.30(t,J=7.2 Hz,3H), 1.30–1.34(m,3H), 3.10–3.25(m,4H), 3.30(s,3H), 3.48–3.68(m,6H), 4.45(d,J=13.6 Hz,2H), 5.35–5.43(m,1H), 6.93(d,J=8.8 Hz,1H), 7.55(d,J=5.2 Hz,1H), 8.02(s,1H), 8.10(d,J=5.2 Hz,1H), 8.35(s,1H), 8.43(dd,J=8.8,2.4 Hz,1H), 8.93(d,J=2.4 Hz,1H).
MS(FAB) m/z 413(M+H)$^+$.

Free compound:
$^1$H-NMR(400 MHz,CDCl$_3$); δ (ppm) 1.16(t,J=7.2 Hz,3H), 1.38(d,J=6.4 Hz,3H), 2.52(q,J=7.2 Hz,2H), 2.68(t,J=4.8 Hz,4H), 3.43(s,3H), 3.56–3.66(m,2H), 3.85(t,J=4.8 Hz,4H), 5.46–5.50(m,1H), 6.83(d,J=8.8 Hz,1H), 7.34(d,J=5.6 Hz,1H), 7.57(d,J=5.6 Hz,1H), 7.58(s,1H), 8.25(dd,J=8.8,2.4 Hz,1H), 8.88(d,J=2.4 Hz,1H).

Example 268

Synthesis of 5-[2-(2-hydroxyethoxy)pyridin-5-yl]-7-(4-ethylpiperazin-1-yl)thieno[2,3-c]pyridine Oxalate

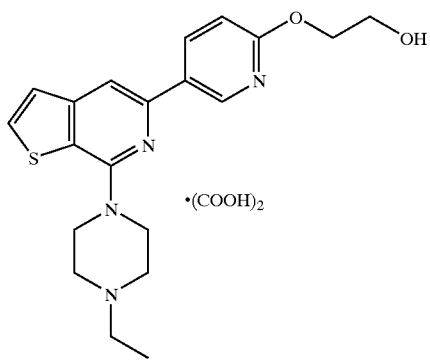

In the same manners sequentially as in Examples 161-2 and 20, a yellow oil was obtained from 5-bromo-2-(2-benzyloxyethoxy)pyridine (610 mg) and 5-bromo-7-(4-ethylpiperazin-1-yl)thieno[2,3-c]pyridin (200 mg). To the resulting oil were added methanol (15 ml) and palladium/carbon catalyst (230 mg), and the mixture was reacted in hydrogen atmosphere at room temperature overnight. The resulting residue was basified by adding a 1N aqueous solution of sodium hydroxide thereto, and then extracted with ethyl acetate. The resulting organic layer was washed with brine, dried and evaporated. Sequentially, the resulting residue was purified by NH-silica gel column chromatography (ethyl acetate/hexane system), to give a yellow oil (69 mg, yield; 38%). The resulting oil was converted into an oxalate in a conventional manner, to give the oxalate of the title compound as white crystals.

Oxalate:
m.p.; 124–125° C.
$^1$H-NMR(400 MHz,DMSO-d$_6$); δ (ppm) 1.21(t,J=7.2 Hz,3H), 3.01(br,2H), 3.20(br,4H), 3.55–3.62(m,2H), 3.72–3.78(m,2H), 3.89(br,2H), 4.30–4.35(m,2H), 6.93(d,J=8.4 Hz,1H), 7.54(d,J=5.2 Hz,1H), 7.99(s,1H), 8.07(d,J=5.2 Hz,1H), 8.41(dd,J=8.4,2.4 Hz,1H), 8.92(d,J=2.4 Hz,1H).
MS(FAB) m/z 385(M+H)$^+$.

Free compound:
$^1$H-NMR(400 MHz,CDCl$_3$); δ (ppm) 1.16(t,J=7.2 Hz,3H), 2.52(q,J=7.2 Hz,2H), 2.68(t,J=5.2 Hz,4H), 3.86(t,J=5.2 Hz,4H), 3.96–3.99(m,2H), 4.50–4.54(m,2H), 6.89(d,J=8.8 Hz,1H), 7.35(d,J=5.6 Hz,1H), 7.59(d,J=5.6 Hz,1H), 7.59(s,1H), 8.31(dd,J=8.8, 2.4 Hz,1H), 8.85(d,J=2.4 Hz,1H).

Example 269

Synthesis of 5-[2-(2-methoxyethoxy)pyridin-5-yl]-7-(4-ethylpiperazin-1-yl)-thieno[2,3-c]pyridine hydrochloride

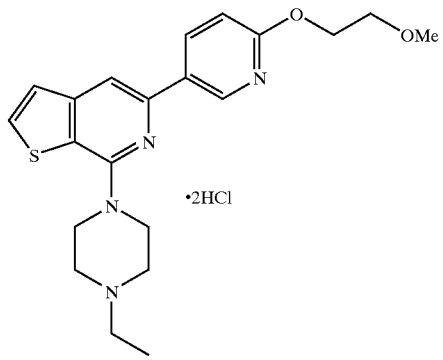

In the same manners sequentially as in Examples 161-2 and 20, a colorless oil was obtained (192 mg, yield; 79%) from 5-bromo-2-methoxyethoxypyridine (607 mg) and 5-bromo-7-(4-ethylpiperazin-1-yl)thieno[2,3-c]pyridine (200 mg). The resulting oil was converted into a hydrochloride in a conventional manner, to give the hydrochloride of the title compound as yellow crystals.

Hydrochloride:
m.p.; 116–118° C.
$^1$H-NMR(400 MHz,CDCl$_3$); δ (ppm) 1.31(t,J=7.2 Hz,3H), 3.15–3.35(m,4H), 3.32(s,3H), 3.58–3.64(m,4H), 3.69(t,J=8.0 Hz,2H), 4.42–4.48(m,4H), 6.96(d,J=8.4 Hz,1H), 7.55(d,J=5.6 Hz,1H), 8.02(s,1H), 8.10(d,J=5.6 Hz,1H), 8.44(dd,J=8.4,2.4 Hz,1H), 8.93(d,J=2.4 Hz,1H).
MS(FAB) m/z 399(M+H)$^+$.

Free Compound:

¹H-NMR(400 MHz,CDCl₃); δ (ppm) 1.16(t,J=7.2 Hz,3H), 2.52(q,J=7.2 Hz,2H), 2.68(t,J=4.8 Hz,4H), 3.46(s, 3H), 3.79(t,J=4.8 Hz,2H), 3.85(t,J=4.8 Hz,4H), 4.54(t,J=4.8 Hz,2H), 6.89(d,J=8.8 Hz,1H), 7.34(d,J=5.6 Hz,1H), 7.57(d, J=5.6 Hz,1H), 7.58(s,1H), 8.27(dd,J=8.8, 2.4 Hz,1H), 8.88 (d,J=2.4 Hz,1H).

Example 270

Synthesis of 5-[4-(4-hydroxycyclohexen-1-yl) phenyl]-7-(4-ethylpiperazin-1-yl)thieno[2,3-c] pyridine hydrochloride

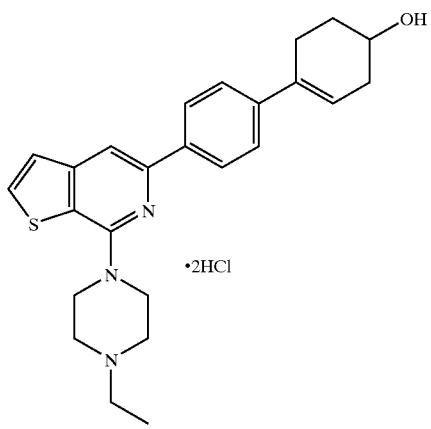

In the same manners sequentially as in Examples 161-2 and 20, an oil was obtained from 1-bromo-4-(4-acetoxycyclohexen-1-yl)benzene (477 mg) and 5-bromo-7-(4-ethylpiperazin-1-yl)thieno[2,3-c]pyridine (200 mg). To the resulting oil were added methanol (10 ml) and a 1N aqueous solution of sodium hydroxide (1 ml), and the mixture was heated under reflux for 1 hr. The reaction solution was partitioned between ethyl acetate and water. The resulting organic layer was washed with water, dried and concentrated. The resulting residue was purified by silica gel column chromatography (hexane/ethyl acetate system), to give a colorless oil (175 mg, yield; 68%). The resulting oil was converted into a hydrochloride in a conventional manner, to give the hydrochloride of the title compound as white crystals.

Hydrochloride:

m.p.; 168–170° C.

¹H-NMR(400 MHz,DMSO-d₆); δ (ppm) 1.31(t,J=7.2 Hz,3H), 1.60–1.70(m,1H), 2.05–2.15(m,1H), 2.40–2.60(m, 2H), 3.19(br,5H), 3.54–3.66(m,5H), 3.80(br,1H), 4.43(d,J= 14.0 Hz,2H), 6.15(br,1H), 7.53(d,J=8.4 Hz,2H), 7.57(d,J= 5.2 Hz,1H), 8.05(s,1H), 8.08(d,J=5.2 Hz,1H), 8.10(d,J=8.4 Hz,2H).

MS(FAB) m/z 420(M+H)⁺.

Free Compound:

¹H-NMR(400 MHz,CDCl₃); δ (ppm) 1.17(t,J=7.6 Hz,3H), 1.82–1.89(m,1H), 2.02–2.07(m,1H), 2.22–2.28(m, 1H), 2.53(q,J=7.6 Hz,2H), 2.50–2.66(m,3H), 2.70(t,J=5.2 Hz,4H), 3.86(t,J=5.2 Hz,4H), 4.06–4.11(m,1H), 6.08–6.09 (m,1H), 7.34(d,J=5.6 Hz,1H), 7.47(d,J=8.8 Hz,2H), 7.56(d, J=5.6 Hz,1H), 7.68(s,1H), 8.06(d,J=8.8 Hz,2H).

Example 271

Synthesis of 7-(1-ethylpiperazin-4-yl)-5-(4-pentanoylphenyl)phenyl)thieno[2,3-c]pyridine dihydrochloride (271-1) 4-Tributylstannylvalerophenone

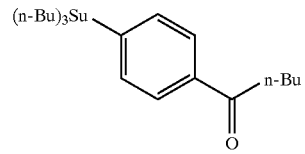

In the same manner as in Example 161-2, the title compound was obtained as a colorless oil (1.297 mg, yield; 58%) from 4-bromovalerophenone (1.206 g).

¹H-NMR(400 MHz,CDCl₃); δ (ppm) 0.88(9H,t,J=7.2 Hz), 0.95(3H,t,J=7.2 Hz), 1.06–1.76(20H,m), 2.95(2H,t,J= 7.6 Hz), 7.57(2H,d,J=8 Hz), 7.87(2H,d,J=8 Hz).

(271-2) 7-(1-Ethylpiperazin-4-yl)-5-(4-pentanoylphenyl) thieno[2,3-c]pyridine dihydrochloride

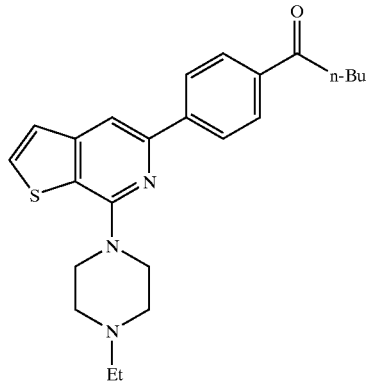

In the same manner as in Example 161-3, the hydrochloride of the title compound was obtained as yellow crystals (118 mg, yield; 68%) from 4-tributylstannylvalerophenone (269 mg) and 7-(1-ethylpiperazin-4-yl)-5-bromothieno[2,3-c]pyridine (120 mg).

Hydrochloride:

m.p.; 109–114° C.

¹H-NMR(400 MHz,DMSO-d₆); δ (ppm) 0.90(3H,t,J=7.4 Hz), 1.30(3H,t,J=7.2 Hz), 1.30–1.40(2H,m), 1.56–1.64(2H, m), 3.03(2H,t,J=7.4 Hz), 3.13–3.24(4H,m), 3.56–3.66(4H, m), 4.43(2H,d,J=14 Hz), 7.59(1H,d,J=5.4 Hz), 8.05(2H,d, J=8.4 Hz), 8.10(1H,d,J=5.4 Hz), 8.15(1H,s), 8.26(2H,d,J= 8.4 Hz), 11.30–11.40(1H,br-s).

ESI-Mass; 408(MH⁺).

Example 272

Synthesis of 7-(1-ethylpiperazin-4-yl)-5-[4-(3-methylbutanoyl)phenyl]thieno[2,3-c]pyridine dihydrochloride (272-1) 4-Bromoisovalerophenone

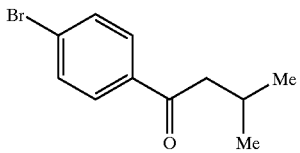

Aluminum chloride (32.8 g) was suspended in 1,2-dichloroethane (200 ml), and then under ice-cooling, a solution of bromobenzene (21.6 ml) and isovaleryl chloride (25 ml) in 1,2-dichloroethane (20 ml) was added dropwise thereto and the resulting mixture was stirred for 1 hr. Thereafter, the mixture was stirred at room temperature for 1 hr, and continuously at 60° C. for 1 hr. After cooling as it was, the reaction mixture was poured onto ice in small portions. The reaction mixture was extracted with chloroform, and the resulting organic layer was washed with 5N sodium hydroxide and brine, dried (over MgSO$_4$) and evaporated. The resulting residue was purified by silica gel column chromatography (ethyl acetate/hexane system), to give the title compound as a brown solid (26.105 g, yield; 53%).

$^1$H-NMR(400 MHz,CDCl$_3$); δ (ppm) 0.99(6H,d,J=6.8 Hz), 2.21–2.37(1H,m), 2.80(2H,d,J=6.8 Hz), 7.60(2H,d,J=8.8 Hz), 7.82(2H,d,J=8.8 Hz).

(272-2) 4-Tributylstannylisovalerophenone

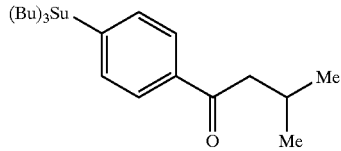

In the same manner as in Example 161-2, the title compound was obtained as a colorless oil (1.493 mg, yield; 51%) from 4-bromoisovalerophenone (1.577 g).

$^1$H-NMR(400 MHz,CDCl$_3$); δ (ppm) 0.89(9H,t,J=7.4 Hz), 0.99(6H,d,J=6.8 Hz), 1.06–1.11(6H,m), 1.28–1.38(6H, m), 1.50–1.58(6H,m), 2.24–2.36(1H,m), 2.82(2H,d,J=7.2 Hz), 7.57(2H,d,J=8 Hz), 7.86(2H,d,J=8 Hz).

(272-3) 7-(1-Ethylpiperazin-4-yl)-5-[4-(3-methylbutanoyl)phenyl]thieno[2,3-c]pyridinedihydrochloride

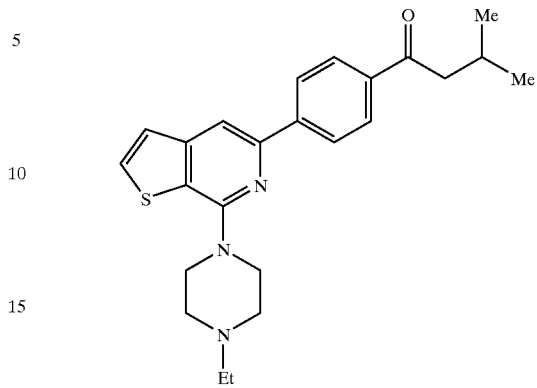

In the same manner as in Example 161-3, the hydrochloride of the title compound was obtained as yellow crystals (130 mg, yield; 63%) from 4-tributylstannylisovalerophenone (322 mg) and 7-(1-ethylpiperazin-4-yl)-5-bromothieno[2,3-c]pyridine (140 mg).

Hydrochloride:

m.p.; 139–141° C.

$^1$H-NMR(400 MHz,DMSO-d$_6$); δ (ppm) 0.94(6H,d,J=6.4 Hz), 1.30(3H,t,J=7.2 Hz), 2.11–2.21(1H,m), 2.91(2H,d,J= 7.2 Hz), 3.13–3.23(4H,m), 3.56–3.66(4H.m), 4.43(2H,d,J= 14 Hz), 7.59(1H,d,J=5.2 Hz), 8.05(2H,d,J=8.4 Hz), 8.10(1H, d,J=5.2 Hz), 8.15(1H,s), 8.26(2H,d,J=8.4 Hz), 11.15–11.25 (1H,br-s).

ESI-Mass; 408(MH$^+$).

Example 273

Synthesis of 7-(1-ethylpiperazin-4-yl)-5-[4-(N-cyclohexylamide)phenyl]thieno[2,3-c]pyridinecarboxamide dihydrochloride (273-1) 4-Bromo-N-cyclohexylbenzamide

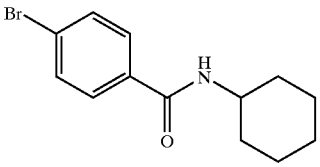

Cyclohexylamine (9.111 g) was dissolved in tetrahydrofuran (100 ml), followed by the addition of 4-bromobenzoyl chloride (5.04 g)/tetrahydrofuran solution (30 ml) under ice-cooling, and the mixture was stirred for 20 min. The reaction mixture was partitioned between ethyl acetate and water. The resulting organic layer was washed with water, dried (over MgSO$_4$) and evaporated. The resulting residue was recrystallized from ethyl acetate/hexane, to give the title compound as a pale pink solid (5.236 g, yield; 83%).

$^1$H-NMR(400 MHz,CDCl$_3$); δ (ppm) 1.18–1.28(2H,m), 1.38–1.46(2H,m) 1.73–1.79(2H,m), 2.01–2.06(2H,m), 3.80–3.40(1H,m), 5.70–5.90(1H,m), 7.56(2H,d,J=8 Hz), 7.62(2H,d,J=8 Hz).

(273-2) 4-Tributylstannyl-N-cyclohexylbenzamide

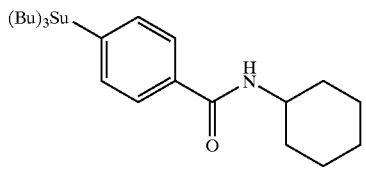

In the same manner as in Example 161-2, the title compound was obtained as a colorless solid (798 mg, yield; 40%) from 4-bromo-N-cyclohexylbenzamide (1.129 g).
¹H-NMR(400 MHz,CDCl₃); δ (ppm) 0.88(9H,t,J=7.2 Hz), 1.04–2.04(28H,m), 3.59–4.01(1H,m), 5.95(1H,d,J=8.4 Hz), 7.52(2H,d,J=8 Hz), 7.67(2H,d,J=8 Hz).

(273-1) 7-(1-Ethylpiperazin-4-yl)-5-[4-N-cyclohexylamide) phenyl]thieno[2,3-c]pyridinedihydrochloride

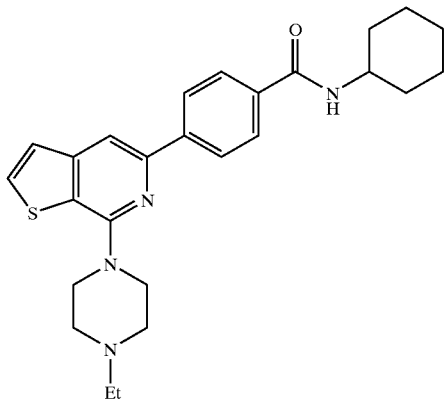

In the same manner as in Example 161-3, the hydrochloride of the title compound was obtained as a pale yellow amorphous (yield; 14%) from 4-tributylstannyl-N-cyclohexylbenzamide (457 mg) and 7-(1-ethylpiperazin-4-yl)-5-bromothieno[2,3-c]pyridine (228 mg) Hydrochloride:
m.p.; 160–165° C.
¹H-NMR(400 MHz,DMSO-d₆); δ (ppm) 1.03–1.20(1H, m), 1.29(3H,t,J=7.2 Hz), 1.27–1.35(4H,m), 1.57–1.85(3H, m), 3.14–3.23(4H,m), 3.56(2H,t,J=14 Hz), 3.63(2H,t,J=14 Hz), 3.63(2H,d,12 Hz), 3.70–3.82(1H,m), 4.43(2H,d,J=14 Hz), 7.58(1H,d,J=5.6 Hz), 7.94(2H,d,J=8.8 Hz), 8.09(1H,d, J=5.6 Hz), 8.12(1H,s), 8.19(2H,d,J=8.8 Hz), 8.26(1H,d,J=8 Hz), 10.85–10.95(1H,br-s).
ESI-Mass; 449(MH⁺).

Example 274

Synthesis of 7-(1-ethylpiperazin-4-yl)-5-[4-(pyrrolidinyl-1-carbonyl)phenyl]thieno[2,3-c] pyridine dihydrochloride (274-1) (4-Bromobenzoyl)pyrrolidine

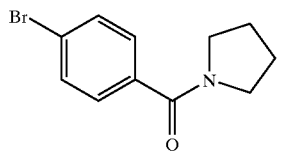

In the same manner as in Example 273-1, the titled compound was obtained as a colorless solid (5.07 g, yield; 87%) from 4-bromobenzoyl chloride (5.027 g) and pyrrolidine (6.543 g).

¹H-NMR(400 MHz,CDCl₃); δ (ppm) 1.89(2H,qui,J=6.8 Hz), 1.97(2H,qui,J=6.8 Hz), 3.41(2H,t,J=6.8 Hz), 3.63(2H, t,J=6.8 Hz) 7.40(2H,d,J=8.8 Hz), 7.54(2H,d,J=8.8 Hz).

(274-2) (4-Tributylstannylbenzoyl)pyrrolidine

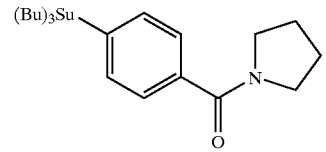

In the same manner as in Example 161-2, the title compound was obtained as a colorless oil (976 mg, yield; 53%) from (4-bromobenzoyl)pyrrolidine (1.574 g).

¹H-NMR(400 MHz,CDCl₃); δ (ppm) 0.88(9H,t,J=7.4 Hz), 1.03–1.08(6H,m), 1.29–1.37(6H,m), 1.49–1.56(6H,m), 1.84–1.99(4H,m), 3.45(2H,t,J=6.6 Hz), 3.65(2H,t,J=7 Hz), 7.44(2H,d,J=8 Hz), 7.48(2H,d,J=8 Hz).

(274-3) 7-(1-Ethylpiperazin-4-yl)-5-[4-(pyrrolidinyl-1-carbonyl)phenyl]thieno[2,3-c]pyridinedihydrochloride

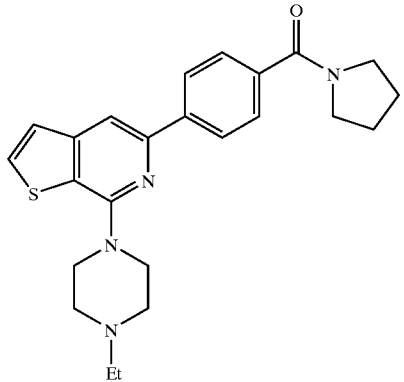

In the same manner as in Example 161-3, the hydrochloride of the title compound was obtained as a yellow amorphous (183 mg, yield; 57%) from (4-tributylstannylbenzoyl) pyrrolidine (564 mg) and 7-(1-ethylpiperazin-4-yl)-5-bromothieno[2,3-c]pyridine (223 mg).

Hydrochloride:

m.p.; 143–146° C.

¹H-NMR(400 MHz,DMSO-d₆); δ (ppm) 1.29(3H,t,J=7.2 Hz), 1.76–1.90(4H,m), 3.14–3.23(4H,m), 3.42(4H,t,J=6.4 Hz), 3.47(4H,t,J=6.8 Hz), 3.57(2H,d,J=8.4 Hz), 3.62(2H,d, J=12 Hz), 4.42(2H,d,J=14 Hz), 7.57(1H,d,J=5.6 Hz), 8.09 (1H,d,J=5.6 Hz), 8.10(1H,s), 8.18(2H,d,J=8.8 Hz), 10.95–11.05(1H,br-s).

ESI-Mass; 421(MH⁺).

Example 275

Synthesis of 5-[4-(2-hydroxyethoxy)phenyl]-7-[4-(2-hydroxyethyl)piperazin-1-yl]thieno[3,2-c]pyridine oxalate

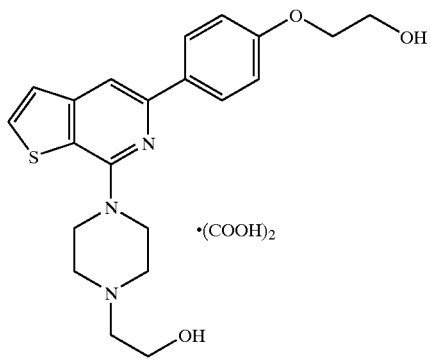

5-(4-Hydroxyphenyl)-7-(piperazin-1-yl)thieno[2,3-c]pyridine (139 mg) was dissolved in DMF (6 ml), followed by the addition of 60% sodium hydride (33 mg) and ethyl bromoacetate (0.068 ml), and the mixture was reacted at 60° C. for 1 hr. The reaction solution was poured into an aqueous solution of saturated ammonium chloride and extracted with ethyl acetate. The organic layer was washed with water, dried and evaporated. To the resulting residue were added tetrahydrofuran (10 ml) and 1.0 M lithium aluminum hydride/tetrahydrofuran solution (0.9 ml), and the mixture was reacted under ice-cooling for 10 min. To the resulting reaction solution were then sequentially added water (0.03 ml), a 5N aqueous solution of sodium hydroxide (0.03 ml) and water (0.09 ml), and the mixture was stirred at room temperature for 30 min. The resulting residue was filtered, washed with ethyl acetate and then purified by NH-silica gel chromatography (hexane/ethyl acetate system), to give a colorless oil (30 mg, yield; 21%). The resulting oil was converted into an oxalate in a conventional manner, to obtain the oxalate of the title compound as white crystals.

Oxalate:

m.p.; 105–107° C.

$^1$H-NMR(400 MHz,DMSO-d$_6$); δ (ppm) 2.93(br,2H), 3.12(br,4H), 3.70(t,J=4.8 Hz,2H), 3.75(t,J=4.8 Hz,2H), 3.85(br,4H), 4.05(t,J=4.8 Hz,2H), 7.04(d,J=8.8 Hz,2H), 7.51(d,J=5.6 Hz,1H), 7.90(s,1H), 8.01(d,J=5.6 Hz,1H), 8.07(d,J=8.8 Hz,2H).

MS(FAB) m/z 400(M+H)$^+$.

Free Compound:

$^1$H-NMR(400 MHz,CDCl$_3$); δ (ppm) 2.66(t,J=5.6 Hz,2H), 2.76(t,J=4.8 Hz,4H), 3.69(t,J=5.6 Hz,2H), 3.82(t,J=4.8 Hz,4H), 4.00(t,J=4.4 Hz,2H), 4.15(t,J=4.4 Hz,2H), 7.01(d,J=8.8 Hz,2H), 7.34(d,J=5.6 Hz,1H), 7.56(d,J=5.6 Hz,1H), 7.64(s,1H), 8.05(d,J=8.8 Hz,2H).

Example 276

Synthesis of 5-(4-methoxyphenyl)-7-[4-(2-hydroxyethyl)piperazin-1-yl]thieno[2,3-c]pyridine hydrochloride

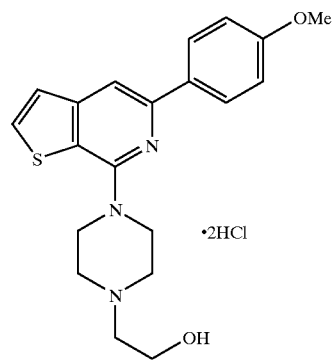

DMSO (6 ml) and 4-hydroxyethylpiperazine (6 ml) were added to 7-chloro-5-(4-methoxyphenyl)thieno[2,3-c]pyridine (920 mg), and the mixture was reacted at 140° C. overnight. The reaction solution was partitioned between ethyl acetate and water. The resulting organic layer was washed with water, dried and evaporated. The resulting residue was purified by NH-silica gel column chromatography (hexane/ethyl acetate system), to give a yellow oil (350 mg, yield; 28%). The resulting oil was converted into a hydrochloride in a conventional manner, to give the hydrochloride of the title compound as yellow crystals.

Hydrochloride:

m.p.; 129–131° C.

$^1$H-NMR(400 MHz,DMSO-d$_6$); δ (ppm) 3.25–3.32(m, 4H), 3.56–3.70(m,6H), 3.84(s,3H), 4.41(t,J=14.4 Hz,2H), 7.05(d,J=8.8 Hz,2H), 7.54(d,J=5.6 Hz,1H), 7.96(s,1H), 8.05(d,J=5.6 Hz,1H), 8.09(d,J=8.8 Hz,2H).

MS(FAB) m/z 370(M+H)$^+$.

Free Compound:

$^1$H-NMR(400 MHz,CDCl$_3$); δ (ppm) 2.65(t,J=5.2 Hz,2H), 2.76(t,J=5.2 Hz,4H), 3.69(t,J=5.2 Hz,2H), 3.82(t, J=5.2 Hz,4H), 3.87(s,3H), 6.99(d,J=8.8 Hz,2H), 7.33(d,J=5.6 Hz,1H), 7.56(d,J=5.6 Hz,1H), 7.63(s,1H), 8.04(d,J=8.8 Hz,2H).

Example 277

Synthesis of 4-(4-ethylpiperazin-1-yl)-6-(4-methoxyphenyl)thieno[3,4-c]pyridine oxalate

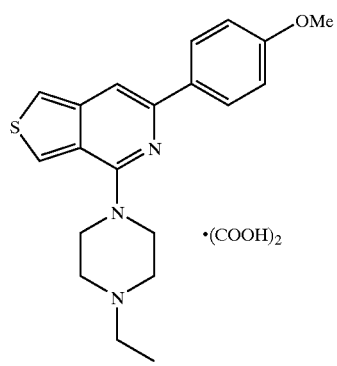

In the same manner as in Example 10, the free compound of the title compound was obtained (57 mg, yield; 13%)

from 4-chloro-6-(4-methoxyphenyl)thieno[3,4-c]pyridine (356 mg) and ethylpiperazine (6 ml). The resulting free compound was converted into an oxalate in a conventional manner, to give the oxalate of the title compound as white crystals.

Oxalate:
¹H-NMR(400 MHz,DMSO-d₆); δ (ppm) 1.25(t,J=7.2 Hz,3H), 3.12(q,J=7.2 Hz,2H), 3.32(br,4H), 3.81(s,3H), 3.93 (br,4H), 7.01(d,J=8.8 Hz,2H), 7.59(s,1H), 7.93(d,J=2.4 Hz,1H), 8.04(d,J=8.8 Hz,2H), 8.46(br,1H).

Free Compound:
¹H-NMR(400 MHz,CDCl₃); δ (ppm) 1.18(t,J=7.2 Hz,3H), 2.55(q,J=7.2 Hz,2H), 2.73(br,4H), 3.85(br,4H), 3.87(s,3H), 6.97(d,J=8.4 Hz,2H), 7.36(s,1H), 7.52(d,J=3.2 Hz,1H), 7.86(d,J=3.2 Hz,1H), 8.04(d,J=8.8 Hz,2H).

Example 278

Synthesis of 4-(4-ethylpiperazin-1-yl)-6-[4-(2-hydroxyethoxy)phenyl]thieno-[3,4-c]pyridine oxalate (278-1) 3-Formyl-4-bromothiophene

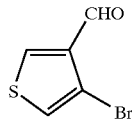

3,4-Dibromothiophene (30 g) was dissolved in diethyl ether (150 ml), followed by the addition of 2.5M n-butyl lithium (60 ml) at −78° C. Subsequently, DMF (14 ml)/diethyl ether solution (50 ml) was added thereto, and the mixture was stirred for 3 hr with heating under reflux. The reaction solution was poured into 1N hydrochloric acid, and then extracted with ethyl acetate. The resulting organic layer was washed with an aqueous solution of saturated sodium bicarbonate and brine, dried and evaporated. The resulting residue was purified by silica gel column chromatography (hexane/ethyl acetate system), to give a colorless oil (14.7 g, yield; 62%).

¹H-NMR(400 MHz,CDCl₃); δ (ppm) 7.37(d,J=3.6 Hz,1H), 8.17(d,J=3.6 Hz,1H), 9.96(s,1H).

(278-2) 4-Methoxymethoxy-1-ethynylbenzene

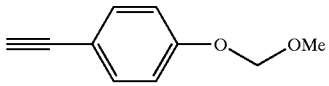

Paraiodophenol (25 g) was dissolved in DMF (100 ml), followed by the addition of potassium t-butoxide (25 g) and methoxymethyl chloride (13 ml), and the mixture was reacted at 60° C. overnight. The reaction solution was poured into water and extracted with ethyl acetate. The organic layer was washed with water and brine, dried and evaporated. The resulting residue was subjected to a silica gel short column, to give 4-methoxymethoxy-1-iodobenzene as an oil (26.5 g, yield; 88%).

To the resulting oil (26.5 g) were added trimethylsilylacetylene (28 ml), pyridine (50 ml), triethylamine (100 ml), CuI (0.35 g) and Pd(PPh₃)₂Cl₂ (0.7 g), and the mixture was reacted at 60° C. overnight. The reaction solution was poured into 1N hydrochloric acid, and the organic layer was washed with an aqueous solution of saturated sodium bicarbonate and brine, dried and evaporated, to give an oil.

The resulting oil was dissolved in a methanol (90 ml), followed by the addition of a 1N aqueous solution of sodium hydroxide (10 ml), and the mixture was heated under reflux for 1 hr. The reaction solution was partitioned between ethyl acetate and water. The organic phase was washed with water, dried and concentrated. The solvent was evaporated, to give the title compound as a yellow oil (11.4 g, yield; 70%).

¹H-NMR(400 MHz,CDCl₃); δ (ppm) 3.00(s,1H), 3.47(s, 3H), 5.18(s,2H), 6.98(d, J=8.8 Hz,2H), 7.42(d,J=8.8 Hz,2H).

(278-3) 4-Chloro-6-[4-(methoxymethoxy)phenyl]thieno[3, 4-c]pyridine

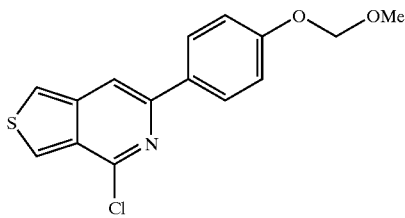

3-Formyl-4-bromothiophene (14.7 g) was dissolved in DMF (100 ml), followed by the addition of triethylamine (100 ml) CuI (0.25 g), Pd(PPh₃)₂Cl₂ (0.5 g) and 4-methoxymethoxy-1-ethynylbenzene (11.4 g), and the mixture was reacted at 70° C. overnight. The reaction solution was filtered through Celite, poured into 1N hydrochloric acid, and then extracted with ethyl acetate. The organic layer was washed with an aqueous solution of saturated sodium bicarbonate and brine, dried and evaporated. The resulting residue was purified by silica gel column chromatography (hexane/ethyl acetate system), to give 3-{[4-(methoxymethoxy)phenyl]ethynyl}-4-formylthiophene as a colorless oil (12.8 g, yield; 47%).

The resulting oil (12.8 g) was dissolved in ethanol (150 ml), followed by the addition of water (50 ml), hydroxylamine hydrochloride (4.9 g) and sodium acetate (7.7 g), and the mixture was heated under reflux for 3 hr. The reaction solution was evaporated, and then extracted with ethyl acetate. The organic layer was washed with brine, dried and evaporated, and then purified by silica gel column chromatography (hexane/ethyl acetate system), to give 3-{[4-(methoxymethoxy)phenyl]ethynyl}-4-formylthiophene oxime as a brown oil (10.5 g, yield; 77%).

The resulting brown oil (10.5 g) was dissolved in n-butanol (100 ml), followed by the addition of water (25 ml) and potassium carbonate (7.5 g), and the resulting mixture was reacted with heating under reflux overnight. The reaction solution was evaporated and extracted with ethyl acetate. The organic layer was washed with brine, dried and evaporated, and then purified by silica gel column chromatography (dichloromethane/methanol system), to give 6-[4-(methoxymethoxy)phenyl]thieno[3,4-c]pyridine N-oxide as a yellow oil (2.6 g, yield; 25%).

The resulting yellow oil (2.6 g) was dissolved in chloroform (100 ml), followed by the addition of diisopropylamine (16 ml) and phosphorus oxychloride (1.7 ml), and the mixture was reacted with heating under reflux for 20 min. The reaction solution was ice-cooled, followed by the addition of methanol and evaporation. The resulting residue was partitioned between ethyl acetate and water, and the resulting ethyl acetate layer was washed with an aqueous solution of saturated sodium bicarbonate and brine, dried and evaporated. The resulting residue was purified by silica gel column chromatography (hexane/ethyl acetate system), to give the title compound as a colorless oil (1.1 g, yield; 39%).

¹H-NMR(400 MHz,CDCl₃); δ (ppm) 3.50(s,3H), 5.23(s, 2H), 7.12(d,J=8.8 Hz,2H), 7.53(s,1H), 7.65(d,J=8.8 Hz,2H), 7.74(s,1H),8.79(s,1H).

(278-4) 4-(4-Ethylpiperazin-1-yl)-6-(4-methoxymethoxyphenyl)thieno[3,4-c]pyridine or compound identified by the following analysis data and synthetic procedures

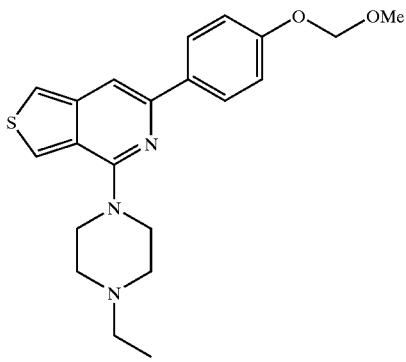

In the same manner as in Example 1, a yellow oil was obtained (695 mg, yield; 51%) from 4-chloro-6-(4-methoxymethoxyphenyl)thieno[3,4-c]pyridine (1.1 g), potassium carbonate (1 g), ethylpiperazine (0.8 ml) and DMF (10 ml).

$^1$H-NMR(400 MHz,CDCl$_3$); δ (ppm) 1.17(t,J=7.2 Hz,3H), 2.53(q,J=7.2 Hz,2H), 2.70(t,J=4.8 Hz,4H), 3.56(s, 3H), 3.84(t,J=4.8 Hz,4H), 5.22(s,2H), 7.10(d,J=8.8 Hz,2H), 7.35(d,J=0.8 Hz,1H), 7.52(d,J=3.2 Hz,1H), 7.86(dd, J=3.2, 0.8 Hz,1H), 8.02(d,J=8.8 Hz,2H).

(278-5) 4-(4-Ethylpipeprazin-1-yl)-6-[4-(2-hydroxyethoxy)phenyl]thieno[3,4-c]pyridine or compound identified by the following analysis data and synthetic procedures

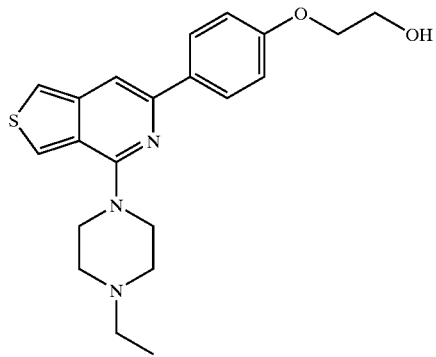

4-(4-Ethylpiperazin-1-yl)-6-[4-(methoxymethoxy)phenyl]thieno[3,4-c]-pyridine (695 mg) was dissolved in ethanol (10 ml), followed by the addition of a 5N aqueous solution of hydrochloric acid (1 ml), and the mixture was reacted for 1 hr with heating under reflux. The reaction solution was neutralized with a 1N aqueous solution of sodium hydroxide and then extracted with ethyl acetate. The organic layer was washed with brine, dried and evaporated, and then purified by silica gel column chromatography (dichloromethane/methanol system), to give 4-(4-ethylpiperazin-1-yl)-6-(4-hydroxyphenyl)thieno[3,4-c]pyridine as a yellow oil (70 mg, yield; 11%).

4-(4-Ethylpiperazin-1-yl)-6-(4-hydroxyphenyl)thieno[3,4-c]pyridine (70 mg) was dissolved in DMF (10 ml), followed by the addition of 2-bromoethoxy(t-butyl)dimethylsilane (300 mg) and 60% sodium hydride (33 mg) and the mixture was reacted at 60° C. overnight. The reaction mixture was poured into an aqueous solution of saturated ammonium chloride and extracted with ethyl acetate. The organic layer was washed with water and brine, dried and evaporated, to give 4-(4-ethylpiperazin-1-yl)-6-{4-[2-(t-butyl)dimethylsilyloxyethoxy]phenyl}- thieno[3,4-c]pyridine as an oil. The resulting oil was then dissolved in tetrahydrofuran (5 ml), followed by the addition of 1.0M tetrabutylammonium fluoride/tetrahydrofuran solution (5 ml), and the mixture was stirred at room temperature for 1 hr. The reaction solution was partitioned between ethyl acetate and water. The organic layer was washed with water, dried and concentrated. The resulting residue was purified by NH-silica gel column chromatography (hexane/ethyl acetate system), to give a colorless oil (18 mg, yield; 23%). The resulting oil was converted into an oxalate in a conventional manner, to give the oxalate of the title compound as white crystals.

Oxalate:

m.p.; 130° C. (decomp.)

$^1$H-NMR(400 MHz,DMSO-d$_6$); δ (ppm) 1.27(t,J=7.2 Hz,3H), 3.19(br,4H), 3.39(br,6H), 3.74(br,2H), 4.04(t,J=4.8 Hz,2H), 7.01(d,J=8.8 Hz,2H), 7.61(s,1H), 7.94(d,J=2.8 Hz,1H), 8.03(d,J=8.8 Hz,2H), 8.48(d,J=2.8 Hz,1H).

MS(FAB) m/z 384(M+H)$^+$.

Free Compound:

$^1$H-NMR(400 MHz,CDCl$_3$); δ (ppm) 1.20(t,J=7.2 Hz,3H), 2.58(q,J=7.2 Hz,2H), 2.77(br,4H), 3.89(br,4H), 3.99(t,J=4.4 Hz,2H), 4.15(t,J=4.0 Hz,2H), 6.99(d,J=8.8 Hz,2H), 7.36(s,1H), 7.53(d,J=3.2 Hz,1H), 7.85(d,J=3.2 Hz,1H), 8.03(d,J=8.8 Hz,2H).

Example 279

Synthesis of 4-(4-methylpiperazin-1-yl)-6-[4-(2-hydroxyethoxy)phenyl]thieno[3,2-c]pyridine hydrochloride

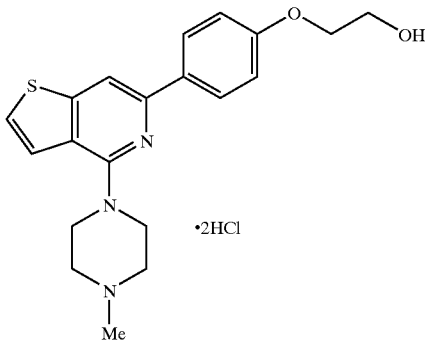

4-(4-Methylpiperazin-1-yl)-6-(4-hydroxyphenyl)thieno[3,2-c]pyridine (413 mg) obtained from 4-chloro-6-(4-methoxyphenyl)thieno[3,2-c]pyridine and N-methylpiperazine in the same manner as in Example 289-6 was dissolved in DMF (10 ml), followed by the addition of potassium carbonate (526 mg) and 2-bromoethanol (0.18 ml). The resulting mixture was stirred at 80° C. for 2 days, and then the resulting reaction mixture was partitioned between ethyl acetate and water. The resulting organic layer was washed with water, dried and evaporated. The resulting residue was purified by NH-silica gel column chromatography (hexane/ethyl acetate system), to give a yellow oil (202 mg, yield; 43%). The resulting oil was converted into a hydrochloride in a conventional manner, to give the title compound as yellow crystals.

Hydrochloride:

m.p.; 148–150° C.

$^1$H-NMR(400 MHz,DMSO-$d_6$); δ (ppm) 2.85(d,J=4.4 Hz,3H), 3.27–3.33(m,2H), 3.47–3.55(m,4H), 3.75(t,J=4.8 Hz,2H), 4.00–4.06(m,2H), 4.21(d,J=13.2 Hz,2H), 7.04(d,J=8.8 Hz,2H), 7.61(d,J=5.6 Hz,1H), 7.78(d,J=5.6 Hz,1H), 8.10 (d,J=8.8 Hz,2H), 8.18(s,1H).

MS(FAB) m/z 370(M+H)$^+$.

Free Compound:

$^1$H-NMR(400 MHz,CDCl$_3$); δ (ppm) 2.39(s,3H), 2.66(t, J=4.8 Hz,4H), 3.69(t,J=4.8 Hz,4H), 3.99(t,J=4.8 Hz,2H), 4.14(t,J=4.8 Hz,2H), 7.00(d,J=8.8 Hz,2H), 7.32(d,J=5.6 Hz,1H), 7.39(d,J=5.6 Hz,1H), 7.72(s,1H), 8.05(d,J=8.8 Hz,2H).

Example 280

Synthesis of 4-(4-ethylpiperazin-1-yl)-6-(4-hydroxyphenyl)thieno[3,2-c]pyridine hydrochloride

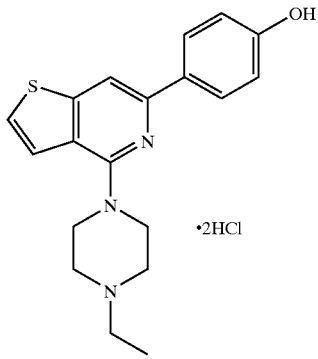

4-(4-Ethylpiperazin-1-yl)-6-(4-methoxyphenyl)thieno[3, 2-c]pyridine (1.85 g) was dissolved in 48% hydrobromic acid (15 ml), and the mixture was reacted for 6 hr with heating under reflux. The reaction solution was ice-cooled, and then basified by adding a 8N aqueous solution of sodium hydroxide thereto. A 28% aqueous solution of ammonia was added to the resulting solution, followed by the extraction with ethyl acetate. The resulting organic layer was washed with water, dried and evaporated. The resulting crystals were washed with hexane and subsequently with diethyl ether, and then dried, to give white crystals (1.44 g, yield; 81%). The resulting crystals were converted into a hydrochloride in a conventional manner, to give the title compound as white crystals.

Hydrochloride:

m.p.; 173–175° C.

$^1$H-NMR(400 MHz,DMSO-$d_6$); δ (ppm) 1.31(t,J=7.2 Hz,3H), 3.13–3.30(m,4H), 3.49–3.60(m,4H), 4.19(d,J=14.0 Hz,2H), 6.88(d,J=8.8 Hz,2H), 7.60(d,J=5.6 Hz,1H), 7.77(d, J=5.6 Hz,1H), 7.79(d,J=8.8 Hz,2H), 8.11(s,1H).

MS(FAB) m/z 340(M+H)$^+$.

Free Compound:

$^1$H-NMR(400 MHz,DMSO-$d_6$); δ (ppm) 1.06(t,J=7.2 Hz,3H), 2.41(q,J=7.2 Hz,2H), 2.59(t,J=4.8 Hz,4H), 3.54(t, J=4.8 Hz,4H), 6.84(d,J=8.8 Hz,2H), 7.48(d,J=5.6 Hz,1H), 7.66(d,J=5.6 Hz,1H), 7.98(d,J=8.8 Hz,2H), 9.64(s,1H).

Example 281

Synthesis of 4-(4-ethylpiperazin-1-yl)-6-[4-(1-hydroxyethyl)phenyl]thieno[3,2-c]pyridine oxalate (281-1) 6-(4-Bromophenyl)-5H-thieno[3,2-c]pyridine-4-one

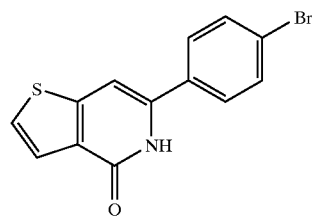

To a solution of N-methyl-2-methylthiophene-3-carboxamide (13.0 g) in tetrahydrofuran (130 ml) was dropwise added 2.5 M butyl lithium (74 ml) at −70° C. The reaction solution was stirred at −70° C. for 2 hr, followed by the addition of 4-bromobenzonitrile (15.3 g) at once. After the dry ice/acetone bath was removed, the reaction mixture was back to room temperature. Three hours later, an aqueous solution of saturated ammonium chloride and ether were added thereto, and then the resulting mixture was further stirred for 1 hr. The resulting white precipitates were collected by filtration, and washed with water, ether and n-hexane in this order. The resulting product was dried to give the title compound (4.9 g, yield; 19%).

(281-2) 4-(4-Ethylpiperazin-1-yl)-6-(4-bromophenyl)thieno [3,2-c]pyridine

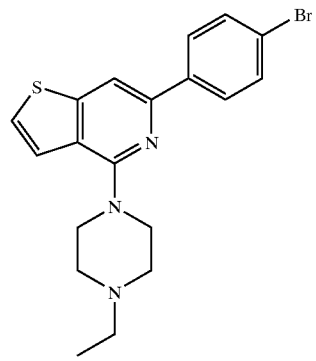

6-(4-Bromophenyl)-5H-thieno[3,2-c]pyridin-4-one (4.87 g) was added to phosphorus oxychloride (30 ml), and the resulting mixture was heated at 100° C. for 3 hr. The reaction solution was evaporated, and to the resulting residue were added ethyl acetate and water. The organic layer was washed with water, an aqueous solution of saturated sodium bicarbonate and brine, and dried over magnesium sulfate. The solvent was evaporated, to give 4-chloro-6-(4-bromophenyl) thieno[3,2-c]pyridine.

Then, the resulting compound was heated with N-ethylpiperazine (50 ml) at 100° C. for 2 hr. The reaction mixture was evaporated, and to the resulting residue were added potassium carbonate and water, and the resulting mixture was extracted with ethyl acetate. The organic layer was washed with water and brine, and dried over magnesium sulfate. The solvent was removed, and the resulting residue was purified by NH-silica gel column chromatography (ethyl acetate/hexane system), to give the title compound as a pale brown oil (3.76 g, yield; 58.8%).

$^1$H-NMR(400 MHz,CDCl$_3$); δ (ppm) 1.16(3H,t,J=7.2 Hz), 2.53(2H,q,J=7.2 Hz), 2.68(4H,br), 3.71(4H,br), 7.37

(1H,d,J=5.6 Hz), 7.41(1H,d,J=5.6 Hz), 7.56(2H,d,J=8.4 Hz), 7.76(1H,s), 7.96(2H,d,J=8.4 Hz).

(281-3) 6-[4-(3,3-Dimethyl-3-hydroxy-1-propynyl)phenyl]-(4-ethylpiperazin-1-yl)thieno[3,2-c]pyridine or compound identified by the following analysis data and synthetic procedures

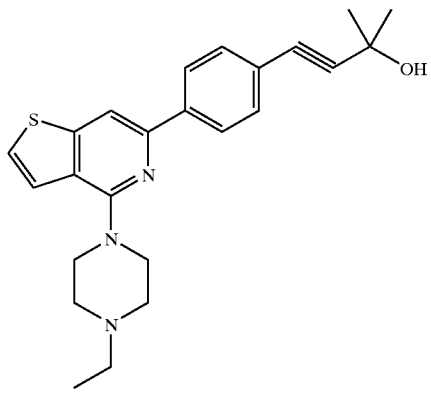

6-(4-Bromophenyl)-4-(4-ethylpiperazin-1-yl)thieno[3,2-c]pyridine (0.96 g) was heated under reflux in the presence of bistriphenylphosphine dichloride (48 mg), triphenylphosphine (174 mg) and cuprous iodide (46 mg), in 2-methyl-3-butyn-2-ol (0.26 g), pyridine (15 ml) and triethylamine (30 ml) for 1.5 hr. The reaction solution was evaporated, and the resulting residue was purified by NH-silica gel column chromatography (ethyl acetate/hexane system), to give 0.80 g of the title compound as a pale yellow oil.

$^1$H-NMR(400 MHz,CDCl$_3$); δ (ppm) 1.16(3H,t,J=7.2 Hz), 1.63(6H,s), 2.53(2H,q,J=7.2 Hz), 2.68(4H,br), 3.70 (4H,br), 7.36(1H,d,J=5.6 Hz), 7.41(1H,d,J=5.6 Hz), 7.47 (2H,d,J=8.4 Hz), 7.78(1H,s), 8.03(2H,d,J=8.4 Hz).

(281-4) 6-(4-Ethynylphenyl)-(4-ethylpiperazin-1-yl)thieno[3,2-c]pyridine

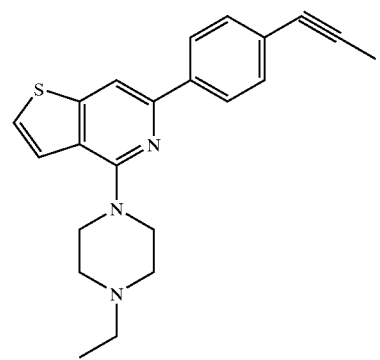

6-[4-(3,3-Dimethyl-3-hydroxy-1-propynyl)phenyl]-(4-ethylpiperazin-1-yl)thieno[3,2-c]pyridine (0.80 g) was dissolved in 1-butanol (15 ml), followed by the addition of potassium hydroxide (0.47 g), and the mixture was heated under reflux for 20 min. The reaction solution was evaporated, and the resulting residue was partitioned between ethyl acetate and water, and then extracted with ethyl acetate. The organic layer was washed with water and brine, and dried over magnesium sulfate. The solvent was removed, and the resulting residue was dissolved in ether, and then filtered through NH-silica gel. The resulting filtrate was concentrated, to give 0.59 g of the title compound as a pale yellow oil.

$^1$H-NMR(400 MHz,CDCl$_3$); δ (ppm) 1.16(3H,t,J=7.2 Hz) 2.53(2H,q,J=7.2 Hz), 2.68(4H,br), 3.13(1H,s), 3.70(4H,br), 7.37(1H,d,J=5.6 Hz), 7.41(1H,d,J=5.6 Hz), 7.58(2H,d,J=8.4 Hz), 7.80(1H,s), 8.06(2H,d,J=8.4 Hz).

(281-5) 6-(4-Acetylphenyl)-(4-ethylpiperazin-1-yl)thieno[3,2-c]pyridine

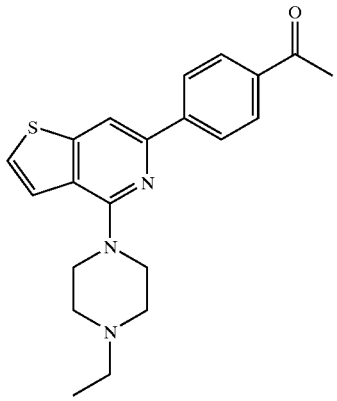

6-(4-Ethynylphenyl)-(4-ethylpiperazin-1-yl)thieno[3,2-c]pyridine (0.59 g) was reacted in formic acid (15 ml) at 100° C. for 12 hr. The reaction solution was evaporated, basified with an aqueous solution of potassium carbonate, and then extracted with ethyl acetate. The organic layer was washed with water and brine, dried and concentrated. The resulting residue was purified by NH-silica gel column chromatography (ethyl acetate/hexane system), to give 0.37 g of the title compound as a pale yellow oil.

$^1$H-NMR(400 MHz,CDCl$_3$); δ (ppm) 1.17(3H,t,J=7.2 Hz), 2.56(2H,q,J=7.2 Hz), 2.64(3H,s), 2.73(4H,br), 3.13 (1H,s), 3.73(4H,br), 7.40–7.43(2H,m), 7.86(1H,s), 8.04(1H, s), 8.10(2H,d,J=8.4 Hz)

(281-6) 4-(4-Ethylpiperazin-1-yl)-6-[4-(1-hydroxyethyl)phenyl]thieno[3,2-c]pyridine

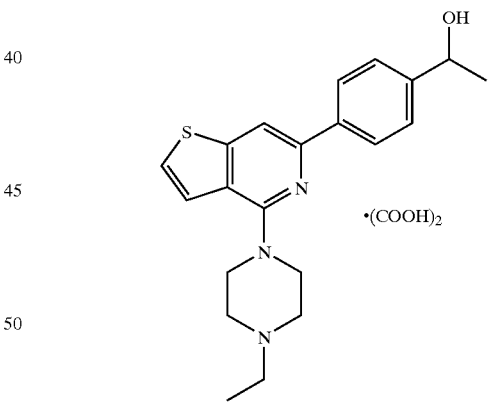

6-(4-Acetylphenyl)-(4-ethylpiperazin-1-yl)thieno[3,2-c]pyridine (0.37 g) was dissolved in methanol (10 ml), followed by the addition of sodium tetrahydroborate (50 mg) at room temperature. The resulting mixture was reacted for 30 min. The reaction solution was concentrated, and the resulting residue was partitioned between ethyl acetate and water. The organic layer was washed with water and brine, dried and concentrated. The resulting residue was purified by NH-silica gel column chromatography (ethyl acetate), to give 0.31 g of the title compound as a pale yellow oil.

Free Compound:

$^1$H-NMR(400 MHz,CDCl$_3$); δ (ppm) 1.17(t,J=7.2 Hz,3H), 1.34(d,J=6.0 Hz,3H), 2.54(q,J=7.2 Hz,2H), 2.70(m, 4H), 3.71(m,4H), 4.96(q,J=6.4 Hz,1H), 7.35(d,J=5.6 Hz,1H), 7.41(d,J=5.6 Hz,1H), 7.47(d,J=8.0 Hz,2H), 7.78(s, 1H), 8.07(d,J=8.0 Hz,2H).

The resulting free compound was converted into an oxalate in a conventional manner, to give 0.29 g of the title compound as a white powder.

Oxalate:

m.p.; 134–135° C.

$^1$H-NMR(400 MHz,DMSO-d$_6$); δ (ppm) 1.25(t,J=7.2 Hz,3H), 1.36(d,J=6.0 Hz,3H), 3.11(q,J=7.2 Hz,2H), 3.31(m, 4H), 3.80(m,4H), 4.78(q,J=6.4 Hz,1H), 7.44(d,J=8.4 Hz,2H), 7.63(d,J=5.6 Hz,1H), 7.81(d,J=5.6 Hz,1H), 8.09(d, J=8.4 Hz,2H), 8.22(s,1H).

MS(FAB) m/z 368(M+H)$^+$.

Example 282

Synthesis of 4-(4-ethylpiperazin-1-yl)-6-[4-(1-hydroxypropyl)phenyl]thieno-[3,2-c]pyridine oxalate (282-1) 6-[4-(1,3-Dioxolan-2-yl)phenyl]5H-thieno[3,2-c]pyridin-4-one

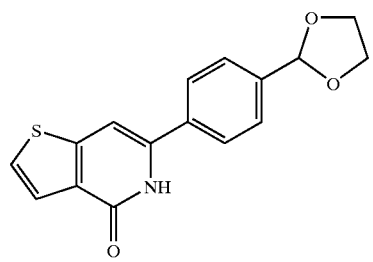

To a solution of N-methyl-2-methylthiophene-3-carboxamide (18.5 g) in tetrahydrofuran (350 ml) was dropwise added 2.5M n-butyl lithium (100 ml) at –70° C. The resulting solution was stirred at –70° C. for 1.5 hr, followed by the addition of a solution of 4-(1,3-dioxolan-2-yl)benzonitrile (20.9 g) in tetrahydrofuran (100 ml) at once. After the dry ice/acetone bath was removed, the reaction mixture was back to room temperature. Three hours later, an aqueous solution of saturated ammonium chloride was added thereto, and the organic layer was separated, washed with water and dried. The filtrate was concentrated, and the resulting solid was washed with ethyl acetate, tetrahydrofuran/ether and n-hexane in this order. The resulting solid was then dried, to give the title compound as white crystals (6.24 g, yield; 31.7%).

$^1$H-NMR(400 MHz,DMSO-d$_6$); δ (ppm) 3.94–4.10(4H, m), 5.79(1H,s), 7.24(1H,s), 7.48–7.56(3H,m), 7.63(2H,d,J= 5.6 Hz), 7.78(2H,d,J=8.4 Hz), 11.67(1H,br-s).

(282-2) 4-(4-Ethylpiperazin-1-yl)-6-(4-formylphenyl)thieno [3,2-c]pyridine

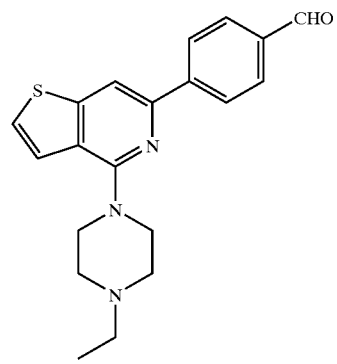

Phosphorus oxychloride (22.7 g) was added to 6-[4-(1,3-dioxolan-2-yl)phenyl]-5H-thieno[3,2-c]pyridin-4-one (6.2 g) at room temperature, and the mixture was reacted at 70° C. for 2 hr. The reaction solution evaporated, and to the resulting residue was added an aqueous solution of potassium carbonate, and then the resulting mixture was extracted with ethyl acetate and dried. The solvent was evaporated, to give 4-chloro-6-[4-(1,3-dioxolan-2-yl)phenyl]-5H-thieno[3, 2-c]pyridine.

Then, the resulting compound was reacted with N-ethylpiperazine (40 ml) at 120° C. for 12 hr. The reaction solution was evaporated, and the resulting residue was extracted with ethyl acetate. The organic layer was extracted with a 2N aqueous solution of hydrochloric acid (100 ml), and then treated at 50° C. for 1 hr. The reaction solution was cooled, basified with a 8N aqueous solution of sodium hydroxide and then extracted with ethylacetate. The organic layer was washed with water and brine, dried and concentrated. The resulting residue was purified by silica gel column chromatography (toluene/acetone system), to give 0.40 g of the title compound as a pale yellow oil.

$^1$H-NMR(400 MHz,CDCl$_3$); δ (ppm) 1.17(t,J=7.2 Hz,3H), 2.54(q,J=7.2 Hz,2H), 2.70(m,4H), 3.73(m,4H), 7.41–7.44(m,2H), 7.88(s,1H), 7.96(d,J=8.4 Hz,2H), 8.25(d, J=8.4 Hz,2H), 10.07(s,1H).

(282-3) 4-(4-Ethylpiperazin-1-yl)-6-[4-(1-hydroxypropyl) phenyl]thieno[3,2-c]pyridine

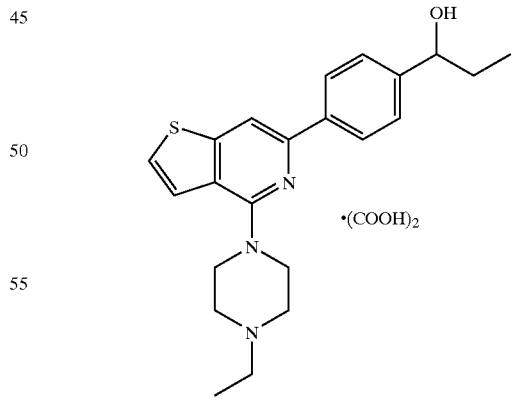

To a solution of 4-(4-ethylpiperazin-1-yl)-6-(4-formylphenyl)thieno-[3,2-c]pyridine (0.20 g) in tetrahydrofuran (20 ml) was added 3M ethylmagnesium bromide/ diethyl ether solution (0.5 ml), and the mixture was reacted at room temperature for 30 min. To the resulting reaction solution was added an aqueous solution of ammonium chloride, and the mixture was extracted with ethyl acetate.

The organic layer was washed with water and brine, and dried. The resulting product was filtered through NH silica gel and washed with ethyl acetate. The filtrate was concentrated, to give 0.17 g of the title compound as white crystals.

Free Compound:

$^1$H-NMR(400 MHz,CDCl$_3$); δ (ppm) 0.96(t,J=7.2 Hz,3H), 1.17(t,J=7.2 Hz,3H), 1.74–1.90(m,2H), 2.54(q,J=7.2 Hz,2H), 2.70(m,4H), 3.71(m,4H), 4.64(m,1H), 7.34(d, J=5.6 Hz,1H), 7.39–7.45(m,3H), 7.79(s,1H), 8.07(d,J=8.0 Hz,2H).

The free compound was converted into an oxalate in a conventional manner, to give 0.16 g of the title compound as a white powder.

Oxalate:
m.p.; 130–131° C.
$^1$H-NMR(400 MHz,DMSO-d$_6$); δ (ppm) 0.84(t,J=7.2 Hz,3H), 1.23(d,J=6.0 Hz,3H), 1.59–1.70(m,2H), 3.07(q,J=7.2 Hz,2H), 3.27(m,4H), 3.78(m,4H), 4.48(t,J=6.4 Hz,1H), 7.40(d,J=8.4 Hz,2H), 7.62(d,J=5.6 Hz,1H), 7.78(d,J=5.6 Hz,1H), 8.09(d,J=8.4 Hz,2H), 8.12(s,1H).
MS(ESI) m/z 382(M+H)$^+$.

Example 283

Synthesis of 4-(4-ethylpiperazin-1-yl)-6-[4-1-hydroxybutyl)phenyl]thieno[3,2-c]pyridine oxalate

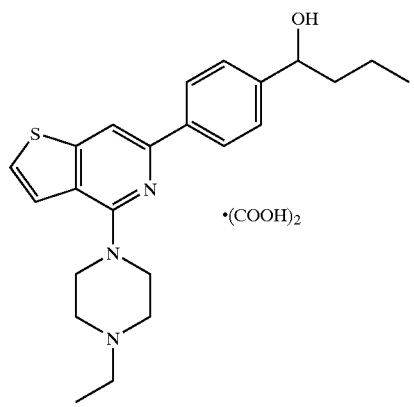

To a solution of 4-(4-ethylpiperazin-1-yl)-6-(4-formylphenyl)thieno[3,2-c]pyridine (0.20 g) obtained in Example 282-2 in tetrahydrofuran (20 ml) was added 2M n-propylmagnesium bromide/diethyl ether solution (1.0 ml), and the mixture was reacted at room temperature for 30 min. To the resulting reaction solution was added an aqueous solution of ammonium chloride, and the mixture was extracted with ethyl acetate. The organic layer was washed with water and brine, dried and filtered through NH silica gel, followed by washing with ethyl acetate. The resulting filtrate was concentrated, to give 0.16 g of the title compound as a white solid.

Free Compound:

$^1$H-NMR(400 MHz,CDCl$_3$); δ (ppm) 0.95(t,J=7.2 Hz,3H), 1.16(d,J=6.0 Hz,3H), 1.28–1.53(m,2H), 1.63–1.89 (m,2H), 2.53(q,J=7.2 Hz,2H), 2.70(m,4H), 3.71(m,4H), 4.76 (m,J=6.4 Hz,1H), 7.34(d,J=5.6 Hz,1H), 7.39–7.45(m,2H), 7.78(s,1H), 8.07(d,J=8.0 Hz,2H).

The resulting free compound was converted into an oxalate in a conventional manner, to give the title compound (0.14 g) as a white powder.

Oxalate:
m.p.; 135–136° C.
$^1$H-NMR(400 MHz,DMSO-d$_6$); δ (ppm) 0.85(t,J=7.2 Hz,3H), 1.22(t,J=7.2 Hz,3H), 1.20–1.68(m,4H), 3.11(m, 2H), 3.26(m,4H), 3.77(m,4H), 4.57(m,1H), 7.39(d,J=8.4 Hz,2H), 7.63(d,J=5.6 Hz,1H), 7.79(d,J=5.6 Hz,1H), 8.07(d, J=8.4 Hz,2H), 8.19(s,1H).

Example 284

Synthesis of 4-(1-ethylpiperazin-4-yl)-6-[3-(2-hydroxyethoxy)phenyl]thieno-[3,2-c]pyridine dihydrochloride (284-1) 2-Methyl-3-thiophenecarboxaldehyde

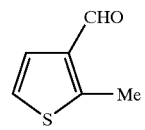

2-(Thiophen-3-yl)-1,3-dioxolane (5.076 g) was dissolved in tetrahydrofuran (50 ml), to which was then added 2.5M n-butyl lithium/hexane solution (13 ml) at −20° C. in nitrogen atmosphere, and the mixture was stirred for 1.5 hr. Subsequently, methyl iodide (2.6 ml) was added to the resulting reaction mixture at −70° C., and the mixture was stirred for 30 min. After the cooling bath was removed, subsequently, the mixture was stirred at room temperature overnight. The reaction mixture was partitioned between ethyl acetate and water. The organic layer was washed with water, dried (over MgSO$_4$) and evaporated. The resulting residue was dissolved in tetrahydrofuran (30 ml), followed by the addition of 1N hydrochloric acid (30 ml), and the mixture was stirred for 1 hr at room temperature. The resulting product was extracted with ethyl acetate, and the organic layer was washed with water, dried (over MgSO$_4$) and evaporated. The resulting residue was purified by silica gel column chromatography (ethyl acetate/hexane system), to give the title compound (3.258 g, yield; 81%) as a pale yellow oil.

$^1$H-NMR(400 MHz,CDCl$_3$); δ (ppm) 2.79(3H,s), 7.07 (1H,d,J=5.4 Hz), 7.38(1H,d,J=5.4 Hz), 10.04(1H,s).

(284-2) 2-Methyl-3-cyanothiophene

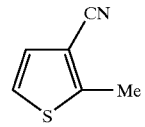

2-Methyl-3-thiophenecarboxaldehyde (3.258 g) was dissolved in ethanol (50 ml), followed by the addition of an aqueous solution (25 ml) of hydroxylamine hydrochloride (2.515 g) and sodium acetate (4.266 g), and the mixture was then stirred at 70° C. for 25 min. The reaction mixture was evaporated, and the resulting residue was partitioned between ethyl acetate and water. The organic layer was washed with water, dried (over MgSO$_4$) and evaporated. The resulting residue was dissolved in methylene chloride (20 ml), followed by the addition of triethylamine (8 ml) and subsequent dropwise addition of trifluoromethanesulfonic anhydride (6 ml) under stirring at −70° C. in nitrogen atmosphere. An aqueous solution of saturated sodium bicarbonate was added to the reaction mixture and extracted with chloroform. The organic layer was washed with water, dried (over MgSO$_4$) and evaporated. The resulting residue was purified by silica gel column chromatography (ethyl acetate/hexane system), to give the title compound as a brown oil (2.108 g, yield; 65%).

¹H-NMR(400 MHz,CDCl₃); δ (ppm) 2.67(3H,s), 7.11 (1H,d,J=5.4 Hz), 7.14(1H,d,J=5.4 Hz).

(284-3) 2-Bromomethyl-3-cyanothiophene

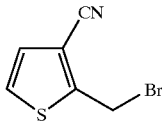

2-Methyl-3-cyanothiophene (2.108 g) was dissolved in benzene (30 ml), followed by the addition of N-bromosuccinimide (4.8 g) and 70% benzoyl peroxide (202 mg), and the mixture was stirred at 80° C. for 2 hr. The reaction mixture was cooled, and the resulting precipitates were filtered off. Then the filtrate was diluted with ethyl acetate, washed with an aqueous solution of saturated sodium bicarbonate, dried (over MgSO₄) and then evaporated. The resulting residue was purified by silica gel column chromatography (ethyl acetate/hexane system), to give the title compound as a yellow oil (2.746 g, yield; 82%).

¹H-NMR(400 MHz,CDCl₃); δ (ppm) 4.80(2H,s), 7.18 (1H,d,J=5.4 Hz), 7.39(1H,d,J=5.4 Hz).

(284-4) 2-Cyanomethyl-3-cyanothiophene

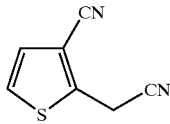

2-Bromomethyl-3-cyanothiophene (2.746 g) was dissolved in toluene (40 ml), followed by the addition of a solution of sodium cyanide (2.002 g)/water (15 ml), and the mixture was stirred at 80° C. overnight. The reaction mixture was diluted with ethyl acetate and washed with an aqueous solution of saturated sodium bicarbonate, dried (over MgSO₄) and evaporated. The resulting residue was purified by silica gel column chromatography (ethyl acetate/hexane system), to give the title compound as a pale yellow solid (823 mg, yield; 43%).

¹H-NMR(400 MHz,CDCl₃); δ (ppm) 4.13(2H,s), 7.23 (1H,d,J=5.2 Hz), 7.41(1H,d,J=5.2 Hz).

(285-5) 6-Amino-4-bromothieno[3,2-c]pyridine

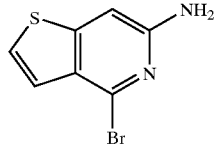

2-Cyanomethyl-3-cyanothiophene (823 mg) was added to a solution (30 ml) of 25% hydrogen bromide in acetic acid, and the resulting mixture was stirred under ice-cooling for 90 min, which was neutralized with a 8N aqueous solution of sodium hydroxide and then extracted with ethyl acetate. The organic layer was washed with water, dried (over MgSO₄) and evaporated. The residue was purified by silica gel column chromatography (ethyl acetate/hexane system), to give the title compound as a yellow solid (894 mg, yield; 70%).

¹H-NMR(400 MHz,CDCl₃); δ (ppm) 4.49(2H,br-s), 6.85 (1H,d,J=0.8 Hz), 7.14(1H,d,J=5.6 Hz), 7.25(1H,dd,J=5.6 Hz,0.8 Hz).

(284-6) 4-(1-Ethylpiperazin-4-yl)-6-[3-(2-hydroxyethoxy) phenyl]thieno[3,2-c]pyridine dihydrochloride

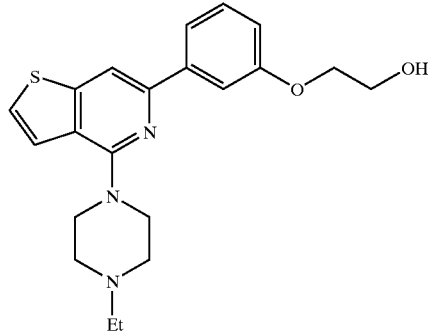

6-Amino-4-bromothieno[3,2-c]pyridine (894 mg) was treated in the same manner as in Example 245-1, to obtain a mixture of 4,6-dibromothieno[3,2-c]pyridine and 4,6,7-tribromothieno[3,2-c]pyridine (6:4). Continuously, the mixture was treated in the same manner as in Example 245-2 and then treated with 3-tributylstannylphenoxyethyl acetate (394 mg) in the same manner as in Example 300-4. Then, the reaction mixture was dissolved in N,N-dimethylformamide (15 ml), followed by the addition of t-butyldimethylsilyl chloride (241 mg) and imidazole (136 mg), and the mixture was stirred for 1 hr at room temperature. The reaction solution was partitioned between ethyl acetate and water. The organic layer was washed with water, dried (over MgSO₄) and evaporated. The residue was dissolved in tetrahydrofuran (12 ml), followed by the addition of 2.5M n-butyl lithium/hexane solution (480 ml) in nitrogen atmosphere at −70° C., and the mixture was stirred for 30 min. Then, an aqueous solution of saturated ammonium chloride was added thereto, and the mixture was extracted with ethyl acetate. The organic layer was washed with water, dried (over MgSO₄) and evaporated. The residue was purified by (NH) silica gel column chromatography (ethyl acetate/hexane system). The resulting product was then converted into a hydrochloride in a conventional manner, to give the hydrochloride of the title compound as a colorless amorphous (288 mg, yield; 15%).

Hydrochloride:

m.p.; 126–130° C.

¹H-NMR(400 MHz,DMSO-d₆); δ (ppm) 1.29(3H,t,J=7.2 Hz), 3.13–3.27(4H,m), 3.47–3.62(4H,m), 3.74(2H,t,J=5 Hz), 4.07(2H,t,J=5 Hz), 4.20(2H,d,J=13.6 Hz), 6.96(1H,dd, J=8.2 Hz,2.4 Hz), 7.37(1H,t,J=8.2 Hz), 7.63(1H,d,J=5.6 Hz), 7.70(1H,d,J=2.4 Hz), 7.71(1H,d,J=8.4 Hz), 7.83(1H,d, J=5.6 Hz), 8.28(1H,s), 11.00–11.10(1H,br-s).

ESI-Mass; 384(MH⁺).

Example 285

Synthesis of 4-(1-ethylpiperazin-4-yl)-6-[4-(3-hydroxybutyl)phenyl]thieno[3,2-c]pyridine hydrochloride (285-1) 4-(1-Ethylpiperazin-4-yl)-6-bromothieno[3,2-c]pyridine

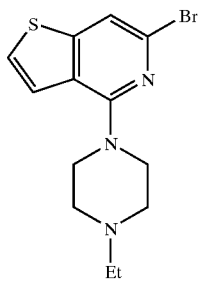

2-Cyanomethylthiophene-3-carboxylic acid (2.331 g) was treated in the same manner as in Example 300-1, to give the title compound as a yellow oil (183 mg, yield; 4%).

$^1$H-NMR(400 MHz,CDCl$_3$); δ (ppm) 1.14(3H,t,J=7.2 Hz), 2.50(2H,q,J=7.2 Hz), 2.63(4H,t,J=5 Hz), 3.66(4H,t,J=5 Hz), 7.30(1H,d,J=5.6 Hz), 7.35(1H,d,J=5.6 Hz,0.8 Hz), 7.43 (1H,d,J=0.8 Hz).

(285-2) 4-(1-Ethylpiperazin-4-yl)-6-[4-(3-(hydroxybutyl)phenyl]thieno[3,2-c]pyridine hydrochloride

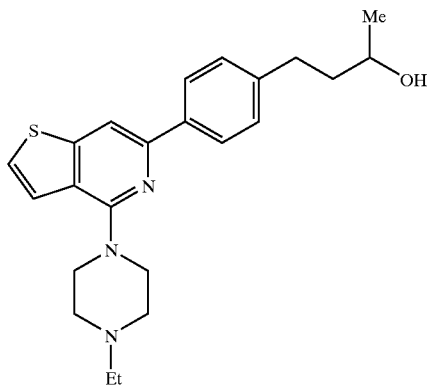

In the same manner as in Example 167-3, the hydrochloride of the title compound was obtained as a pale yellow amorphous (98 mg, yield; 33%) from 4-[3-(t-butyldimethylsilyloxy)butyl]-1-bromobenzene (889 mg) and 4-(1-ethylpiperazin-4-yl)-6-bromothieno[3,2-c]pyridine (183 mg).

Hydrochloride:

m.p.; 122–124° C.

$^1$H-NMR(400 MHz,DMSO-d$_6$); δ (ppm) 1.08(3H,d,J=6.4 Hz), 1.29(3H,t,J=7.2 Hz), 1.58–1.66(2H,m), 2.57–2.74(2H, m), 3.14–3.25(4H,m), 3.49–3.62(5H,m), 4.19(2H,d,J=8.8 Hz), 7.61(1H,d,J=5.2 Hz), 7.80(1H,d,J=5.2 Hz), 8.03(2H,d, J=8.8 Hz), 8.2(1H,s), 11.00–11.10(1H,br-s).

ESI-Mass; 396(MH$^+$).

Example 286

Synthesis of 4-(1-ethylpiperazin-4-yl)-6-[4-(3-hydroxybutyl)phenyl]thieno[3,2-c]pyridine dihydrochloride

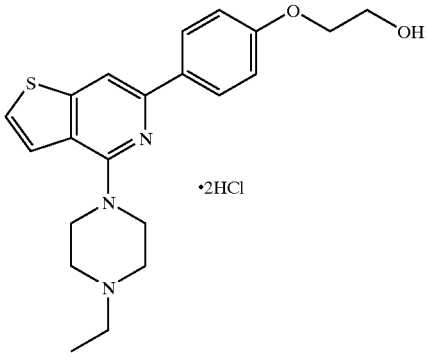

4-(4-Ethylpiperazin-1-yl)-6-(4-hydroxyphenyl)thieno[3,2-c]pyridine (1.01 g) obtained in Example 289-7 was dissolved in DMF (4 ml), followed by the addition of 60% sodium hydride (0.16 g). After the evolution of hydrogen was ceased, 2-(t-butyldimethylsilyloxy)ethyl bromide (1.43 g) was added thereto, and the mixture was stirred at 50° C. overnight. The reaction solution was partitioned between ethyl acetate and water. The organic layer was washed with water, dried and evaporated. The resulting residue was dissolved in THF (10 ml), followed by the addition of 1.0M tetra(n-butyl)ammonium fluoride/THF solution (1.75 ml), and the mixture was stirred at room temperature for 30 min. The solvent was evaporated, and the resulting residue was partitioned between ethyl acetate and water. The resulting product was extracted from the organic layer with 2N hydrochloric acid. The aqueous layer was basified with 2N sodium hydroxide, which was then back-extracted with ethyl acetate. The organic layer was washed with water, dried and evaporated. The resulting residue was purified by silica gel column chromatography (methylene chloride/methanol system) and NH-silica gel column chromatography (ethyl acetate), to give 0.475 g of the free compound of the title compound as a colorless oil.

Free Compound:

$^1$H-NMR(400 MHz,CDCl$_3$); δ (ppm) 1.16(t,J=7.2 Hz,3H), 2.09(br-s,1H), 2.53(q,J=7.2 Hz,2H), 2.70(t,J=4.8 Hz,4H), 3.70(t,J=4.8 Hz,4H), 4.00(br-t,2H), 4.15(t,J=4.4 Hz,2H), 7.00(d,J=9.0 Hz,2H), 7.32(d,J=5.6 Hz,1H), 7.39 (dd,J=0.8, 5.6 Hz,1H), 7.72(d,J=0.8 Hz,1H), 8.05(d,J=9.0 Hz,2H).

The resulting free compound was converted into a hydrochloride in a conventional manner, to give 0.565 g of the title compound as a pale yellow powder.

Hydrochloride:

m.p.; 128–129° C.

$^1$H-NMR(400 MHz,DMSO-d$_6$); δ (ppm) 1.31(t,J=7.2 Hz,3H), 3.18–3.28(m,4H), 3.50(br-t,2H), 3.60(br-d,2H), 3.75(t,J=5.1 Hz,2H), 4.05(t,J=5.1 Hz,2H), 4.22(br-d,2H), 7.05(d,J=8.8 Hz,2H), 7.62(d,J=7.2 Hz,1H), 7.79(d,J=5.6 Hz,1H), 8.10(d, J=8.8 Hz,2H), 8.18(s,1H), 10.76(br-s,1H).

MS(ESI) m/z 384(M+H)$^+$.

Example 287

Synthesis of 4-(4-ethylpiperazin-1-yl)-6-[4-(2-hydroxypropoxy)phenyl]thieno[3,2-c]pyridine (287-1) 1-Bromo-O-(t-butyl)diphenylsilyl-2-propanol

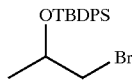

(In the formula, TBDPS represents (t-butyl)diphenylsilyl group.)

A solution of 2-(t-butyl)diphenylsilyloxypropanol of 5.27 g (16.8 mmol) synthetically prepared according to J. Am. Chem. Soc., 1985, 107, 5556, triphenylphosphine of 4.40 g (1.0 equivalent), pyridine of 2.03 ml (1.5 equivalents) and dry THF (50 ml) was stirred under ice-cooling. To the resulting mixture was added dropwise bromide (0.864 ml, 1.0 equivalent), and the mixture was further stirred for 50 min. Ethyl acetate and water were added thereto, and the resulting mixture was stirred. The organic layer was separated, then, it was washed sequentially with an aqueous solution of sodium thiosulfate, water and brine, and dried over magnesium sulfate. The solvent was evaporated, and the resulting residue was purified by silica gel column chromatography (n-hexane/ethyl acetate system). n-Hexane was added to the resulting product to dissolve the product, and the resulting insoluble matters were filtered off. The solvent was evaporated, to give the title compound as a colorless oil (5.706 g, yield; 90%).

$^1$H-NMR(400 MHz,CDCl$_3$); δ (ppm) 1.07(s,9H), 1.22(d, J=6.0 Hz,3H), 3.25(dd,J=6.4, 10.0 Hz), 3.31(dd,J=4.4, 10.0 Hz), 3.96–4.03(m,1H), 7.36–7.46(m,6H), 7.66–7.71(m,4H).

(287-2) 4-(4-Ethylpiperazin-1-yl)-6-[4-(2-t-butyldiphenylsilyloxypropoxy)phenyl]thieno[3,2-c]pyridine

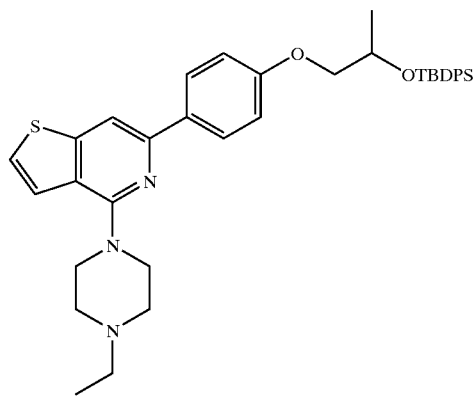

66% sodium hydride (0.26 g, 1.2 equivalents) was washed with n-hexane and was then suspended in DMF of 1 ml, and the mixture was stirred under ice-cooling. To the resulting mixture was added 4-(4-ethylpiperazin-1-yl)-6-(4-hydroxyphenyl)thieno[3,2-c]pyridine of 2.00 g (5.88 mmol) dissolved in DMF of 20 ml, followed by the agitation at room temperature for 45 min. To the resulting product was added 1-bromo-O-(t-butyl)diphenylsilyl-2-propanol of 4.44 g (2.0 equivalents) dissolved in DMF of 15 ml, which was stirred in nitrogen atmosphere at 50° C. for 18 hr. Water was added to the resulting mixture, and then extracted with ethyl acetate. The organic layer was washed sequentially with water (three times) and brine, and dried over magnesium sulfate. The solvent was evaporated, and the resulting residue was purified by NH-silica gel column chromatography (eluent solvent/ethyl acetate system), to give the title compound as a pale yellow oil (3.38 mg, yield; 90%).

$^1$H-NMR(400 MHz,CDCl$_3$); δ (ppm) 1.08(s,9H), 1.16(t, J=7.2 Hz,3H), 1.21(d,J=6.4 Hz,3H), 2.53(q,J=7.2 Hz,2H), 2.70(t,J=4.8 Hz,4H), 3.70(t,J=4.8 Hz,4H), 3.81(dd,J=5.4, 9.2 Hz,1H), 3.97(dd,J=6.0, 9.2 Hz,1H), 4.17–4.24(m,1H), 7.80(d,J=8.8 Hz,2H), 7.31(d,J=5.6 Hz,1H), 7.34–7.45(m, 7H), 7.70–7.74(m,5H), 7.97(d,J=8.8 Hz,2H).

(287-3) 4-(4-Ethylpiperazin-1-yl)-6-[4-(2-hydroxypropoxy)phenyl]thieno[3,2-c]pyridine

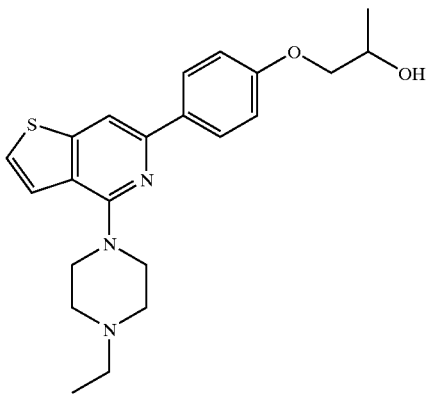

4-(4-Ethylpiperazin-1-yl)-6-[4-(2-t-butyldiphenylsilyloxypropoxy)phenyl]thieno[3,2-c]pyridine of 3.38 g (5.31 mmol) was dissolved in THF of 20 ml and stirred at room temperature. To the mixture was added 1.0M tetrabutylammonium fluoride/THF solution of 10.6 ml (2.0 equivalents), and the mixture was stirred for 8 hr. The solvent was evaporated, and to the resulting residue was added water, and the mixture was extracted with ethyl acetate. The organic layer was washed sequentially with water (three times) and brine, and dried over magnesium sulfate. The solvent was evaporated, and the resulting residue was purified by NH-silica gel column chromatography (n-hexane/ethyl acetate system), to give the title compound as a colorless oil (1.65 g, yield; 78%).

The resulting compound was converted into a hydrochloride in a conventional manner, and then reprecipitated with ethanol/diisopropyl ether/water, to give 1.91 g of the hydrochloride of the title compound as a pale yellow powder.

Hydrochloride:

$^1$H-NMR(400 MHz,DMSO-d$_6$); δ (ppm) 1.17(d,J=7.2 Hz,3H), 1.31(t,J=7.2 Hz,3H), 3.18–3.28(m,4H), 3.49(br-t, 2H), 3.60(br-d,2H), 3.83–3.91(m,2H), 3.94–4.01(m,1H), 4.21(br-d,2H), 7.04(d,J=9.2 Hz,2H), 7.62(d,J=5.6 Hz,1H), 7.79(d,J=5.6 Hz,1H), 8.07–8.11(m,3H), 8.18(s,1H), 10.72 (br-s,1H).

MS(FAB) m/z 398(M+H)$^+$.

Free Compound:

$^1$H-NMR(400 MHz,CDCl$_3$); δ (ppm) 1.16(t,J=7.2 Hz,3H), 1.31(d,J=6.4 Hz,3H), 2.53(q,J=7.2 Hz,2H), 2.70(t, J=4.8 Hz,4H), 3.70(t,J=4.8 Hz,4H), 3.86(dd,J=8.0, 9.2 Hz,1H), 4.01(dd,J=3.0, 9.2 Hz,1H), 4.20–4.27(m,1H), 6.99 (d,J=8.8 Hz,2H), 7.32(d,J=5.4 Hz,1H), 7.39(dd,J=0.4, 5.4 Hz,1H), 7.72(d,J=7.2 Hz,1H), 8.05(d,J=8.8 Hz,2H).

Example 288

Synthesis of 6-[4-(2-methyl-2-hydroxypropoxy)phenyl]-4-(4-methylpiperazin-1-yl)thieno[3,2-c]pyridine hydrochloride

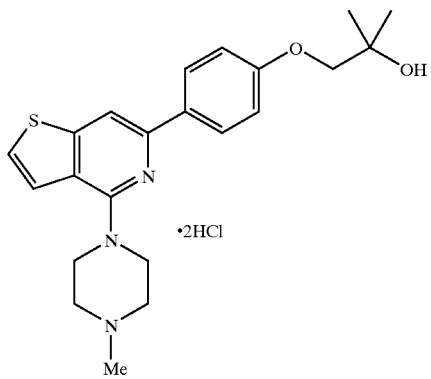

4-(4-Methylpiperazin-1-yl)-6-(4-hydroxyphenyl)thieno[3,2-c]pyridine (543 mg) was dissolved in DMF (20 ml), followed by the addition of 60% sodium hydride (87 mg). The mixture was stirred at room temperature for 30 min, to which was then added ethyl bromoacetate (0.185 ml) at 0° C., and the mixture was stirred for 15 min. The reaction solution was partitioned between ethyl acetate and water. The organic layer was washed with water, dried and evaporated. The resulting residue was dissolved in THF (30 ml), followed by the addition of 3.0M methylmagnesium bromide/ether solution (3.3 ml) under ice-cooling, and the mixture was reacted at room temperature for 1.5 hr. The reaction solution was partitioned between ethyl acetate and water. The organic layer was washed with water, dried and evaporated. The resulting residue was purified by NH-silica gel column chromatography (hexane/ethyl acetate system), to give a colorless oil (209 mg, yield; 31%).

The resulting oil was converted into a hydrochloride in a conventional manner, to give the title compound as yellow crystals.

Hydrochloride:

m.p.; 135–138° C.

$^1$H-NMR(400 MHz,DMSO-d$_6$); δ (ppm) 1.23(s,6H), 2.86 (d,J=4.8 Hz,3H), 3.25–3.33(m,2H), 3.45(t,J=13.2 Hz,2H), 3.54(d,J=11.2 Hz,2H), 3.78(s,2H), 4.21(d,J=14.0 Hz,2H), 7.04(d,J=8.8 Hz,2H), 7.61(d,J=5.6 Hz,1H), 7.78(d,J=5.6 Hz,1H), 8.09(d,J=8.8 Hz,2H), 8.18(s,1H).

MS(FAB) m/z 398(M+H)$^+$.

Free Compound:

$^1$H-NMR(400 MHz,CDCl$_3$); δ (ppm) 1.37(s,6H), 2.39(s, 3H), 2.66(t,J=4.8 Hz,4H), 3.69(t,J=4.8 Hz,4H), 3.86(s,2H), 7.00(d,J=8.8 Hz,2H), 7.32(d,1H,J=5.6 Hz), 7.38(d,J=5.6 Hz,1H), 7.73(s,1H), 8.05(d,J=8.8 Hz,2H).

Example 289

Synthesis of 6-[4-(2-methyl-2-hydroxypropoxy)phenyl]-4-(4-propylpiperazin-1-yl)thieno[3,2-c]pyridine hydrochloride

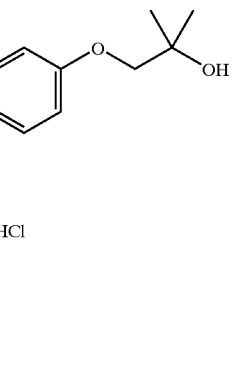

In the same manner as in Example 289, a yellow compound was obtained (240 mg, yield; 35%) from 4-(4-propylpiperazin-1-yl)-6-(4-hydroxyphenyl)thieno[3,2-c]pyridine (603 mg), ethyl bromoacetate (0.18 ml) and 3.0M methylmagnesium bromide (1.6 ml). The resulting compound was converted into a hydrochloride in a conventional manner, to give the hydrochloride of the title compound as yellow crystals.

Hydrochloride:

m.p.; 133–135° C.

$^1$H-NMR(400 MHz,DMSO-d$_6$); δ (ppm) 1.19(t,J=7.2 Hz,3H), 1.23(s,6H), 1.70–1.81(m,2H), 3.03–3.13(m,4H), 3.20–3.30(m,2H), 3.50–3.61(m,2H), 3.78(s,2H), 4.19(d,J=12.8 Hz,2H), 7.04(d,J=8.8 Hz,2H), 7.61(d,J=5.6 Hz,1H), 7.78(d,J=5.6 Hz,1H), 8.10(d,J=8.8 Hz,2H), 8.18(s,1H).

MS(FAB) m/z 426(M+H)$^+$.

Free Compound:

$^1$H-NMR(400 MHz,CDCl$_3$); δ (ppm) 0.95(t,J=7.6 Hz,3H), 1.37(s,6H), 1.56–1.61(m,2H), 2.38–2.43(m,2H), 2.68(t,J=5.2 Hz,4H), 3.69(t,J=5.2 Hz, 4H), 3.86(s, 2H), 7.00(d, J=8.8 Hz,2H), 7.31(d, J=5.6 Hz, 1H), 7.39(d,J=5.6 Hz, 1H), 7.72(s, 1H), 8.05(d, J=8.8 Hz, 2H).

Example 290

Synthesis of 6-[4-(2-methyl-2-hydroxypropoxy)phenyl]-4-(4-ethylpiperazin-1-yl)thieno[3,2-c]pyridine dihydrochloride (290-1) 2-Methyl-3-thiophenecarboxylic acid

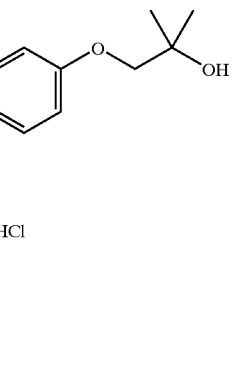

To a solution of 1.5M-lithium diisopropylamide/cyclohexane solution (600 ml) and THF (300 ml) was dropwise added 3-thiophenecarboxylic acid (50.0 g)/THF (150 ml) under vigorous stirring at −70° C. After the reaction mixture was stirred, as it was, at −70° C. for 2 hr, methyl iodide (60.0 g) was added dropwise to the reaction mixture. After the dry ice/acetone bath was removed, the mixture was reacted overnight. The resulting reaction solution was acidified by adding 5N hydrochloric acid thereto, and then extracted with ethyl acetate. The organic layer was washed with water and brine, dried and evaporated, to give 54 g of the title compound.

(290-2) 2-Methyl-3-thiophenecarboxylate chloride

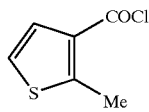

2-Methyl-3-thiophenecarboxylic acid (54 g) was reacted with thionyl chloride (100 ml) at 60° C. for 1.5 hr. The reaction solution was evaporated, and to the resulting residue was added THF (100 ml×2), and then excess thionyl chloride was removed, to give 60.5 g of the title compound.

(290-3) N-Methyl-2-methylthiophene-3-carboxamide

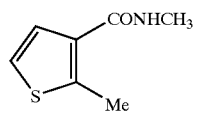

2-Methyl-3-thiophenecarboxylate chloride (60.5 g)/THF (300 ml) solution was added dropwise to a 40% aqueous solution of methylamine (400 ml) at 0° C. Ethyl acetate (2 l) was added thereto, and then the organic layer was washed sequentially with water, a 5N aqueous solution of hydrochloride acid, an aqueous solution of saturated of saturated sodium bicarbonate, water and brine, dried and evaporated. The resulting residue was crystallized from n-hexane, to give the title compound as a white powder (43.5 g, yield; 71.8%).

$^1$H-NMR (400 MHz, CDCl$_3$); δ (ppm) 2.70(3H, s), 2.96 (3H, d, J=7.2 Hz), 5.82(1H,br), 7.03(1H, d,J=5.2 Hz), 7.08 (1H, d, J=5.2 Hz).

(290-4) 6-(4-Methoxyphenyl)-5H-thieno[3,2-c]pyridin-4-one

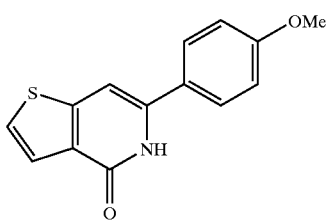

To a solution of N-methyl-2-methylthiophene-3-carboxamide (36.0 g) in THF (500 ml) was added dropwise 2.5M n-BuLi/THF solution (200 ml) at −70° C. The reaction solution was stirred at −70° C. for 2 hr. followed by the addition of anisonitrile (31.0 g) at once. After the dry ice/acetone bath was removed, the reaction mixture was back to room temperature. Three hours later, an aqueous solution of saturated ammonium chloride and ether were added thereto, and then the mixture was further stirred for 1 hr. The resulting white precipitates were collected by filtration, washed with water, ether and n-hexane in this order, and then dried, to give the title compound (17.9 g, yield; 30%).

$^1$H-NMR (400 MHz, DMSO-d$_6$); δ (ppm) 3.81(3H,s), 7.04(2H,d,J=8.4 Hz), 7.15(1H,s), 7.47(1H, d,J=5.2 Hz), 7.56(1H,d,J=2.5 Hz), 7.73(2H,d,J=8.4 Hz).

(290-5) 4-Chloro-6-(4-methoxyphenyl)thieno[3,2-c] pyridine

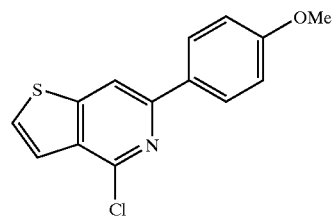

6-(4-Methoxyphenyl)-5H-thieno[3,2-c]pyridin-4-one (9.1 g) was added to phosphorus oxychloride (90 g), and the mixture was heated at 120° C. for 3 hr. The reaction solution was evaporated, and to the resulting residue were added ethyl acetate and water. The organic layer was washed with water, an aqueous solution of saturated sodium bicarbonate and brine, and dried over magnesium sulfate. The solvent was evaporate, and the resulting residue was purified by silica gel column chromatography (ethyl acetate/hexane system), to give the title compound as a white powder (6.6 g, yield; 73%).

$^1$H-NMR (400 MHz, CCDl$_3$); δ (ppm) 3.86(3H,s), 7.01 (2H,d,J=8.8 Hz), 7.50(2H,m), 8.01(2H,d,J=8.8 Hz), 8.06 (1H,s).

(290-6) 4-(4-Ethylpiperazin-1-yl)-6-(4-methoxyphenyl) thieno[3,2-c]pyridine

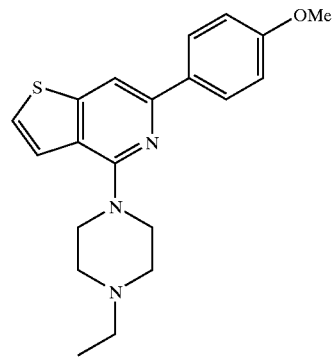

A mixture of 4-chloro-6-(4-methoxyphenyl)thienol[3,2-c] pyridine (6.6 g) and N-ethylpiperazine (30 ml) was heated at 130° C. for 2 hr. The reaction mixture was evaporated, and to the resulting residue were added potassium carbonate and water. The resulting mixture was extracted with ethyl acetate, and the resulting organic layer was washed with water and brine, and dried over magnesium sulfate. The solvent was removed, and the resulting residue was purified by silica gel column chromatography (methylene chloride/methanol system), to give the title compound as a pale brown oil (5.2 g, yield; 61.5%).

$^1$H-NMR (400 MHz, CDCl$_3$): δ (ppm) 1.17(3H,t,J=7.2 Hz), 2.55(2H,q,J=7.2 Hz), 2.72(4H,br), 3.71(4H,br), 6.99 (2H,d,J=8.8 Hz), 7.32(1H,d,J=6.0 Hz), 7.38(1H,dd,J=6.0, 0.8 Hz), 7.73(1H,d,J=0.8 Hz), 8.05(2H,d,J=8.8 Hz).

(290-7) 4-(4-Ethylpiperazin-1-yl)-6-(4-hydroxyphenyl)thieno[3,2-c]pyridine

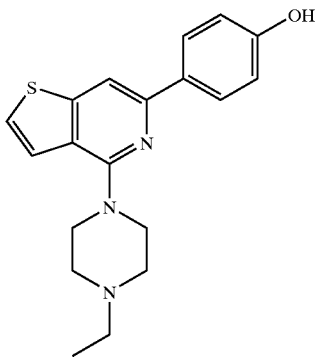

4-(4-Ethylpiperazin-1-yl)-6-(4-methoxyphenyl)thieno[3,2-c]pyridine (5.2 g) was dissolved in 48% hydrobromic acid (50 ml), and the mixture was reacted at 130° C. for 1.5 hr. The reaction solution was evaporated, basified with potassium carbonate and extracted with chloroform. The chloroform layer was washed with water, dried and evaporated. The resulting residue was purified by NH-silica gel column chromatography (ethyl acetate), to give the title compound as a pale brown powder (4.0 g, yield; 80%).

$^1$H-NMR (400 MHz, CDCl$_3$); δ (ppm) 1.21(3H,t,J=7.2 Hz), 2.62(2H,q,J=7.2 Hz), 7.82(4H,br), 3.76(4H,br), 6.92 (2H,d,J=8.4 Hz), 7.33(1H,d,J=5.6 Hz), 7.37(1H,d,J=5.6 Hz), 7.73(1H,s), 7.99(2H,d,J=8.4 Hz).

(290-8) 6-[4-(2-Methyl-2-hydroxy)propoxyphenyl]-(4-ethylpiperazin-1-yl)thieno[3,2-c]pyridinehydrochloride

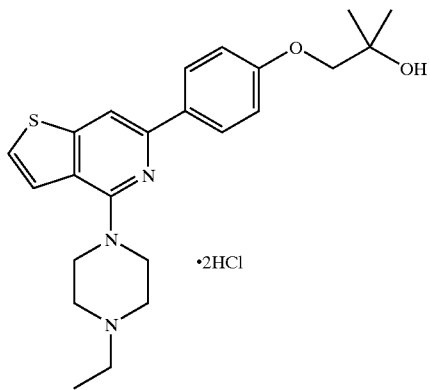

4-(4-Ethylpiprazin-1-yl)-6-(4-hydroxyphenyl)thieno[3,2-c]pyridine (1.10 g) was dissolved in DMF (30 ml), followed by the addition of 60% sodium hydride (0.18 g). After the evolution of hydrogen was ceased, ethyl bromoacetate (0.55 g) was added thereto, which was then stirred at 0° C. for 30 min. The reaction solution was partitioned between ethyl acetate and water. The organic layer was washed with water, dried and evaporated. The resulting residue was dissolved in THF (30 ml), followed by the addition of 3M methylmagnesium bromide/ether solution (3.3 ml) under ice-cooling, and the mixture was reacted at room temperature for 1.5 hr. The reaction solution was partitioned between ethyl acetate and water, and the aqueous layer was extracted from the organic layer with 2N hydrochloric acid. The aqueous layer was basified with 2N sodium hydroxide and back-extracted with ethyl acetate. The organic layer was washed with water, dried and evaporated. The resulting residue was purified by silica gel column chromatography (methylene chloride/methanol system) and NH-silica gel chromatography (ethyl acetate), to give the free compound of the title compound as a colorless oil (0.71 g, yield; 53.2%).

The resulting oil was converted into a hydrochloride in a conventional manner, to give 0.72 g of the title compound as a pale yellow powder.

Hydrochloride:
3.28(m,2H), 3.40(q, J=7.2 Hz,2H), 3.50(br-t,2H), 3.62(br-d,2H), 3.97(br-d,2H), 6.90(d,J=8.8 Hz,2H), 7.55(t,J=8.0 Hz,1H), 7.71(t,J=8.0 Hz,1H), 7.93(s,2H), 7.91–7.96(m,1H), 8.04(d,J=8.8 Hz,2H), 8.08(d,J=8.8 Hz,2H), 10.92(br-s,1H).
MS(FAB) m/z 378(M+H)$^+$.

Example 291

Synthesis of 4-[4-ethylpiperazin-1-yl)-6-[4-(3-hydroxy-3-methylbutyl)phenyl]thieno[3,2-c]pyridine dihydrochloride

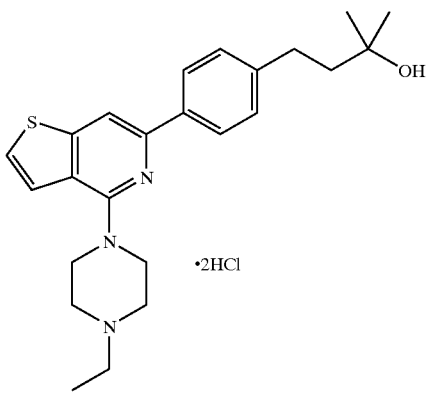

6-(4-Bromophenyl)-4-(4-ethylpiperazin-1-yl)thieno[3,2-c]pyridine (1.265 g) and 2-methyl-3-butyn-2-ol (915 µl) were heated under reflux in the presence of bistriphenylphosphine dichloride (44 mg), triphenylphosphine (165 mg) and cuprous iodide (22 mg) in DMF (12 ml) and triethylamine (20 ml) for 1.5 hr. The reaction solution was evaporated, and the resulting residue was purified by NH-silica gel column chromatography (ethyl acetate/hexane system), to give 6-[4-(3-methyl-3-hydroxy-1-butynyl)phenyl]-(4-ethylpiperazin-1-yl)thieno[3,2-c]pyridine (0.414 g) as a pale yellow oil.

6-[4-(3-Methyl-3-hydroxy-1-butynyl)phenyl]-(4-ethylpiperazin-1-yl)thieno[3,2-c]pyridine (0.299 g) was dissolved in a mixture solution of benzene (30 ml)/THF (15 ml), and the hydrogenation reaction was conducted with a catalyst of chlorotristriphenylphosphinerhodium. The reaction solution was filtered and washed with methanol, and the resulting filtrate was concentrated. The resulting residue was purified by NH-silica gel column chromatography (ethyl acetate/hexane system), to give 0.097 g of 4-(4-ethylpiperazin-1-yl)-6-[4-(3-hydroxy-3-methylbutyl)phenyl)thieno[3,2-c]pyridine of as a pale yellow oil.

Free compound:
$^1$H-NMR (400 MHz, CDCl$_3$): δ (ppm) 1.16(t,J=7.2 Hz,3H), 1.31(s,6H), 1.81–1.85(m,2H), 2.52(q,J=7.2 Hz,2H), 2.69(t,J=5.0 Hz,4H), 2.73–2.77(m,2H), 3.70(t,J=5.0 Hz,4H), 7.28(d,J=8.4 Hz,2H), 7.32(d,J=5.6 Hz,1H), 7.39 (dd,J=0.8.5.6 Hz,1H), 7.76(d,J=0.8 Hz,1H), 8.01(d,J=8.4 Hz,2H).

The resulting oil was converted into a hydrochloride in a conventional manner, to give the title compound (0.72 g) as a pale yellow powder.

Hydrochloride:

m.p.; 116–117.5° C.

¹H-NMR (400 MHz, DMSO-$d_6$); δ (ppm) 1.16(s,6H), 1.31(t,J=7.2 Hz,3H), 1.65–1.69(m,2H), 2.65–2.69(m,2H), 3.17–3.28(m,4H), 3.51(br-t,2H), 3.60(br-d,2H), 4.22(br-d, 2H), 7.30(d,J=8.4 Hz,2H), 7.63(d,J=5.6 Hz,1H), 7.82(d,J= 5.6 Hz,1H), 8.06(d,J=8.4 Hz,2H), 8.22(s,1H), 10.80(br-s, 1H).

MS(FAB) m/z 410(M+H)⁺.

Example 292

Synthesis of 6-[4-(4-methyl-4-hydroxypentyloxy) phenyl]-4-(4-ethylpiperazin-1-yl)thieno[3,2-c] pyridine

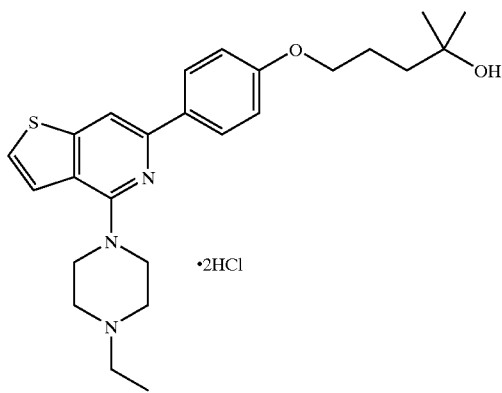

In the same manner as in Example 289, a yellow compound was obtained (359 mg, yield; 55%) from 4-(4-ethylpiperazin-1-yl)-6-(4-hydroxyphenyl)thieno[3,2-c] pyridine (816 mg), ethyl-4-bromobutyrate (0.42 ml) and 3.0M methylmagnesium bromide/THF solution (1.3 ml). The resulting compound was converted into a hydrochloride in a conventional manner, to give the hydrochloride of the title compound as yellow crystals.

Hydrochloride:

m.p.; 116–118° C.

¹H-NMR (400 MHz,DMSO-$d_6$); δ (ppm) 1.12(s,6H), 1.30(t,J=7.2 Hz,3H), 1.48–1.52(m,2H), 1.74–1.82(m,2H), 3.17–3.28(m,4H), 3.48(t,J=12.0 Hz,2H), 3.58–3.62(m,2H), 4.02(t,J=5.6 Hz,2H), 4.02(d,J=14.0 Hz,2), 7.02(d,J=8.8 Hz,2H), 7.61(d,J=5.6 Hz,1H), 7.78(d,J=5.6 Hz,1H), 8.09(d, J=8.8 Hz,2H), 8.17(s,1H).

MS(FAB) m/z 440(M+H)⁺.

Free compound:

¹H-NMR(400 MHz, CDCl₃); δ (ppm) 1.16(t,J=7.6 Hz,3H), 1.27(s,6H), 1.65–1.69(m,2H), 1.89–1.94(m,2H), 2.52(q,J=7.6 Hz,2H), 2.69(t,J=4.8 Hz,4H), 3.69(t,J=4.8 Hz,4H), 4.05(t,J=6.4 Hz,2H), 6.97(d,J=8.4 Hz,2H), 7.31(d, J=5.6 Hz,1H), 7.39(d,J=5.6 Hz,1H), 7.71(s,1H), 8.03(d,J= 8.4 Hz,2H).

Example 293

Synthesis of 4-(4-propylpiperazin-1-yl)-6-[4-(2-hydroxyethoxy)phenyl]thieno[3,2-c]pyridine

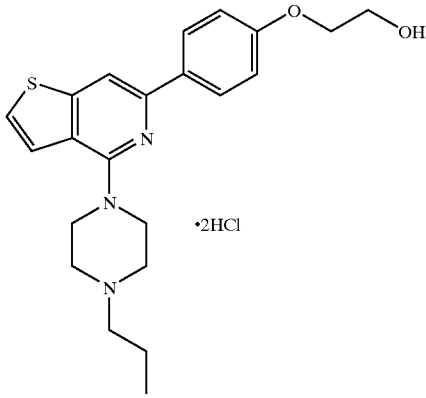

In the same manner as in Example 289, a yellow compound was obtained (310 mg, yield; 82%) from 4-(4-propylpiperazin-1-yl)-6-(4-hydroxyphenyl)thieno[3,2-c] pyridine (603 mg) and 2-bromoethanol (0.24 ml). The resulting compound was converted into a hydrochloride in a conventional manner, to give the hydrochloride of the title compound as yellow crystals.

Hydrochloride:

m.p.; 128–130° C.

¹H-NMR(400 MHz,DMSO-$d_6$); δ (ppm), 1.20(t,J=7.2 Hz,3H), 1.76–2.09(m,2H), 3.02–3.12(m,2H), 3.23–3.29(m, 2H), 3.59–3.62(m,4H), 3.75(t,J=4.8 Hz,2H), 4.05(t,J=4.8 Hz,2H), 4.19(d,J=13.6 Hz,2H), 7.04(d,J=8.8 Hz,2H), 7.61 (d,J=5.6 Hz,1H), 7.78(d,J=5.6 Hz,1H), 8.10(d,J=8.8 Hz,2H), 8.18(s,1H).

MS(FAB) m/z 398 (M+H)⁺.

Free compound:

¹H-NMR(400 MHz,CDCl₃); δ (ppm) 0.95(t,J=7.6 Hz,3H), 1.56–1.62(m,2H), 2.39–2.43(m,2H), 2.68(t,J=5.2 Hz,4H), 3.68(t,J=4.8 Hz,4H), 4.00(br-t,2H), 4.15(t,J=4.8 Hz,2H), 7.00(d,J=8.8 Hz,2H), 7.32(d,J=5.6 Hz,1H), 7.39(d, J=5.6 Hz,1H), 7.72(s,1H), 8.05(d,J=8.8 Hz,2H).

Example 294

Synthesis of 6-[4-(2-methyl-2-hydroxypropoxy) phenyl]-4-[4-(2-fluoroethyl)piperazin-1-yl]thieno[3, 2-c]pyridine

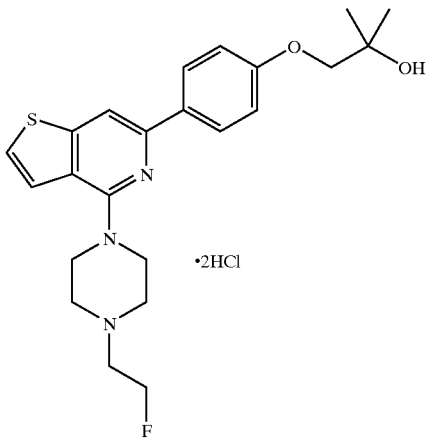

In the same manner as in Example 289, a yellow compound was obtained (245 mg, yield; 34%) from 4-[4-(2- fluoroethyl)piperazin-1-yl]-6-(4-hydroxyphenyl)thieno[3,2-c]pyridine (600 mg), ethyl bromoacetate (0.18 ml) and 3.0M methylmagnesium bromide (1.7 ml). The resulting compound was converted into a hydrochloride in a conventional manner, to give the hydrochloride of the title compound as yellow crystals.

Hydrochloride:

m.p.; 135–137° C.

$^1$H-NMR(400 MHz,DMSO-$d_6$); δ (ppm) 1.23(s,6H), 3.35–3.45(m,2H), 3.54–3.65(m,6H), 3.78(s,2H), 4.22(d,J=13.6 Hz,2H), 4.92(t,J=4.4 Hz,1H), 5.04(t,J=4.4 Hz,1H), 7.04(d,J=8.8 Hz,2H), 7.63(d,J=5.6 Hz,1H), 7.79(d,J=5.6 Hz,1H), 8.10(d,J=8.8 Hz,2H), 8.19(s,1H).

MS(FAB) m/z 430(M+H)$^+$.

Free compound:

$^1$H-NMR(400 MHz,CDCl$_3$); δ (ppm) 1.37(s,6H), 2.77–2.80(m,1H), 2.79(t,J=4.8 Hz,4H), 2.85(t,J=5.2 Hz,1H), 3.70(t,J=4.8 Hz,4H), 3.85(s,2H), 4.59(t,J=4.8 Hz,1H), 4.71(t,J=4.8 Hz,1H), 7.00(d,J=8.8 Hz,2H), 7.32(d, J=5.6 Hz,1H), 7.38(d,J=5.6 Hz,1H), 7.73(s,1H), 8.04(d,J=8.8 Hz,2H).

Example 295

Synthesis of 4-[4-(2-fluoroethyl)piperazin-1-yl]-6-[4-(2-hydroxyethoxy)phenyl]thieno[3,2-c]pyridine

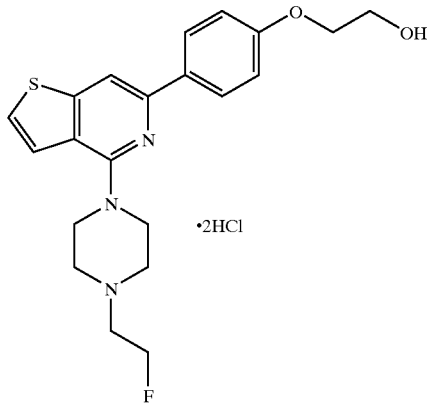

In the same manner as in Example 289, a yellow compound was obtained (231 mg, yield; 68%) from 4-[4-(2-fluorethyl)piperazin-1-yl]-6-(4-hydroxyphenyl)thieno[3,2-c]pyridine (300 mg) and 2-bromoethanol (0.12 ml). The resulting compound was converted into a hydrochloride in a conventional manner, to give the hydrochloride of the title compound as yellow crystals.

Hydrochloride:

m.p.; 138–140° C.

$^1$H-NMR(400 MHz,DMSO-$d_6$); δ (ppm) 3.36–3.43(m, 2H), 3.53–3.66(m,6H), 3.75(t,J=4.8 Hz,2H), 4.05(t,J=4.8 Hz,2H), 4.23(d,J=13.6 Hz,2H), 4.92(t,J=4.4 Hz,1H), 5.03(d, J=4.4 Hz,1H), 7.05(d,J=8.8 Hz,2H), 7.63(d,J=5.6 Hz,1H), 7.79(d,J=5.6 Hz,1H), 8.10(d,J=8.8 Hz,2H), 819(s,1H).

MS(FAB) m/z 402(M+H)$^+$.

Free compound:

$^1$H-NMR(400 MHz,CDCl$_3$): δ (ppm) 2.77–2.85(m,1H), 2.79(t,J=4.4 Hz,4H), 2.85(t,J=5.2 Hz,1H), 3.70(t,J=4.4 Hz,4H), 3.99(brt,2H), 4.15(t,J=4.0 Hz,2H), 4.59(t,J=4.8 Hz,1H), 4.71(t,J=4.8 Hz,1H), 7.00(d,J=8.8 Hz,2H), 7.33(d, J=5.6 Hz,1H), 7.39(d,J=5.6 Hz,1H), 7.73(s,1H), 8.05(d,J=8.8 Hz,2H).

Example 296

Synthesis of 6-[4-(2-methyl-2-hydroxypropoxy) phenyl]-4-[4-(2-hydroxyethyl)piperazin-1-yl]thieno] 3,2-c]pyridine hydrochloride

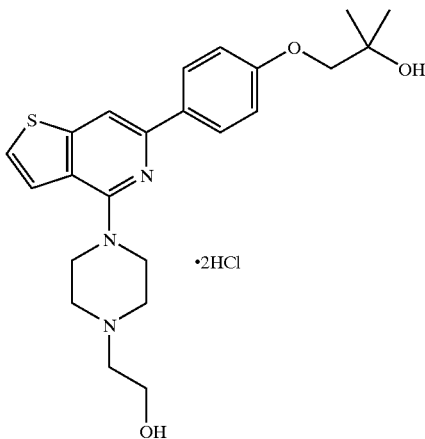

In the same manner as in Example 289, a yellow compound (234 mg, yield; 32%) was obtained from 4-[4-(2-hydroxyethyl)piperazin-1-yl]-6-(4-hydroxyphenyl)thieno[3,2-c]pyridine (600 mg), ethyl bromoacetate (0.18 ml) and 3.0M methylmagnesium bromide/THF solution (1.7 ml). The resulting compound was converted into a hydrochloride in a conventional manner, to give the hydrochloride of the title compound as yellow crystals.

Hydrochloride:

m.p.; 139–142° C.

$^1$H-NMR(400 MHz,DMSO-$d_6$); δ (ppm) 1.23(s,6H), 3.25–3.40(m,2H), 3.55(t,J=13.2 Hz,44H), 3.65(d,J=12.0 Hz,2H), 3.78(s,2H), 3.84(br,2H), 4.20(d,J=13.2 Hz,2H), 7.05(d,J=8.8 Hz,2H), 7.63(d,J=5.6 Hz,1H), 7.79(d,J=5.6 Hz,1H), 8.10(d,J=8.8 Hz,2H), 8.19(s,1H).

MS(FAB) m/z 428(M+H)$^+$.

Free compound:

$^1$H-NMR(400 MHz,CDCl$_3$); δ (ppm) 1.38(s,6H), 2.67(t, J=5.2 Hz,2H), 2.78(t,J=5.2 Hz,4H), 3.67–3.71(m,6H), 3.86 (s,2H), 7.02(d,J=8.8 Hz,2H), 7.38(d,J=5.6 Hz,1H), 7.38(d, J=5.6 Hz,1H), 7.74(s,1H), 8.04(d,J=8.8 Hz,2H).

Example 297

Synthesis of 6-[4-(2-methyl-2-hydroxypropoxy)phenyl]-4-[4-(2-phenylethyl)piperazin-1-yl]thieno[3,2-c]pyridine

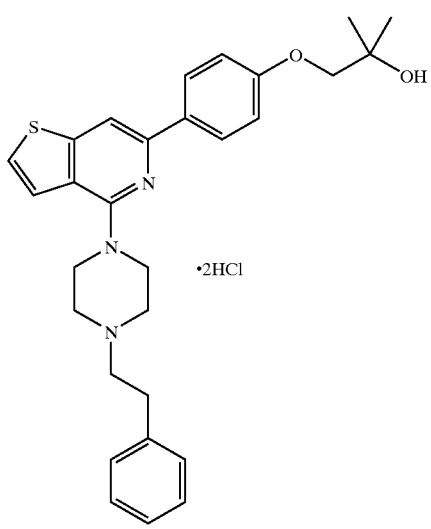

In the same manner as in Example 289, a yellow compound was obtained (485 mg, yield; 69%) from 4-(4-phenylethylpiperazin-1-yl)-6-(4-hydroxyphenyl)thieno[3,2-c]pyridine (605 mg), ethyl bromoacetate (0.18 ml) and 3.0M methylmagnesium bromide solution (1.2 ml). The resulting compound was converted into a hydrochloride in a conventional manner, to give the hydrochloride of the title compound as yellow crystals.

Hydrochloride:

m.p.; 140–142° C.

$^1$H-NMR(400 MHz,DMSO-d$_3$); δ (ppm) 1.23(s,6H), 3.12–3.16(m,2H), 3.30–3.45(m,4H), 3.56(br-t,2H), 3.71(d,J=11.6 Hz,2H), 3.78(s,2H), 4.23(d,J=14.0 Hz,2H), 7.05(d,J=8.8 Hz,2H), 7.23–7.39(m,5H), 7.63(d,J=5.6 Hz,1H), 7.79 (d,J=5.6 Hz,1H), 8.01(d,J=8.8 Hz,2H), 8.18(s,1H).

MS(FAB) m/z 488(M+H)$^+$.

Free compound:

$^1$H-NMR(400 MHz,CDCl$_3$); δ (ppm) 1.38(s,6H), 2.69–2.74(m,2H), 2.78(t,J=4.8 Hz,4H), 2.87–2.91(m,2H), 3.71(t,J=4.8 Hz,4H), 3.86(s,2H), 7.44(d,J=8.8 Hz,2H), 7.20–7.33(m,5H), 7.33(d,J=5.6 Hz,1H), 7.40(d,J=5.6 Hz,1H), 7.74(s,1H), 8.05(d,J=8.8 Hz,2H).

Example 298

Synthesis of 7-(1-ethylpiperazin-4-yl)-5-[3-(2-hydroxyethoxy)phenyl]furo[2,3-c]pyridine dihydrochloride

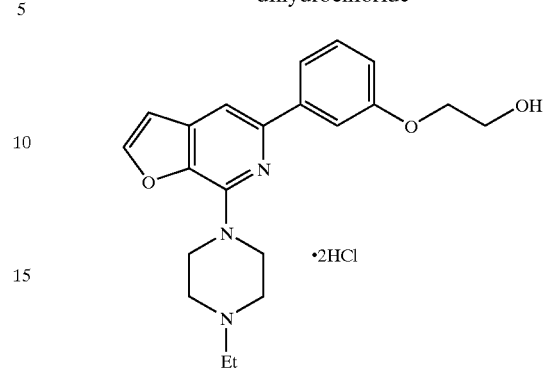

In the same manner as in Example 301-4, the hydrochloride of the title compound was obtained as pale yellow crystals (215 mg, yield; 83%) from 7-(1-ethylpiperazin-4-yl)-5-bromofuro[2,3-c]pyridine (200 mg) and 3-tributylstannylphenoxyethyl acetate (563 mg).

Hydrochloride:

m.p.; 117–121° C.

$^1$H-NMR(400 MHz,DMSO-d$_6$); δ (ppm) 1.28(3H,t,J=7.2 Hz), 3.07–3.18(2H,m), 3.56(2H,t,J=14.8 Hz), 3.61(2H,d,J=11.6 Hz), 3.74(2H,t,J=5 Hz), 4.72(2H,d,J=14.8 Hz), 6.93 (1H,dd,J=8 Hz,2.4 Hz), 7.02(1H,d,J=2.4 Hz), 7.34(1H,t,J=8 Hz), 7.60(1H,s), 7.61(1H,d,J=8 Hz), 7.71(1H,s), 8.15(1H,d,J=2.4 Hz), 11.00–11.10(1H,br-s). FAB-Mass; 368(MH$^+$).

Example 299

Synthesis of 7-(1-ethylpiperazin-4-yl)-5-[4-(3-hydroxypropyl)phenyl]furo[2,3-c]pyridine dihydrochloride (299-1) 3-(4-Bromophenyl)-2-propyn-1-ol

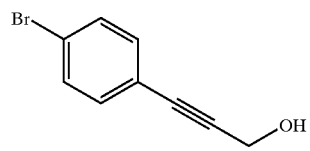

In the same manner as in Example 139-1, the title compound was obtained as a yellow solid (13.792 g, yield; 93%) from 4-bromoiodobenzene (19.804 g) and propargyl alcohol (4.5 ml).

$^1$H-NMR(400 MHz,CDCl$_3$); δ (ppm) 1.75(1H,t,J=6.4 Hz), 4.49(2H,d,J=6.4 Hz), 7.30(2H,d,J=8.8 Hz), 7.45(2H,d,J=8.8 Hz).

(299-2) 3-(4-Bromophenyl)-1-propanol

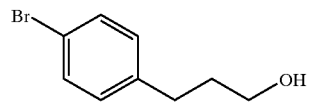

In the same manner as in Example 139-2, the title compound was obtained as a brown solid (4.64 g, yield, 88%) from 3-(4-bromophenyl)-2-propyn-1-ol (5.276 g).

$^1$H-NMR(400 MHz, CDCl$_3$); δ (ppm) 1.40(1H,br-s), 1.82–1.90(2H,m), 2.67(2H,t,J=7.8 Hz), 3.66(2H,t,J=6.2 Hz), 7.07(2H,d,J=8.8 Hz), 7.40(2H,d,J=8.8 Hz).

(299-3) 4-[3-(t-Butyldimethylsilyloxy)propyl]-1-bromobenzene

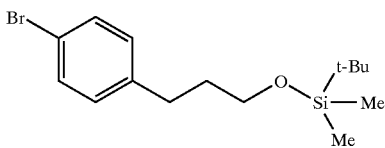

In the same manner as in Example 163-1, the title compound was obtained as a colorless oil (2.263 g, yield; 100%) from 3-(4-bromophenyl)-1-propanol (1.513 g) and t-butyldimethylsilyl chloride (1.161 g).

$^1$H-NMR(400 MHz,CDCl$_3$): δ (ppm) 0.04(6H,s), 0.90 (9H,s), 1.76–1.83(2H,m), 2.63(2H,t,J=7.8 Hz), 3.61(2H,t,J= 6.2 Hz), 7.06(2H,d,J=8.8 Hz), 7.39(2H,d,J=8.8 Hz).

(299-4) 7-(1-Ethylpiperazin-4-yl)-5-[4-(3-hydroxypropyl)phenyl]furo[2,3-c]pyridine

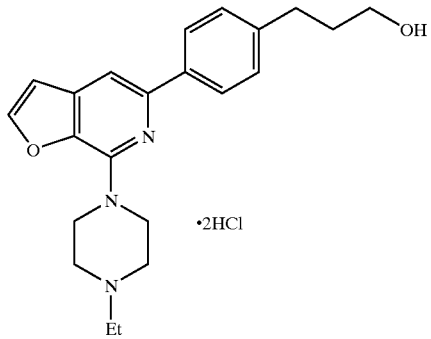

In the same manner as in Example 167-2, the hydrochloride of the title compound as colorless crystals (recrystallized from ethanol/isopropyl ether) (417 mg, yield; 83%) from 4-[3-(t-butyldimethylsilyloxy)propyl]-1-bromobenzene (2.263 g) and 7-(1-ethylpiperazin-4-yl)-5-bromofuro[2,3-c]pyridine (380 mg).

Hydrochloride:

m.p.; 126–130° C.

$^1$H-NMR(400 MHz,DMSO-d$_6$); δ (ppm) 1.28(3H,t,J=7.2 Hz), 1.63–1.78(2H,m), 2.63(2H,t,J=7.8 Hz), 3.06–3.18 (4H, m), 3.42(2H,t,J=6.4 Hz), 3.56(2H, t,J=14.4 Hz), 3.60(2H,d, J=10.8 Hz), 4.73(2H,d,J=14.4 Hz), 7.02(1H,d,J=2.4 Hz), 7.26(2H,d,J=8.8 Hz), 7.65(1H,s), 7.95(2H,d,J=8.8 Hz), 8.13 (1H,d,J=2.4 Hz), 11.05(1H,br-s). FAB-MASS; 366(MH$^+$).

Example 300

Synthesis of 7-(1-ethylpiperazin-4-yl)-5-[4-(3-hydroxybutyl)phenyl]furo[2,3-c]pyridine dihydrochloride (300-1) 4-(4-Bromophenyl)-3-butyn-2-ol

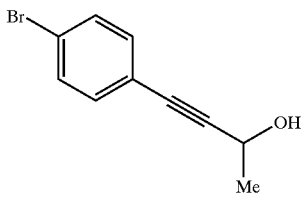

In the same manner as in Example 139-1, the title compound was obtained as a brown solid (13.792 g, yield; 93%) from 4-bromoiodobenzene (16.609 g) and 3-butyn-2-ol (4.526 g).

$^1$-NMR(400 MHz,CDCl$_3$); δ (ppm) 1.55(3H,d,J=6.8 Hz), 1.85(1H,d,J=5.2 Hz), 4.71–4.78(1H,m), 7.34(2H,d,J=8.8 Hz), 7.44(2H,d,J=8.8 Hz).

(300-2) 3-(4-Bromophenyl)-1-methyl-1-propanol

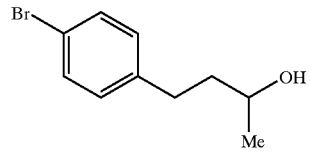

In the same manner as in Example 139-2, the title compound was obtained as brown oil (4.259 g, yield; 37%) from 4-(4-bromophenyl)-3-butyn-2-ol (11.791 g).

$^1$H-NMR(400 MHz,CDCl$_3$); δ (ppm) 1.23(3H,d,J=6 Hz), 1.32(1H,s), 1.70–1.79(2H,m), 2.59–2.76(2H,m), 3.76–3.86 (1H,m), 7.08(2H,d,J=8.8 Hz), 7.40(2H,d,J=8.8 Hz).

(300-3) 7-(1-Ethylpiperazin-4-yl)-5-[4-(3-hydroxybutyl)phenyl]furo[2,3-c]pyridine

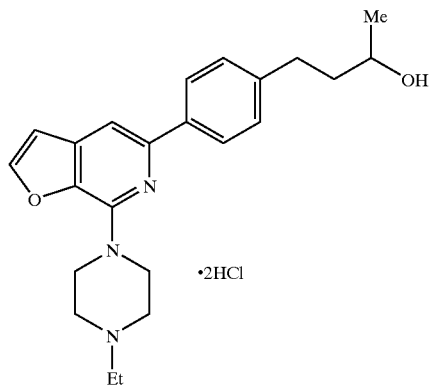

3-(4-Bromophenyl)-1-methyl-1-propanol (2.186 g) and t-butyldimethylsilyl chloride (1.575 g) were treated in the same manner as in Example 163-1, to give 4-[3-(t-butyldimethylsilyloxy)-3-methylpropan-1-yl]-1-bromobenzene as a colorless oil (2.396 g). Subsequently, the resulting compound was treated with 7-(1-ethylpiperazin-4-yl)-5-bromofuro[2,3-c]pyridine (404 mg), in the same manner as in Example 167-2, to give the hydrochloride of the title compound as colorless crystals (recrystallized from ethanol/isopropyl ether) (390 mg, yield; 69%).

Hydrochloride:

m.p.; 175–177° C.

$^1$H-NMR(400 MHz,DMSO-d$_6$); δ (ppm) 1.08(3H,d,J=6 Hz), 1.28(3H,t,J=7.2 Hz), 1.58–1.65(2H,m), 2.55–2.73(2H, m), 3.07–3.18(4H,m), 3.50–3.64(5H,m), 4.73(2H,d,J=14.8 Hz), 7.01(1H,d,J=2.4 Hz), 7.26(2H,d,J=8.8 Hz), 7.65(1H,s), 7.94(2H,d,J=8.8 Hz), 8.14(1H,d,J=2.4 Hz), 10.95(1H,br-s). FAB-Mass; 380(MH$^+$).

Example 301

Synthesis of 7-(1-Ethylpiperazin-4-yl)-5-[4-(2-hydroxyethoxy)phenyl]furo[2,3-c]pyridine oxalate (301-1) 7-(1-Ethylpiperazin-4-yl)-5-bromofuro[2,3-c]pyridine

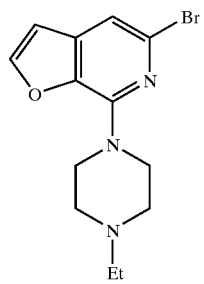

Phosphorus oxychloride (20.214 g) and phorphorus tribromide (40 ml) were added to 3-cyanomethyl-2-furancarboxylic acid (9.046 g) synthesized according to *Bull. Soc. chim. Fr.*, No. 5–6, II-270, 1978, and the resulting mixture was stirred at 140° C. for 3 hr. After cooling as it was, ethanol was added thereto in small portions until exothermic reaction was ceased. The reaction solution was evaporated, and to the resulting residue was added 1-ethylpiperazine (240 ml), and the resulting mixture was stirred for 20 min, and then evaporated. The resulting residue was partitioned between ethyl acetate and water. The resulting organic layer was washed with water, dried (over MgSO$_4$) and evaporated. The resulting residue was purified by (NH) silica gel column chromatography (ethyl acetate/hexane system), to give the title compound as a pale yellow solid (9.594 g, yield; 56%).

$^1$H-NMR(400 MHz,CDCl$_3$): δ (ppm) 1.14(3H,t,J=7.2 Hz), 2.47(2H,q,7J=0.2 Hz), 2.58(4H,t,J=5.2 Hz), 3.92(4H,t,J=5.2 Hz), 6.64(1H,d,J=2 Hz), 7.02(1H,s), 7.60(1H,d,J=2 Hz).

(301-2) 4-Bromophenoxyethyl acetate or compound identified by the following analysis data and synthetic procedures

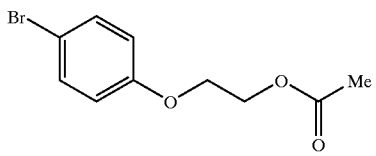

2-Bromophenol (26.128 g) was dissolved in N,N-dimethylformamide (70 ml), followed by the addition of 2-bromoethyl acetate (32.224 g) and potassium carbonate (21 g), and the mixture was stirred at 100° C. overnight. After cooling as it was, the resulting insoluble matters were filtered off. The resulting filtrate was evaporated, and the resulting residue was purified by (NH) silica gel column chromatography (ethyl acetate/hexane system), to give the title compound as a pale yellow oil (33.915 g, yield; 87%).

$^1$H-NMR(400 MHz, CDCl$_3$); δ (ppm) 2.10(3H,s), 4.14 (2H,t,J=4.6 Hz), 6.80(2H,d,J×8.8 Hz), 7.38(2H,d,J=8.8 Hz).

(301-3) 4-Tributylstannylphenoxyethyl acetate or compound identified by the following analysis data and synthetic procedures

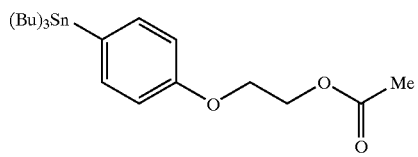

In the same manner as in Example 161-2, the title compound was obtained as a colorless oil (3.452 g, yield; 35%) from 4-bromophenoxyethyl acetate (5.182 g) and bis(tributyltin) (11 ml).

$^1$H-NMR(400 MHz,CDCl$_3$); δ (ppm) 0.88(9H,t,J=7.2 Hz), 1.00–1.05(6H,m), 1.27–1.37(6H,m), 1.48–1.57(6H,m), 2.10(3H,s), 4.17(2H,t,J=4.8 Hz), 6.91(2H,d,J=8.8 Hz), 7.37 (2H,d,J=8.8 Hz), (301-4) 7-(1-Ethylpiperazin-4-yl)-5-[4-(2-hydroxyethoxy)phenyl]furo[2,3-c]pyridine oxalate

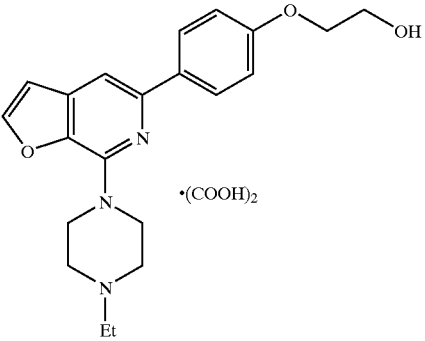

7-(1-Ethylpiperazin-4-yl)-5-bromofuro[2,3-c]pyridine (564 mg) and 4-tributylstannylphenoxyethyl acetate (3.452 g) were treated in the same manner as in Example 161.3, and the resulting product was dissolved in ethanol (16 ml), followed by the addition of a 1N aqueous solution of sodium hydroxide (6 ml), and the mixture was stirred at 70° C. for 1 hr. The reaction mixture was evaporated, and then partitioned between ethyl acetate and water. The resulting organic layer was washed with water, dried (over MgSO$_4$) and evaporated. The resulting residue was purified by (NH) silica gel column chromatography (ethyl acetate/hexane system). Then, the resulting product was converted into an oxalate in a conventional manner, to give the oxalate of the title compound as colorless crystals (417 mg, yield; 90%).

Oxalate:

m.p.; 145–152° C.

$^1$H-NMR(400 MHz,DMSO-d$_6$); δ (ppm) 1.19(3H,t,J=7.2 Hz), 2.98(2H,q,J=7.2 Hz), 3.14–3.22(4H,m), 3.72(2H,t,J=5 Hz), 3.96–4.10(4H,br-s), 4.02(2H,t,J=5 Hz), 6.98(1H,d,J=2 Hz), 6.99(2H,d,J=8.8 Hz), 7.57(1H,s), 7.98(2H,d,J=8.8 Hz), 8.10(1H,d,J=2 Hz). FAB-Mass; 368(MH$^+$).

Example 302

Synthesis of 7-(1-ethylpiperazin-4-yl)-5-{4-[(R)-2-hydroxy-1-methylethoxy]phenyl}furo[2,3-c]pyridine dihydrochloride

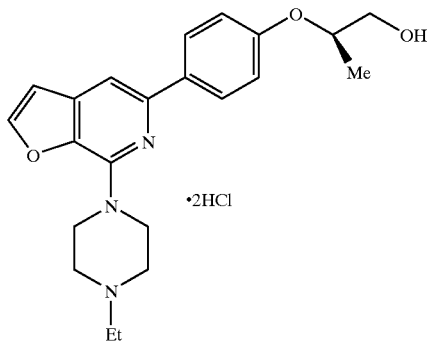

In the same manner as in Example 301-4, the hydrochloride of the title compound was obtained as a pale yellow amorphous (348 mg, yield; 67%) from 7-(1-ethylpiperazin-4-yl)-5-bromofuro[2,3-c]pyridine (373 mg) and 2-(4-tributylstannylphenoxy)-(R)-2-methylethyl acetate (889 mg). Hydrochloride:
$^1$H-NMR(400 MHz,DMSO-$d_6$); δ (ppm) 1.21(3H,d,J=6.4 Hz), 1.28(3H,t,J=7.2 Hz), 3.06–3.18(4H,m), 3.46(1H,dd,J=11.2 Hz, 5 Hz), 3.56(2H,dd,J=11.2 Hz,5.6 Hz), 3.56–3.62 (3H,m), 4.88–4.90(1H,m), 4.71(2H,d,J=14.4 Hz), 6.99(2H, d,J=8.8 Hz), 7.00(1H,d,J=2 Hz), 7.59(1H,s), 7.96(2H,d,J= 8.8 Hz), 8.12(1H,d,J=2 Hz), 11.15(1H,br-s). FAB-Mass; 382(MH$^+$).

Example 303

Synthesis of 7-(1-ethylpiperazin-4-yl)-5-{4-[(S)-2-hydroxy-1-methylethoxy]phenyl}furo[2,3-c]pyridine dihydrochloride

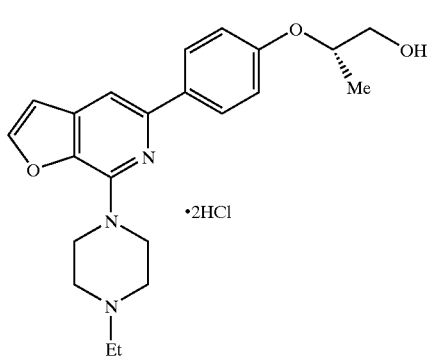

In the same manner as in Example 301-4, the hydrochloride of the title compound was obtained as a pale yellow amorphous (348 mg, yield; 67%) from 7-(1-ethylpiperazin-4-yl)-5-bromofuro[2,3-c]pyridine (373 mg) and 2-(4-tributylstannylphenoxy)-(S)-2-methylethyl acetate (889 mg).
Hydrochloride:
$^1$H-NMR(400 MHz,DMSO-$d_6$); δ (ppm) 1.21(3H,d,J=-6 Hz), 1.28(3H,t,J=7.2 Hz), 3.05–3.18 (4H,m), 3.46(1H,dd,J=11.2 Hz,4.8 Hz), 3.54(1H,dd,J=11.2 Hz,5.6 Hz), 3.60(4H,t, J=11.2 Hz), 4.43–4.50(1H,m), 4.71(2H,d,J=14.4 Hz), 6.99 (2H,d,J=8.8 Hz), 7.00(1H,d,J=2.4 Hz), 7.50(1H,s), 7.96(2H, d,J=8.8 Hz), 8.13(1H,d,J=2.4 Hz), 11.20(1H,br-s). FAB-Mass; 382(MH$^+$).

Example 304

Synthesis of 7-(1-ethylpiperazin-4-yl)-5-[4-[(S)-2-hydroxypropoxy]phenyl)furo[2,3-c]pyridine dihydrochloride

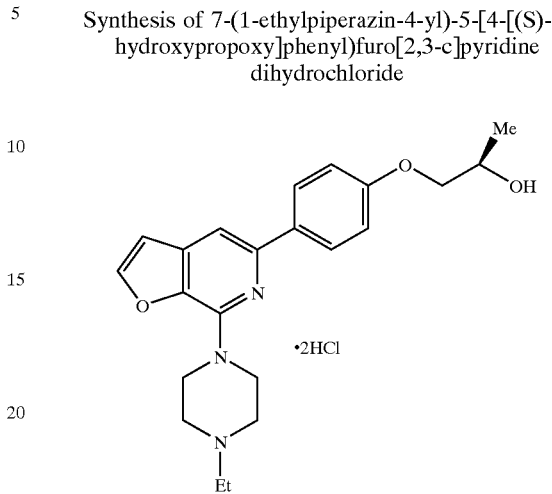

In the same manner as in Example 301-4, the hydrochloride of the title compound was obtained as a pale yellow amorphous (348 mg, yield; 67%) from 7-(1-ethylpiperazin-4-yl)-5-bromofuro[2,3-c]pyridine (373 mg) and 2-(4-tributylstannylphenoxy)-(S)-1-methylethyl acetate (889 mg).
Hydrochloride:
$^1$H-NMR(400 MHz,DMSO-$d_6$); δ (ppm) 1.15(3H,d,J=6.4 Hz), 1.28(3H,t,J=7.2 Hz), 3.05–3.18(4H,m), 3.57(2H,t,J= 14.4 Hz), 3.59(2H,d,J=12.4 Hz), 3.79–3.88(2H,m), 3.92–4.00(1H,m), 4.71(2H,d,J=14.4 Hz), 6.98(2H,d,J=8.8 Hz), 6.99(1H,d,J=2 Hz), 7.60(1H,d,J=2 Hz), 7.60(1H,s), 7.99(2H,d,J=8.8 Hz), 8.12(1H,d,J=2 Hz), 11.65(1H,br-s). FAB-Mass; 382(MH$^+$).

Example 305

Synthesis of 2-(1-ethylpiperazin-4-yl)-5-{4-[(R)-2-hydroxypropoxy]phenyl}furo[2,3-c]pyridine dihydrochloride

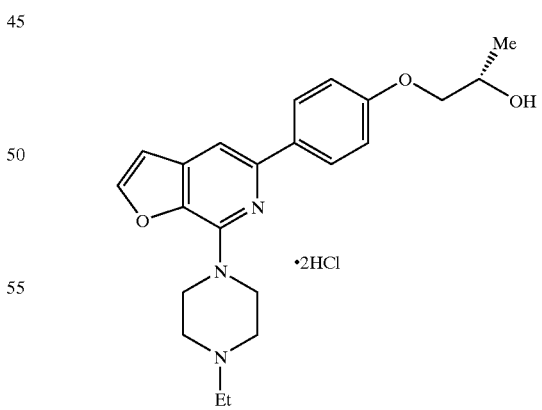

In the same manner as in Example 301-4, the hydrochloride of the title compound was obtained as a pale yellow amorphous (73 mg, yield; 17%) from 7-(1-ethylpiperazin-4-yl)-5-bromofuro[2,3-c]pyridine (373 mg) and 2-[4-tributylstannylphenoxy)-(R)-1-methylethyl acetate (920 mg). Hydrochloride:

¹H-NMR(400 MHz,DMSO-d₆); δ (ppm) 1.15(3H,d,J=6.4 Hz), 1.28(3H,t,J=7.2 Hz), 3.60–3.18(4H,m), 3.52–3.62(4H,m), 3.79–3.88(2H,m), 3.91–3.99(1H,m), 4.72(2H,d,J=14.8 Hz), 6.98(2H,d,J=8.8 Hz), 6.99(1H,d,J=2 Hz), 7.60(1H,s), 7.97(2H,d,J=8.8 Hz), 8.12(1H,d,J=2 Hz), 11.10(1H,br-s). FAB-Mass; 382(MH⁺).

Example 306

Synthesis of 7-(1-ethylpiperazin-4-yl)-5-[4-(3-hydroxy-3-methylbutoxy)phenyl]furo[2,3-c]pyridine dihydrochloride (306-1) 7-(1-Ethylpiperazin-4-yl)-5-[(4-ethoxycarbonylmethoxy)phenyl]furo[2,3-c]pyridine

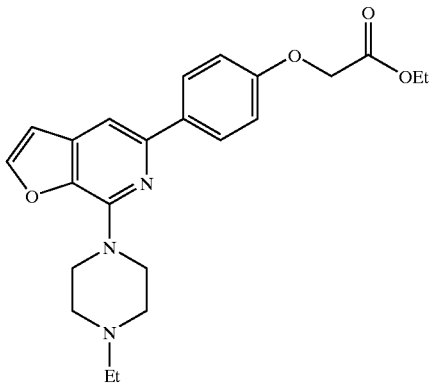

In the same manner as in Example 161-3, the titled compound was obtained as a colorless oil (484 mg, yield; 80%) from 7-(1-ethylpiperazin-4-yl)-5-bromofuro[2,3-c]pyridine (465 mg) and ethyl 2-(4-tributylstannylphenoxy) acetate.

¹H-NMR(400 MHz,CDCl₃); δ (ppm) 1.16(3H,t,J=7.2 Hz), 1.31(3H,t,J=7.2 Hz), 2.50(2H,q,J=7.2 Hz), 2.65(4H,t,J=5 Hz), 3.99(4H,t,J=5 Hz), 4.29(2H,q,J=7.25 Hz), 4.67(1H,s), 6.73(1H,d,J=2.4 Hz), 6.97(2H,d,J=8.8 Hz), 7.32(1H,s), 7.61(1H,d,J=2.4 Hz), 7.98(2H,d,J=8.8 Hz), (306-2) 7-(1-Ethylpiperazin-4-yl)-5-[4-(3-hydroxy-3-methylbutoxy)phenyl]furo[2,3-c]pyridine dihydrochloride

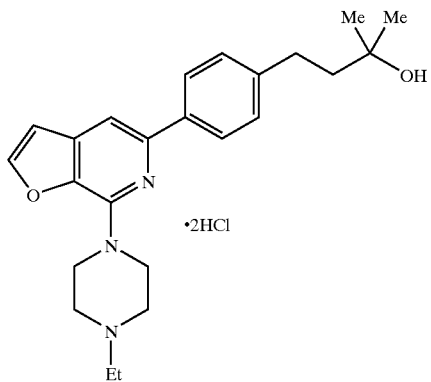

In the same manner as in Example 260-3, the hydrochloride of the titled compound was obtained as a colorless solid (435 mg, yield; 75%) from 7-(1-ethylpiperazin-4-yl)-5-[(4-ethoxycarbonylmethoxy)phenyl]furo[2,3-c]pyridine (484 mg) and 3M methylmagnesium bromide/ether solution (2 ml).

Hydrochloride:
m.p.; 123–125° C.
¹H-NMR(400 MHz,DMSO-d₆); δ (ppm) 1.20(6H,s), 1.28 (3H,t,J=7.2 Hz), 3.10–3.18(4H,m), 3.56(2H,t,J=14.4 Hz), 3.60(2H,d,J=11.2 Hz), 4.71(2H,d,J=14.4 Hz), 6.99(2H,d,J= 8.8 Hz), 7.00(1H,d,J=2 Hz), 7.60(1H,s), 7.98(2H,d,J=8.8 Hz), 8.12(1H,d,J=2 Hz), 11.05–11.15(1H,br-s). FAB-Mass; 396(MH⁺).

Example 307

Synthesis of 7-(1-ethylpiperazin-4-yl)-5-{trans-2-[4-(2-hydroxyethoxy)phenyl]ethyl}furo[2,3-c]pyridine oxalate

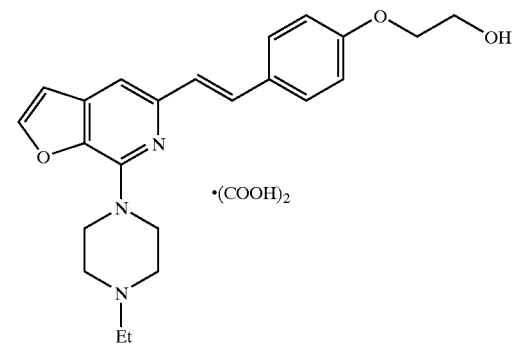

In the same manner as in Example 189, the oxalate of the title compound was obtained as a yellow amorphous (106 mg, yield; 17%) from 7-(1-ethylpiperazin-4-yl)-5-bromofuro[2,3-c]pyridine (372 mg) and 2-(4-vinylphenoxy) ethanol (264 mg). Oxalate:

¹H-NMR(400 MHz,DMSO-d₆); δ (ppm) 1.21(3H,t,J=7.2 Hz), 3.03(2H,q,J=7.2 Hz), 3.16–3.26(4H,m), 3.71(2H,t,J=5 Hz), 3.94–4.14(4H,m), 3.99(2H,t,J=5 Hz), 6.94(2H,d,J=8.8 Hz), 6.97(1H,d,J=2 Hz), 7.08(1H,d,J=16 Hz), 7.15(1H,s), 7.46(1H,d,J=16 Hz), 7.53(2H,d,J=8.8 Hz), 0.08(1H,d,J=2 Hz). FAB-Mass; 394(MH⁺).

Example 308

Synthesis of 7-(1-ethylpiperazin-4-yl)-5-{trans-2-[2-(2-hydroxyethyl}phenyl]ethenyl]furo[2,3-c]pyridine oxalate

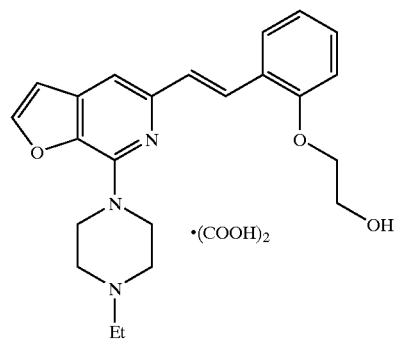

In the same manner as in Example 189, the oxalate of the title compound was obtained as a yellow amorphous (366 mg, yield; 67%) from 7-(1-ethylpiperazin-4-yl)-5-bromofuro[2,3-c]pyridine (372 mg) and 2-(2-vinylphenoxy) ethanol (246 mg).
Oxalate:
¹H-NMR(400 MHz,DMSO-d₆); δ (ppm) 1.21(3H,t,J=7.2 Hz), 3.02(2H,q,J=7.2 Hz), 3.14–3.26(4H,m), 3.80(2H,t,J=5

Hz), 4.05(2H,t,J=5 Hz), 6.96(1H,dd,J=7.8 Hz,7.4 Hz), 6.98 (1H,d,J=2.4 Hz), 7.03(1H,d,J=8.2 Hz), 7.16(1H,s), 7.23(1H, dd,J=8.2 Hz,7.4 Hz), 7.24(1H,d,J=15.6 Hz), 7.65(1H,dd,J= 7.8 Hz,2 Hz), 7.88(1H,d,J=15.6 Hz), 8.09(1H,d,J=2.4 Hz). FAB-Mass; 394(MH$^+$).

Example 309

Synthesis of 1-(1-ethylpiperazin-4-yl)-3-[4-(2-hydroxy-2-methylpropoxy)phenyl]isoquinoline dihydrochloride (309-1) 1-(1-Ethylpiperazin-4-yl)-3-[(4-ethoxycarbonylmethoxy)phenyl]isoquinoline or compound identified by the following analysis data and synthetic procedures

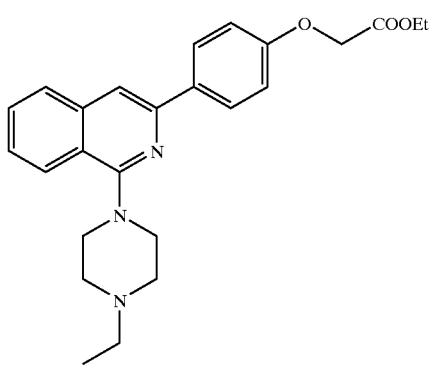

In the same manner as in Example 161-3, the title compound was obtained as a pale yellow oil (473 mg, 73%) from 1-(1-ethylpiperazin-4-yl)-3-bromoiosquinoline (480 mg) and ethyl 2-(4-tributylstannylphenoxy)acetate.

$^1$H-NMR(400 MHz,CDCl$_3$); δ (ppm) 1.17(3H,t,J=7.2 Hz), 1.32(3H,t,J=7.2 Hz), 2.55(2H,q,J=7.2 Hz), 2.75(4H,t, J=4.4 Hz), 3.58(4H,t,J=4.4 Hz), 4.29(2H,q,J=7.2 Hz), 4.68 (2H,s), 7.01(2H,d,J=8.8 Hz), 7.43(1H,ddd,J=8 Hz, 7 Hz,1.2 Hz), 7.56(1H,ddd,J=8 Hz,7 Hz,1.2 Hz), 7.61(1H,s), 7.76 (1H,d,J=8 Hz), 8.06(1H,d,J=8 Hz), 8.12(2H,d,J=8.8 Hz).

(309-2) 1-(1-Ethylpiperazin-4-yl)-3-[4-(2-hydroxy-2-methylpropoxy)phenyl]isoquinoline dihydrochloride or compound identified by the following analysis data and synthetic procedures

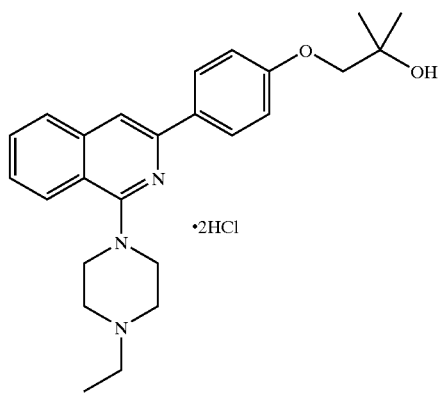

In the same manner as in Example 260-3, the hydrochloride of the title compound was obtained as yellow crystals (172 mg, yield; 36%) from 1-(1-ethylpiperazin-4-yl)-3-[(4-ethoxycarbonylmethoxy)phenyl]isoquinoline (473 mg) and 3M methylmagnesium bromide/ether solution (1.8 ml).

Hydrochloride:
m.p.; 129–134° C.
$^1$H-NMR(400 MHz,DMSO-d$_6$); δ (ppm) 1.21(6H,s), 1.31 (3H,t,J=7.2 Hz), 3.20(1H,q,J=7.2 Hz), 3.22(1H,q,J=7.2 Hz), 3.31(1H,t,J=11.2 Hz), 3.34(1H,t,J=11.2 Hz), 3.60(2H,d,J= 1.2 Hz), 3.77(2H,s), 3.95(2H,d,J=13.6 Hz), 7.05(2H,d,J=8.8 Hz), 7.55(1H,ddd,J=8 Hz,7 Hz,1.2 Hz), 7.70(1H,ddd,J=8 Hz,7 Hz,1.2 Hz), 7.93(1H,dd,J=8 Hz,1.2 Hz), 7.98(1H,s), 8.07(1H,dd,J=8 Hz,1.2 Hz), 8.13(2H,d,J=8.8 Hz), 11.15(1H, br-s). FAB-Mass; 406(MH$^+$).

Example 310

Synthesis of 1-(1-ethylpiperazin-4-yl)-3-(3-phenyl-3-hydroxy-1-propynyl)isoquinoline hydrochloride

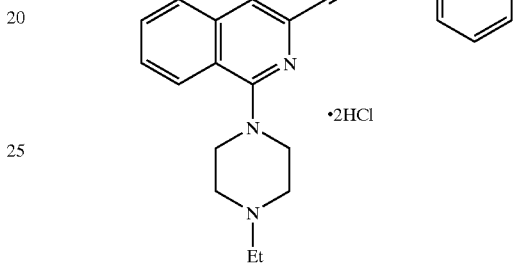

In the same manner as in Example 177, the title compound was obtained as a brown solid (1.222 g, yield; 77%) from 1-phenyl-2-propyn-1-ol (858 mg) and 1-(1-ethylpiperazin-4-yl)-3-bromoisoquinoline (1.386 mg).

The resulting compound was converted into a hydrochloride in a conventional manner.

Hydrochloride:
m.p.; 203–209° C.
Free form:
$^1$H-NMR(400 MHz,CDCl$_3$); δ (ppm) 1.15(3H,t,J=7.2 Hz), 2.54(2H,q,7J=0.2 Hz), 2.72(4H,t,J=4.4 Hz), 3.51(4H, t,J=4.4 Hz), 5.76(1H,s), 7.32–7.53(5H,m), 7.59(1H,ddd,J=8 Hz,7 Hz,1.2 Hz), 7.65–7.70(3H,m), 8.04(1H,dd,J=8 Hz,1.2 Hz).
ESI-Mass; 372(MH$^+$).

Example 311

Synthesis of 1-(1-ethylpiperazin-4-yl)-8-methyl-3-(4-methoxyphenyl)isoquinoline hydrochloride (311-1) 2,6-Dimethyl-N-methylbenzamide or compound identified by the following analysis data and synthetic procedures

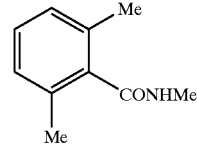

In the same manner as in Example 225-1, the title compound was obtained as a colorless solid (10.761 g, yield; 100%) from 2,6-dimethylbenzoic acid (10.125 g).

$^1$H-NMR(400 MHz,CDCl$_3$); δ (ppm) 2.31(6H,s), 3.02 (3H,d,J=4.8 Hz), 5.64(1H,br-s), 7.01(2H,d,J=8 Hz), 7.15 (1H,t,J=8 Hz).

(311-2) 8-Methyl-3-(4-methoxyphenyl)isoquinolin-1-(2H)-one

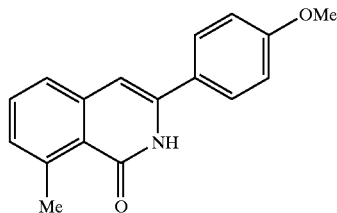

In the same manner as in Example 10, the title compound was obtained as a colorless solid (168 mg, yield; 2%) from 2,6-dimethyl-N-methylbenzamide (4.986 g) and anisonitrile (4.128 g).

$^1$H-NMR(400 MHz,CDCl$_3$); δ (ppm) 2.96(3H,s), 3.88 (3H,s), 6.65(1H,s), 7.01(2H,d,J=8.8 Hz), 7.18(1H,d,J=7.6 Hz), 7.38(1H,d,J=7.6 Hz), 7.47(1H,t,J=7.6 Hz), 7.74(2H,d, J=8.8 Hz), 10.41(1H,br-s).

(311-3) 1-(1-Ethylpiperazin-4-yl)-8-methyl-(4-methoxyphenyl)isoquinoline hydrochloride

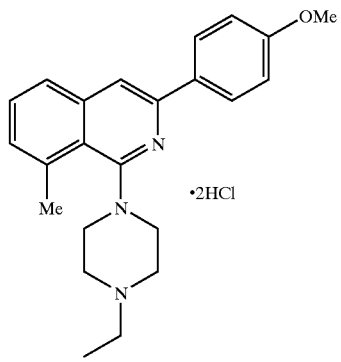

5-Methyl-3-(4-methoxyphenyl)isoquinolin-1-(2H)-one (168 mg) was treated in the same manner as in Example 252-3, to give the hydrochloride of the title compound (recrystallized from ethanol/isopropyl ether) (215 mg, yield; 78%) as yellow crystals.

Hydrochloride:

m.p.; 248–253° C.

$^1$H-NMR(400 MHz,DMSO-d$_6$); δ (ppm) 1.31(3H,t,J=7.2 Hz), 2.68(3H,s), 3.20(1H,q,J=7.2 Hz), 3.22(1H,q,J=7.2 Hz), 3.31(1H,t,J=10.5 Hz), 3.34(1H,t,J=10.5 Hz), 3.48(2H,t,J= 13.6 Hz), 3.60(2H,d,J=10.5 Hz), 3.81(3H,s), 3.93(2H,d,J= 13.6 Hz), 7.05(2H,d,J=8.8 Hz), 7.44(1H,dd,J=8.2 Hz,6.8 Hz), 7.54(1H,d,J=6.8 Hz), 7.93(1H,d,J=8.2 Hz), 7.93(1H,s), 8.18(2H,d,J=8.8 Hz), 10.95(1H,br-s).

ESI-Mass; 362(MH$^+$).

Example 312

Synthesis of 1-(1-ethylpiperazin-4-yl)-4-methyl-3-(4-methoxyphenyl)isoquinoline hydrochloride

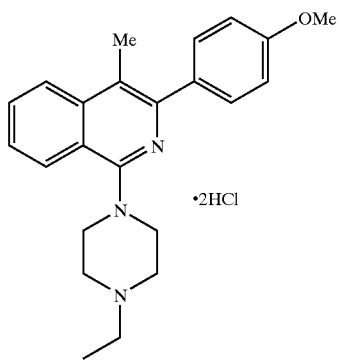

In the same manner as in Example 252-3, 1-(-ethylpiperazin-4-yl)-4-chloro-3-(4-methoxyphenyl) isoquinoline (318 mg), 3M methylmagnesium bromide/ ether solution (5.3 ml) and [1,3-bis(diphenylphosphino) propane]nickel(II) chloride (70 mg) were dissolved and suspended in toluene (14 ml), and then the mixture was stirred in nitrogen atmosphere at 80° C. for 4 days and treated, to give the hydrochloride of the title compound as a pale yellow amorphous (36 mg, yield: 10%).
Hydrochloride:
$^1$H-NMR(400 MHz,DMSO-d$_6$); δ (ppm) 1.30(3H,t,J=7.2 Hz), 2.52(3H,s), 3.18(1H,q,J=7.2 Hz), 3.19(1H,q,J=7.2 Hz), 3.29(1H,t,J=10.7 Hz), 3.32(1H,t,J=10.7 Hz), 3.47–3.56(4H, m), 3.81(3H,s), 3.85(2H,d,J=13.6 Hz), 7.04(2H,d,J=8.8 Hz), 7.56(2H,d,J=8.8 Hz), 7.65(1H,t,J=8.4 Hz), 7.83(1H,t,J=8.4 Hz), 8.08(1H,d,8.4 Hz), 10.30(1H,br-s).
ESI-Mass; 362(MH$^+$).

Example 313

Synthesis of 1-[1-(2-cyanoethyl)piperazin-4-yl]-3-(4-methoxyphenyl)isoquinoline dihydrochloride or compound identified by the following analysis data and synthetic procedures

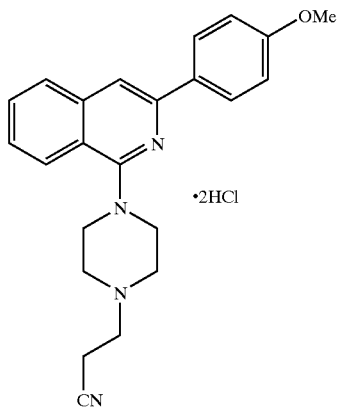

In the same manner as in Example 236-3, the hydrochloride of the title compound was obtained as yellow crystals (recrystallized from ethanol) (346 mg, yield; 80%) from 1-piperazinyl-3-(4-methoxphenyl)isoquinoline (319 mg) and 3-bromopropionitrile (100 ml).

Hydrochloride:

m.p.; 164–166° C.

$^1$H-NMR(400 Hz,DMSO-d$_6$); δ (ppm) 3.23(2H,t,J=7.2 Hz), 3.38–3.54(4H,m), 3.57(2H,t,J=7.2 Hz), 3.60–3.68(2H, br-d), 3.81(3H,s), 3.96–4.04(2H,br-d), 7.05(2H,d,J=8.8 Hz), 7.56(1H,ddd,J=8 Hz,7 Hz,1.2 Hz), 7.70(1H,ddd,J=8 Hz,7 Hz,1.2 Hz), 6.93(1H,d,J=8 Hz), 7.98(1H,s), 8.07(1H,d,J=8 Hz), 8.13(2H,d,J=8.8 Hz).

ESI-Mass; 373(MH$^+$).

Example 314

Synthesis of 1-[1-(carbamoylmethyl)piperazin-4-yl]-3-(4-methoxyphenyl)isoquinoline dihydrochloride

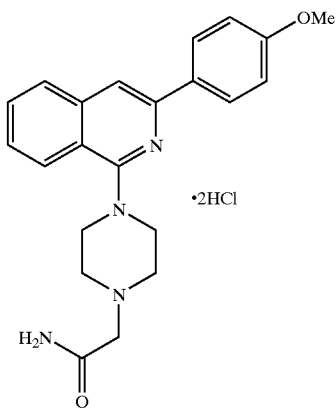

In the same manner as in Example 236-3, the hydrochloride of the title compound was obtained as yellow crystals (recrystallized from ethanol/isopropyl ether) (228 mg, yield; 50%) from 1-piperazinyl-3-(4-methoxyphenyl)isoquinoline (319 mg) and bromoacetamide (166 mg).

Hydrochloride:

m.p.; 153–155° C.

$^1$H-NMR(400 MHz,DMSO-d$_6$); δ (ppm) 3.46–3.57(4H, m), 3.58–3.66(2H,m), 3.81(3H,s), 3.92–4.02(2H,br-d), 4.05 (2H,s), 7.05(2H,d,J=8.8 Hz), 7.55(1H,ddd,J=8 Hz,7 Hz,1.2 Hz), 7.70(1H,ddd,J=8 Hz,7 Hz,1.2 Hz), 7.73(1H,s), 7.93 (1H,d,J=8 Hz), 7.97(1H,s), 8.06(1H,d,J=8 Hz), 8.07(1H,s), 8.13(2H,d,J=8.8 Hz).

ESI-Mass; 377(MH$^+$).

Example 315

Synthesis of 1-(4-ethylsulfonylpiperazin-1-yl)-3-(4-methoxyphenyl)isoquinoline hydrochloride

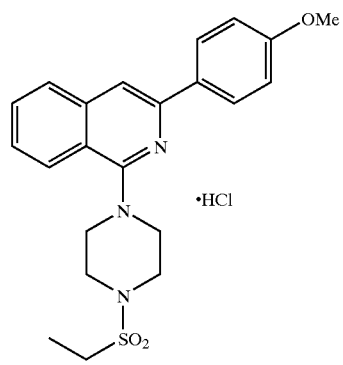

1-Piperazinyl-3-(4-methoxyphenyl)isoquinoline (140 mg) was dissolved in tetrahydrofuran (2 ml), followed by the addition of triethylamine (0.12 ml) and ethynylsulfonyl chloride (0.08 ml), and the mixture was reacted for 2 hr. The reaction solution was partitioned between ethyl acetate and a 2N aqueous solution of sodium hydroxide. The resulting organic layer was washed with water and brine and dried. The resulting product was recrystallized from hexane/ethyl acetate, to give the title compound (139 mg, yield; 77%). The resulting compound was converted into an oxalate in a conventional manner, to give the oxalate of the title compound as white crystals.

Oxalate:
$^1$H-NMR(400 MHz,DMSO-d$_6$); δ (ppm) 1.28(t,J=7.2 Hz,3H), 3.18(q,J=7.2 Hz,2H), 3.52(br,8H), 3.83(s,3H), 7.07 (d,J=8.8 Hz,2H), 7.57(d,J=8.0 Hz,1H), 7.72(d,J=8.0 Hz,1H), 7.94(d,J=8.0 Hz,1H), 7.95(s,1H), 8.10(d,J=8.0 Hz,1H), 8.14 (d,J=8.8 Hz,2H).

MS(FAB) m/z 412(M+H)$^+$.

Free compound:
$^1$H-NMR(400 MHz,CDCl$_3$); δ (ppm) 1.44(t,J=7.6 Hz,3H), 3.05(q,J=7.6 Hz,2H), 3.61(br,8H), 3.88(s,3H), 7.01 (d,J=8.8 Hz,2H), 7.47(ddd,J=8.4,8.0,1.2 Hz,1H), 7.60(ddd, J=8.4,8.0,1.2 Hz,1H), 7.68(s,1H), 7.80(d,J=8.0 Hz,1H), 8.01 (d,J=8.4 Hz,1H), 8.09(d,J=8.8 Hz,2H).

Example 316

Synthesis of 4-piperidinyl-6-[4-(2-methyl-2-hydroxypropoxy)phenyl]thieno[3,2-c]pyridine hydrochloride

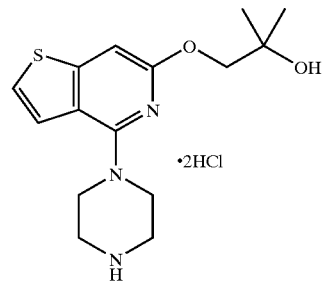

In the same manner as in Example 289, an oil was obtained from 4-[4-(t-butoxycarbonyl)piperazin-1-yl]-6-(4-hydroxyphenyl)thieno[3,2-c]pyridine (872 mg), ethyl bromoacetate (0.32 ml) and 3.0M ethylmagnesium bromide/ THF solution (1.7 ml). THF (10 ml) and a 5N aqueous solution of hydrochloride acid (2 ml) were added to the resulting oil, and the mixture was heated under reflux at 60° C. for 20 min. The reaction solution was cooled, and then basified with an aqueous solution of saturated sodium bicarbonate. Then, the mixture was extracted with ethyl acetate. The resulting organic layer was washed with water, dried and concentrated. The resulting residue was purified by NH-silica gel column chromatography (hexane/ethyl acetate system), to give the free compound of the title compound as a colorless oil (534 mg, yield; 66%). The resulting free compound was converted into a hydrochloride in a conventional manner, to give the hydrochloride of the title compound as white crystals.

Hydrochloride:

m.p.; 154–156° C.

$^1$H-NMR(400 MHz,DMSO-d$_6$); δ (ppm) 1.23(s,6H), 3.34 (br,4H), 3.73(br,4H), 3.78(s,2H), 7.04(d,J=8.8 Hz,2H), 7.62 (d,J=5.2 Hz,1H), 7.77(d,J=5.2 Hz,1H), 8.09(d,J=8.8 Hz,2H), 8.18(s,1H).

MS(FAB) m/z 384(M+H)$^+$.

Free compound:

$^1$H-NMR(400 MHz,CDCl$_3$); δ (ppm) 1.37(s,6H), 3.12(t, J=4.8 Hz,4H), 3.61(t,J=4.8 Hz,4H), 3.86(s,2H), 7.00(d,J=8.8 Hz,2H), 7.32(d,J=5.6 Hz,1H), 7.39(d,J=5.6 Hz,1H), 7.73(s, 1H), 8.04(d,J=8.8 Hz,2H).

Example 317

Synthesis of 7-(1-ethylpiperazin-4-yl)-5-[4-(3-hydroxypropoxy)phenyl]furo[2,3-c]pyridine dihydrochloride

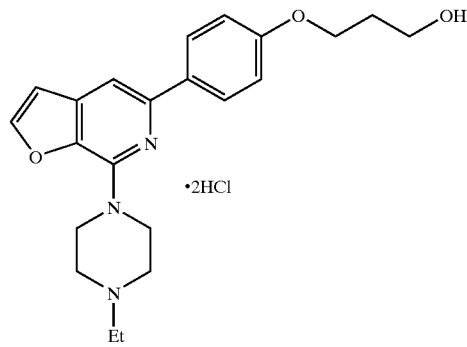

In the same manner as in Example 161-2, the hydrochloride of the title compound was obtained as a colorless amorphous (353 mg, yield; 67%) from 7-(1-ethylpiperazin-4-yl)-5-bromofuro[2,3-c]pyridine (373 mg) and 1-(4-tributylstannylphenoxy)-3-tetrahydropyranyloxypropane (1.404 g).

$^1$H-NMR(400 MHz,DMSO-d$_6$); δ (ppm) 1.28(3H,t,J=7.2 Hz), 1.86(2H,qui,J=6.4 Hz), 3.06–3.18(4H,m), 3.50–3.62 (6H,m). 4.07(2H,t,J=6.4 Hz), 4.72(2H,d,J=14.4 Hz), 6.99 (2H,d,J=8.8 Hz), 7.00(1H,d,J=2 Hz), 7.60(1H,m), 7.97(2H, d,J=8.8 Hz), 8.12(1H,d,J=2 Hz). FAB-Mass; 382(MH$^+$).

Example 318

Synthesis of 1-(4-ethylpiperazin-1-yl)-3-(4-methylphenyl)isoquinoline hydrochloride (318-1) 1-Benzyl-4-(1-ethynyl)piperidine

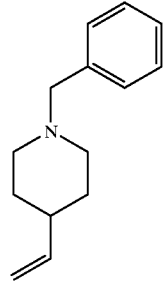

Ethyl triphenylphosphonium bromide (25 g) was suspended in tetrahydrofuran (100 ml), followed by the addition of 60% sodium hydride (2.68 g) under ice-cooling, and the mixture was stirred at room temperature for 2 hr. The reaction solution was ice-cooled again, followed by the addition of 1-benzyl-4-piperidone (11.55 g), and the resulting mixture was stirred at room temperature overnight. The reaction mixture was partitioned between ethyl acetate and water. The resulting organic layer was washed with water, dried (over MgSO$_4$) and evaporated. The resulting residue was purified by silica gel column chromatography (ethyl acetate/hexane system), to give the title compound as a colorless oil (6.08 g, yield, 52%).

$^1$H-NMR(400 MHz,CDCl$_3$); δ (ppm) 1.57(3H,d,J=6.8 Hz), 2.19(2H,t,J=5.6 Hz), 2.26(2H,t,J=5.6 Hz), 2.40(2H,t, J=5.6 Hz), 2.41(2H,t,J=5.6 Hz), 3.51(2H,s); 5.18(1H,q,J=6.8 Hz), 7.22–7.36(5H,m).

(318-2) 4-Ethylpiperidine

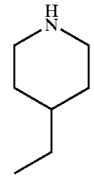

1-Benzyl-4-(1-ethylene)piperidine (6.084 g) was dissolved in methanol (60 ml), followed by the addition of 20% palladium hydroxide/carbon catalyst (617 mg), and the resulting mixture was stirred in hydrogen atmosphere overnight at room temperature. After the resulting insoluble matters were filtered off, the resulting filtrate was evaporated and partitioned between methylene chloride and an aqueous solution of saturated sodium bicarbonate; the resulting organic layer was dried (over MgSO$_4$) and evaporated, to give the title compound as a pale yellow oil (1.042 g, yield; 28%).

$^1$H-NMR(400 MHz,CDCl$_3$); δ (ppm) 0.89(3H,t,J=7.2 Hz), 1.18–1.33(5H,m), 1.75(2H,d,J=12 Hz), 2.66(2H,t,J= 11.6 Hz), 3.19(2H,d,J=11 Hz), 5.00(1H,br-s).

(318-3) 1-(4-Ethylpiperidin-1-yl)-3-(4-methoxyphenyl)isoquinoline hydrochloride

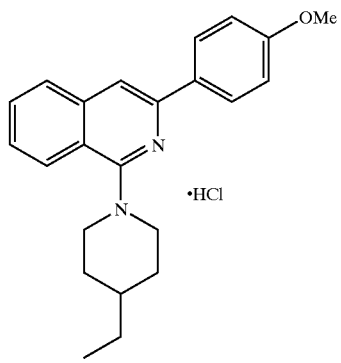

1-Chloro-3-(4-methoxyphenyl)isoquinoline (405 mg) and 4-ethylpiperidine (168 mg) were dissolved in N,N-dimethylformamide (5 ml), followed by the addition of triethylamine (251 ml), and the mixture was stirred at 80° C. overnight. The reaction mixture was partitioned between ethyl acetate and water. The resulting organic layer was washed with water, dried (over MgSO$_4$) and evaporated. The resulting residue was purified by silica gel column chromatography (ethyl acetate/hexane system). Then the resulting product was converted into a hydrochloride in a conventional manner, and then recrystallized from ethanol/isopropyl ether, to give the hydrochloride of the title compound as a colorless crystals (87 mg, yield; 13%).
Hydrochloride:
  m.p.; 109–114° C.
  $^1$H-NMR(400 MHz,DMSO-d$_6$); δ (ppm) 0.92(3H,t,J=7.2 Hz), 1.30–1.38(2H,br-quin), 1.40–1.53(3H,m), 1.80–1.90 (2H,br-d), 3.02–3.12(2H,br-t), 3.88–3.98(2H,br-d), 7.05 (2H,d,J=8.8 Hz), 7.56(1H,ddd,J=8 Hz,7 Hz,1.2 Hz), 7.72 (1H,ddd,J=8 Hz,7 Hz,1.2 Hz), 7.83(1H,s), 7.90(1H,d,J=8 Hz), 8.03(1H,d,J=8 Hz), 8.05(2H,d,J=8.8 Hz).
  ESI-Mass; 347(MH$^+$).

Example 319

Synthesis of 1-{N-[2-(2-dimethylamino)ethyl]-N-methylamino}-3-(4-methoxyphenyl)isoquinoline dihydrochloride

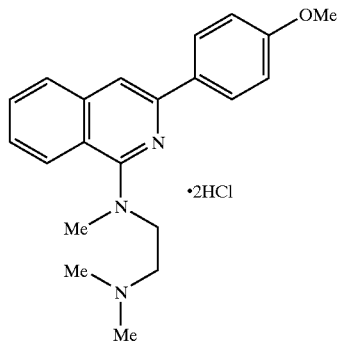

In the same manner as in Example 2, the hydrochloride of the title compound was obtained as yellow crystals (recrystallized in ethanol/isopropyl ether) (433 mg, yield; 58%) from 1-chloro-3-(4-methoxyphenyl)isoquinoline (514 mg) and N,N,N'-trimethylethylenediamine (4.8 ml).
Hydrochloride:
  m.p.; 160–162° C.
  $^1$H-NMR(400 MHz,DMSO-d$_6$); δ (ppm) 2.79(3H,s), 2.81 (3H,s), 3.13(3H,s), 3.45(1H,t,J=6.4 Hz), 3.46(1H,t,J=6.4 Hz), 3.81(3H,s), 3.87(2H,t,J=6.4 Hz), 7.04(2H,d,J=8.8 Hz), 7.52(1H,ddd,J=8 Hz,6.8 Hz,1.2 Hz), 7.61(1H,ddd,J=8 Hz,6.8 Hz,1.2 Hz), 7.87(1H,s), 7.89(1H,d,J=8 Hz), 8.11(2H,d,J=8.8 Hz), 8.18(1H,d,J=8 Hz), 10.08(1H,br-s).
  ESI-Mass; 336(MH$^+$).

Example 320

Synthesis of 1-(4-morpholinyl)-3-(4-methoxyphenyl)isoquinoline hydrochloride

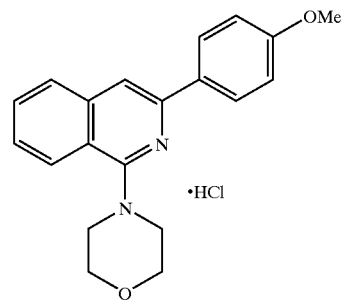

In the same manner as in Example 2, the hydrochloride of the title compound was obtained as yellow crystals (recrystallized in ethanol) (371 mg, yield; 56%) from 1-chloro-3-(4-methoxyphenyl)isoquinoline (468 mg) and morpholine (3.1 ml).
Hydrochloride:
  m.p.; 137–139° C.
  $^1$H-NMR(400 MHz, DMSO-d$_6$); δ (ppm) 3.38(4H,t,J=4.4 Hz), 3.80(3H,s), 3.87(4H,t,J=4.4 Hz), 7.04(2H,d,J=8.8 Hz), 7.51(1H,ddd,J=8.4 Hz,7 Hz,1.2 Hz), 7.66(1H,ddd,J=8 Hz,7 Hz,1.2 Hz), 7.89(1H,d,J=8 Hz), 7.90(1H,s), 8.07(1H,d,J=8.4 Hz), 8.13(2H,d,J=8.8 Hz).
  ESI-Mass; 321(MH$^+$).

Example 321

Synthesis of 1-(1-ethyl-2-pyrrolidinyl)methylamino-3-(4-methoxyphenyl)isoquinoline dihydrochloride

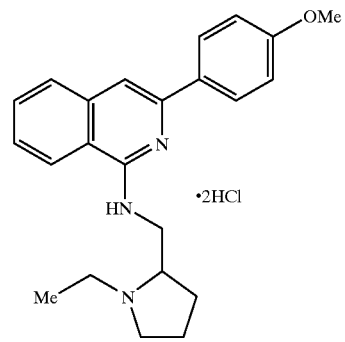

In the same manner as in Example 2, the hydrochloride of the title compound was obtained as a brown amorphous (85 mg, yield; 11%) from 1-chloro-3-(4-methoxyphenyl)isoquinoline (486 mg) and 2-aminomethyl-1-ethylpyrrolidine (5.2 ml).
Hydrochloride:
  $^1$H-NMR(400 MHz,DMSO-d$_6$); δ (ppm) 1.18(3H,t,J=6.8 Hz), 1.20–1.35(1H,m), 1.85–2.00(4H,m), 2.15–2.25(1H,m), 3.03–3.15(2H,m), 3.35–3.45(1H,m), 3.50–3.60(1H,m), 3.85–3.95(1H,m), 3.95–4.05(1H,m), 4.15–4.25(1H,m), 7.05 (2H,d,J=8.8 Hz), 7.47(1H,s), 7.50–7.58(1H,m), 7.66–7.75 (1H,m), 7.82(1H,d,J=8.4 Hz), 7.98(2H,d,J=8.8 Hz), 8.38–8.54(1H,m).

ESI-Mass; 362(MH⁺).

Example 322

Synthesis of 3-(4-methoxyphenyl)-1-[2-(2-pyridyl) ethyl]aminoisoquinoline hydrochloride

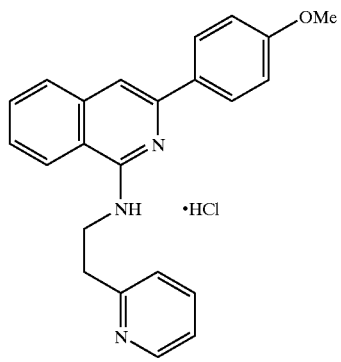

In the same manner as in Example 10-1, the free compound of the title compound was obtained (107 mg, yield; 69%) from 1-chloro-3-(4-methoxyphenyl)isoquinoline (117 mg) and 2-(2-aminoethyl)pyridine (0.52 ml). The resulting free compound was converted into a hydrochloride in a conventional manner, to give the hydrochloride of the title compound as yellow crystals.

Hydrochloride:

m.p.; 138–140° C.

¹H-NMR(400 MHz,DMSO-d₆); δ (ppm) 3.30(t,J=7.2 Hz,2H), 3.83(s,3H), 4.01(br-t,2H), 7.40(d,J=8.8 Hz,2H), 7.37(dd,J=7.6,5.6 Hz,1H), 7.43(s,1H), 7.45(t,J=8.0 Hz,1H), 7.49(d,J=7.6 Hz,1H), 7.62(t,J=8.0 Hz,1H), 7.76(d,J=8.0 Hz,1H), 7.89(t,J=7.6 Hz,1H), 8.10(d,J=8.8 Hz,2H), 8.20(d, J=8.0 Hz,1H), 8.54(dd,J=5.6,0.8 Hz,1H).

MS(FAB) m/z 356(M+H)⁺

Free compound:

¹H-NMR(400 MHz,CDCl₃); δ (ppm) 3.27(t,J=6.4 Hz,2H), 3.88(s,3H), 4.11–4.16(m,2H), 6.40(br-t,1H), 6.99 (d,J=8.8 Hz,2H), 7.16(ddd,J=7.6,4.8,1.2 Hz,1H), 7.23(d,J= 7.6 Hz,1H), 7.32(s,1H), 7.38(dt,J=8.0, 1.2 Hz,1H), 7.54(dt, J=8.0, 21.2 Hz,1H), 7.61(dt,J=7.6, 2.0 Hz,1H), 7.69(d,J=8.0 Hz,1H), 7.75(d,J=8.0 Hz,1H), 8.13(d,J=8.8 Hz,2H), 8.62 (dd,J=4.8, 1.2 Hz,1H).

Example 323

Synthesis of 1-[2-(4-morpholinyl)ethyl]amino-3-(4-methoxyphenyl)isoquinoline dihydrochloride

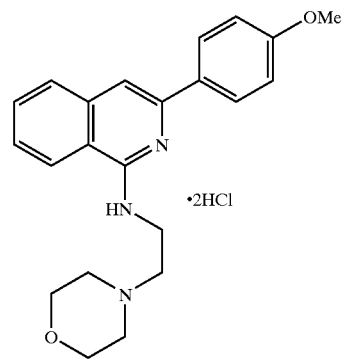

1-Chloro-3-(4-methoxyphenyl)isoquinoline (405 mg) and 4-(2-aminoethyl)morpholine (394 mg) were dissolved in N,N-dimethylformamide (5 ml), followed by the addition of potassium carbonate (415 ml), and the resulting mixture was stirred at 120° C. overnight. The reaction mixture was partitioned between ethyl acetate and water. The resulting organic layer was washed with water, dried (over MgSO₄) and evaporated. The resulting residue was purified by silica gel column chromatography (methylene chloride/methanol system). Then, the resulting product was converted into a hydrochloride in a conventional manner, and then recrystallized from ethanol/isopropyl ether, to give the hydrochloride of the title compound as pale yellow crystals (190 mg, yield; 27%).

Hydrochloride:
m.p.; 135–136° C.
¹H-NMR(400 MHz,DMSO-d₆); δ (ppm) 3.28–3.52(2H, m), 3.48–3.56(2H,m), 3.81(3H,s), 3.84–3.94(4H,m), 4.06–4.16(4H,m), 7.05(2H,d,J=8.8 Hz), 7.47(1H,s), 7.50–7.58(1H,m), 7.66–7.78(1H,m), 7.82(1H,d,J=8 Hz), 7.94–8.06(2H,m), 8.40–8.58(1H,m).
ESI-Mass; 364(MH⁺).

Example 324

Synthesis of 1-(1-imidazolyl)-3-(4-methoxyphenyl) isoquinoline hydrochloride

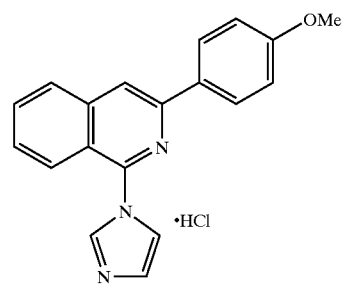

1-Chloro-3-(4-methoxyphenyl)isoquinoline (405 mg) and imidazole (204 mg) were dissolved in N,N-dimethylformamide (5 ml), followed by the addition of 60% sodium hydride (60 mg), and the resulting mixture was stirred at 80° C. for 6 hr. The reaction mixture was partitioned between ethyl acetate and water. The resulting organic layer was washed with water, dried (over MgSO₄)

and evaporated. The resulting residue was purified by silica gel column chromatography (methylene chloride/methanol system), and then the resulting product was converted into a hydrochloride in a conventional manner, to give the hydrochloride of the title compound as a pale yellow amorphous (255 mg, yield; 53%).

Hydrochloride:

$^1$H-NMR(400 MHz,DMSO-d$_6$); δ (ppm) 3.83(3H,s), 7.10 (2H,d,J=8.8 Hz), 7.90–7.96(2H,m), 8.00(1H,s), 8.17–8.23 (3H,m), 8.40(1H,s), 8.69(1H,s), 9.80(1H,s).

ESI-Mass; 302(MH$^+$).

Example 325

Synthesis of 1-[4-(piperidin-1-yl)piperidine-1-yl]-3-(4-methoxyphenyl)isoquinoline dihydrohcloride

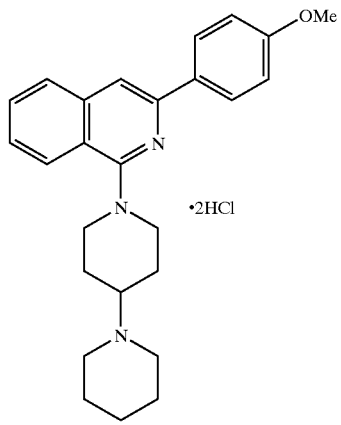

In the same manner as in Example 321, the hydrochloride of the title compound was obtained as yellow crystals (recrystallized in ethanol/isopropyl ether) (278 mg, yield; 40%) from 1-chloro-3-(4-methoxyphenyl)isoquinoline (405 mg) and 4-(piperidin-1-yl)piperidine (425 mg).

Hydrochloride:

m.p.; 223–238° C.

$^1$H-NMR(400 MHz,DMSO-d$_6$); δ (ppm) 1.67–1.75(1H, m), 1.78–1.86(4H,m), 1.97–2.09(2H,m), 2.19–2.26(2H,m), 2.90–3.08(5H,m), 3.36–3.50(3H,m), 3.80(3H,s), 3.96–4.04 (2H,m), 7.04(2H,d,J=8.8 Hz), 7.53(1H,ddd,J=8 Hz,7 Hz,1.2 Hz), 7.67(1H,ddd,J=8 Hz,7 Hz,1.2 Hz), 7.89(1H,s), 7.90 (1H,d,J=8 Hz), 8.01(1H,d,J=8 Hz), 8.12(2H,d,J=8.8 Hz).

ESI-Mass; 402(MH$^+$).

Example 326

Synthesis of 1-(1,4,5,6-tetrahydropyrimidin-1-yl)-3-(4-methoxyphenyl)isoquinoline hydrochloride

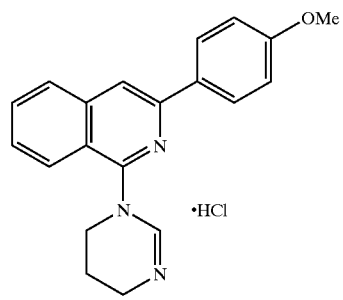

In the same manner as in Example 324, the hydrochloride of the title compound was obtained as a brown amorphous (80 mg, yield; 13%) from 1-chloro-3-(4-methoxyphenyl) isoquinoline (405 mg) and 1,4,5,6-tetrahydropyrimidine (370 mg).

Hydrochloride:

$^1$H-NMR(400 MHz,DMSO-d$_6$); δ (ppm) 2.24(2H,qui,J= 5.6 Hz), 3.58(2H,t,J=5.6 Hz), 4.15(2H,t,J=5.6 Hz), 7.09(2H, d,J=8.8 Hz), 7.74(1H,ddd,J=8 Hz,7 Hz,1.2 Hz), 7.88(1H, ddd,J=8 Hz,7 Hz,1.2 Hz), 8.11(1H,d,J=8 Hz), 8.13(1H,d,J=8 Hz), 8.16(2H,d,J=8.8 Hz), 8.50(1H,s), 8.91(1H,d,J=6 Hz), 11.02(1H,br-s).

ESI-Mass; 318(MH$^+$).

Example 327

Synthesis of 1-(1-ethylhomopiperazin-4-yl)-3-(4-methoxyphenyl)isoquinoline dihydrochloride (327-1) 1-(1-Formylhomopiperazin-4-yl)-3-(4-methoxyphenyl)isoquinoline

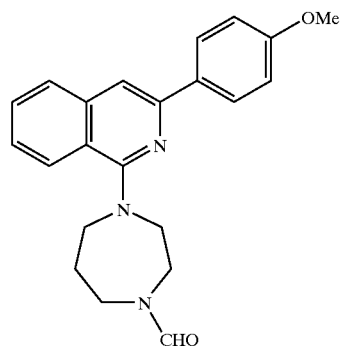

In the same manner as in Example 2, the title compound was obtained as a brown oil (3.173 g, yield; 68%) from 1-chloro-3-(4-methoxyphenyl)isoquinoline (3.506 g) and 1-formylhomopiperazine (5 g).

$^1$H-NMR(400 MHz,CDCl$_3$); δ (ppm) 2.06–2.16(2H,m), 3.59(1H,t,J=6 Hz), 3.67–3.98(5H,m), 3.85(3H,s), 3.83–3.91 (2H,m), 6.99(1H,d,J=8.8 Hz), 7.00(1H,d,J=8.8 Hz), 7.41 (0.5H,ddd,J=8 Hz,7 Hz,1.2 Hz), 7.42(0.5H,ddd,J=8 Hz,7 Hz,1.2 Hz), 7.55(0.5H,ddd,J=8 Hz,7 Hz,1.2 Hz), 7.56(0.5H, ddd,J=8 Hz,7 Hz,1.2 Hz), 7.58(1H,s), 7.74(1H,d,J=8 Hz), 7.99(0.5H,d,J=8 Hz), 8.00(0.5H,d,J=8 Hz), 8.05(1H,d,J=8.8 Hz), 8.06(1H,d,J=8.8 Hz), 8.14(0.5H,s), 8.18(0.5H,s).

(327-2) 1-(1-Homopiperazinyl)-3-(4-methoxyphenyl)isoquinoline

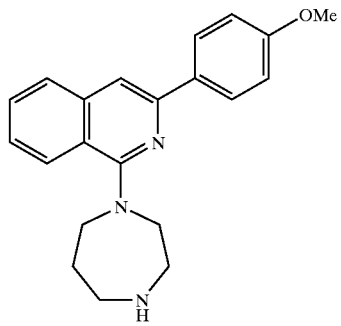

In the same manner as in Example 236, the title compound was obtained as a pale yellow solid (2.467 g, yield; 84%) from 1-(1-formylhomopiperazin-4-yl)-3-(4-methoxyphenyl)isoquinoline (3.173 g).

$^1$H-NMR(400 MHz,CDCl$_3$); δ (ppm) 2.01–2.08(2H,m), 3.09(2H,t,J=5.8 Hz), 3.20–3.23(2H,m), 3.85–3.90(7H,m), 7.00(2H,d,J=8.8 Hz), 7.39(1H,ddd,J=8 Hz,7 Hz,1.2 Hz), 7.53(1H, s) 7.55(1H,ddd,J=8 Hz,7 Hz,1.2 Hz), 7.74(1H,d, J=8 Hz), 8.10(2H,d,J=8.8 Hz).

(327-3) 1-(1-Ethylhomopiperazin-4-yl)-3-(4-methoxyphenyl)isoquinolinehydrochloride

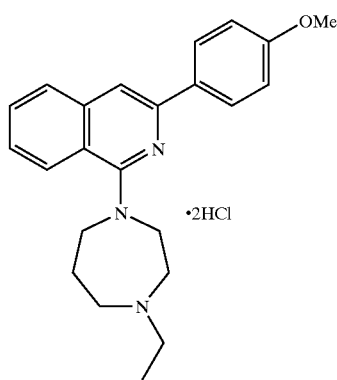

In the same manner as in Example 236, the hydrochloride of the title compound was obtained as yellow crystals (recrystallized from ethanol/isopropyl ether) (228 mg, yield; 82%) from 1-(1-homopiperazinyl)-3-(4-methoxyphenyl)isoquinoline (355 mg) and 1-bromoethane (87 ml).

Hydrochloride:

m.p.; 124–125° C.

$^1$H-NMR(400 MHz,DMSO-d$_6$); δ (ppm) 1.28(3H,t,J=7.2 Hz), 2.15–2.25(1H,m), 2.30–2.45(1H,m), 3.15–3.28(3H,m), 3.50–3.60(2H,m), 3.68–3.78(2H,m), 3.80(3H,s), 3.90–4.08 (2H,m), 4.10–4.18(1H,m), 7.03(2H,d,J=8.8 Hz), 7.48(1H, ddd,J=8.4 Hz,7 Hz,1.2 Hz), 7.65(1H,ddd,J=8.4 Hz,7 Hz,1.2 Hz), 7.80(1H,s), 7.87(1H,d,J=8.4 Hz), 8.04(1H,d,J=8.4 Hz), 8.10(1H,d,J=8.8 Hz), 10.62(1H,br-s).

ESI-Mass; 362(MH$^+$).

Example 328

Synthesis of 3-(4-methoxyphenyl)-1-(4-ethylpiperazin-1-yl)methylisoquinoline oxalate

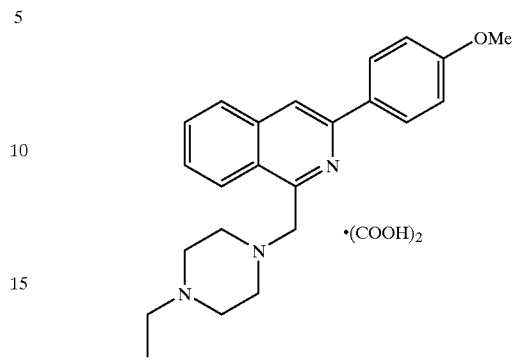

3-(4-Methoxyphenyl)-1-chloroisoquinoline (3.25 g) was dissolved in tetrahydrofuran (30 ml), followed by the addition of 3.0M ethylmagnesium bromide diethyl ether solution (12 ml) and NiCl$_2$ (dppp) (50 mg) at 0° C. After the mixture was reacted overnight at room temperature, the resulting reaction solution was poured into an aqueous solution of saturated ammonium chloride and extracted with ethyl acetate. The resulting organic layer was washed with water and brine, dried and evaporated, to give 3-(4-methoxyphenyl)-1-methylisoquinoline as an oil (3.3 g, yield; 100%).

To the resulting oil (3.3 g) were added chloroform (30 ml) and m-chloroperbenzoic acid (MCPBA, 4.4 g) under ice-cooling, and the mixture was reacted at room temperature for 1 hr. To the resulting reaction solution was added a 2N aqueous solution of sodium hydroxide, and the mixture was stirred 10 min, and then extracted with ethyl acetate. The resulting organic layer was washed with water and brine, dried and then purified by NH-silica gel column chromatography (hexane/ethyl acetate system), to give 3-(4-methoxyphenyl)-1-methylisoquinoline N-oxide as a yellow oil (2.42 g, yield; 76%).

To the resulting oil (2.4 g) were added chloroform (10 ml) and p-toluenesulfonyl chloride (1.9 g), and the mixture was reacted at 50° C. overnight. To the reaction solution was added an aqueous solution of saturated sodium bicarbonate, and the mixture was stirred for 10 min and then extracted with ethyl acetate. The resulting organic layer was washed with water and brine, dried and purified by silica gel column chromatography (hexane/ethyl acetate system), to give 3-(4-methoxyphenyl)-1-chloromethylisoquinoline (783 mg, yield; 30%).

In the same manner as in Example 1, the title compound was obtained (995 mg, yield; 99%) from 3-(4-methoxyphenyl)-1-chloromethylisoquinoline (783 mg) and ethylpiperazine (0.57 ml).

The resulting compound was converted into an oxalate in a conventional manner, to give the oxalate of the title compound as white crystals.

Oxalate:

m.p.; 219–221° C.

$^1$H-NMR(400 MHz,DMSO-d$_6$); δ (ppm) 1.18(t,J=7.2 Hz,3H), 2.87(br,4H), 3.04(q,J=7.2 Hz,2H), 3.14(br,4H), 3.84(s,3H), 4.26(s,2H), 7.09(d,J=8.8 Hz,2H), 7.62(dt,J=8.4, 1.2 Hz,1H), 7.76(dt,J=8.4,1.2 Hz,1H), 8.01(d,J=8.4 Hz,1H), 8.19(d,J=8.8 Hz,2H), 8.28(s,1H), 8.43(d,J=8.4 Hz,1H).

MS(FAB) m/z 362(M+H)$^+$.

Free Compound:

¹H-NMR(400 MHz,CDCl₃); δ (ppm) 1.08(t,J=7.2 Hz,3H), 2.42(q,J=7.2 Hz,2H), 2.50(br,4H), 2.72(br,4H), 3.88(s,3H), 4.20(s,2H), 7.03(d,J=8.8 Hz,2H), 7.52(t,J=8.4 Hz,1H), 7.63(t,J=8.4 Hz,1H), 7.82(d,J=8.4 Hz,1H), 7.90(s,1H), 8.11(d,J=8.8 Hz,2H), 8.45(d,J=8.4 Hz,1H).

Example 329

Synthesis of 1-(4-Ethylpiperazin-1-yl)-3-[3-(2-hydroxyethoxy)phenyl]isoquinoline dihydrochloride

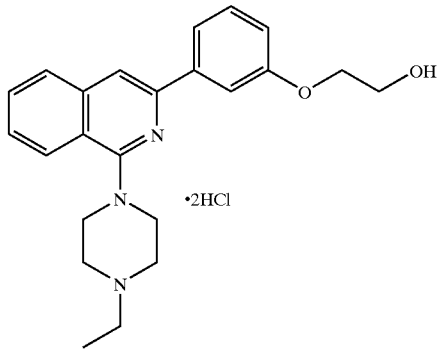

According to the methods of Examples 10-1 and 10-2, 1-(4-ethylpiperazin-1-yl)-3-[2-(t-butyldimethylsilyloxy)ethoxy]phenylisoquinoline (0.59 g) was obtained from N-methyl-2-methylbenzamide (5.97 g) and 3-methoxybenzonitrile (5.33 g).

The resulting 1-(4-ethylpiperazin-1-yl)-3-[2-(t-butyldimethylsilyloxy)ethoxy]phenylisoquinoline (0.58 g) was dissolved in tetrahydrofuran (5 ml), to which was then added 1.0M tetrabutylammonium fluoride/tetrahydrofuran solution (1.42 ml), and the mixture was stirred for 7.5 hr. The solvent was evaporated, and the resulting residue was dissolved in ethyl acetate. The resulting solution was washed with water (four times) and brine, and then dried over magnesium sulfate. The solvent was evaporated, and the resulting residue was purified by silica gel column chromatography (chloroform/methanol system), to give 0.32 g of the free compound of the title compound as a pale yellow oil.

The resulting free compound was converted into a hydrochloride in a conventional manner, and then recrystallized from ethanol/ether, to give 0.34 g of the title compound as a yellow powder.

Hydrochloride:

¹H-NMR(400 MHz,DMSO-d₆); δ (ppm) 1.18(t,J=7.2 Hz,3H), 2.56(q,J=7.2 Hz,2H), 2.77(br-t,4H), 3.59(br-t,4H), 4.02(t,J=4.5 Hz,2H), 4.20(t,J=4.5 Hz,2H), 6.94(dd,J=2.6,8.2 Hz,1H), 7.38(t,J=8.0 Hz,1H), 7.47(br-t,1H), 7.59(br-t,1H), 7.70(s,1H), 7.75(br-d,1H), 7.79(d,J=8.0 Hz,1H), 7.82(br-t,1H), 8.08(d,J=8.4 Hz,1H).

MS(FAB) m/z 378(M+H)⁺.

Example 330

Synthesis of 1-(4-Ethylpiperazin-1-yl)-3-(4-ethoxyphenyl)isoquinoline dihydrochloride

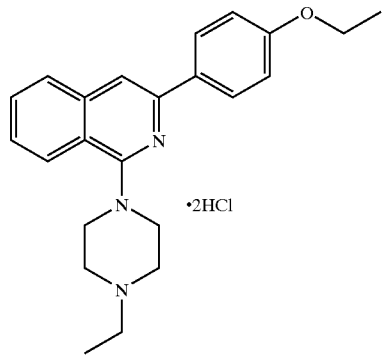

According to the method of Example 7, 1-(4-ethylpiperazin-1-yl)-3-(4-hydroxyphenyl)isoquinoline was obtained.

Sodium hydride (0.04 g) was washed with n-hexane, suspended in N,N-dimethylformamide (2 ml) and stirred under ice-cooling. The resulting 1-(4-ethylpiperazin-1-yl)-3-(4-hydroxyphenyl)isoquinoline (0.25 g) described above was added thereto, and the mixture was stirred at room temperature for 35 min. The mixture was again ice-cooled, followed by the addition of ethyl iodide (90 ml), and the mixture was stirred in nitrogen atmosphere at 50° C. for 1.5 hr. Water was added to the reaction solution, and then extracted with ethyl acetate. The resulting extract was washed with water and brine, and dried over magnesium sulfate. The solvent was evaporated, and the resulting residue was purified by silica gel column chromatography (chloroform/methanol system), to give 0.22 g of the free compound of the title compound as a pale yellow oil.

Free Compound:

¹H-NMR(400 MHz,CDCl₃); δ (ppm) 1.17(t,J=7.2 Hz,3H), 1.44(t,J=7.0 Hz,3H), 2.54(q,J=7.2 Hz,2H), 2.74(br-t,4H), 3.58(br-t,4H), 4.08(q,J=7.0 Hz,2H), 6.98(d,J=8.8 Hz,2H), 7.41(br-t,1H), 7.54(br-t,1H), 7.60(s,1H), 7.74(d,J=8.0 Hz,1H), 8.05(d,J=8.4 Hz,1H), 8.11(d,J=8.8 Hz,2H).

The resulting free compound was converted into a hydrochloride in a conventional manner, and then recrystallized from ethanol/ether, to give the title compound as a yellow powder.

Hydrochloride:

m.p.; 197–198° C. (decomp.)

¹H-NMR(400 MHz,DMSO-d₆); δ (ppm) 1.33(t,J=7.2 Hz,3H), 1.37(t,J=6.8 Hz,3H), 3.20–3.27(m,2H), 3.31–3.39 (m,2H), 3.51(br-t,2H), 3.62(br-d,2H), 3.98(br-d,2H), 4.10(q, J=6.8 Hz,2H), 7.05(d,J=9.2 Hz,2H), 7.57(br-t,1H), 7.72(br-t,1H), 7.95(d,J=8.0 Hz,1H), 7.99(s,1H), 8.10(d,J=8.4 Hz,1H), 8.14(d,J=9.2 Hz,2H), 10.86(br-s,1H).

MS(FAB) m/z 362(M+H)⁺.

Example 331

Synthesis of 1-(4-ethylpiperazin-1-yl)-3-[4-(3-hydroxypropoxy)phenyl]isoquinoline dihydrochloride

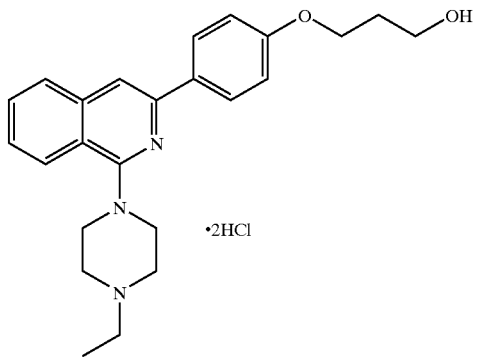

According to the method of Example 7, 1-(4-ethylpiperazin-1-yl)-3-(4-hydroxyphenyl)isoquinoline was obtained.

Sodium hydride (0.08 g) was washed with n-hexane, suspended in N,N-dimethylformamide (4 ml) and stirred under ice-cooling. The resulting 1-(4-ethylpiperazin-1-yl)-3-(4-hydroxyphenyl)isoquinoline (0.49 g) described above was added thereto, and the mixture was stirred at room temperature for 25 min. The mixture was again ice-cooled, followed by the addition of 3-(tetrahydropyranyloxy)propyl bromide (0.50 g), and the mixture was stirred in nitrogen atmosphere at 50° C. overnight. Water was added to the reaction solution, and then extracted with ethyl acetate. The resulting extract was washed with water and brine, and dried over magnesium sulfate. The solvent was evaporated, and the resulting residue was purified by silica gel column chromatography (chloroform/methanol system), to give 0.66 g of the tetrahydropyranyl-protected compound of the titled compound as a pale yellow oil.

Methanol (5 ml) and 2N hydrochloric acid (5 ml) were added to the protected compound (0.65 g) described above, and the mixture was left as it was at room temperature for 1.5 hr. The solvent was evaporated, and then a 5N aqueous solution of sodium hydroxide was added to the resulting residue. The mixture was extracted with ethyl acetate. The resulting extract was washed with brine, and dried over magnesium sulfate. The solvent was evaporated, and the resulting residue was purified by silica gel column chromatography (chloroform/methanol system), to give 0.43 g of the free compound of the title compound as a pale yellow oil.

Free form:
$^1$H-NMR(400 MHz,CDCl$_3$); δ (ppm) 1.18(t,J=7.4 Hz,3H), 2.08(quintet,J=6.0 Hz,2H), 2.56(q,J=7.4 Hz,2H), 2.76(br-t,4H), 3.58(br-t,4H), 3.90(t,J=6.0 Hz,2H), 4.20(t,J=6.0 Hz,2H), 7.00(d,J=8.8 Hz,2H), 7.43(br-t,1H), 7.56(br-t,1H), 7.61(s,1H), 7.76(d,J=7.6 Hz,1H), 8.06(d,J=8.4 Hz,1H), 8.12(d,J=8.8 Hz,2H).

The resulting free compound was converted into a hydrochloride in a conventional manner, and then recrystallized from ethanol/IPE, to give the title compound as a yellow powder.

Hydrochloride:
m.p.; 112–113° C. (decomp.)
$^1$H-NMR(400 MHz,DMSO-d$_6$); δ (ppm) 1.32(t,J=7.4 Hz,3H), 1.90(quintet,J=6.2 Hz,2H), 3.22–3.28(m,2H), 3.34–3.48(m,4H), 3.59(t,J=6.2 Hz,2H), 3.64(br-d,2H), 4.00 (br-d,2H), 4.11(t,J=6.2 Hz,2H), 7.06(d,J=8.8 Hz,2H), 7.57(br-t,1H), 7.72(br-t,1H), 7.95(d,J=8.4 Hz,1H), 8.00(s,1H), 8.10(d,J=8.0 Hz,1H), 8.14(d,J=8.8 Hz,2H), 10.37(br-s,1H).
MS(FAB) m/z 392(M+H)$^+$.

Example 332

Synthesis of 1-(4-ethylpiperazin-1-yl)-3-(3,4-ethylenedioxyphenyl)isoquinoline dihydrochloride

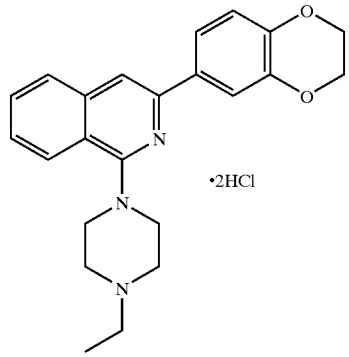

According to the method of Example 10-1, N-methyl-2-methylbenzamide (5.97 g) and 3,4-ethylenedioxybenzonitrile (6.41 g) were reacted, to give 3-(3,4-ethylenedioxyphenyl)isoquinolin-1-one (3.58 g).

The resulting 3-(3,4-ethylenedioxyphenyl)isoquinolin-1-one (1.94 g) was reacted with phosphorus oxychloride (20 ml) according to the method of Example 10-2, to give 1-chloro-3-(3,4-ethylenedioxyphenyl)isoquinoline. The resulting compound was reacted, as it was, with N-ethylpiperazine (6 ml) at 100° C. overnight. The reaction solution was evaporated, and to the resulting residue were added ethyl acetate and purified water. The resulting ethyl acetate layer was washed with water and brine, and dried over magnesium sulfate. The solvent was evaporated, and the resulting residue was purified by silica gel column chromatography (chloroform/methanol system), to give 1.63 g of the free compound of the title compound as a pale yellow oil.

Free form:
$^1$H-NMR(400 MHz,CDCl$_3$); δ (ppm) 1.17(t,J=7.2 Hz,3H), 2.55(q,J=7.2 Hz,2H), 2.75(br-t,4H), 3.57(br-t,4H), 4.32(s,4H), 6.95(d,J=8.4 Hz,1H), 7.43(br-t,1H), 7.56(br-t,1H), 7.59(s,1H), 7.66(dd,J=0.8,8.4 Hz,1H), 7.74–7.77(m,1H), 8.05(d,J=8.0 Hz,1H).

The resulting free compound was converted into a hydrochloride in a conventional manner, and then recrystallized from ethanol/IPE, to give the title compound as a yellow powder.

Hydrochloride:
m.p.; 141–143° C.
$^1$H-NMR(400 MHz,DMSO-d$_6$); δ (ppm) 1.33(t,J=7.2 Hz,3H), 3.20–3.26(m,2H), 3.30–3.37(m,2H), 3.51(br-t,2H), 3.62(br-d,2H), 3.97(br-d,2H), 4.30(s,4H), 6.98(d,J=8.4 Hz,1H), 7.58(br-t,1H), 7.68–7.74(m,3H), 7.95(d,J=8.0 Hz,1H), 7.99(s,1H), 8.09(d,J=8.4 Hz,1H), 11.01(s,1H).
MS(FAB) m/z 376(M+H)$^+$.

Example 333

Synthesis of 1-(4-ethylpiperazin-1-yl)-3-[4-(3-(methoxypropyl)phenyl]isoquinoline dihydrochloride

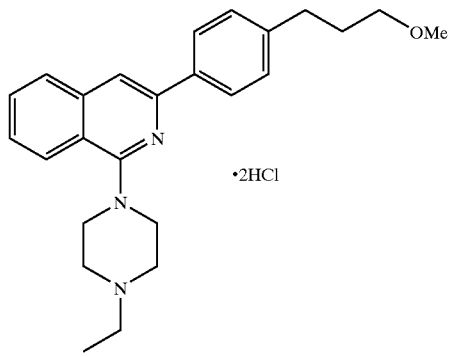

According to the method of Example 10-1, N-methyl-2-methylbenzamide (3.75 g) and 4-(3-methoxypropyl)benzonitrile (4.40 g) were reacted, to give 3-[4-(3-methoxypropyl)phenyl]isoquinolin-1-one (1.98 g).

The resulting 3-[4-(3-methoxypropyl)phenyl]isoquinolin-1-one (1.85 g) was reacted with phosphorus oxychloride (20 ml) according to the method of Example 10-2, to give 1-chloro-3-[4-(3-methoxypropyl)phenyl]isoquinoline. The resulting compound was reacted, as it was, with N-ethylpiperazine (6 ml) at 100° C. overnight. The reaction solution was evaporated, and to the resulting residue were added ethyl acetate and purified water. The resulting ethyl acetate layer was washed with water and brine, and dried over magnesium sulfate. The solvent was evaporated, and the resulting residue was purified by silica gel column chromatography (chloroform/methanol system), to give 0.63 g of the free compound of the title compound as a pale yellow oil.

Free Compound:

$^1$H-NMR(400 MHz,CDCl$_3$); δ (ppm) 1.15(t,J=7.2 Hz,3H), 1.88–1.95(m,2H), 2.52(q,J=7.2 Hz,2H), 2.71–2.74 (m,6H), 3.33(s,3H), 3.39(t,J=6.4 Hz,2H), 3.56(br-t,4H), 7.27(d,J=8.0 Hz,2H), 7.41(br-t,1H), 7.53(br-t,1H), 7.64(s, 1H), 7.73(d,J=8.0 Hz,1H), 8.04(d,J=8.0 Hz,1H), 8.08(d,J= 8.0 Hz,2H).

The resulting free compound was converted into a hydrochloride in a conventional manner, and then recrystallized from ethanol/IPE, to give the free compound of the title compound as a yellow powder.

Hydrochloride:

m.p.; 191–192° C. (decomp.)

$^1$H-NMR(400 MHz,DMSO-d$_6$); δ (ppm) 1.06(t,J=7.2 Hz,3H), 1.33(t,J=7.4 Hz,3H), 1.81–1.88(m,2H), 2.68(br-t, 2H), 3.19–3.25(m,2H), 3.25(s,3H), 3.30–3.38(m,2H), 3.35 (t,J=6.4 Hz,2H), 3.54(br-t,2H), 3.62(br-d,2H), 3.99(br-d, 2H), 7.34(d,J=8.4 Hz,2H), 7.60(br-t,1H), 7.74(br-t,1H), 7.98 (d,J=8.0 Hz,1H), 8.06(s,1H), 8.11–8.13(m,3H), 11.09(br-s, 1H).

MS(FAB) m/z 390(M+H)$^+$.

Example 334

Synthesis of 1-(4-ethylpiperazin-1-yl)-3-[4-(n-butyl)phenyl]isoquinoline dihydrochloride

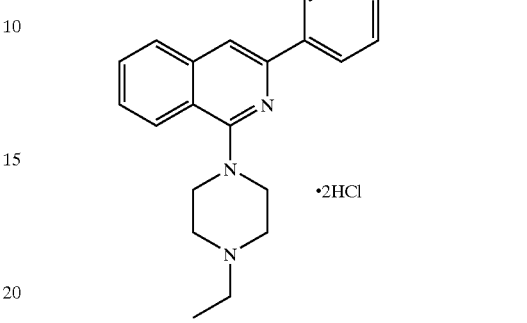

According to the method of Example 10-1, N-methyl-2-methylbenzamide (4.28 g) and 4-(n-butyl)benzonitrile (4.57 g) were reacted, to give 3-[4-(n-butyl)phenyl]isoquinolin-1-one (2.51 g).

The resulting 3-[4-(n-butyl)phenyl]isoquinolin-1-one (2.44 g) was reacted with phosphorus oxychloride (20 ml) according to the method of Example 10-2, to give 1-chloro-3-[4-(n-butyl)phenyl]isoquinoline. The resulting compound was reacted, as it was, with N-ethylpiperazine (11 ml) at 100° C. overnight. The reaction solution was evaporated, and to the resulting residue were added ethyl acetate and purified water. The resulting ethyl acetate layer was washed with water and brine, and dried over magnesium sulfate. The solvent was evaporated, and the resulting residue was purified by silica gel column chromatography (chloroform/methanol system), to give 1.78 g of the free compound of the title compound as a pale yellow oil.

Free Compound:

$^1$H-NMR(400 MHz,CDCl$_3$); δ (ppm) 0.95(t,J=7.2 Hz,3H), 1.18(t,J=7.2 Hz,3H), 1.35–1.44(m,2H), 1.61–1.68 (m,2H), 2.55(q,J=7.2 Hz,2H), 2.67(t,J=7.8 Hz,2H), 2.76(br-t,4H), 3.59(br-t,4H), 7.28(d,J=8.4 Hz,2H), 7.44(br-t,1H), 7.57(br-t,1H), 7.67(s,1H), 7.78(d, J=8.0 Hz,1H), 8.06–8.09 (m,3H).

The resulting free compound was converted into a hydrochloride in a conventional manner, and then recrystallized from ethanol/IPE, to give the title compound as a yellow powder.

Hydrochloride:

m.p.; 190–192° C. (decomp.)

¹H-NMR(400 MHz,DMSO-d₆); δ (ppm) 0.92(t,J=7.4 Hz,3H), 1.29–1.39(m,5H), 1.56–1.64(m,2H), 2.64(t,J=7.6 Hz,2H), 3.19–3.26(m,2H), 3.30–3.39(m,2H), 3.54–3.63(m, 4H), 3.98(br-d,2H), 7.33(d,J=8.4 Hz,2H), 7.60(br-t,1H), 7.74(br-t,1H), 7.98(d,J=8.0 Hz,1H), 8.05(s,1H), 8.11(d,J= 8.4 Hz,2H), 11.33(br-s,1H).

MS(FAB) m/z 374(M+H)⁺.

Example 335

Synthesis of 1-(4-ethylpiperazin-1-yl)-3-(4-methoxypyridin-2-yl)isoquinoline dihydrochloride

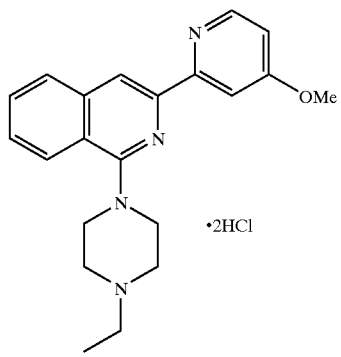

According to the method of Example 10-1, N-methyl-2-methylbenzamide (4.96 g) and 2-cyano-4-methoxypyridine (4.46 g) were reacted, to give 3-(4-methoxypyridin-2-yl)isoquinolin-1-one (2.51 g).

The resulting 3-(4-methoxypyridin-2-yl)isoquinolin-1-one (0.85 g) was reacted with phosphorus oxychloride (10 ml) according to the method of Example 10-2, to give 1-chloro-3-(4-methoxypyridin-2-yl)isoquinoline. The resulting compound was reacted, as it was, with N-ethylpiperazine (2.5 ml) at 100° C. overnight. The reaction solution was evaporated, and to the resulting residue were added ethyl acetate and purified water. The resulting ethyl acetate layer was washed with water and brine, and dried over magnesium sulfate. The solvent was evaporated, and the resulting residue was purified by silica gel column chromatography (chloroform/methanol system), to give 0.40 g of the free compound of the title compound as a pale yellow oil.

Free Compound:

¹H-NMR(400 MHz,CDCl₃); δ (ppm) 1.18(t,J=7.2 Hz,3H), 2.56(q,J=7.2 Hz,2H), 2.77(br-t,4H), 3.58(br-t,4H), 3.95(s,3H), 6.80(dd,J=2.6,5.6 Hz,1H), 7.50(br-t,1H), 7.60 (br-t,1H), 7.88(d,J=8.0 Hz,1H), 8.11(d,J=8.4 Hz,1H), 8.12 (d,J=2.6 Hz,1H), 8.40(s,1H), 8.51(d,J=5.6 Hz,1H).

The resulting free compound was converted into a hydrochloride in a conventional manner, and then recrystallized from ethanol/IPE, to give the title compound as a yellow powder.

Hydrochloride:

m.p.; 172–173° C. (decomp.)

¹H-NMR(400 MHz,DMSO-d₆); δ (ppm) 1.34(t,J=7.2 Hz,3H), 3.20–3.26(m,2H), 3.32–3.40(m,2H), 3.59–3.68(m, 4H), 4.18(s,3H), 4.22(br-d,2H), 7.50(br-d,1H), 7.80(br-t, 1H), 7.90(br-t,1H), 8.09(d,J=7.6 Hz,1H), 8.22(d,J=8.4 Hz,1H), 8.26(d,J=2.0 Hz,1H), 8.73(s,1H), 8.77(d,J=6.8 Hz,1H), 11.36(br-s,1H).

MS(FAB) m/z 349(M+H)⁺.

Example 336

Synthesis of 1-(4-ethylpiperazin-1-yl)-3-[4-(1,3-dioxolan-2-ylmethyloxy)phenyl]isoquinoline

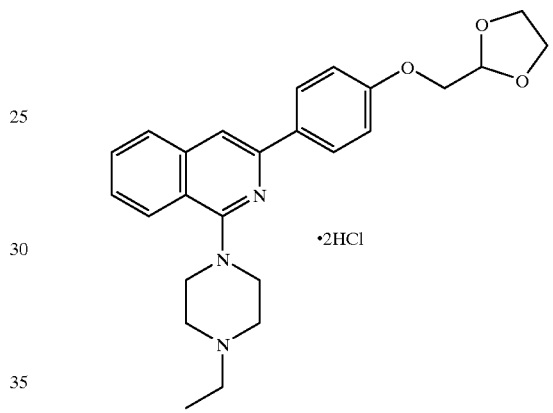

According to the method of Example 7, 1-(4-ethylpiperazin-1-yl)-3-(4-hydroxyphenyl)isoquinoline was prepared.

The resulting 1-(4-ethylpiperazin-1-yl)-3-(4-hydroxyphenyl)isoquinoline (0.53 g) was dissolved in N,N-dimethylformamide (5 ml), to which were added potassium carbonate (0.24 g) and 2-bromomethyl-1,3-dioxolane (250 ml), and the mixture was stirred at 90° C. overnight. Water was added to the reaction solution, and then the mixture was extracted with ethyl acetate. The extract was washed with brine, and dried over magnesium sulfate. The solvent was evaporated, and the resulting residue was purified by silica gel column chromatography (chloroform/methanol system), to give 0.47 g of the title compound as a pale yellow oil.

Free Compound:

¹H-NMR(400 MHz,CDCl₃); δ (ppm) 1.17(t,J=7.4 Hz,3H), 2.55(q,J=7.4 Hz,2H), 2.75(br-t,4H), 3.58(br-t,4H), 3.97–4.10(m,4H), 4.11(d,J=4.0 Hz,2H), 5.33(t,J=4.0 Hz,1H), 7.03(d,J=8.6 Hz,2H), 7.43(br-t,1H), 7.56(br-t,1H), 7.61(s,1H), 7.76(d,J=7.6 Hz,1H), 8.06(d,J=8.4 Hz,1H), 8.11 (d,J=8.6 Hz,2H).

MS(FAB) m/z 420(M+H)⁺.

Example 337

Synthesis of 1-(4-ethylpiperazin-1-yl)-3-[4-(2,3-dihydroxypropoxy)phenyl]isoquinoline dihydrochloride

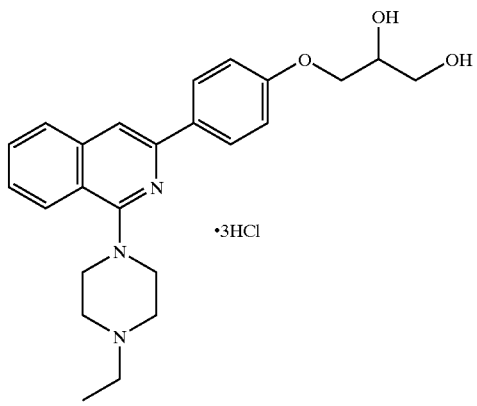

According to the method of Example 7, 1-(4-ethylpiperazin-1-yl)-3-(4-hydroxyphenyl)isoquinoline was prepared.

Sodium hydride (0.07 g) was washed with n-hexane, suspended in N,N-dimethylformamide (0.5 ml) and stirred under ice-cooling, to which was then added the resulting 1-(4-ethylpiperazin-1-yl)-3-(4-hydroxyphenyl)isoquinoline (0.52 g) dissolved in N,N-dimethylformamide (5 ml), and the mixture was stirred at room temperature for 20 min. The mixture was again ice-cooled, followed by the addition of (2,2-dimethyl-1,3-dioxolan-4-yl)methyl tosylate (0.67 g), and the mixture was stirred overnight in nitrogen atmosphere at 50° C. Water was added to the reaction solution, followed by the extraction with ethyl acetate. The extract was washed with water and brine, and then dried over magnesium sulfate. The solvent was evaporated, and the resulting residue was purified by silica gel column chromatography (chloroform/methanol system), to give 0.55 g of the acetonide-protected compound of the title compound as a pale yellow oil.

2N Hydrochloric acid (25 ml) was added to the above-mentioned protected compound (0.53 g) to dissolve, and the mixture was then left to stand at room temperature for 1 hr. A 8N aqueous solution of sodium hydroxide was added thereto, and the resulting solution was extracted with ethyl acetate. The extract was washed with a 10% aqueous solution of sodium carbonate and brine, and then dried over magnesium sulfate. The solvent was evaporated, and the resulting residue was purified by silica gel column chromatography (chloroform/methanol system), to give the free compound of the title compound as a pale yellow oil.

Free Compound:
$^1$H-NMR(400 MHz,CDCl$_3$); δ (ppm) 1.18(t,J=7.2 Hz,3H), 2.55(q,J=7.2 Hz,2H), 2.76(br-t,4H), 3.58(br-t,4H), 3.79(dd,J=5.2,11.6 Hz,1H), 3.88(dd,J=4.0,11.6 Hz,1H), 4.10–4.18(m,3H), 7.01(d,J=9.2 Hz,2H), 7.44(br-t,1H), 7.57(br-t,1H) 7.62(s,1H), 7.77(d,J=8.0 Hz,1H), 8.06(d,J=8.4 Hz,1H), 8.25(d,J=9.2 Hz,2H).

The resulting free compound was converted into a hydrochloride in a conventional manner, and then recrystallized from ethanol/IPE, to give 0.26 g of the title compound as a yellow powder.

Hydrochloride:
m.p.; 133–135° C. (decomp.)
$^1$H-NMR(400 MHz,DMSO-d$_6$); δ (ppm) 1.47(t,J=7.2 Hz,3H), 3.36–3.41(m,2H), 3.52–3.58(m,2H), 3.66–3.82(m, 6H), 3.99–4.09(m,2H), 4.16(dd,J=4.4,9.6 Hz,1H), 4.29(br-d,2H), 7.13(d,J=8.8 Hz,2H), 7.71(br-t,1H), 7.86(br-t,1H), 7.88(s,1H), 7.97(d,J=8.8 Hz,2H), 8.01(d,J=8.0 Hz,1H), 8.24 (d,J=8.4 Hz,1H), 10.79(br-s,1H).
MS(FAB) m/z 408(M+H)$^+$.

Example 338

Synthesis of 1-(4-ethylpiperazin-1-yl)-3-(4-carbamoylmethoxyphenyl)isoquinoline dihydrochloride

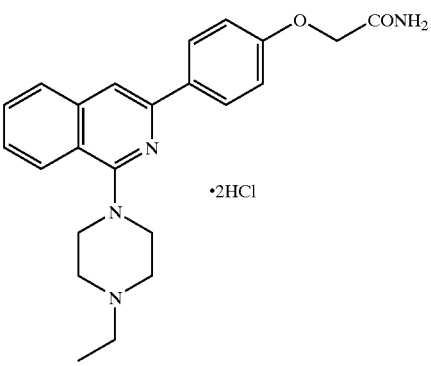

According to the method of Example 7, 1-(4-ethylpiperazin-1-yl)-3-(4-hydroxyphenyl)isoquinoline was prepared.

The resulting 1-(4-ethylpiperazin-1-yl)-3-(4-hydroxyphenyl)isoquinoline (0.57 g) was dissolved in N,N-dimethylformamide (5 ml), to which were added potassium carbonate (0.24 g) and ethyl bromoacetate (210 ml), and the mixture was stirred at room temperature for 2 days. Water was added to the reaction solution, followed by the extraction with ethyl acetate. The extract was washed with water and brine, and dried over magnesium sulfate. The solvent was evaporated, and the resulting residue was purified by silica gel column chromatography (chloroform/methanol system), to give obtain 1-(4-ethylpiperazin-1-yl)-3-[4-(ethoxycarbonylmethoxy)phenyl]isoquinoline (0.57 g) as a pale yellow viscous oil.

To the resulting 1-(4-ethylpiperazin-1-yl)-3-[4-(ethoxycarbonylmethoxy)phenyl]isoquinoline (0.55 g) was added a solution of 10% ammonia/ethanol (20 ml) for dissolution, and the mixture was sealed and left to stand at room temperature for 2 days. The solvent was evaporated, and the resulting residue was purified by recrystallization (chloroform/n-hexane system), to give 0.47 g of the free compound of the title compound as a colorless powder.

Free Compound:
$^1$H-NMR(400 MHz,CDCl$_3$); δ (ppm) 1.18(t,J=7.2 Hz,3H), 2.55(q,J=7.2 Hz,2H), 2.76(br-t,4H), 3.59(br-t,4H), 4.58(s,2H), 5.64(br-s,1H), 6.59(br-s,1H), 7.03(d,J=8.8 Hz,2H), 7.45(br-t,1H), 7.58(br-t,1H), 7.63(s,1H), 7.78(d,J=8.0 Hz,1H), 8.07(d,J=8.4 Hz,1H), 8.15(d,J=8.8 Hz,2H).

The resulting free compound was converted into a hydrochloride in a conventional manner, and then recrystallized from ethanol/IPE, to give the title compound (0.26 g) as a yellow powder.

Hydrochloride:
$^1$H-NMR(400 MHz,DMSO-d$_6$); δ (ppm) 1.33(t,J=7.2 Hz,3H), 3.20–3.27(m,2H), 3.31–3.39(m,2H), 3.50(br-t,2H), 3.62(br-d,2H), 4.00(br-d,2H), 4.51(s,2H), 7.09(d,J=9.0

Hz,2H), 7.44(br-s,1H), 7.56–7.60(m,2H), 7.73(br-t,1H), 7.96(d,J=8.0 Hz,1H), 8.01(s,1H), 8.10(d,J=8.4 Hz,1H), 8.16(d,J=9.0 Hz,2H), 10.78(br-s,1H).

MS(FAB) m/z 391(M+H)+.

Example 339

Synthesis of 1-(4-ethylpiperazin-1-yl)-3-(4-trifluoromethoxyphenyl)isoquinoline dihydrochloride

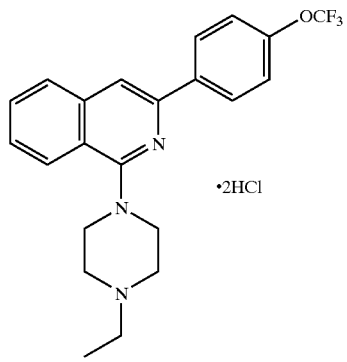

According to the method of Example 10-1, N-methyl-2-methylbenzamide (5.97 g) and 4-trifluoromethoxybenzonitrile (7.49 g) were reacted, to give 3-(4-trifluoromethoxyphenyl)isoquinolin-1-one (3.04 g).

The resulting 3-(4-trifluoromethoxyphenyl)isoquinolin-1-one (3.01 g) was reacted with phosphorus oxychloride (20 ml) according to the method of Example 10-2, to give 1-chloro-3-(4-trifluoromethoxyphenyl)isoquinoline, which was then reacted as it was with N-ethylpiperazine (40 ml) at 90° C. overnight. The reaction solution was evaporated, and to the resulting residue were added ethyl acetate and purified water. The ethyl acetate layer was washed with water and brine, and dried over magnesium sulfate. The solvent was evaporated, and the resulting residue was purified by silica gel column chromatography (chloroform/methanol system), to give 3.65 g of the free compound of the title compound as a pale yellow oil.

Free Compound:

$^1$H-NMR(400 MHz,CDCl$_3$); δ (ppm) 1.18(t,J=7.4 Hz,3H), 2.56(q,J=7.4 Hz,2H), 2.76(br-t,4H), 3.59(br-t,4H), 7.31(d, J=8.8 Hz,2H), 7.48(br-t,1H), 7.60(br-t,1H), 7.67(s,1H), 7.80(d,J=7.6 Hz,1H), 8.08(d,J=8.4 Hz,1H), 8.19(d,J=8.8 Hz,2H).

The resulting free compound was converted into a hydrochloride in a conventional manner, and then recrystallized from ethanol/ether, to give the title compound as a yellow powder.

Hydrochloride:

m.p.; 113–115° C.

$^1$H-NMR(400 MHz,DMSO-d$_6$); δ (ppm) 1.35(t,J=7.4 Hz,3H), 3.19–3.26(m,2H), 3.30–3.39(m,2H), 3.56–3.63(m,4H), 4.01(br-d,2H), 7.51(d,J=8.4 Hz,2H), 7.64(br-t,1H), 7.77(br-t,1H), 8.01(d,J=8.4 Hz,1H), 8.14(br-d,1H), 8.15(s,1H), 8.33(d,J=8.4 Hz,2H), 11.45(br-s,1H).

MS(FAB) m/z 402(M+H)+.

Example 340

Synthesis of 1-(4-ethylpiperazin-1-yl)-3-[4-(2-hydroxyethoxy)-3-methoxyphenyl]isoquinoline dihydrochloride

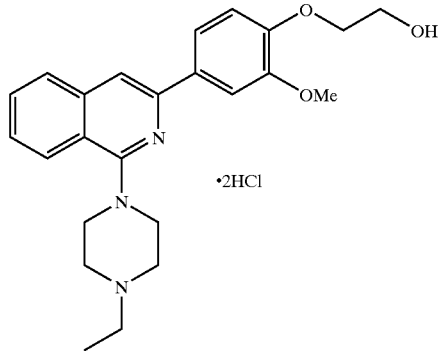

According to the method of Example 10-1, N-methyl-2-methylbenzamide (5.97 g) and 4-(2-benzyloxyethoxy)-3-methoxybenzonitrile (9.57 g) were reacted, to give 3-[4-(2-benzyloxyethoxy)-3-methoxyphenyl]isoquinolin-1-one (3.20 g).

The resulting 3-[4-(2-benzyloxyethoxy)-3-methoxyphenyl]isoquinolin-1-one (3.15 g) was reacted with phosphorus oxychloride (20 ml) according to the method of Example 10-2, to give 3-[4-(2-benzyloxyethoxy)-3-methoxyphenyl]-2-chloroisoquinoline. Then, N-ethylpiperazine (30 ml) and potassium carbonate (1.83 g) were added to the resulting compound as it was. The resulting mixture was reacted at 90° C. overnight. The reaction solution was evaporated, and to the resulting residue were added ethyl acetate and purified water. The ethyl acetate layer was washed with water and brine, and dried over magnesium sulfate. The solvent was evaporated, to give 3-[4-(2-benzyloxyethoxy)-3-methoxyphenyl]-1-(4-ethylpiperazin-1-yl)isoquinoline.

The resulting compound was dissolved in methanol (100 ml), followed by the addition of 10% palladium/carbon catalyst (0.50 g), and then the overnight catalytic reduction was conducted at atmospheric pressure. The catalyst was filtered off, and the solvent was evaporated. Water was added to the resulting residue, to which was then added sodium carbonate to adjust the resulting solution to pH 8, to give 1-(4-ethylpiperazin-1-yl)-3-[4-(2-hydroxyethoxy)-3-methoxyphenyl]isoquinoline as an insoluble matter. The filtrate was extracted with ethyl acetate, washed with brine, and dried over magnesium sulfate. The solvent was evaporated, and the resulting 1-(4-ethylpiperazin-1-yl)-3-[4-(2-hydroxyethoxy)-3-methoxyphenyl]isoquinoline was combined with the same compound previously collected by filtration, recrystallized from chloroform/n-hexane, to give 1.20 g of the free compound of the title compound as a colorless powder.

Free Compound:

$^1$H-NMR(400 MHz,CDCl$_3$); δ (ppm) 1.18(t,J=7.2 Hz,3H), 2.56(q,J=7.2 Hz,2H), 2.77(br-s,4H), 3.58(br-s,4H), 3.97(t,J=4.4 Hz,2H), 4.00(s,3H), 4.20(t,J=4.4 Hz,2H), 7.03(d,J=8.4 Hz,1H), 7.45(br-t,1H), 7.59(br-t,1H), 7.64(s,1H), 7.69(dd,J=2.0,8.4 Hz,1H), 7.78(d,J=8.0 Hz,1H), 7.86(d,J=2.0 Hz,1H), 8.08(d,J=8.0 Hz,1H).

The resulting free compound was converted into a hydrochloride in a conventional manner, and then reprecipitated with ethanol/IPE, to give the title compound as a yellow powder.

m.p.: 128–129° C.

$^1$H-NMR(400 MHz,DMSO-$d_6$); δ (ppm) 1.33(t,J=7.4 Hz,3H), 3.20–3.26(m,2H), 3.31–3.39(m,2H), 3.53(br-t,2H), 3.63(br-d,2H), 3.76(t,J=5.2 Hz,2H), 3.90(s,3H), 4.00(br-d, 2H), 4.05(t,J=5.2 Hz,2H), 7.09(d,J=8.4 Hz,1H), 7.58(br-t, 1H), 7.73(br-t,1H), 7.76–7.80(m,2H), 7.96(d,J=8.4 Hz,1H), 8.04(s,1H), 8.10(d,J=8.0 Hz,1H), 10.95(br-s,1H).

MS(FAB) m/z 408(M+H)$^+$.

Example 341

Synthesis of 1-(4-ethylpiperazin-1-yl)-3-(4-methylthiophenyl)isoquinoline dihdyrochloride

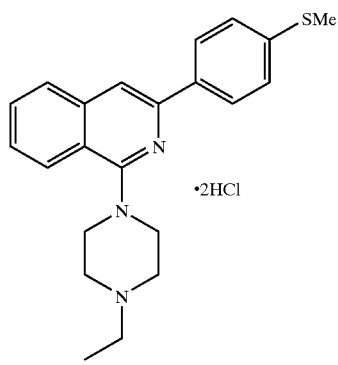

According to the method of Example 10-1, N-methyl-2-methylbenzamide (5.97 g) and 4-cyanothioanisole (5.97 g) were reacted, to give 3-(4-methylthiophenyl)isoquinolin-1-one (5.00 g).

The resulting 3-(4-methylthiophenyl)isoquinolin-1-one (0.73 g) was reacted with phosphorus oxychloride (5 ml) according to the method of Example 10-2, to give 1-chloro-3-(4-methylthiophenyl)isoquinoline. Then, N-ethylpiperazine (10 ml) and potassium carbonate (0.36 g) were added to the resulting product as it was. The resulting mixture were reacted at 100° C. overnight. The reaction solution was evaporated, and the resulting residue were added ethyl acetate and purified water. The ethyl acetate layer was washed with water and brine, and dried over magnesium sulfate. The solvent was evaporated, and the resulting residue was purified by silica gel column chromatography (chloroform/methanol system), to give 0.95 g of the free compound of the title compound as a pale yellow oil.

Free Compound:

$^1$H-NMR(400 MHz,CDCl$_3$); δ (ppm) 1.18(t,J=7.2 Hz,3H), 2.54(s,3H), 2.56(q,J=7.2 Hz,2H), 2.76(br-t,4H), 3.58(br-t,4H), 7.35(d,J=8.4 Hz,2H), 7.45(br-t,1H), 7.58(br-t,1H), 7.66(s,1H), 7.78(d,J=8.0 Hz,1H), 8.07(d,J=8.4 Hz,1H), 8.11(d,J=8.4 Hz,2H).

The resulting free compound was converted into a hydrochloride in a conventional manner, and then recrystallized from ethanol/IPE, to give the title compound as a yellow powder.

Hydrochloride:

m.p.; 215–218° C. (decomp.)

$^1$H-NMR(400 MHz,DMSO-$d_6$); δ (ppm) 1.34(t,J=7.4 Hz,3H), 2.54(s,3H), 3.19–3.26(m,2H), 3.31–3.38(m,2H), 3.54(br-t,2H), 3.62(br-d,2H), 3.99(br-d,2H), 7.39(d,J=8.6 Hz,2H), 7.60(br-t,1H), 7.74(br-t,1H), 7.98(d,J=7.6 Hz,1H), 8.08(s,1H), 8.11(d,J=8.4 Hz,1H), 8.16(d,J=8.6 Hz,2H), 11.14(br-s,1H).

MS(FAB) m/z 364(M+H)$^+$.

Example 342

Synthesis of 1-(4-ethylpiperazin-1-yl)-3-(4-methylsulfonylphenyl)isoquinoline dihydrochloride

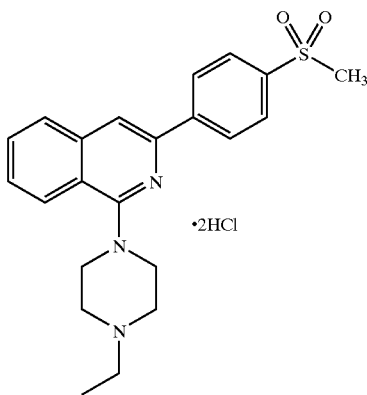

According to the method of Example 10-1, N-methyl-2-methylbenzamide (5.97 g) and 4-cyanothioanisole (5.97 g) were reacted, to give 3-(4-methylthiophenyl)isoquinolin-1-one (5.00 g).

The resulting 3-(4-methylthiophenyl)isoquinolin-1-one (2.18 g) was reacted with phosphorus oxychloride (20 ml) according to the method of Example 10-2, to give 1-chloro-3-(4-methoxythiophenyl) isoquinoline. N-Formylpiperazine (4.66 g), potassium carbonate (1.13 g) and dimethyl sulfoxide (20 ml) were added to the resulting product as it was, and the resulting mixture was reacted at 100° C. overnight. The reaction solution was evaporated, and to the resulting residue were added ethyl acetate and purified water. The ethyl acetate layer was washed with water (six times) and brine, and dried over magnesium sulfate. The solvent was evaporated, and the resulting residue was purified by silica gel column chromatography (ethyl acetate/n-hexane system), to give 1-(4-formylpiperazin-1-yl)-3-(4-methylthiophenyl)isoquinoline (2.03 g) as a colorless amorphous.

The resulting 1-(4-formylpiperazin-1-yl)-3-(4-methylthiophenyl)isoquinoline (0.80 g) was dissolved in chloroform (40 ml), and the mixture was stirred under ice-cooling, to which was then added m-chloroperbenzoic acid (2.63 g) dissolved in chloroform (20 ml), and the mixture was stirred overnight. A 5N aqueous solution of sodium hydroxide was added to the resulting mixture, which was then extracted with chloroform. The organic layer was washed sequentially with water and brine, and dried over magnesium sulfate. The solvent was evaporated, and the resulting residue was purified by silica gel column chromatography (ethyl acetate/n-hexane system), to give 1-(4-formylpiperazin-1-yl)-3-(4-methylsulfonylphenyl) isoquinoline (0.80 g).

To the resulting 1-(4-formylpiperazin-1-yl)-3-(4-methylsulfonylphenyl)isoquinoline (0.78 g) were added ethanol (30 ml) and a 8N aqueous solution of sodium hydroxide (740 ml), followed by heating under reflux in nitrogen atmosphere for 4 hr. The solvent was evaporated, and to the resulting residue were added water and ethyl acetate, and the organic layer was separated. Then, it was washed with brine, dried over magnesium sulfate. The solvent was evaporated, to give 1-(piperazin-1-yl)-3-(4-methylsulfonylphenyl)isoquinoline (0.62 g) as a pale yellow amorphous.

The resulting 1-(piperazin-1-yl)-3-(4-methylsulfonylphenyl)isoquinoline (0.61 g) was dissolved in N,N-dimethylformamide (5 ml), followed by the addition of triethylamine (255 ml) and ethyl iodide (146 ml), and the mixture was sealed for overnight reaction at 50° C. Water was added to the reaction solution, and then it was extracted with ethyl acetate. The ethyl acetate layer was washed with water (three times) and brine, and dried over magnesium sulfate. The solvent was evaporated, and the resulting residue was recrystallized from ethyl acetate/n-hexane, to give 0.46 g of the free compound of the title compound as a pale brown powder.

Free Compound:
$^1$H-NMR(400 MHz,CDCl$_3$); δ (ppm) 1.18(t,J=7.2 Hz,3H), 2.57(q,J=7.2 Hz,2H), 2.77(br-t,4H), 3.10(s,3H), 3.60(br-t,4H), 7.54(br-t,1H), 7.64(br-t,1H), 7.78(s,1H), 7.84 (d,J=8.0 Hz,1H), 8.03(d,J=8.4 Hz,2H), 8.11(d,J=8.4 Hz,1H), 8.36(d,J=8.4 Hz,2H).

The resulting free compound was converted into a hydrochloride in a conventional manner, and then recrystallized from ethanol/IPE, to give the title compound as a yellow powder.

Hydrochloride:
m.p.; 216.5–218° C. (decomp.)
$^1$H-NMR(400 MHz,DMSO-d$_6$); δ (ppm) 1.33(t,J=7.2 Hz,3H), 3.23(br-s,2H), 3.28(s,3H), 3.31–3.40(m,2H), 3.55 (br-t,2H), 3.63(br-d,2H), 4.04(br-d,2H), 7.68(br-t,1H), 7.80 (br-t,1H), 8.05(d,J=7.6 Hz,1H), 8.06(d,J=8.4 Hz,2H), 8.16 (d,J=8.4 Hz,1H), 8.28(s,1H), 8.46(d,J=8.4 Hz,2H), 11.02(br-s,1H).
MS(FAB) m/z 396(M+H)$^+$.

Example 343

Synthesis of 1-(4-ethylpiperazin-1-yl)-3-[4-(2-hydroxy-3-methoxypropoxy)phenyl]isoquinoline dihydrochloride

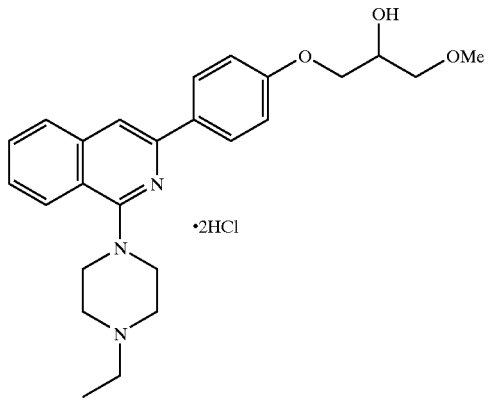

According to the method of Example 7, 1-(4-ethylpiperazin-1-yl)-3-(4-hydroxyphenyl)isoquinoline was obtained.

To the resulting 1-(4-ethylpiperazin-1-yl)-3-(4-hydroxyphenyl)isoquinoline (0.52 g) were added dimethyl sulfoxide (5 ml), 2-(methoxymethyl)oxirane (3 ml) and potassium carbonate (0.21 g), and the resulting mixture was reacted in a sealed tube at 120° C. for 1 day. Water was added to the reaction solution, and then it was extracted with ethyl acetate. The ethyl acetate layer was washed with water (six times) and brine, and dried over magnesium sulfate. The solvent was evaporated, and the resulting residue was purified by silica gel column chromatography (chloroform/methanol system), to give 0.15 g of the free compound of the title compound as a pale yellow oil.

Free Compound:
$^1$H-NMR(400 MHz,CDCl$_3$) δ (ppm) 1.17(t,J=7.2 Hz,3H), 2.55(q,J=7.2 Hz,2H), 2.76(br-t,4H), 3.43(s,3H), 3.55–3.61 (m,6H), 4.05–4.12(m,2H), 4.18–4.23(m,1H), 7.01(d,J=9.2 Hz,2H), 7.43(br-t,1H), 7.56(br-t,1H), 7.61(s,1H), 7.76(d,J= 8.0 Hz,1H), 8.05(d,J=8.0 Hz,1H), 8.11(d,J=8.8 Hz,2H).

The resulting free compound was converted into a hydrochloride in a conventional manner, and then reprecipitated with ethanol/IPE, to give the title compound as a yellow powder.

Hydrochloride:
m.p.; 216.5–218° C. (decomp.)
$^1$H-NMR(400 MHz,DMSO-d$_6$); δ (ppm) 1.33(t,J=7.2 Hz,3H), 3.20–3.26(m,2H), 3.30(s,3H), 3.33–3.55(m,6H), 3.62(br-d,2H), 3.94–4.04(m,5H), 7.07(d,J=9.0 Hz,2H), 7.57 (br-t,1H), 7.72(br-t,1H), 7.96(d,J=8.0 Hz,1H), 8.00(s,1H), 8.10(d,J=8.8 Hz,1H), 8.15(d,J=9.0 Hz,2H), 10.99(br-s,1H).
MS(FAB) m/z 422(M+H)$^+$.

Example 344

Synthesis of 1-(4-ethylpiperazin-1-yl)-3-(2-methoxypyridin-5-yl)isoquinoline

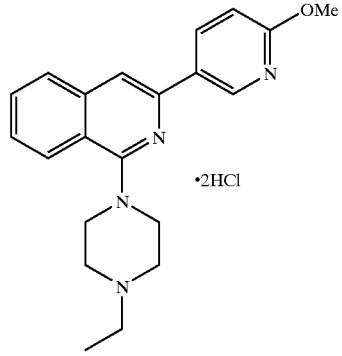

2-Methoxy-5-tributylstannylpyridine (1.41 g) and 3-bromo-1-(4-ethylpiperazin-1-yl)isoquinoline (0.57 g) obtained in Example 28-2 were heated under reflux in the presence of tetrakistriphenylphosphinepalladium(0) (0.10 g) in xylene in nitrogen atmosphere for 30 min. After cooling, the reaction solution was filtered and extracted in 2N hydrochloric acid. The aqueous layer was washed with ethyl acetate twice. The resulting aqueous layer was adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, and the resulting residue was purified by silica gel column chromatography (chloroform/methanol system), to give 0.38 g of the free compound of the title compound as a pale brown powder.

Free Compound:
$^1$H-NMR(400 MHz,CDCl$_3$); δ (ppm) 1.16(t,J=7.2 Hz,3H), 2.53(q,J=7.2 Hz,2H), 2.72(br-t,4H), 3.57(br-t,4H), 4.00(s,3H), 6.82(d,J=8.8 Hz,1H), 7.43(br-t,1H), 7.54(s,1H), 7.55(br-t,1H), 7.74(d,J=8.0 Hz,1H), 8.04(d,J=8.4 Hz,1H), 8.30(dd,J=2.4,8.8 Hz,1H), 8.97(d,J=2.4 Hz,1H).
MS(FAB) m/z 349(M+H)+.

Example 345

Synthesis of 1-(4-ethylpiperazin-1-yl)-[4-(1-hydroxy-1-methylethyl)phenyl]isoquinoline

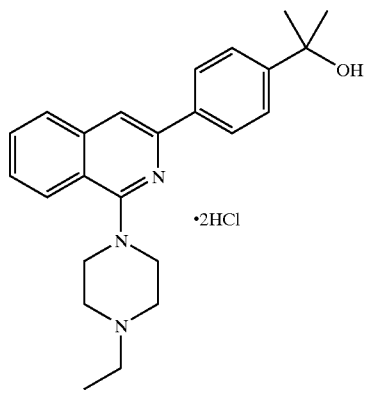

4-(2-Methyl-1,3-dioxolan-2-yl)phenylboric acid (0.41 g) and 3-bromo-1-(4-ethylpiperazin-1-yl)isoquinoline (0.62 g) were reacted in the presence of tetrakistriphenylphosphinepalladium(0) (0.11 g) in toluene (50 ml) and a 10% aqueous solution of sodium carbonate (30 ml) in nitrogen atmosphere at 120° C. for 30 min. The organic layer was separated, washed with brine and dried over magnesium sulfate. The solvent was evaporated, and the resulting residue was purified by silica gel column chromatography (chloroform/methanol system), to give 1-(4-ethylpiperazin-1-yl)-3-[4-(2-methyl-1,3-dioxolan-2-yl)phenyl]isoquinoline.

The resulting compound was dissolved in ethyl acetate and extracted with 2N hydrochloric acid. The aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, to give 0.55 g of 1-(4-ethylpiperazin-1-yl)-3-(4-acetylphenyl)isoquinoline as a pale brown viscous oil.

The resulting 1-(4-ethylpiperazin-1-yl)-3-(4-acetylphenyl)isoquinoline (0.10 g) was dissolved in tetrahydrofuran (10 ml) and stirred under ice-cooling, to which was then added 3.0M methylmagnesium bromide/ether solution (1.1 ml), and the mixture was further stirred for 1.5 hr. An aqueous solution of saturated ammonium chloride, a 10% aqueous solution of sodium carbonate and ethyl acetate were added to the resulting mixture, the mixture was stirred. The organic layer was separated, and then it was washed with brine, and dried over magnesium sulfate. The solvent was evaporated, and the resulting residue was purified by silica gel column chromatography (chloroform/methanol system), to give 0.05 g of the free compound of the title compound as a pale brown amorphous.
Free Compound:
$^1$H-NMR(400 MHz,CDCl$_3$); δ (ppm) 1.17(t,J=7.2 Hz,3H), 1.63(s,6H), 2.56(q,J=7.2 Hz,2H), 2.76(br-t,4H), 3.59(br-t,4H), 7.45(br-t,1H), 7.56–7.61(m,3H), 7.68(s,1H), 7.78(d,J=8.0 Hz,1H), 8.07(d,J=7.6 Hz,1H), 8.14(d,J=8.4 Hz,2H).
MS(FAB) m/z 376(M+H)+.

Example 346

Synthesis of 1-(4-ethylpiperazin-1-yl)-3-{4-(N-(2-hydroxyethyl)carbamoyl]phenyl}isoquinoline dihydrochloride

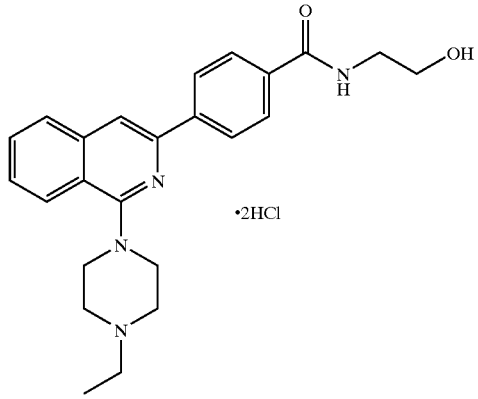

N-(2-Benzyloxyethyl)-4-tributylstannylbenzamide (1.23 g) and 3-bromo-1-(4-ethylpiperazin-1-yl)isoquinoline (0.49 g) were heated under reflux in the presence of tetrakistriphenylphosphinepalladium(0) (0.13 g) in xylene in nitrogen atmosphere for 3 hr. After cooling, the reaction solution was filtered and concentrated. The resulting residue was purified by silica gel column chromatography (chloroform/methanol system). The resulting product was dissolved in ethyl acetate and extracted with 2N hydrochloric acid. The aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, to give 1-(4-ethylpiperazin-1-yl)-3-{4-[N-(2-benzyloxyethyl)carbamoyl]phenyl}isoquinoline (0.17 g) as a pale brown viscous oil.

The resulting 1-(4-ethylpiperazin-1-yl)-3-{4-[N-(2-benzyloxyethyl)carbamoyl]phenyl}isoquinoline (0.17 g) was converted into a hydrochloride in a conventional manner. The resulting hydrochloride was dissolved in methanol (10 ml), followed by the addition of 10% palladium/carbon catalyst (0.03 g), and the catalytic reduction was conducted at atmospheric pressure for 2 days. The catalyst was filtered off, and the solvent was evaporated. Water was added to the resulting residue, to which was then added sodium carbonate to adjust the resulting solution to pH 8, and the resulting mixture was extracted with ethyl acetate. The extract was washed with brine, and dried over magnesium sulfate. The solvent was evaporated, and the resulting residue was purified by silica gel column chromatography (chloroform/methanol system), to give 0.05 g of the free compound of the title compound as a pale brown amorphous.
Free Compound:
$^1$H-NMR(400 MHz,CDCl$_3$); δ (ppm) 1.17(t,J=7.2 Hz,3H), 2.56(q,J=7.2 Hz,2H), 2.76(br-t,4H), 2.84(br-s,1H), 3.58(br-t,4H), 3.65(br-q,2H), 3.85(t,J=5.0 Hz,2H), 6.88(t,J=5.6 Hz,1H), 7.48(br-t,1H), 7.58(br-t,1H), 7.69(s,1H), 7.75 (d,J=7.6 Hz,1H), 7.87(d,J=8.4 Hz,2H), 8.06(d,J=8.0 Hz,1H), 8.19(d,J=8.4 Hz,2H).

The resulting free compound was converted into a hydrochloride in a conventional manner, and then reprecipitated with ethanol/IPE, to give the title compound as a yellow powder.

Hydrochloride:
m.p.; 154–155° C.
$^1$H-NMR(400 MHz,DMSO-d$_6$); δ (ppm) 1.33(t,J=7.2 Hz,3H), 3.20–3.27(m,2H), 3.32–3.40(m,4H), 3.51–3.57(m,4H), 3.64(br-d,2H), 4.02(br-d,2H), 7.65(br-t,1H), 7.78(br-t,1H), 8.00–8.03(m,3H), 8.14(d,J=8.4 Hz,1H), 8.22(s,1H), 8.29(d,J=8.4 Hz,2H), 8.58(t,J=5.6 Hz,1H), 10.96(br-s,1H).
MS(FAB) m/z 405(M+H)$^+$.

Example 347

Synthesis of 1-(4-ethylpiperazin-1-yl)-3-{4-[N-(2-hydroxyethyl)sulfamoyl]phenyl}isoquinoline dihydrochloride

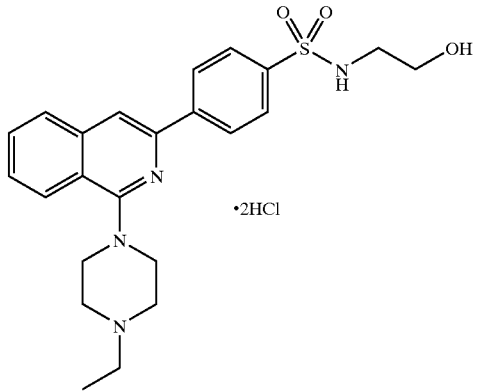

N-(2-Benzyloxyethyl)4-tributylstannylbenzenesulfonamide (0.92 g) and 3-bromo-1-(4-ethylpiperazin-1-yl)isoquinoline (0.42 g) were heated under reflux in the presence of tetrakistriphenylphosphinepalladium(0) (0.09 g) in xylene in nitrogen atmosphere for 45 min. After cooling, the reaction solution was filtered and concentrated. The residue was purified by silica gel column chromatography (chloroform/methanol system). The resulting product was dissolved in ethyl acetate and extracted with 2N hydrochloric acid. The aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, to give 1-(4-ethylpiperazin-1-yl)-3-{4-[N-(2-benzyloxyethyl)sulfamoyl]phenyl}isoquinoline (0.34 g) as a pale brown oil.

The resulting 1-(4-ethylpiperazin-1-yl)-3-{4-[N-(2-benzyloxyethyl)sulfamoyl]phenyl}isoquinoline (0.34 g) was converted into a hydrochloride in a conventional manner. The resulting hydrochloride was dissolved in methanol (20 ml), followed by the addition of 10% palladium/carbon catalyst (0.08 g), and the catalytic reduction was conducted at atmospheric pressure for 2 days. The catalyst was filtered off, and the solvent was evaporated. Water was added to the resulting residue, to which was then added sodium carbonate to adjust the resulting solution to pH 8, and the resulting mixture was extracted with ethyl acetate. The extract was washed with brine, and dried over magnesium sulfate. The solvent was evaporated, and the resulting residue was purified by silica gel column chromatography (chloroform/methanol system), give 0.19 g of the free compound of the title compound as a pale brown amorphous.
Free Compound:
$^1$H-NMR(400 MHz,CDCl$_3$); δ (ppm) 1.18(t,J=7.2 Hz,3H), 2.57(q,J=7.2 Hz,2H), 2.77(br-t,4H), 3.16(br-q,2H), 3.60(br-t,2H), 3.72(t,J=5.0 Hz,2H), 4.93(t,J=5.8 Hz,1H), 7.53(br-t,1H), 7.64(br-t,1H), 7.76(s,1H), 7.82(d,J=8.8 Hz,1H), 7.96(d,J=8.4 Hz,2H), 8.10(d,J=7.6 Hz,1H), 8.32(d,J=8.4 Hz,2H).

The resulting free compound was converted into a hydrochloride in a conventional manner, and then reprecipitated with ethanol/IPE, to give the title compound as a yellow powder.
Hydrochloride:
m.p.; 136–138.5° C.
$^1$H-NMR(400 MHz,DMSO-d$_6$); δ (ppm) 1.33(t,J=7.2 Hz,3H), 2.84(br-q,2H), 3.21–3.28(m,2H), 3.34–3.41(m,2H), 3.39(t,J=6.4 Hz,2H), 3.51(br-t,2H), 3.63(br-d,2H0,4.04(br-d,2H), 7.67(br-t,1H), 7.71(br-t,1H), 7.79(br-t,1H), 7.93(d,J=8.6 Hz,2H), 8.04(d,J=8.0 Hz,1H), 8.16(d,J=8.4 Hz,1H), 8.24(s,1H), 8.40(d,J=8.6 Hz,2H), 10.69(br-s,1H).
MS(FAB) m/z 441(M+H)$^+$.

Example 348

Synthesis of 1-(4-ethylpiperazin-1-yl)-3-[4-(1-hydroxyethyl)phenyl]isoquinoline dihydrochloride or compound identified by the following analytical data and synthetic procedures

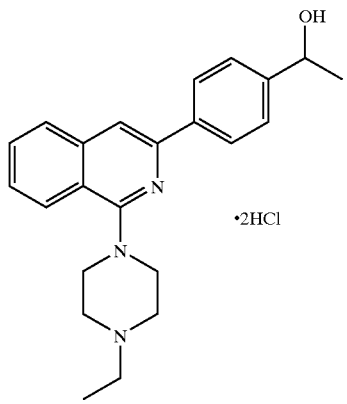

1-(4-Ethylpiperazin-1-yl)-3-(4-acetylphenyl)isoquinoline (0.20 g) obtained as an intermediate in Example 345 was dissolved in methanol (20 ml), followed by the addition of sodium borohydride until the starting material disappeared on TLC. The solvent was evaporated, and to the resulting residue were added water and a 8N aqueous solution of sodium hydroxide to adjust the resulting solution to pH 10, which was then extracted with ethyl acetate. Then, the extract was washed with a 10% aqueous solution of sodium carbonate and brine, and dried over magnesium sulfate. The solvent was evaporated, and the resulting residue was purified by silica gel column chromatography (chloroform/methanol system), to give 0.13 g of the free compound of the title compound as a pale brown amorphous.
Free Compound:
$^1$H-NMR(400 MHz,CDCl$_3$); δ (ppm) 1.17(t,J=7.2 Hz,3H), 1.54(d,J=6.4 Hz,3H), 2.43(br-s,1H), 2.55(q,J=7.2 Hz,2H), 2.74(br-t,4H), 3.57(br-t,4H), 4.95(q,J=6.4 Hz,1H), 7.45(br-t,1H), 7.47(d,J=8.4 Hz,2H), 7.58(br-t,1H), 7.67(s,1H), 7.77(d,J=8.0 Hz,1H), 8.06(d,J=8.4 Hz,1H), 8.14(d,J=8.4 Hz,2H).

The resulting free compound was converted into a hydrochloride in a conventional manner, and then reprecipitated with ethanol/IPE, to give the title compound as a yellow powder.

Hydrochloride:

m.p.; 135.5–136° C.

$^1$H-NMR(400 MHz,DMSO-d$_6$); δ (ppm) 1.33(t,J=7.2 Hz,3H), 1.37(d,J=6.4 Hz,3H), 3.20–3.27(m,2H), 3.32–3.39 (m,2H), 3.51(br-t,2H), 3.63(br-d,2H), 4.01(br-d,2H), 4.79(q, J=6.4 Hz,1H), 7.47(d,J=8.4 Hz,2H), 7.61(br-t,1H), 7.74(br-t,1H), 7.99(d,J=8.4 Hz,1H), 8.07(s,1H), 8.12(d,J=8.0 Hz,1H), 8.15(d,J=8.4 Hz,2H), 10.79(br-s,1H).

MS(FAB) m/z 362(M+H)$^+$.

Example 349

Synthesis of 1-(4-ethylpiperazin-1-yl)-3-[4-propylsulfonyl)phenyl]isoquinoline dihydrochloride

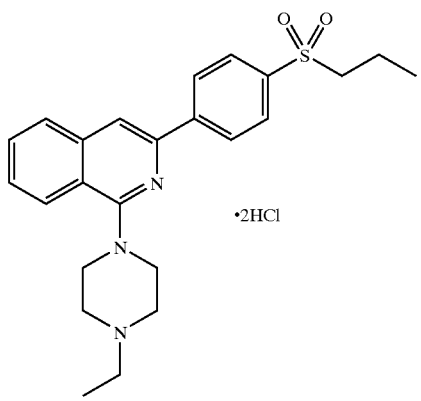

(4-Tributylstannylphenyl)propylsulfone (1.24 g) and 3-bromo-1-(4-ethylpiperazin-1-yl)isoquinoline (0.54 g) were heated under reflux in the presence of tetrakistriphenylphosphinepalladium(0) (0.15 g) in xylene in nitrogen atmosphere for 1 day. After cooling, the reaction solution was diluted with ethyl acetate and filtered. The filtrate was extracted with 2N hydrochloric acid, and the resulting aqueous layer was washed with ethyl acetate, adjusted to pH 10 with a 8N aqueous solution of sodium hydroxide, which was then extracted with ethyl acetate. The extract was washed with a 10% aqueous solution of sodium carbonate and brine, and dried over magnesium sulfate. The solvent was evaporated, and the resulting residue was purified by silica gel column chromatography (chloroform/methanol system), to give 0.60 g of the free compound of the title compound as a pale brown amorphous.

Free Compound:

$^1$H-NMR(400 MHz,CDCl$_3$); δ (ppm) 1.01(t,J=7.2 Hz,3H), 1.18(t,J=7.2 Hz,3H), 1.77–1.83(m,2H), 2.56(q,J=7.2 Hz,2H), 2.77(br-t,4H), 3.09–3.13(m,2H), 3.59(br-t,4H), 7.54(br-t,1H), 7.62(br-t,1H), 7.83(br-d,1H), 7.98(d,J=8.8 Hz,2H), 8.10(br-d,1H), 8.35(d,J=8.8 Hz,2H).

The resulting free compound was converted into a hydrochloride in a conventional manner, and then reprecipitated with ethanol/IPE, to give the title compound as a yellow powder.

Hydrochloride:

m.p.; 240.5–242° C. (decomp.)

$^1$H-NMR(400 MHz,DMSO-d$_6$); δ (ppm) 0.94(t,J=7.4 Hz,3H), 1.34(t,J=7.2 Hz,3H), 1.55–1.65(m,2H), 3.20–3.27 (m,2H), 3.28–3.40(m,4H), 3.50–3.64(m,4H), 4.03(br-d,2H), 7.68(br-t,1H), 7.80(br-t,1H), 8.02(d,J=8.4 Hz,2H), 8.05(d, J=7.6 Hz,1H), 8.16(d,J=8.4 Hz,1H), 8.28(s,1H), 8.47(d,J= 8.4 Hz,2H), 11.25(br-s,1H).

MS(FAB) m/z 424(M+H)$^+$.

Example 350

Synthesis of 1-(4-ethylpiperazin-1-yl)-3-{4-[(3-methoxypropyl)sulfonyl]phenyl}isoquinoline

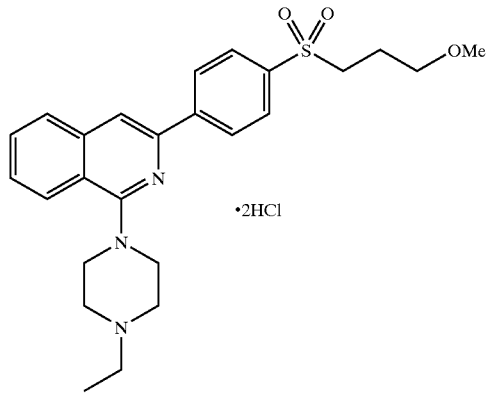

(4-Tributylstannylphenyl)(3-methoxypropyl)sulfone (1.70 g) and 3-bromo-1-(4-ethylpiperazin-1-yl)isoquinoline (0.93 g) were heated under reflux in the presence of tetrakistriphenylphosphinepalladium(0) (0.20 g) in xylene in nitrogen atmosphere for 1 day. After cooling, the reaction solution was diluted with ethyl acetate and filtered. The filtrate was extracted with 2N hydrochloric acid, and the resulting aqueous layer was washed with ethyl acetate and adjusted to pH 10 with a 8N aqueous solution of sodium hydroxide, which was then extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 0.87 g of the free compound of the title compound as a pale brown amorphous.

Free Compound:

$^1$H-NMR(400 MHz,CDCl$_3$); δ (ppm) 1.18(t,J=7.2 Hz,3H), 1.99–2.06(m,2H), 2.57(q,J=7.2 Hz,2H), 2.77(br-t, 4H), 3.22–3.26(m,2H), 3.28(s,3H), 3.44(t,J=6.2 Hz,2H), 3.61(br-t,4H), 7.53(br-t,1H), 7.64(br-t,1H), 7.78(s,1H), 7.84 (d,J=8.0 Hz,1H), 7.99(d,J=8.6 Hz,2H), 8.11(d,J=8.4 Hz,1H), 8.35(d,J=8.6 Hz,2H).

The resulting free compound was converted into a hydrochloride in a conventional manner, and then recrystallized from ethanol/ether, to give the title compound as a yellow powder.

Hydrochloride:

m.p.; 177.5–180° C.

$^1$H-NMR(400 MHz,DMSO-d$_6$); δ (ppm) 1.33(t,J=7.2 Hz,3H), 1.76–1.83(m,2H), 3.18(s,3H), 3.21–3.28(m,2H), 3.33–3.39(m,6H), 3.53(br-t,2H), 3.64(br-d,2H), 4.04(br-d, 2H), 7.68(br-t,1H), 7.80(br-t,1H), 8.03(d,J=8.8 Hz,2H), 8.05 (d,J=8.0 Hz,1H), 8.17(d,J=8.0 Hz,1H), 8.29(s,1H), 8.47(d, J=8.8 Hz,2H), 10.85(br-s,1H).

MS(FAB) m/z 454(M+H)$^+$.

Example 351

Synthesis of 1-(4-ethylpiperazin-1-yl)-3-[4-(2-hydroxyethyl)phenyl]isoquinoline dihydrochloride

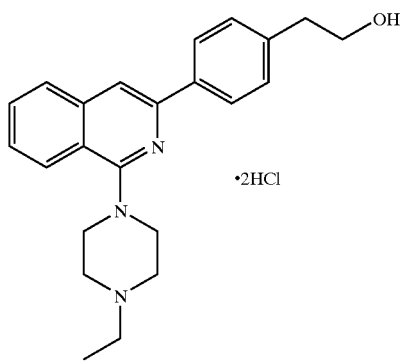

4-(2-Benzyloxyethyl)phenylboric acid (0.40 g) and 3-bromo-1-(4-ethylpiperazin-1-yl)isoquinoline (0.65 g) were heated under reflux in the presence of tetrakistriphenylphosphinepalladium(0) (0.09 g) in toluene (50 ml) and a 10% aqueous solution of sodium carbonate (30 ml) in nitrogen atmosphere for 1 hr. To the mixture was additionally added 4-(2-benzyloxyethyl)phenylboric acid (0.40 g), and the mixture was heated under reflux for 1.5 hr. 4-(2-Benzyloxyethyl)phenylboric acid (0.40 g) was again added, and the mixture was heated under reflux overnight. The organic layer was separated, and it was extracted with 2N hydrochloric acid twice. The resulting aqueous layer was washed with ethyl acetate, adjusted to pH 10 with a 8N aqueous solution of sodium hydroxide, extracted with ethyl acetate, washed with a 10% aqueous solution of sodium carbonate and brine, and then dried over magnesium sulfate. The solvent was evaporated, and the resulting residue was purified by silica gel column chromatography (chloroform/methanol system, and then ethyl acetate/acetone system), to give 1-(4-ethylpiperazin-1-yl)-3-[4-(2-benzyloxyethyl)phenyl]isoquinoline (0.48 g) as a colorless viscous oil.

The resulting 1-(4-ethylpiperazin-1-yl)-3-[4-(2-benzyloxyethyl)phenyl]isoquinoline (0.46 g) was converted into a hydrochloride in a conventional manner. The resulting hydrochloride was then dissolved in methanol (50 ml), followed by the addition of 10% palladium/carbon catalyst (0.10 g), and the catalytic reduction was conducted at atmospheric pressure overnight. The catalyst was filtered off, while the solvent was evaporated. Water was added thereto, followed by the addition of a 1N aqueous solution of sodium hydroxide to adjust the pH 8, and then the mixture was extracted with ethyl acetate. The extract was washed with brine, dried over magnesium sulfate, and evaporated. The solvent was evaporated, and the resulting residue was purified by silica gel column chromatography (chloroform/methanol system), to give 0.24 g of the free compound of the title compound as a pale brown viscous oil.

Free compound:

$^1$H-NMR (400 MHz, CDCl$_3$); δ (ppm) 1.18 (t, J=7.2 Hz, 3H), 2.56 (q, J=7.2 Hz, 2H), 2.76 (br-t, 4H), 2.94 (t, J=6.6 Hz, 2H), 3.59 (br-t, 4H), 3.91 (t, J=6.6 Hz, 2H), 7.34 (d, J=8.4 Hz, 2H), 7.46 (br-t, 1H), 7.59 (br-t, 1H), 7.68 (s, 1H), 7.79 (d, J=8.0 Hz, 1H), 8.08 (d, J=8.4 Hz, 1H), 8.12 (d, J=8.4 Hz, 2H).

The resulting free compound was converted into a hydrochloride in a conventional manner, and then recrystallized from ethanol/ether, to give the title compound as a yellow powder.

Hydrochloride:
m.p.; 134–136° C.
$^1$H-NMR (400 MHz, DMSO-d$_6$); δ (ppm) 1.33 (t, J=7.2 Hz, 3H), 2.79 (t, J=7.0 Hz, 2H), 3.19–3.26 (m, 2H), 3.30–3.38 (m, 2H), 3.55 (br-t, 2H), 3.62 (br-d, 2H), 3.65 (t, J=7.0 Hz, 2H), 3.99 (br-d, 2H), 7.36 (d, J=8.4 Hz, 2H), 7.60 (br-t, 1H), 7.74 (br-t, 1H), 7.98 (d, J=8.0 Hz, 1H), 8.05 (s, 1H), 8.11 (d, J=8.4 Hz, 2H), 8.11 (d, J=8.4 Hz, 1H), 11.12 (br-s, 1H).
MS(FAB) m/z 362 (M+H)*.

Example 352

Synthesis of 1-(4-ethylpiperazin-1-yl)-3-[4-(3-hydroxypropyl)sulfonylphenyl]isoquinoline dihydrochloride

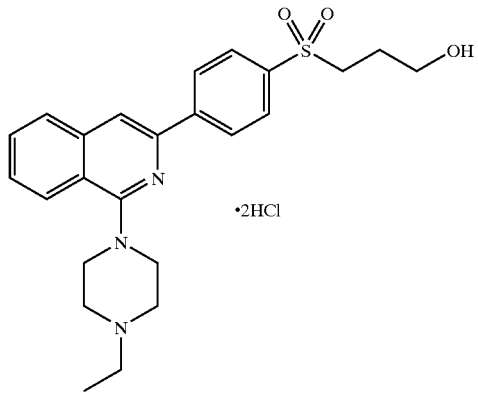

(4-Tributylstannylphenyl)(3-benzyloxypropyl)sulfone (5.78 g) and 3-bromo-1-(4-ethylpiperazin-1-yl)isoquinoline (2.13 g) were heated under reflux in the presence of tetrakistriphenylphosphinepalladium(0) (0.58 g) in xylene in nitrogen atmosphere for 7 hr. After cooling, the reaction solution was diluted with ethyl acetate and filtered. The filtrate was extracted with 2N hydrochloric acid, and the resulting aqueous layer was washed with ethyl acetate and adjusted to pH 10 with a 8N aqueous solution of sodium hydroxide, which was then extracted with ethyl acetate. The extract was washed with a 10% aqueous solution of sodium carbonate and brine, and dried over magnesium sulfate. The solvent was evaporated, and the resulting residue was purified by silica gel column chromatography (chloroform/methanol system), to give 1-(4-ethylpiperazin-1-yl)-3-[4-(3-benzyloxypropyl)sulfonylphenyl]isoquinoline (2.56 g) as a pale brown amorphous.

The resulting 1-(4-ethylpiperazin-1-yl)-3-[4-(2-benzyloxyethyl)sulfonylphenyl]isoquinoline (2.56 g) was converted into a hydrochloride in a conventional manner. The resulting hydrochloride was then dissolved in methanol (50 ml), followed by the addition of 10% palladium/carbon catalyst (0.07 g), and the catalytic reduction was conducted at atmospheric pressure overnight. The 10% palladium/carbon catalyst (0.05 g) was additionally added thereto, and the catalytic reduction was conducted at atmospheric pressure for 1 day. The catalyst was filtered off, while the solvent was evaporated. Water was added to the resulting residue, followed by the addition of a 1N aqueous solution of sodium hydroxide to adjust to pH 8, and the mixture was extracted with ethyl acetate. The extract was washed with brine and dried over magnesium sulfate. The solvent was evaporated, and the resulting residue was purified by silica gel column chromatography (chloroform/methanol system), to give 1.23 g of the free compound of the title compound as a pale yellow amorphous.

Free compound:
$^1$H-NMR (400 MHz, CDCl$_3$); δ (ppm) 1.18 (t, J=7.2 Hz, 3H), 1.98–2.05 (m, 2H), 2.56 (q, J=7.2 Hz, 2H), 2.76 (br-t, 4H), 3.27–3.31 (m, 2H), 3.59 (br-t, 4H), 3.75 (t, J=6.0 Hz, 2H), 7.53 (br-t, 1H), 7.64 (br-t, 1H), 7.77 (s, 1H), 7.83 (d, J=7.6 Hz, 1H), 7.99 (d, J=8.4 Hz, 2H), 8.09 (d, J=8.4 Hz, 1H), 8.34 (d, J=8.4 Hz, 2H).

The resulting free compound was converted into a hydrochloride in a conventional manner, and then recrystallized from ethanol/ether, to give the title compound as yellow needles.

Hydrochloride:
m.p.; 213–215° C. (decomp.)
$^1$H-NMR (400 MHz, DMSO-d$_6$); δ (ppm) 1.33 (t, J=7.2 Hz, 3H), 1.67–1.74 (m, 2H), 3.22–3.28 (m, 2H), 3.33–3.44 (m, 6H), 3.51 (br-t, 2H), 3.64 (br-d, 2H), 4.05 (br-d, 2H), 7.68 (br-t, 1H), 7.80 (br-t, 1H), 8.02 (d, J=8.4 Hz, 2H), 8.05 (d, J=8.0 Hz, 1H), 8.17 (d, J=8.8 Hz, 1H), 8.29 (s, 1H), 8.47 (d, J=8.4 Hz, 2H), 10.68 (br-s, 1H).
MS(FAB) m/z 439 (M+H)*.

Example 353

Synthesis of 1-(4-ethylpiperazin-1-yl)-3-[4-(N-propylsulfamoyl)phenyl]isoquinoline dihydrochloride

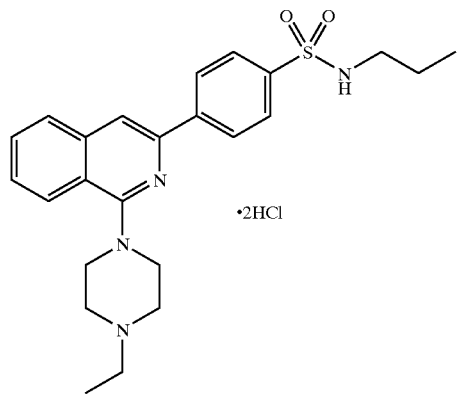

N-Propyl-4-tributylstannylbenzenesulfonamide (1.05 g) and 3-bromo-1-(4-ethylpiperazin-1-yl)isoquinoline (0.46 g) were heated under reflux in the presence of tetrakistriphenylphosphinepalladium(0) (0.12 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, and the resulting residue was purified by silica gel column chromatography (chloroform/methanol system), to give 0.41 g of the free compound of the title compound as a pale brown amorphous.

Free compound:
$^1$H-NMR (400 MHz, CDCl$_3$); δ (ppm) 0.89 (t, J=7.2 Hz, 3H), 1.18 (t, J=7.2 Hz, 3H), 1.52 (tq, J=7.2, 7.2 Hz, 2H), 2.57 (q, J=7.2 Hz, 2H), 2.77 (br-t, 4H), 2.97 (q, J=7.2 Hz, 2H), 3.60 (br-t, 4H), 4.38 (br-t, 1H), 7.52 (br-t, 1H), 7.63 (br-t, 1H), 7.77 (s, 1H), 7.83 (d, J=8.4 Hz, 1H), 7.95 (d, J=8.4 Hz, 2H), 8.10 (d, J=8.4 Hz, 1H), 8.31 (d, J=8.4 Hz, 2H).

The resulting free compound was converted into a hydrochloride in a conventional manner, and then reprecipitated with ethanol/ether, to give the title compound as a pale brown powder.

Hydrochloride:
m.p.; 226.5–227.5° C. (decomp.)
$^1$H-NMR (400 MHz, DMSO-d$_6$); δ (ppm) 0.81 (t, J=7.2 Hz, 3H), 1.33 (t, J=7.2 Hz, 3H), 1.40 (tq, J=7.2 Hz, 2H), 2.74 (br-q, 2H), 3.22–3.28 (m, 2H), 3.32–3.41 (m, 2H), 3.50 (br-t, 2H), 3.64 (br-d, 2H), 4.05 (br-d, 2H), 7.65–4.70 (m, 2H), 7.79 (br-t, 1H), 7.91 (d, J=8.8 Hz, 2H), 8.03 (d, J=8.0 Hz, 1H), 8.16 (d, J=8.4 Hz, 1H), 8.24 (s, 1H), 8.40 (d, J=8.8 Hz, 2H), 10.56 (br-s, 1H).
MS(FAB) m/z 439 (M+H)*.

Example 354

Synthesis of 1-(4-ethylpiperazin-1-yl)-3-{4-[N-(2-methoxyethyl)sulfamoyl]phenyl}isoquinoline dihydrochloride

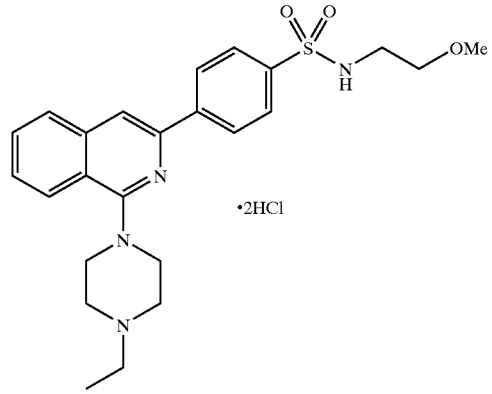

N-(2-Methoxyethyl)-4-tributylstannylbenzenesulfonamide (1.07 g) and 3-bromo-1-(4-ethylpiperazin-1-yl)isoquinoline (0.45 g) were heated under reflux in the presence of tetrakistriphenylphosphinepalladium(0) (0.12 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, and the resulting residue was purified by silica gel column chromatography (chloroform/methanol system), to give 0.43 g of the free compound of the title compound as a pale brown amorphous.

Free compound:
$^1$H-NMR (400 MHz, CDCl$_3$); δ (ppm) 1.18 (t, J=7.2 Hz, 3H), 2.57 (q, J=7.2 Hz, 2H), 2.77 (br-t, 4H), 3.17 (dt, J=5.0, 6.0 Hz, 2H), 3.28 (s, 3H), 3.43 (t, J=5.0 Hz, 2H), 3.60 (br-t, 4H), 4.87 (t, J=6.0 Hz, 1H), 7.52 (br-t, 1H), 7.63 (br-t, 1H), 7.77 (s, 1H), 7.84 (d, J=8.0 Hz, 1H), 7.95 (d, J=8.4 Hz, 2H), 8.10 (d, J=9.2 Hz, 1H), 8.31 (d, J=8.4 Hz, 2H).

The resulting free compound was converted into a hydrochloride in a conventional manner, and then reprecipitated with ethanol/ether, to give the title compound as a pale brown powder.

Hydrochloride:
m.p.; 222–224° C. (decomp.)
¹H-NMR (400 MHz, DMSO-d₆); δ (ppm) 1.34 (t, J=7.2 Hz, 3H), 2.95 (dt, J=5.8 Hz, 2H), 3.18 (s, 3H), 3.20–3.27 (m, 2H), 3.33 (t, J=5.8 Hz, 2H), 3.36 (br-t, 2H), 3.56 (br-t, 2H), 3.63 (br-d, 2H), 4.04 (br-d, 2H), 7.67 (br-t, 1H), 7.79 (br-t, 1H), 7.84 (t, J=5.8 Hz, 1H), 7.93 (d, J=8.4 Hz, 2H), 8.03 (d, J=7.6 Hz, 1H), 8.16 (d, J=8.0 Hz, 1H), 8.24 (s, 1H), 8.40 (d, J=8.4 Hz, 2H), 11.09 (br-s, 1H).
MS(FAB) m/z 455 (M+H)*.

Example 355

Synthesis of 1-(4-ethylpiperazin-1-yl)-3-[4-(3-fluoropropyl)sulfonylphenyl]isoquinoline dihydrochloride

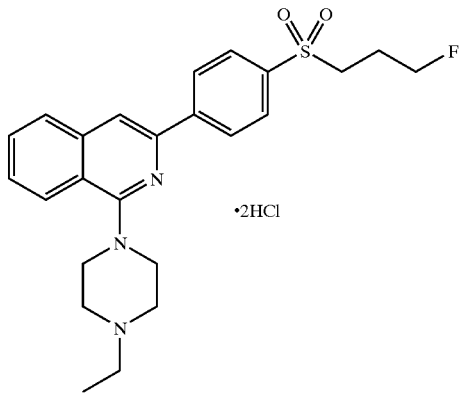

Diethylaminosulfur trifluoride (DAST, 0.14 ml) was added to anhydrous methylene chloride (3 ml), and the resulting mixture was stirred at −78° C. in nitrogen atmosphere, to which was then added a solution of 1-(4-ethylpiperazin-1-yl)-3-[4-(3-hydroxypropyl)sulfonylphenyl]isoquinoline (0.31 g) obtained in Example 352 in methylene chloride (5 ml), and the mixture was further stirred for 6 hr. DAST (0.09 ml) was further added thereto, and the resulting mixture was further stirred overnight. The bulk temperature was raised to room temperature. The reaction solution was diluted with chloroform, followed by the addition of a 10% aqueous solution of sodium carbonate. The organic layer was separated, and then it was washed with brine and dried over magnesium sulfate. The solvent was evaporated, and the resulting residue was purified by silica gel column chromatography (chloroform/methanol system), to give 0.23 g of the free compound of the title compound as a pale brown viscous oil.
Free compound:
¹H-NMR (400 MHz, CDCl₃); δ (ppm) 1.18 (t, J=7.2 Hz, 3H), 2.11–2.26 (m, 2H), 2.56 (q, J=7.2 Hz, 2H), 2.77 (br-t, 4H), 3.26–3.30 (m, 2H), 3.60 (br-t, 4H), 4.53 (dt, J=5.6, 46.8 Hz, 2H), 7.53 (br-t, 1H), 7.64 (br-t, 1H), 7.77 (s, 1H), 7.83 (d, J=8.0 Hz, 1H), 7.99 (d, J=8.4 Hz, 2H), 8.10 (d, J=8.4 Hz, 1H), 8.36 (d, J=8.8 Hz, 2H).
The resulting free compound was converted into a hydrochloride in a conventional manner, and then recrystallized from ethanol/ether, to give the title compound as pale yellow needles.
Hydrochloride:
m.p.; 224–225° C. (decomp.)
¹H-NMR (400 MHz, DMSO-d₆); δ (ppm) 1.33 (t, J=7.2 Hz, 3H), 1.90–2.04 (m, 2H), 3.22–3.28 (m, 2H), 3.32–3.41 (m, 2H), 3.44–3.54 (m, 4H), 3.64 (br-d, 2H), 4.05 (br-d, 2H), 4.50 (dt, J=6.0, 46.8 Hz, 2H), 7.69 (br-t, 1H), 7.81 (br-t, 1H), 8.03–8.06 (m, 3H), 8.17 (d, J=8.4 Hz, 1H), 8.30 (s, 1H), 8.48 (d, J=8.4 Hz, 2H), 10.62 (br-s, 1H).
MS(FAB) m/z 442 (M+H)*.

Example 356

Synthesis of 1-(4-ethylpiperazin-1-yl)-3-[4-(pyrrolidin-1-yl)sulfonylphenyl]isoquinoline dihydrochloride

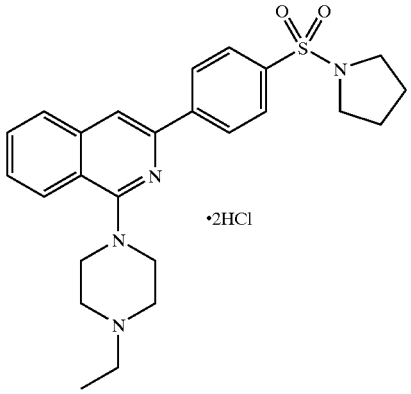

Pyrrolidine 4-tributylstannylbenzenesulfonamide (1.17 g) and 3-bromo-1-(4-ethylpiperazin-1-yl)isoquinoline (0.64 g) were heated under reflux in the presence of tetrakistriphenylphosphinepalladium(0) (0.09 g) in xylene in nitrogen atmosphere overnight. After cooling, the reaction solution was diluted with ethyl acetate and filtered. The filtrate was extracted with 2N hydrochloric acid. The aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (toluene/acetone system), to give 0.47 g of the free compound of the title compound as a pale brown amorphous.
Free compound:
¹H-NMR (400 MHz, CDCl₃); δ (ppm) 1.18 (t, J=7.2 Hz, 3H), 1.76–1.79 (m, 4H), 2.57 (q, J=7.2 Hz, 2H), 2.77 (br-t, 4H), 3.28–3.31 (m, 2H), 3.60 (br-t, 4H), 7.52 (br-t, 1H), 7.64 (br-t, 1H), 7.77 (s, 1H), 7.83 (d, J=8.0 Hz, 1H), 7.92 (d, J=8.6 Hz, 2H), 8.10 (d, J=8.4 Hz, 1H), 8.32 (d, J=8.6 Hz, 2H).
The resulting free compound was converted into a hydrochloride in a conventional manner, and then reprecipitated with ethanol/ether, to give the title compound as a pale brown powder.
Hydrochloride:
m.p.; 238.5–240° C. (decomp.)
¹H-NMR (400 MHz, DMSO-d₆); δ (ppm) 1.34 (t, J=7.2 Hz, 3H), 1.65–1.68 (m, 4H), 3.18–3.27 (m, 6H), 3.32–3.40 (m, 2H), 3.56 (br-t, 2H), 3.63 (br-d, 2H), 4.02 (br-d, 2H), 7.68 (br-t, 1H), 7.80 (br-t, 1H), 7.94 (d, J=8.8 Hz, 2H), 8.05 (d, J=7.6 Hz, 1H), 8.16 (d, J=8.8 Hz, 1H), 8.27 (s, 1H), 8.45 (d, J=8.4 Hz, 2H), 11.17 (br-s, 1H).
MS(FAB) m/z 451 (M+H)*.

Example 357

Synthesis of 1-(4-ethylpiperazin-1-yl)-3-[4-(N-ethylsulfamoyl)phenyl]isoquinoline dihydrochloride

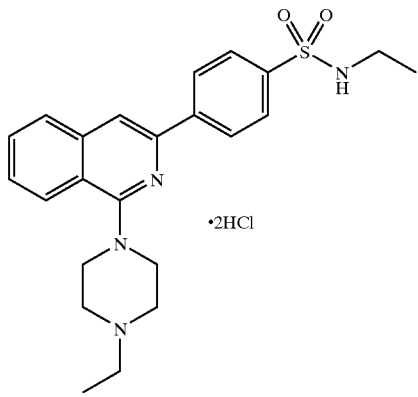

N-Ethyl-4-tributylstannylbenzenesulfonamide (1.05 g) and 3-bromo-1-(4-ethylpiperazin-1-yl)isoquinoline (0.61 g) were heated under reflux in the presence of tetrakistriphenylphosphinepalladium(0) (0.09 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give the free compound of the title compound (0.49 g) as a pale brown amorphous.

Free compound:

$^1$H-NMR (400 MHz, CDCl$_3$); δ (ppm) 1.14 (t, J=7.2 Hz, 3H), 1.18 (t, J=7.2 Hz, 3H), 2.57 (q, J=7.2 Hz, 2H), 2.77 (br-t, 4H), 3.07 (dq, J=6.0, 7.2 Hz, 2H), 3.60 (br-t, 4H), 4.30 (t, J=6.0 Hz, 1H), 7.52 (br-t, 1H), 7.63 (br-t, 1H), 7.77 (s, 1H), 7.83 (d, J=8.8 Hz, 1H), 7.95 (d, J=8.4 Hz, 2H), 8.10 (d, J=8.4 Hz, 1H), 8.31 (d, J=8.4 Hz, 2H).

The resulting free compound was converted into a hydrochloride in a conventional manner, and then reprecipitated with ethanol/ether, to give the title compound as a pale brown powder.

Hydrochloride:

m.p.; 147–149° C.

$^1$H-NMR (400 MHz, DMSO-d$_6$); δ (ppm) 1.00 (t, J=7.2 Hz, 3H), 1.33 (t, J=7.2 Hz, 3H), 2.79–2.86 (m, 2H), 3.21–3.27 (m, 2H), 3.32–3.4 (m, 2H), 3.53 (br-t, 2H), 3.63 (br-d, 2H), 4.04 (br-d, 2H), 7.64–7.69 (m, 2H), 7.79 (br-t, 1H), 7.92 (d, J=8.4 Hz, 2H), 8.03 (d, J=7.6 Hz, 1H), 8.16 (d, J=8.4 Hz, 1H), 8.24 (s, 1H), 8.41 (d, J=8.4 Hz, 2H), 10.86 (br-s, 1H).

MS(FAB) m/z 425 (M+H)$^+$.

Example 358

Synthesis of 1-(4-ethylpiperazin-1-yl)-3-[4-(N-methyl-N-propylsulfamoyl)phenyl]isoquinoline dihydrochloride

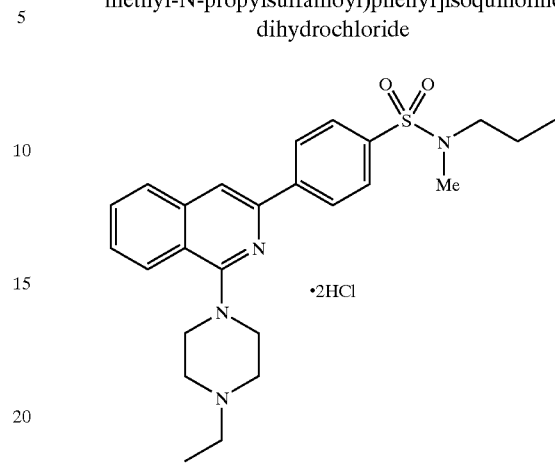

N-Methyl-N-propyl-4-tributylstannylbenzenesulfonamide (2.00 g) and 3-bromo-1-(4-ethylpiperazin-1-yl)isoquinoline (0.64 g) were heated under reflux in the presence of tetrakistriphenylphosphinepalladium(0) (0.15 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 0.56 g of the free compound of the title compound as a pale brown amorphous.

Free compound:

$^1$H-NMR (400 MHz, CDCl$_3$); δ (ppm) 0.95 (t, J=7.2 Hz, 3H), 1.18 (t, J=7.2 Hz, 3H), 1.59 (tq, J=7.2, 7.2 Hz, 2H), 2.57 (q, J=7.2 Hz, 2H), 2.75–2.78 (77H), 3.01 (t, J=7.2 Hz, 2H), 3.60 (br-t, 4H), 7.52 (br-t, 1H), 7.63 (br-t, 1H), 7.77 (s, 1H), 7.83 (d, J=8.0 Hz, 1H), 7.87 (d, J=8.6 Hz, 2H), 8.10 (d, J=8.0 Hz, 1H), 8.18 (d, J=8.6 Hz, 2H).

The resulting free compound was converted into a hydrochloride in a conventional manner, and then reprecipitated with ethanol/ether, to give the title compound as a pale brown powder.

Hydrochloride:

m.p.; 199.5–200.5° C. (decomp.)

$^1$H-NMR (400 MHz, DMSO-d$_6$); δ (ppm) 0.86 (t, J=7.2 Hz, 3H), 1.34 (t, J=7.2 Hz, 3H), 1.50 (tq, J=7.2, 7.2 Hz, 2H), 2.70 (s, 3H), 2.95 (t, J=7.2 Hz, 2H), 3.20–3.27 (m, 2H), 3.32–3.40 (m, 2H), 3.56 (br-t, 2H), 3.63 (br-d, 2H), 4.02 (br-d, 2H), 7.68 (br-t, 1H), 7.80 (br-t, 1H), 7.90 (d, J=8.8 Hz, 2H), 8.05 (d, J=7.6 Hz, 1H), 8.16 (d, J=8.4 Hz, 1H), 8.26 (s, 1H), 8.44 (d, J=8.4 Hz, 2H), 11.18 (br-s, 1H).

MS(FAB) m/z 453 (M+H)$^+$.

Example 359

Synthesis of 1-(4-ethylpiperazin-1-yl)-3-[4-(N,N-diethylsulfamoyl)phenyl]isoquinoline dihydrochloride

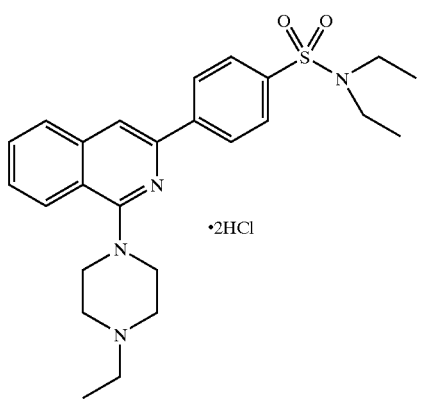

·2HCl

N,N-Diethyl-4-tributylstannylbenzenesulfonamide (1.29 g) and 3-bromo-1-(4-ethylpiperazin-1-yl)isoquinoline (0.55 g) were heated under reflux in the presence of tetrakistriphenylphosphinepalladium(0) (0.10 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 0.48 g of the free compound of the title compound as a pale brown amorphous.

Free compound:

$^1$H-NMR (400 MHz, CDCl$_3$); δ (ppm) 1.17 (t, J=7.2 Hz, 6H), 1.18 (t, J=7.2 Hz, 3H), 2.57 (q, J=7.2 Hz, 2H), 2.77 (br-t, 4H), 3.28 (q, j=7.2 Hz, 4H), 3.60 (br-t, 4H), 7.52 (br-t, 1H), 7.63 (br-t, 1H), 7.76 (s, 1H), 7.83 (d, J=8.8 Hz, 1H), 7.90 (d, J=8.4 Hz, 2H), 8.10 (d, J=8.4 Hz, 1H), 8.29 (d, J=8.4 Hz, 2H).

The resulting free compound was converted into a hydrochloride in a conventional manner, and then reprecipitated with ethanol/ether, to give the title compound as a pale brown powder.

Hydrochloride:

m.p.; 210–212° C. (decomp.)

$^1$H-NMR (400 MHz, DMSO-d$_6$); δ (ppm) 1.07 (t, J=7.2 Hz, 6H), 1.34 (t, J=7.2 Hz, 3H), 3.18–3.26 (m, 6H), 3.32–3.39 (m, 2H), 3.56 (br-t, 2H), 3.62 (br-d, 2H), 4.02 (br-d, 2H), 7.67 (br-t, 1H), 7.79 (br-t, 1H), 7.92 (d, J=8.8 Hz, 2H), 8.04 (d, J=8.0 Hz, 1H), 8.16 (d, J=8.4 Hz, 1H), 8.25 (s, 1H), 8.41 (d, J=8.8 Hz, 2H), 11.22 (br-s, 1H).

MS(FAB) m/z 453 (M+H)*.

Example 360

Synthesis of 1-(4-ethylpiperazin-1-yl)-3-{4-[N-(1-methylpropyl)sulfamoyl]phenyl}isoquinoline dihydrochloride

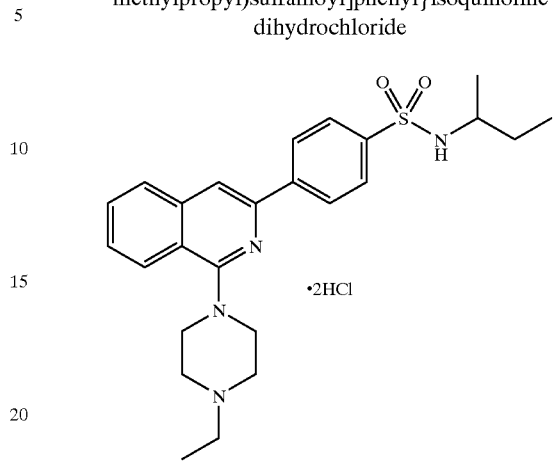

·2HCl

N-(1-Methylpropyl)-4-tributylstannylbenzenesulfonamide (0.98 g) and 3-bromo-1-(4-ethylpiperazin-1-yl)isoquinoline (0.42 g) were heated under reflux in the presence of tetrakistriphenylphosphinepalladium(0) (0.08 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 0.36 g of the free compound of the title compound as a pale brown amorphous.

Free compound:

$^1$H-NMR (400 MHz, CDCl$_3$); δ (ppm) 0.83 (t, J=7.2 Hz, 3H), 1.06 (d, J=6.4 Hz, 3H), 1.17 (t, J=7.2 Hz, 3H), 1.39–1.47 (m, 2H), 2.56 (q, J=7.2 Hz, 2H), 2.76 (br-t, 4H), 3.28–3.34 (m, 1H), 3.59 (br-t, 4H), 4.75 (d, J=8.0 Hz, 1H), 7.51 (br-t, 1H), 7.61 (br-t, 1H), 7.76 (s, 1H), 7.80 (d, J=8.0 Hz, 1H), 7.98 (d, J=8.8 Hz, 2H), 8.09 (d, J=8.0 Hz, 1H), 8.31 (d, J=8.8 Hz, 2H).

The resulting free compound was converted into a hydrochloride in a conventional manner, and then reprecipitated with ethanol/ether, to give the title compound as a pale brown powder.

Hydrochloride:

m.p.; 155–156° C.

$^1$H-NMR (400 MHz, DMSO-d$_6$); δ (ppm) 0.74 (t, J=7.2 Hz, 3H), 0.90 (d, J=6.4 Hz, 3H), 1.30–1.37 (m, 5H), 3.08–3.27 (m, 3H), 3.33–3.40 (m, 2H), 3.54 (br-t, 2H), 3.63 (br-d, 2H), 4.04 (br-d, 2H), 7.62 (d, J=7.6 Hz, 1H), 7.67 (br-t, 1H), 7.79 (br-t, 1H), 7.93 (d, J=8.4 Hz, 2H), 8.03 (d, J=8.4 Hz, 1H), 8.15 (d, J=8.0 Hz, 1H), 8.25 (s, 1H), 8.40 (d, J=8.4 Hz, 2H), 10.95 (br-s, 1H).

MS(FAB) m/z 453 (M+H)*.

Example 361

Synthesis of 1-(4-ethylpiperazin-1-yl)-3-[4-(N-methylsulfamoyl)phenyl]isoquinoline dihydrochloride

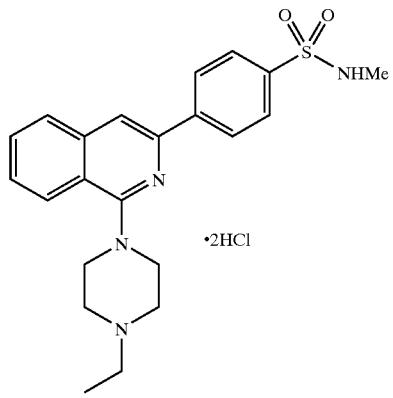

·2HCl

N-Methyl-4-tributylstannylbenzenesulfonamide (1.23 g) and 3-bromo-1-(4-ethylpiperazin-1-yl)isoquinoline (0.73 g) were heated under reflux in the presence of tetrakistriphenylphosphinepalladium(0) (0.10 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the reuslting residue was purified by silica gel column chromatography (chloroform/methanol system), to give 0.38 g of the free compound of the title compound as a pale brown amorphous.

Free compound:

$^1$H-NMR (400 MHz, CDCl$_3$); δ (ppm) 1.18 (t, J=7.2 Hz, 3H), 2.57 (q, J=7.2 Hz, 2H), 2.71 (s, 1.5H), 2.72 (s, 1.5H), 2.77 (br-t, 4H), 3.60 (br-t, 4H), 4.35 (br-q, 1H), 7.53 (br-t, 1H), 7.64 (br-t, 1H), 7.77 (s, 1H), 7.83 (d, J=8.0 Hz, 1H), 7.95 (d, J=8.4 Hz, 2H), 8.10 (d, J=8.0 Hz, 2H), 8.32 (d, J=8.8 Hz, 2H).

The resulting free compound was converted into a hydrochloride in a conventional manner, and then recrystallized from ethanol/IPE, to give the title compound as a pale brown powder.

Hydrochloride:

m.p.; 170–172° C.

$^1$H-NMR (400 MHz, DMSO-d$_6$); δ (ppm) 1.34 (t, J=7.2 Hz, 3H), 2.46 (br-d, 3H), 3.20–3.27 (m, 2H), 3.32–3.40 (m, 2H), 3.56 (br-t, 2H), 3.63 (br-d, 2H), 4.03 (br-d, 2H), 7.57 (br-s, 1H), 7.67 (br-t, 1H), 7.79 (br-t, 1H), 7.91 (d, J=8.4 Hz, 2H), 8.04 (d, J=8.0 Hz, 1H), 8.16 (d, J=8.0 Hz, 1H), 8.24 (s, 1H), 8.42 (d, J=8.4 Hz, 2H), 11.11 (br-s, 1H).

MS(FAB) m/z 411 (M+H)*.

Example 362

Synthesis of 1-(4-ethylpiperazin-1-yl)-3-[4-(N,N-dimethylsulfamoyl)phenyl]isoquinoline dihydrochloride

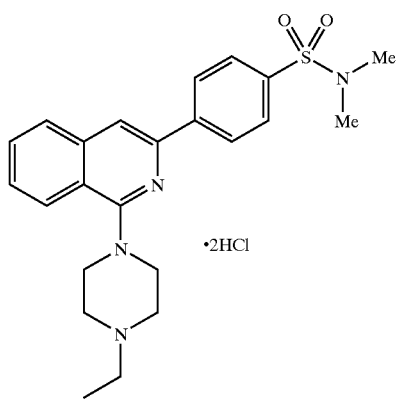

·2HCl

N,N-Dimethyl-4-tributylstannylbenzenesulfonamide (1.21 g) and 3-bromo-1-(4-ethylpiperazin-1-yl)isoquinoline (0.55 g) were heated under reflux in the presence of tetrakistriphenylphosphinepalladium(0) (0.10 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 0.51 g of the free compound of the title compound as a pale brown amorphous.

Free compound:

$^1$H-NMR (400 MHz, CDCl$_3$); δ (ppm) 1.18 (t, J=7.2 Hz, 3H), 2.57 (q, J=7.2 Hz, 2H), 2.75 (s, 6H), 2.77 (br-t, 4H), 3.61 (br-t, 4H), 7.53 (br-t, 1H), 7.64 (br-t, 1H), 7.78 (s, 1H), 7.87 (d, J=8.8 Hz, 2H), 8.11 (br-d, 1H), 8.34 (d, J=8.8 Hz, 2H).

The resulting free compound was converted into a hydrochloride in a conventional manner, and then reprecipitated with ethanol/ether, to give the title compound as a pale brown powder.

Hydrochloride:

m.p.; 155–156° C.

$^1$H-NMR (400 MHz, DMSO-d$_6$); δ (ppm) 1.34 (t, J=7.2 Hz, 3H), 2.66 (s, 6H), 3.21–3.27 (m, 2H), 3.33–3.40 (m, 2H), 3.54 (br-t, 2H), 3.63 (br-d, 2H), 4.03 (br-d, 2H), 7.68 (br-t, 2H), 7.80 (br-t, 2H), 7.88 (d, J=8.6 Hz, 2H), 8.05 (d, J=8.4 Hz, 1H), 8.28 (s, 1H), 8.46 (d, J=8.6 Hz, 2H), 10.97 (br-s, 1H).

MS(FAB) m/z 425 (M+H)*.

Example 363

Synthesis of 1-(4-ethylpiperazin-1-yl)-3-[4-(N-cyclopropylsulfamoyl)phenyl]isoquinoline dihydrochloride

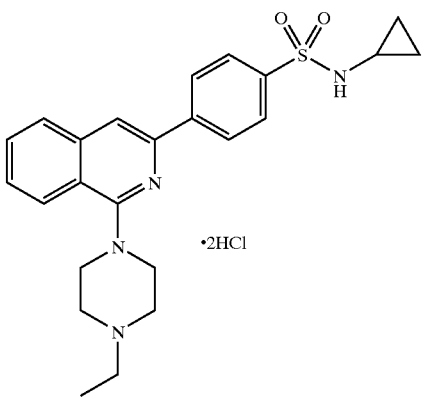

N-Cyclopropyl-4-tributylstannylbenzenesulfonamide (1.00 g) and 3-bromo-1-(4-ethylpiperazin-1-yl)isoquinoline (0.56 g) were heated under reflux in the presence of tetrakistriphenylphosphinepalladium(0) (0.08 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 0.43 g of the free compound of the title compound as a pale brown amorphous.

Free compound:

$^1$H-NMR (400 MHz, DMSO-$d_6$); δ (ppm) 0.39–0.52 (m, 4H), 1.08 (t, J=7.2 Hz, 3H), 2.15 (br-s, 1H), 2.68 (br-t, 4H), 3.47 (br-t, 4H), 7.62 (br-t, 1H), 7.74 (br-t, 1H), 7.92 (d, J=8.6 Hz, 2H), 7.96–7.99 (m, 2H), 7.10 (d, J=8.0 Hz, 1H), 8.13 (s, 1H), 8.42 (d, J=8.6 Hz, 2H).

The resulting free compound was converted into a hydrochloride in a conventional manner, and then reprecipitated with ethanol/IPE, to give the title compound as a pale brown powder.

Hydrochloride:

m.p.; 158–159.5° C.

$^1$H-NMR (400 MHz, DMSO-$d_6$); δ (ppm) 0.39–0.53 (m, 4H), 1.34 (t, J=7.2 Hz, 3H), 2.16 (br-s, 1H), 3.20–3.27 (m, 2H), 3.32–3.40 (m, 2H), 3.56 (br-t, 2H), 3.63 (br-d, 2H), 4.04 (br-d, 2H), 7.67 (br-t, 1H), 7.80 (br-t, 1H), 7.94 (d, J=8.4 Hz, 2H), 8.00–8.05 (m, 2H), 8.16 (d, J=8.6 Hz, 1H), 8.25 (s, 1H), 8.43 (d, J=8.6 Hz, 2H), 11.14 (br-s, 1H).

MS(FAB) m/z 437 (M+H)$^+$.

Example 364

Synthesis of 1-(4-ethylpiperazin-1-yl)-3-[4-(N-ethylcarbamoyl)phenyl]isoquinoline dihydrochloride

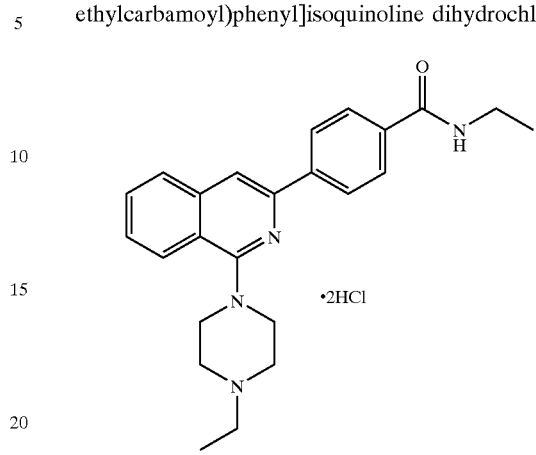

N-Ethyl-4-tributylstannylbenzamide (1.35 g) and 3-bromo-1-(4-ethylpiperazin-1-yl)isoquinoline (0.82 g) were heated under reflux in the presence of tetrakistriphenylphosphinepalladium(0) (0.12 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 0.58 g of the free compound of the title compound as a pale yellow powder.

Free compound:

$^1$H-NMR (400 MHz, CDCl$_3$); δ (ppm) 1.18 (t, J=7.2 Hz, 3H), 1.29 (t, J=7.2 Hz, 3H), 2.56 (q, J=7.2 Hz, 2H), 2.77 (br-t, 4H), 3.54 (dq, J=5.6, 7.2 Hz, 2H), 3.60 (br-t, 4H), 6.14 (br-t, 1H), 7.50 (br-t, 1H), 7.61 (br-t, 1H), 7.75 (s, 1H), 7.82 (d, J=8.0 Hz, 1H), 7.86 (d, J=8.8 Hz, 2H), 8.09 (d, J=8.4 Hz, 1H), 8.24 (d, J=8.8 Hz, 2H).

The resulting free compound was converted into a hydrochloride in a conventional manner, and then recrystallized from ethanol/IPE, to give the title compound as a pale brown powder.

Hydrochloride:

m.p.; 160–160.5° C.

$^1$H-NMR (400 MHz, DMSO-$d_6$); δ (ppm) 1.16 (t, J=7.2 Hz, 3H), 1.34 (t, J=7.2 Hz, 3H), 3.20–3.27 (m, 2H), 3.29–3.40 (m, 2H), 3.55 (br-t, 2H), 3.63 (br-d, 2H), 4.02 (br-d, 2H), 7.64 (br-t, 1H), 7.77 (br-t, 1H), 7.99 (d, J=8.4 Hz, 2H), 8.02 (d, J=8.0 Hz, 1H), 8.14 (d, J=8.4 Hz, 1H), 8.21 (s, 1H), 8.29 (d, J=8.4 Hz, 2H), 8.59 (d, J=5.4 Hz, 1H), 11.07 (br-s, 1H).

MS(FAB) m/z 389 (M+H)$^+$.

Example 365

Synthesis of 1-(4-ethylpiperazin-1-yl)-3-[4-(N-methylcarbamoyl)phenyl]isoquinoline dihydrochloride

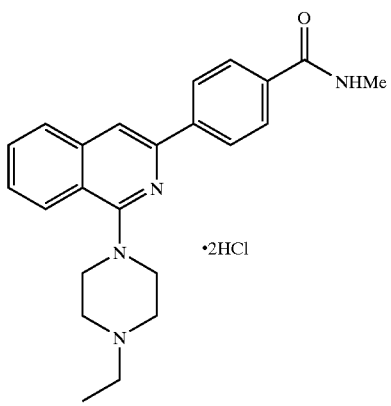

N-Methyl-4-tributylstannylbenzamide (1.35 g) and 3-bromo-1-(4-ethylpiperazin-1-yl)isoquinoline (0.82 g) were heated under reflux in the presence of tetrakistriphenylphosphinepalladium(0) (0.12 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 0.58 g of the title compound as a pale yellow powder.

Free compound:

$^1$H-NMR (400 MHz, CDCl$_3$); δ (ppm) 1.18 (t, J=7.2 Hz, 3H), 2.57 (q, J=7.2 Hz, 2H), 2.77 (br-t, 4H), 3.05 (s, 1.5H), 3.06 (s, 1.5H), 3.60 (br-t, 4H), 6.21 (br-q, 1H), 7.49 (br-t, 1H), 7.61 (br-t, 1H), 7.75 (s, 1H), 7.80 (d, J=8.4 Hz, 1H), 7.86 (d, J=8.4 Hz, 2H), 8.09 (d, J=8.4 Hz, 1H), 8.23 (d, J=8.4 Hz, 2H).

The resulting free compound was converted into a hydrochloride in a conventional manner, and then recrystallized from ethanol/IPE, to give the title compound as a pale brown powder.

Hydrochloride:

m.p.; 161.5–163° C.

$^1$H-NMR (400 MHz, DMSO-d$_6$); δ (ppm) 1.33 (t, J=7.2 Hz, 3H), 2.82 (s, 1.5H), 2.83 (s, 1.5H), 3.21–3.27 (m, 2H), 3.32–3.40 (m, 2H), 3.53 (br-t, 2H), 3.64 (br-d, 2H), 4.02 (br-d, 2H), 7.65 (br-t, 1H), 7.77 (br-t, 1H), 7.98 (d, J=8.4 Hz, 2H), 8.02 (d, J=7.6 Hz, 1H), 8.14 (d, J=8.4 Hz, 1H), 8.21 (s, 1H), 8.29 (d, J=8.4 Hz, 2H), 8.55 (br-q, 1H), 10.90 (br-s, 1H).

MS(FAB) m/z 375 (M+H)$^+$.

Example 366

Synthesis of 1-(4-ethylpiperazin-1-yl)-3-[4-(ethylsulfonyl)phenyl]isoquinoline dihydrochloride

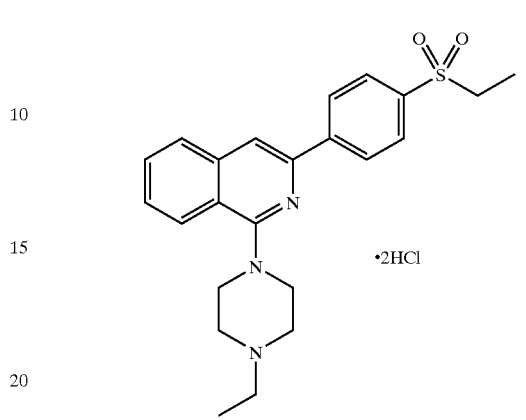

Ethyl (4-tributylstannylphenyl)sulfone (1.53 g) and 3-bromo-1-(4-ethylpiperazin-1-yl)isoquinoline (0.71 g) were heated under reflux in the presence of tetrakistriphenylphosphinepalladium(0) (0.13 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 by a 8N aqueous solution of sodium hydroxide, extracted in ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 0.68 g of the free compound of the title compound as a pale brown amorphous.

Free compound:

$^1$H-NMR (400 MHz, CDCl$_3$); δ (ppm) 1.18 (t, J=7.2 Hz, 3H), 1.32 (t, J=7.2 Hz, 3H), 2.57 (q, J=7.2 Hz, 2H), 2.77 (br-t, 4H), 3.16 (q, J=7.2 Hz, 2H), 3.61 (br-t, 4H), 7.53 (br-t, 1H), 7.64 (br-t, 1H), 7.79 (s, 1H), 7.84 (d, J=8.0 Hz, 1H), 7.99 (d, J=8.4 Hz, 2H), 8.11 (d, J=8.4 Hz, 1H), 8.36 (d, J=8.4 Hz, 2H).

The resulting free compound was converted into a hydrochloride in a conventional manner, and then reprecipitated with ethanol/IPE, to give the title compound as a yellow powder.

Hydrochloride:

m.p.; 150–151.5° C.

$^1$H-NMR (400 MHz, DMSO-d$_6$); δ (ppm) 1.14 (t, J=7.2 Hz, 3H), 1.34 (t, J=7.2 Hz, 3H), 3.20–3.27 (m, 2H), 3.32–3.40 (m, 4H), 3.55 (br-t, 2H), 3.63 (br-d, 2H), 4.04 (br-d, 2H), 7.68 (br-t, 1H), 7.80 (br-t, 1H), 8.01 (d, J=8.4 Hz, 2H), 8.05 (d, J=8.0 Hz, 1H), 8.16 (d, J=8.4 Hz, 1H), 8.29 (s, 1H), 8.47 (d, J=8.4 Hz, 2H), 11.07 (br-s, 1H).

MS(FAB) m/z 410 (M+H)$^+$.

Example 367

Synthesis of 1-(4-ethylpiperazin-1-yl)-3-(3-fluoro-4-methoxyethoxyphenyl)isoquinoline dihydrochloride

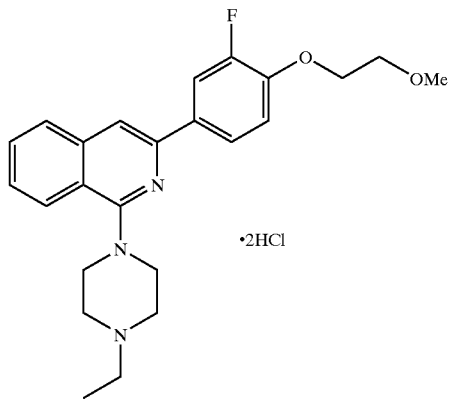

4-Benzyloxy-3-fluorophenylboric acid (1.97 g) and 3-bromo-1-(4-ethylpiperazin-1-yl)isoquinoline (2.57 g) were heated under reflux in the presence of tetrakistriphenylphosphinepalladium(0) (0.09 g) in toluene (250 ml) and a 10% aqueous solution of sodium carbonate (150 ml) in nitrogen atmosphere for 2 hr. 4-Benzyloxy-3-fluorophenylboric acid (0.99 g) was additionally added thereto, and the mixture was heated under reflux for 30 min. 4-Benzyloxy-3-fluorophenylboric acid (1.43 g) was again added thereto, and the mixture was heated under reflux overnight. The organic layer was separated and extracted with 2N hydrochloric acid twice, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give obtain 1-(4-ethylpiperazin-1-yl)-3-(4-benzyloxy-3-fluorophenyl)isoquinoline (3.19 g) as a brown viscous oil.

The resulting 1-(4-ethylpiperazin-1-yl)-3-(4-benzyloxy-3-fluorophenyl)isoquinoline (3.19 g) was converted into a hydrochloride in a conventional manner. The resulting hydrochloride was dissolved in methanol (200 ml), followed by the addition of 10% palladium/carbon catalyst (0.31 g), and the catalytic reduction was conducted at atmospheric pressure for 3 days. The catalyst was filtered off, while the solvent was evaporated. Water was added to the resulting residue, followed by the addition of an aqueous solution of saturated sodium bicarbonate, and then the mixture was extracted with chloroform. The extract was washed with brine and dried over magnesium sulfate. The solvent was evaporated, and the resulting residue was purified by silica gel column chromatography (chloroform/methanol system), to give obtain 1-(4-ethylpiperazin-1-yl)-3-(3-fluoro-4-hydroxyphenyl)isoquinoline (1.01 g) as a pale brown viscous oil.

Sodium hydride (0.03 g) was washed with n-hexane, suspended in N,N-dimethylformamide (2 ml) and stirred under ice-cooling. To the resulting mixture was added the resulting 1-(4-ethylpiperazin-1-yl)-3-(3-fluoro-4-hydroxyphenyl)isoquinoline (0.20 g) dissolved in N,N-dimethylformamide (2 ml), and the mixture was stirred at room temperature for 50 min. The mixture was again ice-cooled, followed by the addition of 2-methoxyethyl bromide (79 ml), and the mixture was stirred in nitrogen atmosphere at 50° C. overnight. Water was added to the reaction solution, and the mixture was extracted with ethyl acetate. The organic layer was washed with water and brine, and dried over magnesium sulfate. The solvent was evaporated, and the resulting residue was purified by silica gel column chromatography (chloroform/methanol system), to give 0.16 g of the free compound of the title compound as a pale brown viscous oil.

Free compound:
$^1$H-NMR (400 MHz, CDCl$_3$); δ (ppm) 1.17 (t, J=7.2 Hz, 3H), 2.55 (q, J=7.2 Hz, 2H), 2.75 (br-t, 4H), 3.47 (s, 3H), 3.58 (br-t, 4H), 3.79–3.82 (m, 2H), 4.24–4.26 (m, 2H), 7.06 (dd, J=8.6, 8.6 Hz, 1H), 7.45 (br-t, 1H), 7.57 (br-t, 1H), 7.59 (s, 1H), 7.76 (d, J=8.0 Hz, 1H), 7.85–7.88 (m, 1H), 7.95 (dd, J=2.0, 12.8 Hz, 1H), 8.06 (d, J=8.4 Hz, 1H).

The resulting free compound was converted into a hydrochloride in a conventional manner, and then reprecipitated with ethanol/IPE, to give the title compound as a pale yellowish brown powder.

Hydrochloride:
m.p.; 112.5–114° C.
$^1$H-NMR (400 MHz, DMSO-d$_6$); δ (ppm) 1.33 (t, J=7.2 Hz, 3H), 3.20–3.27 (m, 2H), 3.31–3.39 (m, 2H), 3.34 (s, 3H), 3.52 (br-t, 2H), 3.63 (br-d, 2H), 3.71–3.73 (m, 2H), 4.00 (br-d, 2H), 4.24–4.26 (m, 2H), 7.31 (dd, J=8.8, 8.8 Hz, 1H), 7.60 (br-t, 1H), 7.74 (br-t, 1H), 7.95–8.06 (m, 3H), 8.08 (s, 1H), 8.11 (d, J=8.4 Hz, 1H), 10.96 (br-s, 1H).
MS(FAB) m/z 410 (M+H)*.

Example 368

Synthesis of 1-(4-ethylpiperazin-1-yl)-3-(3,5-difluoro-4-methoxyethoxyphenyl)isoquinoline dihydrochloride

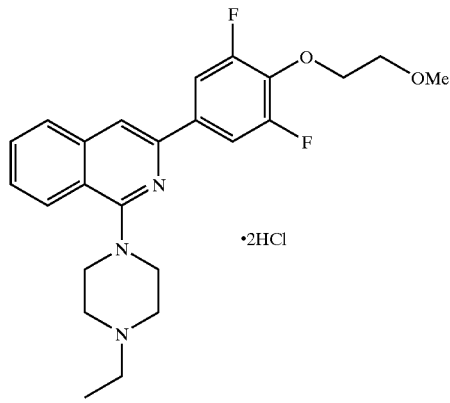

4-Benzyloxy-3,5-difluorophenylboric acid (1.97 g) and 3-bromo-1-(4-ethylpiperazin-1-yl)isoquinoline (5.20 g) were heated under reflux in the presence of tetrakistriphenylphosphinepalladium(0) (0.50 g) in toluene (250 ml) and a 10% aqueous solution of sodium carbonate (150 ml) in nitrogen atmosphere for 1 hr. 4-Benzyloxy-3,5-difluorophenylboric acid (1.15 g) was additionally added thereto, and the mixture was heated under reflux for 1 hr. 4-Benzyloxy-3,5-difluorophenylboric acid (1.15 g) was additionally added to the resulting mixture, and then heated under reflux overnight. The organic layer was separated and extracted with 2N hydrochloric acid twice. The resulting aqueous layer was washed with ethyl acetate, adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 1-(4-ethylpiperazin-1-yl)-3-(4-benzyloxy-3,5-difluorophenyl)isoquinoline (6.44 g) as a brown viscous oil.

The resulting 1-(4-ethylpiperazin-1-yl)-3-(4-benzyloxy-3,5-difluorophenyl)isoquinoline (6.44 g) was converted into a hydrochloride in a conventional manner. The hydrochloride was dissolved in methanol (200 ml), followed by the addition of 10% palladium/carbon catalyst (0.48 g), and then the catalytic reduction was conducted at atmospheric pressure overnight. The catalyst was filtered off, while the solvent was evaporated. Water was added to the resulting residue, followed by the addition of an aqueous solution of saturated sodium bicarbonate, and the mixture was extracted with chloroform. The extract was washed with brine, dried over magnesium sulfate, and the solvent was evaporated, to give obtain 1-(4-ethylpiperazin-1-yl)-3-(3,5-difluoro-4-hydroxyphenyl)isoquinoline (3.36 g) as a pale brown amorphous.

Sodium hydride (0.04 g) was washed with n-hexane, suspended in N,N-dimethylformamide (2 ml) and stirred under ice-cooling. The above-described 1-(4-ethylpiperazin-1-yl)-3-(3,5-difluoro-4-hydroxyphenyl)isoquinoline (0.30 g) dissolved in N,N-dimethylformamide (2 ml) was added thereto, and the mixture was stirred at room temperature for 50 min. The mixture was again ice-cooled, followed by the addition of 2-methoxyethyl bromide (115 ml), and the mixture was stirred in nitrogen atmosphere at 50° C. overnight. Water was added to the reaction solution, and then it was extracted with ethyl acetate. The extract was washed with water and brine, and dried over magnesium sulfate. The solvent was evaporated, and the resulting residue was purified by silica gel column chromatography (chloroform/methanol system), to give 0.26 g of the free compound of the title compound as a brown viscous oil.

Free compound:

$^1$H-NMR (400 MHz, CDCl$_3$); δ (ppm) 1.17 (t, J=7.2 Hz, 3H), 2.55 (q, J=7.2 Hz, 2H), 2.75 (br-t, 4H), 3.46 (s, 3H), 3.56 (br-t, 4H), 3.74–3.76 (m, 2H), 4.32–4.34 (m, 2H), 7.47 (br-t, 1H), 7.57 (s, 1H), 7.59 (br-t, 1H), 7.69–7.77 (m, 3H), 8.06 (d, J=8.0 Hz, 1H).

The resulting free compound was converted into a hydrochloride in a conventional manner, and then reprecipitated with methanol/ether, to give the title compound as a pale yellowish brown powder.

Hydrochloride:

m.p.; 110–112° C.

$^1$H-NMR (400 MHz, DMSO-d$_6$); δ (ppm) 1.34 (t, J=7.2 Hz, 3H), 3.19–3.26 (m, 2H), 3.30–3.37 (m, 2H), 3.31 (s, 3H), 3.55 (br-t, 2H), 3.62 (br-d, 2H), 3.65–3.67 (m, 2H), 4.01 (br-d, 2H), 4.28–4.30 (m, 2H), 7.64 (br-t, 1H), 7.77 (br-t, 1H), 7.93–7.80 (m, 3H), 8.13 (d, J=8.4 Hz, 1H), 8.18 (s, 1H), 11.20 (br-s, 1H).

MS(FAB) m/z 428 (M+H)*.

Example 369

Synthesis of 1-(4-ethylpiperazin-1-yl)-3-[3-fluoro-4-(2-hydroxyethoxy)phenyl]isoquinoline dihydrochloride

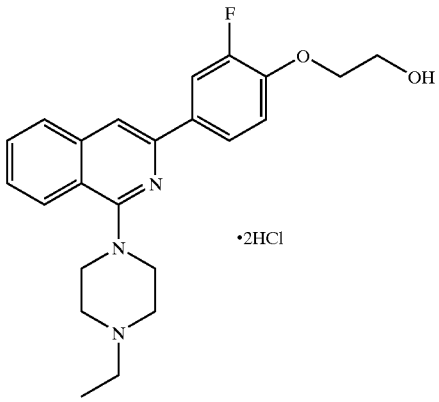

Sodium hydride (0.08 g) was washed with n-hexane, suspended in N,N-dimethylformamide (0.5 ml) and stirred under ice-cooling, to which was then added 1-(4-ethylpiperazin-1-yl)-3-(3-fluoro-4-hydroxyphenyl)isoquinoline (0.50 g) obtained in the same manner as in Example 367 dissolved in N,N-dimethylformamide (2 ml), and the mixture was stirred at room temperature for 30 min. The mixture was again ice-cooled, followed by the addition of 2-(tert-butyldimethylsilyloxy)ethyl bromide (0.51 g) dissolved in N,N-dimethylformamide (1 ml), and the mixture was stirred in nitrogen atmosphere at 50° C. overnight. Water was added to the reaction solution, and the mixture was extracted with ethyl acetate. The extract was washed with water and brine, and dried over magnesium sulfate. The solvent was evaporated, and the resulting residue was purified by silica gel column chromatography (chloroform/methanol system), to give obtain 1-(4-ethylpiperazin-1-yl)-3-{3-fluoro-4-[2-(tert-butyldimethylsilyloxy)ethoxy]phenyl}isoquinoline (0.62 g) as a pale brown viscous oil.

The resulting 1-(4-ethylpiperazin-1-yl)-3-{3-fluoro-4-[2-(tert-butyldimethylsilyloxy)ethoxy]phenyl}isoquinoline (0.62 g) was dissolved in tetrahydrofuran (6 ml), to which was then added 1.0M tetrabutylammonium fluoride/tetrahydrofuran solution (1.46 ml), and the mixture was stirred for 2 hr. The solvent was evaporated, and the resulting residue was dissolved in ethyl acetate, washed with water (three times) and brine, and dried over magnesium sulfate. The solvent was evaporated, and the resulting residue was purified by silica gel column chromatography (chloroform/methanol system), to give 0.42 g of the free compound of the title compound as a yellow powder.

Free compound:

$^1$H-NMR (400 MHz, CDCl$_3$); δ (ppm) 1.18 (t, J=7.2 Hz, 3H), 2.56 (q, J=7.2 Hz, 2H), 2.76 (br-t, 4H), 3.58 (br-t, 4H), 4.02 (t, J=4.4 Hz, 2H), 4.22 (t, J=4.4 Hz, 2H), 7.07 (dd, J=8.6, 8.6 Hz, 1H), 7.46 (br-t, 1H), 7.59 (br-t, 1H), 7.61 (s, 1H), 7.78 (d, J=8.4 Hz, 1H), 7.87–7.90 (m, 1H), 7.96 (dd, J=2.2, 13.0 Hz, 1H), 8.07 (d, J=8.4 Hz, 1H).

The resulting free compound was converted into a hydrochloride in a conventional manner, and then reprecipitated with ethanol/ether, to give the title compound as a pale yellowish brown powder.

Hydrochloride:
m.p.; 119–120° C.
$^1$H-NMR (400 MHz, DMSO-d$_6$); δ (ppm) 1.33 (t, J=7.2 Hz, 3H), 3.20–3.27 (m, 2H), 3.31–3.38 (m, 2H), 3.52 (br-t, 2H), 3.63 (br-d, 2H), 3.77 (t, J=5.0 Hz, 2H), 4.00 (br-d, 2H), 4.15 (t, J=5.0 Hz, 2H), 7.31 (dd, J=8.8, 8.8 Hz, 1H), 7.60 (br-t, 1H), 7.74 (br-t, 1H), 7.96 (d, J=8.0 Hz, 1H), 7.97–8.00 (m, 1H), 8.04 (dd, J=2.0, 13.2 Hz, 1H), 8.07 (s, 1H), 8.11 (d, J=8.4 Hz, 1H), 10.93 (br-s, 1H).
MS(FAB) m/z 396 (M+H)*.

Example 370

Synthesis of 1-(4-ethylpiperazin-1-yl)-3-[3,5-difluoro-4-(2-hydroxyethoxy)phenyl]isoquinoline

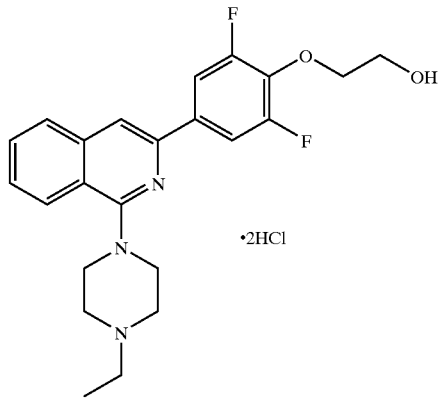

Sodium hydride (0.07 g) was washed with n-hexane, suspended in N,N-dimethylformamide (0.5 ml) and stirred under ice-cooling, to which was then added 1-(4-ethylpiperazin-1-yl)-3-(3,5-difluoro-4-hydroxyphenyl)isoquinoline (0.52 g) obtained in the same manner as in Example 368 dissolved in N,N-dimethylformamide (2 ml), and the mixture was stirred at room temperature for 50 min. The mixture was again ice-cooled, followed by the addition of 2-(tert-butyldimethylsilyloxy)ethyl bromide (0.51 g) dissolved in N,N-dimethylformamide (1 ml), and the mixture was stirred in nitrogen atmosphere at 50° C. overnight. Water was added to the reaction solution, and the mixture was extracted with ethyl acetate. The extract was washed with water and brine, and dried over magnesium sulfate. The solvent was evaporated, and the resulting residue was purified by silica gel column chromatography (chloroform/methanol system), to give 1-(4-ethylpiperazin-1-yl)-3-{3,5-difluoro-4-[2-(tert-butyldimethylsilyloxy)ethoxy]phenyl}isoquinoline (0.62 g) as a brown viscous oil.

The resulting 1-(4-ethylpiperazin-1-yl)-3-{3,5-difluoro-4-[2-(tert-butyldimethylsilyloxy)ethoxy]phenyl}isoquinoline (0.62 g) was dissolved in tetrahydrofuran (6 ml), to which was then added 1.0M tetrabutylammonium fluoride/tetrahydrofuran solution (1.41 ml), and the mixture was stirred for 75 min. The solvent was evaporated, and the resulting residue was dissolved in ethyl acetate, washed with (three times) and brine, and dried over magnesium sulfate. The solvent was evaporated, and the resulting residue was purified by silica gel column chromatography (chloroform/methanol system), to give 0.46 g of the free compound of the title compound as a pale brown powder.
Free compound:
$^1$H-NMR (400 MHz, CDCl$_3$); δ (ppm) 1.18 (t, J=7.2 Hz, 3H), 2.56 (q, J=7.2 Hz, 2H), 2.76 (br-t, 4H), 3.58 (br-t, 4H), 3.93 (t, J=4.4 Hz, 2H), 4.31 (t, J=4.4 Hz, 2H), 7.49 (br-t, 1H), 7.60 (s, 1H), 7.61 (br-t, 1H), 7.72–7.80 (m, 3H), 8.08 (d, J=8.4 Hz, 1H).

The resulting free compound was converted into a hydrochloride in a conventional manner, and then recrystallized from ethanol/ether, to give the title compound as a yellowish brown powder.
Hydrochloride:
m.p.; 112.5–114° C.
$^1$H-NMR (400 MHz, DMSO-d$_6$); δ (ppm) 1.33 (t, J=7.2 Hz, 3H), 3.20–3.27 (m, 2H), 3.30–3.38 (m, 2H), 3.52 (br-t, 2H), 3.63 (br-d, 2H), 3.71 (d, J=5.0 Hz, 2H), 4.20 (d, J=5.0 Hz, 2H), 7.64 (br-t, 1H), 7.77 (br-t, 1H), 7.92–7.99 (m, 3H), 8.13 (d, J=8.0 Hz, 1H), 8.18 (s, 1H), 10.97 (br-s, 1H).
MS(FAB) m/z 414 (M+H)*.

Example 371

Synthesis of 1-(4-ethylpiperazin-1-yl)-3-[3,5-difluoro-4-(2-fluoroethoxy)phenyl]isoquinoline dihydrochloride

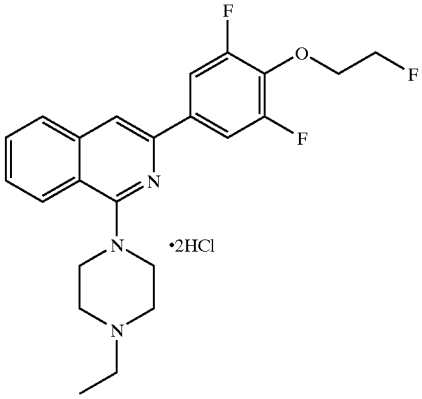

Sodium hydride (0.05 g) was washed with n-hexane, suspended in N,N-dimethylformamide (0.5 ml) and stirred under ice-cooling, to which was then added 1-(4-ethylpiperazin-1-yl)-3-(3,5-difluoro-4-hydroxyphenyl)isoquinoline (0.31 g) obtained in the same manner as in Example 368 dissolved in N,N-dimethylformamide (2 ml), and the mixture was stirred at room temperature for 35 min. The resulting mixture was again ice-cooled, followed by the addition of 2-fluoroethyl bromide (95 ml), and the mixture was stirred in nitrogen atmosphere at 50° C. overnight. Water was added to the reaction solution, and the mixture was extracted with ethyl acetate extraction. The extract was washed with water and brine, and dried over magnesium sulfate. The solvent was evaporated, and the resulting residue was purified by silica gel column chromatography (chloroform/methanol system), to give 0.20 g of the free compound of the title compound as a brown viscous oil.
Free compound:
$^1$H-NMR (400 MHz, CDCl$_3$); δ (ppm) 1.18 (t, J=7.2 Hz, 3H), 2.56 (q, J=7.2 Hz, 2H), 2.75 (br-t, 4H), 3.57 (br-t, 4H), 4.43 (dt, J=4.0, 28.4 Hz, 2H), 4.75 (dt, J=4.0, 47.2 Hz, 2H), 7.48 (br-t, 1H), 7.58 (s, 1H), 7.60 (br-t, 1H), 7.70–7.78 (m, 3H), 8.07 (d, J=8.8 Hz, 1H).

The resulting free compound was converted into a hydrochloride in a conventional manner, and then reprecipitated with ethanol/ether, to give the title compound as a pale yellow powder.

Hydrochloride:

m.p.; 105.0–105.5° C.

$^1$H-NMR (400 MHz, DMSO-d$_6$); δ (ppm) 1.32 (t, J=7.2 Hz, 3H), 3.21–3.28 (m, 2H), 3.31–3.39 (m, 2H), 3.48 (br-t, 2H), 3.64 (br-d, 2H), 4.03 (br-d, 2H), 4.43 (dt, J=3.8, 30.4 Hz, 2H), 4.73 (dt, J=3.8, 48.0 Hz, 2H), 7.65 (br-t, 1H), 7.78 (br-t, 1H), 7.96–8.02 (m, 3H), 8.13 (d, J=8.4 Hz, 1H), 8.20 (s, 1H), 10.57 (br-s, 1H).

MS(FAB) m/z 416 (M+H)*.

Example 372

Synthesis of 1-[4-(2-hydroxyethyl)piperazin-1-yl]-3-[4-(N-ethylsulfamoyl)phenyl]isoquinoline oxalate

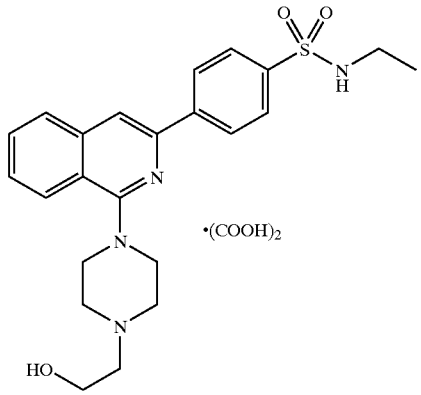

N-Ethyl-4-tributylstannylbenzenesulfonamide (1.42 g) and 3-bromo-1-(4-formylpiperazin-1-yl)isoquinoline (0.82 g) were heated under reflux in the presence of tetrakistriphenylphosphinepalladium(0) (0.12 g) in xylene in nitrogen atmosphere overnight. After cooling, the reaction solution was diluted with ethyl acetate and filtered. The filtrate was extracted with 5N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (toluene/acetone system), to give 1-(4-formylpiperazin-1-yl)-3-[4-(N-ethylsulfamoyl)phenyl]isoquinoline (0.45 g).

To the resulting 1-(4-formylpiperazin-1-yl)-3-[4-(N-ethylsulfamoyl)phenyl]isoquinoline (0.45 g) were added ethanol (20 ml) and a 8N aqueous solution of sodium hydroxide (651 ml), and the mixture was heated under reflux in nitrogen atmosphere for 1.5 hr. The solvent was evaporated, and to the resulting residue were added water and ethyl acetate. The organic layer was separated. Then it was washed with brine, and dried over magnesium sulfate. The solvent was evaporated, to give 1-(piperazin-1-yl)-3-[4-(N-ethylsulfamoyl)phenyl]isoquinoline (0.49 g) as a colorless powder.

The resulting 1-(piperazin-1-yl)-3-[4-(N-ethylsulfamoyl)phenyl]isoquinoline (0.49 g) was dissolved in N,N-dimethylformamide (10 ml), followed by the addition of triethylamine (290 ml) and ethylene bromohydrin (185 ml), and the reaction mixture was reacted at 50° C. overnight in nitrogen atmosphere. Water was added to the reaction solution, and the mixture was extracted with ethyl acetate. The ethyl acetate layer was washed with water (four times) and brine, and dried over magnesium sulfate. The solvent was evaporated, and the resulting residue was purified by silica gel column chromatography (chloroform/methanol system), to give 0.20 g of the free compound of the title compound as a colorless powder.

Free compound:

$^1$H-NMR (400 MHz, CDCl$_3$); δ (ppm) 1.14 (t, J=7.2 Hz, 3H), 2.71 (t, J=5.4 Hz, 2H), 2.84 (br-t, 4H), 3.07 (dq, J=6.2, 7.2 Hz, 2H), 3.59 (br-s, 4H), 3.71 (t, J=5.4 Hz, 2H), 4.30 (t, J=6.2 Hz, 1H), 7.54 (br-t, 1H), 7.65 (br-t, 1H), 7.79 (s, 1H), 7.84 (d, J=8.0 Hz, 1H), 7.96 (d, J=8.6 Hz, 2H), 8.10 (d, J=8.4 Hz, 1H), 8.31 (d, J=8.6 Hz, 2H).

The resulting free compound was converted into an oxalate in a conventional manner, and then recrystallized from ethanol/IPE, to give the title compound as a colorless powder.

Oxalate:

m.p.; 172–174° C.

$^1$H-NMR (400 MHz, DMSO-d$_6$); δ (ppm) 1.00 (t, J=7.2 Hz, 3H), 2.79–2.86 (m, 2H), 2.92 (br-s, 2H), 3.15 (br-s, 4H), 3.61 (br-s, 4H), 3.70 (t, J=7.2 Hz, 2H), 7.61–7.67 (m, 2H), 7.77 (br-t, 1H), 7.91 (d, J=8.6 Hz, 2H), 8.01 (d, J=8.0 Hz, 1H), 8.12 (d, J=8.4 Hz, 1H), 8.18 (s, 1H), 8.40 (d, J=8.6 Hz, 2H).

MS(FAB) m/z 441 (M+H)*.

Example 373

Synthesis of 1-[4-(2-hydroxyethyl)piperazin-1-yl]-3-[4-(propylsulfonyl)phenyl]isoquinoline oxalate

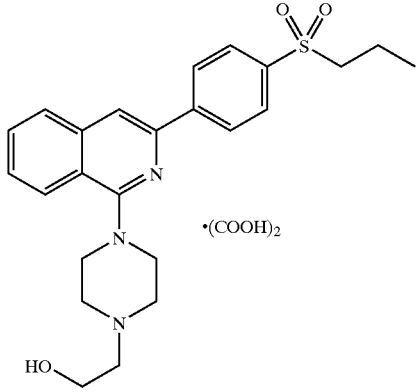

Propyl-(4-tributylstannylphenyl)sulfone (1.59 g) and 3-bromo-1-(4-formylpiperazin-1-yl)isoquinoline (0.93 g) were heated under reflux in the presence of tetrakistriphenylphosphinepalladium(0) (0.13 g) in xylene in nitrogen atmosphere overnight. After cooling, the reaction solution was diluted with ethyl acetate and filtered. The filtrate was extracted with 5N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (toluene/acetone system), to give 1-(4-formylpiperazin-1-yl)-3-[4-(propylsulfonyl)phenyl]isoquinoline (0.76 g).

To the resulting 1-(4-formylpiperazin-1-yl)-3-[4-(propylsulfonyl)phenyl]isoquinoline (0.72 g) were added ethanol (25 ml) and a 8N aqueous solution of sodium hydroxide (1.06 ml), and the mixture was heated under reflux in nitrogen atmosphere for 1.5 hr. The solvent was evaporated, and to the resulting residue were added water and ethyl acetate. The organic layer was separated. Then, it was washed with brine, and dried over magnesium sulfate. The solvent was evaporated, to give 1-(piperazin-1-yl)-3-[4-(propylsulfonyl)phenyl]isoquinoline (0.61 g) as a colorless powder.

The resulting 1-(piperazin-1-yl)-3-[4-(propylsulfonyl)phenyl]isoquinoline (0.61 g) was dissolved in N,N-dimethylformamide (10 ml), followed by the addition of triethylamine (401 μl) and ethylene bromohydrin (255 μl), and the resulting reaction mixture was reacted at 50° C. overnight in nitrogen atmosphere. Water was added to the reaction solution, and the mixture was extracted with ethyl acetate. The ethyl acetate layer was washed with water (four times) and brine, and dried over magnesium sulfate. The solvent was evaporated, and the resulting residue was purified by silica gel column chromatography (chloroform/methanol system), to give 0.59 g of the free compound of the title compound as a colorless powder.
Free compound:
$^{1}$H-NMR (400 MHz, CDCl$_3$); δ (ppm) 1.02 (t, J=7.2 Hz, 3H), 1.74–1.83 (m, 2H), 2.71 (t, J=5.4 Hz, 2H), 2.85 (br-t, 4H), 3.09–3.13 (m, 2H), 3.59 (br-s, 4H), 3.71 (t, J=5.4 Hz, 2H), 7.55 (br-t, 1H), 7.65 (br-t, 1H), 7.81 (s, 1H), 7.85 (d, J=8.0 Hz, 1H), 7.99 (d, J=8.4 Hz, 2H), 8.10 (d, J=8.4 Hz, 1H), 8.35 (d, J=8.4 Hz, 2H).

The resulting free compound was converted into an oxalate in a conventional manner, and then recrystallized from ethanol/IPE, to give the title compound as a colorless powder.
Oxalate:
m.p.; 127–129° C.
$^{1}$H-NMR (400 MHz, DMSO-d$_6$); δ (ppm) 0.94 (t, J=7.2 Hz, 3H), 1.55–1.64 (m, 2H), 3.04 (br-s, 2H), 3.27 (br-s, 4H), 3.31–3.35 (m, 2H), 3.66 (br-s, 4H), 3.73 (t, J=5.6 Hz, 2H), 7.66 (br-t, 1H), 7.78 (br-t, 1H), 8.01 (d, J=8.4 Hz, 2H), 8.03 (br-d, 1H), 8.14 (d, J=8.4 Hz, 1H), 8.24 (s, 1H), 8.46 (d, J=8.4 Hz, 2H).
MS(FAB) m/z 440 (M+H)*.

Example 374

Synthesis of 1-(4-ethylpiperazin-1-yl)-3-(phenylthio)isoquinoline oxalate

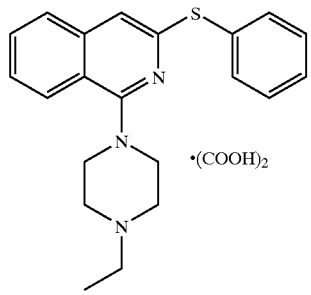

3-Bromo-1-(4-ethylpiperazin-1-yl)isoquinoline (0.51 g) was dissolved in tetrahydrofuran (20 ml) and cooled to −78° C. in nitrogen atmosphere. To the mixture was added dropwise 2.5M (n-butyl)lithium/hexane solution (0.73 ml), and the mixture was further stirred for 1 hr. Subsequently, diphenyl disulfide (0.40 g) dissolved in tetrahydrofuran (10 ml) was added thereto, and the temperature was raised to room temperature under stirring overnight. Water was added thereto, and the mixture was extracted with ethyl acetate. The extract was washed with a 2N aqueous solution of sodium hydroxide (three times) and brine, and dried over magnesium sulfate. The solvent was evaporated, and the resulting residue was purified by silica gel column chromatography (toluene/acetone system), to give 0.35 g of the free compound to the title compound as a yellow viscous oil.
Free compound:
$^{1}$H-NMR (400 MHz, CDCl$_3$); δ (ppm) 1.14 (t, J=7.2 Hz, 3H), 2.51 (q, J=7.2 Hz, 2H), 2.65 (br-t, 4H), 3.46 (br-t, 4H), 6.87 (s, 1H), 7.34–7.66 (m, 8H), 7.96 (d, J=8.0 Hz, 1H).

The resulting free compound was converted into an oxalate in a conventional manner, and then recrystallized from ethanol/IPE, to give the title compound as a colorless powder.
Oxalate:
m.p.; 181.5–183° C.
$^{1}$H-NMR (400 MHz, DMSO-d$_6$); δ (ppm) 1.22 (t, J=7.2 Hz, 3H), 3.02–3.09 (m, 2H), 3.22 (br-s, 4H), 3.53 (br-s, 4H), 7.44–7.79 (m, 9H), 8.02 (d, J=8.4 Hz, 1H).
MS(FAB) m/z 350 (M+H)*.

Example 375

Synthesis of 1-(4-ethylpiperazin-1-yl)-3-[4-(2-oxopropyl)phenyl]isoquinoline dihydrochloride

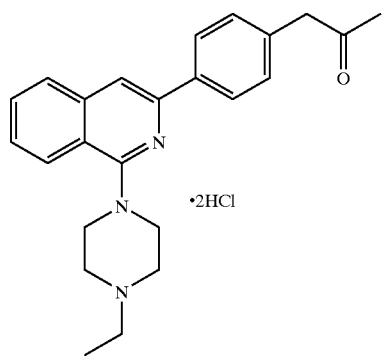

(4-Tributylstannyl)phenyl acetone (2.23 g) and 3-bromo-1-(4-ethylpiperazin-1-yl)isoquinoline (1.41 g) were heated under reflux in the presence of tetrakistriphenylphosphinepalladium(0) (0.21 g) in xylene in nitrogen atmosphere overnight. After cooling, the reaction solution was diluted with ethyl acetate and filtered. The filtrate was extracted with 2N hydrochloric acid, and the aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (toluene/acetone system), to give 0.97 g of the free compound of the title compound as a pale brown amorphous.
Free compound:
$^{1}$H-NMR (400 MHz, CDCl$_3$); δ (ppm) 1.18 (t, J=7.2 Hz, 3H), 2.19 (s, 3H), 2.56 (q, J=7.2 Hz, 2H), 2.76 (br-t, 4H), 3.59 (br-t, 4H), 3.75 (s, 2H), 7.31 (d, J=8.4 Hz, 2H), 7.47 (br-t, 1H), 7.59 (br-t, 1H), 7.69 (s, 1H), 7.79 (d, J=8.0 Hz, 1H), 8.08 (d, J=8.0 Hz, 1H), 8.15 (d, J=7.2 Hz, 2H).

The resulting free compound was converted into a hydrochloride in a conventional manner, and then reprecipitated with methanol/IPE, to give the title compound as a yellow powder.

Hydrochloride:

m.p.; 125–126° C.

$^1$H-NMR (400 MHz, CDCl$_3$); δ (ppm) 1.32 (t, J=7.2 Hz, 3H), 2.17 (s, 3H), 3.21–3.28 (m, 2H), 3.31–3.40 (m, 2H), 3.49 (br-t, 2H), 3.63 (br-d, 2H), 3.84 (s, 2H), 4.01 (br-d, 2H), 7.33 (d, J=8.4 Hz, 2H), 7.61 (br-t, 1H), 7.75 (br-t, 1H), 7.99 (d, J=7.6 Hz, 1H), 8.08 (s, 1H), 8.13–8.16 (m, 3H), 10.59 (br-s, 1H).

MS(FAB) m/z 374 (M+H)*.

Example 376

Synthesis of 1-(4-ethylpiperazin-1-yl)-3-[4-(2-hydroxypropyl)phenyl]isoquinoline oxalate

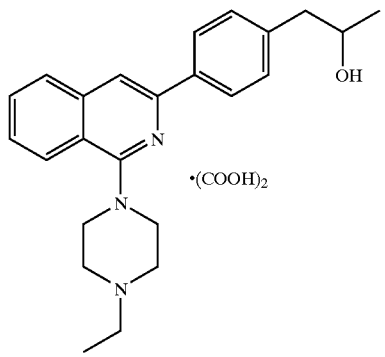

1-(4-Ethylpiperazin-1-yl)-3-[4-(2-oxopropyl)phenyl]isoquinoline (0.27 g) obtained in the previous Example was dissolved in methanol (40 ml), to which was then gradually added sodium borohydride. The disappearance of the starting material was confirmed by TLC; and then, the solvent was evaporated. Water was added to the resulting mixture, and then the mixture was extracted with ethyl acetate. The resulting product was washed with brine, and dried over magnesium sulfate. The solvent was evaporated, to give 0.25 g of the free compound of the title compound as a colorless viscous oil.

Free compound:

$^1$H-NMR (400 MHz, CDCl$_3$); δ (ppm) 1.18 (t, J=7.0 Hz, 3H), 1.29 (d, J=6.0 Hz, 3H), 2.57 (q, J=7.2 Hz, 2H), 2.73–2.78 (m, 5H), 2.86 (dd, J=4.6, 13.4 Hz, 1H), 3.60 (br-t, 4H), 4.04–4.13 (m, 1H), 7.32 (d, J=8.4 Hz, 2H), 7.46 (br-t, 1H), 7.59 (br-t, 1H), 7.68 (s, 1H), 7.79 (d, J=8.0 Hz, 1H), 8.08 (d, J=8.4 Hz, 1H), 8.13 (d, J=8.4 Hz, 2H).

The resulting free compound was converted into an oxalate in a conventional manner, and then reprecipitated with ethanol/IPE, to give the title compound as a pale brown powder.

Hydrochloride:

m.p.; 174–176° C.

$^1$H-NMR (400 MHz, DMSO-d$_6$); δ (ppm) 1.07 (t, J=6.4 Hz, 3H), 1.26 (t, J=7.2 Hz, 3H), 2.63 (dd, J=6.2, 13.4 Hz, 1H), 2.76 (dd, J=6.6, 13.4 Hz, 1H), 3.15 (br-q, 2H), 3.39 (br-s, 4H), 3.67 (br-s, 4H), 3.83–3.91 (m, 1H), 7.33 (d, J=8.4 Hz, 2H), 7.59 (br-t, 1H), 7.73 (br-t, 1H), 7.97 (d, J=8.0 Hz, 1H), 8.03 (s, 1H), 8.09–8.12 (m, 3H).

MS(FAB) m/z 376 (M+H)$^+$.

Example 377

Synthesis of 1-(4-Ethylpiperazin-1-yl)-3-[4-(2-Hydroxy-2-Methylpropyl)Phenyl]Isoquinoline Oxalate

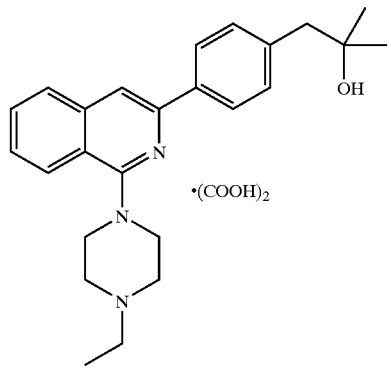

1-(4-Ethylpiperazin-1-yl)-3-[4-(2-oxopropyl)phenyl]isoquinoline (0.27 g) obtained in Example 375 was dissolved in tetrahydrofuran (10 ml), and the mixture was stirred under ice-cooling. To the resulting mixture was added 3.0M methylmagnesium bromide/ether solution (0.44 ml), and the resulting mixture was further stirred for 20 min. Then, an aqueous solution of ammonium chloride and ethyl acetate were added thereto, and the mixture was stirred, to separate the organic layer. The resulting organic layer was washed with brine, dried over magnesium sulfate and the solvent was evaporated, to give 0.25 g or the free compound of the title compound as a pale brown amorphous.

Free compound:

$^1$H-NMR (400 MHz, CDCl$_3$); δ (ppm) 1.18 (t, J=7.2 Hz, 3H), 1.28 (s, 6H), 2.56 (q, J=7.2 Hz, 2H), 2.77 (br-t, 4H), 2.84 (s, 2H), 3.60 (br-t, 4H), 7.32 (d, J=8.2 Hz, 2H), 7.46 (br-t, 1H), 7.59 (br-t, 1H), 7.69 (s, 1H), 7.79 (d, J=8.4 Hz, 1H), 8.08 (d, J=8.4 Hz, 1H), 8.13 (d, J=8.2 Hz, 2H).

The resulting free compound was converted into an oxalate in a conventional manner, and then reprecipitated with ethanol/IPE, to give the title compound as a pale brown powder.

Oxalate:

m.p.; 184–186° C. (decomp.)

$^1$H-NMR (400 MHz, DMSO-d$_6$); δ (ppm) 1.10 (s, 6H), 1.26 (t, J=7.2 Hz, 3H), 2.17 (s, 2H), 3.12–3.18 (m, 2H), 3.39 (br-s, 4H), 3.67 (br-s, 4H), 7.34 (d, J=8.0 Hz, 2H), 7.59 (br-t, 1H), 7.73 (br-t, 1H), 7.97 (d, J=7.6 Hz, 1H), 8.04 (s, 1H), 8.08–8.12 (m, 3H).

MS(FAB) m/z 390 (M+H)$^+$.

Example 378

Synthesis of 1-(4-Ethylpiperazin-1-yl)-3-(2-Pyridylthio)Isoquinoline Oxalate

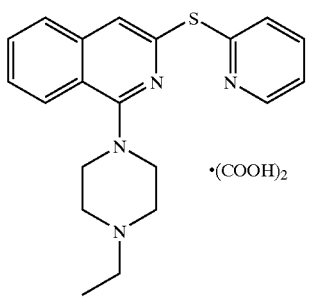

3-Bromo-1-(4-ethylpiperazin-1-yl)isoquinoline (0.44 g) was dissolved in tetrahydrofuran (20 ml), and the mixture was cooled to −78° C. in nitrogen atmosphere. To the resulting mixture was added dropwise 2.5M-(n-butyl) lithium/hexane solution (0.57 ml), and the mixture was further stirred for 30 min. Subsequently, di(2-pyridyl) disulfide (0.31 g) dissolved in tetrahydrofuran (5 ml) was added to the resulting mixture, of which the temperature was raised to room temperature under overnight stirring. Water was added thereto, and the mixture was extracted with ethyl acetate extraction. The resulting extract was washed with a 2N aqueous solution of sodium hydroxide (three times) and brine sequentially, and dried over magnesium sulfate. The solvent was evaporated, and the resulting residue was purified by silica gel column chromatography (toluene/acetone system), to give 0.05 g of the free compound of the title compound as a yellow viscous oil.

Free compound:

$^1$H-NMR (400 MHz, CDCl$_3$); δ (ppm) 1.14 (t, J=7.2 Hz, 3H), 2.51 (q, J=7.2 Hz, 2H), 2.65 (br-t, 4H), 3.46 (br-t, 4H), 7.09 (ddd, J=1.1, 4.9, 7.5 Hz, 1H), 7.39–7.41 (m, 1H), 7.46–7.61 (m, 4H), 7.66 (d, J=8.0 Hz, 1H), 8.03 (d, J=8.4 Hz, 1H), 8.49–8.51 (m, 1H).

The resulting free compound was converted into an oxalate in a conventional manner, and then recrystallized from ethanol/IPE, to give the title compound as a colorless powder.

Oxalate:

m.p.; 178–181° C. (decomp.)

$^1$H-NMR (400 MHz, DMSO-d$_6$); δ (ppm) 1.20 (t, J=7.2 Hz, 3H), 3.02 (br-s, 2H), 3.20 (br-s, 4H), 3.51 (br-s, 4H), 7.25 (ddd, J=0.8, 4.9, 7.4 Hz, 1H), 7.34 (ddd, J=0.8, 0.8, 7.4 Hz, 1H), 7.65 (br-t, 1H), 7.70–7.78 (m, 2H), 7.71 (s, 1H), 7.90 (d, J=8.8 Hz, 1H), 7.10 (d, J=8.0 Hz, 1H), 8.47–8.49 (m, 1H).

MS(FAB) m/z 351 (M+H)$^+$.

Example 379

Synthesis of 1-(4-Ethylpiperazin-1-yl)-3-(4-Butyrylphenyl)Isoquinoline Dihydrochloride

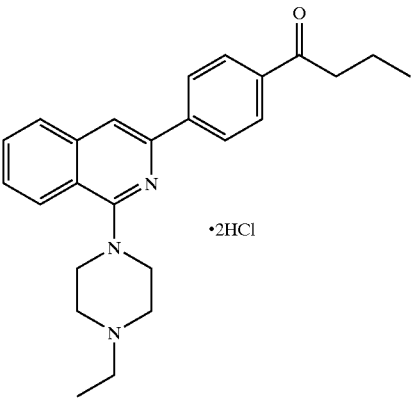

(n-Propyl) [(4-tributylstannyl)phenyl]ketone (1.57 g) and 3-bromo-1-(4-ethylpiperazin-1-yl)isoquinoline (0.99 g) were heated under reflux in the presence of tetrakistriphenylphosphinepalladium(0) (0.14 g), in xylene in nitrogen atmosphere overnight. After cooling, the reaction solution was diluted with ethyl acetate and filtered. The resulting filtrate was extracted with 2N hydrochloric acid. The resulting aqueous layer was washed with ethyl acetate, adjusted to pH 10 with a 8N aqueous solution of sodium hydroxide, and then extracted with ethyl acetate. The resulting organic layer was washed with a 10% sodium carbonate and brine, and dried over magnesium sulfate. The solvent was evaporated, and the resulting residue was purified by silica gel column chromatography (toluene/acetone system), to give 0.84 g of the free compound of the title compound as a pale brown amorphous.

Free compound:

$^1$H-NMR (400 MHz, CDCl$_3$); δ (ppm) 1.04 (t, J=7.2 Hz, 3H), 1.18 (t, J=7.2 Hz, 3H), 1.81 (tq, J=7.2, 7.2 Hz, 2H), 2.56 (q, J=7.2 Hz, 2H), 2.77 (br-t, 4H), 3.00 (t, J=7.2 Hz, 2H), 3.61 (br-t, 4H), 7.51 (br-t, 1H), 7.62 (br-t, 1H), 7.78 (s, 1H), 7.83 (d, J=8.0 Hz, 1H), 8.06 (d, J=8.4 Hz, 2H), 8.10 (d, J=8.4 Hz, 1H), 8.26 (d, J=8.4 Hz, 2H).

The resulting free compound was converted into a hydrochloride in a conventional manner, and then reprecipitated with methanol/IPE, to give the title compound as a yellow powder.

Hydrochloride:

m.p.; 110–112.5° C. (decomp.)

$^1$H-NMR (400 MHz, DMSO-d$_6$); δ (ppm) 0.96 (t, J=7.2 Hz, 3H), 1.34 (t, J=7.2 Hz, 3H), 1.68 (tq, J=7.2, 7.2 Hz, 2H), 3.06 (t, J=7.2 Hz, 2H), 3.20–3.29 (m, 2H), 3.32–3.40 (m, 2H), 3.55 (br-t, 2H), 3.63 (br-d, 2H), 4.03 (br-d, J=7.2 Hz, 2H), 7.66 (br-t, 1H), 7.79 (br-t, 1H), 8.04 (d, J=8.0 Hz, 1H), 8.10 (d, J=8.4 Hz, 2H), 8.15 (d, J=8.4 Hz, 1H), 8.25 (s, 1H), 8.35 (d, J=8.4 Hz, 2H), 11.03 (br-s, 1H).

MS(FAB) m/z 388 (M+H)$^+$.

Example 380

Synthesis of 1-(4-Ethylpiperazin-1-yl)-3-[4-(1-Hydroxyiminobutyl)Phenyl]Isoquinoline

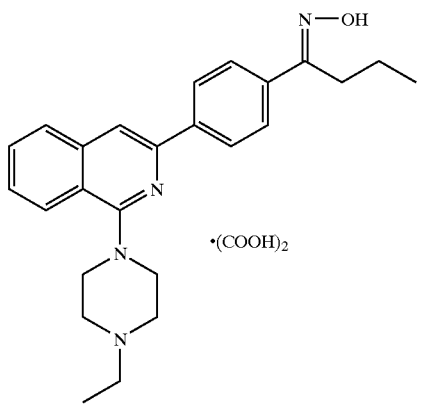

·(COOH)$_2$ 1-(4-Ethylpiperazin-1-yl)-3-(4-butyrylphenyl)isoquinoline (0.27 g) obtained in the previous Example was dissolved in ethanol (40 ml), to which was then added a solution of hydroxylamine hydrochloride (0.14 g) and sodium acetate (0.22 g) dissolved in water (10 ml), and the mixture was heated under reflux. The solvent was evaporated, and the resulting residue was purified by NH-silica gel column chromatography (ethyl acetate/methanol system), to give 0.23 g of the free compound of the title compound as a pale brown amorphous.

Free compound:

$^1$H-NMR (400 MHz, CDCl$_3$); δ (ppm) 1.00 (t, J=7.2 Hz, 3H), 1.19 (t, J=7.2 Hz, 3H), 1.60–1.67 (m, 4H), 2.59 (q, J=7.2 Hz, 2H), 2.79–2.85 (m, 6H), 3.63 (br-t, 4H), 7.47 (br-t, 1H), 7.60 (Br-t, 1H), 7.72–7.75 (m, 2H), 7.80 (br-d, 1H), 8.08 (br-d, 1H), 8.18–8.21 (m, 2H), 8.32 (br-s, 1H).

The resulting free compound was converted into an oxalate in a conventional manner, and then recrystallized from methanol/IPE, to give the title compound as a colorless powder.

Oxalate:

m.p.; 179.5–180° C.

$^1$H-NMR (400 MHz, DMSO-d$_6$); δ (ppm) 0.94 (t, J=7.2 Hz, 3H), 1.26 (t, J=7.2 Hz, 3H), 1.47–1.57 (m, 2H), 2.76 (br-t, 2H), 3.11 (br-q, 2H), 3.35 (br-s, 4H), 3.67 (br-s, 4H), 7.62 (br-t, 1H), 7.75 (br-t, 1H), 7.78 (d, J=8.4 Hz, 2H), 8.00 (d, J=8.0 Hz, 1H), 8.11 (s, 1H), 8.12 (d, J=8.4 Hz, 1H), 8.22 (d, J=8.4 Hz, 2H), 11.19 (br-s, 1H).

MS(FAB) m/z 403 (M+H)$^+$.

Example 381

Synthesis of 1-(4-Ethylpiperazin-1-yl)-3-yl)-3-[4-(N-Methyl-N-Propylcarbamoyl)Phenyl]Isoquinoline

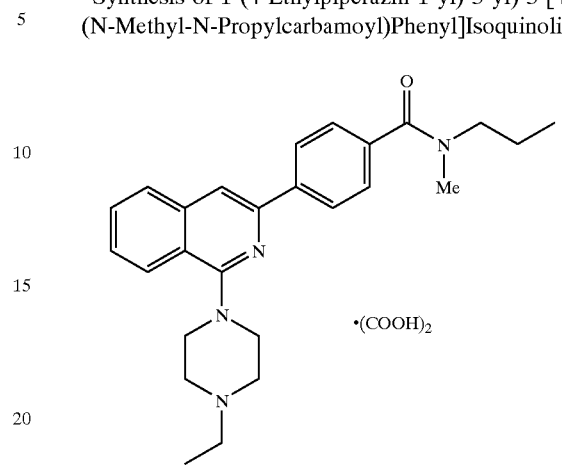

·(COOH)$_2$

N-Methyl-N-propyl-4-tributylstannylbenzamide (2.36 g) and 3-bromo-1-(4-ethylpiperazin-1-yl)isoquinoline (1.02 g) were heated under reflux overnight in the presence of tetrakistriphenylphosphinepalladium(0) (0.15 g) in xylene in nitrogen atmosphere. After cooling, the reaction solution was diluted with ethyl acetate and filtered. The filtrate was extracted with 2N hydrochloric acid. The aqueous layer was washed with ethyl acetate and adjusted to pH 10 by a 8N aqueous solution of sodium hydroxide, and then extracted with ethyl acetate, washed with a 10% aqueous solution of sodium carbonate and brine and dried over magnesium sulfate. The solvent was evaporated, and the resulting residue was purified by silica gel column chromatography (chloroform/methanol system), to give 0.72 g of the free compound of the title compound as a pale yellow powder.

Free compound:

$^1$H-NMR (400 MHz, CDCl$_3$); δ (ppm) 0.80 (br-t, 1.5H), 1.01 (br-t, 1.5H), 1.18 (t, J=7.2 Hz, 3H), 1.56–1.75 (m, 2H), 2.56 (q, J=7.2 Hz, 2H), 2.77 (br-t, 4H), 3.00–3.54 (m, 5H), 3.60 (br-t, 4H), 7.48 (br-t, 1H), 7.60 (br-t, 1H), 7.73 (s, 1H), 7.80 (d, J=8.4 Hz, 1H), 8.09 (d, J=7.6 Hz, 1H), 8.21 (d, J=8.4 Hz, 2H).

The resulting free compound was converted into a oxalate in a conventional manner, and then recrystallized from ethanol/IPE, to give the title compound as a pale brown powder.

Oxalate:

m.p.; 131–132° C.

$^1$H-NMR (400 MHz, DMSO-d$_6$); δ (ppm) 0.71 (br-s, 1.5H), 0.93 (br-s, 1.5H), 1.26 (t, J=7.2 Hz, 3H), 1.51–1.67 (br-d, 2H), 2.94–3.66 (m, 15H), 7.50 (br-t, t, 1H), 7.76 (br-t, 1H), 8.01 (d, J=7.6 Hz, 1H), 8.12–8.15 (m, 2H), 8.26 (d, J=8.4 Hz, 2H).

MS(FAB) m/z 417 (M+H)$^+$.

Example 382

Synthesis of 1-(4-Ethylpiperazin-1-yl)-3-{4-[N-(2-Hydroxyethyl)-N-Methylcarbamoyl]Phenyl}Isoquinoline

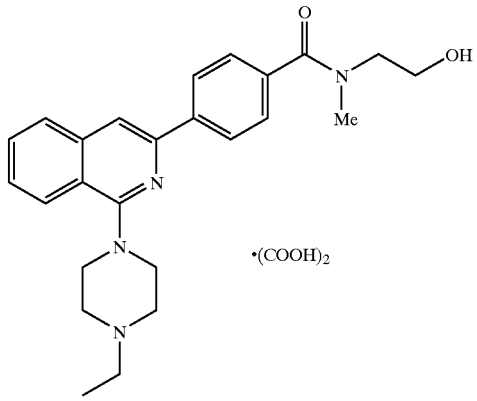

N-Methyl-N-(2-benzyloxyethyl)-4-tributylstannylbenzamide (1.93 g) and 3-bromo-1-(4-ethylpiperazin-1-yl)isoquinoline (0.93 g) were heated under reflux overnight in the presence of tetrakistriphenylphosphinepalladium(0) (0.13 g) in xylene in nitrogen atmosphere. After cooling, the reaction solution was diluted with ethyl acetate and filtered. The filtrate was extracted with 2N hydrochloric acid. The aqueous layer was washed with ethyl acetate and adjusted to pH 10 by a 8N aqueous solution of sodium hydroxide, which was then extracted with ethyl acetate, washed with a 10% aqueous solution of sodium carbonate and brine, and then dried over magnesium sulfate. The solvent was evaporated, and the resulting residue was purified by silica gel column chromatography (chloroform/methanol system), to give 1-(4-ethylpiperazin-1-yl)-3-{4-[N-(2-benzyloxyethyl)-N-methylcarbamoyl]phenyl}isoquinoline (0.69 g) as a pale yellow viscous oil.

Sequentially, the resulting 1-(4-ethylpiperazin-1-yl)-3-{4-[N-(2-benzyloxyethyl)-N-methylcarbamoyl]phenyl}isoquinoline (0.69 g) was converted into a hydrochloride in a conventional manner and then dissolved in methanol (50 ml). To the resulting solution was added 10% palladium/carbon catalyst (0.20 g), and the catalytic reduction was conducted at a atmospheric pressure overnight. The catalyst was filtered off, while the solvent was evaporated, and the resulting residue was purified by silica gel column chromatography (chloroform/methanol system), to give 0.41 g of the free compound of the title compound as a pale yellow amorphous.

Free compound:
$^1$H-NMR (400 MHz, CDCl$_3$); δ (ppm) 1.18 (t, J=7.2 Hz, 3H), 2.57 (q, J=7.2 Hz, 2H), 2.77 (br-t, 4H), 3.13 (br-s, 3H), 3.60 (br-t, 4H), 3.77 (br-s, 2H), 3.94 (br-s, 2H), 7.49 (br-t, 1H), 7.57 (br-d, 2H), 7.61 (br-t, 1H), 7.74 (s, 1H), 7.81 (d, J=8.0 Hz, 1H), 8.09 (d, J=8.4 Hz, 1H), 8.22 (d, J=8.0 Hz, 2H).

The resulting free compound was converted into an oxalate in a conventional manner, and then recrystallized from ethanol/IPE, to give the title compound as a pale brown powder.

Oxalate:
m.p.; 116–118° C.
$^1$H-NMR (400 MHz, DMSO-d$_6$); δ (ppm) 1.26 (t, J=7.2 Hz, 3H), 3.01 (s, 3H), 3.12 (br-q, 2H), 3.36 (br-s, 6H), 3.52 (br-s, 2H), 3.67 (br-s, 4H), 7.54 (d, J=8.4 Hz, 2H), 7.63 (br-t, 1H), 7.76 (br-t, 1H), 8.00 (d, J=8.0 Hz, 1H), 8.12–8.14 (m, 2H), 8.24 (br-d, 2H).
MS(FAB) m/z 419 (M+H)$^+$.

Example 383

Synthesis of 1-(4-Ethylpiperazin-1-yl)-3-[4-(3-Hydroxy-1-Methylpropyl)Phenyl]Isoquinoline Oxalate

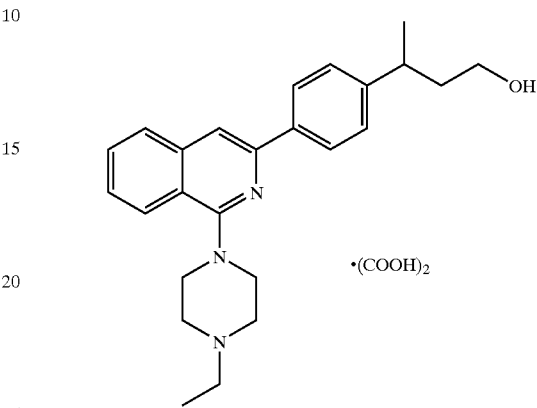

Ethyl 3-(4-Tributylstannylphenyl)butyrate (5.46 g) and 3-bromo-1-(4-ethylpiperazin-1-yl)isoquinoline (1.33 g) were heated under reflux overnight in the presence of tetrakistriphenylphosphinepalladium(0) (0.19 g) in xylene in nitrogen atmosphere. After cooling, the reaction solution was diluted with ethyl acetate and filtered. The filtrate was extracted with 2N hydrochloric acid. The aqueous layer was washed with ethyl acetate, adjusted to pH 10 with a 8N aqueous solution of sodium hydroxide, and then extracted in ethyl acetate. The organic layer was washed with a 10% aqueous solution of sodium carbonate and brine, and dried over magnesium sulfate. The solvent was evaporated, and the resulting residue was purified by silica gel column chromatography (chloroform/methanol system), to give 1-(4-ethylpiperazin-1-yl)-3-[4-(1-ethoxycarbonylpropan-2-yl)phenyl]isoquinoline (1.34 g) as a pale yellow viscous oil.

Subsequently, the resulting 1-(4-ethylpiperazin-1-yl)-3-[4-(1-ethoxycarbonylpropan-2-yl)phenyl]isoquinoline (0.69 g) was dissolved in tetrahydrofuran (10 ml). The solution was added to a suspension of lithium aluminum hydride (0.12 g) in tetrahydrofuran (20 ml) under cooling with a cooler of sodium chloride and ice, and the mixture was stirred for another 20 min. Water (120 ml), a 5N aqueous solution of sodium hydroxide (120 ml) and water (360 ml) were added to the reaction solution in this order, and then the resulting precipitates were filtered off. The solvent was evaporated, and the resulting residue was purified by silica gel column chromatography (toluene/acetone system), to give 0.32 g of the free compound of the title compound as a pale brown viscous oil.

Free compound:
$^1$H-NMR (400 MHz, CDCl$_3$); δ (ppm) 1.18 (t, J=7.2 Hz, 3H), 1.33 (d, J=7.2 Hz, 3H), 1.91 (dt, J=7.2, 7.2 Hz, 2H), 2.56 (q, J=7.2 Hz, 2H), 2.76 (br-t, 4H), 2.96 (tq, J=7.2, 7.2 Hz, 1H), 3.55–3.66 (m, 6H), 7.31 (d, J=8.2 Hz, 2H), 7.45 (br-t, 1H), 7.58 (br-t, 1H), 7.67 (s, 1H), 7.79 (d, J=8.0 Hz, 1H), 8.08 (d, J=8.4 Hz, 1H), 9.06 (d, J=8.2 Hz, 2H).

The resulting free compound was converted into an oxalate in a conventional manner, and then recrystallized from ethanol/IPE, to give the title compound as a pale brown powder.

Oxalate:
 m.p.; 106–108° C.
 ¹H-NMR (400 MHz, DMSO-d₆); δ (ppm) 1.24 (d, J=6.8 Hz, 3H), 1.25 (t, J=7.2 Hz, 3H), 1.74 (br-q, 1H), 2.86–2.95 (m, 1H), 3.11 (br-s, 2H), 3.28–3.38 (m, 6H), 3.65 (br-s, 4H), 7.34 (d, J=8.4 Hz, 2H), 7.59 (br-t, 1H), 7.73 (br-t, 1H), 7.97 (d, J=8.0 Hz, 1H), 8.03 (s, 1H), 8.11 (br-d, 3H).
 MS(FAB) m/z 390 (M+H)⁺.

Example 384

Synthesis of 1-(4-Ethylpiperazin-1-yl)-3-[4-(N-Propylcarbamoyl)-3-Fluorophenyl]Isoquinoline Dihydrochloride

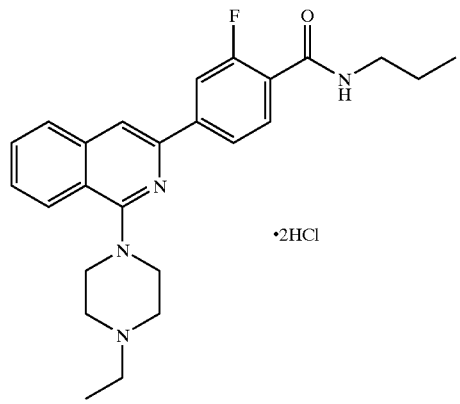

N-Propyl-3-fluoro-4-tributylstannylbenzamide (2.23 g) and 3-bromo-1-(4-ethylpiperazin-1-yl)isoquinoline (0.96 g) were heated under reflux overnight in the presence of tetrakistriphenylphosphinepalladium(0) (0.14 g) in xylene in nitrogen atmosphere. After cooling, the reaction solution was diluted with ethyl acetate and filtered. The filtrate was extracted with 2N hydrochloric acid. The aqueous layer was washed with ethyl acetate, adjusted to pH 10 with a 8N aqueous solution of sodium hydroxide, and then extracted with ethyl acetate. The organic layer was washed with a 10% aqueous solution of sodium carbonate and brine, and dried over magnesium sulfate. The solvent was evaporated, and the resulting residue was purified by silica gel column chromatography (chloroform/methanol system), to give 0.83 g of the free compound of the title compound as a pale yellow powder.
Free compound:
 ¹H-NMR (400 MHz, CDCl₃); δ (ppm) 1.02 (t, J=7.2 Hz, 3H), 1.18 (t, J=7.2 Hz, 3H), 1.68 (tq, J=7.2, 7.2 Hz, 2H), 2.56 (q, J=7.2 Hz, 2H), 2.77 (br-t, 4H), 3.46–3.51 (m, 2H), 3.60 (br-t, 4H), 6.80–6.86 (m, 1H), 7.52 (br-t, 1H), 7.63 (br-t, 1H), 7.75 (s, 1H), 7.82 (d, J=8.0 Hz, 1H), 7.98–8.02 (m, 2H), 8.09 (d, J=8.0 Hz, 1H), 8.19 (dt, J=8.2 Hz, 1H).

The resulting free compound was converted into a hydrochloride in a conventional manner, and then reprecipitated with ethanol/IPE, to give the title compound as a pale brown powder.
Hydrochloride:
 m.p.; 124–125° C. (decomp.)
 ¹H-NMR (400 MHz, DMSO-d₆); δ (ppm) 0.92 (t, J=7.6 Hz, 3H), 1.33 (t, J=7.2 Hz, 3H), 1.55 (tq, J=7.2 Hz, 2H), 3.21–3.27 (m, 4H), 3.32–3.39 (m, 2H), 3.53 (br-t, 2H), 3.64 (br-d, 2H), 4.03 (br-d, 2H), 7.67 (br-t, 1H), 7.73 (dd, J=7.8 Hz, 1H), 7.79 (br-t, 1H), 8.02 (d, J=7.6 Hz, 1H), 8.07 (br-d, 1H), 8.10 (dd, J=1.8, 8.2 Hz, 1H), 8.15 (d, J=8.0 Hz, 1H), 8.26 (s, 1H), 8.36 (br-t, 1H), 10.89 (br-s, 1H).

MS(FAB) m/z 421 (M+H)⁺.

Example 385

Synthesis of 1-(4-Ethylpiperazin-1-yl)-3-[3-Fluoro-4-(2-Hydroxyethyl)Phenyl]Isoquinoline Dihydrochloride

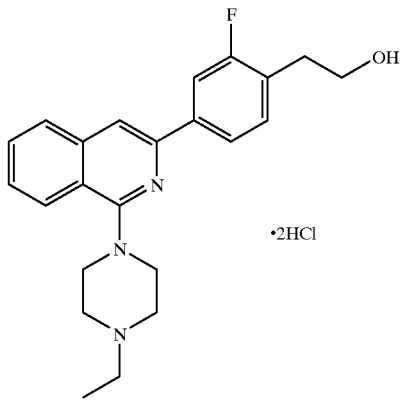

2-(3-Fluoro-4-tributylstannylphenyl)ethyl acetate (2.77 g) and 3-bromo-1-(4-ethylpiperazin-1-yl)isoquinoline (1.19 g) were heated under reflux overnight in the presence of tetrakistriphenylphosphinepalladium(0) (0.17 g) in xylene in nitrogen atmosphere. After cooling, the reaction solution was diluted with ethyl acetate and filtered. The filtrate was extracted with 2N hydrochloric acid. The aqueous layer was washed with ethyl acetate, adjusted to pH 10 with a 8N aqueous solution of sodium hydroxide, and then extracted with ethyl acetate. The organic layer was washed with a 10% aqueous solution of sodium carbonate and brine, and dried over magnesium sulfate. The solvent was evaporated, to give a mixture (1.44 g) of 1-(4-ethylpiperazin-1-yl)-3-[3-fluoro-4-(2-acetoxyethyl)phenyl]isoquinoline as a brown viscous oil and the starting material.

Subsequently, the resulting mixture (1.44 g) was dissolved in methanol (30 ml). A 5N aqueous solution of sodium hydroxide (11.8 ml) was added thereto, and the resulting mixture was stirred at room temperature for 2 hr. After the solvent was evaporated, water was added to the resulting residue, and then the mixture was extracted with ethyl acetate. The extract was washed with a 10% aqueous solution of sodium carbonate and brine, and dried over magnesium sulfate. The solvent was evaporated, and the resulting residue was purified by silica gel column chromatography (toluene/acetone system), to give 0.91 g of the free compound of the title compound as a pale yellow solid.
Free compound:
 ¹H-NMR (400 MHz, CDCl₃); δ (ppm) 1.18 (t, J=7.2 Hz, 3H), 2.56 (q, J=7.2 Hz, 2H), 3.76 (br-t, 4H), 2.98 (t, J=6.6 Hz, 2H), 3.59 (br-t, 4H), 3.91 (t, J=6.6 Hz, 2H), 7.33 (dd, J=8.0 Hz, 1H), 7.48 (br-t, 1H), 7.60 (br-t, 1H), 7.66 (s, 1H), 7.79 (d, J=8.0 Hz, 1H), 7.86–7.91 (m, 2H), 8.08 (d, J=8.4 Hz, 1H).

The resulting free compound was converted into a hydrochloride in a conventional manner, and then reprecipitated with ethanol/IPE, to give the title compound as a pale brown powder.
Hydrochloride:
 m.p.; 213–215° C. (decomp.)
 ¹H-NMR (400 MHz, DMSO-d₆); δ (ppm) 1.33 (t, J=7.2 Hz, 3H), 2.82 (t, J=6.8 Hz, 2H), 3.20–3.27 (m, 2H), 3.31–3.39 (m, 2H), 3.51 (br-t, 2H), 3.63 (br-d, 2H), 3.65 (t, J=6.8 Hz, 2H), 4.01 (br-d, 2H), 7.45 (dd, J=8.0 Hz, 1H), 7.63 (br-t, 1H), 7.76 (br-t, 1H), 7.93–8.00 (m, 3H), 8.12–8.13 (m, 2H), 10.78 (br-s, 1H).

MS(FAB) m/z 380 (M+H)⁺.

Example 386

Synthesis of 1-(4-Ethylpiperazin-1-yl)-3-[4-(3-Hydroxy-2-Methylpropyl)Phenyl]Isoquinoline Oxalate

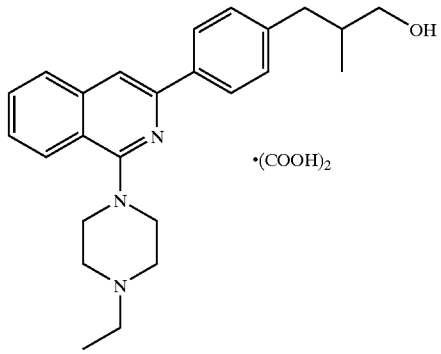

Methyl 2-methyl-3-(4-tributylstannylphenyl)propionate (2.69 g) and 3-bromo-1-(4-ethylpiperazin-1-yl)isoquinoline (1.16 g) were heated under reflux overnight in the presence of tetrakistriphenylphosphinepalladium(0) (0.17 g) in xylene in nitrogen atmosphere. After cooling, the reaction solution was diluted with ethyl acetate and filtered. The filtrate was extracted with 2N hydrochloric acid. The aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, and the resulting residue was purified by silica gel column chromatography (toluene/acetone system), to give obtain 1-(4-ethylpiperazin-1-yl)-3-[4-(2-methoxycarbonylpropyl)phenyl]isoquinoline (1.34 g) in pale yellow viscous oil.

Subsequently, the resulting 1-(4-ethylpiperazin-1-yl)-3-[4-(2-methoxycarbonylpropyl)phenyl]isoquinoline (1.34 g) was dissolved in tetrahydrofuran (10 ml). The solution was added to a suspension of lithium aluminum hydride (0.13 g) in tetrahydrofuran (20 ml) under cooling with a cooler of sodium chloride and ice, and the mixture was further stirred for 30 min. Water (130 ml), a 5N aqueous solution of sodium hydroxide (130 ml) and water (390 ml) were added to the reaction solution in this order, and the resulting precipitates were filtered off. The solvent was evaporated, and the resulting residue was purified by silica gel column chromatography (toluene/acetone system), to give 0.62 g of the free compound of the title compound as a pale brown viscous oil.

Free compound:
¹H-NMR (400 MHz, CDCl₃); δ (ppm) 0.96 (d, J=6.8 Hz, 3H), 1.18 (t, J=7.2 Hz, 3H), 1.96–2.05 (m, 1H), 2.49 (dd, J=8.0, 13.6 Hz, 1H), 2.56 (q, J=7.2 Hz, 2H), 2.76 (br-t, 4H), 2.82 (dd, J=6.4, 13.6 Hz, 1H), 3.52 (dd, J=6.0, 10.8 Hz, 1H), 3.58 (dd, J=6.0, 10.8 Hz, 1H), 3.59 (br-t, 4H), 7.28 (d, J=8.2 Hz, 2H), 7.45 (br-t, 1H), 7.58 (br-t, 1H), 7.68 (s, 1H), 7.78 (d, J=7.6 Hz, 1H), 8.07 (br-d, 1H), 8.10 (d, J=8.2 Hz, 2H).

The resulting free compound was converted into an oxalate in a conventional manner, and then recyrstallized from ethanol/IPE, to give the title compound as a pale brown powder.

Oxalate:
m.p.; 195–196° C.
¹H-NMR (400 MHz, DMSO-d₆); δ (ppm) 0.82 (d, J=6.8 Hz, 3H), 1.26 (t, J=7.2 Hz, 3H), 1.79–1.88 (m, 2H), 2.35 (dd, J=8.6, 13.2 Hz, 1H), 2.78 (dd, J=5.6, 13.2 Hz, 1H), 3.12 (br-q, 2H), 3.26 (dd, J=6.0, 10.4 Hz, 1H), 3.31 (dd, J=6.0, 10.4 Hz, 1H), 3.36 (br-s, 4H), 3.66 (br-s, 4H), 7.30 (d, J=8.0 Hz, 2H), 7.59 (br-t, 1H), 7.73 (br-t, 1H), 7.97 (d, J=8.0 Hz, 1H), 8.04 (s, 1H), 8.11 (d, J=8.0 Hz, 2H).

MS(FAB) m/z 390 (M+H)⁺.

Example 387

Synthesis of 1-(4-Ethylpiperazin-1-yl)-3-[4-(1,2-Dihydroxyethyl)Phenyl]Isoquinoline Dihydrochloride

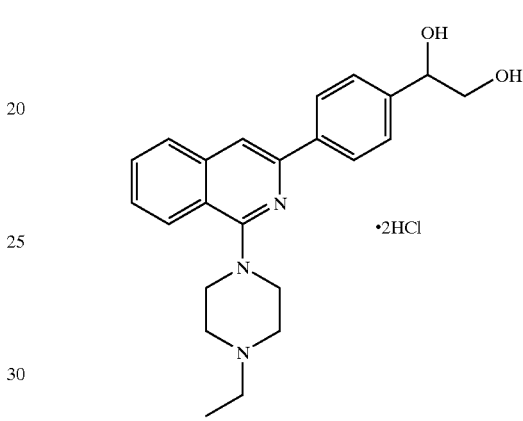

2,2-Dimethyl-3-(4-tributylstannylphenyl)-1,3-dioxolane (3.64 g) and 3-bromo-1-(4-ethylpiperazin-1-yl)isoquinoline (1.05 g) were heated under reflux overnight in the presence of tetrakistriphenylphosphinepalladium(0) (0.15 g) in xylene in nitrogen atmosphere. After cooling, the reaction solution was diluted with ethyl acetate and filtered. To the filtrate was added 2N hydrochloric acid, and the mixture was stirred at room temperature for 2 hr. The aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, and the resulting residue was purified by silica gel column chromatography (toluene/acetone system) and then recrystallized from chloroform/n-hexane, to give 0.73 g of the free compound of the title compound as a pale brown powder.

Free compound:
¹H-NMR (400 MHz, CDCl₃); δ (ppm) 1.18 (t, J=7.2 Hz, 3H), 2.56 (q, J=7.2 Hz, 2H), 2.76 (br-t, 4H), 3.58 (br-t, 4H), 3.72 (dd, J=8.0, 11.2 Hz, 1H), 3.82 (dd, J=3.6, 11.2 Hz, 1H), 4.90 (dd, J=3.6, 8.0 Hz, 1H), 7.45–7.49 (m, 3H), 7.59 (br-t, 1H), 7.69 (s, 1H), 7.80 (d, J=8.0 Hz, 1H), 8.08 (d, J=8.4 Hz, 1H), 8.17 (d, J=8.4 Hz, 2H).

The resulting free compound was converted into a hydrochloride in a conventional manner, and then recrystallized from ethanol/IPE, to give the title compound as a pale brown powder.

Hydrochloride:
m.p.; 132–133° C.
¹H-NMR (400 MHz, DMSO-d₆); δ (ppm) 1.33 (t, J=7.2 Hz, 3H), 3.20–3.27 (m, 2H), 3.31–3.39 (m, 2H), 3.48 (d, J=6.0 Hz, 2H), 3.35 (br-t, 2H), 3.63 (br-d, 2H), 4.00 (br-d, 2H), 4.61 (t, J=6.0 Hz, 1H), 7.47 (d, J=8.4 Hz, 2H), 7.61

(br-t, 1H), 7.74 (br-t, 1H), 7.99 (d, J=7.6 Hz, 1H), 8.07 (s, 1H), 8.11–8.15 (m, 3H), 10.94 (br-s, 1H).
MS(FAB) m/z 378 (M+H)+.

Example 388

Synthesis of 1-(4-Ethylpiperazin-1-yl)-3-[4-(3-Hydroxy-3-Methylbutyl)Phenyl]Isoquinoline Dihydrochloride

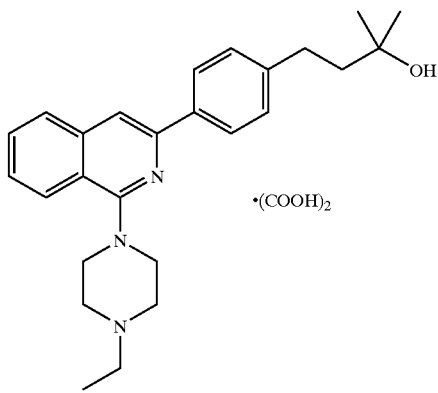

4-(4-Tributylstannylphenyl)-2-butanone (2.46 g) and 3-bromo-1-(4-ethylpiperazin-1-yl)isoquinoline (1.41 g) were heated under reflux in the presence of tetrakistriphenylphosphinepalladium(0) (0.22 g) in xylene in nitrogen atmosphere overnight. After cooling, the reaction solution was diluted with ethyl acetate and filtered. The filtrate was extracted in 2N hydrochloric acid, and the resulting aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, and the resulting residue was purified by silica gel column chromatography (toluene/acetone system), to give 1-(4-ethylpiperazin-1-yl)-3-[4-(3-oxobutyl)phenyl]isoquinoline (1.07 g) as a pale yellow viscous oil.

The resulting 1-(4-ethylpiperazin-1-yl)-3-[4-(3-oxobutyl)phenyl]isoquinoline (0.50 g) was dissolved in tetrahydrofuran (50 ml), and the mixture was stirred under ice-cooling, to which was then added 3.0M methylmagnesium bromide/ether solution (860 μl). The resulting mixture was stirred for 30 min. Then, 3.0M methylmagnesium bromide/ethyl ether solution (860 μl) was additionally added thereto, and the resulting mixture was stirred for 2 hr. An aqueous solution of saturated ammonium chloride was added to the mixture and extracted with ethyl acetate. The organic layer was washed with brine and dried over magnesium sulfate. The solvent was evaporated, and the resulting residue was purified by silica gel column chromatography (toluene/acetone system), to give 0.21 g of the free compound of the title compound as a colorless viscous oil.
Free compound:
$^1$H-NMR (400 MHz, CDCl$_3$); δ (ppm) 1.18 (t, J=7.2 Hz, 3H), 1.32 (s, 6H), 1.82–1.86 (m, 2H), 2.56 (q, J=7.2 Hz, 2H), 2.75–2.79 (m, 6H), 3.59 (br-t, 4H), 7.31 (d, J=8.0 Hz, 2H), 7.45 (br-t, 1H), 7.58 (br-t, 1H), 7.67 (s, 1H), 7.78 (d, J=8.0 Hz, 1H), 8.07 (br-d, 1H), 8.09 (d, J=8.0 Hz, 2H).

The resulting free compound was converted into an oxalate in a conventional manner, and then recrystallized from ethanol/IPE, to give the title compound as a pale brown powder.

Oxalate:
m.p.; 205–206° C.
$^1$H-NMR (400 MHz, DMSO-d$_6$); δ (ppm) 1.17 (s, 6H), 1.26 (t, J=7.2 Hz, 3H), 1.66–1.70 (m, 2H), 2.66–2.70 (m, 2H), 3.12 (br-q, 2H), 3.36 (br-s, 4H), 3.66 (br-s, 4H), 7.33 (d, J=8.0 Hz, 2H), 7.59 (br-t, 1H), 7.73 (br-t, 1H), 7.97 (d, J=8.0 Hz, 1H), 8.03 (s, 1H), 8.09–8.12 (m, 3H).
MS(FAB) m/z 404 (M+H)+.

Example 389

Synthesis of 1-(4-Ethylpiperazin-1-yl)-3-[4-(3-Hydroxy-2,2-Dimethylpropyl)Phenyl]Isoquinoline Oxalate

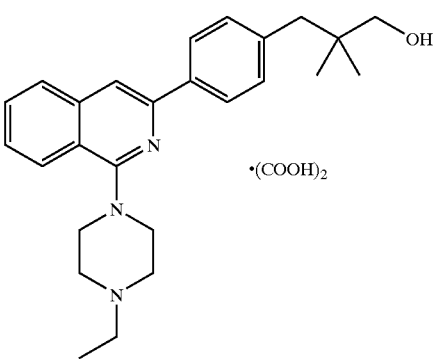

Methyl 2,2-dimethyl-3-(4-tributylstannylphenyl)propionate (2.81 g) and 3-bromo-1-(4-ethylpiperazin-1-yl)isoquinoline (1.18 g) were heated under reflux overnight in the presence of tetrakistriphenylphosphinepalladium(0) (0.17 g) in xylene in nitrogen atmosphere. After cooling, the reaction solution was diluted with ethyl acetate and filtered. The filtrate was extracted with 2N hydrochloric acid, and the resulting aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, and the resulting residue was purified by silica gel column chromatography (toluene/acetone system), to give 1-(4-ethylpiperazin-1-yl)-3-[4-(2-methoxycarbonyl-2-methylpropyl)phenyl]isoquinoline (1.51 g) as a brown viscous oil.

The resulting 1-(4-ethylpiperazin-1-yl)-3-[4-(2-methoxycarbonyl-2-methylpropyl)phenyl]isoquinoline (1.51 g) was dissolved in tetrahydrofuran (10 ml). The solution was added to a suspension of lithium aluminum hydride (0.14 g) in tetrahydrofuran (20 ml) under cooling with a cooler of sodium chloride and ice, and the mixture was stirred for another 30 min. To the resulting solution were sequentially added water (140 ml), a 5N aqueous solution of sodium hydroxide (140 ml) and water (420 ml), and the resulting precipitates were filtered off. The solvent was evaporated, and the resulting residue was purified by silica gel column chromatography (toluene/acetone system), to give 0.90 g of the free compound of the title compound as a pale brown viscous oil.
Free compound:
hu 1H-NMR (400 MHz, CDCl$_3$); δ (ppm) 0.93 (s, 6H), 1.18 (t, J=7.2 Hz, 3H), 2.56 (q, J=7.2 Hz, 2H), 2.64 (s, 2H), 2.76 (br-t, 4H), 3.36 (s, 2H), 3.60 (br-t, 4H), 7.27 (d, J=8.0 Hz, 2H), 7.45 (br-t, 1H), 7.58 (br-t, 1H), 7.68 (s, 1H), 7.79 (d, J=8.0 Hz, 1H), 8.08 (br-d, 1H), 8.09 (d, J=8.0 Hz, 2H).

The resulting free compound was converted into an oxalate in a conventional manner, and then recrystallized from ethanol/IPE, to give the title compound as a pale brown powder.
Oxalate:
m.p.; 194–195° C.
¹H- NMR (400 MHz, DMSO-d₆); δ (ppm) 0.80 (s, 6H), 1.26 (t, J=7.2 Hz, 3H), 2.56 (s, 2H), 3.10–3.16 (m, 2H), 3.12 (s, 2H), 3.38 (br-s, 4H), 3.68 (br-s, 4H), 7.28 (d, J=8.0 Hz, 2H), 7.59 (br-t, 1H), 7.73 (br-t, 1H), 7.97 (d, J=8.0 Hz, 1H), 8.04 (s, 1H), 8.10 (d, J=8.0 Hz, 2H), 8.11 (br-d, 1H).
MS(FAB) m/z 404 (M+H)⁺.

Example 390

Synthesis of 1-(4-Ethylpiperazin-1-yl)-3-[3,5-Difluoro-4-(2-Hydroxyethoxy)Phenyl]Isoquinoline Oxalate

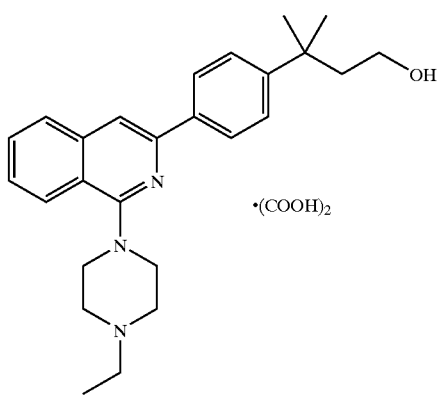

3-Methyl-3-(4-tributylstannylphenyl)butyl acetate (4.05 g) and 3-bromo-1-(4-ethylpiperazin-1-yl)isoquinoline (1.10 g) were heated under reflux overnight in the presence of tetrakistriphenylphosphinepalladium(0) (0.16 g) in xylene in nitrogen atmosphere. After cooling, the reaction solution was diluted with ethyl acetate and filtered. The filtrate was extracted with 2N hydrochloric acid, and the resulting aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, to give a mixture (1.32 g) of 1-(4-ethylpiperazin-1-yl)-3-[4-(3-acetoxy-1,1-dimethylpropyl)phenyl]isoquinoline as a brown viscous oil and the starting material.

The resulting mixture (1.32 g) was then dissolved in methanol (30 ml), to which was then added a 5N aqueous solution of sodium hydroxide (3.00 ml), and the mixture was stirred at room temperature for 1.5 hr. The solvent was evaporated, and water was added to the resulting residue and the resulting mixture was extracted with ethyl acetate. The organic layer was washed with a 10% aqueous solution of sodium carbonate and brine, and dried over magnesium sulfate. The solvent was evaporated, and the resulting residue was purified by silica gel column chromatography (toluene/acetone system), to give 0.74 g of the free compound of the title compound as a pale yellow solid.
Free compound:
¹H-NMR (400 MHz, CDCl₃); δ (ppm) 1.18 (t, J=7.2 Hz, 3H), 1.40 (s, 6H), 2.01 (t, J=7.4 Hz, 2H), 2.56 (q, J=7.2 Hz, 2H), 2.76 (br-t, 4H), 3.55 (t, J=7.2 Hz, 2H), 3.59 (br-t, 4H), 7.43–7.47 (m, 3H), 7.58 (br-t, 1H), 7.68 (s, 1H), 7.79 (d, J=8.0 Hz, 1H), 8.07 (d, J=8.0 Hz, 1H), 8.12 (d, J=8.4 Hz, 2H).

The resulting free compound was converted into an oxalate in a conventional manner, and then recrystallized from ethanol/ether, to give the title compound as a pale brown powder.
Oxalate:
m.p.; 134–135° C.
¹H-NMR (400 MHz, DMSO-d₆); δ (ppm) 1.26 (t, J=7.2 Hz, 3H), 1.32 (s, 6H), 1.85 (t, J=7.6 Hz, 2H), 3.12 (br-q, 2H), 3.23 (d, J=7.6 Hz, 2H), 3.36 (br-s, 4H), 3.67 (br-s, 4H), 7.48 (d, J=8.4 Hz, 2H), 7.60 (br-t, 1H), 7.73 (br-t, 1H), 7.98 (d, J=8.0 Hz, 1H), 8.03 (s, 1H), 8.11 (br-d, 1H), 8.12 (d, J=8.4 Hz, 2H).
MS(FAB) m/z 404 (M+H)⁺.

Example 391

Synthesis of 1-(4-Ethylpiperazin-1-yl)-3-[4-(1,3-Dihydroxy-2,2-Dimethylpropyl)Phenyl]Isoquinoline Dihydrochloride

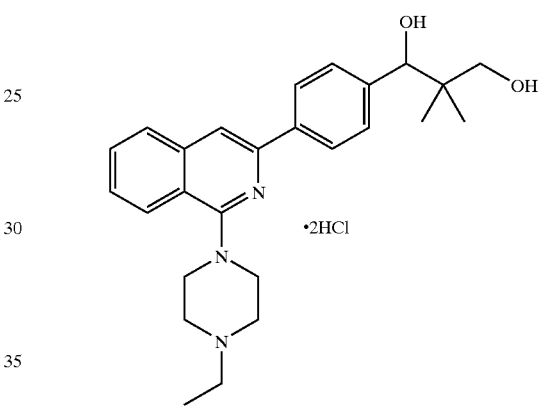

2,2,5,5-Tetramethyl-4-(4-tributylstannylphenyl)-1,3-dioxane (3.22 g) and 3-bromo-1-(4-ethylpiperazin-1-yl)isoquinoline (1.27 g) were heated under reflux overnight in the presence of tetrakistriphenylphosphinepalladium(0) (0.18 g) in xylene in nitrogen atmosphere. After cooling, the reaction solution was diluted with ethyl acetate and filtered. To the filtrate was added 2N hydrochloric acid. The resulting mixture was stirred at room temperature for 20 min. The resulting aqueous layer was washed with ethyl acetate, adjusted to pH 10 with a 8N aqueous solution of sodium hydroxide, and then extracted with ethyl acetate. The organic layer was washed with a 10% aqueous solution of sodium carbonate and brine, and dried over magnesium sulfate. The solvent was evaporated, and the resulting residue was purified by silica gel column chromatography (toluene/acetone system) and recrystallized from chloroform/n-hexane, to give 0.93 g of the free compound of the title compound as a pale brown powder.
Free compound:
¹H-NMR (400 MHz, CDCl₃); δ (ppm) 0.91 (s, 3H), 0.94 (s, 3H), 1.18 (t, J=7.2 Hz, 3H), 2.56 (q, J=7.2 Hz, 2H), 2.75 (br-t, 4H), 3.54–3.65 (m, 6H), 4.73 (s, 1H), 7.44 (d, J=8.4 Hz, 2H), 7.46 (br-t, 1H), 7.59 (br-t, 1H), 7.69 (s, 1H), 7.79 (d, J=8.4 Hz, 1H), 8.07 (d, J=8.4 Hz, 1H), 8.15 (d, J=8.4 Hz, 2H).

The resulting free compound was converted into a hydrochloride in a conventional manner, and then recrystallized from ethanol/ether, to give the title compound as a pale brown powder.

Hydrochloride:

m.p.; 150.5–151.5° C.

¹H-NMR (400 MHz, DMSO-d₆); δ (ppm) 0.70 (s, 3H), 0.84 (s, 3H), 1.33 (t, J=7.2 Hz, 3H), 3.16 (d, J=10.2 Hz, 1H), 3.21–3.27 (m, 2H), 3.34 (d, J=10.2 Hz, 1H), 3.32–3.39 (m, 2H), 3.51 (br-t, 2H), 3.63 (br-d, 2H), 4.01 (br-d, 2H), 4.56 (s, 1H), 7.42 (d, J=8.4 Hz, 2H), 7.60 (br-t, 1H), 7.74 (br-t, 1H), 7.99 (d, J=8.0 Hz, 1H), 8.08 (s, 1H), 8.11 (br-d, 1H), 8.13 (d, J=8.4 Hz, 2H), 10.79 (br-s, 1H).

MS(FAB) m/z 420 (M+H)⁺.

Example 392

Synthesis of 1-(4-Ethylpiperazin-1-yl)-3-{4-[4-(2-Hydroxyethyl)Tetrahydropyran-4-yl]Phenyl}Isoquinoline Dihydrochloride

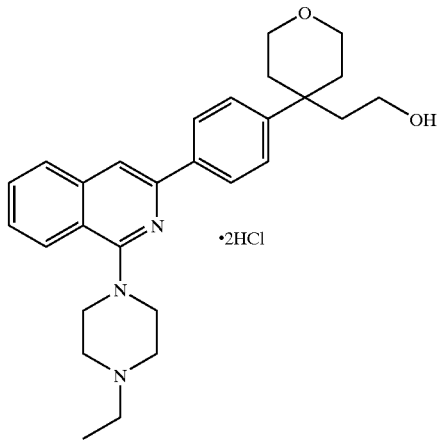

4-(2-Acetoxyethyl)-4-(4-tributylstannylphenyl)tetrahydropyran (2.20 g) and 3-bromo-1-(4-ethylpiperazin-1-yl)isoquinoline (0.83 g) were heated under reflux overnight in the presence of tetrakistriphenylphosphinepalladium(0) (0.12 g) in xylene in nitrogen atmosphere. After cooling, the reaction solution was diluted with ethyl acetate and filtered. The filtrate was extracted with 2N hydrochloric acid, and the resulting aqueous layer was washed with ethyl acetate, adjusted to pH 10 with a 8N aqueous solution of sodium hydroxide, and then extracted with ethyl acetate. The extract was washed with a 10% sodium carbonate and brine, and dried over magnesium sulfate. The solvent was evaporated, to give a mixture (1.14 g) of 1-(4-ethylpiperazin-1-yl)-3-{4-[4-(2-acetoxyethyl)tetrahydropyran-4-yl]phenyl}isoquinoline as a brown viscous oil and the starting material.

The resulting mixture (1.14 g) was subsequently dissolved in methanol (30 ml), followed by the addition of a 5N aqueous solution of sodium hydroxide (2.35 ml), and the mixture was stirred at room temperature for 5 hr. The solvent was evaporated. To the resulting residue was added water, and the mixture was extracted with ethyl acetate. The extract was washed with a 10% aqueous solution of sodium carbonate and brine, and dried over magnesium sulfate. The solvent was evaporated, and the resulting residue was purified by silica gel column chromatography (toluene/acetone system), to give 0.83 g of the free compound of the title compound as a pale yellow solid.

¹H-NMR (400 MHz, CDCl₃); δ (ppm) 1.18 (t, J=7.2 Hz, 3H), 1.92–1.99 (m, 2H), 1.98 (t, J=7.2 Hz, 2H), 2.25 (br-d, 2H), 2.57 (q, J=7.2 Hz, 2H), 2.77 (br-t, 4H), 3.46 (t, J=7.2 Hz, 2H), 3.59–3.65 (m, 6H), 3.80–3.85 (m, 2H), 7.41 (d, J=8.4 Hz, 2H), 7.47 (br-t, 1H), 7.60 (br-t, 1H), 7.70 (s, 1H), 7.80 (d, J=8.0 Hz, 1H), 8.08 (d, J=8.0 Hz, 1H), 8.17 (d, J=8.4 Hz, 2H).

The resulting free compound was converted into a hydrochloride in a conventional manner, and then reprecipitated with ethanol/ether, to give the title compound as a pale brown powder.

Hydrochloride:

m.p.; 138–139° C.

¹H-NMR (400 MHz, DMSO-d₆); δ (ppm) 1.34 (t, J=7.2 Hz, 3H), 1.82–1.88 (m, 4H), 2.10 (br-d, 2H), 3.08–3.16 (m, 2H), 3.18–3.26 (m, 2H), 3.31–3.39 (m, 2H), 3.45 (br-t, 2H), 3.53–3.63 (m, 4H), 3.68–3.74 (m, 2H), 4.00 (br-d, 2H), 7.47 (d, J=8.4 Hz, 2H), 7.61 (br-t, 1H), 7.75 (br-t, 1H), 8.00 (d, J=8.0 Hz, 1H), 8.08 (s, 1H), 8.12 (d, J=8.4 Hz, 1H), 8.17 (d, J=8.4 Hz, 2H), 11.11 (br-s, 1H).

MS(FAB) m/z 446 (M+H)⁺.

Example 393

Synthesis of 1-(4-Ethylpiperazin-1-yl)-3-(2-Hydroxymethylindan-5-yl)Isoquinoline Dihydrochloride

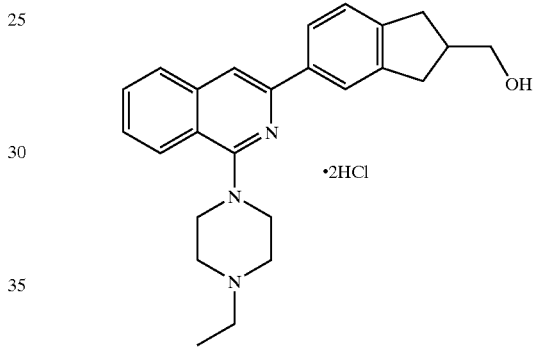

2-Ethoxycarbonyl-5-(tributylstannyl)indane (3.04 g) and 3-bromo-1-(4-ethylpiperazin-1-yl)isoquinoline (0.87 g) were heated under reflux overnight in the presence of tetrakistriphenylphosphinepalladium(0) (0.12 g) in xylene in nitrogen atmosphere. After cooling, the reaction solution was diluted with ethyl acetate and filtered. The filtrate was extracted with 2N hydrochloric acid, and the resulting aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, to give 1-(4-ethylpiperazin-1-yl)-3-(2-ethoxycarbonylindan-5-yl)isoquinoline (1.06 g) as a brown viscous oil.

The resulting 1-(4-ethylpiperazin-1-yl)-3-(2-ethoxycarbonylindan-5-yl)isoquinoline (1.06 g) was dissolved in tetrahydrofuran (6 ml). Under cooling with a cooler of sodium chloride and ice, the solution was added to a suspension of lithium aluminum hydride (0.10 g) in tetrahydrofuran (10 ml), and the mixture was stirred for 20 min. To the resulting solution were sequentially added water (100 ml), a 5N aqueous solution of sodium hydroxide (100 ml) and water (300 ml), and the resulting precipitates were filtered off. The solvent was evaporated, and the resulting residue was purified by silica gel column chromatography (toluene/acetone system), to give 0.35 g of the free compound of the title compound as a pale yellow amorphous.

Free compound:

¹H-NMR (400 MHz, CDCl₃); δ (ppm) 1.18 (t, J=7.2 Hz, 3H), 2.56 (q, J=7.2 Hz, 2H), 2.72–2.86 (m, 7H), 3.09–3.20 (m, 2H), 3.58 (br-t, 4H), 3.70 (d, J=6.8 Hz, 2H), 7.29 (d, J=8.0 Hz, 1H), 7.44 (br-t, 1H), 7.57 (br-t, 1H), 7.66 (s, 1H), 7.78 (d, J=8.4 Hz, 1H), 7.95 (br-d, 1H), 8.01 (s, 1H), 8.07 (d, J=8.4 Hz, 1H).

The resulting free compound was converted into a hydrochloride in a conventional manner, and then reprecipitated with ethanol/IPE, to give the title compound as a pale brown powder.

Hydrochloride:

m.p.; 136.5–138° C.

¹H-NMR (400 MHz, DMSO-d₆); δ (ppm) 1.33 (t, J=7.2 Hz, 3H), 2.57–2.65 (m, 1H), 2.70–2.80 (m, 2H), 2.96–3.07 (m, 2H), 3.21–3.27 (m, 2H), 3.31–3.40 (m, 2H), 3.41 (d, J=6.8 Hz, 2H), 3.49 (br-t, 2H), 3.64 (br-d, 2H), 3.98 (br-d, 2H), 7.32 (d, J=8.0 Hz, 2H), 7.59 (br-t, 1H), 7.73 (br-t, 1H), 7.97 (d, J=8.0 Hz, 2H), 8.03 (br-d, 1H), 8.04 (s, 1H), 8.11 (d, J=8.0 Hz, 1H), 10.79 (br-s, 1H).

MS(FAB) m/z 388 (M+H)⁺.

Example 394

Synthesis of 1-(4-Ethylpiperazin-1-yl)-3-[(3,4-Dihydroxymethyl)Phenyl]Isoquinoline Dihydrochloride

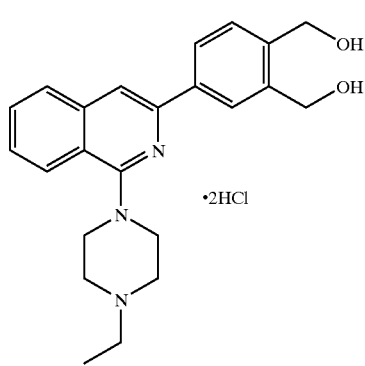

3,4-Bis(acetoxymethyl)tributylstannylbenzene (1.91 g) and 3-bromo-1-(4-ethylpiperazin-1-yl)isoquinoline (1.00 g) were heated under reflux overnight in the presence of tetrakistriphenylphosphinepalladium(0) (0.14 g) in xylene in nitrogen atmosphere. After cooling, the reaction solution was diluted with ethyl acetate and filtered. The filtrate was extracted with 2N hydrochloric acid, and the resulting aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, to give a mixture (1.36 g) of 1-(4-ethylpiperazin-1-yl)-3-[3,4-bis(acetoxymethyl)phenyl] isoquinoline as a brown viscous oil and the starting material.

The resulting mixture (1.36 g) was then dissolved in methanol (30 ml), to which was then added a 5N aqueous solution of sodium hydroxide (7.22 ml), and the mixture was stirred at room temperature for 1 hr. The solvent was evaporated, and to the resulting residue was added water, and then the mixture was extracted with ethyl acetate. The extract was washed with a 10% aqueous solution of sodium carbonate and brine, and dried over magnesium sulfate. The solvent was evaporated, and the resulting residue was puri- fied by silica gel column chromatography (toluene/acetone system), to give 0.79 g of the free compound of the title compound as a pale yellow solid.

¹H-NMR (400 MHz, CDCl₃); δ (ppm) 1.17 (t, J=7.2 Hz, 3H), 2.55 (q, J=7.2 Hz, 2H), 2.76 (br-t, 4H), 3.58 (br-t, 4H), 4.81 (s, 2H), 4.87 (s, 2H), 7.46 (d, J=7.6 Hz, 1H), 7.48 (br-t, 1H), 7.60 (br-t, 1H), 7.70 (s, 1H), 7.79 (d, J=8.0 Hz, 1H), 8.07–8.11 (m, 2H), 8.17 (d, J=1.6 Hz, 1H).

The resulting free compound was converted into a hydrochloride in a conventional manner, and then reprecipitated with ethanol/IPE, to give the title compound as a pale brown powder.

Hydrochloride:

¹H-NMR (400 MHz, DMSO-d₆); δ (ppm) 1.34 (t, J=7.2 Hz, 3H), 3. (m, 2H), 3.32–3.40 (m, 2H), 3.54 (br-t, 2H), 3.64 (br-d, 2H), 3.99 (br-d, 2H), 4.61 (s, 2H), 4.64 (s, 2H), 7.53 (d, J=8.2 Hz, 1H), 7.61 (br-t, 1H), 7.74 (br-t, 1H), 8.02 (d, J=8.0 Hz, 1H), 8.07 (s, 1H), 8.08 (dd, J=2.0, 8.2 Hz, 1H), 8.12 (d, J=8.8 Hz, 1H), 8.23 (d, J=2.0 Hz, 1H), 11.11 (br-s, 1H).

MS(FAB) m/z 378 (m+H)⁺. m.p.; 130.5–132° C. (decomp.)

Example 395

Synthesis of 1-(4-Ethylpiperazin-1-yl)-3-[4-(1,4-Dioxan-2-yl)Phenyl]Isoquinoline Dihydrochloride

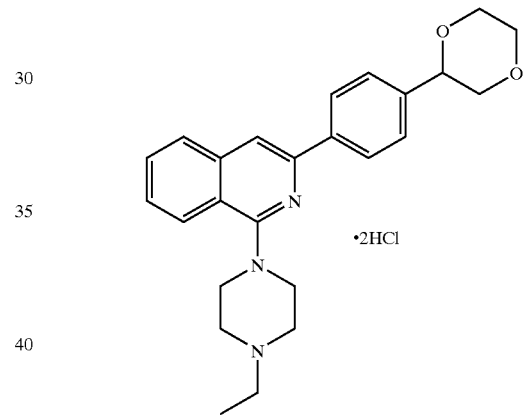

2-(4-Tributylstannylphenyl)-1,4-dioxane (2.63 g) and 3-bromo-1-(4-ethylpiperazin-1-yl)isoquinoline (1.15 g) were heated under reflux overnight in the presence of tetrakistriphenylphosphinepalladium(0) (0.16 g) in xylene in nitrogen atmosphere. After cooling, the reaction solution was diluted with ethyl acetate and filtered. The filtrate was extracted with 2N hydrochloric acid, and the resulting aqueous layer was washed with ethyl acetate, adjusted to pH 10 with a 8N aqueous solution of sodium hydroxide, and then extracted with ethyl acetate. The extract was washed with a 10% aqueous solution of sodium carbonate and brine, and dried over magnesium sulfate. The solvent was evaporated, and the resulting residue was purified by silica gel column chromatography (chloroform/methanol system), to give 0.41 g of the free compound of the title compound as a pale brown viscous oil.

Free compound:

¹H-NMR (400 MHz, CDCl₃); δ (ppm) 1.18 (t, J=7.2 Hz, 3H), 2.56 (q, J=7.2 Hz, 2H), 2.76 (br-t, 4H), 3.03 (d, J=4.8 Hz, 2H), 3.59 (br-t, 4H), 3.84–3.90 (m, 2H), 3.93–3.99 (m, 2H), 5.12 (t, J=4.8 Hz, 1H), 7.38 (d, J=8.2 Hz, 2H), 7.45 (br-t, 1H), 7.58 (br-t, 1H), 7.67 (s, 1H), 7.78 (d, J=8.0 Hz, 1H), 8.07 (d, J=7.6 Hz, 1H), 8.11 (d, J=8.2 Hz, 2H).

The resulting free compound was converted into a hydrochloride in a conventional manner, and then reprecipitated with ethanol/ether, to give the title compound as a yellow powder.

Hydrochloride:

m.p.; 163–166° C. (decomp.)

$^1$H-NMR (400 MHz, DMSO-d$_6$); δ (ppm) 1.33 (t, J=7.2 Hz, 3H), 3.21–3.28 (m, 2H), 3.31–3.39 (m, 2H), 3.39 (d, J=0.4 Hz, 2H), 3.50 (br-t, 2H), 3.63 (br-d, 2H), 3.76–3.92 (m, 4H), 4.01 (br-d, 2H), 5.03 (t, J=0.4 Hz, 1H), 7.38–7.41 (m, 1H), 7.58–7.63 (m, 1H), 7.72–7.78 (m, 1H), 7.99 (br-d, 1H), 8.07–8.16 (m, 5H).

MS(FAB) m/z 404 (M+H)$^+$.

Example 396

Synthesis of 1-(4-Ethylpiperazin-1-yl)-3-[4-(Tetrahydrofuran-2-yl)Phenyl]Isoquinoline Dihydrochloride

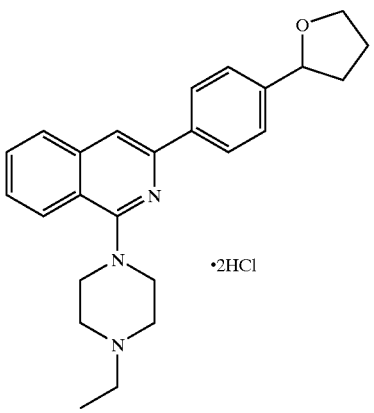

2-(4-Tributylstannylphenyl)tetrahydrofuran (1.88 g) and 3-bromo-1-(4-ethylpiperazin-1-yl)isoquinoline (1.18 g) were heated under reflux in the presence of tetrakistriphenylphosphinepalladium(0) (0.17 g) in xylene in nitrogen atmosphere. After cooling, the reaction solution was diluted with ethyl acetate and filtered. The filtrate was extracted with 2N hydrochloric acid, and the resulting aqueous layer was washed with ethyl acetate. Then, it was adjusted to pH 10 with a 8N aqueous solution of sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 0.78 g of the free compound of the title compound as a pale yellow viscous oil.

Free compound:

$^1$H-NMR (400 MHz, CDCl$_3$); δ (ppm) 1.18 (t, J=7.2 Hz, 3H), 1.81–1.90 (m, 1H), 1.99–2.07 (m, 2H), 2.32–2.40 (m, 1H), 2.56 (q, J=7.2 Hz, 2H), 2.76 (br-t, 4H), 3.59 (br-t, 4H), 3.97 (dt, J=6.4, 8.0 Hz, 1H), 4.14 (dt, J=6.8, 8.4 Hz, 1H), 4.97 (t, J=7.0 Hz, 1H, 7.43 (d, J=8.2 Hz, 2H), 7.45 (br-t, 1H), 7.58 (br-t, 1H), 7.69 (s, 1H), 7.79 (d, J=8.4 Hz, 1H), 8.08 (d, J=8.8 Hz, 1H), 8.14 (d, J=8.2 Hz, 2H).

The resulting free compound was converted into a hydrochloride in a conventional manner, and then reprecipitated with ethanol/ether, to give the title compound as a yellow powder.

Hydrochloride:

m.p.; 129–130° C.

$^1$H-NMR (400 MHz, DMSO-d$_6$); δ (ppm) 1.33 (t, J=7.2 Hz, 3H), 1.66–1.75 (m, 1H), 1.93–2.01 (m, 2H), 2.30–2.38 (m, 1H), 3.20–3.27 (m, 2H), 3.31–3.39 (m, 2H), 3.52 (br-t, 2H), 3.63 (br-d, 2H), 3.81–3.87 (m, 1H), 3.98–4.05 (m, 3H), 4.87 (t, J=7.2 Hz, 1H), 7.45 (d, J=8.4 Hz, 2H), 7.61 (br-t, 1H), 7.75 (br-t, 1H), 7.99 (d, J=8.4 Hz, 1H), 8.08 (s, 1H), 8.12 (d, J=8.8 Hz, 1H), 8.16 (d, J=8.4 Hz, 2H), 10.92 (br-s, 1H).

MS(FAB) m/z 388 (M+H)$^+$.

Example 397

Synthesis of 1-(4-Ethylpiperazin-1-yl)-3-[4-(cis-4-Hydroxycyclohexyl)Phenyl]Isoquinoline Dihydrochloride

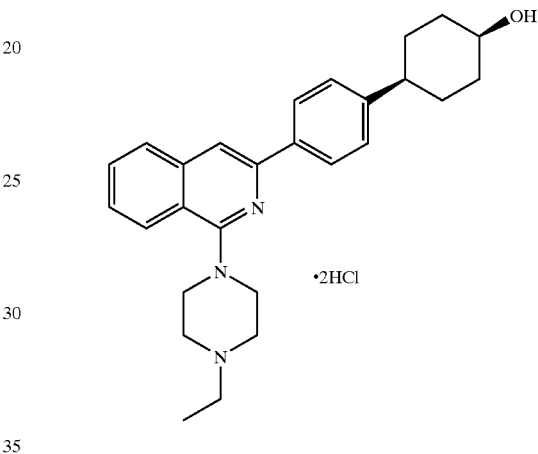

cis-4-(Tributylstannylphenyl)cyclohexyl acetate (1.37 g) and 3-bromo-1-(4-ethylpiperazin-1-yl)isoquinoline (1.11 g) were heated under reflux in the presence of tetrakistriphenylphosphinepalladium(0) (0.16 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 with a 8N aqueous solution of sodium hydroxide, extracted with ethyl acetate, washed with a 10% aqueous solution of sodium carbonate and brine, and dried over magnesium sulfate. The solvent was evaporated, to give a mixture (1.24 g) of 1-(4-ethylpiperazin-1-yl)-3-[4-(cis-4-acetoxycyclohexyl)phenyl]isoquinoline as a brown viscous oil and the starting material.

Then, the resulting mixture (1.24 g) was dissolved in methanol (20 ml). To the solution was added a 5N aqueous solution of sodium hydroxide (2.72 ml), and the mixture was stirred at room temperature for 3.5 hr. The solvent was evaporated, and to the resulting residue was added water. The resulting mixture was extracted with ethyl acetate, washed with a 10% aqueous solution of sodium carbonate and brine, and dried over magnesium sulfate. The solvent was evaporated, and the resulting residue was purified by silica gel column chromatography (toluene/acetone system), to give 0.52 g of the free compound of the title compound as a pale brown amorphous.

$^1$H-NMR (400 MHz, CDCl$_3$); δ (ppm) 1.18 (t, J=7.2 Hz, 3H), 1.17 (br-t, 4H), 1.94 (br-t, 4H), 2.56 (q, J=7.2 Hz, 2H), 2.61 (br-t, 1H), 2.76 (br-t, 4H), 3.59 (br-t, 4H), 4.16 (s, 1H), 7.35 (d, J=8.4 Hz, 2H), 7.45 (br-t, 1H), 7.58 (br-t, 1H), 7.67

(s, 1H), 7.78 (d, J=8.0 Hz, 1H), 8.07 (br-d, 1H), 8.10 (d, J=8.4 Hz, 2H).

The resulting free compound was converted into a hydrochloride in a conventional manner, and then reprecipitated with ethanol/IPE, to give the title compound as a pale brown powder.
Hydrochloride:
m.p.; 152–153° C.
$^1$H-NMR (400 MHz, DMSO-$d_6$); δ (ppm) 1.32 (t, J=7.2 Hz, 3H), 1.57 (br-t, 4H), 1.77 (br-d, 2H), 1.84–1.94 (m, 2H), 2.58 (br-t, 1H), 3.21–3.28 (m, 2H), 3.31–3.39 (m, 2H), 3.47 (br-t, 2H), 3.64 (br-d, 2H), 3.92 (br-s, 1H), 4.00 (br-d, 2H), 7.36 (d, J=8.6 Hz, 2H), 7.60 (br-t, 1H), 7.74 (br-t, 1H), 7.98 (br-d, 1H), 8.05 (s, 1H), 8.11 (d, J=8.6 Hz, 2H), 10.56 (br-s, 1H).
MS(FAB) m/z 416 (M+H)$^+$.

Example 398

Synthesis of 1-(4-Ethylpiperazin-1-yl)-3-[4-(trans-4-Hydroxycyclohexyl)Phenyl]Isoquinoline Dihydrochloride

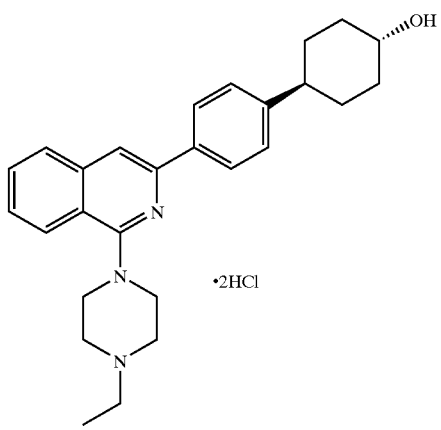

Trans-4-(tributylstannylphenyl)cyclohexyl acetate (0.56 g) and 3-bromo-1-(4-ethylpiperazin-1-yl)isoquinoline (0.46 g) were heated under reflux in the presence of tetrakistriphenylphosphinepalladium(0) (0.06 g) in xylene in nitrogen atmosphere overnight. After cooling, the reaction solution was diluted with ethyl acetate and filtered. The filtrate was extracted with 2N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, to give a mixture (0.44 g) of 1-(4-ethylpiperazin-1-yl)-3-[4-(trans-4-acetoxycyclohexyl)phenyl]isoquinoline as a brown viscous oil and the starting material.

The resulting mixture (0.44 g) was then dissolved in methanol (8 ml), to which was then added a 5N aqueous solution of sodium hydroxide (987 ml), and the mixture was stirred at room temperature for 3 hr. The solvent was evaporated, and to the resulting residue was added water, and the mixture was extracted with ethyl acetate. The extract was washed with a 10% aqueous solution of sodium carbonate and brine, and dried over magnesium sulfate. The solvent was evaporated, and the resulting residue was purified by silica gel column chromatography (toluene/acetone system), to give 0.13 g of the free compound of the title compound as a pale brown amorphous.

$^1$H-NMR (400 MHz, CDCl$_3$); δ (ppm) 1.17 (t, J=7.2 Hz, 3H), 1.40–1.50 (m, 2H), 1.53–1.63 (m, 2H), 1.97 (br-d, 2H), 2.12 (br-d, 2H), 2.52–2.59 (m, 1H), 2.55 (q, J=7.2 Hz, 2H), 2.75 (br-t, 4H), 3.58 (br-t, 4H), 3.67–3.74 (m, 1H), 7.30 (d, J=8.4 Hz, 2H), 7.44 (br-t, 1H), 7.57 (br-t, 1H), 7.66 (s, 1H), 7.77 (d, J=8.0 Hz, 1H), 8.06–8.10 (m, 3H).

The resulting free compound was converted into a hydrochloride in a conventional manner, and then reprecipitated with ethanol/IPE, to give the title compound as a pale brown powder.
Hydrochloride:
m.p.; 157–158° C. (decomp.)
$^1$H-NMR (400 MHz, DMSO-$d_6$); δ (ppm) 1.27–1.37 (m, 2H), 1.33 (t, J=7.2 Hz, 3H), 1.47–1.58 (m, 2H), 1.82 (br-d, 2H), 1.95 (br-d, 2H), 3.20–3.27 (m, 2H), 3.31–3.38 (m, 2H), 3.46–3.53 (m, 3H), 3.63 (br-d, 2H), 3.99 (br-d, 2H), 7.36 (d, J=8.4 Hz, 2H), 7.60 (br-t, 1H), 7.74 (br-t, 1H), 7.98 (d, J=8.0 Hz, 1H), 8.04 (s, 1H), 8.09–8.12 (m, 3H), 10.77 (br-s, 1H).
MS(FAB) m/z 416 (M+H)$^+$.

Example 399

Synthesis of 1-(4-Ethylpiperazin-1-yl)-3-[4-(tetrahydropyran-4-yl)Methylphenyl]Isoquinoline Dihydrochloride

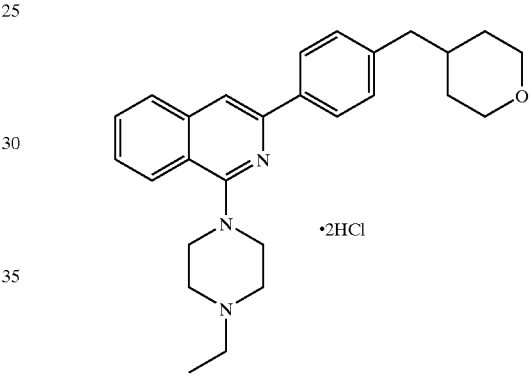

4-(Tetrahydrofuran-4-yl)methyltributylstannylbenzene (0.67 g) and 3-bromo-1-(4-ethylpiperazin-1-yl)isoquinoline (0.59 g) were heated under reflux in the presence of tetrakistriphenylphosphinepalladium(0) (0.08 g) in xylene in nitrogen atmosphere overnight. After cooling, the reaction solution was diluted with ethyl acetate and filtered. The filtrate was extracted in 2N hydrochloric acid, and the resulting aqueous layer was washed with ethyl acetate. Then, it was adjusted to pH 10 with a 8N aqueous solution sodium hydroxide, extracted with ethyl acetate, washed with a 10% aqueous solution of sodium carbonate and brine, and dried over magnesium sulfate. The solvent was evaporated, and the resulting residue was purified by silica gel column chromatography (chloroform/methanol system), to give 0.30 g of the free compound of the title compound as a pale yellow viscous oil.
Free compound:
$^1$H-NMR (400 MHz, CDCl$_3$); δ (ppm) 1.18 (t, J=7.2 Hz, 3H), 132–1.43 (m, 2H), 1.61 (br-d, 2H), 1.75–1.86 (m, 1H), 2.56 (q, J=7.2 Hz, 2H), 2.61 (d, J=6.8 Hz, 2H), 2.76 (br-t, 4H), 3.35 (br-t, 2H), 3.59 (br-t, 4H), 3.96 (br-q, 2H), 7.24–7.26 (m, 2H), 7.45 (br-t, 1H), 7.58 (br-t, 1H), 7.68 (s, 1H), 7.79 (d, J=8.0 Hz, 1H), 8.07–8.11 (m, 3H).

The resulting free compound was converted into a hydrochloride in a conventional manner, and then reprecipitated with in ethanol/ether, to give the title compound as a yellow powder.

Hydrochloride:
m.p.; 182–184° C. (decomp.)
¹H-NMR (400 MHz, DMSO-d₆); δ (ppm) 1.19–1.30 (m, 2H), 1.33 (t, J=7.2 Hz, 3H), 1.51 (br-d, 2H), 1.72–1.84 (m, 1H), 2.58 (d, J=7.2 Hz, 2H), 3.20–3.28 (m, 4H), 3.31–3.39 (m, 2H), 3.53 (br-t, 2H), 3.62 (br-d, 2H), 3.82 (br-q, 2H), 3.99 (br-d, 2H), 7.31 (d, J=8.4 Hz, 2H), 7.60 (br-t, 1H), 7.74 (br-t, 1H), 7.98 (d, J=7.6 Hz, 1H), 8.06 (s, 1H), 8.12 (br-d, 3H), 11.00 (br-s, 1H).
MS(FAB) m/z 416 (M+H)⁺.

Example 400

Synthesis of 4-Chloro-1-(4-Ethylpiperazin-1-yl)-3-(4-Methoxyphenyl)Isoquinoline Dihydrochloride

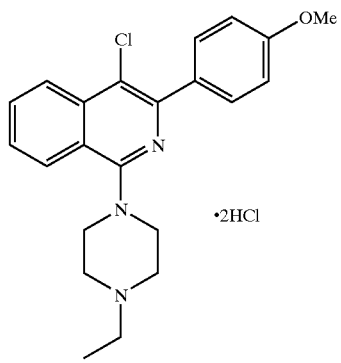

Phosphorus pentachloride (12.50 g) was added to 3-(4-methoxyphenyl)-1,2-dihydroisoquinolin-2-one (5.03 g) obtained in Example 10-1, and the mixture was stirred at 140° C. overnight. Water was added to the reaction solution, and the mixture was extracted with ethyl acetate. The extract was washed sequentially with a 10% aqueous solution of sodium carbonate and brine, and dried over magnesium sulfate. The solvent was evaporated, and the resulting residue was purified by silica gel column chromatography (ethyl acetate/n-hexane system) and recrystallized from chloroform/n-hexane, to give 1,4-dichloro-3-(4-methoxyphenyl)isoquinoline (2.17 g).

To the resulting 1,4-dichloro-3-(4-methoxyphenyl) isoquinoline (0.30 g) were added potassium carbonate (0.14 g), N-ethylpiperazine (126 ml) and N,N-dimethylformamide (10 ml). The resulting mixture was stirred at room temperature overnight. To the mixture was then added N-ethylpiperazine (126 ml), and the mixture was stirred at room temperature for 4 hr. Still additionally, N-ethylpiperazine (378 ml) was added thereto, and the mixture was stirred at 50° C. for 1.5 hr. To the reaction solution was added water, and the mixture was extracted with ethyl acetate. The extract was washed sequentially with water (four times) and brine, and dried over magnesium sulfate. The solvent was evaporated, and the resulting residue was purified by silica gel column chromatography (ethyl acetate/acetone system), to give 0.10 g of the free compound of the title compound as a colorless viscous oil.
Free compound:
¹H-NMR (400 MHz, CDCl₃); δ (ppm) 1.16 (t, J=7.2 Hz, 3H), 2.54 (q, J=7.2 Hz, 2H), 2.72 (br-t, 4H), 3.52 (br-t, 4H), 3.88 (s, 3H), 7.01 (d, J=9.0 Hz, 2H), 7.53 (br-t, 1H), 7.72 (br-t, 1H), 7.88 (d, J=9.0 Hz, 2H), 8.09 (d, J=8.0 Hz, 1H), 8.27 (d, J=8.0 Hz, 1H).
The resulting free compound was converted into a hydrochloride in a conventional manner, and then recrystallized from ethanol/IPE, to give the title compound as a yellow powder.

Hydrochloride:
m.p.; 200.5–201.5° C. (decomp.)
¹H-NMR (400 MHz, DMSO-d₆); δ (ppm) 1.31 (t, J=7.2 Hz, 3H), 3.18–3.25 (m, 2H), 3.28–3.36 (m, 2H), 3.50 (br-t, 2H), 3.58 (br-d, 2H), 3.84 (s, 3H), 3.95 (br-d, 2H), 7.08 (d, J=9.0 Hz, 2H), 7.74 (br-t, 1H), 7.81 (d, J=9.0 Hz, 2H), 7.93 (br-t, 1H), 8.20 (d, J=8.0 Hz, 1H), 8.26 (d, J=8.0 Hz, 1H), 10.95 (br-s, 1H).
MS(FAB) m/z 382, 384 (M+H)⁺.

Example 401

Synthesis of 1-(4-Ethylpiperazin-1-yl)-3-[4-(cis-4-Hydroxytetrahydropyran-2-yl)Phenyl]Isoquinoline Dihydrochloride

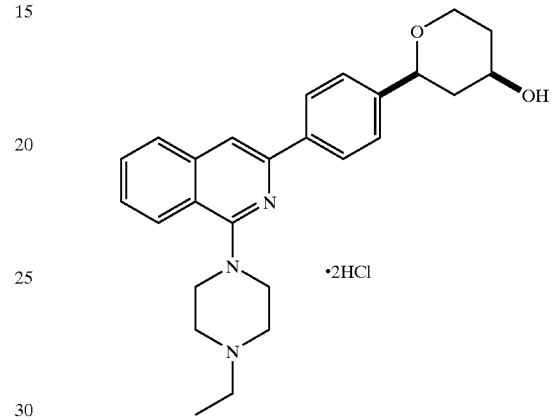

cis-4-Acetoxy-2-(tributylstannylphenyl)tetrahydrofuran (1.81 g) and 3-bromo-1-(4-ethylpiperazin-1-yl)isoquinoline (0.98 g) were heated under reflux in the presence of tetrakistriphenylphosphinepalladium(0) (0.14 g) in xylene in nitrogen atmosphere overnight. After cooling, the reaction solution was diluted with ethyl acetate and filtered. The filtrate was extracted in 2N hydrochloric acid, and the resulting aqueous layer was washed with ethyl acetate. Then, it was adjusted to pH 10 by a 8N aqueous solution of sodium hydroxide, extracted with ethyl acetate, washed with a 10% aqueous solution of sodium carbonate and brine, and dried over magnesium sulfate. The solvent was evaporated, to give a mixture of 1-(4-ethylpiperazin-1-yl)-3-[4-(cis-4-acetoxytetrahydropyran-2-yl)phenyl]isoquinoline as a brown viscous oil and the starting material.

Then, the resulting mixture was dissolved in methanol (20 ml). To the solution was added a 5N aqueous solution of sodium hydroxide (3.0 ml), and the mixture was stirred at room temperature overnight. The solvent was evaporated, and to the resulting residue was added water, and the mixture was then extracted with ethyl acetate. The extract was washed with brine and dried over magnesium sulfate. The solvent was evaporated, and the resulting residue was purified by silica gel column chromatography (chloroform/methanol system), to give 0.75 g of the free compound of the title compound as a pale brown amorphous.
¹H-NMR (400 MHz, CDCl₃); δ (ppm) 1.18 (t, J=7.2 Hz, 3H), 1.55–1.72 (m, 2H), 1.97–2.03 (m, 1H), 2.21–2.27 (m, 1H), 2.56 (q, J=7.2 Hz, 2H), 2.76 (br-t, 4H), 3.59–3.65 (m, 5H), 3.94–4.02 (m, 1H), 4.19–4.24 (m, 1H), 4.39 (dd, J=2.0, 11.4 Hz, 1H), 7.42–7.48 (m, 1H), 7.45 (d, J=8.4 Hz, 2H), 7.58 (br-t, 1H), 7.69 (s, 1H), 7.79 (d, J=8.0 Hz, 1H), 8.08 (d, J=8.0 Hz, 1H), 8.15 (d, J=8.4 Hz, 2H).
The resulting free compound was converted into a hydrochloride in a conventional manner, and then recrystallized from ethanol/IPE, to give the title compound as a yellow powder.

Hydrochloride:

m.p.; 148–149.5° C.

$^1$H-NMR (400 MHz, DMSO-d$_6$); δ (ppm) 1.28–1.36 (m, 1H), 1.34 (t, J=7.2 Hz, 3H), 1.39–1.49 (m, 1H), 1.81–1.86 (m, 1H), 2.06–2.11 (m, 1H), 3.20–3.26 (m, 2H), 3.31–3.39 (m, 2H), 3.48–3.64 (m, 5H), 3.74–3.82 (m, 1H), 3.99 (br-d, 2H), 4.02–4.07 (m, 1H), 4.38 (dd, J=1.6, 11.2 Hz, 1H), 7.46 (d, J=8.4 Hz, 2H), 7.61 (br-t, 1H), 7.75 (br-t, 1H), 7.99 (d, J=8.4 Hz, 1H), 8.09 (s, 1H), 8.12 (d, J=8.4 Hz, 1H), 8.16 (d, J=8.4 Hz, 2H), 11.09 (br-s, 1H).

MS(FAB) m/z 418 (M+H)$^+$.

Example 402

Synthesis of 1-(4-Ethylpiperazin-1-yl)-3-[4-(trans-4-Hydroxytetrahydropyran-2-yl)Phenyl]Isoquinoline Dihydrochloride

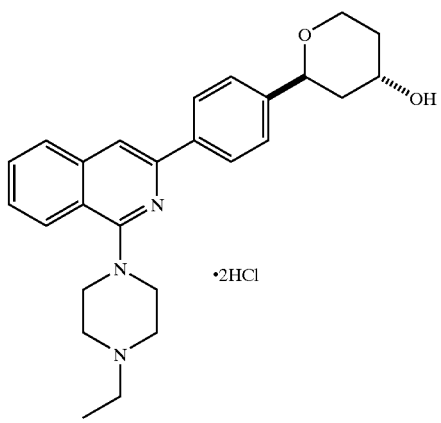

trans-4-Acetoxy-2-(tributylstannylphenyl) tetrahydropyran (3.35 g) and 3-bromo-1-(4-ethylpiperazin-1-yl)isoquinoline (1.36 g) were heated under reflux in the presence of tetrakistriphenylphosphinepalladium(0) (0.19 g) in xylene in nitrogen atmosphere overnight. After cooling, the reaction solution was diluted with ethyl acetate and filtered. The filtrate was extracted with 2N hydrochloric acid, and the resulting aqueous phase was washed with ethyl acetate. Then, it was adjusted to pH 10 by a 8N aqueous solution of sodium hydroxide, extracted with ethyl acetate, washed with brine, and dried over magnesium sulfate. The solvent was evaporated, to give a mixture of 1-(4-ethylpiperazin-1-yl)-3-[4-(trans-4-acetoxytetrahydropyran-2-yl)phenyl]isoquinoline as a brown viscous oil and the starting material.

Then, the resulting mixture was dissolved in methanol (20 ml). To the solution was added a 5N aqueous solution of sodium hydroxide (3.0 ml), and the mixture was stirred at room temperature overnight. The solvent was evaporated, and to the residue was added water, and the mixture was extracted with ethyl acetate. The extract was washed with brine and dried over magnesium sulfate. The solvent was evaporated, and the resulting residue was purified by silica gel column chromatography (chloroform/methanol system), to give 1.06 g of the free compound of the title compound as a brown amorphous.

$^1$H-NMR (400 MHz, CDCl$_3$); δ (ppm) 1.18 (t, J=7.2 Hz, 3H), 1.64–1.70 (m, 1H), 1.88–2.06 (m, 3H), 2.56 (q, J=7.2 Hz, 2H), 2.76 (br-t, 4H), 3.59 (br-t, 4H), 3.95–4.00 (m, 1H), 4.07–4.13 (m, 1H), 4.34–4.37 (m, 1H), 4.89 (dd, J=4.8, 9.2 Hz, 1H), 7.45 (br-t, 1H), 7.46 (d, J=8.4 Hz, 2H), 7.58 (br-t, 1H), 7.69 (s, 1H), 7.79 (d, J=8.0 Hz, 1H), 8.07 (d, J=8.4 Hz, 1H), 8.14 (d, J=8.4 Hz, 2H).

The resulting free compound was converted into a hydrochloride in a conventional manner, and then recrystallized from ethanol/IPE, to give the title compound as a yellow powder.

Hydrochloride:

m.p.; 151–152.5° C. (decomp.)

$^1$H-NMR (400 MHz, DMSO-d$_6$); δ (ppm) 1.34 (t, J=7.2 Hz, 3H), 1.55 (br-d, 1H), 1.68 (br-t, 1H), 1.75–1.86 (m, 2H), 3.19–3.26 (m, 2H), 3.31–3.39 (m, 2H), 3.53–3.64 (m, 4H), 3.82 (dd, J=4.6, 10.6 Hz, 1H), 3.92–4.00 (m, 4H), 4.79 (dd, J=2.0, 11.2 Hz, 1H), 7.44 (d, J=8.2 Hz, 2H), 7.61 (br-t, 1H), 7.75 (br-t, 1H), 7.99 (d, J=8.0 Hz, 1H), 8.08 (s, 1H), 8.12 (d, J=8.4 Hz, 1H), 8.16 (d, J=8.2 Hz, 2H), 11.29 (br-s, 1H).

MS(FAB) m/z 418 (M+H)$^+$.

Example 403

Synthesis of 1-(4-ethylpiperazin-1-yl)-3-[4-(2-hydroxypropoxy)phenyl]isoquinoline Dihydrochloride

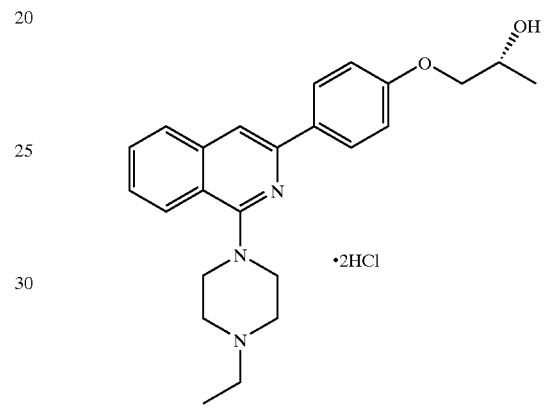

According to the method of Example 7, 1-(4-ethylpiperazin-1-yl)-3-(4-hydroxyphenyl)isoquinoline was obtained. In the same manner as in Example 287, subsequently, 1-(4-ethylpiperazin-1-yl)-3-{4-[2-(R)-(tert-butyldimethylsilyloxy)propoxy]phenyl}isoquinoline (0.43 g) was obtained.

To the resulting 1-(4-ethylpiperazin-1-yl)-3-[4-[2-(R)-(tert-butyldimethylsilyloxy)propoxy]phenyl)isoquinoline (0.43 g) were added methanol (10 ml) and 2N hydrochloric acid (50 ml) and dissolved, and the resulting mixture was stirred at room temperature for 4.5 hr. The solvent was evaporated, and the resulting residue was adjusted to pH 10 by a 8N aqueous solution of sodium hydroxide, which was then extracted with ethyl acetate. The extract was washed with brine and dried over magnesium sulfate. The solvent was evaporated, and the resulting residue was purified by silica gel column chromatography (chloroform/methanol system), to give 0.22 g of the free compound of the title compound as a colorless amorphous.

Free compound:

$^1$H-NMR (400 MHz, CDCl$_3$); δ (ppm) 1.18 (t, J=7.2 Hz, 3H), 1.32 (d, J=6.4 Hz, 3H), 2.56 (q, J=7.2 Hz, 2H), 2.76 (br-t, 4H), 3.59 (br-t, 4H), 3.87 (dd, J=8.0, 9.2 Hz, 1H), 4.02 (dd, J=2.8, 8.2 Hz, 1H), 4.20–4.28 (m, 1H), 7.01 (d, J=8.8 Hz, 2H), 7.44 (br-t, 1H), 7.57 (br-t, 1H), 7.62 (s, 1H), 7.77 (d, J=8.0 Hz, 1H), 8.06 (d, J=8.4 Hz, 1H), 8.12 (d, J=8.8 Hz, 2H).

The resulting free compound was converted into a hydrochloride in a conventional manner, and then reprecipitated with ethanol/ether, to give the title compound as a yellow powder.

Hydrochloride:
m.p.; 112–114° C.
$^1$H-NMR (400 MHz, DMSO-d$_6$); δ (ppm) 1.18 (d, J=6.0 Hz, 3H), 1.33 (t, J=7.2 Hz, 3H), 3.21–3.28 (m, 2H), 3.31–3.39 (m, 2H), 3.48 (br-t, 2H), 3.63 (br-d, 2H), 3.85–4.02 (m, 5H), 7.07 (d, J=8.8 Hz, 2H), 7.58 (br-t, 1H), 7.72 (br-t, 1H), 7.96 (d, J=8.4 Hz, 1H), 8.00 (s, 1H), 8.10 (d, J=8.0 Hz, 1H), 8.15 (d, J=8.8 Hz, 2H), 10.68 (br-s, 1H).
MS(FAB) m/z 392 (M+H)$^+$.

Example 404

Synthesis of 1-(4-ethylpiperazin-1-yl)-3-[4-(2-hydroxy-1-methylethoxy)phenyl]isoquinoline Dihydrochloride

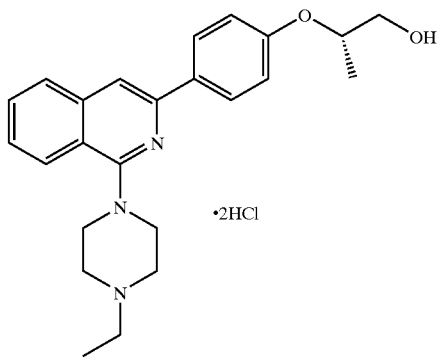

According to the method of Example 7, 1-(4-ethylpiperazin-1-yl)-3-(4-hydroxyphenyl)isoquinoline was obtained. In the same manner as in Example 287, subsequently, 1-(4-ethylpiperazin-1-yl)-3-{4-[2-trityloxy-1-(S)-methylethoxy)]phenyl}isoquinoline (1.21 g) in colorless viscous oil was prepared.

To the resulting 1-(4-ethylpiperazin-1-yl)-3-{4-[2-trityloxy-1-(S)-methylethoxy]phenyl}isoquinoline (1.21 g) were added benzene (10 ml), methanol (50 ml) and 2N hydrochloric acid (10 ml) and dissolved, and the resulting mixture was stirred at room temperature for 45 min. The solvent was evaporated, and the resulting residue was adjusted to pH 10 by a 8N aqueous solution of sodium hydroxide, which was then extracted with ethyl acetate. The extract was washed with brine and dried over magnesium sulfate. The solvent was evaporated, to give 0.36 g of the free compound of the title compound as a colorless amorphous.

Free compound:
$^1$H-NMR (400 MHz, CDCl$_3$); δ (ppm) 1.18 (t, J=7.2 Hz, 3H), 1.32 (d, J=6.0 Hz, 3H), 2.56 (q, J=7.2 Hz, 2H), 2.76 (br-t, 4H), 3.59 (br-t, 4H), 3.75 (dd, J=6.4, 11.6 Hz, 1H), 3.80 (dd, J=3.6, 11.6 Hz, 1H), 4.55–4.62 (m, 1H), 7.03 (d, J=8.8 Hz, 2H), 7.44 (br-t, 1H), 7.57 (br-t, 1H), 7.62 (s, 1H), 7.77 (d, J=8.0 Hz, 1H), 8.06 (d, J=7.2 Hz, 1H), 8.12 (d, J=8.8 Hz, 2H).

The resulting free compound was converted into a hydrochloride in a conventional manner, and then reprecipitated with ethanol/ether, to give the title compound as a yellow powder.

Hydrochloride:
m.p.; 128–129° C.
$^1$H-NMR (400 MHz, DMSO-d$_6$); δ (ppm) 1.25 (d, J=6.0 Hz, 3H), 1.33 (t, J=7.2 Hz, 3H), 3.20–3.26 (m, 2H), 3.31–3.38 (m, 2H), 3.48–3.63 (m, 6H), 4.48–4.56 (m, 1H), 7.07 (d, J=9.0 Hz, 2H), 7.57 (br-t, 1H), 7.72 (br-t, 1H), 7.95 (d, J=8.0 Hz, 1H), 7.99 (s, 1H), 8.10 (d, J=8.4 Hz, 1H), 8.13 (d, J=9.0 Hz, 2H), 11.03 (br-s, 1H).

MS(FAB) m/z 392 (M+H)$^+$.

Example 405

Synthesis of 1-(4-ethylpiperazin-1-yl)-3-(2-methoxypyridin-4-yl)isoquinoline

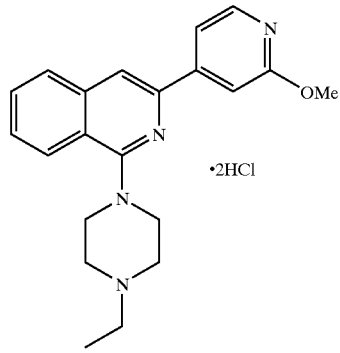

To 3-(2-methoxypyridin-4-yl)isoquinolin-1-one (1.22 g) obtained by reacting N-methyl-o-toluamide (2.90 g) and 4-cyano-2-methoxypyridine (2.60 g) according to the method of Example 10-1 was added phosphorus oxychloride (25.7 g), and the resulting mixture was heated at 100° C. for 2 hr. The reaction solution was evaporated, and to the resulting residue were added ethyl acetate and purified water. The ethyl acetate layer was washed with water, an aqueous solution of saturated sodium bicarbonate and brine, and dried over magnesium sulfate. The solvent was evaporated, and the resulting 1-chloro-3-(2-methoxyphenyl)isoquinoline was reacted as it was with N-ethylpiperazine (20 ml) at 120° C. for 8 hr. The reaction solution was evaporated, and to the resulting residue were added ethyl acetate and purified water. The ethyl acetate layer was washed with water and brine, and dried over magnesium sulfate. The solvent was evaporated, and the resulting residue was purified by silica gel column chromatography (methylene chloride/methanol system), to the free compound of the title compound as a pale yellow oil (0.62 g, yield: 9.2%).

The resulting free compound was converted into a hydrochloride in a conventional manner, to give a yellow powder.

Hydrochloride:

$^1$H-NMR (400 MHz, DMSO-d$_6$); δ (ppm) 1.32 (t, J=7.2 Hz, 3H), 3.18–3.28 (m, 2H), 3.28–3.41 (m, 2H), 3.48–3.67 (m, 4H), 3.94 (s, 3H), 3.99–4.08 (m, 2H), 7.62 (br-s, 1H), 7.66–7.73 (m, 1H), 7.77–7.84 (m, 2H), 8.04 (br-d, 1H), 8.16 (br-d, 1H), 8.28–8.33 (m, 2H), 10.98 (m, 1H). m.p.; 174–176° C.

MS(FAB) m/z 349 (M+H)$^+$.

Example 406

Synthesis of 1-(4-ethylpiperazin-1-yl)-3-(2-benzyloxypyridin-4-yl)isoquinoline and 1-(4-ethylpiperazin-1-yl)-3-(2-chloropyridin-4-yl)isoquinoline

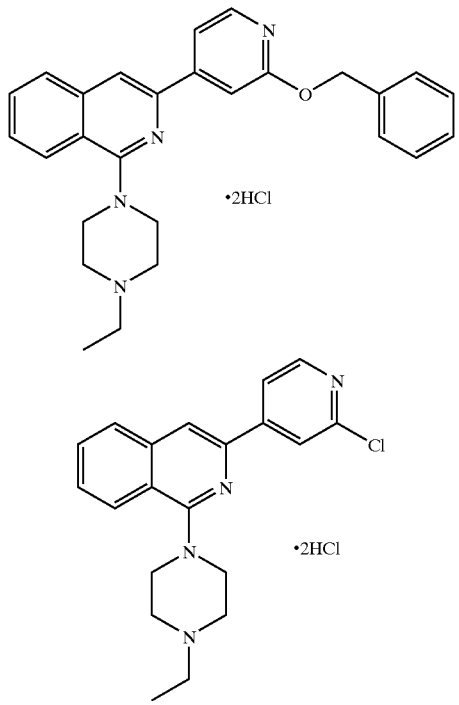

To 3-(2-benzyloxypyridin-4-yl)isoquinolin-1-one (2.84 g) obtained by reacting N-methyl-o-toluamide (3.00 g) and 4-cyano-2-benzyloxypyridine (4.20 g) according to the method of Example 10-1 was added phosphorus oxychloride (37.7 g), and the resulting mixture was heated at 100° C. for 2 hr. The reaction solution was evaporated, and to the resulting residue were added ethyl acetate and purified water. The ethyl acetate layer was washed with water and brine, and dried over magnesium sulfate. The solvent was evaporated, and the resulting 1-chloro-3-(2-benzyloxypyridin-4-yl)isoquinoline was reacted as it was with N-ethylpiperazine (20 ml) at 120° C. for 8 hr. The reaction solution was evaporated, and to the resulting residue were added ethyl acetate and purified water. The ethyl acetate layer was washed with water and brine, and dried over magnesium sulfate. The solvent was evaporated, and the resulting residue was purified by silica gel column chromatography (methylene chloride/methanol system), to give 1-(4-ethylpiperazin-1-yl)-3-(2-benzyloxypyridin-4-yl)isoquinoline (0.21 g) and 1-(4-ethylpiperazin-1-yl)-3-(2-chloropyridin-4-yl)isoquinoline (0.32 g), as pale yellow oils.

These resulting compounds were individually converted into hydrochlorides in conventional methods, to give a yellow amorphous and a yellow powder. 1-(4-Ethylpiperazin-1-yl)-3-(2-benzyloxypyridin-4-yl)isoquinoline hydrochloride (yellow amorphous):

$^1$H-NMR (400 MHz, DMSO-d$_6$); δ (ppm) 1.32 (t, J=7.2 Hz, 3H), 3.18–3.40 (m, 4H), 3.41–3.53 (m, 2H), 3.58–3.66 (m, 2H), 3.96–4.07 (m, 2H), 5.42 (s, 2H).

MS(FAB) m/z 425 (M+H)$^+$. 1-(4-Ethylpiperazin-1-yl)-3-(2-chloropyridin-4-yl)isoquinoline hydrochloride (yellow powder):

$^1$H-NMR (400 MHz, DMSO-d$_6$); δ (ppm) 1.32 (t, J=7.2 Hz, 3H), 3.18–3.41 (m, 4H), 3.44–3.56 (m, 2H), 3.58–2.66 (m, 2H), 4.00–4.08 (m, 2H), 7.68–7.75 (m, 1H), 7.79–7.85 (m, 1H), 8.05 (br-d, 1H), 8.15–8.21 (m, 2H), 8.24 (s, 1H), 8.42 (s, 1H), 8.55 (d, J=5.6 Hz, 1H). m.p.; 165–167° C.

Example 407

Synthesis of 1-(4-ethylpiperazin-1-yl)-3-[2-(2-methoxyethoxy)pyridin-4-yl]isoquinoline

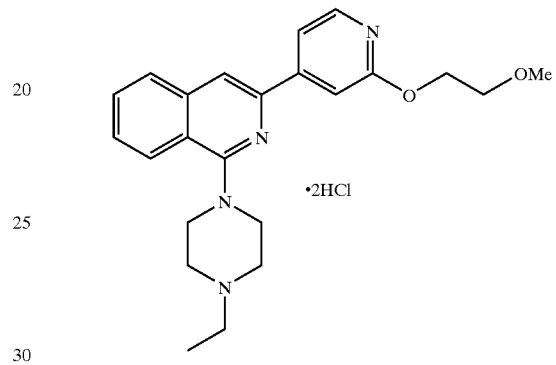

60% oily sodium hydride (0.20 g) was added gradually to 2-methoxyethanol (50 ml), under ice-cooling. To the resulting solution was added 1-(4-ethylpiperazin-1-yl)-3-(2-chloropyridin-4-yl)isoquinoline chloropyridin-4-yl)isoquinoline (0.20 g) obtained in the previous Example, and the mixture was heated under reflux for 3 days. The reaction solution was evaporated, and to the resulting residue were added ethyl acetate and purified water. The ethyl acetate layer was washed with water and brine, and dried over magnesium sulfate. The solvent was evaporated, and the resulting residue was purified by silica gel column chromatography (methylene chloride/methanol system), to give the title compound (0.12 g) as a pale yellow oil.

The resulting compound was converted into a hydrochloride in a conventional manner, to give a yellow powder.

Hydrochloride:

$^1$H-NMR (400 MHz, DMSO-d$_6$); δ (ppm) 1.34 (t, J=7.2 Hz, 3H), 3.17–3.27 (m, 2H), 3.27–3.41 (m, 2H), 3.50–3.67 (m, 4H), 3.69–3.74 (m, 2H), 3.97–4.07 (m, 2H), 4.44–4.49 (m, 2H), 7.64 (br-s, 1H), 7.66–7.75 (m, 1H), 7.76–7.85 (m, 1H), 8.01–8.06 (m, 1H), 8.14–8.20 (m, 1H), 8.29 (d, J=5.6 Hz, 1H), 8.34 (s, 1H), 11.52 (m, 1H). m.p.; 139–140° C.

MS(FAB) m/z 393 (M+H)$^+$.

Example 408

Synthesis of 1-(4-ethylpiperazin-1-yl)-3-(4-carbamoylphenyl)isoquinoline

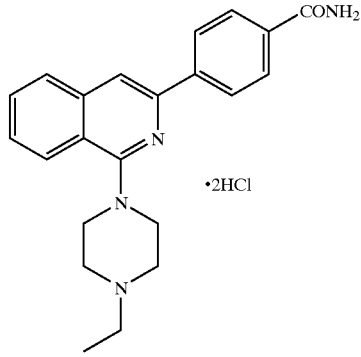

1-(4-Ethylpiperazin-1-yl)-3-(4-cyanophenyl)isoquinoline (1.0 g) obtained in Example 62 was reacted in concentrated sulfuric acid (40 ml) at 60° C. for 5 hr. The reaction solution was cooled and then poured over ice, and was then adjusted to pH 8 to 9 by a 8N aqueous solution of sodium hydroxide. The resulting white precipitates were collected by filtration, washed with water and dried, to give the title compound (0.25 g, yield; 23.8%).

The resulting compound was converted into a hydrochloric in a conventional manner, to give a yellow powder (0.21 g). Hydrochloride:

$^1$H-NMR (400 MHz, DMSO-d$_6$); δ (ppm) 1.34 (t, J=7.2 Hz, 3H), 3.18–3.28 (m, 2H), 3.30–3.41 (m, 2H), 3.51–3.67 (m, 4H), 3.98–4.06 (m, 2H), 7.43 (m, 1H), 7.62–7.67 (m, 1H), 7.75–7.80 (m, 1H), 8.02 (d, J=8.4 Hz, 2H), 8.05–8.12 (m, 1H), 8.14 (d, J=8.4 Hz, 1H), 8.21 (s, 1H), 8.28 (d, J=8.4 Hz, 2H), 11.14 (m, 1H). m.p.; 197–199° C.

MS(FAB) m/z 361 (M+H)$^+$.

Example 409

Synthesis of 1-(4-ethylpiperazin-1-yl)-3-[4-(cyclohexylhydroxymethyl)phenyl]isoquinoline

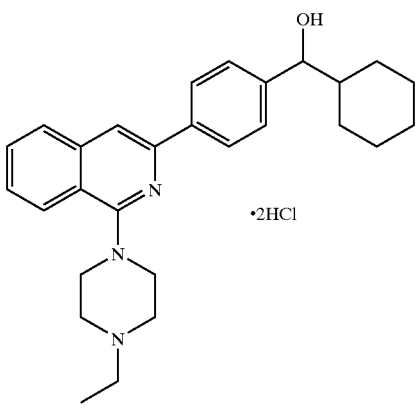

To a solution of 1-(4-ethylpiperazin-1-yl)-3-(4-formylphenyl)isoquinoline (0.35 g) obtained as an intermediate product in Example 17, in tetrahydrofuran (5 ml) was added 2M cyclohexylmagnesium chloride/ether solution (1 ml) at room temperature, and the mixture was reacted for 0.5 hr. The reaction solution was diluted with ethyl acetate, washed sequentially with an aqueous solution of saturated ammonium chloride, water and brine, and dried over magnesium sulfate. The solvent was evaporated, and the resulting residue was purified by silica gel column chromatography (methylene chloride/methanol system), to give the title compound (0.21 g) as a pale yellow oil.

The resulting compound was converted into a hydrochloride in a conventional manner, to give a yellow powder (0.18 g).
Hydrochloride:

$^1$H-NMR (400 MHz, DMSO-d$_6$); δ (ppm) 1.34 (t, J=7.2 Hz, 3H), 0.90–1.90 (m, 11H), 3.17–3.28 (m, 2H), 3.29–3.41 (m, 2H), 3.50–3.66 (m, 4H), 3.96–4.05 (m, 2H), 4.32 (d, J=6.4 Hz, 1H), 7.40 (d, J=8.4 Hz, 2H), 7.58–7.64 (m, 1H), 7.72–7.77 (m, 1H), 7.99 (d, J=8.4 Hz, 1H), 8.07 (s, 1H), 8.10–8.16 (m, 3H), 11.28 (m, 1H). m.p.; 153–155° C.

MS(FAB) m/z 430 (M+H)$^+$.

Example 410

Synthesis of 1-(4-ethylpiperazin-1-yl)-3-[4-(4-hydroxytetrahydropyran-4-yl)phenyl]isoquinoline

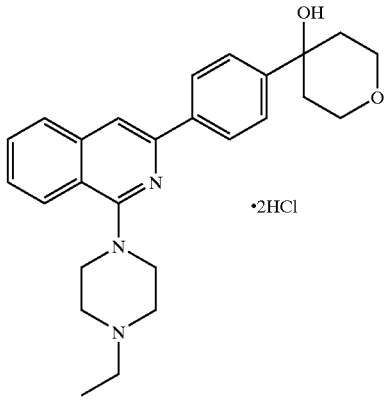

To 3-(4-bromophenyl)isoquinolin-1-one (3.86 g) obtained by reacting N-methyl-o-toluamide (7.50 g) and 4-bromobenzonitrile (9.10 g) according to the method of Example 10-1 was added phosphorus oxychloride (38.6 g), and the resulting mixture was heated at 100° C. for 2 hr. The reaction solution was evaporated, and to the resulting residue were added ethyl acetate and purified water. The ethyl acetate layer was washed with water, an aqueous solution of saturated sodium bicarbonate and brine, and dried over magnesium sulfate. The solvent was evaporated, and the resulting 1-chloro-3-(4-bromophenyl)isoquinoline was reacted as it was with N-ethylpiperazine (30 ml) at 120° C. for 8 hr. The reaction solution was evaporated, and to the resulting residue were added ethyl acetate and purified water. The ethyl acetate layer was washed with water and brine, and dried over magnesium sulfate. The solvent was evaporated, and the resulting residue was purified by silica gel column chromatography (methylene chloride/methanol system), to give 3-(4-bromophenyl)-1-(4-ethylpiperazin-1-yl)isoquinoline (1.62 g) as a pale yellow oil.

A solution of the resulting 3-(4-bromophenyl)-1-(4-ethylpiperazin-1-yl)isoquinoline (0.61 g) in tetrahydrofuran (30 ml) was cooled to −78° C., followed by the dropwise addition of 1.6M n-BuLi (1.1 ml) in nitrogen atmosphere. Fifteen minutes later, a solution of tetrahydropyran-4-one (0.17 g) in tetrahydrofuran (1 ml) was added thereto, and the temperature of the reaction mixture was gradually raised to room temperature. Three hours later, an aqueous solution of saturated ammonium chloride was added thereto, and the mixture was extracted with ethyl acetate. The ethyl acetate layer was washed with water and brine, and dried over magnesium sulfate. The solvent was evaporated, and the resulting residue was purified by silica gel column chromatography (methylene chloride/methanol system), to give the title compound as a pale yellow oil (0.21 g, yield; 32.1%).

The resulting compound was converted into a hydrochloride in a conventional manner, to give a yellow amorphous.
Free compound:
¹H-NMR (400 MHz, CDCl₃); δ (ppm) 1.17 (t, J=7.2 Hz, 3H), 1.76 (br-d, 2H), 2.20–2.30 (m, 2H), 2.55 (q, J=7.2 Hz, 2H), 2.76 (m, 4H), 3.58 (m, 4H), 3.89–4.02 (m, 4H), 7.43–7.48 (m, 1H), 7.56–7.62 (m, 1H), 7.59 (d, J=8.4 Hz, 2H), 7.68 (s, 1H), 7.77 (d, J=8.0 Hz, 1H), 8.08 (d, J=8.0 Hz, 1H), 8.16 (d, J=8.4 Hz, 2H).
MS(FAB) m/z 418 (M+H)⁺.

Example 411

Synthesis of 1-(4-ethylpiperazin-1-yl)-3-{4-[bis(1,3-thiazol-2-yl)hydroxymethyl]phenyl}isoquinoline

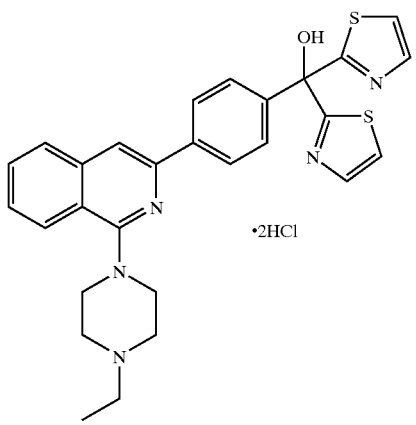

A solution of thiazole (0.75 g) in tetrahydrofuran (40 ml) was cooled to −78° C., followed by the dropwise addition of 2.5M n-BuLi (3.8 ml). Fifteen minutes later, a solution of 1-(4-ethylpiperazin-1-yl)-3-(4-formylphenyl)isoquinoline (1.0 g) obtained as an intermediate in Example 17, in tetrahydrofuran (20 ml) was added dropwise thereto. The temperature of the reaction solution was gradually raised to room temperature. The reaction solution was diluted with ethyl acetate, washed with an aqueous solution of saturated ammonium chloride, water and brine, and then dried over magnesium sulfate. The solvent was evaporated, and the resulting residue was purified by silica gel column chromatography (methylene chloride/methanol system), to give the title compound (0.27 g) as a pale yellow oil.
Free compound:
¹H-NMR (400 MHz, CDCl₃); δ (ppm) 1.16 (t, J=7.2 Hz, 3H), 2.55 (d, J=7.2 Hz, 2H), 2.74 (m, 4H), 3.57 (m, 4H), 5.75 (br-s, 1H), 7.37 (d, J=3.2 Hz, 2H), 7.45 (br-t, 1H), 7.56 (br-t, 1H), 7.65 (s, 1H), 7.73–7.80 (m, 3H), 7.82 (d, J=3.2 Hz, 2H), 8.05 (d, J=8.0 Hz, 1H), 8.14 (d, J=8.0 Hz, 2H).
The resulting compound was converted into a hydrochloride in a conventional manner, to give a yellow powder (0.18 g).
Hydrochloride:
¹H-NMR (400 MHz, DMSO-d₆); δ (ppm) 1.37 (t, J=7.2 Hz, 3H), 3.17–3.62 (m, 8H), 3.96–4.03 (m, 2H), 7.70–7.76 (m, 5H), 7.80 (d, J=3.2 Hz, 2H), 7.96 (br-d, 1H), 8.05 (s, 1H), 8.09 (br-d, 1H), 8.14 (d, J=8.0 Hz, 2H). m.p.; 157–158° C.

MS(FAB) m/z 514 (M+H)⁺.

As a by-product, 1-(4-ethylpiperazin-1-yl)-3-[4-(1,3-thiazol-2-yl)carbonylphenyl]isoquinoline (0.18 g) was obtained.

Example 412

Synthesis of 1-(4-ethylpiperazin-1-yl)-3-[4-(1,3-thiazol-2-yl)hydroxymethylphenyl]isoquinoline

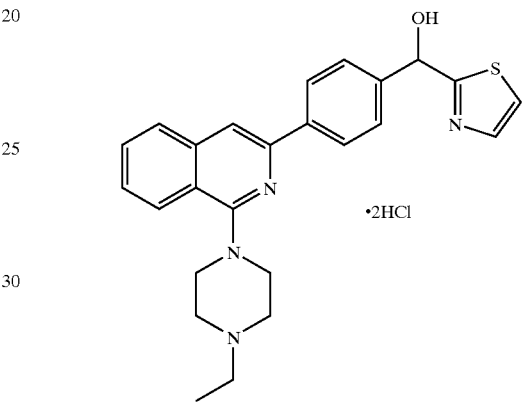

1-(4-Ethylpiperazin-1-yl)-3-[4-(1,3-thiazol-2-yl)carbonylphenyl]isoquinoline (0.18 g) was dissolved in methanol (10 ml) and was reacted with sodium borohydride (0.02 g). The reaction solution was concentrated. The resulting residue was partitioned between ethyl acetate (50 ml) and water (20 ml). The ethyl acetate layer was washed with water and brine, and dried over magnesium sulfate. The solvent was evaporated, and the resulting residue was purified by silica gel column chromatography (methylene chloride/methanol system), to give the title compound (0.12 g) as a pale yellow oil.

Free compound:

¹H-NMR (400 MHz, CDCl₃); δ (ppm) 1.18 (t, J=7.2 Hz, 3H), 2.58 (d, J=7.2 Hz, 2H), 2.77 (m, 4H), 3.60 (m, 4H), 6.15 (s, 1H), 7.29 (br-s, 1H), 7.44 (t, J=8.0 Hz, 1H), 7.55–7.60 (m, 1H), 7.58 (d, J=8.0 Hz, 2H), 7.66 (s, 1H), 7.72 (d, J=2.8 Hz, 2H), 7.77 (d, J=8.0 Hz, 1H), 8.04 (d, J=8.0 Hz, 1H), 8.16 (d, J=8.0 Hz, 2H).

MS(FAB) m/z 431 (M+H)⁺.

The resulting compound was converted into a hydrochloride in a conventional manner, to give a yellow powder (0.10 g).

Example 413

Synthesis of 1-(4-ethylpiperazin-1-yl)-3-[(3-pyridyl)hydroxymethyl]isoquinoline

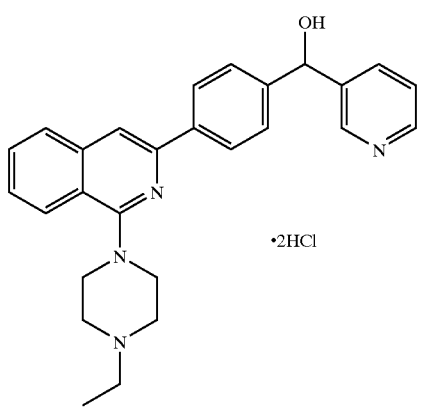

·2HCl

A solution of 1-(4-ethylpiperazin-1-yl)-3-bromoisoquinoline (0.39 g) obtained in Example 28-2, in tetrahydrofuran (10 ml) was cooled to −78° C., followed by the dropwise addition of 2.5M n-BuLi (0.6 ml). Fifteen minutes later, a solution of 3-formylpyridine (0.2 g) in tetrahydrofuran (3 ml) was added dropwise thereto. The temperature of the reaction solution was gradually raised to room temperature. The reaction solution was diluted with ethyl acetate, washed with brine, water and an aqueous solution of saturated sodium chloride, and dried over magnesium sulfate. The solvent was evaporated, and the resulting residue was purified by silica gel column chromatography (methylene chloride/methanol system), to give the title compound (0.15 g) as a pale yellow oil.

Free compound:

$^1$H-NMR (400 MHz, CDCl$_3$); δ (ppm) 1.17 (t, J=7.2 Hz, 3H), 2.57 (d, J=7.2 Hz, 2H), 2.74 (m, 4H), 3.55 (m, 4H), 5.80 (s, 1H), 7.00 (s, 1H), 7.23–7.28 (m, 1H), 7.46 (br-t, 1H), 7.57 (br-t, 1H), 7.65 (br-d, 1H), 7.75 (br-d, 1H), 8.04 (br-d, 2H), 8.52 (br-d, 1H), 8.72 (s, 1H).

The resulting compound was converted into an oxalate in a conventional manner, to give a pale yellow powder (0.17 g).

Oxalate:

$^1$H-NMR (400 MHz, DMSO-d$_6$); δ (ppm) 1.25 (t, J=7.2 Hz, 3H), 3.14 (q, J=7.2 Hz, 2H), 3.21–3.70 (m, 8H), 7.33 (dd, J=8.0, 1.2 Hz, 1H), 7.58 (t, J=7.6 Hz, 1H), 7.68 (s, 1H), 7.72 (t, J=7.6 Hz, 1H), 7.83 (d, J=7.6 Hz, 1H), 7.95 (d, J=8.0 Hz, 1H), 7.95 (d, J=8.0 Hz, 1H), 8.43 (dd, J=4.8, 1.6 Hz, 1H), 8.71 (d, J=1.6 Hz, 1H). m.p.; 174–175° C.

MS(FAB) m/z 349 (M+H)$^+$.

Example 414

Synthesis of 1-(4-ethylpiperazin-1-yl)-3-(1-indanon-5-yl)isoquinoline

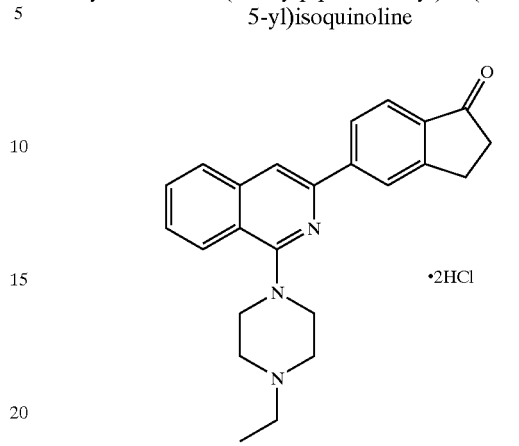

·2HCl

5-Bromo-1-indanone (3.0 g) and hexabutylditin (8.2 g) were reacted in the presence of tetrakistriphenylphosphinepalladium(0) (0.3 g) in xylene (50 ml) at 140° C. for 2 hr. After the reaction solution was back to room temperature, it was directly subjected to and purified by silica gel column chromatography (ethyl acetate/hexane system), to give 5-tributylstannyl-1-indanone (1.20 g) as a pale yellow oil. The resulting compound was subsequently reacted with 1-(4-ethylpiperazin-1-yl)-3-bromoisoquinoline (0.6 g) in the presence of tetrakistriphenylphosphinepalladium(0) (0.3 g) in xylene (50 ml) at 140° C. for 4 hr. The reaction solution was extracted with a 2N aqueous solution of hydrochloric acid (20 ml), again basified with sodium carbonate, and then extracted with ethyl acetate. The ethyl acetate layer was washed with water and brine, and dried over magnesium sulfate. The solvent was evaporated, and the resulting residue was purified by silica gel column chromatography (methylene chloride/methanol system), to give the title compound (0.41 g) as a pale yellow oil.

Free compound:

$^1$H-NMR (400 MHz, CDCl$_3$); δ (ppm) 1.18 (t, J=7.2 Hz, 3H), 2.56 (d, J=7.2 Hz, 2H), 2.73–2.81 (m, 6H), 3.20–3.26 (m, 2H), 3.60 (m, 4H), 7.50 (t, J=7.6 Hz, 1H), 7.62 (t, J=7.6 Hz, 1H), 7.79 (s, 1H), 7.81–7.86 (m, 2H), 8.09 (br-d, 1H), 8.15 (br-d, 1H), 8.29 (s, 1H).

The titled compound (0.21 g) was converted into a hydrochloride in a conventional manner, to give a yellow powder (0.19 g).

Hydrochloride:

$^1$H-NMR (400 MHz, DMSO-d$_6$); δ (ppm) 1.32 (t, J=7.2 Hz, 3H), 2.68–2.74 (m, 2H), 3.19–3.52 (m, 6H), 3.63 (br-d, 2H), 4.02 (br-d, 2H), 7.68 (br-t, 1H), 7.75–7.83 (m, 2H), 8.04 (d, J=8.0 Hz, 1H), 8.16 (d, J=8.0 Hz, 1H), 8.26–8.30 (m, 1H), 8.29 (s, 1H), 8.40 (s, 1H). m.p.; 233° C. (decomp.)

MS(FAB) m/z 372 (M+H)$^+$.

Example 415

Synthesis of 1-(4-ethylpiperazin-1-yl)-3-(1-hydroxyindan-5-yl)isoquinoline

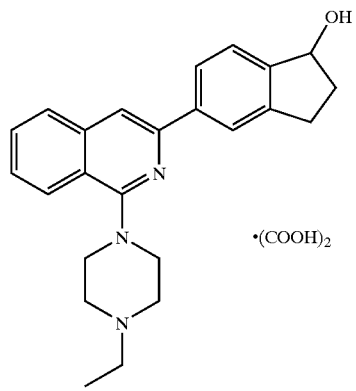

1-(4-Ethylpiperazin-1-yl)-3-(1-indanon-5-yl)isoquinoline (0.20 g) obtained in the previous Example was dissolved in methanol (20 ml), followed by the addition of sodium borohydride (0.10 g) at room temperature, and the mixture was reacted for 15 min. The reaction solution was concentrated, and the resulting residue was partitioned between ethyl acetate and water. The ethyl acetate layer was separated, washed with water and brine, and dried over magnesium sulfate. The solvent was evaporated, and the resulting residue was purified by silica gel column chromatography (methylene chloride/methanol system), to give the title compound (0.12 g) as a pale yellow oil.

Free compound:

$^1$H-NMR (400 MHz, CDCl$_3$); δ (ppm) 1.16 (t, J=7.2 Hz, 3H), 1.96–2.07 (m, 1H), 2.50–2.60 (m, 3H), 2.75 (m, 4H), 2.86–2.96 (m, 1H), 3.10–3.21 (m, 1H), 3.58 (m, 4H), 5.29–5.33 (m, 1H), 7.46 (br-t, 1H), 7.51 (d, J=8.0 Hz, 1H), 7.58 (br-t, 1H), 7.67 (s, 1H), 7.77 (d, J=8.0 Hz, 1H), 8.03–8.09 (m, 2H), 8.05 (s, 1H).

The title compound was converted into an oxalate in a conventional manner, to give a pale yellow powder (0.11 g).

Oxalate:

$^1$H-NMR (400 MHz, DMSO-d$_6$); δ (ppm) 1.25 (t, J=7.2 Hz, 3H), 1.78–1.88 (m, 1H), 2.35–2.43 (m, 1H), 2.75–2.86 (m, 1H), 2.94–3.08 (m, 1H), 3.09–3.70 (m, 10H), 5.10 (br-t, 1H), 7.45 (d, J=8.4 Hz, 1H), 7.60 (br-t, 1H), 7.73 (br-t, 1H), 7.97 (d, J=8.4 Hz, 1H), 8.04 (s, 1H), 8.05 (s, 1H), 8.11 (d, J=8.8 Hz, 1H). m.p.; 193–195° C.

MS(FAB) m/z 374 (M+H)$^+$.

Example 416

Synthesis of 1-(4-ethylpiperazin-1-yl)-3-[4-(3-hydroxy-3-methylbutyl)-3-fluorophenyl]isoquinoline

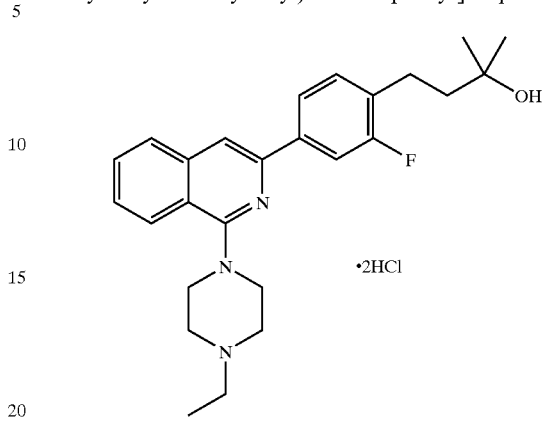

To a suspension of 60% oily sodium hydride (0.18 g) in tetrahydrofuran (25 ml) was added triethylphosphonoacetate ester (1.0 g), under ice-cooling. After the evolution of the hydrogen was ceased, a solution of 1-(4-ethylpiperazin-1-yl)-3-(3-fluoro-4-formylphenyl)isoquinoline (0.65 g) obtained in Example 28-3 in tetrahydrofuran (10 ml) was added dropwise to the resulting reaction solution. After stirring for 2 hr, purified water was added to the reaction solution, and the mixture was extracted with ethyl acetate. The ethyl acetate layer was washed with water and brine, and dried over magnesium sulfate. The solvent was removed, and the resulting residue was dissolved in ethanol (10 ml), followed by the hydrogenation in the presence of platinum oxide (0.05 g). After the catalyst was filtered off and washed with ethanol, the resulting filtrate was concentrated. To a solution of the resulting residue in tetrahydrofuran (10 ml) was added 3M methylmagnesium bromide/ether solution (1 ml), and the mixture was reacted at room temperature for 1 hr. An aqueous solution of ammonium chloride was added to the reaction solution, and then the mixture was extracted with ethyl acetate. The resulting ethyl acetate layer was washed with water and brine, and dried over magnesium sulfate. The solvent was evaporated, and the resulting residue was purified by silica gel column chromatography (methylene chloride/methanol system), to give 0.28 g of the title compound as a pale yellow oil.

Free compound:

$^1$H-NMR (400 MHz, CDCl$_3$); δ (ppm) 1.16 (t, J=7.2 Hz, 3H), 1.31 (s, 6H), 1.77–1.85 (m, 2H), 2.55 (q, J=7.2 Hz, 3H), 2.73–2.81 (m, 6H), 3.57 (m, 4H), 7.27 (t, J=8.0 Hz, 1H), 7.45 (br-t, 1H), 7.58 (br-t, 1H), 7.65 (s, 1H), 7.77 (d, J=8.4 Hz, 1H), 7.82–7.79 (m, 2H), 8.06 (d, J=8.0 Hz, 1H).

The resulting title compound was converted into a hydrochloride in a conventional manner, to give a pale yellow powder (0.20 g).

Hydrochloride:

$^1$H-NMR (400 MHz, DMSO-d$_6$); δ (ppm) 1.18 (s, 6H), 1.33 (t, J=7.2 Hz, 3H), 1.62–1.69 (m, 2H), 2.66–2.75 (m, 2H), 3.18–3.29 (m, 2H), 3.36 (br-q, 2H), 3.51 (br-t, 2H), 3.63 (br-d, 2H), 4.00 (br-d, 2H), 7.41 (t, J=8.0 Hz, 1H), 7.63 (br-t, 1H), 7.76 (br-t, 1H), 7.91–8.00 (m, 3H), 8.10–8.15 (m, 2H), 10.86 (m, 1H). m.p.; 206–207° C.

MS(FAB) m/z 422 (M+H)$^+$.

Example 417

Synthesis of 1-(4-ethylpiperazin-1-yl)-3-[3-cyano-4-(2-hydroxyethoxy)phenyl]isoquinoline

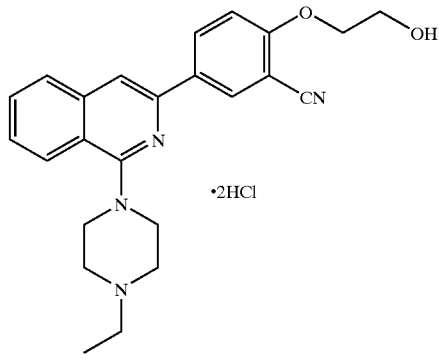

•2HCl 2-(2-Benzyloxyethoxy)-5-bromobenzonitrile (2.01 g) and hexabutylditin (3.84 g) were reacted in xylene (50 ml) in the presence of tetrakistriphenylphosphinepalladium(0) (0.20 g) at 140° C. for 1.5 hr. After the reaction solution was back to room temperature, it was directly subjected to silica gel column chromatography (ethyl acetate/hexane system), to give 2-(2-benzyloxyethoxy)-5-tributylstannylbenzonitrile (1.70 g) as a pale yellow oil. Further, the resulting compound was reacted as it was with 1-(4-ethylpiperazin-1-yl)-3-bromoisoquinoline (0.48 g) in xylene (50 ml) in the presence of tetrakistriphenylphosphinepalladium(0) (0.21 g) at 140° C. for 4 hr. The reaction solution was extracted with a 2N aqueous solution of hydrochloric acid (20 ml) and basified again with sodium carbonate, and then extracted with ethyl acetate. The ethyl acetate layer was washed with water and brine, and dried over magnesium sulfate. The solvent was evaporated, and the resulting residue was purified by silica gel column chromatography (methylene chloride/methanol system), to give 1-(4-ethylpiperazin-1-yl)-3-[3-cyano-4-(2-benzyloxyethoxy)phenyl]isoquinoline (0.52 g) as a pale yellow oil.

1-(4-Ethylpiperazin-1-yl)-3-[3-cyano-4-(2-benzyloxyethoxy)phenyl]isoquinoline (0.50 g) was dissolved in methanol (20 ml), followed by the hydrogenation in the presence of 10% palladium/carbon catalyst (0.05 g) at room temperature. After the catalyst was filtered off and washed with methanol, the resulting filtrate was concentrated, to give 0.28 g of the title compound as a pale yellow oil.

Free compound:
$^1$H-NMR (400 MHz, CDCl$_3$); δ (ppm) 1.18 (t, J=7.2 Hz, 3H), 2.56 (q, J=7.2 Hz, 3H), 2.77 (m, 4H), 3.58 (m, 4H), 4.05 (m, 3H), 4.24 (m, 3H), 7.08 (d, J=8.0 Hz, 1H), 7.47 (br-t, 1H), 7.60 (s, 1H), 7.58–7.63 (m, 1H), 7.78 (d, J=8.0 Hz, 1H), 8.06 (d, J=8.0 Hz, 1H), 8.35 (d, J=8.0 Hz, 1H), 8.39 (s, 1H).

The resulting title compound was converted into a hydrochloride in a conventional manner, to give a yellow powder (0.25 g).

Hydrochloride:
$^1$H-NMR (400 MHz, DMSO-d$_6$); δ (ppm) 1.33 (t, J=7.2 Hz, 3H), 3.20–3.29 (m, 2H), 3.36 (br-q, 2H), 3.51 (br-t, 2H), 3.64 (br-d, 2H), 3.78–3.83 (m, 12H), 4.02 (br-d, 2H), 7.43 (br-d, 1H), 7.62 (br-t, 1H), 7.76 (br-t, 1H), 7.96 (d, J=8.4 Hz, 1H), 8.13 (d, J=8.4 Hz, 1H), 8.16 (s, 1H), 8.46–8.53 (m, 2H), 10.76 (m, 1H). m.p.; 162–164° C.
MS(FAB) m/z 403 (M+H)$^+$.

Example 418

Synthesis of 1-(4-ethylpiperazin-1-yl)-3-[3-(3-hydroxypropyl)phenyl]isoquinoline

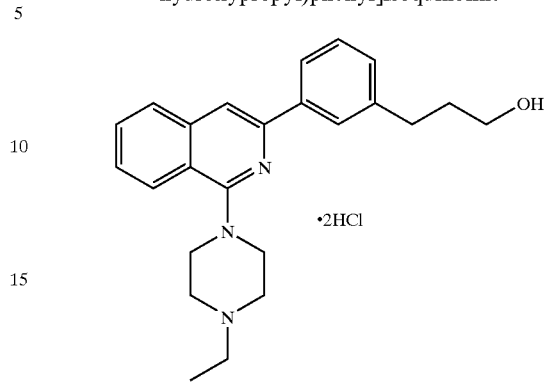

•2HCl

Ethyl 3-(3-bromophenyl)propionate (3.3 g) and hexabutylditin (7.5 g) were reacted in xylene (50 ml) in the presence of tetrakistriphenylphosphinepalladium(0) (0.50 g) at 140° C. for 1.5 hr. After the reaction solution was back to room temperature, it was directly subjected to silica gel column chromatography (ethyl acetate/hexane system), to give 1-(2-ethoxycarbonylethyl)-3-tributylstannylbenzene (2.70 g) as a pale yellow oil. Further, the resulting compound was reacted as it was with 1-(4-ethylpiperazin-1-yl)-3-bromoisoquinoline (1.13 g) in xylene (30 ml) in the presence of tetrakistriphenylphosphinepalladium(0) (0.3 g) at 140° C. for 4 hr. The reaction solution was extracted with a 2N aqueous solution of hydrochloric acid (20 ml) and basified again with sodium carbonate, and the mixture was extracted with ethyl acetate. The ethyl acetate layer was washed with water and brine, and dried over magnesium sulfate. The solvent was evaporated, and the resulting residue was purified by silica gel column chromatography (methylene chloride/methanol system), to give 1-(4-ethylpiperazin-1-yl)-3-[3-(2-ethoxycarbonylethyl)phenyl]isoquinoline (0.85 g) as a pale yellow oil.

A solution of 1-(4-ethylpiperazin-1-yl)-3-[3-(2-(2-ethoxycarbonylethyl)phenyl)isoquinoline (0.85 g) in tetrahydrofuran (10 ml) was added dropwise into a suspension of lithium aluminum hydride (0.1 g) in tetrahydrofuran (30 ml) at room temperature, and the mixture was stirred for 30 min. The reaction mixture was cooled, water (1 ml), a 5N aqueous solution of sodium hydroxide (1 ml) and water (3 ml) were sequentially added thereto, and then the mixture was stirred at room temperature for 1 hr. After the resulting precipitates were filtered off and washed with ethyl acetate, the resulting filtrate was concentrated. The resulting residue was purified by silica gel column chromatography (methylene chloride/methanol system), to give the title compound (0.51 g) as a pale yellow oil.

The resulting compound was converted into a hydrochloride in a conventional manner, to give a yellow powder (0.50 g).

Hydrochloride:
$^1$H-NMR (400 MHz, DMSO-d$_6$); δ (ppm) 1.33 (t, J=7.2 Hz, 3H), 1.76–1.85 (m, 2H), 2.75 (br-t, 2H), 3.19–3.28 (m, 2H), 3.30–3.41 (m, 2H), 3.47 (t, J=7.2 Hz, 3H), 3.52 (br-t, 2H), 3.64 (br-d, 2H), 4.00 (br-d, 2H), 7.26 (d, J=8.0 Hz, 1H), 7.42 (t, J=8.0 Hz, 1H), 7.61 (br-t, 1H), 7.75 (br-t, 1H), 7.98–8.04 (m, 3H), 8.10 (s, 1H), 7.99 (d, J=8.0 Hz, 1H), 8.12 (br-d, 1H). m.p.; 101–103° C.

MS(FAB) m/z 376 (M+H)+.

Example 419

Synthesis of 1-(4-ethylpiperazin-1-yl)-3-benzylisoquinoline

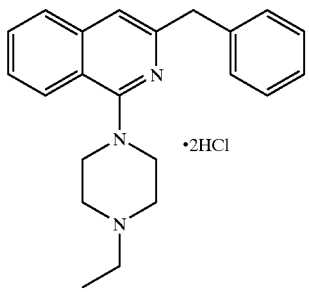

•2HCl

To a mixture solution of 1-(4-ethylpiperazin-1-yl)-3-bromoisoquinoline (0.71 g) cooled to 0° C. and [1,3-bis(diphenylphosphino)propane]dichloronickel(II) (0.05 g) in diethyl ether (20 ml) was dropwise added 1M benzylmagnesium chloride/ether solution (4.5 ml) in nitrogen atmosphere. The reaction mixture was stirred at room temperature overnight. The reaction solution was diluted with ether (30 ml), washed with water and brine, and then dried over magnesium sulfate. The solvent was removed, and the resulting residue was purified by silica gel column chromatography (ethyl acetate/acetone system), to give the title compound (0.44 g; 59.5%) as a pale yellow oil.

Free compound:

1H-NMR (400 MHz, CDCl3); δ (ppm) 1.16 (t, J=7.2 Hz, 3H), 2.54 (q, J=7.2 Hz, 2H), 2.73 (m, 4H), 3.49 (m, 4H), 4.12 (s, 2H), 6.98 (s, 1H), 7.19 (t, J=8.0 Hz, 1H), 7.24–7.30 (m, 2H), 7.36 (d, J=8.0 Hz, 2H), 7.40 (d, J=8.0 Hz, 1H), 7.51 (t, J=8.0 Hz, 1H), 7.61 (d, J=8.0 Hz, 1H), 8.00 (d, J=8.0 Hz, 1H).

The resulting compound was converted into a hydrochloride in a conventional manner, to give a yellow powder (0.49 g).

Hydrochloride:

1H-NMR (400 MHz, DMSO-d6); δ (ppm) 1.36 (t, J=7.2 Hz, 3H), 3.35 (q, J=7.2 Hz, 2H), 3.50 (br-t, 2H), 3.77–3.88 (m, 6H), 4.26–4.34 (m, 4H), 4.31 (s, 2H), 7.26–7.40 (m, 6H), 7.74 (dt, J=8.4, 1.2 Hz, 1H), 7.61 (d, J=8.0 Hz, 1H), 7.74 (dt, J=8.0, 0.8 Hz, 1H), 8.15 (d, J=8.0 Hz, 1H). m.p.; 118–119° C.

MS(FAB) m/z 332 (M+H)+.

Example 420

Synthesis of 1-(4-ethylpiperazin-1-yl)-3-(2-hydroxy-2-phenylethyl)isoquinoline

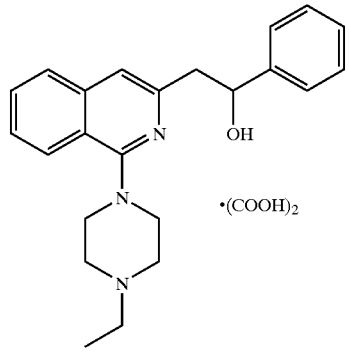

•(COOH)2

A mixed solution of 1-(4-ethylpiperazin-1-yl)-3-bromoisoquinoline (1.00 g), acetophenone (1.50 g) and tert-butoxypotassium (1.40 g) in dimethyl sulfoxide (50 ml) was irradiated with light (450 W; mercury-vapor lamp) at room temperature for 5 hr. Water (200 ml) was added to the reaction solution, and the mixture was extracted with ethyl acetate. The resulting organic layer was washed with water and brine, and then extracted with a 2N aqueous solution of hydrochloric acid (100 ml). The resulting aqueous layer was basified with sodium carbonate and extracted with ethyl acetate. The ethyl acetate layer was washed with water and brine, and dried over magnesium sulfate. The solvent was removed, to give 1-(4-ethylpiperazin-1-yl)-3-phenacylisoquinoline (1.0 g) as a pale yellow oil.

To a solution of the resulting 1-(4-ethylpiperazin-1-yl)-3-phenacylisoquinoline (0.92 g) in methanol (30 ml) was added sodium borohydride (0.12 g) at room temperature. One hr later, the reaction mixture was concentrated. The resulting residue was partitioned between ethyl acetate and water, and extracted with ethyl acetate. The resulting organic layer was washed with water and brine, and dried over magnesium sulfate. The solvent was removed, to give the title compound (0.81 g) as a pale yellow oil.

Free compound:

1H-NMR (400 MHz, CDCl3); δ (ppm) 1.17 (t, J=7.2 Hz, 3H), 2.56 (q, J=7.2 Hz, 2H), 2.77 (m, 4H), 3.14 (d, J=6.8 Hz, 2H), 3.55 (m, 4H), 5.15 (br-t, 1H), 6.75 (br-s, 1H), 7.02 (s, 1H), 7.22–7.28 (m, 1H), 7.35 (t, J=8.0 Hz, 2H), 7.42–7.49 (m, 3H), 7.58 (t, J=8.0 Hz, 1H), 7.65 (d, J=8.0 Hz, 1H), 8.05 (d, J=8.0 Hz, 1H).

The resulting compound was converted into an oxalate in a conventional manner, to give a pale yellow powder (0.88 g).

Oxalate:

1H-NMR (400 MHz, DMSO-d6); δ (ppm) 1.26 (t, J=7.2 Hz, 3H), 3.00–3.64 (m, 12H), 5.08 (t, J=6.8 Hz, 1H), 7.19–7.37 (m, 6H), 7.56 (t, J=8.0 Hz, 1H), 7.68 (t, J=8.0 Hz, 1H), 7.80 (d, J=8.0 Hz, 1H), 8.07 (d, J=8.0 Hz, 1H).

Melting point; 148–149° C.

Example 421

Synthesis of 3-benzamide-1-(4-ethylpiperazin-1-yl)isoquinoline

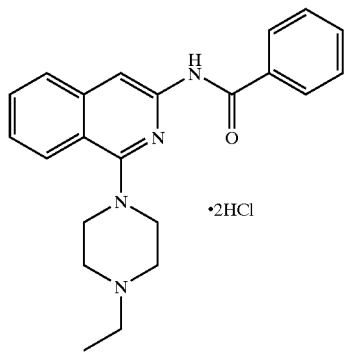

To a suspension of α-cyanotolunitrile (20.0 g) in acetic acid (50 ml) was added 25% hydrogen bromide/acetate solution (150 ml), and the mixture was reacted at room temperature overnight. The resulting precipitates were collected by filtration and then added to a 10% aqueous solution of potassium carbonate. The yellow powder was changed to a pale yellow powder. The resulting powder was collected by filtration, washed with water and hexane, and dried at 50° C. under reduced pressure, to give 3-amino-1-bromoisoquinoline (28.5 g; 90.8%).

3-Amino-1-bromoisoquinoline (10.3 g) and 1-ethylpiperazine (10.5 g) were reacted in the presence of potassium carbonate (13.8 g) in N,N-dimethylformamide (80 ml) at room temperature for 3 days. The reaction solution was concentrated, followed by the addition of purified water (500 ml), and the resulting mixture was stirred under ice-cooling for 1 hr. The resulting ocherous precipitates were collected by filtration, washed with a small amount of ice-water and hexane, and then dried at 50° C. under reduced pressure, to give 3-amino-1-(4-ethylpiperazin-1-yl)isoquinoline (4.5 g).

To a solution of 3-amino-1-(4-ethylpiperazin-1-yl) isoquinoline (0.5 g) in pyridine (10 ml) was added benzoyl chloride (0.28 g), and the mixture was reacted at room temperature for 5 hr. The reaction solution was concentrated, and then extracted with ethyl acetate. The ethyl acetate layer was washed with water and brine, and dried over magnesium sulfate. The solvent was removed, and the resulting residue was purified by NH-silica gel column chromatography (ethyl acetate/hexane system), to give the title compound (0.57 g, %) as a pale yellow solid.

Free compound:
$^1$H-NMR (400 MHz, CDCl$_3$); δ (ppm) 1.17 (t, J=7.2 Hz, 3H), 2.56 (q, J=7.2 Hz, 2H), 2.73 (m, 4H), 3.45 (m, 4H), 7.36 (t, J=8.0 Hz, 1H), 7.48–7.60 (m, 4H), 7.78 (d, J=8.0 Hz, 1H), 7.93–8.02 (m, 3H), 8.27 (s, 1H), 8.38 (s, 1H).

The resulting title compound was converted into a hydrochloride in a conventional manner, to give a yellow powder (0.58 g).
Hydrochloride:
$^1$H-NMR (400 MHz, DMSO-d$_6$); δ (ppm) 1.32 (t, J=7.2 Hz, 3H), 3.14–3.38 (m, 4H), 3.48–3.60 (m, 4H), 3.92 (br-d, 2H), 7.45–7.68 (m, 5H), 7.89 (d, J=8.4 Hz, 1H), 7.98–8.08 (m, 3H), 8.21 (s, 1H), 10.45 (s, 1H), 11.15 (m, 1H). m.p.; 160–162° C.
MS(FAB) m/z 362 (M+H)$^+$.

Example 422

Synthesis of 3-benzenesulfoneamide-1-(4-ethylpiperazin-1-yl)isoquinoline

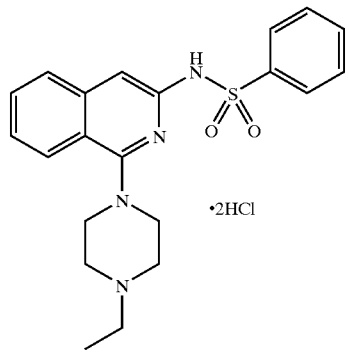

To a solution of 3-amino-1-(4-ethylpiperazin-1-yl) isoquinoline (0.4 g) in pyridine (10 ml) was added benzoylsulfonyl chloride (0.29 g), and the mixture was stirred at room temperature for 5 hr. The reaction solution was concentrated, and then extracted with ethyl acetate. The ethyl acetate layer was washed with water and brine, and then dried over magnesium sulfate. The solvent was removed, and the resulting residue was purified by NH-silica gel column chromatography (ethyl acetate/hexane system), to give the title compound (0.48 g) as a pale yellow solid.
Free compound:
$^1$H-NMR (400 MHz, CDCl$_3$); δ (ppm) 1.14 (t, J=7.2 Hz, 3H), 2.48 (q, J=7.2 Hz, 2H), 2.62 (m, 4H), 3.35 (m, 4H), 7.16 (s, 1H), 7.33 (br-t, 1H), 7.42 (br-t, 2H), 7.48–7.53 (m, 2H), 7.64 (d, J=8.0 Hz, 1H), 7.88–7.94 (m, 2H).

The resulting title compound was converted into a hydrochloride in a conventional manner, to give a yellow amorphous (0.54 g).
Hydrochloride:
$^1$H-NMR (400 MHz, DMSO-d$_6$); δ (ppm) 1.32 (t, J=7.2 Hz, 3H), 3.15–3.26 (m, 2H), 3.27–3.39 (m, 2H), 3.48–3.60 (m, 4H), 3.94 (br-d, 2H), 7.48–7.71 (m, 5H), 7.90 (d, J=8.0 Hz, 1H), 8.00–8.08 (m, 3H), 8.23 (s, 1H), 10.45 (s, 1H), 10.98 (m, 1H). m.p.; amorphous
MS(ESI) m/z 397 (M+H)$^+$.

Example 423

Synthesis of 1-(4-ethylpiperazin-1-yl)-3-(4-methoxybenzenesulfonamide)isoquinoline

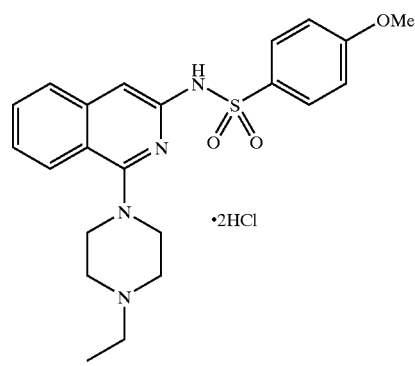

To a solution of 3-amino-1-(4-ethylpiperazin-1-yl) isoquinoline (0.4 g) in pyridine (10 ml) was added 4-methoxybenzenesulfonyl chloride (0.33 g), and the mixture was reacted at room temperature for 5 hr. The reaction solution was concentrated, and then extracted with ethyl acetate. The ethyl acetate layer was washed with water and brine, and then dried over magnesium sulfate. The solvent was removed, and the resulting residue was purified by NH-silica gel column chromatography (ethyl acetate/hexane system), to give the title compound (0.52 g, %) as a pale yellow solid.

Free compound:
$^1$H-NMR (400 MHz, DMSO-$d_6$); δ (ppm) 1.05 (t, J=7.2 Hz, 3H), 2.38 (q, J=7.2 Hz, 2H), 2.50 (m, 4H), 3.20 (m, 4H), 3.79 (s, 3H), 6.87 (s, 1H), 7.05 (d, J=8.0 Hz, 2H), 7.36 (br-t, 1H), 7.55 (br-t, 2H), 7.68 (d, J=8.0 Hz, 1H), 7.84 (d, J=8.0 Hz, 2H), 7.80–7.88 (m, 1H), 10.54 (m, 1H).

The resulting title compound was converted into a hydrochloride in a conventional manner, to give a pale yellow amorphous (0.59 g).

Hydrochloride:
$^1$H-NMR (400 MHz, DMSO-$d_6$); δ (ppm) 1.30 (t, J=7.2 Hz, 3H), 3.10–3.25 (m, 2H), 3.40 (br-t, 2H), 3.51 (br-d, 2H), 3.71 (br-d, 2H), 3.79 (s, 3H), 6.98 (s, 1H), 7.11 (d, J=9.2 Hz, 2H), 7.40 (br-t, 1H), 7.60 (br-t, 1H), 7.76 (d, J=8.0 Hz, 1H), 7.87 (d, J=9.2 Hz, 2H), 7.93 (br-d, 1H), 10.80 (s, 1H), 11.09 (m, 1H).
MS(ESI) m/z 427 (M+H)$^+$.

Example 424

Synthesis of 1-(4-ethylpiperazin-1-yl)-3-(4-methoxyphenoxymethyl)isoquinoline Hydrochloride

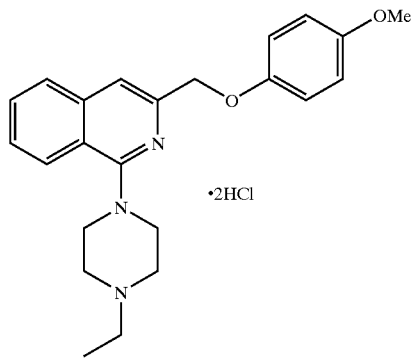

A solution of 4-(4-ethylpiperidin-1-yl)-3-bromoisoquinoline (1.03 g) in tetrahydrofuran (20 ml) was cooled to −78° C., followed by the dropwise addition of 1.7M tert-butyllithium (3 ml). Fifteen minutes later, N,N-dimethylformamide (0.5 ml) was added thereto and the temperature of the reaction solution was raised to room temperature. To the reaction solution was added an aqueous solution of ammonium chloride, and the mixture was extracted with ethyl acetate, followed by washing with water and brine, drying and evaporating. The resulting residue was dissolved in methanol (15 ml), and reacted with sodium borohydride (0.4 g). The solvent was removed, the resulting residue was extracted with ethyl acetate extraction, followed by washing with water and brine, drying and evaporating. The resulting residue was purified by silica gel column chromatography (methylene chloride/methanol system), to give 4-(4-ethylpiperidin-1-yl)-3-hydroxymethylisoquinoline (0.46 g, 52.7%) as a pale yellow oil.

A solution of 4-(4-ethylpiperazin-1-yl)-3-hydroxymethylisoquinoline (0.25 g), 4-methoxyphenol (0.12 g) and triphenylphosphine (0.29 g) in tetrahydrofuran (20 ml) was cooled to −30° C., followed by the dropwise addition of diethyl azodicarboxylate (0.19 g). The temperature of the reaction was raised gradually to room temperature, and the reaction was conducted for further 12 hr. The reaction solution was diluted with ethyl acetate (50 ml) and extracted with a 2N aqueous solution of hydrochloric acid. Then the mixture was basified with a 5N aqueous solution of sodium hydroxide and extracted with ethyl acetate. The ethyl acetate layer was washed with water and brine, dried and evaporated. The resulting residue was purified by silica gel column chromatography (methylene chloride/methanol system), to give the title compound (0.21 g) as a pale yellow oil.

The resulting title compound was converted into a hydrochloride in a conventional manner, to give a yellow powder (0.18 g).

Hydrochloride:
$^1$H-NMR (400 MHz, DMSO-$d_6$); δ (ppm) 1.32 (t, J=7.2 Hz, 3H), 3.16–3.38 (m, 4H), 3.45 (br-t, 2H), 3.59 (br-d, 2H), 3.69 (s, 3H), 3.89 (br-d, 2H), 5.15 (s, 2H), 6.88 (dd, J=8.8, 1.6 Hz, 2H), 7.02 (dd, J=8.8, 1.6 Hz, 2H), 7.57 (s, 1H), 7.62 (br-t, 1H), 7.74 (br-t, 1H), 7.94 (d, J=8.0 Hz, 1H), 8.12 (d, J=8.4 Hz, 1H), m.p.; 101–102° C.
MS(ESI) m/z 378 (M+H)$^+$.

Example 425

Synthesis of 1-(4-ethylpiperazin-1-yl)-3-[4-(2-hydroxyethoxy)-2-methoxyphenyl]isoquinoline

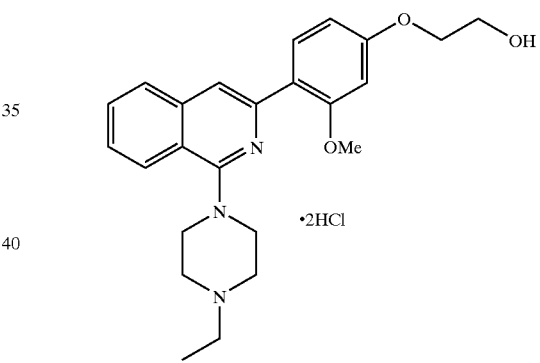

According to Example 36-1, N-methyl-o-toluamide (1.70 g) and 4-(2-benzyloxyethoxy)-2-methoxybenzonitrile (3.30 g) were reacted, to give 3-[4-(2-benzyloxyethoxy)-2-methoxyphenyl]isoquinolin-1-one (0.47 g).

The resulting 3-[4-(2-benzyloxyethoxy)-2-methoxyphenyl]isoquinolin-1-one (0.47 g) was added to phosphorus oxychloride (10 ml), and the mixture was reacted at room temperature overnight. The reaction solution was evaporated, and to the resulting residue were added ethyl acetate and purified water. The ethyl acetate layer was washed with water, an aqueous solution of sodium bicarbonate and brine, and dried over magnesium sulfate. The solvent was evaporated, and the resulting 1-chloro-3-[4-(2-benzyloxyethoxy)-2-methoxyphenyl]isoquinoline was reacted as it was with N-ethylpiperazine (5 ml) in the presence of potassium carbonate (1.2 g) at 120° C. for 24 hr. The reaction solution was evaporated, and to the resulting residue were added ethyl acetate and purified water. The ethyl acetate layer was washed with water and brine, and dried over magnesium sulfate. The solvent was evaporated, and the resulting residue was purified by NH-silica gel column chromatography (ethyl acetate/hexane system), to give 1-(4-ethylpiperazin-1-yl)-3-[4-(2-benzyloxyethoxy)-2-methoxyphenyl]isoquinoline hydrochloride (0.11 g) as a yellow powder.

1-(4-Ethylpiperazin-1-yl)-3-[4-(2-benzyloxyethoxy)-2-methoxyphenyl]isoquinoline hydrochloride (0.10 g) was dissolved in methanol (20 ml), followed by the hydrogenation in the presence of 10% palladium/carbon catalyst (0.03 g) at room temperature for 6 hr. The catalyst was filtered off. The resulting solution was washed with methanol, and then the filtrate was evaporated. The resulting residue was crystallized from ethanol/ether, to give the title compound (0.04 g) as a yellow powder.
Hydrochloride:
$^1$H-NMR (400 MHz, D$_2$O); δ (ppm) 1.37 (t, J=7.2 Hz, 3H), 3.35 (q, J=7.2 Hz, 2H), 3.42–3.60 (m, 2H), 3.70–3.95 (m, 6H), 3.92 (s, 3H), 4.16 (m, 2H), 4.25 (br-d, 2H), 6.70 (s+d, 2H), 7.57 (d, J=8.0 Hz, 1H), 7.66 (s, 1H), 7.72–7.77 (m, 1H), 7.94 (m, 2H), 8.10 (d, J=8.4 Hz, 1H). m.p.; 140–142° c.
MS(FAB) m/z 408 (M+H)$^+$.

Example 426

Synthesis of 1-(4-ethylpiperazin-1-yl)-3-[4-(2-hydroxycyclohexyloxy)phenyl]isoquinoline Hydrochloride

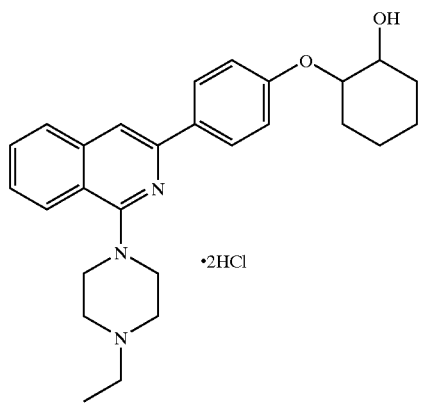

1-(4-Ethylpiperazin-1-yl)-3-(4-hydroxyphenyl)isoquinoline (380 mg) obtained in Example 7 was dissolved in tetrahydrofuran (20 ml), followed by the addition of 60% oily sodium hydride (48 mg) at room temperature. Thirty minutes later, the solvent was removed. To the resulting residue was added cyclohexene oxide (15 ml), and the mixture was reacted at 150° C. for 3 hr. After cooling, the reaction solution was diluted with ethyl acetate and extracted with a 5N aqueous solution of hydrochloric acid. The aqueous layer was basified with a 8N aqueous solution of sodium hydroxide and extracted with ethyl acetate. The organic phase was washed with water and brine, and dried over magnesium sulfate. The solvent was removed, and the resulting residue was purified by NH-silica gel column chromatography (ethyl acetate/hexane system), to give the free compound of the title compound as a pale yellow oil.

The resulting free compound was converted into a hydrochloride in a conventional manner, to give the title compound (240 mg) as a yellow powder.
Hydrochloride:
$^1$H-NMR (400 MHz, DMSO-d$_6$); δ (ppm) 1.23–1.42 (m, 7H), 1.59–1.68 (m, 2H), 1.85–1.94 (m, 1H), 2.00–2.08 (m, 1H), 3.20–3.66 (m, 9H), 3.97 (br-d, 2H), 4.10–4.20 (m, 1H), 7.07 (d, J=8.0 Hz, 2H), 7.52–7.61 (m, 1H), 7.66–7.75 (m, 1H), 7.90–8.14 (m, 5H), 10.82 (m, 1H). m.p.; 143–144° C.
MS(ESI) m/z 432 (M+H)$^+$.

Example 427

Synthesis of 4-(4-ethylpiperazin-1-yl)-2-(4-methoxyphenyl)quinazoline Dihydrochloride

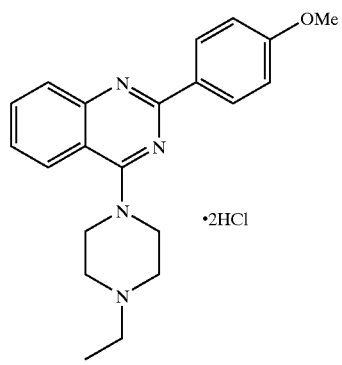

A mixture of 4-(1-ethylpiperazin-4-yl)-2-chloroquinazoline (0.56 g), 4-methoxyphenylboric acid (0.46 g), tetrakistriphenylphosphinepalladium(0) (0.12 g), toluene (50 ml) and a 10% aqueous solution of sodium carbonate (30 ml) was vigorously stirred in nitrogen atmosphere at 100° C. for 1 hr. To the resulting mixture was additionally added 4-methoxyphenylboric acid (0.31 g), and the mixture was further stirred for 2 hr. To the resulting mixture was again added 4-methoxyphenylboric acid (0.31 g), and the mixture was further stirred for 1 hr. To the resulting mixture was further added 4-methoxyphenylboric acid (0.31 g), and the mixture was further stirred overnight. The resulting insoluble matters were filtered off, and then the organic layer was separated and extracted with 2N hydrochloric acid twice, followed by the addition of a 8N aqueous solution of sodium hydroxide to adjust the resulting mixture to pH 10. The resulting mixture was extracted with ethyl acetate twice. The extract was washed with brine and dried over magnesium sulfate. The solvent was evaporated, and the resulting residue was purified by NH silica gel column chromatography (ethyl acetate/n-hexane system), to give 0.58 g of the free compound of the title compound as a pale yellow viscous oil.
Free compound:
$^1$H-NMR (400 MHz, CDCl$_3$); δ (ppm) 1.16 (t, J=7.2 Hz, 3H), 2.53 (q, J=7.2 Hz, 2H), 2.70 (t, J=5.0 Hz, 4H), 3.89 (s, 3H), 3.90 (t, J=5.0 Hz, 4H), 7.00 (d, J=8.8 Hz, 2H), 7.37 (ddd, J=1.2, 8.4, 8.4 Hz, 1H), 7.70 (ddd, J=1.2, 8.4, 8.4 Hz, 1H), 7.88 (dd, J=1.2, 8.4 Hz, 1H), 7.93 (dd, J=1.2, 8.4 Hz, 1H), 8.51 (d, J=8.8 Hz, 2H).

The resulting free compound was converted into a hydrochloride in a conventional manner, and then reprecipitated with ethanol/IPE, to give the title compound as a yellow powder.
Hydrochloride:
m.p.; 224.5–226° C. (decomp.)
$^1$H-NMR (400 MHz, DMSO-d$_6$); δ (ppm) 1.31 (t, J=7.2 Hz, 3H), 3.15–3.21 (m, 2H), 3.24–3.32 (m, 2H), 3.65 (br-d, 2H), 4.03 (br-s, 2H), 4.84 (br-s, 2H), 7.19 (d, J=8.8 Hz, 2H), 7.67 (br-t, 1H), 8.02 (br-t, 1H), 8.20 (br-d, 1H), 8.28 (br-s, 1H), 8.54 (d, J=8.8 Hz, 2H), 11.64 (br-s, 1H).
MS(ESI) m/z 349 (M+H)$^+$.

Example 428

Synthesis of 1-(4-ethylpiperazin-1-yl)-3-(4-methoxyphenyl)-7-azaisoquinoline

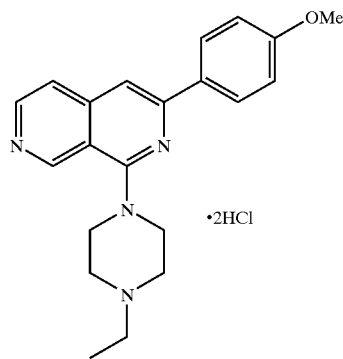

4-Chloro-3-cyanopyridine (1.50 g) and 4-methoxyphenylacetylene (1.60 g) were reacted in the presence of dichlorobistriphenylphosphinepalladium (0.14 g), cuprous iodide (75 mg) and triethylamine (10 ml) in N,N-dimethylformamide (25 ml) in nitrogen atmosphere at 100° C. overnight. The reaction mixture was poured into water (100 ml), and the mixture was extracted with ethyl acetate. The resulting organic layer was washed with water and brine, and dried over magnesium sulfate. The solvent was evaporated, and the resulting residue was purified by silica gel column chromatography (ethyl acetate/hexane system), to give 4-(4-methoxyphenylethynyl)-3-cyanopyridine (2.13 g, 95%) as a pale yellow oil.

4-(4-Methoxyphenylethynyl)-3-cyanopyridine (2.10 g) was reacted in polyphosphoric acid (10 ml) at 120° C. for 15 min. Water (40 ml) was added to the reaction mixture, and then the mixture was adjusted to pH 6.5 by potassium carbonate and extracted with ethyl acetate. The ethyl acetate layer was washed with water and brine, and dried over magnesium sulfate. The solvent was removed, ammonium acetate (10 g) was added to the resulting residue, and the mixture was reacted at 140° C. overnight. After cooling, the reaction solution was diluted with water (100 ml) and extracted with dichloroethane. The resulting organic layer was washed with water and brine, and dried over magnesium sulfate. The solvent was removed, to give 3-(4-methoxyphenyl)-7-aza-2H-dihydroisoquinolin-1-one acetate (1.70 g, 58%).

3-(4-Methoxyphenyl)-7-aza-2H-dihydroisoquinolin-1-one acetate (0.25 g) was reacted with phosphorus oxychloride (10 g) at 100° c. for 4 hr. The mixture was concentrated, followed by the addition of water, neutralization with potassium carbonate and extraction with ethyl acetate. The organic layer was washed with water and brine, and dried over magnesium sulfate. The organic layer was filtered through silica gel and washed with ethyl acetate. The resulting filtrate was concentrated, to give 1-chloro-3-(4-methoxyphenyl)-7-azaisoquinoline (0.12 g). 1-Ethylpiperidine (10 ml) and potassium carbonate (0.5 g) were added thereto, and the mixture was reacted at 80° C. for 6 hr. The reaction mixture was evaporated, and the resulting residue was partitioned between ethyl acetate and water. The ethyl acetate layer was washed with water and brine, and dried over magnesium sulfate. The resulting residue was purified by silica gel column chromatography (ethyl acetate/hexane system), to give the title compound (0.10 g, 65%) as a pale yellow oil.

Free compound:
$^1$H-NMR (400 MHz, CDCl$_3$); δ (ppm) 1.17 (t, J=7.2 Hz, 3H), 2.55 (q, J=7.2 Hz, 2H), 2.75 (m, 4H), 3.70 (m, 4H), 3.88 (s, 3H), 7.01 (d, J=8.0 Hz, 2H), 7.48 (s, 1H), 7.52 (d, J=8.0 Hz, 1H), 8.12 (d, J=8.0 Hz, 2H), 8.54 (d, J=8.0 Hz, 1H), 9.40 (br-d, 1H).

The resulting title compound was converted into a hydrochloride in a conventional manner, to give a yellow powder (0.11 g).

Hydrochloride:
$^1$H-NMR (400 MHz, DMSO-d$_6$); δ (ppm) 1.33 (t, J=7.2 Hz, 3H), 3.15–4.00 (m, 8H), 3.85 (s, 1H), 4.34 (br-d, 2H), 7.13 (d, J=8.4 Hz, 2H), 8.12(s,1H), 8.16(br-d,1H), 8.24(d, J=8.4 Hz,2H), 8.63(m,1H), 9.63(br-s,1H), 11.52(m,1H).
m.p.; 222° C. (decomp.)
MS(ESI) m/z 349(M+H)$^+$.

Example 429

Synthesis of 7-(4-ethylpiperazin-1yl)-5-[2-(3-hydroxypropyl)pyridin-5-yl]thieno[2,3-c]pyridine hydrochloride

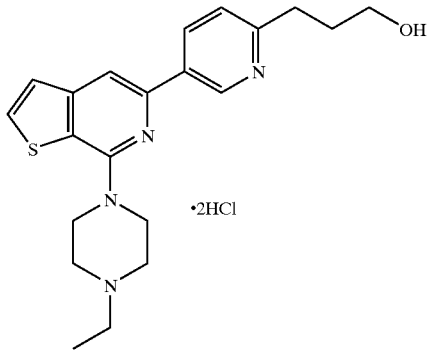

3-Cyanomethyl-2-thiophenecarboxylic acid (7.50 g) was reacted in phosphorus tribromide (40 ml) at 170° C. for 5 hr. The reaction was back to room temperature. Under cooling, water was added to the reaction mixture, followed by the neutralization with potassium carbonate and extraction with ethyl acetate. The organic layer was washed with water and brine, and dried over magnesium sulfate. The resulting residue was purified by silica gel column chromatography (ethyl acetate/hexane system), to give 5,7-dibromothieno[2,3-c]pyridine (2.04 g, 15.5%) as a pale brown solid.

5,7-Dibromothieno[2,3-c]pyridine (2.04 g), 1-ethylpiperidine (0.95 g) and potassium carbonate (2.0 g) were reaacted in N,N-dimethylformamide (15 ml) at 70° C. for 2 hr. The reaction mixture was evaporated, and the resulting residue was partitioned between ethyl acetate and water. The ethyl acetate layer was washed with water and brine, and dried over magnesium sulfate. The resulting residue was purified by silica gel column chromatography (ethyl acetate/methanol system), to give 7-(4-ethylpiperidin-1-yl)-5-bromothieno[2,3-c]pyridine (1.95 g) as a brown oil.

5-Bromo-2-[3-(tert-butyldimethylsilyloxy)propyl]pyridine (3.26 g) and hexabutylditin (5.80 g) were heated in the presence of tetrakistriphenylphosphinepalladium(0) in xylene, to give 2-[3-(tert-butyldimethylsilyloxy)propyl]-5-tributylstannylpyridine (1.80 g).

The resulting compound and 7-(4-ethylpiperidin-1-yl)-5-bromothieno[2,3-c]pyridine (0.54 g) previously were reacted in the presence of tetrakistriphenylphosphinepalladium(0) (0.20 g) in xylene in nitrogen atmosphere for 1 hr. A 2N aqueous solution of hydrochloric acid (30 ml) was added to the reaction solution, and the mixture was stirred for 30 min. Then, the aqueous layer was separated, basified with a 5N aqueous solution of sodium hydroxide, and then back-extracted with ethyl acetate. The ethyl acetate layer was washed with water and brine, dried and evaporated. The resulting residue was purified by silica gel column chromatography (methylene chloride/methanol system), to give the title compound (0.31 g) as a pale yellow oil.

The resulting title compound was converted into a hydrochloride in a conventional manner, to give a yellow powder (0.38 g).

Hydrochloride:

$^1$H-NMR(400 MHz,DMSO-d$_6$); δ (ppm) 1.32(t,J=7.2 Hz,3H), 1.89–1.98(m,2H), 3.08–3.27(m,5H), 3.49(t,J=6.4 Hz,2H), 3.58–3.70(m,4H), 4.48(br-d,2H), 7.62(d,J=5.2 Hz, 1H), 7.99(d,J=8.0 Hz,1H), 8.19(d,J=5.2 Hz,1H), 8.32(s,1H), 8.07(d,J=8.0 Hz,1H), 9.34(br-s,1H), 11.34(m,1H). m.p.; 204–205° C.

MS(ESI) m/z 383(M+H)$^+$.

Example 430

Synthesis of 7-(4-ethylpiperazin-1-yl)-5-[3-(2-hydroxyethoxy)styryl]thieno [2,3-c]pyridine hydrochloride

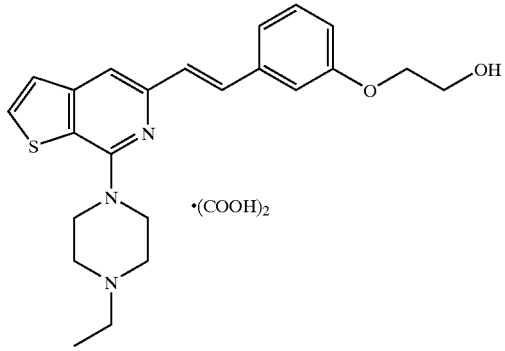

7-(4-Ethylpiperidin-1-yl)-5-bromothieno[2,3-c]pyridine (300 mg) and 3-(2-hydroxyethoxy)styrene (300 mg) were reacted in the presence of palladium acetate (30 mg), tri-o-toluylphosphine (81 mg) and triethylamine (2 ml) in N,N-dimethylformamide (15 ml) in nitrogen atmosphere for 6 hr. After cooling, the reaction solution was diluted with ethyl acetate (200 ml), washed with water and brine, dried and evaporated. The resulting residue was purified by silica gel column chromatography (methylene chloride/methanol system), to give the title compound (100 mg) as a pale yellow oil.

Free compound:

$^1$H-NMR(400 MHz,CDCl$_3$); δ (ppm) 1.16(t,J=7.2 Hz,3H), 2.53(q,J=7.2 Hz,2H), 2.69(m,4H), 3.82(m,4H), 3.98(m,2H), 4.15(m,2H), 7.01(t,J=8.0 Hz,2H), 7.13(d,J=18.0 Hz,1H), 7.22(s,1H), 7.21–7.25(d,1H), 7.29(d,J=5.2 Hz,1H), 7.55(d,J=5.2 Hz,2H), 7.65(br-d,1H), 8.07(d,J=18.0 Hz,1H).

The resulting title compound was converted into an oxalate in a conventional manner, to give a white powder (57 mg).

Oxalate:

$^1$H-NMR(400 MHz,DMSO-d$_6$); δ (ppm) 1.25(br-t,3H), 3.04–3.80(m,10H), 3.76(br-t,2H), 4.06(br-t,2H), 6.86–6.91 (m,1H), 7.19–7.36(m,3H), 7.51(s,1H), 7.54(d,J=5.2 Hz,1H), 7.62(d,J=8.0 Hz,1H), 8.05(d,J=5.2 Hz,1H). m.p.; 98–99° C.

MS(FAB) m/z 410(M+H)$^+$.

Example 431

Synthesis of 7-(4-ethylpiperazin-1-yl)-5-[4-(2-hydroxyethoxy)styryl]thieno[2,3-c]pyridine hydrochloride

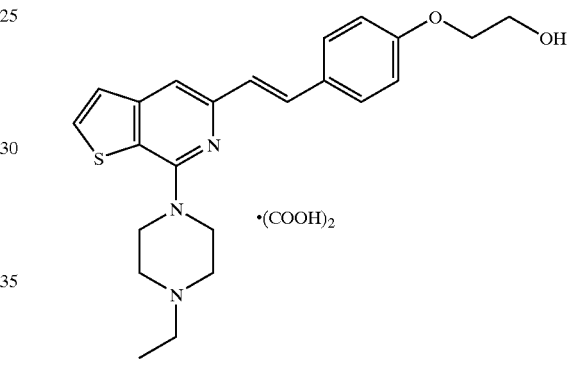

7-(4-Ethylpiperidin-1-yl)-5-bromothieno[2,3-c]pyridine (300 mg) and 4-(2-hydroxyethoxy)styrene (300 mg) were reacted in the presence of palladium acetate (30 mg), tri-o-toluylphosphine (81 mg) and triethylamine (2 ml) in N,N-dimethylformamide (15 ml) in nitrogen atmosphere for 6 hr. After cooling, the reaction solution was diluted with ethyl acetate (200 ml), washed with water and brine, dried and evaporated. The resulting residue was purified by silica gel column chromatography (methylene chloride/methanol system), to give the title compound (120 mg) as a pale yellow oil.

The resulting title compound was converted into an oxalate in a conventional manner, to give a white powder (68 mg).

Oxalate:

$^1$H-NMR(400 MHz,DMSO-d$_6$); δ (ppm) 1.25(br-t,3H), 3.09(br-q,2H), 3.29(m,4H), 3.73(t,J=5.2 Hz), 3.80–3.99(m, 4H), 4.02(t,J=5.2 Hz,1H), 6.97(d,J=8.4 Hz,2H), 7.16(d,J=12 Hz,1H), 7.46(s,1H), 7.51(d,J=5.2 Hz,1H), 7.58(d,J=8.4 Hz,1H), 7.60(d,J=12.0 Hz,1H), 8.03(d,J=5.2 Hz,1H). m.p.; 143–145° C.

MS(ESI) m/z 410(M+H)$^+$.

Example 432

Synthesis of 7-(4-ethylpiperazin-1-yl)-5-[4-(3-hydroxypropyl)phenyl]thieno[2,3-c]pyridine hydrochloride

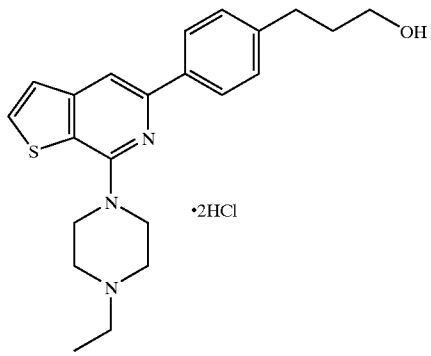

7-(4-Ethylpiperidin-1-yl)-5-bromothieno[2,3-c]pyridine (200 mg) and ethyl 3-(4-tributylstannylphenyl)propionate (400 mg) were reacted in the presence of tetrakistriphenylphosphinepalladium(0) (50 mg) in xylene (10 ml) in nitrogen atmosphere for 5 hr. After cooling, the reaction solution was diluted with ethyl acetate (200 ml) and extracted with a 2N aqueous solution of hydrochloride acid. The resulting solution was basified with a 5N aqueous solution of sodium hydroxide and extracted with ethyl acetate. The ethyl acetate layer was washed with water and brine, dried and evaporated. The resulting residue was purified by silica gel column chromatography (methylene chloride/methanol system), to give 7-(4-ethylpiperazin-1-yl)-5-[4-(ethoxycarbonylethyl)phenyl]thieno[2,3-c]pyridine (0.20 g) as a pale yellow oil.

The resulting compound (0.20 g) was dissolved in tetrahydrofuran (5 ml), and added dropwise into a suspension of lithium aluminum hydride (0.07 g) in tetrahydrofuran (20 ml) at room temperature. The reaction mixture was stirred for 1 hr, followed by the sequential addition of water (0.07 ml), a 5N aqueous solution of sodium hydroxide (0.07 ml) and water (0.21 ml), and the mixture was stirred at room temperature for 1 hr. The resulting precipitates were filtered off, while the resulting filtrate was washed with ethyl acetate. The filtrate was evaporated, and the resulting residue was purified by silica gel column chromatography (methylene chloride/methanol system), to give the title compound as a pale yellow oil (0.12 g).

The resulting title compound was converted into a hydrochloride in a conventional manner, to give a yellow powder (0.10 g).

Hydrochloride:

$^1$H-NMR(400 MHz,DMSO-$d_6$); δ (ppm) 1.31(t,J=7.2 Hz,3H), 1.71–1.80(m,2H), 2.67(t,J=7.2 Hz,2H), 3.14–3.26 (m,4H), 3.44(t,J=7.2 Hz,2H), 3.55(br-t,2H), 3.64(br-d,2H), 4.43(br-d,2H), 7.32(d,J=8.0 Hz,2H), 7.56(d,J=5.6 Hz,1H), 8.01(s,1H), 8.05(d,J=8.0 Hz,2H), 8.07(d,J=5.6 Hz,1H), 10.82(m,1H), m.p.; 112–113° C.

MS(FAB) m/z 382 (M+H)$^+$.

Example 433

Synthesis of 7-(4-ethylpiperazin-1-yl)-5-[4-(3-hydroxypropyl)-3-methoxyphenyl]thieno[2,3-c]-pyridine hydrochloride

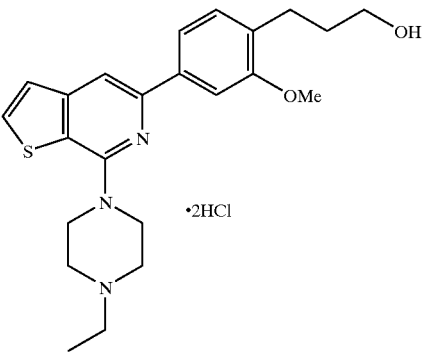

5-Bromo-2-(3-acetoxypropyl)anisole (2.27 g) and hexabutylditin (5.28 g) were heated in the presence of tetrakistriphenylphosphinepalladium(0) in xylene, to give 2-(3-acetoxypropyl)-5-tributylstannylanisole (0.92 g).

The resulting compound and 7-(4-ethylpiperidin-1-yl)-5-bromothieno[2,3-c]pyridine (0.21 g) were reacted in the presence of tetrakistriphenylphosphinepalladium(0) (0.12 g) in xylene in nitrogen atmosphere for 1 hr. The reaction solution was evaporated, and the resulting residue was purified by silica gel column chromatography (methylene chloride/methanol system), to give 7-(4-ethylpiperazin-1-yl)-5-[4-(3-acetoxypropyl)-3-methoxyphenyl]thieno [2,3-c] pyridine (42 mg) as a pale yellow oil.

The resulting compound was dissolved in methanol (15 ml), and reacted with a 2N aqueous solution of sodium hydroxide (5 ml) at room temperature overnight. The reaction solution was concentrated, and the resulting residue was extracted with ethyl acetate. The ethyl acetate layer was washed with water and brine, and dried over magnesium sulfate. The solvent was evaporated, to give the free compound of the title compound.

The resulting free compound was converted into a hydrochloride in a conventional manner, to give 31 mg of the title compound as a yellow powder.

Free compound:

$^1$H-NMR(400 MHz,CDCl$_3$); δ (ppm) 1.17–1.25(m,3H), 1.80–1.92(m,2H), 2.62(m,2H), 2.68–2.84(m,6H), 3.63(m, 2H), 3.83–3.98(m,4H), 3.95(s,3H), 7.22(d,J=8.0 Hz,1H), 7.36(d,J=5.2 Hz,1H), 7.58(m,2H), 7.67(s,2H).

Hydrochloride:

$^1$H-NMR(400 MHz,DMSO-$d_6$); δ (ppm) 1.31(t,J=7.2 Hz,3H), 1.66–1.75(m,2H), 2.62(t,J=7.6 Hz,2H), 3.14–3.25 (m,4H), 3.44(q,J=6.4 Hz,2H), 3.55–3.68(m,4H), 3.91(s,3H), 4.43(br-d,2H), 7.23(d,J=8.0 Hz,1H), 7.57(d,J=5.2 Hz,1H), 7.65(dd,J=8.0,1.6 Hz,1H), 7.69(br-s,1H), 8.06(s,1H), 8.08 (d,J=5.2 Hz,1H), 11.10(m,1H). m.p.; 114–115° C.

MS(FAB) m/z 412(M+H)$^+$.

Example 434

Synthesis of 7-(4-ethylpiperazin-1-yl)-5-[4-(3-hydroxypropoxy)phenyl]thieno[2,3-c]pyridine dihydrochloride

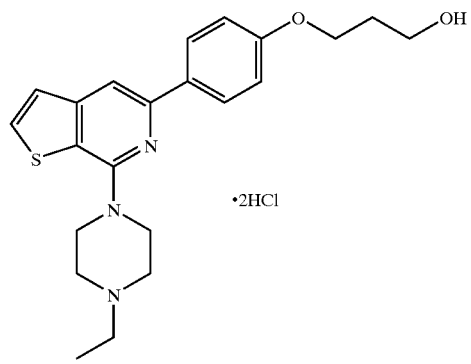

·2HCl

In the same manner as in Example 162-2, 1-[4-(tributylstannyl)phenoxy]-3-(tetrahydropyran-2-YL)oxypropane (1.73 g) was obtained as a colorless oil from 1-(4-bromophenoxy)-3-(tetrahydropyran-2-yloxy)propane (2.08 g) and bis(tributyltin) (3.3 ml).

The resulting compound and 7-(1-ethylpiperazin-4-yl)-5-bromothieno[2,3-c]pyridine (0.29 g) were reacted in the same manner as in Example 300-4, to give a reaction solution containing 7-(4-ethylpiperazin-1-yl)-5-[4-[3-(tetrahydropyran-2-yl)oxypropoxy]phenyl]thieno[2,3-c]pyridine. Ethyl acetate and 2N hydrochloric acid were added to the reaction solution, and the resulting insoluble matters were filtered off. The aqueous layer was separated, while the organic layer was extracted with 2N hydrochloric acid. The aqueous layers were combined and washed with ethyl acetate thrice. The pH of the resulting solution was adjusted to pH 10 by adding a 8N aqueous soluton of sodium hydroxide thereto, and the resulting solution was extracted with ethyl acetate thrice. The extract was washed with brine and dried over magnesium sulfate. The solvent was evaporated, and the resulting residue was purified by NH silica gel column chromatography (ethyl acetate/n-hexane system), to give 0.26 g of the free compound of the title compound as a colorless amorphous.

Free compound:

$^1$H-NMR(400 MHz,CDCl$_3$); δ (ppm) 1.16(t,J=7.2 Hz,3H), 2.09(quintet,J=5.9 Hz,2H), 2.52(q,J=7.2 Hz,2H), 2.69(t,J=5.0 Hz,4H), 3.85(t,J=5.0 Hz,4H), 3.90(t,J=5.9 Hz,2H), 4.20(t,J=5.9 Hz,2H), 6.99(d,J=9.2 Hz,2H), 7.33(d,J=5.6 Hz,1H), 7.55(d,J=5.6 Hz,1H), 7.61(s,1H), 8.04(d,J=9.2 Hz,2H).

The resulting free compound was converted into a hydrochloride in a conventional manner, and then reprecipitated with ethanol/ether, to give the title compound as a pale yellow powder.

Hydrochloride:

m.p.; 126–127° C.

$^1$H-NMR(400 MHz,DMSO-d$_6$); δ (ppm) 1.31(t,J=7.2 Hz,3H), 1.89(quintet,J=6.2 Hz,2H), 3.16–3.23(m,4H), 3.53–3.66(m,4H), 3.58(t,J=6.2 Hz,2H), 4.10(t,J=6.2 Hz,2H), 3.42(br-d,2H), 7.04(d,J=8.8 Hz,2H), 7.54(d,J=5.2 Hz,1H), 7.96(s,1H), 8.05–8.09(m,3H), 10.99(br-s,1H).

MS(FAB) m/z 398(M+H)$^+$.

Example 435

Synthesis of 7-(4-ethylpiperazin-1-yl)-5-[4-(2-hydroxypropoxy)phenyl]thieno[2,3-c]pyridine dihydrochloride.

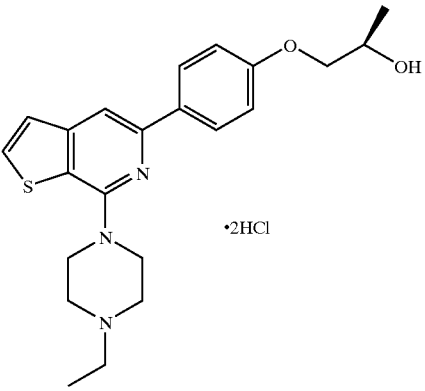

·2HCl

In the same manner as in Example 161-2, 2-(R)-acetoxy-1-[4-(tributylstannyl)phenoxy]propane (1.31 g) was obtained as a colorless oil from 2-(R)-acetoxy-1-(4-bromophenoxy)propane (1.94 g) and bis(tributyltin) (3.6 ml).

The resulting compound and 7-(1-ethylpiperazin-4-yl)-5-bromothieno[2,3-c]pyridine (0.29 g) were reacted in the same manner as in Example 300-4, to give a reaction solution containing 7-(4-ethylpiperazin-1-yl)-5-{4-[2-(R)-acetoxypropoxy]phenyl}thieno[2,3-c]pyridine. Ethyl acetate and 2N hydrochloric acid were added to the reaction solution, and the resulting insoluble matters were filtered off. The aqueous layer was separated, while the organic layer was extracted with 2N hydrochloric acid. The aqueous layers were combined and washed with ethyl acetate twice. The pH of the resulting solution was adjusted to pH 10 by adding a 8N aqueous solution of sodium hydroxide thereto, and subsequently, methanol was added thereto until the reaction solution became homogeneous. The reaction solution was left as it was at room temperature for 45 min. The solvent was evaporated, and then water was added thereto and the mixture was extracted with ethyl acetate thrice. After washing with brine and drying over magnesium sulfate, the solvent was evaporated. The resulting residue was purified by NH silica gel column chromatography (ethyl acetate/n-hexane system), to give 0.22 g of the free compound of the title compound as a colorless viscous oil.

Free compound:

$^1$H-NMR(400 MHz,CDCl$_3$); δ (ppm) 1.16(t,J=7.2 Hz,3H), 1.31(d,J=6.4 Hz,3H), 3.27(br-s1H), 2.52(q,J=7.2 Hz,2H), 2.69(t,J=5.0 Hz,4H), 3.84–3.88(m,5H), 4.01(dd,J=3.2,9.2 Hz,1H), 4.19–4.28(m,1H), 7.00(d,J=8.8 Hz,2H), 7.33(d,J=5.4 Hz,1H), 7.55(d,J=5.4 Hz,1H), 7.62(s,1H), 8.05 (d,J=8.8 Hz,2H).

The resulting free compound was converted into a hydrochloride in a conventional manner, and then reprecipitated with ethanol/ether, to give the title compound as a yellow powder.

Hydrochloride:

m.p.; 126–127° C.

$^1$H-NMR(400 Mhz,DMSO-d$_6$); δ (ppm) 1.18(d,J=6.4 Hz,3H), 1.31(t,J=7.2 Hz,3H), 3.16–3.24(m,2H), 3.55(br-t, 2H), 3.64(br-d,2H), 3.84(dd,J=5.2,9.6 Hz,1H), 3.89(dd,J=6.0,9.6 Hz,1H), 3.95–4.01(m,1H), 4.42(br-d,2H), 7.05(d,J=

8.8 Hz,2H), 7.54(d,J=5.6 Hz,1H), 7.97(s,1H), 8.05–8.09(m, 3H), 10.91(br-s,1H).

MS(FAB) m/z 398(M+H)$^+$.

Example 436

Synthesis of 7-(4-ethylpiperazin-1-yl)-5-[4-(2-hydroxypropyl)phenyl]thieno[2,3-c]pyridine dihydrochloride.

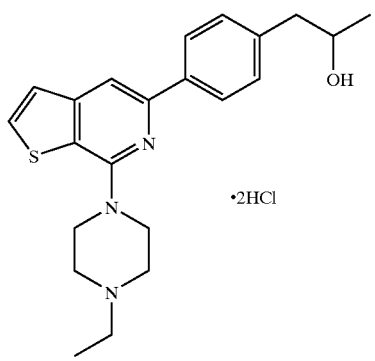

In the same manner as in Example 161-2, 1-[4-(tributylstannyl)phenyl]propan-2-one (1.98 g) was obtained as a colorless oil from 1-(4-bromophenyl)propan-2-one(2.09 g) and bis(tributyltin) (5.0 ml).

The resulting compound and 7-(1-ethylpiperazin-4-yl)-5-bromothieno[2,3-c]pyridine (0.29 g) were reacted in the same manner as in Example 300-4, to give 7-(4-ethylpiperazin-1-yl)-5-[4-(2-oxypropyl)phenyl]thieno[2,3-c]pyridine (0.20 g).

Then, the resulting 7-(4-ethylpiperazin-1-yl)-5-[4-(2-oxopropyl)phenyl]thieno [2,3-c]pyridine (0.20 g) was dissolved in tetrahydrofuran (5 ml). The resulting solution was added to a suspension of lithium aluminum hydride (0.04 g) in tetrahydrofuran (1 ml) under cooling with a cooler of sodium chloride/ice. Further, the resulting mixture was stirred for 15 min. Water (40 ml), a 5N aqueous solution of sodium hydroxide (40 ml) and water (120 ml) were sequentially added to the reaction solution, which was then diluted with ethyl acetate, and the resulting precipitates were filtered off. The solvent was evaporated, and the resulting residue was purified by NH silica gel column chromatography (ethyl acetate/n-hexane system), to give 0.55 g of the free compound of the title compound as a colorless viscous oil.

Free compound:

$^1$H-NMR(400 MHz,CDCl$_3$); δ (ppm) 1.16(t,J=7.2 Hz,3H), 1.27(d,J=6.0 Hz,3H), 2.52(q,J=7.2 Hz,2H), 2.68(t, J=5.0 Hz,4H), 2.75(dd,J=8.0,13.6 Hz,1H), 2.84(dd,J=4.0, 13.6 Hz,1H), 3.85(t,J=5.0 Hz,4H), 4.02–4.10(m,1H), 7.30 (d,J=8.4 Hz,2H), 7.33(d,J=5.6 Hz,1H), 7.55(d,J=5.6 Hz,1H), 7.65(s,1H), 8.04(d,J=8.4 Hz,2H).

The resulting free compound was converted into a hydrochloride in a conventional manner, and then reprecipitated with ethanol/ether, to give the titled compound as a pale yellow powder.

Hydrochloride:

m.p.; 66–67° C.

$^1$H-NMR(400 MHz,DMSO-d$_6$); δ (ppm) 1.06(d,J=6.4 Hz,3H), 1.03(t,J=7.2 Hz,3H), 2.62(dd,J=6.4,13.2 Hz,1H), 2.75(dd,J=6.8,13.2 Hz,1H), 3.17–3.23(m,2H), 3.55(br-t, 2H), 3.64(br-d,2H), 3.83–3.91(m,1H), 4.43(br-d,2H), 7.31 (d,J=8.2 Hz,2H), 7.56(d,J=5.2 Hz,1H), 8.01(s,1H), 8.04(d, J=8.2 Hz,2H), 8.07(d,J=5.2 Hz,1H), 10.79(br-s,1H).

MS(FAB) m/z 382(M+H)$^+$.

Example 437

Synthesis of 7-(4-ethylpiperazin-1-yl)-5-[3-chloro-4-(2-hydroxyethoxy)phenyl]thieno[2,3-c]pyridine

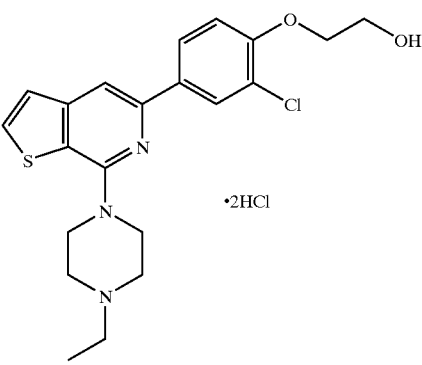

In the same manner as in Example 161-2, 2-acetoxy-1-[2-chloro-4-(tributylstannyl)phenoxy]ethane (0.58 g) was obtained as a colorless oil from 2-acetoxy-1-(4-bromo-2-chlorophenoxy)ethane (1.32 g) and bis(tributyltin) (2.3 ml).

The resulting compound and 7-(1-ethylpiperazin-4-yl)-5-bromothieno[2,3-c]pyridine (0.19 g) were reacted in the same manner as in Example 300-4, to give a reaction solution containing 7-(4-ethylpiperazin-1-yl)-5-[4-(2-acetoxyethoxy)-3-chlorophenyl]thieno[2,3-c]pyridine. Ethyl acetate and 2N hydrochloric acid were added to the reaction solution, and the resulting insoluble matters were filtered off. The aqueous layer was separated, while the organic layer was extracted with 2N hydrochloric acid. The resulting aqueous layers were combined and washed with ethyl acetate twice. The pH of the resulting solution was adjusted to pH 10 by adding a 8N aqueous solution of sodium hydroxide, and then the solution was extracted with ethyl acetate twice. The extract was washed with brine, dried over magnesium sulfate, and the solvent was evaporated. Methanol (6 ml) was added to the resulting residue and dissolved, followed by the addition of a 8N aqueous solution of sodium hydroxide (0.75 ml). The resulting mixture was left as it was at room temperature for 45 min, and then the solvent was evaporated. Water was added to the resulting residue, and then the mixture was extracted with ethyl acetate thrice. The extract was washed with brine, dried over magnesium sulfate, and the solvent was evaporated. The resulting residue was purified by NH silica gel column chromatography (ethyl acetate/n-hexane system), to give the title compound (0.03 g) as a colorless viscous oil.

Free compound:

$^1$H-NMR(400 MHz,CDCl$_3$); δ (ppm) 1.17(t,J=7.2 Hz,3H), 2.52(q,J=7.2 Hz,2H), 2.69(t,J=4.8 Hz,4H), 3.85(t, J=4.8 Hz,4H), 4.30(t,J=4.8 Hz,2H), 4.50(t,J=4.8 Hz,2H), 7.01(d,J=8.4 Hz,1H), 7.34(d,J=5.6 Hz,1H), 7.57(d,J=5.6 Hz,1H), 7.60(s,1H), 7.95(dd,J=2.4,8.4 Hz,1H), 8.13(d,J=2.4 Hz,1H).

MS(FAB) m/z 418, 420(M+H)$^+$.

Example 438

Synthesis of 7-(4-ethylpiperazin-1-yl)-5-[4-(1-methyl-2-hydroxyethoxy)phenyl]thieno[2,3-c]pyridine dihydrochloride

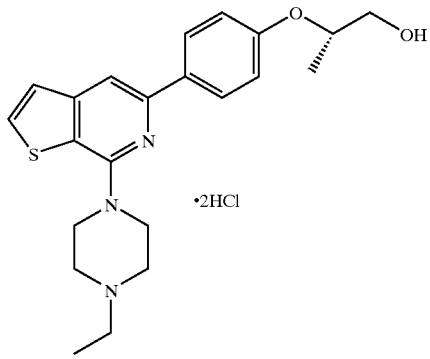

In the same manner as in Example 161-2, 1-(S)-acetoxy-2-[4-(tributylstannyl)phenoxy]propane (1.12 g) was obtained as a colorless oil from 1-(S)-acetoxy-2-(4-bromophenoxy)propane (1.61 g) and bis(tributyltin) (3.0 ml).

The resulting compound and 7-(1-ethylpiperazin-4-yl)-5-bromothieno[2,3-c]pyridine (0.19 g) were reacted in the same manner as in Example 300-4, to give a reaction solution containing 7-(4-ethylpiperazin-1-yl)-5-[4-(S)-(1-acetoxypropan-2-yl)oxyphenyl]thieno[2,3-c]pyridine. Ethyl acetate and 2N hydrochloric acid were added to the reaction solution and dissolved, and the resulting insoluble matters were filtered off. The aqueous layer was separated, while the organic layer was extracted with 2N hydrochloric acid. The resulting aqueous layers were combined and washed with ethyl acetate twice. The pH of the resulting solution was adjusted to pH 10 by adding a 8N aqueous solution of sodium hydroxide thereto, and the solution was extracted with ethyl acetate twice. The extract was washed with brine, dried over magnesium sulfate, and the solvent was evaporated. To the resulting residue was added methanol (6 ml) and dissolved, followed by the addition of a 8N aqueous solution of sodium hydroxide (1.48 ml). The resulting solution was left as it was at room temperature for 2 hr, and then the solvent was evaporated. Water was added to the residue, and the mixture was extracted with ethyl acetate thrice. Then, it was washed with brine, dried and the solvent was evaporated. The resulting residue was purified by NH silica gel column chromatography (ethyl acetate/n-hexane system), to give 0.15 g of the free compound of the title compound as a colorless viscous oil).

Free compound:
$^1$H-NMR(400 MHz,CDCl$_3$); δ (ppm) 1.16(t,J=7.2 Hz,3H), 1.31(d,J=6.4 Hz,3H), 2.37(br-s,1H), 2.52(q,J=7.2 Hz,2H), 2.69(t,J=5.0 Hz,4H), 3.84–3.88(m,5H), 4.01(dd,J=3.2,9.2 Hz,1H), 4.19–4.28(m,1H), 7.00(d,J=8.8 Hz,2H), 7.33(d,J=5.4 Hz,1H), 7.55(d,J=5.4 Hz,1H), 7.62(s,1H), 8.05(d,J=8.8 Hz,2H).

The resulting free compound was converted into a hydrochloride in a conventional manner, and then reprecipitated with ethanol/ether, to give the title compound as a yellow powder.

Hydrochloride:
m.p.; 126–127° C.
$^1$H-NMR(400 MHz,DMSO-d$_6$); δ (ppm) 1.18(d,J=6.4 Hz,3H), 1.31(t,J=7.2 Hz,3H), 3.16–3.24(m,2H), 3.55(br-t, 2H), 3.64(br-d,2H), 3.84(dd,J=5.2,9.6 Hz,1H), 3.89(dd,J=6.0,9.6 Hz,1H), 3.95–4.01(m,1H), 4.42(br-d,2H), 7.05(d,J=8.8 Hz,2H), 7.54(d,J=5.6 Hz,1H), 7.97(s,1H), 8.05–8.09(m,3H), 10.91(br-s,1H).
MS(FAB) m/z 398(M+H)$^+$.

Example 439

Synthesis of 7-(4-ethylpiperazin-1-yl)-5-[4-(3-hydroxy-3-methylbutyl)phenyl]thieno[2,3-c]pyridine dihydrochloride

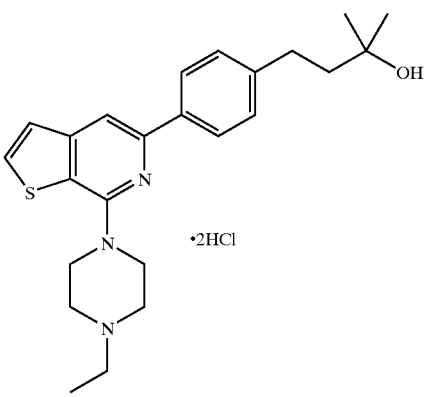

In the same manner as in Example 161-2, 4-[4-(tributylstannyl)phenyl]butan-2-one (1.61 g) was obtained as a colorless oil from 4-(4-bromophenyl)butan-2-one (1.36 g) and bis(tributyltin) (3.0 ml).

The resulting compound and 7-(1-ethylpiperazin-4-yl)-5-bromothieno[2,3-c]pyridine (0.33 g) were reacted in the same manner as in Example 300-4, to give 7-(4-ethylpiperazin-1-yl)-5-[4-(3-oxobutyl)phenyl]thieno[2,3-c]pyridine (0.23 g).

The resulting 7-(4-ethylpiperazin-1-yl)-5-[4-(3-oxobutyl)phenyl]thieno[2,3-c]pyridine (0.23 g) was dissolved in tetrahydrofuran (10 ml), and the resulting mixture was stirred under ice cooling. To the resulting mixture was added 3.0M methylmagnesium bromide/ether solution (0.39 ml), and the mixture was further stirred for 3 hr. Then, 3.0 M methylmagnesium bromide/ether solution (0.39 ml) was further added thereto, and the mixture was further stirred for 4.5 hr. Then, an aqueous solution of saturated ammonium chloride and ethyl acetate were added to the mixture, and the mixture was stirred. The organic layer was separated, and then it was washed with brine and dried over magnesium sulfate. The solvent was evaporated, and the resulting residue was purified by NH silica gel column chromatography (ethyl acetate/n-hexane system), to give 0.10 g of the free compound of the title compound as a colorless viscous oil.

Free compound:
$^1$H-NMR(400 MHz,CDCl$_3$); δ (ppm) 1.16(t,J=7.2 Hz,3H), 1.31(s,6H), 1.81–1.86(m,2H), 2.52(q,J=7.2 Hz,2H), 2.69(t,J=5.0 Hz,4H), 2.74–2.78(m,2H), 3.85(t,J=5.0 Hz,4H), 7.29(d,J=8.4 Hz,2H), 7.33(d,J=5.4 Hz,1H), 7.55(d,J=5.4 Hz,1H), 7.65(s,1H), 8.02(d,J=8.4 Hz,2H).

The resulting free compound was converted into a hydrochloride in a conventional manner, and then reprecipitated with ethanol/ether, to give the title compound as a yellow powder.

Hydrochloride:
m.p.; 122–133.5° C.
$^1$H-NMR(400 MHz,DMSO-d$_6$); δ (ppm) 1.17(s,6H), 1.32 (t,J=7.2 Hz,3H), 1.65–1.70(m,2H), 2.65–2.70(m,2H), 3.15–3.24(m,4H), 3.57–3.65(m,4H), 4.42(br-d,2H), 7.31(d, J=8.0 Hz,2H), 7.56(d,J=5.4 Hz,1H), 8.00(s,1H), 8.04(d,J= 8.0 Hz,2H), 8.08(d,J=5.4 Hz,1H), 11.28(br-s,1H).
MS(FAB) m/z 410(M+H)⁺.

Example 440

Synthesis of 7-(4-ethylpiperazin-1-yl)-5-[4-(3-hydroxybutyl)phenyl]thieno[2,3-c]pyridine dihydrochloride.

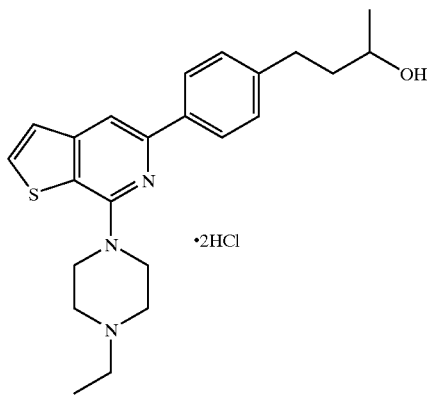

In the same manner as in Example 161-2, 4-[4-(tributylstannyl)phenyl]butan-2-one (1.59 g) was obtained as a colorless oil from 4-(4-bromophenyl)butan-2-one (1.29 g) and bis(tributyltin) (2.9 ml).

The resulting compound and 7-(1-ethylpiperazin-4-yl)-5-bromothieno[2,3-c]pyridine (0.22 g) were reacted in the same manner as in Example 300-4, to give 7-(4-ethylpiperazin-1-yl)-5-[4-(3-oxobutyl)phenyl]thieno[2,3-c]pyridine.

The resulting 7-(4-ethylpiperazin-1-yl)-5-[4-(3-oxobutyl)phenyl]thieno[2,3-c]pyridine was dissolved in tetrahydrofuran (5 ml). The resulting solution was added to a suspension of lithium aluminum hydride (0.04 g) in tetrahydrofuran (1 ml) under ice-cooling, and the mixture was further stirred for 15 min. Water (40 ml), a 5N aqueous solution of solution hydroxide (40 ml) and water (120 ml) were sequentially added to the reaction solution. then, the resulting mixture was diluted with ethyl acetate, and the resulting precipitates were filtered off. The solvent was evaporated, and the resulting residue was purified by NH silica gel column chromatography (ethyl acetate/n-hexane-system), to give 0.18 g of the free compound of the title compound as a colorless viscous oil.
Free compound:
¹H-NMR(400 MHz,CDCl₃); δ (ppm) 1.16(t,J=7.2 Hz,3H), 1.25(d,J=3.2 Hz), 1.78–1.85(m,2H), 2.52(q,J=7.2 Hz,2H), 2.69(t,J=5.0 Hz,4H), 2.65–2.8(m,2H), 3.84–3.89 (m,5H), 7.29(d,J=8.4 Hz,2H), 7.34(d,J=5.4 Hz,1H), 7.56(d, J=5.4 Hz,1H), a7.66(s,1H), 8.02(d,J=8.4 Hz,2H).

The resulting free compound was converted into a hydrochloride in a conventional manner, and then reprecipitated with ethanol/ether, to give the title compound as a yellow powder.
Hydrochloride:
m.p.; 110.5–112° C.
¹H-NMR(400 MHz,DMSO-d₆); δ (ppm) 1.10(d,J=6.0 Hz,3H), 1.31(t,J=7.2 Hz,3H), 1.62–1.68(m,2H), 2.60–2.76 (m,2H), 3.15–3.23(m,4H), 3.57–3.65(m,4H), 4.42(br-d,2H), 7.31(d,J=8.4 Hz,2H), 7.56(d,J=5.4 Hz,1H), 8.00(s,1H), 8.04 (d,J=8.0 Hz,2H), 8.08(d,J=5.4 Hz,1H), 11.26(br-s,1H).
MS(FAB) m/z 396(M+H)⁺.

Example 441

Synthesis of 7-(4-ethylpiperazin-1-yl)-5-[4-(3-hydroxy-2-methylpropyl)phenyl]thieno[2,3-c] pyridine dihydrochloride

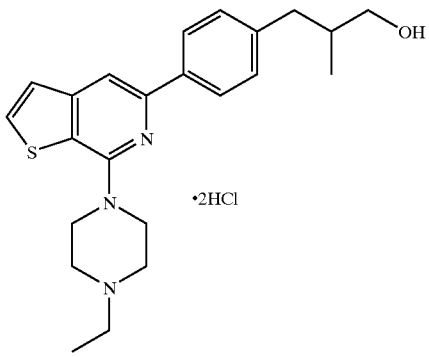

In the same manner as in Example 161-2, methyl 2-methyl-3-[4-tributylstannyl)phenyl]propionate (1.52 g) was obtained as a colorless oil from methyl 3-(4-bromophenyl)-2-methylpropionate (1.36 g) and bis (tributyltin) (2.7 ml).

The resulting compound and 7-(1-ethylpiperazin-4-yl)-5-bromothieno[2,3-c]pyridine (0.22 g) were reacted in the same manner as in Example 300-4, to give 7-(4-ethylpiperazin-1-yl)-5-[4-(2-methoxycarbonylpropyl) phenyl]thieno[2,3-c]pyridine.

The resulting 7-(4-ethylpiperazin-1-yl)-5-[4-(2-methoxycarbonylpropyl)phenyl]thieno[2,3-c]pyridine was dissolved in tetrahydrofuran (5 ml). The resulting solution was added to a suspension of lithium aluminum hydride (0.05 g) in tetrahydrofuran (0.5 ml) under ice-cooling, and the mixture was further stirred for 20 min. Water (50 ml), a 5N aqueous solution of sodium hydroxide (50 ml) and water (150 ml) were sequentially added thereto. The resulting mixture was then diluted with ethyl acetate, and the resulting precipitates were filtered off. The solvent was evaporated, and the resulting residue was purified by NH silica gel column chromatography (ethyl acetate/n-hexane system), to give 0.17 g of the free compound of the titled compound as a colorless viscous oil.
Free compound:
¹H-NMR(400 MHz,CDCl₃); δ (ppm) 0.94(d,J=6.8 Hz,3H), 1.16(t,J=7.2 Hz,3H), 1.93–2.02(m,1H), 2.46(dd,J= 8.2,13.6 Hz,1H), 2.51(q,J=7.2 Hz,2H), 2.68(t,J=5.0 Hz,4H), 2.81(dd,J=6.0,13.6 Hz,1H), 3.49(dd,J=6.0,10.4 Hz,1H), 3.55(dd,J=6.0,10.4 Hz,1H), 3.85(t,J=5.0 Hz,4H), 7.25(d,J= 8.4 Hz,2H), 7.32(d,J=5.6 Hz,1H), 7.54(d,J=5.6 Hz,1H), 7.65 (s,1H), 8.01(d,J=8.4 Hz,2H).

The resulting free compound was converted into a hydrochloride in a conventional manner, and then reprecipitated with ethanol/ether, to give the title compound as a yellow powder.
Hydrochloride:
m.p.; 108–110° C.
¹H-NMR(400 MHz,DMSO-d₆); δ (ppm) 0.82(d,J=6.8 Hz,3H), 1.32(t,J=7.2 Hz,3H), 1.79–1.88(m,1H), 2.35(dd,J= 8.2,13.2 Hz,1H), 2.78(dd,J=5.6,13.2 Hz,1H), 3.15–3.24(m, 4H), 3.26(dd,J=6.2,10.4 Hz,1H), 3.31(dd,J=6.0,10.4

Hz,1H), 3.62(br-t,4H), 4.42(br-d,2H), 7.29(d,J=8.0 Hz,2H), 7.57(d,J=5.4 Hz,1H), 8.01(s,1H), 8.05(d,J=8.4 Hz,1H), 8.08 (d,J=5.4 Hz,1H), 11.28(br-s,1H).
MS(FAB) m/z 396 (M+H)$^+$.

Example 442

Synthesis of 7-(4-ethylpiperazin-1-yl)-5-[4-(3-hydroxy-2,2-dimethylpropyl)phenyl]thieno[2,3-c]pyridine dihydrochloride

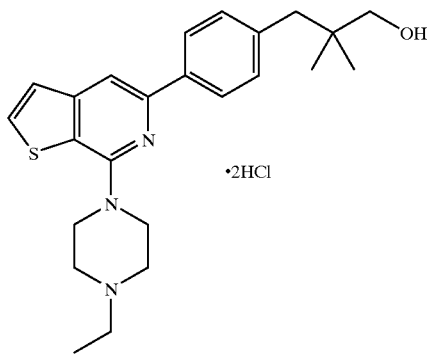

In the same manner as in Example 161-2, methyl 2,2-dimethyl-3-[4-(tributylstannyl)phenyl]propionate (1.51 g) was obtained as a colorless oil from methyl 3-(4-bromophenyl)-2,2-dimethylpropionate (1.29 g) and bis (tributyltin) (2.4 ml).

The resulting compound and 7-(1-ethylpiperazin-4-yl)-5-bromothieno[2,3-c]pyridine (0.23 g) were reacted in the same manner as in Example 300-4, to give 7-(4-ethylpiperazin-1-yl)-5-[4-(2-methoxycarbonyl-2-methylpropyl)phenyl]thieno[2,3-c]pyridine.

The resulting 7-(4-ethylpiperazin-1-yl)-5-[4-(2-methoxycarbonylpropyl)phenyl]thieno[2,3-c]pyridine was dissolved in tetrahydrofuran (5 ml). The resulting solution was added to a suspension of lithium aluminum hydride (0.05 g) in tetrahydrofuran (1 ml) under ice-cooling, and the mixture was further stirred from 30 min. Water (50 ml), a 5N aqueous solution of sodium hydroxide (50 ml) and water (150 ml) were sequentially added thereto. The resulting mixture was then diluted with ethyl acetate, and the resulting precipitates were filtered off. The solvent was evaporated, and the resulting residue was purified by NH silica gel column chromatography (ethyl acetate/n-hexane system), to give 0.22 g of the title compound as a colorless viscous oil.
Free compound:
$^1$H-NMR(400 MHz,CDCl$_3$); δ (ppm) 0.91(s,6H), 1.16(t, J=7.2 Hz,3H), 1.93(br-s,1H), 2.51(q,J=7.2 Hz,2H), 2.62(s, 2H), 2.68(t,J=5.0 Hz,4H), 3.34(s,2H), 3.85(t,J=5.0 Hz,4H), 7.24(d,J=8.2 Hz,2H), 7.32(d,J=5.4 Hz,1H), 7.54(d,J=5.4 Hz,1H), 7.66(s,1H), 8.01(d,J=8.2 Hz,2H).

The resulting free compound was converted into a hydrochloride in a conventional manner, and then reprecipitated with ethanol/ether, to give the title compound as a yellow powder.
Hydrochloride:
m.p.; 113–114° C.
$^1$H-NMR(400 MHz,DMSO-d$_6$); δ (ppm) 0.81(s,6H), 1.32 (t,J=7.2 Hz,3H), 1.92(s,2H), 3.12(s,2H), 3.15–3.24(m,4H), 3.62–368(m,4H), 4.43(br-d,2H), 7.27(d,J=8.2 Hz,2H), 7.57 (d,J=5.4 Hz,1H), 8.02(s,1H), 8.04(d,J=8.2 Hz,2H), 8.09(d, J=5.4 Hz,1H), 11.49(br-s,1H).
MS(FAB) m/z 410(M+H)$^+$.

Example 443

Synthesis of 7-(4-ethylpiperazin-1-yl)-5-[4-(3-hydroxy-1,1-dimethylpropyl)phenyl]thieno[2,3-c]pyridine dihydrochloride

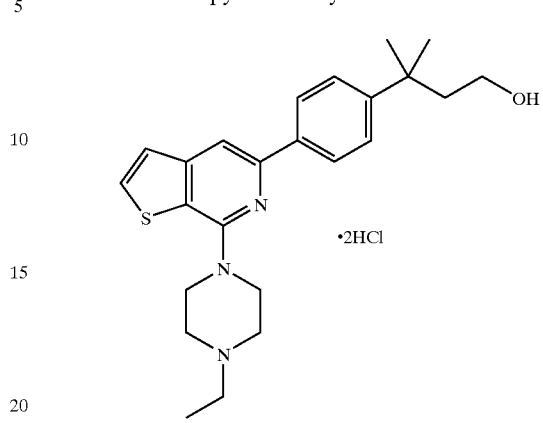

In the same manner as in Example 161-2, 3-acetoxy-1,1-dimethyl-1-[4-(tributylstannyl)phenoxy]propane (1.36 g) was obtained as a colorless oil from 1-acetoxy-3-(4-bromophenoxy)-3-methylbutane (1.34 g) and bis(tributyltin) (2.4 ml).

The resulting compound and 7-(1-ethylpiperazin-4-yl)-5-bromothieno[2,3-c]pyridine (0.20 g) were reacted in the same manner as in Example 300-4, to give a reaction solution containing 7-(4-ethylpiperazin-1yl)-5-[4-(3-acetoxy-1,1-dimethylpropyl)phenyl]thieno[2,3-c]pyridine. Ethyl acetate and 2N hydrochloric acid were added to the reaction solution, and the resulting insoluble matters were filtered off. The aqueous layer was separated, while the organic layer was extracted with 2N hydrochloride acid. The aqueous layers were combined and washed with ethyl acetate twice. The pH of the resulting solution was adjusted to pH 10 by adding a 8N aqueous solution of sodium hydroxide thereto, and the solution was extracted with ethyl acetate twice. The extract was washed with brine, dried over magnesium sulfate, and the solvent was evaporated. Methanol (10 ml) was added to the resulting residue and dissolved, followed by the addition of a 8N aqueous solution of sodium hydroxide (0.75 ml). The resulting solution was left as it was at room temperature for 2 hr, and then the solvent was evaporated. Water was added to the resulting residue, and then the mixture was extracted with ethyl acetate thrice. The extract was washed with brine, dried over magnesium sulfate, and the solvent was evaporated. The resulting residue was purified by NH silica gel column chromatography (ethyl acetate/n-hexane system), to give 0.16 g of the free compound of the title compound as a colorless viscous oil.
Free compound:
$^1$H-NMR(400 MHz,CDCl$_3$); δ (ppm) 1.15(t,J=7.2 Hz,3H), 1.38(s,6H), 1.98(t,J=7.6 Hz,2H), 2.50(q,J=7.2 Hz,2H), 2.67(t,J=5.0 Hz,2H), 3.51(t,J=7.6 Hz,2H), 3.84(t, J=5.0 Hz,4H), 7.32(d,J=5.4 Hz, 1H), 7.43(d,J=8.4 Hz,2H), 7.53(d,J=5.4 Hz,1H), 7.64(s,1H), 8.03(d,J=8.4 Hz,2H).

The resulting free compound was converted into a hydrochloride in a conventional manner, and then reprecipitated with ethanol/IPE, to give the title compound as a yellow powder.
Hydrochloride:
m.p.; 125.5–127.5° C.
$^1$H-NMR(400 MHz,DMSO-d$_6$); δ (ppm)1.30(t,J=7.2 Hz,3H), 1.32(s,6H), 1.85(t,J=7.8 Hz,2H), 3.15–3.25(m,2H), 3.57(br-t,2H), 3.64(br-d,2H), 4.44(br-d,2H), 7.46(d,J=8.4 Hz,2H), 7.57(d,J=5.4 Hz,1H), 8.01(s,1H), 8.06(d,J=8.4 Hz,2H), 8.08(d,J=5.4 Hz,1H), 10.89(br-s,1H).
MS(FAB) m/z 410(M+H)+.

Example 444

Synthesis of 7-(4-ethylpiperazin-1-yl)-5-[4-(2-hydroxypropylthio)phenyl]thieno[2,3-c]pyridine dihydrochloride

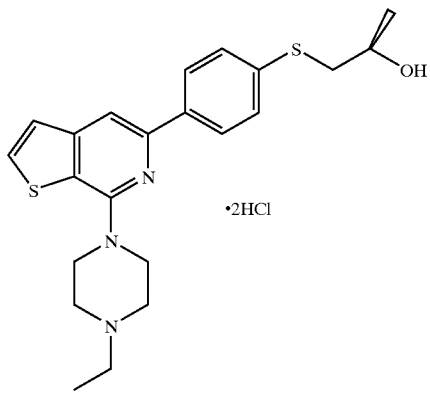

In the manner as in Example 161-2, (R)-2-acetoxy-1-[4-(tributylstannyl)phenylthio]propane (0.79 g) was obtained as a colorless oil from (R)-2-acetoxy-1-(4-bromophenylthio)propane (1.14 g) and bis(tributyltin) (2.2 ml).

The resulting compound and 7-(1-ethylpiperazin-4-yl)-5-bromothieno[2,3-c]pyridine (0.20 g) were reacted in the same manner as in Example 300-4, to give a reaction solution containing 7-(4-ethylpiperazin-1-yl)-5-[4-(R)-2-acetoxypropylthio]phenyl]thieno[2,3-c]pyridine. Ethyl acetate and 2N hydrochloric acid were added to the reaction solution, and the resulting insoluble matters were filtered off. The aqueous layer was separated, while the organic layer was extracted with 2N hydrochloric acid. The aqueous layer were combined and washed with ethyl acetate twice. The pH of the resulting solution was adjusted to pH 10 by adding a 8N aqueous solution of sodium hydroxide thereto, and the resulting solution was extracted with ethyl acetate twice. The extract was washed with brine, dried over magnesium sulfate, and the solvent was evaporated. Methanol (10 ml) was added to the resulting residue and dissolved, followed by the addition of a 8N aqueous solution of sodium hydroxide (0.74 ml). The resulting solution was left as it was at room temperature for 2 hr, and then the solvent was evaporated. Water was added to the resulting residue, and then the resulting mixture was extracted with ethyl acetate thrice. The resulting extract was washed with brine, dried over magnesium sulfate, and the solvent was evaporated. The resulting residue was purified by NH silica gel column chromatography (ethyl acetate/n-hexane system), to give 0.14 g of the free compound of the title compound as a colorless viscous oil.
Free compound:
$^1$H-NMR(400 MHz,CDCl$_3$); δ (ppm) 1.16(t,J=7.2 Hz,3H), 1.29(d,J=6.4 Hz,3H), 2.51(q,J=7.2 Hz,2H), 2.68(t, J=5.0 Hz,4H), 2.89(dd,J=8.6,13.6 Hz,1H), 3.15(dd,J=3.6, 13.6 Hz,1H), 7.46(d,J=8.4 Hz,2H), 7.56(d,J=5.4 Hz,1H), 7.64(s,1H), 8.03(d,J=8.4 Hz,2H).

The resulting free compound was converted into a hydrochloride in a conventional manner, and then reprepitated with ethanol/IPE, to give the title compound as a yellow powder.

Hydrochloride:
m.p.; 98.5–99.5° C.
$^1$H-NMR(400 MHz,DMSO-d$_6$); δ (ppm) 0.19(d,J=6.0 Hz,3H), 1.30(T,J=7.2 Hz,3H), 2.97(dd,J=6.2,13.2 Hz,1H), 3.08(dd,J=6.0,13.2 Hz,1H), 3.16–3.23(m,4H), 3.56(br-t, 2H), 3.64(br-d,2H), 4.43(br-d,2H), 7.43(d,J=8.8 Hz,2H), 7.56(d,J=5.2 Hz,1H), 8.03(s,1H), 8.06–8.09(m,3H), 10.87 (br-s,1H).
MS(ESI) m/z 414(M+H)+.

Example 445

Synthesis of 7-(4-ethylpiperazin-1-yl)-5-(4-methanesulfonylphenyl)thieno)[2,3-c]pyridine dihydrochloride

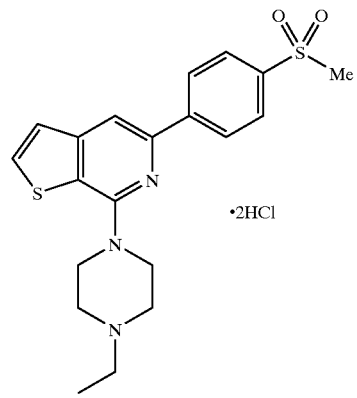

In the same manner as in Example 161-2, 1-methanesulfonyl-4-(tributylstannyl)benzene (0.58 g) was obtained as a colorless oil from 4-methanesulfonylbromobenzene (1.50 g) and bis (tributyltin) (3.6 ml).

The resulting compound and 7-(1-ethylpiperazin-4-yl)-5-bromothieno[2,3-c]pyridine (0.18 g) were reacted in the same manner as in Example 300-4, to give a reaction solution containing 7-(4-ethylpiperazin-1-yl)-5-(4-methanesulfonylphenyl)thieno[2,3-c]pyridine. Ethyl acetate and 2N hydrochloride acid were added to the reaction solution, and the resulting insoluble matters were filtered off. The aqueous layer was separated, while the organic layer was extracted with 2N hydrochloric acid. The aqueous layers were combined and washed with ethyl acetate. The pH of the resulting solution was adjusted to pH 10 by adding a 8N aqueous solution of sodium hydroxide thereto, and the resulting solution was extracted with ethyl acetate twice. After washing with brine and drying over magnesium sulfate, the solvent was evaporated. The resulting residue was purified by NH silica gel column chromatography (ethyl acetate/n-hexane system), to give 0.19 g of the free compound of the title compound as a pale brown viscous oil.
Free compound:
$^1$H-NMR(400 MHz,CDCl$_3$); δ (ppm) 1.17(t,J=7.2 Hz,3H), 2.53(q,=J=7.2 Hz,2H), 2.71(t,J=5.0 Hz,4H), 3.10(s, 3H), 3.88(t,J=5.0 Hz,4H), 7.40(d,J=5.2 Hz,1H), 7.64(d,J= 5.2 Hz,1H), 7.75(s,1H), 8.02(d,J=8.4 Hz,2H), 8.29(d,J=8.4 Hz,2H).

The resulting free compound was converted into a hydrochloride in a conventional manner, and then reprepitated with ethanol/IPE, to give the title compound as a yellow powder.

Hydrochloride:
m.p.; 222.5–225° C. (decomp.)
$^1$H-NMR(400 MHz,DMSO-d$_6$); δ (ppm) 1.30(t,J=7.2 Hz,3H), 3.18–3.28(m,4H), 3.28(s,3H), 3.55(br-t,2H), 3.66(br-d,2H), 4.48(br-d,2H), 7.62(d,J=5.4 hz,1H), 8.03(d,=J=8.4 Hz,2H), 8.15(d,J=5.4 Hz,1H), 8.21(s,1H), 8.40(d,J=8.4 Hz,2H), 10.59(br-s,1H).
MS(FAB) m/z 402(M+H)$^+$.

Example 446

Synthesis of 7-(4-ethylpiperazin-1-yl)-5-[4-(1-hydroxybutyl)phenyl]thieno[2,3-c]pyridine dihydrochloride

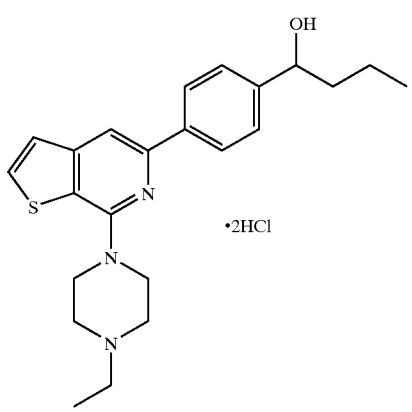

In the same manner as in Example 161-2, 1-[4-(tributylstannyl)phenyl]butan-1-one (1.74 g) was obtained as a colorless oil from 1-(4-bromophenyl)butan-1-one (1.91 g) and bis(tributyltin) (4.7 ml).

The resulting compound and 7-(1-ethylpiperazin-4-yl)-5-bromothieno[2,3-c]pyridine (0.22 g) were reacted in the same manner as in Example 300-4, to give 7-(4-ethylpiperazin-1-yl)-5-(4-butyrylphenyl)thieno[2,3-c]pyridine (0.17 g).

The resulting 7-(4-ethylpiperazin-1-yl)-5-(4-butyrylphenyl)thieno[2,3-c]pyridine (0.17 g) was dissolved in tetrahydrofuran (6 ml). The resulting solution was added to a suspension of lithium aluminum hydride (0.02 g) in tetrahydrofuran (0.5 ml) under ice-cooling, and the mixture was further stirred for 25 min. To the reaction solution were sequentially added water (20 ml), a 5N aqueous solution of sodium hydroxide (20 ml) and water (60 ml). The resulting mixture was diluted with ethyl acetate, and then the resulting precipitates were filtered off. The solvent was evaporated, and the resulting residue was purified by NH silica gel column chromatography (ethyl acetate/n-hexane system), to give 0.13 g of the free compound of the title compound as a colorless viscous oil.
Free compound:
$^1$H-NMR(400 MHz,CDCl$_3$); δ (ppm) 0.94(t,J=7.2 Hz,3H), 1.15(t,J=7.2 Hz,3H), 1.29–1.40(m,1H), 1.40–1.52(m,1H), 1.66–1.75(m,1H), 1.78–1.88(m,1H), 2.42(br-s,1H), 2.49(q,J=7.2 Hz,2H), 2.66(t,J=5.0 Hz,4H), 3.82(t,J=5.0 Hz,4H), 4.71(br-t,1H), 7.32(d,J=5.4 Hz,1H), 7.41(d,J=8.2 Hz,2H), 7.54(d,J=5.4 Hz,1H), 8.06(d,J=8.2 Hz,2H).

The resulting free compound was converted into a hydrochloride in a conventional manner, and then reprecipitated with ethanol/ether, to give the title compound as a yellow powder.

Hydrochloride:
m.p.; 112–114° C.
$^1$H-NMR(400 MHz,DMSO-d$_6$); δ (ppm) 0.88(t,J=7.4 Hz,3H), 1.06(t,J=6.8 Hz,3H), 1.23–1.42(m,2H), 1.52–1.69(m,2H), 3.15–3.23(m,4H), 3.58–3.66(m,4H), 4.42(br-d,2H), 4.58(t,J=6.4 Hz,1H), 7.43(d,J=8.2 Hz,2H), 7.57(d,J=5.6 Hz,1H), 8.02(s,1H), 8.08(d,J=8.2 Hz,2H), 8.09(d,J=5.6 Hz,1H), 11.46(BR-S,1H).
MS(FAB) m/z 396(M+H)$^+$.

Example 447

Synthesis of 7-(4-ethylpiperazin-1-yl)-5-[4-(N-methylcarbamoyl)phenyl]thieno[2,3-c]pyridine dihydrochloride

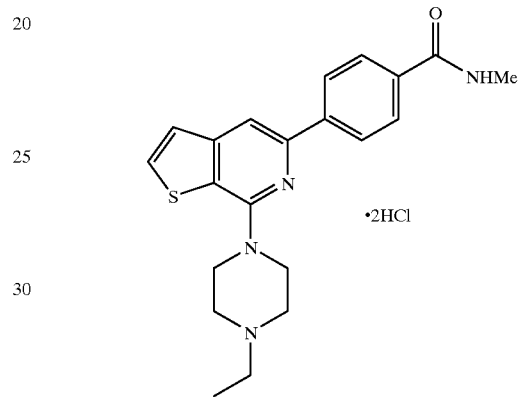

In the same manner as in Example 161-2, N-methyl-4-(tributylstannyl)benzamide (0.90 g) was obtained as a colorless oil from N-methyl-4-bromobenzamide (1.13 g) and bis(tributyltin) (2.9 ml).

The resulting compound and 7-(1-ethylpiperazin-4-yl)-5-bromothieno[2,3-c]pyridine (0.19 g) were reacted in the same manner as in Example 300-4, to give 0.16 g of the free compound of the title compound as a colorless viscous oil.

Free compound:
$^1$H-NMR(400 MHz,CDCl$_3$); δ (ppm) 1.15(t,J=7.2 Hz,3H), 2.51(q,J=7.2 Hz,2H), 3.68(t,J=5.0 Hz,4H), 3.03(d, J=4.8 Hz,3H), 3.85(t,J=5.0 Hz,4H), 6.35(br-q,1H), 7.33(d, J=5.4 Hz,1H), 7.57(d,J=5.4 Hz,1H), 7.69(s,1H), 7.84(d,J=9.0 Hz,2H), 8.14(d,J=9.0 Hz,2H).

The resulting free compound was converted into a hydrochloride in a conventional manner, and then reprecipitated with ethanol/IPE, to give the title compound as a yellow powder.

Hydrochloride:
m.p.; 150.5–152° C.
$^1$H-NMR(400 MHz,DMSO-d$_6$); δ (ppm) 1.30(t,J=7.2 Hz,3H), 2.82(d,J=3.6 Hz,3H), 3.18–3.26(m,4H), 3.55(br-t, 2H), 3.66(br-d,2H), 4.47(br-d,2H), 7.59(d,J=5.4 Hz,1H), 7.95(d,J=8.4 Hz, 1H), 8.11(d,J=5.4 Hz,1H), 8.15(s,1H), 8.22(d,J=8.4 Hz,2H), 8.53(br-s,1H), 10.65(br-s,1H).
MS(FAB) m/z 381(M+H)$^+$.

Example 448

Synthesis of 7-(4-ethylpiperazin-1-yl)-5-[4-(N-ethylcarbamoyl)phenyl]thieno[2,3-c]pyridine dihydrochloride

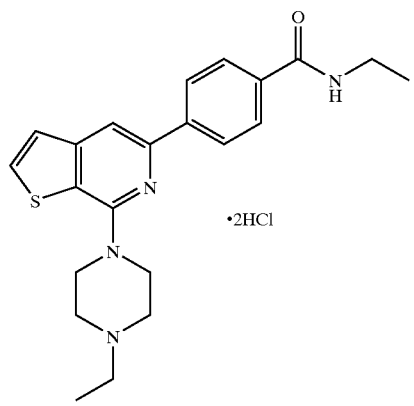

In the same manner as in Example 161-2, N-ethyl-4-(tributylstannyl)benzamide (0.84 g) was obtained as a colorless oil from N-ethyl-4-bromobenzamide (1.11 g) and bis(tributyltin) (2.7 ml).

The resulting compound and 7-(1-ethylpiperazin-4-yl)-5-bromothieno[2,3-c]pyridine (0.19 g) were reacted in the same manner as in Example 300-4, to give 0.19 g of the free compound of the title compound as a colorless viscous oil.

Free compound:

$^1$H-NMR(400 MHz,CDCl$_3$); δ (ppm) 1.16(t,J=7.2 Hz,3H), 1.27(t,J=7.2 Hz,3H), 2.51(q,J=7.2 Hz,2H), 2.68(t,J=5.0 Hz,4H), 3.52(qd,J=5.2,7.2 Hz,2H), 3.85(t,J=5.0 Hz,4H), 6.26(br-t,1H), 7.34(d,J=5.4 Hz,1H), 7.57(d,J=5.4 Hz,1H), 7.70(s,1H), 7.84(d,J=8.2 Hz,2H), 8.14(d,J=8.2 Hz,2H).

The resulting free compound was converted into a hydrochloride in a conventional manner, and then recrystallized from ethanol/IPE, to give the title compound as a pale yellow powder.

Hydrochloride:

m.p.; 142–143° C.

$^1$H-NMR(400 MHz,DMSO-d$_6$); δ (ppm) 1.15(t,J=7.2 Hz,3H), 1.31(t,J=7.2 Hz,3H), 3.17–3.25(m, 4H), 3.29–3.35 (m,2H), 3.58(br-t,2H), 3.66(br-d,2H), 4.46(br-d,2H), 7.59(d, J=5.6 Hz,1H), 7.96(d,J=8.4 Hz,2H), 8.10(d,J=5.6 Hz,1H), 8.15(s,1H), 8.22(d,J=8.4 Hz,2H), 8.57(t,J=5.4 Hz,1H), 10.97(br-s,1H).

MS(FAB) m/z 395(M+H)$^+$.

Example 449

Synthesis of 7-(4-ethylpiperazin-1-yl)-5-[4-(N-propylcarbamoyl)phenyl]thieno[2,3-c]pyridine dihydrochloride

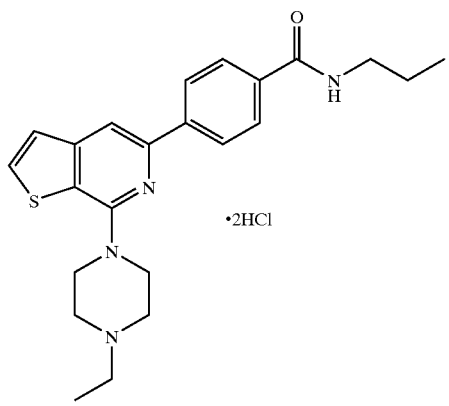

In the same manner as in Example 161-2, N-ethyl-4-(tributylstannyl)benzamide (0.66 g) was obtained as a colorless oil from N-propyl-4-bromobenzamide (1.13 g) and bis(tributyltin) (2.6 ml).

The resulting compound and 7-(1-ethylpiperazin-4-yl)-5-bromothieno[2,3-c]pyridine (0.21 g) were reacted in the same manner as in Example 300-4, to give 0.21 g of the free compound of the title compound as a colorless viscous oil.

Free compound:

$^1$H-NMR(400 MHz,CDCl$_3$); δ (ppm) 0.99(t,J=7.4 Hz,3H), 1.15(t,J=7.2 Hz,3H), 1.66(qt,J=7.2,7.2 Hz,2H), 2.50(q,J=7.2 Hz,2H), 2.67(t,J=5.0 Hz,4H), 3.44(br-q,2H), 3.85(t,J=5.0 Hz,4H), 6.36(t,J=5.6 Hz,1H), 7.32(d,J=5.4 Hz,1H), 7.56(d,J=5.4 Hz,2H), 7.68(s,1H), 7.84(d,J=8.8 Hz,2H), 8.14(d,J=8.4 Hz,2H).

The resulting free compound was converted into a hydrochloride in a conventional manner, and then reprecipitated with ethanol/IPE, to give the title compound as a pale yellow powder.

Hydrochloride:

m.p.; 136.5–138° C.

$^1$H-NMR(400 MHz,DMSO-d$_6$); δ (ppm) 0.91(t,J=7.2 Hz,3H), 1.30(t,J=7.2 Hz,3H), 1.56(qt,J=7.2,7.2 Hz,2H), 3.18–3.27(m, 6H), 3.55(br-t,2H), 3.66(br-d,2H), 4.47(br-d, 2H), 7.60(d,J=5.4 Hz,1H), 7.96(d,J=8.4 Hz,2H), 8.11(d,J= 5.4 Hz,1H), 8.14(s,1H), 8.22(d,J=8.4 Hz,2H), 8.54(t,J=5.6 Hz,1H), 10.63(br-s,1H).

MS(FAB) m/z 409(M+H)$^+$.

Example 450

Synthesis of 7-(4-ethylpiperazin-1-yl)-5-(4-ethanesulfonylphenyl)thieno[2,3-c]pyridine dihydrochloride

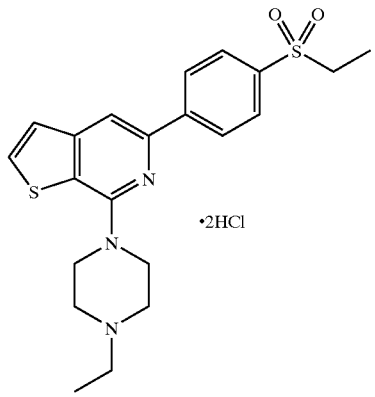

·2HCl

In the same manner as in Example 161-2, 4-ethanesulfonyl-4-(tributylstannyl)benzene (0.70 g) was obtained as a colorless oil from 4-ethanesulfonylbromobenzene (1.23 g) and bis(tributyltin) (2.7 ml).

The resulting compound and 7-(1-ethylpiperazin-4-yl)-5-bromothieno[2,3-c]pyridine (0.18 g) were reacted in the same manner as in Example 300-4, to give a reaction solution containing 7-(4-ethylpiperazin-1-yl)-5-(4-ethanesulfonylphenyl)thieno[2,3-c]pyridine. To the resulting reaction solution were added ethyl acetate and 2N hydrochloric acid, and the resulting insoluble matters were filtered off. The aqueous layer was separated, while the organic layer was extracted with 2N hydrochloric acid. The aqueous layers were combined and washed with ethyl acetate. The pH of the resulting solution was adjusted to pH 10 by adding a 8N aqueous solution of sodium hydroxide thereto, and the resulting solution was extracted with ethyl acetate twice. After washing with brine and drying over magnesium sulfate, the solvent was evaporated. The resulting residue was purified by NH silica gel column chromatography (ethyl acetate/n-hexane system), to give 0.20 g of the free compound of the title compound as a pale brown viscous oil.

Free compound:

$^1$H-NMR(400 MHz,CDCl$_3$); δ (ppm) 1.16(t,J=7.4 Hz,3H), 1.31(t,J=7.4 Hz,3), 2.52(q,J=7.4 Hz,2H), 2.69(t,J=5.0 Hz,4H), 3.15(q,J=7.4 Hz,2H), 3.87(t,J=5.0 Hz,4H), 7.38 (d,J=5.4 Hz,1H), 7.61(d,J=5.4 Hz,1H), 7.74(s,1H), 7.97(d, J=8.6 Hz,2H), 8.28(d,J=8.6 Hz,2H).

The resulting free compound was converted into a hydrochloride in a conventional manner, and then reprecipitated with ethanol/IPE, to give the title compound as a yellow powder.

Hydrochloride:

m.p.; 230–232.0° C. (decomp.)

$^1$H-NMR(400 MHz,DMSO-d$_6$); δ (ppm) 1.14(t,J=7.4 Hz,3H), 1.30(t,J=7.4 Hz,3H), 3.18–3.26(m,4H), 3.35(q,J=7.4 Hz,2H), 3.54(br-t,2H), 3.66(br-d,2H), 4.49(br-d,2H), 7.62(d,J=5.4 Hz,1H), 7.99(d,J=8.6 Hz,2H), 8.14(d,J=5.4 Hz,1H), 8.21(s,1H), 8.41(d,J=8.6 Hz,2H), 10.48(br-s,1H).

MS(ESI) m/z 416(M+H)$^+$.

Example 451

Synthesis of 7-(4-ethylpiperazin-1-yl)-5-(4-propanesulfonylphenyl)thieno[2,3-c]pyridine dihydrochloride

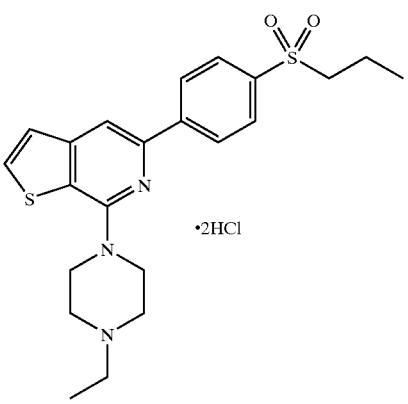

·2HCl

In the same manner as in Example 161-2, 1.09 g of 1-propanesulfonyl-4-(tributylstannyl)benzene was obtained as a colorless oil from 4-propanesulfonylbromobenzene (1.40 g) and bis(tributyltin) (3.0 ml).

The resulting compound and 7-(1-ethylpiperazin-4-yl)-5-bromothieno[2,3-c]pyridine (0.18 g) were reacted in the same manner as in Example 300-4, to give a reaction solution containing 7-(4-ethylpiperazin-1-yl)-5-(4-propanesulfonylphenyl)thieno[2,3-c]pyridine. To the resulting reaction solution were added ethyl acetate and 2N hydrochloric acid, and the resulting insoluble matters were filtered off. The aqueous layer was separated, while the organic layer was extracted with 2N hydrochloric acid. The aqueous layers were combined and washed with ethyl acetate. The pH of the solution was adjusted to pH 10 by adding a 8N aqueous sodium hydroxide thereto, and then the solution was extracted with ethyl acetate twice. It was washed with brine, dried over magnesium sulfate, and then the solvent was evaporated. The resulting residue was purified by NH silica gel column chromatography (ethyl acetate/n-hexane system), to give 0.19 g of the free compound of the title compound as a pale brown viscous oil.

Free compound:

$^1$H-NMR(400 MHz,CDCl$_3$); δ (ppm) 1.01(t,J=7.4 Hz,3H), 1.16(t,J=7.2 Hz,3H), 1.73–1.83(m,2H), 2.52(q,J=7.2 Hz,2H), 2.69(t,J=5.0 Hz,4H), 3.08–3.12(m,2H), 3.87(t, J=5.0 Hz,4H), 7.38(d,J=5.6 Hz,1H), 7.62(d,J=5.6 Hz,1H), 7.74(s,1H), 7.97(d,J=8.6 Hz,2H), 7.27(d,J=8.6 Hz,2H).

The resulting free compound was converted into a hydrochloride in a conventional manner, and then reprecipitated with ethanol/IPE, to give the title compound as a yellow powder.

Hydrochloride:

m.p.; 230.5–233.5° C. (decomp.)

$^1$H-NMR(400 MHz,DMSO-d$_6$); δ (ppm) 0.94(t,J=7.4 Hz,3H), 1.30(t,J=7.2 Hz,3H), 1.55–1.64(m,2H), 3.17–3.27 (m,4H), 3.31–3.35(m,2H), 3.54(br-t,2H), 3.66(br-d,2H), 3.49(br-d,2H), 7.62(d,J=5.6 Hz,1H), 7.99(d,J=8.4 Hz,2H), 8.14(d,J=5.6 Hz,1H), 8.21(s,1H), 8.40(d,J=8.4 Hz,2H), 10.47(br-s,1H).

Example 452

Synthesis of 7-(4-ethylpiperazin-1-yl)-5-[4-(N-butylcarbamoyl)phenyl]thieno[2,3-c]pyridine dihydrochloride

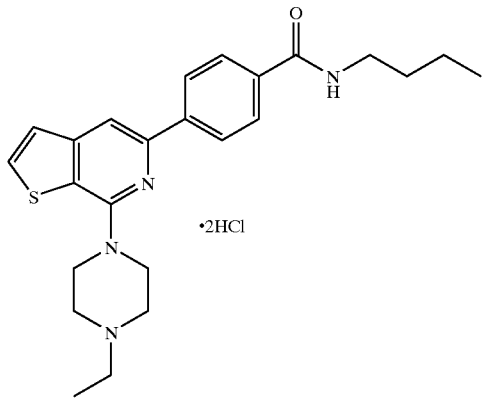

In the same manner as in Example 161-2, N-butyl-4-(tributylstannyl)benzamide (0.80 g) was obtained as a colorless oil from N-butyl-4-bromobenzamide (1.21 g) and bis(tributyltin) (2.6 ml).

The resulting compound and 7-(1-ethylpiperazin-4-yl)-5-bromothieno[2,3-c]pyridine (0.20 g) were reacted in the same manner as in Example 300-4, to give 0.20 g of the free compound of the title compound as colorless crystals.

Free compound:

$^1$H-NMR(400 MHz,CDCl$_3$); δ (ppm) 0.96(t,J=7.2 Hz,3H), 1.15(t,J=7.2 Hz,3H), 1.42(tq,J=7.2,7.2 Hz,2H), 1.57–1.65(m,2H), 2.50(q,J=7.2 Hz,2H), 2.66(t,J=5.0 Hz,4H), 3.44–3.49(m,2H), 3.84(t,J=5.0 Hz,4H), 6.38(t,J=5.4 Hz,1H), 7.31(d,J=5.6 Hz,2H), 7.55(d,J=5.6 Hz,1H), 7.67(s,1H), 7.84(d,J=8.2 Hz,2H), 8.13(d,J=8.4 Hz,2H).

The resulting free compound was converted into a hydrochloride in a conventional manner, and then reprecipitated with ethanol/IPE, to give the title compound as a pale yellow powder.

Hydrochloride:

m.p.; 127.5–128° C.

$^1$H-NMR(400 MHz,DMSO-d$_6$); δ (ppm) 0.92(t,J=7.2 Hz,3H), 1.30(t,J=7.2 Hz,3H), 1.30–1.40(m,2H), 1.50–1.57 (m,2H), 3.18–3.31(m,6H), 3.54(br-t,2H), 3.66(br-d,2H), 4.47(br-d,2H), 7.59(d,J=5.6 Hz,1H), 7.96(d,J=8.4 Hz,2H), 8.11(d,J=5.6 Hz,1H), 8.14(s,1H), 8.22(d,J=8.4 Hz,1H), 8.52(t,J=5.8 Hz,1H), 10.57(br-s,1H).

MS(FAB) m/z 423(M+H)$^+$.

Example 453

Synthesis of 7-(4-ethylpiperazin-1-yl)-5-[4-(N-cyclopentylcarbamoyl)phenyl]thieno[2,3-c]pyridine dihydrochloride

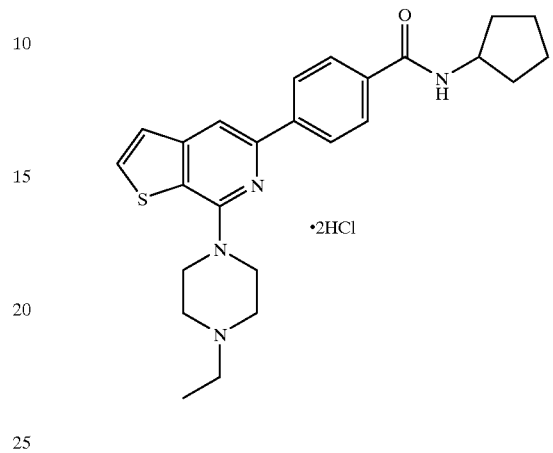

In the same manner as in Example 161-2, N-cyclopentyl-4-(tributylstannyl)benzamide (0.92 g) was obtained as a colorless oil from N-cyclopentyl-4-bromobenzamide (1.22 g) and bis(tributyltin) (2.5 ml).

7-(1-Ethylpiperazin-4-yl)-5-bromothieno[2,3-c]pyridine (0.21 g) was reacted with the resulting compound in the same manner as in Example 300-4, to give 0.21 g of the free compound of the title compound as colorless crystals.

$^1$H-NMR(400 MHz,CDCl$_3$); δ (ppm) 1.15(t,J=7.2 Hz,3H), 1.47–1.56(m,2H), 1.60–1.78(m,4H), 2.06–2.14(m, 2H), 2.50(q,J=7.2 Hz,2H), 2.66(t,J=5.0 Hz,4H), 3.84(t,J=5.0 Hz,4H), 4.38–4.47(m,1H), 6.26(d,J7.6 Hz,1H), 7.31(d,J=5.2 Hz,1H), 7.55(d,J=5.2 Hz,1H), 7.68(s,1H), 7.83(d,J=8.4 Hz,2H), 8.13(d,J=8.4 Hz,2H).

The resulting free compound was converted into a hydrochloride in a conventional manner, and then reprecipitated with ethanol/IPE, to give the title compound as a pale yellow powder.

Hydrochloride:

m.p.; 148–149° C.

$^1$H-NMR(400 MHz,DMSO-d$_6$); δ (ppm) 1.30(t,J=7.2 Hz,3H), 1.52–1.62(m,4H), 1.67–1.74(m,2H), 1.86–1.95(m, 2H), 3.18–3.26(m,4H), 3.55(br-t,2H), 3.66(br-d,2H), 4.26 (br-q,1H), 4.46(br-d,2H), 7.60(d,J=5.4 Hz,1H), 7.96(d,J=8.4 Hz,2H), 8.11(d,J=5.4 Hz,1H), 8.14(s,1H),8.21(d,J=8.4 Hz,2H), 8.35(d,J=7.6 Hz,1H), 10.65(br-s,1H).

MS(FAB) m/z 435(M+H)$^+$.

Example 454

Synthesis of 7-(4-Ethylpiperazin-1-yl)-5-[4-(cis-4-hydroxytetrahydropyran-2-yl)phenyl]thieno[2,3-c]pyridine dihydrochloride

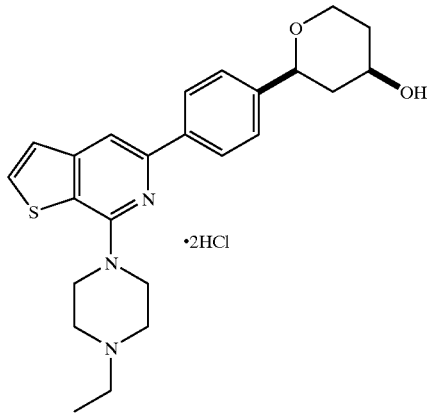

In the same manner as in Example 161-2, cis-4-acetoxy-2-[4-(tributylstannyl)phenyl]tetrahydropyran (1.00 g) was obtained as a colorless oil from cis-4-acetoxy-2-(4-bromophenyl)tetrahydropyran (1.20 g) and bis(tributyltin) (2.2 ml).

The resulting compound and 7-(1-ethylpiperazin-4-yl)-5-bromothieno[2,3-c]pyridine (0.21 g) were reacted in the same manner as in Example 300-4, to give a reaction solution containing 7-(4-ethylpiperazin-1-yl)-5-[4-(cis-4-acetoxytetrahydropyran-2-yl)phenyl]thieno[2,3-c]pyridine. To the resulting reaction solution were added ethyl acetate and 2N hydrochloric acid, and the resulting insoluble matters were filtered off. The aqueous layer was separated, while the organic phase was extracted with 2N hydrochloric acid. The aqueous layers were combined and washed with ethyl acetate twice. The pH of the solution was adjusted to pH 10 by adding a 8N aqueous solution of sodium hydroxide thereto, and then the solution was extracted with ethyl acetate twice. After washing with brine and drying over magnesium sulfate, the solvent was evaporated. Methanol (10 ml) was added to the resulting residue and dissolved, followed by the addition of a 5N aqueous solution of sodium hydroxide (1 ml). The resulting solution was left as it was at room temperature for 1 hr, and then the solvent was evaporated. Water was added to the resulting residue, and then the mixture was extracted with ethyl acetate thrice. The extract was washed with brine, dried over magnesium sulfate, and then the solvent was evaporated. The resulting residue was purified by NH silica gel column chromatography (ethyl acetate/n-hexane system), to give 0.20 g of the free compound of the title compound as a colorless amorphous.

Free compound:
$^1$H-NMR(400 MHz,CDCl$_3$); δ (ppm) 1.15(t,J=7.2 Hz,3H), 1.53–1.70(m,2H), 1.93–1.99(m,1H), 2.15(br-s,1H), 2.16–2.22(m,1H), 2.51(q,J=7.2 Hz,2H), 2.68(t,J=5.0 Hz,4H), 3.59(dt,J=2.0,12.4 Hz), 3.85(t,J=5.0 Hz,4H), 3.89–3.97(m,1H), 4.16–4.21(m,1H), 4.34–4.37(m,1H), 7.33 (d,J=5.4 Hz,1H), 7.54(d,J=5.4 Hz,1H), 7.66(s,1H), 8.06(d, J=8.4 Hz,2H).

The resulting free compound was converted into a hydrochloride in a conventional manner, and then reprecipitated with ethanol/ether, to give the title compound as a yellow powder.

Hydrochloride:
m.p.; 157–159° C.
$^1$H-NMR(400 MHz,DMSO-d$_6$); δ (ppm) 1.04(d,J=6.0 Hz,3H), 1.31(t,J=7.4 Hz,3H), 1.38–1.48(m,1H), 1.80–1.86 (m,1H), 2.04–2.10(m1H), 3.16–3.24(m,4H), 4.48–3.66(m, 5H), 3.73–3.81(m,1H), 4.02–4.06(m,1H), 4.37(dd,J=1.6, 11.2 Hz,1H), 4.43(br-d,2H), 7.43(d,J=8.4 Hz,2H), 7.57(d,J= 5.4 Hz,1H), 8.03(s,1H), 8.08(d,J=5.4 Hz,1H), 8.09(d,J=8.4 Hz,2H), 10.94(br-s,1H).
MS(FAB) m/z 424(M+H)$^+$.

Example 455

Synthesis of 7-(4-ethylpiperazin-1-yl)-5-[4-(trans-4-hydroxytetrahydropyran-2-yl)phenyl]thieno[2,3-c]pyridine dihydrochloride

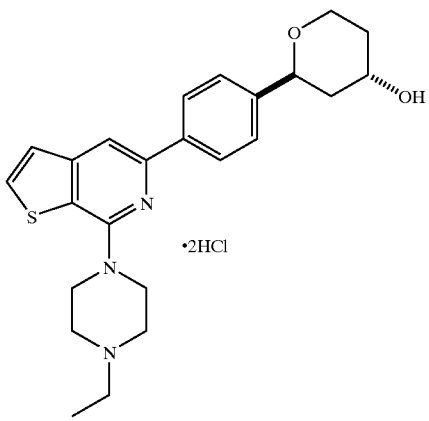

In the same manner as in Example 161-2, trans-4-acetoxy-2-[4-(tributylstannyl)phenyl]tetrahydropyran (1.29 g) was obtained as a colorless oil from trans-4-acetoxy-2-(4-bromophenyl)tetrahydropyran (1.31 g) and bis (tributyltin) (2.4 ml).

The resulting compound and 7-(1-ethylpiperazin-4-yl)-5-bromothieno[2,3-c]pyridine (0.21 g) were reacted in the same manner as in Example 300-4, to give a reaction solution containing 7-(4-ethylpiperazin-1-yl)-5-[4-(trans-4-acetoxytetrahydropyran-2-yl)phenyl]thieno[2,3-c]pyridine. To the resulting reaction solution were added ethyl acetate and 2N hydrochloric acid, and the resulting insoluble matters were filtered off. The aqueous layer was separated, while the organic layer was extracted with 2N hydrochloric acid. The aqueous layers were combined and washed with ethyl acetate twice. The pH of the solution was adjusted to pH 10 by adding a 8N aqueous solution of sodium hydroxide thereto, and then the solution was extracted with ethyl acetate twice. The extract was washed with brine, dried over magnesium sulfate and the solvent was evaporated. Methanol (10 ml) was added to the resulting residue and dissolved, followed by the addition of a 5N aqueous solution of sodium hydroxide solution (1 ml). The resulting solution was left as it was at room temperature for 1 hr, and then the solvent evaporated. Water was added thereto, and then the mixture was extracted with ethyl acetate thrice. The extract was washed with brine, dried over magnesium sulfate, and then the solvent was evaporated. The resulting residue was purified by NH silica gel column chromatography (ethyl acetate/n-hexane system), to give 0.18 g of the free compound of the title compound as a colorless amorphous.

Free compound:
$^1$H-NMR(400 MHz, CDCl$_3$); δ (ppm) 1.16(t,J=7.2 Hz,3H), 1.64(br-d,1H), 1.88–1.91(m,2H), 1.94–2.03(m,1H), 2.06(br-s,1H), 2.51(q,J=7.2 Hz,2H), 2.68(t,J=5.02 Hz,4H), 3.85(t,J=5.0 Hz,4H), 3.95(ddd,J=1.6,5.2,11.6 Hz,1H), 4.09 (br-dt,1H), 4.31(br-quintet,1H), 4.84–4.92(m,1H), 7.32(d,J=5.4 Hz,1H), 7.43(d,J=8.4 Hz,2H), 7.54(d,J=5.4 Hz,1H), 7.66 (s,1H), 7.06(d,J=8.4 Hz,2H).

The resulting free compound was converted into a hydrochloride in a conventional manner, and then reprecipitated with ethanol/ether, to give the title compound as a yellow powder.

m.p.; 146–148° C.
$^1$H-NMR(400 MHz,DMSO-d$_6$); δ (ppm) 1.30(t,J=7.2 Hz,3H), 1.54(br-d,1H), 1.68(br-t,1H), 1.74–1.84(m,2H), 1.17–1.24(m4H), 3.54(br-t,2H), 3.65(br-d,2H), 3.81(br-q, 1H), 3.94(br-t,1H), 4.11(br-quintet,1H), 4.43(br-d2H), 4.77 (br-d,1H), 7.41(d,J=8.4 Hz,2H), 7.57(d,J=5.6 Hz,1H), 8.03 (s,1H), 8.08(d,J=5.6 Hz,1H), 8.09(d,J=8.4 Hz,2H), 10.71(br-s,1H).
MS(FAB) m/z 424(M+H)$^+$.

Example 456

Synthesis of 7-(4-Ethylpiperazin-1-yl)-5-[4-(trans-4-hydroxytetrahydropyran-2-yl)phenyl]thieno[2,3-c]pyridine dihydrochloride

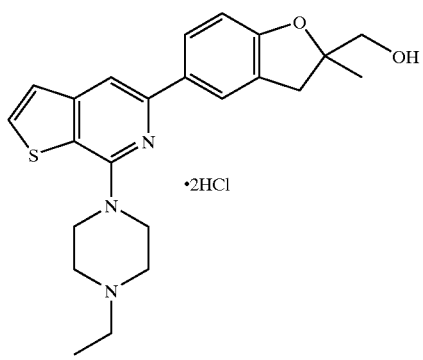

In the same manner as in Example 161-2, 1.10 g of 2-ethoxycarbonyl-2,3-dihydro-2-methyl-5-(tributylstannyl)benzofuran was obtained as a colorless oil from 5-bromo-2-ethoxycarbonyl-2,3-dihydro-2-methylbenzofuran (1.34 g) and bis(tributyltin) (2.6 ml).

The resulting compound and 7-(1-ethylpiperazin-4-yl)-5-bromothieno[2,3-c]pyridine (0.29 g) were reacted in the same manner as in Example 300-4, to give 7-(4-ethylpiperazin-1-yl)-5-(2-ethoxycarbonyl-2,3-dihydro-2-methylbenzofuran-5-yl)thieno[2,3-c]pyridine.

The resulting 7-(4-ethylpiperazin-1-yl)-5-(2-ethoxycarbonyl-2,3-dihydro-2-methylbenzofuran-5-yl)thieno[2,3-c]pyridine was dissolved in tetrahydrofuran (10 ml). The resulting solution was added to a suspension of lithium aluminum hydroxide (0.06 g) in tetrahydrofuran (1 ml) under cooling on ice, and further stirred for 15 min. To the resulting reaction solution were sequentially added water (60 ml), a 5N aqueous solution of sodium hydroxide (60 ml) and water (180 ml). The resulting mixture was diluted with ethyl acetate, and then the resulting precipitates were filtered off. The solvent was evaporate, and the resulting residue was purified by NH silica gel column chromatography (ethyl acetate/n-hexane system), to give 0.20 g of the free compound of the title compound as a colorless viscous oil.
Free compound:
$^1$H-NMR(400 MHz,CDCl$_3$); δ (ppm) 1.15(t,J=7.2 Hz,3H), 1.46(s,3H), 2.50(q,J=7.2 Hz,2H), 2.61(br-s,1H), 2.67(t,J=5.0 Hz,4H), 2.96(d,J=15.6 Hz,1H), 3.31(d,J=15.6 Hz,1H), 3.64(d,J=11.6 Hz,1H), 3.69(d,J=11.6 Hz,1H), 3.82 (t,J=5.0 Hz,4H), 6.80(d,J=8.4 Hz,1H), 7.28(d,J=5.4 Hz,1H), 7.51(d,J=5.4 Hz,1H), 7.55(s,1H), 7.84(dd,J=1.4,8.4 Hz,1H), 7.90(d,J=1.4 Hz,1H).

The resulting free compound was converted into a hydrochloride in a conventional manner, and then reprecipitated with ethanol/ether, to give the title compound as a yellow powder.
Hydrochloride:
m.p.; 138–140° C. (decomp.)
$^1$H-NMR(400 MHz,DMSO-d$_6$); δ (ppm) 1.32(t,J=7.2 Hz,3H), 1.38(s,3H), 2.91(d,J=15.8 Hz,1H), 3.15–3.2(m,4H), 3.30(d,J=15.8 Hz,1H), 3.45(d,J=7.0 Hz,1H), 3.49(d,J=7.0 Hz,1H), 3.55–3.65(m,4H), 4.39(br-d,2H), 6.79(d,J=8.6 Hz,1H), 7.52(d,J=5.6 Hz,1H), 7.88(dd,J=1.6,8.6 Hz,1H), 7.91(s,1H), 7.95(br-s,1H), 8.05(d,J=5.6 Hz,1H), 11.25(br-s, 1H).
MS(FAB) m/z 410(M+H)$^+$.

Example 457

Synthesis of 7-(4-Ethylpiperazin-1-yl)-5-[4-(cyclohexylhydroxymethyl)phenyl]thieno[2,3-c]pyridine dihydrochloride

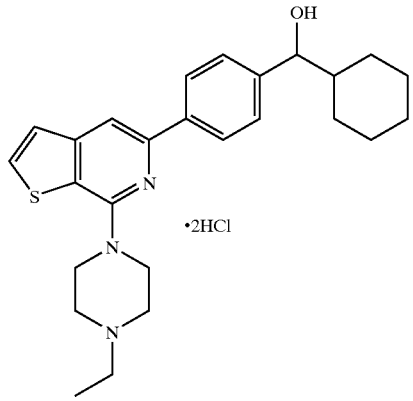

In the same manner as in Example 161.2, 1.39 g of 4-(cyclohexylacetoxymethyl)-1-(tributylstannyl)benzene was obtained as a colorless oil from 4-(cyclohexylacetoxymethyl)bromobenzene 1.36 g) and bis (tributyltin) (2.1 ml).

The resulting compound and 7-(1-ethylpiperazin-4-yl)-5-bromothieno[2,3-c]pyridine (0.20 g) were reacted in the same manner as in Example 300-4, to give a reaction solution containing 7-(4-ethylpiperazin-1-yl)-5-[4-(cyclohexylacetoxymethyl)phenyl]thieno[2,3-c]pyridine. To the resulting reaction solution were added ethyl acetate and 2N hydrochloric acid, and then the resulting insoluble matters were filtered off. The aqueous layer was separated, while the organic phase was extracted with 2N hydrochloric acid. The resulting aqueous layers were combined and washed twice with ethyl acetate. The pH of the resulting solution was adjusted to pH 10 by adding 8N sodium hydroxide thereto, and then the solution was extracted with ethylacetate twice. After washing with brine and drying over magnesium sulfate, the solvent was evaporated. Methanol (10 ml) was added to the resulting residue, dissolved, and then a 5N aqueous solution of sodium hydroxide (1 ml) was added thereto. The resulting solution was left as it was at room temperature for 1 hr, and then the solvent was evaporated. Water was added thereto, and then the mixture was extracted with ethyl acetate thrice. After washing with brine and drying over magnesium sulfate, the solvent was evaporated. The resulting residue was purified by NH silica gel column chromatography (ethyl acetate/n-hexane system), to give 0.12 g of the free compound of the title compound as a colorless amorphous.

Free compound:
$^1$H-NMR(400 MHz,CDCl$_3$); δ (ppm) 0.91–1.28(m,3H), 1.16(t,J=7.2 Hz,3H), 1.45(br-d,1H), 1.45(br-d,1H), 1.61–1.69(m,3H), 1.77(br-d,1H) 2.02(br-d,1H), 2.23(br-s,1H), 2.50(q,J=7.2 Hz,2H), 2.66(t,J=5.0 Hz,4H), 3.83(t,J=7.2 Hz,4H), 4.41(d,J=7.2 Hz,1H), 7.32(d,J=5.6 Hz,1H), 7.37(d, J=8.4 Hz,2H), 7.54(d,J=5.6 Hz,1H), 7.64(s,1H), 8.05(d,J=8.4 Hz,2H).

The resulting free compound was converted into a hydrochloride in a conventional manner, and then reprecipitated with ethanol/ether, to give the title compound as a yellow powder.

m.p.; 127.5–129° C.
$^1$H-NMR(400 MHz,DMSO-d$_6$); δ (ppm) 0.92–1.88(m, 4H), 1.32(t,J=7.2 Hz,3H), 1.38(br-d,1H), 1.46–1.70(m,4H), 1.85(br-d,1H), 3.15–3.24(m,4H), 3.57–3.66(m,5H), 4.30(d, J=6.4 Hz,1H), 4.43(br-d2H), 7.38(d,J=8.4 Hz,2H), 7.57(d, J=5.6 Hz,1H), 8.02(s,1H), 8.06–8.09(m3H), 11.41(br-s,1H).
MS(FAB) m/z 436(M+H)$^+$.

Example 458

Synthesis of 7-(4-ethylpiperazin-1-yl)-5-[4-(cyclopentylhydroxymethyl)phenyl]thieno[2,3-c]pyridine dihydrochloride

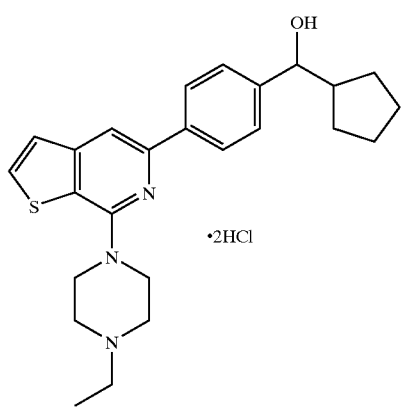

In the same manner as in Example 161-2, 1.21 g of (4-tributylstannylphenyl)cyclopentyl ketone was obtained as a colorless oil from (4-bromophenyl)cyclopentyl ketone (1.57 g) and bis(tributyltin) (3.1 ml).

The resulting compound and 7-(1-ethylpiperazin-4-yl)-5-bromothieno[2,3-c]pyridine (0.22 g) were reacted in the same manner as in the Example 300-4, to give 7-(4-ethylpiperazin-1-yl)-5-[4-(cyclopentylcarbonyl)phenyl]thieno[2,3-c]pyridine.

The resulting 7-(4-ethylpiperazin-1-yl)-5-[4-(cyclopentylcarbonyl)phenyl]thieno[2,3-c]pyridine was dissolved in tetrahydrofuran (5 ml). The resulting solution was added to a suspension of lithium aluminum hydroxide (0.06 g) in tetrahydrofuran (1 ml) under ice-cooling, and the resulting mixture was further stirred for 10 min. To the resulting reaction solution were sequentially added water (60 ml), a 5N aqueous solution of sodium hydroxide (60 ml) and water (180 ml). The resulting mixture was diluted was diluted with ethylacetate, and then the resulting precipitates were filtered off. The solvent was evaporated, and the resulting residue was purified by NH silica gel column chromatography (ethyl acetate/n-hexane system), to give 0.14 g of the free compound of the title compound as a colorless viscous oil.

Free compound:
$^1$H-NMR(400 MHz,CDCl$_3$); δ (ppm) 1.15(t,J=7.2 Hz,3H), 1.14–1.70(m,7H), 1.88–1.95(m,1H), 2.20–2.31(m, 1H) 2.30(br-s,1H), 2.49(q,J=7.2 Hz,2H), 2.66(t,J=5.0 Hz,4H), 3.83(t,J=5.0 Hz,4H), 4.44(d,J=8.4 Hz,1H), 7.32(d, J=5.2 Hz,1H), 7.41(d,J=8.4 Hz,2H), 7.54(d,J=5.2 Hz,1H), 7.64(s,1H), 8.05(d,J=8.4 Hz,2H).

The resulting free compound was converted into a hydrochloride in a conventional manner, and then reprecipitated with ethanol/IPE, to give the title compound as a yellow powder.

Hydrochloride:
m.p.; 128–129° C.
$^1$H-NMR(400 MHz,DMSO-d$_6$); δ (ppm) 1.18–1.61(m, 7H), 1.31(t,J=7.2 Hz,3H), 1.65–1.72(m,1H), 2.07–2.17(m, 1H), 3.16–3.24(m,4H), 3.55–3.66(m,4H), 4.34(d,J=7.6 Hz,1H), 4.43(br-d,2H), 7.42(d,J=8.4 Hz,2H), 7.57(d,J=5.2 Hz,1), 8.02(s,1H), 8.07(d,J=8.4 Hz,2H), 8.07(d,J=5.2 Hz,1H), 11.01(br-s,1H).
MS(FAB) m/z 422(M+H)$^+$.

Example 459

Synthesis of 7-(4-ethylpiperazin-1-yl)-5-(4-methoxyphenyl)thieno[2,3-c]pyridine dihydrochloride

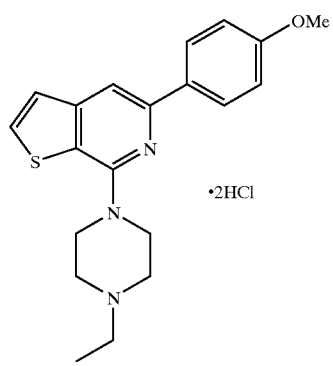

A mixture of 5-bromo-7-(4-ethylpiperazin-1-yl)thieno[2, 3-c]pyridine (0.35 g), 4-methoxyphenylboric acid (0.24 g), tetrakistriphenylphosphinepalladium (0) (0.06 g), toluene (30 ml) and a 10% aqueous solution of sodium carbonate (20 ml) was vigorously stirred in nitrogen atmosphere at 100° C. for 1 hr. To the resulting mixture was added 4-methoxyphenylboric acid (0.16 g), and the resulting mixture was further stirred for 2 hr. To the resulting mixture was added 4-methoxyphenylboric acid (0.16 g), and the resulting mixture was stirred for 6.5 hr. The resulting insoluble matters were filtered off, and then the organic layer was separated. It was extracted with 2N hydrochloric acid twice, adjusted to pH 10 by adding a 8N aqueous solution of sodium hydroxide thereto, and then extracted with ethyl acetate twice. After washing with brine and drying over magnesium sulfate, the solvent was evaporated. The resulting residue was purified by NH silica gel column chromatography (ethyl acetate/n-hexane system), to give 0.34 g of the free compound of the title compound as a pale yellow viscous oil.

Free compound:

¹H-NMR(400 MHz,CDCl₃); δ (ppm) 1.15(t,J=7.2 Hz,3H), 2.50(q,J=7.2 Hz,2H), 2.67(t,J=5.0 Hz,4H), 3.84(t, J=5.0 Hz,4H), 3.85(s,3H), 6.98(d,J=9.0 Hz,2H), 7.30(d,J= 5.2 Hz,1H), 7.51(d,J=5.2 Hz,1H), 7.59(s,1H), 8.04(d,J=9.0 Hz,2H).

The resulting free compound was converted into a hydrochloride in a conventional manner, and then reprecipitated with ethanol/ether, to give the title compound as a yellow powder.

Hydrochloride:

m.p.; 113–115° C.

¹H-HMR(400 MHz,DMSO-d₆); δ (ppm) 1.30(t,J=7.4 Hz,3H), 3.16–3.24(m,4H), 3.53(br-t,2H), 3.65(br-d,2H), 3.82(s,3H), 4.43(br-d,2H), 7.05(d,J=8.8 Hz,2H), 7.54(d,J= 5.4 Hz,1H), 7.97(s,1H), 8.06(d,J=5.4 Hz,1H), 8.09(d,J=8.8 Hz,2H), 10.64(br-s,1H).

MS(ESI) m/z 354(M+H)⁺.

Example 460

Synthesis of 4-(4-ethylpiperazin-1-yl)-6-[4-(1,3-dioxolan-2-yl)methoxyphenyl]thieno[3,2-c]pyridine oxalate

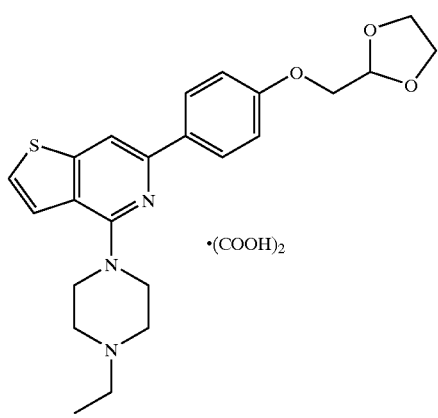

·(COOH)₂

In the same manner as in Example 259, the free compound of 4-(4-ethylpiperazin-1-yl)-6-[4-(1,3-dioxolan-2-yl) methoxyphenyl]thieno[3,2-c]pyridine was obtained as a yellow viscous oil (1.60 g) from 2-bromo-3-thiophenecarboxyaldehyde (5.19 g) and 1-(1,3-dioxolan-2-yl)methoxy-4-ethynylbenzene (5.89 g).

Free compound:

¹H-NMR(400 MHz,CDCl₃); δ (ppm) 1.16(t,J=7.2 Hz,3H), 2.52(q,J=7.2 Hz,2H), 2.69(br-t,4H), 3.70(br-t,4H), 3.96–4.02(m,2H), 4.04–4.12(m,2H), 4.10(d,J=4.0 Hz,2H), 5.33(t,J=4.0 Hz,1H), 7.02(d,J=9.2 Hz,2H), 7.31(d,J=5.6 Hz,1H), 7.39(dd,J=0.8,5.6 Hz,1H), 7.72(d,J=0.8 Hz,1H), 8.04(d,J=9.2 Hz,2H).

The resulting free compound was converted into an oxalate in a conventional manner, and then recrystallized from methanol/ether, to give the title compound as a pale yellow powder.

Oxalate:

m.p.; 188–189° C. (decomp.)

¹H-NMR(400 MHz,DMSO-d₆); δ (ppm) 1.24(t,J=7.2 Hz,3H), 3.08(br-q,2H), 3.28(br-s,4H), 3.76(br-s,4H), 3.86–3.92(m,2H), 3.94–4.00(m,2H), 4.07(d,J=4.0 Hz,2H), 5.23(J=4.0 Hz,1H), 7.06(d,J=9.2 Hz,2H), 7.60(d,J=5.6 Hz,1H), 7.77(d,J=5.6 Hz,1H), 8.10(d,J=9.2 Hz,2H), 8.16(s, 1H).

MS(ESI) m/z 416(M+H)⁺.

Example 461

Synthesis of 4-(4-Ethylpiperazin-1-yl)-6-[4-(2-hydroxyethoxy)phenyl]thieno[3,2-c]pyridine dihydrochloride

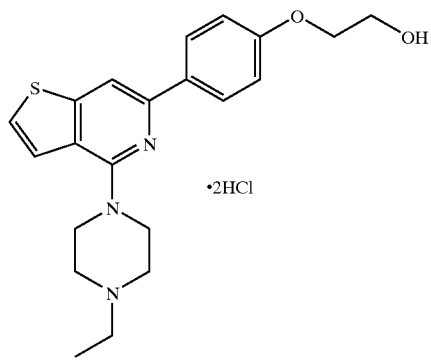

·2HCl 4-(4-Ethylpiperazin-1-yl)-6-(4-hydroxyphenyl)thieno[3, 2-c]pyridine (0.52 g) obtained by the method of Example 280 was treated in the same manner as in Example 417, to give 0.20 g of the free compound of the title compound as pale yellow prisms.

Free compound:

¹H-NMR(400 MHz,CDCl₃); δ (ppm) 1.16(t,J=7.2 Hz,3H), 2.09(br-s,1H), 2.53(q,J=7.2 Hz,2H), 2.70(t,J=4.8 Hz,4H), 3.70(t,J=4.8 Hz,4H), 4.00(br-t2H), 4.15(t,J=4.4 Hz,2H), 7.00(d,J=9.0 Hz,2H), 7.32(d,J=5.6 Hz,1H), 7.39 (dd,J=0.8,5.6 Hz,1H), 7.72(d,J=0.8 Hz,1H), 8.05(d,J=9.0 Hz,2H).

The resulting free compound was converted into a hydrochloride in a conventional manner, and then reprecipitated with ethanol/ether, to give the title compound as a pale yellow powder.

Hydrochloride:

m.p.; 128–129° C.

¹H-NMR(400 MHz,DMSO-d₆); δ (ppm) 1.31(t,J=7.2 Hz,3H), 3.18–3.28(m,4H), 3.50(br-t,2H), 3.60(br-d,2H), 3.75(t,J=5.1 Hz,2H), 4.05(t,J=5.1 Hz,2H), 4.22(br-d,2H), 7.05(d,J=8.8 Hz,2H), 7.62(d,J=7.2 Hz,1H), 7.79(d,J=5.6 Hz,1H), 8.10(d,J=8.8 Hz,2H), 8.18(s,1H), 10.76(br-s,1H).

MS(ESI) m/z 384(M+H)⁺.

Example 462

Synthesis of 4-(4-ethylpiperazin-1-yl)-6-[4-(3-hydroxypropoxy)phenyl]thieno[3,2-c]pyridine dihydrochloride

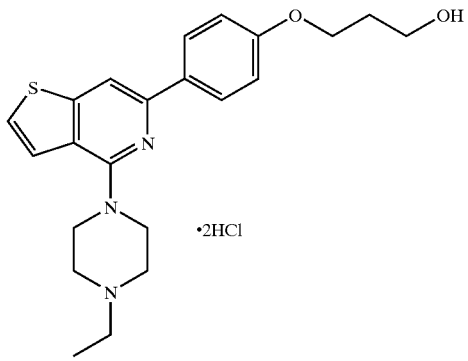

4-(4-Ethylpiperazin-1-yl)-6-(4-hydroxyphenyl)thieno[3,2-c]pyridine (0.40 g) obtained by the method of Example 280 was treated in the same manner as in Example 417, to give 4-(4-ethylpiperazin-1-yl)-6-{4-[2-(3-tetrahydropyran-2-yl)oxypropoxy]phenyl}thieno[3,2-c]pyridine (0.47 g) as a pale yellow viscous oil.

Methanol (5 ml) and 2N hydrochloric acid (2 ml) were added to the resulting 4-(4-ethylpiperazin-1-yl)-6-{4-[2-(3-tetrahydropyran-2-yl)oxypropoxy]phenyl}thieno[3,2-c]pyridine (0.47 g), and the resulting mixture was stirred at room temperature. The solvent was evaporated, and then the pH of the resulting residue was adjusted to pH 10 by adding a 8N aqueous solution of sodium hydroxide thereto. The resulting solution was extracted with ethyl acetate, washed with brine and dried over magnesium sulfate. The solvent was evaporated, and the resulting residue was purified by silica gel column chromatography (chloroform/methanol system), to give 0.18 g of the free compound of the title compound as a pale yellow viscous oil.

Free compound:

$^1$H-NMR(400 MHz,CDCl$_3$); δ (ppm) 1.15(t,J=7.2 Hz,3H), 2.04(tt,J=6.0,6.0 Hz,2H), 2.48–2.53(br-s,1H), 2.51(q,J=7.2 Hz,2H), 2.68(t,J=4.9 Hz,4H), 3.69(t,J=4.9 Hz,4H), 3.85(t,J=6.0 Hz,2H), 4.15(t,J=6.0 Hz,2H), 6.96(d,J=9.0 Hz,2H), 7.29(d,J=5.6 Hz,1H), 7.36(dd,J=1.6,5.6 Hz,1H), 7.69(d,J=1.6 Hz,1H), 8.01(d,J=9.0 Hz,2H).

The resulting free compound was converted into a hydrochloride in a conventional manner, and then reprecipitated with ethanol/ether, to give the title compound as a pale yellow powder.

Hydrochloride:

m.p.; 102–104° C.

$^1$H-NMR(400 MHz,DMSO-d$_6$); δ (ppm) 1.31(t,J=7.2 Hz,3H), 1.89(tt,J=6.2,6.2 Hz,2H), 3.17–3.28(m,4H), 3.50 (br-t,2H), 3.57–3.61(m,2H), 3.58(t,J=6.2 Hz,2H), 4.10(t,J=6.2 Hz,2H), 4.21(br-d2H), 7.02(d,J=8.8 Hz,2H), 7.61(d,J=5.6 Hz,1H), 7.78(d,J=5.6 Hz,1H), 8.10(d,J=5.6 Hz,1H), 8.18 (s,1H), 10.77(br-s,1H).

MS(ESI) m/z 398(M+H)$^+$.

Example 463

Synthesis of 4-(4-ethylpiperazin-1-yl)-6-[4-(2-hydroxy-1-methylethoxy)phenyl]thieno[3,2-c]pyridine dihydrochloride

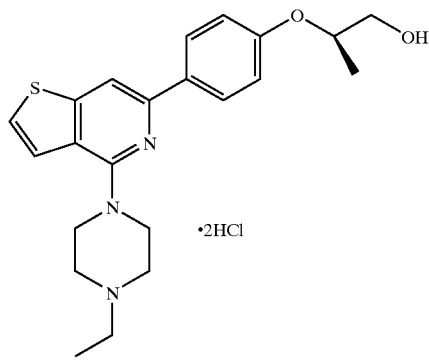

4-(4-Ethylpiperazin-1-yl)-6-(4-hydroxyphenyl)thieno[2,3-c]pyridine (0.31 g) obtained by the method of Example 280 was treated in the same manner as in Example 464, to give 0.16 g of the free compound of the title compound as pale yellow prisms.

Free compound:

$^1$H-NMR(400 MHz,CDCl$_3$); δ (ppm) 1.17(t,J=7.2 Hz,3H), 1.32(d,J=6.4 Hz,3H), 2.53(q,J=7.2 Hz,2H), 2.71(t, J=5.0 Hz,4H), 3.70(t,J=5.0 Hz,4H), 3.75(dd,J=6.4,11.6 Hz,1H), 3.80(dd,J=3.6,11.6 Hz,1H), 4.54–4.61(m,1H), 7.01 (d,J=8.8 Hz,2H), 7.32(d,J=5.6 Hz,1H), 7.39(dd,J=0.8,5.6 Hz,1H), 7.72(d,J=0.8 Hz,1H), 8.04(d,J=8.8 Hz,2H).

The resulting free compound was converted into a hydrochloride in a conventional manner, and then reprecipitated with ethanol/ether, to give the title compound as a pale yellow powder.

Hydrochloride:

m.p.; 124–125° C.

$^1$H-NMR(400 MHz,DMSO-d$_6$); δ (ppm) 1.24(d,J=6.0 Hz,3H), 1.30(t,J=7.2 Hz,3H), 3.18–3.37(m,4H), 3.44–3.51 (m,3H), 3.56–3.61(m,3H), 4.22(br-d,2H), 4.48–4.54(m,1H), 7.04(d,J=9.0 Hz,2), 7.62(d,J=5.6 Hz,1H), 7.79(d,J=5.6 Hz,1H), 8.08(d,J=9.0 Hz,2H), 8.17(s,1H), 10.56(br-s,1H).

MS(FAB) m/z 398(M+H)$^+$.

Example 464

Synthesis of 4-(4-ethylpiperazin-1-yl)-6-[4-(3-hydroxy-1-propynyl)phenyl]thieno[3,2-c]pyridine

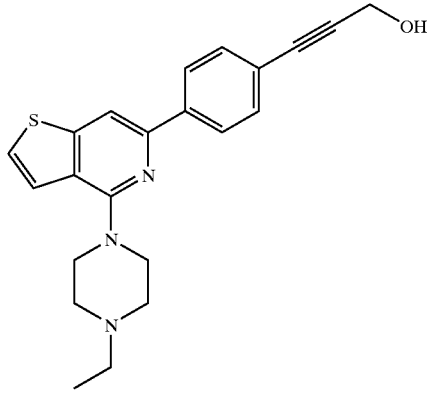

In the same manner as in Example 281-3, 6-(4-bromophenyl)-4-(4-ethylpiperazin-1-yl)thieno[3,2-c]pyridine (1.27 g) and propargyl alcohol (0.92 ml) were reacted, and then recrystallized from chloroform/n-hexane, to give 0.41 g of the title compound as pale yellow needles.

m.p.; 149-5-150.5° C. (decomp.)

$^3$H-NMR(400 MHz,CDCl$_3$); δ (ppm) 1.17(t,J=7.2 Hz,3H), 2.53(q,J=7.2 Hz,2H), 2.70(t,J=5.0 Hz,4H), 3.71(t, J=5.0 Hz,4H), 4.53(s,2H), 7.37(d,J=5.6 Hz,1H), 7.42(dd,J= 0.8,5.6 Hz,1H). 7.52(d,J=8.4 Hz,2H), 7.80(d,J=0.8 Hz,1H), 8.06(d,J=8.4 Hz,2H).

MS(ESI) m/z 378(M+H)$^+$.

Example 465

Synthesis of 4-(4-ethylpiperazin-1-yl)-6-[4-(3-hydroxypropy)phenyl]thieno[3,2-c]pyridine dihydrochloride

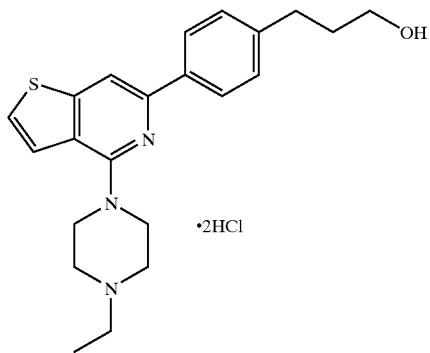

4-(4-Ethylpiperazin-1-yl)-6-[4-(3-hydroxy-1-propynyl) phenyl]thieno[3,2-c]pyridine (0.30 g) obtained in the previous Example was reduced in the same manner as in Example 291, to give 0.10 g of the free compound of the title compound.

Free compound:

$^1$H-NMR(400 MHz,CDCl$_3$); δ (ppm) 1.16(t,J=7.4 Hz,3H), 1.89–1.96(m,2H), 2.52(q,J=7.4 Hz,2H), 2.69(t,J= 4.8 Hz,4H), 2.76(t,J=7.6 Hz,2H), 3.68–3.71(m,6H), 7.28(d, J=8.6 Hz,2H), 7.33(d,J=5.6 Hz,1H), 7.40(dd,J=0.8,5.6 Hz,1H), 7.76(d,J=0.8 Hz,1H), 8.02(d,J=8.6 Hz,2H).

The resulting free compound was converted into a hydrochloride in a conventional manner, and then reprecipitated with ethanol/ether, to give the title compound as a colorless powder.

Hydrochloride:

m.p.; 125.5–126.5° C.

$^1$H-NMR(400 MHz,DMSO-d$_6$); δ (ppm) 1.30(t,J=7.2 Hz,3H), 1.72–1.79(m,2H), 2.67(t,J=7.6 Hz,2H), 3.18–3.29 (m4H), 3.44(t,J=6.4 Hz,2H), 3.48(br-t2H) 3.61(br-d,2H), 4.23(br-d,2H), 7.31(d,J=8.4 Hz,2H), 7.64(d,J=5.6 Hz,1H), 7.82(d,J=5.6 Hz,1H), 8.06(d,J=8.4 Hz,2H), 8.23(s,1H), 10.51(br-s,1H).

MS(ESI) m/z 382(M+H)$^+$.

Example 466

Synthesis of 4-(4-ethylpiperazin-1-yl)-6-[4-(3-hydroxy-3-methyl-1-butynyl)phenyl]thieno[3,2-c] pyridine oxalate

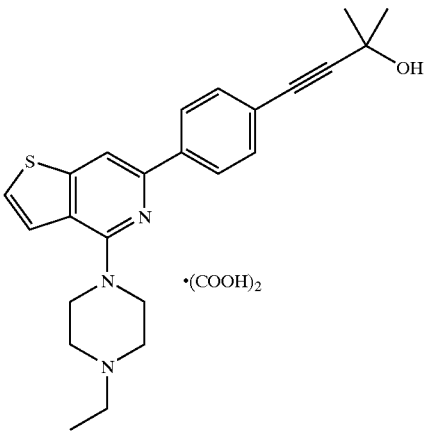

In the same manner as in Example 281-3, 6-(4-bromophenyl)-4-(4-ethylpiperazin-1-yl)thieno[3,2-c]pyridine (0.50 g) was reacted with 2-methyl-3-butyn-2-ol (0.16 ml), to give 0.28 g of the free compound of the title compound as a pale brown amorphous.

Free compound:

$^3$H-NMR(400 MHz,CDCl$_3$); δ (ppm) 1.16(t,J=7.2 Hz,3H), 1.65(s,6H), 2.53(q,J=7.2 Hz,2H), 2.70(t,J=5.0 Hz,4H), 3.71(t,J=5.0 Hz,4H), 7.37(d,J=5.4 Hz,1H), 7.41(dd, J=0.8,5.4 Hz1H), 7.49(d,J=8.2 Hz,2H), 7.80(d,J=0.8 Hz,1H), 8.05(d,J=8.2 Hz,2H).

The resulting free compound was converted into an oxalate in a conventional manner, and then reprecipitated with ethanol/ether, to give the title compound as a colorless powder.

Oxalate:

m.p.; 124.5–125.5° C.

$^1$H-NMR(400 MHz,DMSO-d$_6$); δ (ppm) 1.24(t,J=7.2 Hz,3H), 1.49(s,6H), 3.08(br-q,2H), 3.29(br-t,4H), 3.78(br-t, 4H), 7.49(d,J=8.4 Hz,2H), 7.64(d,J=5.4 Hz,1H), 7.85(d,J= 5.4 Hz,1H), 8.17(d,J=8.2 Hz,2H), 8.29(s,1H).

MS(ESI) m/z 406(M+H)$^+$.

Example 467

Synthesis of 7-(4-ethylpiperazin-1-yl)-5-(4-methoxyphenyl)furo[2,3-c]pyridine dihydrochloride

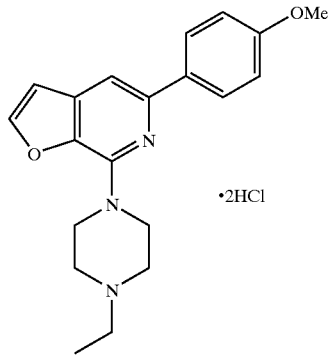

A mixture of 5-bromo-7-(4-ethylpiperazin-1-yl)furo[2,3-c]pyridine (0.34 g) 4-methoxyphenylboric acid (0.25 g), tetrakistriphenylphosphinepalladium(0) (0.06 g), toluene (30 ml) and a 10% aqueous solution of sodium bicarbonate (20 ml) was vigorously stirred in nitrogen atmosphere at 100° C. for 1 hr. To the mixture was then additionally added 4-methoxyphenylboric acid (0.17 g), and the resulting mixture was further stirred overnight. The insoluble matters were filtered off, and the organic layer was separated. Then, it was extracted twice with 2N hydrochloric acid, adjusted to pH 10 by adding a 8N aqueous solution of sodium hydroxide thereto, and then extracted with ethyl acetate twice. It was washed with brine, dried over magnesium sulfate, and then the solvent was evaporated. The resulting residue was purified by NH silica gel column chromatography (ethyl acetate/n-hexane system), to give 0.31 g of the free compound of the title compound as a pale yellow viscous oil.

Free compound:

$^1$H-NMR(400 MHz,CDCl$_3$); δ (ppm) 1.16(t,J=7.2 Hz,3H), 2.50(q,J=7.2 Hz,2H), 2.65(t,J=5.0 Hz,4H), 3.86(s, 3H), 3.99(t,J=5.0 Hz,4H), 6.73(d,J=2.2 Hz,1H), 6.97(d,J=9.0 Hz,2H), 7.32(s,1H), 7.61(d,J=2.2 Hz,1H), 7.97(d,J=9.0 Hz,2H).

The resulting free compound was converted into a hydrochloride in a conventional manner, and then reprecipitated with ethanol/ether, to give the title compound as a yellow powder.

Hydrochloride:

m.p.; 127–128° C.

$^1$H-NMR (400 MHz,DMSO-d$_6$); δ (ppm) 1.29(t,J=7.2 Hz,3H), 3.10–3.20(m,4H), 3.55(br-t,2H), 3.62(br-d,2H), 3.81(s,3H), 4.75(br-d,2H), 7.01(d,J=9.0 Hz,2H), 7.02(d,J=1.8 Hz,1H), 7.63(s,1H), 8.01(d,J=9.0 Hz,2H), 8.14(d,J=1.8 Hz,1H), 10.84(br-s,1H).

MS(ESI) m/z 338(M+H)$^+$.

Example 468

Synthesis of 4-(4-ethylpiperazin-1-yl)-6-(4-methoxyphenyl)furo[3,2-c]pyridine oxalate

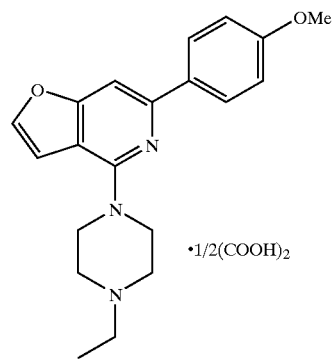

In the same manner as in Example 259, the free compound of the title compound was obtained as a brown viscous oil (0.29 g) from 2-bromo-3-furancarboxyaldehyde (5.79 g) and 4-ethynylanisole (8.74 g).

Free compound:

$^1$H-NMR(400 MHz,CDCl$_3$); δ (ppm) 1.16(t,J=7.2 Hz,3H), 2.50(q,J=7.2 Hz,2H), 2.65(t,J=5.0 Hz,4H), 3.86(t, J=5.0 Hz,4H), 3.86(s,3H), 6.81(dd,J=0.8,2.4 Hz,1H), 6.97 (d,J=9.0 Hz,2H), 7.31(d,J=0.8 Hz,1H), 7.51(d,J=2.4 Hz,1H), 8.01(d,J=9.0 Hz2H).

The resulting free compound was converted into an oxalate in a conventional manner, and then reprecipitated with methanol/ether, to give the title compound as a pale yellow powder.

½ Oxalate:

m.p.; 170–172° C. (decomp.)

$^1$H-NMR(400 MHz,CDCl$_3$); δ (ppm) 1.21(t,J=7.2 Hz3H), 2.96(br-q,2H), 3.13(br-s,4H), 3.81(s,3H), 3.92(br-s,4H), 7.02(d,J=8.8 Hz,2H), 7.22(d,J=2.0 Hz,1H), 7.64(s,1H), 7.98 (d,J=2.0 Hz,1H), 8.08(d,J=8.8 Hz,2H).

MS(FAB) m/z 338(M+H)$^+$.

What is claimed is:

1. A compound represented by the following formula, its pharmaceutically acceptable salt or hydrates thereof

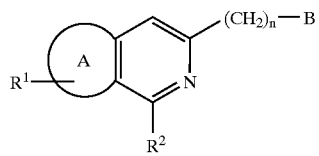

wherein, ring A represents a pyridine ring;

$R^1$ represents a hydrogen atom, a halogen atom, a lower alkyl group or a lower alkoxyl group;

$R^2$ represents a 1-$R^4$-piperazin-4-yl group;

$R^4$ represents a hydrogen atom, a lower alkyl group, a hydroxy lower alkyl group, a halogenated lower alkyl group, a lower cycloalkyl group, an aryl group, an aralkyl group, a 1-piperidyl group, an alkenyl group, a cyano lower alkyl group, a carbamoyl lower alkyl group, a lower acyl group, an aromatic acyl group, a lower alkoxyl carbonyl group, an aryloxycarbonyl group or an aralkyloxycarbonyl group;

n represents 0 or an integer of 1 to 6; and

B represents an optionally substituted aryl group, an optionally substituted aralkyloxy group, an aryl (hydroxy)alkyl group, an aromatic acyl amino group, an arylsulfonylamino group, a lower alkoxyl arylsulfonylamino group, a hydroxy lower alkoxyl styryl group, a lower alkoxy aryloxy group, a 4-phenylpiperidin-1-yl group, a 4-pyridylpiperidin-1-yl group, an arylalkenyl group, an arylalkynyl group, an aromatic acyl alkynyl group, an optionally N-substituted amino lower alkyl group, an optionally substituted arylamino group, an optionally substituted aralkylamino group or a group selected from the groups represented by the following formulae:

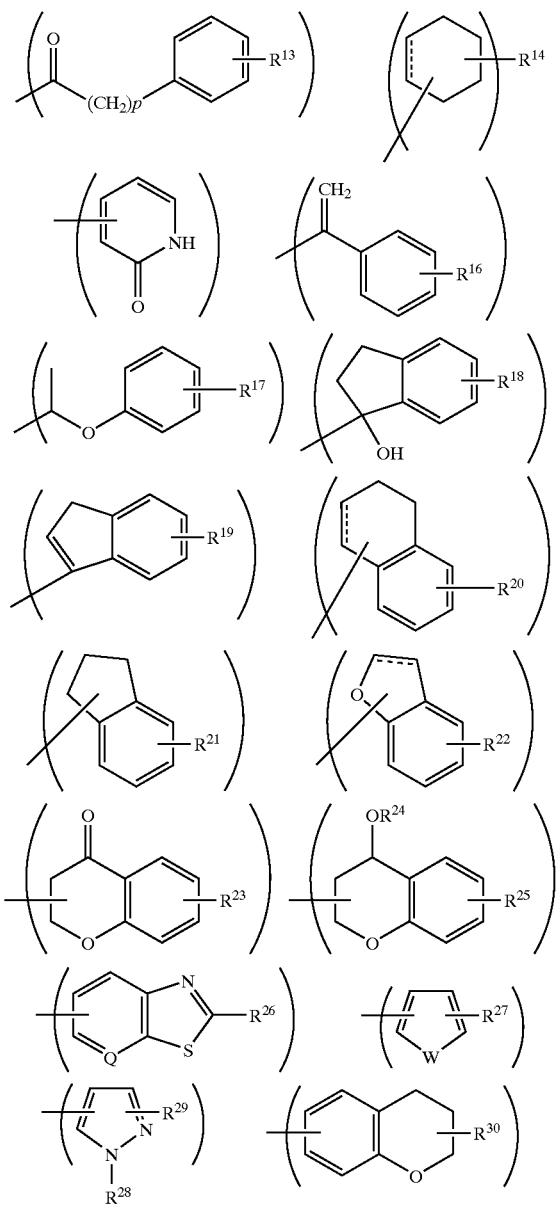

wherein p represents 0 or an integer of 1 to 6;
$R^{13}$, $R^{14}$, $R^{16}$, $R^{17}$, $R^{18}$, $R^{19}$, $R^{20}$, $R^{21}$, $R^{22}$, $R^{23}$, $R^{25}$, $R^{27}$ and $R^{29}$ independently represent a hydrogen atom, a halogen atom, a hydroxyl group, a lower alkyl group, a lower alkoxy group, a hydroxy lower alkyl group, a hydroxy lower alkoxy group or tetrahydropyranyl group;

$R^{24}$ represents a hydrogen atom or a lower alkyl group;
$R^{26}$ represents a hydrogen atom or a hydroxy lower alkyl group;
$R^{28}$ represents a hydrogen atom or a lower alkyl group;
$R^{30}$ represents a hydrogen atom, a lower alkyl group; a lower alkoxy group, a hydroxy lower alkyl group or a hydroxy lower alkoxy group;
W represents sulfur atom or oxygen atom; and
the bond represented by the following formula:

----- is a single or double bond.

2. A compound represented by the following formula, its pharmaceutically acceptable salt or hydrates thereof

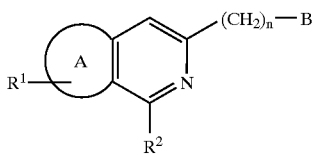

wherein,
ring A represents a pyridine ring;
$R^1$ represents a hydrogen atom, a halogen atom, a lower alkyl group or a lower alkoxy group;
$R^2$ represents a 1-$R^4$-piperazin-4-yl group;
$R^4$ represents a hydrogen atom, a lower alkyl group, a hydroxy lower alkyl group, a halogenated lower alkyl group, a lower cycloalkyl group, an aryl group, an aralkyl group, a 1-piperidyl group, an alkenyl group, a cyano lower alkyl group, a carbamoyl lower alkyl group, a lower acyl group, an aromatic acyl group, a lower alkoxyl carbonyl group, a aryloxycarbonyl group or an aralkyloxycarbonyl group;
n represents 0 or an integer of 1 to 6; and
B represents a group selected from the groups represented by the following formulae:

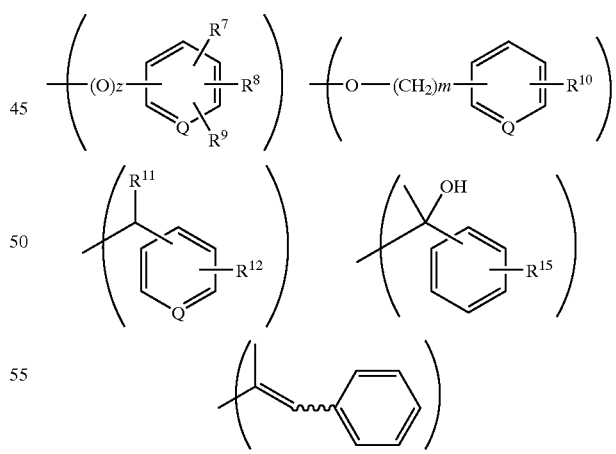

wherein z represents 0 or 1;
Q represents a nitrogen atom or a methine group;
$R^7$, $R^8$ and $R^9$ are the same as or different from each other and each represents a hydrogen atom, a halogen atom, a hydroxy group, a lower alkyl group, a lower alkenyl group, a lower alkynyl group, a lower alkoxy group, a lower thioalkoxyl group, a hydroxy lower thioalkoxyl group, an arylthio group, a heteroarylthio group, a heteroaryl(hydroxy)alkyl group, a halogenated lower alkyl group, a hydroxy lower alkyl group, a dihydroxy lower alkyl group, a halogenated (hydroxy) lower alkyl group, a hydroxyalkenyl group, a hydroxyalkynyl group, a hydroxy lower cycloalkenyl group, a lower alkoxy(hydroxy)alkyl group, a lower alkoxy(hydroxy) alkoxy group, a lower alkoxyalkyl group, a lower alkoxyalkoxy group, a lower thioalkoxyalkoxy group, a lower alkylsulfonylalkoxy group, a hydroxy lower alkoxy group, a dihydroxy lower alkoxy group, a hydroxy lower alkylalkoxy group, a hydroxyimino lower alkyl group, a lower cyclalkyl (hydroxy) alkyl group, an aralkyl group, a hydroxyaralkyl group, a cyano group, a cyano lower alkyl group, an amide group, an N-lower alkylamide group, an N-lower cyclalkylamide group, an N,N-di lower alkylamide group, an N-hydroxy lower alkylamide group, an N-hydroxy lower alkyl-N-lower alkylamide group, an N-arylamide group, a cyclic aminocarbonyl group, a carbamoyl group, an N-lower alkyl carbamoyl group, an N,N-di lower alkyl carbamoyl group, an aminosulfonyl group, a cyclic aminosulfonyl group, an N-lower alkylaminosulfonyl group, an N-lower cycloalkylaminosulfonyl group, an N,N-di lower alkylaminosulfonyl group, an N-hydroxy lower alkylaminosulfonyl group an N-lower alkoxyalkylaminosulfonyl group, an N-halogenated lower alkylsulfonyl group, a pyrrolidinylsulfonyl group, a lower alkylsulfonylaminoalkyl group, an N-lower alkylaminosulfonylalkyl group, an N,N-di lower alkylaminosulfonylalkyl group, a lower acyl group, a lower acylalkyl group, a lower cycloalkyl (hydroxy)methyl group, a tetrahydropyranyl group, a hydroxytetrahydropyranyl group, a hydroxy lower alkyltetrahydropyranyl group, a lower acylaminoalkyl group, a (thiazol-2-yl)hydroxymethyl group, a di(thiazol-2-yl)hydroxymethyl group, a lower alkylsulfonyl group, a lower alkoxyalkylsulfonyl group, a hydroxy lower alkylsulfonyl group, a lower alkylsulfonylalkyl group, an N-lower alkylamidealkyl group, an aryl group, an aralkyl group, a heteroaryl group, a heteroaryl lower alkyl group, a heteroaryl lower alkoxy group, a heteroarylsulfonyl group, a 4-morpholinylsulfonyl group, a 4-oxythiomorpholinylsulfonyl group, a 4-dioxythiomorpholinylsulfonyl group, a 4-morpholinylsulfonyl group, a hydroxy lower cycloalkyl group, a hydroxy lower cycloalkyloxy group, a hydroxycycloalkenyl group, a halogenated hydroxy lower alkyl group, a 4-hydroxypiperidyl group, a 4-lower alkoxypiperidyl group, an ω,ω-lower alkylenedioxyalkyl group, an ω,ω-lower alkylenedioxyalkoxy group, a lower cycloalkylhydroxymethyl group, an aryloxy group, an arylaminosulfonyl group, amino group, a lower alkylamino group, a di lower alkylamino group, a hydroxy lower alkylamino group, a lower acylamino group, a hydroxy lower acylamino group, a lower alkylsulfonylamino group, a pyridyl lower alkoxy group, a lower alkylpyridylalkoxy group, a lower alkoxyhydroxyalkoxy group, a lower thioalkoxyalkoxy group, a lower alkylsulfonylalkoxy group, an N-lower alkylcarbamoyl group, an N,N-di lower alkylcarbamoyl group, an N-hydroxy lower alkylcarbamoyl group, an N-hydroxy lower alkyl-N-lower alkylcarbamoyl group, a halogenated lower alkoxy group, a cyano lower alkoxy group, a hydroxy lower cyclalkoxy group, trifluoromethyl group, a trifluoromethoxy group, an amino lower alkoxy group, an N-lower alkyl aminoalkoxy group, an N,N-di lower alkylaminoalkoxy group, a lower acylalkoxy group, a lower acylaminoalkoxy group, a (1,3-dioxolanyl) lower alkyl group, a (1,3-dioxolanyl) lower alkoxy group, an amido lower alkoxy group, a 4-(hydroxyalkyl) tetrahydropyran-4-yl group, a 2,3-dihydrobenzofuranyl group, a 2-hydroxy-2-alkyl-2,3-dihydrobenzofuranyl group, an indanonyl group, a hydroxyindanyl group, an imidazolyl lower alkoxy group, a succinimide group or a 2-oxazolidon-3-yl group; furthermore, $R^7$ represents a hydrogen atom, while $R^8$ and $R^9$ form a cyclopentanone ring, a hydroxycyclopentane ring, a hydroxylalkylcyclopentane ring, a cyclohexanone ring, hydroxycyclohexane ring, a hydroxyalkylcyclohexane ring, a 2-hydroxymethyl-2-methylcyclopentanone ring, a 1,2-ethylenedioxy ring or a methylenedioxy ring;

m or p represents 0 or an integer of 1 to 6;

$R^{10}$ and $R^{12}$ independently represent a hydrogen atom, a halogen atom, a hydroxyl group, a lower alkyl group, a lower alkoxy group, a hydroxy lower alkyl group, a hydroxy lower alkoxy group or a tetrahydropyranyl group;

$R^{11}$ represents a hydrogen atom, a halogen atom, a hydroxy group, a lower alkyl group or a lower alkoxy group;

W represents sulfur atom or oxygen atom; and the bond represented by the following formula:〰〰 is a trans or cis bond.

3. The compound as claimed in one of claims 1 and 2, wherein $R^1$ is a hydrogen atom.

4. The compound as claimed in one of claims 1 and 2, wherein $R^4$ is ethyl.

5. The compound as claimed in one of claims 1 and 2, wherein B is phenyl, pyridyl, phenyloxy, or pyridyloxy, each of which may be substituted by up to three substituents selected from the group consisting of halogen atoms, lower alkoxy groups, halogenated lower alkyl groups, hydroxy lower alkyl groups, dihydroxy lower alkyl groups, lower alkoxy(hydroxy)alkyl groups, lower alkoxy(hydroxy) alkoxy groups, lower alkoxyalkyl groups, lower alkoxyalkoxy groups, hydroxy lower alkoxy groups, dihydroxy lower alkoxy groups, lower cycloalkyl (hydroxy) alkyl groups, cyano groups, N-lower alkylaminosulfonyl groups, N-lower cycloalkylaminosulfonyl groups, lower acylalkyl groups, hydroxytetrahydropyranyl groups, lower acylaminoalkyl groups, 4-morpholinylsulfonyl groups, hydroxy lower cycloalkyl groups ω,ω-lower alkylenedioxyalkoxy groups, hydroxy lower acylamino groups, lower alkylsulfonylamino groups, halogenated lower alkoxy groups, cyano lower alkoxy groups, N,N-di lower alkylaminoalkoxy groups, and lower acylalkoxy groups.

6. The compound as claimed in one of claims 1 and 2, wherein B is phenyl, pyridyl, phenyloxy, or pyridyloxy, each of which may be substituted by up to three substituents selected from the group consisting of lower alkoxy(hydroxy) alkoxy groups, lower alkoxyalkyl groups, hydroxy lower alkoxy groups, and dihydroxy lower alkoxy groups.

7. A pharmaceutical composition which comprises a pharmaceutically effective dose of the compound as claimed in claim 1 or 2, its pharmaceutically acceptable salt or hydrates thereof, and pharmaceutically acceptable carriers.

8. A method for treating spastic paralysis or for ameliorating myotonia, which comprising the step of administering to a patient a pharmaceutically effective dose of the compound as claimed in claim 1 or 2, its pharmaceutically acceptable salt or hydrates thereof.

* * * * *